United States Patent
Keasling et al.

(10) Patent No.: US 8,158,383 B2
(45) Date of Patent: Apr. 17, 2012

(54) METHODS OF GENERATING PROTEIN VARIANTS

(75) Inventors: Jay D. Keasling, Berkeley, CA (US); Yasuo Yoshikuni, Berkeley, CA (US); Jeffrey Allen Dietrich, Berkeley, CA (US); Farnaz F. Nowroozi, Berkely, CA (US); Patricia C. Babbitt, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1069 days.

(21) Appl. No.: 12/049,008

(22) Filed: Mar. 14, 2008

(65) Prior Publication Data

US 2008/0318292 A1    Dec. 25, 2008

Related U.S. Application Data

(60) Provisional application No. 60/918,417, filed on Mar. 16, 2007.

(51) Int. Cl.
*C12P 21/06* (2006.01)
*C07H 21/02* (2006.01)
*C07K 14/00* (2006.01)

(52) U.S. Cl. ............. 435/69.1; 435/320.1; 435/252.3; 536/23.1; 530/350

(58) Field of Classification Search ............ 530/350; 435/320.1, 252.3, 69.1; 536/23.1
See application file for complete search history.

(56) References Cited

U.S. PATENT DOCUMENTS 7,172,886 B2    2/2007  Keasling et al.
7,888,095 B2 *  2/2011  Keasling et al. ............ 435/232

FOREIGN PATENT DOCUMENTS

WO    WO2006133013 A2    12/2006

OTHER PUBLICATIONS

Rebrin et al. 2001; Effects of carboxyl-terminal truncations on the activity and solubility of human monoamine oxidase B. Journal of Biological Chemistry. 276(31): 29499-29506.*
Lee et al. 2007; published on-line Nov. 7, 2006; Mutations within the membrane domain of HMG-CoA reductase confer resistance to sterol-accelerated degradation. J. Lipid Research 48: 318-327.*
Polakowski et al. 1998; Overexpression of a cytosolic hydroxymethylglutaryl-CoA reductase leads to squalene accumulation in yeast. Applied Microbiology and Biotechnology. 49:66-71.*
Martin, V., et al. Engineering a mevalonate pathway in *Escherichia coli* for production of terpenoids. Nature Biotechnology. 2003, vol. 21, No. 7, pp. 796-802.

* cited by examiner

*Primary Examiner* — Karen Carlson
(74) *Attorney, Agent, or Firm* — Paula A. Borden; Bozicevic, Field & Francis LLP.

(57) ABSTRACT

The present invention provides methods of designing and generating polypeptide variants that have altered properties compared to a parent polypeptide. The present invention further provides a computer program product for carrying out the design of a variant polypeptide. The present invention further provides nucleic acids encoding enzyme variants, as well as vectors and host cells comprising the nucleic acids. The present invention further provides variant enzymes; methods of producing the variant enzymes; and methods of producing compounds using the enzymes.

20 Claims, 74 Drawing Sheets

FIGURE 1A

```
                              *        20         *        40
gi|2961462  : ------------------------MAQISESV--------    :  8
gi|4480457  : ----------------------------MAQI--------    :  4
gi|6251118  : ----------------------------------------    :  -
gi|4480454  : --------------------MALLSIAPLTSTW--CVDKSL   : 19
gi|4480455  : --------------------MSPVSVIPLAYKL--CLPRSL   : 19
gi|2132215  : --------------------MSPVSVIPLAYKL--CLPRSL   : 19
gi|2132215  : --------------------MSPVSVVPLACKL--CLCRSM   : 19
gi|4480458  : --------------------MSPVSVVPLACKL--CLCRSM   : 19
gi|1736792  : --------------------MALVSISPLASKS--CLRKSL   : 19
gi|7381249  : ---------------------MALVSSAPKS---CLHKSL    : 16
gi|2889448  : --------------------MSPVSVISLPSDL--CLPTSF   : 19
gi|5979946  : --------------------MSLISMAPLAPKS--CLHKPF   : 19
gi|2929303  : --------------------MSVISILPLASKS--CLYKSL   : 19
gi|4480453  : -----------------------PRAAGKS----CLHKSL    : 13
gi|2411485  : --------------------MALISTTPIVSRS--CLS---   : 16
gi|3458266  : --------------------MALVSVAPMASRS--CLHKSL   : 19
gi|7381251  : --------------------MALVSILPLSSKS--VLHKSW   : 19
gi|2889448  : --------------------MDLISVLPSASKSCVCLHKPL   : 21
gi|4480460  : ----------------------------------------    :  -
gi|1736792  : --------------------MALVSTAPLASKS--CLHKSL   : 19
gi|2889448  : --------------------MALVSAVPINSKL--CLRRTL   : 19
gi|1508073  : -----------------------TAPLASKS---CLHKSL    : 14
gi|1508074  : -------------------MALLSIVSLQVPK-SCGQKSL    : 20
gi|5979947  : ----------------------------MSS---------   :  3
gi|1736791  : -------------------MALLSIVSLQVPKSCGLKSLI    : 21
gi|7381253  : -------------------MALLSIVSLQVPKSCGLKSLI    : 21
gi|4480448  : --------------------MTSVSVESGTVSCLSSNN      : 18
gi|3252840  : ----------------------MAGVSAVSKV--------    : 10
gi|3252838  : ----------------------------------------    :  -
gi|1508073  : -----------------------AGVSAVSKV--------    :  9
gi|2855836  : -------------MAQLSFNAALKMNALGNKA-IHDPTNC    : 26
gi|1508074  : -------------MAQLSFNAALKMNALGNKA-IHDPTNC    : 26
gi|3576443  : -------------------MALISLSSSAFTF--CLKSK-    : 18
gi|3778921  : -------------MAQLSFNAALKMNALGNKA-IHDPTNC    : 26
gi|4253916  : -------------MAQLSFNAALKMNALGNKA-IHDPTNC    : 26
gi|1457179  : -------------MAQLSFNAALKMNALGNKA-IHDPTNC    : 26
gi|1586560  : -------------MAGVLFANLPCSLQLSPKVPFRQSTNI    : 27
gi|3820148  : -------------MAQLSFNAALKMNALGNKA-IHDPTNC    : 26
gi|3826010  : -------------MAQLSFNAALKMNALGNKA-IHDPTNC    : 26
gi|9965484  : -------------MAQLSFNAALKMNALGNKA-IHDPTNC    : 26
gi|5980027  : ----------------MALPSSSLSSQIHTGATTQC        : 20
gi|7754686  : -------------MALLSSSLSSQIPTGSHP--LTHTQC     : 24
gi|4480452  : --------------------MALISSSLSSQIPTGA        : 16
gi|2889448  : ----------------------------------------    :  -
gi|1508073  : ---------------AHHLTANTQSIPHFSTTL--NAGSSA   : 24
gi|6251118  : MAMPSSSLSSQIPTAAHHLTANAQSIPHFSTTL--NAGSSA   : 39
gi|5979947  : ------------------------MSLEEFYPMATVYVPSST  : 18
```

*         60         *         80
gi|2961462 : ------------------------------------------- :  -
gi|4480457 : ------------------------------------------- :  -
gi|6251118 : ------------------------------------------- :  -
gi|4480454 : V--GSSEAKALLR--KIPTL-----EMCRLTKSVT-P----   : 46
gi|4480455 : MS-SSREVKPLHI--TIPNL-----GMCRRGKSMA-PA---   : 48
gi|2132215 : MS-SSREVKPLHI--TIPNL-----GMCRRGKSMA-PA---   : 48
gi|2132215 : TS-STDELKPLPT--TIPTR-----GMCGRRMSVT-P----   : 47
gi|4480458 : TS-STDELKPLPT--TIPTR-----GMCGRRMSVT-P----   : 47
gi|1736792 : IS-SIHEHKPPYR--TIPNL-----GMRRGKSVT-P----    : 47
gi|7381249 : IRSTHHELKPLRR--TIPTL-----GMCRRGKSFT-P----   : 45
gi|2889448 : IDRSGRELIPLHI--TIPNV-----AMRRQGKLMTRA----   : 49
gi|5979946 : IG-STHEPKVFCRKIPTPTL-----VMCRRAKSV-------   : 47
gi|2929303 : MS-STHELKALCR--PIATL-----GMCRRGKSVM-A----   : 47
gi|4480453 : SS-SAHELKTICR--TIPTL-----GMSRRGKSAT-P----   : 41
gi|2411485 : ---SSHEIKALRR--TIPTL-----GICRPGKSVA-H----   : 42
gi|3458266 : SS-SAHELKTICR--TIPTL-----GMSRRGKSAT-P----   : 47
gi|7381251 : IV-STYEHKAISR--TIPNL-----GLRGRGKSVT-H----   : 47
gi|2889448 : SS-STHKLKPFCK--TIRIL-----VMPRRWEFAR-P----   : 49
gi|4480460 : ----------------MDL----------------------   :  3
gi|1736792 : IS-STHELKALSR--TIPAL-----GMSRRGKSIT-P----   : 47
gi|2889448 : FG-FSHELKAIHS--TVPNL-----GMCRGGKSIA-P----   : 47
gi|1508073 : IS-STHELKALSR--TIPAL-----GMSRRGKSIT-P----   : 42
gi|1508074 : IS-SSNVQKALCISTAVPTL-----RMRRRQKALVI-----   : 50
gi|5979947 : ---IFHEHKPLRK--TIPTLIGKCSTSSRRSVTPA-S----   : 34
gi|1736791 : SSSNVQKALCIST--AVPTL-----RMRRRQKALV-I----   : 50
gi|7381253 : SSSNVQKALCIST--AVPTL-----RMRRRQKALV-I----   : 50
gi|4480448 : ------------------------------------------ :  -
gi|3252840 : ------------------------------------------ :  -
gi|3252838 : ------------------------------------------ :  -
gi|1508073 : ------------------------------------------ :  -
gi|2855836 : RAKSERQMMWVCSRSGRTRV--KMSRGSGGPGPVV-MMSSS  : 64
gi|1508074 : RAKSERQMMWVCSRSGRTRV--KMSRGSGGPGPVV-MMSSS  : 64
gi|3576443 : ---PTHLSKPSPK--SFPTL---------ARKCMR-N----  : 40
gi|3778921 : RAKSEGQMMWVCSKSGRTRV--KMSRGSGGPGPVV-MMSSS  : 64
gi|4253916 : RAKSEGQMMWVCSKSGRTRV--KMSRGSGGPGPVV-MMSSS  : 64
gi|1457179 : RAKSERQMMWVCSRSGRTRV--KMSRGSGGPGPVV-MMSSS  : 64
gi|1586560 : LIPFHKRSSFGFNAQHCVRS-----HLRLRWNCVGIHA---  : 60
gi|3820148 : RAKSEGQMMWVCSKSGRTRV--KMSRGSGGPGPVV-MMSSS  : 64
gi|3826010 : RAKSEGQMMWVCSKSGRPRV--KMSRGSGGPGPVV-MMSSS  : 64
gi|9965484 : RAKSEGQMMWVCSKSGRTRV--KMSRGSGGPGPVV-MMSSS  : 64
gi|5980027 : IPHFHGSLNAGTSAGKRRSL-----YLRWGKGPSK------  : 50
gi|7754686 : IPHFSTTINAGISAGKPRSF---YLRWGKGSNKIIACVGEG  : 62
gi|4480452 : ---HHLTLNAYANTQCIPHFFSTLNAGTSAGKRSSLYLRWG  : 54
gi|2889448 : ------------------------------------------ :  -
gi|1508073 : SKRRSLYLRWGKGSNKIIAC-----VGEGGATSVP------  : 54
```

FIGURE 1C

```
gi|6251118  : SKRRSLYLRWGKGSNKIIAC-----VGEGGATSVP------ :  69
gi|5979947  : L--------------------------------------- :  19
gi|5979947  : ---------------------------------------- :   -

*         100         *         120
gi|2961462  : -----SPSTDLKSTESS---------ITS R G  ED RI :  35
gi|4480457  : -----SKCSSLSAELNE-------SSIISHH G  DD FI :  33
gi|6251118  : ---------MAEISESS-------P RTG H G  DD LI :  26
gi|4480454  : -----STSMCLTTTVSD-DG---Q RIA H P  DD FI :  78
gi|4480455  : -----STSMILTAAVSDDDR---Q RRG Y S  DD FI :  81
gi|2132215  : -----STSMILTAAVSDDDR---Q RRG Y S  DD FI :  81
gi|2132215  : -----SMSMSLNTVVSDNDA---Q RIG Y S  ND FI :  80
gi|4480458  : -----SMSMSLNTVVSDNDA---Q RIG Y S  ND FI :  80
gi|1736792  : -----SMSISLATAAPD-DG---Q RIG Y S  DD FI :  79
gi|7381249  : -----SVSMSLTTAVSD-DG---Q RIG Y S  DD FI :  77
gi|2889448  : -----SMSMNLRTAVSD-DA---I RRG F S  DD LI :  81
gi|5979946  : -----TSSMGTSLDAGH------Q RIG Y S  DD FI :  77
gi|2929303  : -----SKSTSLTTAVSD-DG---Q RIG H S  DD FI :  79
gi|4480453  : -----SMSMSLTTTVSD-DG---Q RMG F S  ND FI :  73
gi|2411485  : -----SINMCLTSVAST-DS---Q RVG Y S  DD FI :  74
gi|3458266  : -----SMSMSLTTTVSD-DG---Q RMG F S  ND FI :  79
gi|7381251  : -----SLRMSLSTAVSDDHG---Q RIVF S  DD FI :  80
gi|2889448  : -----SMSLSTVASEDD------Q RTGGYLS  ND VI :  79
gi|4480460  : -----AVEIAMDLAVDD------E RVG Y S  DD FI :  33
gi|1736792  : -----SISMSSTTVVTD-DG---R RMG F S  DD VI :  79
gi|2889448  : -----SMSMSSTTSVSNEDG---P RIAGH S  DD SI :  80
gi|1508073  : -----SISMSSTTVVTD-DG---R RMG F S  DD VI :  74
gi|1508074  : -----NMKLTTVSHRDDNDGGV-Q RIA H P  ED FI :  85
gi|5979947  : -----ITSMTMETAVSD-DG---Q RVG Y S  DD FI :  66
gi|1736791  : -----NMKLTTVSHRDD-NGGGVQ RIA H P  ED FI :  85
gi|7381253  : -----NMKLTTVSHRDD-NGGGVQ RIA H P  ED FI :  85
gi|4480448  : ----------------------I RTA P P  GY FV :  36
gi|3252840  : -----SSLVCDLSSTSG------I RTA P P  GY LV :  40
gi|3252838  : ------------------------------GY LV :   5
gi|1508073  : -----SSLVCDLSSTSG------I RTA P P  GY LV :  39
gi|2855836  : TGTSKVVSETSSTIVDD------P LSA Y G  HH VI :  99
gi|1508074  : TGTSKVVSETSSTIVDD------P LSA Y G  HH VI :  99
gi|3576443  : -----TMAMATTSVES-------T RTG H G  DD FI :  69
gi|3778921  : TGTSKVVSETSSTIVDD------P LSA Y G  HH VI :  99
gi|4253916  : TGTSKVVSETSSTIVDD------P LSA Y G  HH VI :  99
gi|1457179  : TGTSKVVSETSSTIVDD------P LSA Y G  HH VI :  99
gi|1586560  : -----SAAETRPDQLPQEERF--S LNA Y PA  KD FI :  94
gi|3820148  : TGTSKVVSETSSTIVDD------P LSA Y G  HH VI :  99
gi|3826010  : TGTSKVVSETSSTIVDD------P LSA Y G  HH VI :  99
gi|9965484  : TGTSKVVSETSSTIVDD------P LSA Y G  HH VI :  99
gi|5980027  : -----IVACAGQDPFSV------PTLVKREFPPGF KD HVI :  80
gi|7754686  : TTSLPYQSAEKTDSLSA------PTLVKREFPPGF KD HVI :  97
gi|4480452  : KGSNKIIACVGEDSLSA------PTLVKREFPPGF KD HVI :  89
```

FIGURE 1D

```
gi|2889448  : ---------MSSLAVDD------AE RVG Y P  DDALI :  26
gi|1508073  : -----YQSAEKNDSLSS------STLVKREFPPGF KD LI :  84
gi|6251118  : -----YQSAEKNDSLSS------STLVKREFPPGF KD LI :  99
gi|5979947  : -----PCALSTSSSSSS------ VRTA P P  DYHFV :  49
gi|5979947  : ---MAASTLPSGLSTND------I RTA P P  GY LL :  32
                                       r   h   w     6

*         140         *         160
gi|2961462  : Q L-N P G-APA -------Q  SEKL E I L- -----   :  62
gi|4480457  : Q L-K SNG-APQ -------H  AKL E I N- VVSE-   :  63
gi|6251118  : H L-N P G-APA -------Y LLQKL Q I HL LTE E   :  58
gi|4480454  : Q L-S P G-ATA -------H  QKL G V V- INS L   : 109
gi|4480455  : Q L-S P G-EP  -------R  ERLKG I K- RS S   : 112
gi|2132215  : Q L-S P G-EP  -------R  ETLKG I K- RS S   : 112
gi|2132215  : Q L-T P G-AP  -------I  DGL S V E- NR C   : 111
gi|4480458  : Q L-T P G-AP  -------I  DRL S V E- NR C   : 111
gi|1736792  : Q L-S P G-EP  -------Q  ERL V V K- NS Y   : 110
gi|7381249  : Q L-S P G-EP  -------R  EKL G V E- NS P   : 108
gi|2889448  : Q L-S P G-EP  -------R  ERL G V N- S S   : 112
gi|5979946  : Q L-S P E-ES  -------GD ETL G V E- NS S   : 108
gi|2929303  : Q L-S P G-AS  -------G  ERL G V E- NS S   : 110
gi|4480453  : Q L-S S G-EP  -------R  ERL G V K- NS S   : 104
gi|2411485  : Q LIS P G-APD -------R  DRL G V DI NFKS   : 107
gi|3458266  : Q L-S S G-EP  -------R  ERL G V K- NS S   : 110
gi|7381251  : Q L-S P G-AP  -------R  DRL V V G- TS S   : 111
gi|2889448  : QFL-S P G-ELA -------R  ERL D V D- SS S   : 110
gi|4480460  : Q L-S P G-AS  -------R  ERL G V E- TS S   :  64
gi|1736792  : Q L-P A E-EK  -------L  EKL G V N- NS S   : 110
gi|2889448  : A L-S S E-AP  -------RK DKL G V N- DL S   : 111
gi|1508073  : Q L-P A E-EK  -------L  EKL G VEN- NS S   : 105
gi|1508074  : Q L-S PNG-GS  -------S  ETL E V E- NS P   : 116
gi|5979947  : N LIS P E-AP  -------R  GETL G V E- NS S   :  98
gi|1736791  : Q L-S P G-GS  -------S  ETV E V E- NS -   : 115
gi|7381253  : Q L-S P G-GS  -------S  VTV E V E- NS P   : 116
gi|4480448  : H L-K P THDS  -------R  ETL S I V- L---   :  64
gi|3252840  : H L-K P I-DS  -------R  EVL S I A- LNPAI   :  71
gi|3252838  : H L-K P I-DS  -------R  EVL S I V- LNPAI   :  36
gi|1508073  : H L-K P I-DS  -------R  EVL S I V- LNPAI   :  70
gi|2855836  : Q L-E P RESS  -------Q  DEL VKI D- NA G   : 131
gi|1508074  : Q L-E P RESS  -------Q  DEL VKI D- NA G   : 131
gi|3576443  : Q LPKLP D-APE -------R  DRL G V N- NA R   : 101
gi|3778921  : Q L-E P RESS  -------Q  DEL VKI D- NA G   : 131
gi|4253916  : Q L-E P RESS  -------Q  DEL VKI D- NA G   : 131
gi|1457179  : Q L-E P RESS  -------Q  DEL VKI D- NA G   : 131
gi|1586560  : D L-T PNSHAT KSSVDETINK IQTL K I QC- QS-   : 132
gi|3820148  : Q L-E P RESS  -------Q  DEL VKI D- NA G   : 131
gi|3826010  : Q L-E P RESS  -------Q  DEL VKI D- NA G   : 131
gi|9965484  : Q L-E P RESS  -------Q  DEL VKI D- NA G   : 131
gi|5980027  : E L-MPS KVAP D-------EK IETL T I N- RS G   : 112
```

FIGURE 1E

```
gi|7754686 : D L-T SHKVSAAE-------EK METL S  I N- RS G : 129
gi|4480452 : D L-T SHKVAA D-------EK IETL S  I N- RS G : 121
gi|2889448 : Q L-S P G-ASP      ---RDV EKL G  I E- AS S :  57
gi|1508073 : D L-T SHKVAA D-------EK IETL S  I N- RC G : 116
gi|6251118 : D L-T SHKVAA D-------EK IETL S  I N- RC G : 131
gi|5979947 : Q L-Q P T-DPC       ---G  VETL A  I A- LH--- :  77
gi|5979947 : C L-K P SRDS       ---K  KDTL N  I A- LGAA- :  63
             L                     era    6  e6   f

*        180         *        200
gi|2961462 : LS MDDSCNDSDR------------------------- :  75
gi|4480457 : ------MKDCND--------------------------- :  69
gi|6251118 : MD -GDH-------------------------------- :  64
gi|4480454 : VE -GELITPPN---------------------------- : 120
gi|4480455 : KD -GELITPLN---------------------------- : 123
gi|2132215 : KD -GELITPLN---------------------------- : 123
gi|2132215 : ME -GELMSPLN---------------------------- : 122
gi|4480458 : ME -GELMSPLN---------------------------- : 122
gi|1736792 : LD -GRLMSSFN---------------------------- : 121
gi|7381249 : SE -GESMSPLN---------------------------- : 119
gi|2889448 : NE -GESITPLD---------------------------- : 123
gi|5979946 : MTG---VVSPLN---------------------------- : 117
gi|2929303 : RT -GELVSHVD---------------------------- : 121
gi|4480453 : SE -GELISPHN---------------------------- : 115
gi|2411485 : LE GGN--------------------------------- : 113
gi|3458266 : SE -GELISPHN---------------------------- : 121
gi|7381251 : AE -GELITPLN---------------------------- : 122
gi|2889448 : LE -GEFS------------------------------- : 117
gi|4480460 : IE -GELTS------------------------------ :  72
gi|1736792 : LE -GELMSPLN---------------------------- : 121
gi|2889448 : VE -GVFTSPLS---------------------------- : 122
gi|1508073 : LE -GELMSPLN---------------------------- : 116
gi|1508074 : NNR--ELFGSQN---------------------------- : 126
gi|5979947 : VE AGELITPLN---------------------------- : 110
gi|1736791 : PN -RELFGSQN---------------------------- : 126
gi|7381253 : NNR--ELFGSQN---------------------------- : 126
gi|4480448 : -GGGELMMTPSAYDTAWVARVPSID---GSACPQFPQTVEW : 101
gi|3252840 : TG GESMITPSAYDTAWVARVPAID---GSARPQFPQTVDW : 109
gi|3252838 : TG GESMITPSAYDTAWVARVPAID---GSARPQFPQTVDW :  74
gi|1508073 : TG GESMITPSAYDTAWVARVPAID---GSARPQFPQTVDW : 108
gi|2855836 : DG ----ISPSAYDTAWVARLATIS-SDGSEKPRFPQALNW : 167
gi|1508074 : DG ----ISPSAYDTAWVARVATIS-SDGSEKPRFPQALNW : 167
gi|3576443 : AA -----SSSQ--------------------------- : 108
gi|3778921 : DG ----ISPSAYDTAWVARVATVS-SDGSEKPRFPQALNW : 167
gi|4253916 : DG ----ISPSAYDTAWVARVATVS-SDGSEKPRFPQALNW : 167
gi|1457179 : DG ----ISPSAYDTAWVARVATVS-SDGSEKPRFPQALNW : 167
gi|1586560 : -G -GET-NPSAYDTAWVARIPSID---GSGAPQFPQTLQW : 167
gi|3820148 : DG ----ISPSAYDTAWVARVATIS-SDGSEKPRFPQALNW : 167
gi|3826010 : DG ----ISPSAYDTAWVARVATIS-SDGSEKPRFPQALNW : 167
```

FIGURE 1F

```
gi|9965484 : DGS----ISPSAYDTAWVARVATIS-SDGSEKPRFPQALNW : 167
gi|5980027 : YGE----TNPSAYDTAWVARIPAVD---GSEKPQFPETLEW : 146
gi|7754686 : YGE----TNPSAYDTAWVARIPAVD---GSEHPEFPETLEW : 163
gi|4480452 : YGS----TNPSAYDTAWVARIPAVD---GSEQPEFPETLEW : 155
gi|2889448 : IESGDDEIC------------------------------- :  66
gi|1508073 : YGE----TNPSAYDTAWVARIPAVD---GSDNPHFPETVEW : 150
gi|6251118 : YGE----TNPSAYDTAWVARIPAVD---GSDNPHFPETVEW : 165
gi|5979947 : -GEGGLMTTPSAYDTAWVARVPSID---GSARPQFPQTVQW : 114
gi|5979947 : FGSKEMTTPSAYDTAWVARIPSIDGSSGSARPQFPQTVDW  : 104

*         220         *         240
gi|2961462 : ---------------------------------------- :  -
gi|4480457 : ---------------------------------------- :  -
gi|6251118 : ---------------------------------------- :  -
gi|4480454 : ---------------------------------------- :  -
gi|4480455 : ---------------------------------------- :  -
gi|2132215 : ---------------------------------------- :  -
gi|2132215 : ---------------------------------------- :  -
gi|4480458 : ---------------------------------------- :  -
gi|1736792 : ---------------------------------------- :  -
gi|7381249 : ---------------------------------------- :  -
gi|2889448 : ---------------------------------------- :  -
gi|5979946 : ---------------------------------------- :  -
gi|2929303 : ---------------------------------------- :  -
gi|4480453 : ---------------------------------------- :  -
gi|2411485 : ---------------------------------------- :  -
gi|3458266 : ---------------------------------------- :  -
gi|7381251 : ---------------------------------------- :  -
gi|2889448 : ---------------------------------------- :  -
gi|4480460 : ---------------------------------------- :  -
gi|1736792 : ---------------------------------------- :  -
gi|2889448 : ---------------------------------------- :  -
gi|1508073 : ---------------------------------------- :  -
gi|1508074 : ---------------------------------------- :  -
gi|5979947 : ---------------------------------------- :  -
gi|1736791 : ---------------------------------------- :  -
gi|7381253 : ---------------------------------------- :  -
gi|4480448 : ILKNQLKDGSWGTESHFLLSDRLLATLSCVLALLKWKVADV : 142
gi|3252840 : ILKNQLKDGSWGIQSHFLLSDRLLATLSCVLVLLKWNVGDL : 150
gi|3252838 : ILKNQLKDGSWGIQSHFLLSDRLLATLSCVLVLLKWNVGDL : 115
gi|1508073 : ILKNQLKDGSWGIQSHFLLSDRLLATLSCVLVLLKWNVGDL : 149
gi|2855836 : VFNNQLQDGSWGIESHFSLCDRLLNTTNSVIALSVWKTGHS : 208
gi|1508074 : VFNNQLQDGSWGIESHFSLCDRLLNTTNSVIALSVWKTGHS : 208
gi|3576443 : ---------------------------------------- :  -
gi|3778921 : VLNNQLQDGSWGIESHFSLCDRLLNTVNSVIALSVWKTGHS : 208
gi|4253916 : VLNNQLQDGSWGIESHFSLCDRLLNTVNSVIALSVWKTGHS : 208
gi|1457179 : VLNNQLQDGSWGIESHFSLCDRLLNTVNSVIALSVWKTGHS : 208
gi|1586560 : ILNNQLPDGSWGEECIFLAYDRVLNTLACLLTLKIWNKGDI : 208
```

FIGURE 1G

```
gi|3820148 : VFNNQLQDGSWGIESHFSLCDRLLNTTNSVIALSVWKTGHS : 208
gi|3826010 : VLNNQLQDGSWGIESHFSLCDRLLNTINSVIVLSVWKTGHS : 208
gi|9965484 : VFNNQLQDGSWGIESHFSLCDRLLNTTNSVIALSVWKTGHS : 208
gi|5980027 : ILQNQLKDGSWGEEFYFLAYDRILATLACIITLTIWQTGDT : 187
gi|7754686 : ILQNQLKDGSWGEGFYFLAYDRILATLACIITLTLWRTGET : 204
gi|4480452 : ILQNQLKDGSWGEGFYFLAYDRILATLACIITLTLWRTGEI : 196
gi|2889448 : ---------------------------------------- : -
gi|1508073 : ILQNQLKDGSWGEGFYFLAYDRILATLACIITLTLWRTGET : 191
gi|6251118 : ILQNQLKDGSWGEGFYFLAYDRILATLACIITLTLWRTGET : 206
gi|5979947 : ILKNQLKDGSWGTESHFLLSDRLLATLSCVLALLKWKVGDL : 155
gi|5979947 : ILKNQLKDGSWGTESHFLLSEPLLATISCVLALFKWQVGDL : 145

*         260         *         280
gi|2961462 : ---------------------------------------- : -
gi|4480457 : ---------------------------------------- : -
gi|6251118 : ---------------------------------------- : -
gi|4480454 : ---------------------------------------- : -
gi|4480455 : ---------------------------------------- : -
gi|2132215 : ---------------------------------------- : -
gi|2132215 : ---------------------------------------- : -
gi|4480458 : ---------------------------------------- : -
gi|1736792 : ---------------------------------------- : -
gi|7381249 : ---------------------------------------- : -
gi|2889448 : ---------------------------------------- : -
gi|5979946 : ---------------------------------------- : -
gi|2929303 : ---------------------------------------- : -
gi|4480453 : ---------------------------------------- : -
gi|2411485 : ---------------------------------------- : -
gi|3458266 : ---------------------------------------- : -
gi|7381251 : ---------------------------------------- : -
gi|2889448 : ---------------------------------------- : -
gi|4480460 : ---------------------------------------- : -
gi|1736792 : ---------------------------------------- : -
gi|2889448 : ---------------------------------------- : -
gi|1508073 : ---------------------------------------- : -
gi|1508074 : ---------------------------------------- : -
gi|5979947 : ---------------------------------------- : -
gi|1736791 : ---------------------------------------- : -
gi|7381253 : ---------------------------------------- : -
gi|4480448 : QVEQGIEFIKRNLQAIKDERDQDSLVTDFEIIFPSLLKEAQ : 183
gi|3252840 : QVEQGIEFIKSNLELVKDETDQDSLVTDFEIIFPSLLREAQ : 191
gi|3252838 : QVEQGIEFIKSNLELVKDETDQDSLVTDFEIIFPSLLREAQ : 156
gi|1508073 : QVEQGIEFIKSNLELVKDETDQDSLVTDFEIIFPSLLREAQ : 190
gi|2855836 : QVQQGAEFIAENLRLLNEE---DELSPDFQIIFPALLQKAK : 246
gi|1508074 : QVQQGAEFIAENLRLLNEE---DELSPDFQIIFPALLQKAK : 246
gi|3576443 : ---------------------------------------- : -
gi|3778921 : QVEQGTEFIAENLRLLNEE---DELSPDFEIIFPALLQKAK : 246
gi|4253916 : QVEQGTEFIAENLRLLNEE---DELSPDFEIIFPALLQKAK : 246
```

FIGURE 1H

```
gi|1457179  : QVEQGAEFIAENLRLLNEE---DELSPDFEIIFPALLQKAK : 246
gi|1586560  : QVQKGVEFVRKHMEEMKDEAD-NHRPSGFEVVFPAMLDEAK : 248
gi|3820148  : QVEQGTEFIAENLRLLNEE---DELSPDFEIIFPALLQKAK : 246
gi|3826010  : QVEQGTEFIAENLRLLNEE---DELSPDFEIIFPALLQKAK : 246
gi|9965484  : QVEQGTEFIAENLRLLNEE---DELSPDFEIIFPALLQKAK : 246
gi|5980027  : QVQKGIEFFKTQAGKIEEAD-SHRPSGFEIVFPAMLKEAK  : 227
gi|7754686  : QIRKGIEFFKTQAGKIEDAD-SHRPSGFEIVFPAMLKEAK  : 244
gi|4480452  : QVQKGIEFFKTQAGKIEDAD-SHRPSGFEIVFPAMLKEAK  : 236
gi|2889448  : ---------------------------------------- :   -
gi|1508073  : QVQKGIESFRTQAGKMEDAD-SHRPSGFEIVFPAMLKEAK  : 231
gi|6251118  : QVQKGIEFFRTQAGKMEDAD-SHRPSGFEIVFPAMLKEAK  : 246
gi|5979947  : QVQQGIEFIKSNLEAIKDENDEDSLVTDFDIIFPSLLREAQ : 196
gi|5979947  : QVERGIEFLKSSLEKIKNESDQDSLVTDFEIIFPSMLREAQ : 186

*         300         *         320
gi|2961462  : ---------------------------------------- :   -
gi|4480457  : ---------------------------------------- :   -
gi|6251118  : ---------------------------------------- :   -
gi|4480454  : ---------------------------------------- :   -
gi|4480455  : ---------------------------------------- :   -
gi|2132215  : ---------------------------------------- :   -
gi|2132215  : ---------------------------------------- :   -
gi|4480458  : ---------------------------------------- :   -
gi|1736792  : ---------------------------------------- :   -
gi|7381249  : ---------------------------------------- :   -
gi|2889448  : ---------------------------------------- :   -
gi|5979946  : ---------------------------------------- :   -
gi|2929303  : ---------------------------------------- :   -
gi|4480453  : ---------------------------------------- :   -
gi|2411485  : ---------------------------------------- :   -
gi|3458266  : ---------------------------------------- :   -
gi|7381251  : ---------------------------------------- :   -
gi|2889448  : ---------------------------------------- :   -
gi|4480460  : ---------------------------------------- :   -
gi|1736792  : ---------------------------------------- :   -
gi|2889448  : ---------------------------------------- :   -
gi|1508073  : ---------------------------------------- :   -
gi|1508074  : ---------------------------------------- :   -
gi|5979947  : ---------------------------------------- :   -
gi|1736791  : ---------------------------------------- :   -
gi|7381253  : ---------------------------------------- :   -
gi|4480448  : SLNLGLPYDLPYIRLLQTKRQERLANLSMDKIHG--GTLLS : 222
gi|3252840  : SLRLGLPYDLPYIHLLQTKRQERLAKLSREEIYAVPSPLLY : 232
gi|3252838  : SLRLGLPYDLPYIHLLQTKRQERLAKLSREEIYAVPSPLLY : 197
gi|1508073  : SLRLGLPYDLPYIHLLQTKRQERLAKLSREEIYAVPSPLLY : 231
gi|2855836  : ALGINLPYDLPFIKYLSTTREARLTDVSAAA-DNIPANMLN : 286
gi|1508074  : ALGINLPYDLPFIKYLSTTREARLTDVSAAA-DNIPANMLN : 286
gi|3576443  : ---------------------------------------- :   -
```

FIGURE 1I

```
gi|3778921 : ALGINLPYDLPFIKSLSTTREARLTDVSAAA-DNIPANMLN : 286
gi|4253916 : ALGINLPYDLPFIKSLSTTREARLTDVSAVA-DNIPANMLN : 286
gi|1457179 : ALGINLPYDLPFIKSLSTTREARLTDVSAAA-DNIPANMLN : 286
gi|1586560 : SLGLDLPYHLPFISQIHQKRQKKLQKIPLNVLHNHQTALLY : 289
gi|3820148 : ALGINLPYDLPFIKSLSTTREARLTDVSAAA-DNIPANMLN : 286
gi|3826010 : ALGINLPYDLPFIKYLSTTREARLTDVSAAA-DNIPANMLN : 286
gi|9965484 : ALGINLPYDLPFIKYLSTTREARLTDVSAAA-DNIPANMLN : 286
gi|5980027 : ALGLALPYELPFIQQIIEKREAKLQRLPPDLLYALPTTLLY : 268
gi|7754686 : VLGLDLPYELPFIKQIIEKREAKLERLPTNILYALPTTLLY : 285
gi|4480452 : VLGLDLPYELPFIKQIIEKREAKLERLPTNILYALPTTLLY : 277
gi|2889448 : ---------------------------------------- : -
gi|1508073 : ILGLDLPYDLPFLKQIIEKREAKLKRIPTDVLYALPTTLLY : 272
gi|6251118 : ILGLDLPYDLPFLKQIIEKREAKLKRIPTDVLYALPTTLLY : 287
gi|5979947 : YLDIELPLQPALCKSTPPKRQERLANMSREEIHGVPSPLLY : 237
gi|5979947 : SLHLGLPYDLPYIQLLQTKRQERLANLSREKIHG-GILQLS : 226

*         340         *         360
gi|2961462 : ---------------------------------------- : -
gi|4480457 : ---------------------------------------- : -
gi|6251118 : ---------------------------------------- : -
gi|4480454 : ---------------------------------------- : -
gi|4480455 : ---------------------------------------- : -
gi|2132215 : ---------------------------------------- : -
gi|2132215 : ---------------------------------------- : -
gi|4480458 : ---------------------------------------- : -
gi|1736792 : ---------------------------------------- : -
gi|7381249 : ---------------------------------------- : -
gi|2889448 : ---------------------------------------- : -
gi|5979946 : ---------------------------------------- : -
gi|2929303 : ---------------------------------------- : -
gi|4480453 : ---------------------------------------- : -
gi|2411485 : ---------------------------------------- : -
gi|3458266 : ---------------------------------------- : -
gi|7381251 : ---------------------------------------- : -
gi|2889448 : ---------------------------------------- : -
gi|4480460 : ---------------------------------------- : -
gi|1736792 : ---------------------------------------- : -
gi|2889448 : ---------------------------------------- : -
gi|1508073 : ---------------------------------------- : -
gi|1508074 : ---------------------------------------- : -
gi|5979947 : ---------------------------------------- : -
gi|1736791 : ---------------------------------------- : -
gi|7381253 : ---------------------------------------- : -
gi|4480448 : SLEGIQDIVEWETIMDVQSQDGSFLSSPASTACVFMHTGDM : 263
gi|3252840 : SLEGIQDIVEWERIMEVQSQDGSFLSSPASTACVFMHTGDA : 273
gi|3252838 : SLEGIQDIVEWERIMEVQSQDGSFLSSPASTACVFMHTGDA : 238
gi|1508073 : SLEGIQDIVEWERIMEVQSQDGSFLSSPASTACVFMHTGDA : 272
gi|2855836 : ALEGLEEVIDWNKIMRFQSKDGSFLSSPASTACVLMNTGDE : 327
```

FIGURE 1J

```
gi|1508074 :  ALEGLEEVIDWNKIMRFQSKDGSFLSSPASTACVLMNTGDE : 327
gi|3576443 :  ---------------------------------------- :  -
gi|3778921 :  ALEGLEEVIDWNKIMRFQSKDGSFLSSPASTACVLMNTGDE : 327
gi|4253916 :  ALEGLEEVIDWNKIMRFQSKDGSFLSSPASTACVLMNTGDE : 327
gi|1457179 :  ALEGLEEVIDWNKIMRFQSKDGSFLSSPASTACVLMNTGDE : 327
gi|1586560 :  SLEGLQDVVDWQEITNLQSRDGSFLSSPASTACVFMHTQNK : 330
gi|3820148 :  ALEGLEEVIDWNKIMRFQSKDGSFLSSPASTACVLMNIGDE : 327
gi|3826010 :  ALEGLEEVIDWKKIMRFRSKDGSFLSSPASTACVLMNTGDE : 327
gi|9965484 :  ALEGLEEVMDWKKIMRFQSKDGSFLSSPASTACVLMNTGDE : 327
gi|5980027 :  SLEGLQEIVDWEKIMKLQSKDGSFLSSPASTAAVFMRTGNK : 309
gi|7754686 :  SLEGLQEIVDWEKIIKLQSKDGSFLTSPASTAAVFMRTGNK : 326
gi|4480452 :  SLEGLQEIVDWQKIIKLQSKDGSFLSSPASTAAVFMRTGNK : 318
gi|2889448 :  ---------------------------------------- :  -
gi|1508073 :  SLEGLQEIVEWEKIMKLQSKDGSFLSSPASTAAVFMRTGNK : 313
gi|6251118 :  SLEGLQEIVDWQKIMKLQSKDGSFLSSPASTAAVFMRTGNK : 328
gi|5979947 :  SLEGIEDMVDWERIMDVRSQDGSFLSSPASIACVFMHTGDI : 278
gi|5979947 :  SLEGIEDMVEWERLMDLQSLDGSFLSSPASTAFVFIHTGDL : 267

*         380         *         400         *
gi|2961462 :  ------------------------------K IE VDT  CLGID :  93
gi|4480457 :  ------------------------------R LQ VDIF CLGID :  87
gi|6251118 :  ------------------------------K LQ VDT  CLGID :  82
gi|4480454 :  ------------------------------  LS VDS  RLGID : 138
gi|4480455 :  ------------------------------  LW VDS  RLGID : 141
gi|2132215 :  ------------------------------  LW VDS  RLGID : 141
gi|2132215 :  ------------------------------  LWTVDS  RLGID : 140
gi|4480458 :  ------------------------------  LWTVDS  RLGID : 140
gi|1736792 :  ------------------------------  LW VDS  RLGIA : 139
gi|7381249 :  ------------------------------  LW VDS  RLGID : 137
gi|2889448 :  ------------------------------  LW VDS  RLGID : 141
gi|5979946 :  ------------------------------  LL VDN  RLGIE : 135
gi|2929303 :  ------------------------------H LS VDN  RLGID : 139
gi|4480453 :  ------------------------------  VW VDS  RLGIE : 133
gi|2411485 :  ------------------------------  LL VDD  RLGID : 131
gi|3458266 :  ------------------------------  VW VDS  RLGIE : 139
gi|7381251 :  ------------------------------  LL VDN  RLGID : 140
gi|2889448 :  ------------------------------  LW VDN  RLGID : 135
gi|4480460 :  ------------------------------  LW VDN  RLGIS :  90
gi|1736792 :  ------------------------------  LW VDS  RLGIH : 139
gi|2889448 :  ------------------------------HH LW VDS  RLGID : 140
gi|1508073 :  ------------------------------  LW VDS  GLGIH : 134
gi|1508074 :  ------------------------------T LW VDS  RLGID : 144
gi|5979947 :  ------------------------------  LW VDS  RLGID : 128
gi|1736791 :  ------------------------------T LW VDS  RLGID : 144
gi|7381253 :  ------------------------------T LW VDS  RLGID : 144
gi|4480448 :  KCLDFLNNVLTKFGSSVPCLYPV       LL VDN  RLGID : 304
gi|3252840 :  KCLEFLNSVMIKFGNFVPCLYPV       LL VDN  VRLGIY : 314
gi|3252838 :  KCLEFLNSVMIKFGNFVPCLYPV       LL VDN  VRLGIY : 279
```

FIGURE 1K

```
gi|1508073  : KCLEFLNSVMIKFGNFVPCLYPV    IL VDN VRLGIY : 313
gi|2855836  : KCFTFLNNLLDKFGGCVPCMYSI    IS VDN HLGIG : 368
gi|1508074  : KCFTFLNNLLDKFGGCVPCMYSI    IS VDN HLGIG : 368
gi|3576443  : ----------------------- RLIE VDK RLGIG : 126
gi|3778921  : KCFTLLNNLLDKFGGCVPCMYSI    IS VDN HLGIG : 368
gi|4253916  : KCFTLLNNLLDKFGGCVPCMYSI    IS VDN HLGIG : 368
gi|1457179  : KCFTLLNNLLDKFGGCVPCMYSI    IS VDN HLGIG : 368
gi|1586560  : RCLHFLNFVLSKFGDYVPCHYPL  F IWAVDT RLGID : 371
gi|3820148  : KCFTFLNNLLDKFGGCVPCMYSI    IS VDN HLGIG : 368
gi|3826010  : KCFTFLNNLLDKFGGCVPCMYSI    IS VDN HLGIG : 368
gi|9965484  : KCFTFLNNLLVKFGGCVPCMYSI    IS VDN HLGIG : 368
gi|5980027  : KCLEFLNFVLKKFGNHVPCHYPL  F IWAVDT RLGID : 350
gi|7754686  : KCLEFLNFVLKKFGNHVPCHYPL  F IWAVDT RLGID : 367
gi|4480452  : KCLEFLNFVLKKFGNHVPCHYPL  F IWAVDT RLGID : 359
gi|2889448  : ----------------------YF  IW IDN RLGIS : 84
gi|1508073  : KCLDFLNFVLKKFGNHVPCHYPL  F IWAVDT RLGID : 354
gi|6251118  : KCLDFLNFVLKKFGNHVPCHYPL  F IWAVDT RLGID : 369
gi|5979947  : KCLEFLNNVLTNFGTFVPCLYPV    IL VDN VQLGID : 319
gi|5979947  : KCLAFLNSVLAKFGAFVPCLYHV    IL VDN RLGID : 308
                                        r6  6D   LGI

420         *        440        *
gi|2961462  : FQPEI -L L V -RCWN -  E S DSLKKD  A : 131
gi|4480457  : FQHEIQ-V L V -RYWN LE  I S DSLIKDF A : 126
gi|6251118  : FEHEIQTA L V -RWWN -  E S DSFSKD  A : 121
gi|4480454  : FKNEI -S L V -SYWS -  C  -DSVVND   : 175
gi|4480455  : FKNEI -S L V -SYWN -  C  -DSVVAD   : 178
gi|2132215  : FKNEI -S L V -SYWN -  C  -DSVVAD   : 178
gi|2132215  : FKNEI -ASL V -SYWN -  C  -TSVVTD   : 177
gi|4480458  : FKNEI -ASL V -SYWN -  C  -QSVVTD   : 177
gi|1736792  : FKNEIT-S L V -RYWE N-  C  -DSIVTD   : 176
gi|7381249  : FKKEI -S L V -SYWN -  C  -DSVFPD   : 174
gi|2889448  : FKKEI -S L HV -RYWS -  C  -ESVVTD   : 178
gi|5979946  : FQNEI -S LQ V -SYWS N-  C  -DSVSTD   : 172
gi|2929303  : FQTEI -VSL V -SYWS -  S  -DIVCTD   : 176
gi|4480453  : FKNEI -S L V -SYWS -  C  -ESVVAD   : 170
gi|2411485  : FKKEI -T L VN -SYWN -  C  -ESVVTD   : 168
gi|3458266  : FKNEI -S L V -SYWS -  C  -ESVVAD   : 176
gi|7381251  : FKNEI -A L V -SYWN -  S  -SDSGVAD   : 177
gi|2889448  : FKNEI -S L V -SYWS -  C  -TKSIITN   : 172
gi|4480460  : FENEI -A L V -SYWSD - VR -DSAVPD  I : 127
gi|1736792  : FKDEI -S L V -SYWG N-  C  -ESVVTD   : 176
gi|2889448  : FKDEIN-S L HV -SYWT -  R  -ESGVTD   : 177
gi|1508073  : FKDEI -S L V -SYWG N-  C  -ESAVTD   : 171
gi|1508074  : FQNEI -V L V -SYWK E  C  -DSTFPD   : 182
gi|5979947  : FKDEI -S L V -SHWR E-  C  -ESVATD   : 165
gi|1736791  : FQNEI -V L V -SYWK E-  C  -DSTFPD   : 182
gi|7381253  : FQNEI -V L V -SYWK E-  C  -DSTFPD   : 182
gi|4480448  : FEKEI -E L V -RHWND -  W  -LSPIAD E : 341
```

FIGURE 1L

```
gi|3252840 :  FEKEI -E L V -RHWN      W- LNPIAD E   : 351
gi|3252838 :  FEKEI -E L V -RHWN      W- LNPIAD E   : 316
gi|1508073 :  FEKEI -E L V -RHWN      W- LNPIAD E   : 350
gi|2855836 :  FKQEI -G L V -RHWS      W- DSLVPD     : 405
gi|1508074 :  FKQEI -G L V -RHWS      W- DSLVPD     : 405
gi|3576443 :  FETEIA-E L V -RFWNDI----------SSKD  A : 155
gi|3778921 :  FKQEI -V L V -RHWS      W- DSLVPD     : 405
gi|4253916 :  FKQEI -V L V -RHWS      W- DSLVPD     : 405
gi|1457179 :  FKQEI -V L V -RHWS      W- DSLVPD     : 405
gi|1586560 : YFKKEI -ESL V -RYWDAER   WA-CNPIPD  D  : 409
gi|3820148 :  FKQEI -G L V -RHWS      W- DSLVPD     : 405
gi|3826010 :  FKQEI -V L V -RHWS      W- DCLVPD     : 405
gi|9965484 :  FKQEI -V L V -RHWS      W- DSLVPD     : 405
gi|5980027 : H FKEEI -D L V -SHWD     WA-ENPVPD  D  : 387
gi|7754686 : H FKEEI -D L V -SHWD     WA-ENPIPD  D  : 404
gi|4480452 :  FKEEI -D L V -SHWD      WA-ENPVPD  D  : 396
gi|2889448 :  FENEI -A MEDV SRHWSD    AC -HSVVAD    : 122
gi|1508073 :  FKEEI -E L V -SHWD      WA-ENPVPD  D  : 391
gi|6251118 :  FKEEI -E L V -SHWD      WA-ENPVPD  D  : 406
gi|5979947 :  FEKEI -E L VH-RHWN      W- LNPIAD EI  : 356
gi|5979947 :  FEKEIN-E L V -RYWSNER   W- MNATAD E   : 346
              rhF   EI  a6dyV   W     g  g      l t

460        *         480         *
gi|2961462 : A  F ALR HRYNV SGV ENE   --DNGQ FC---GST-V : 166
gi|4480457 : A  F ALR HRYNV SDV ENE   --NGQ  FC---SST-V : 161
gi|6251118 : A  F ALR HRYNV SGV KNE   --NGK  FC---NFT-G : 156
gi|4480454 : A  L TLR H YPV SDV EQF   --NGQ  AC---SAI-Q : 210
gi|4480455 : A  F TLR H YNV SEV KVFE  --NGQ  AC---SPS-K : 213
gi|2132215 : A  F TLR H YTV SEV KVFE  --NGQ  AC---SPS-K : 213
gi|2132215 : A AXILR H YTV SEV KVFEE  --NGQ  AC---SPS-Q : 212
gi|4480458 : A  L ILRQH YTV SEV KVFEE --NGQ  AC---SPS-Q : 212
gi|1736792 : A  F TLR H YTV PEV KAEQ  --NGQ  VC---SPG-Q : 211
gi|7381249 : AS F TLR H YSV SEV KVFQ  --NGQ  AF---SPS-T : 209
gi|2889448 : A  L TLR H YDV ADV NHF   --SGQ  AC---TLK-Q : 213
gi|5979946 : A  F ILR H YTVFSDV EQF   --KGQ  AS-AWSAN-H : 209
gi|2929303 : A  F ILR H YTVFPDVFEHE   --MGRIAC---SDN-H  : 211
gi|4480453 : A  L TLR H YAV ADV NLE   --NGQ  AC---SPS-Q : 205
gi|2411485 : A  L TLR H YTV SDV NVF   --KNGQ SS---TANIQ : 204
gi|3458266 : A  F TLR H YAV ADV NLF   --NGQ  AC---SPS-Q : 211
gi|7381251 : A  F TLR H YSV SDV EHF EEK KGQ  VC---SAI-Q : 214
gi|2889448 : A  F TLR H YPV ADV KHF   --IGQ  VS---CPS-E : 207
gi|4480460 : A  F TLR H YTV SDVFKVFQ  --RKGE AC---SAI-P : 162
gi|1736792 : A  L TLR H YPV SDVFKAF G---NGQ  SC---SENIQ : 212
gi|2889448 : A  F TLR H YTV SHV DHF   --KGQ  TC---SAI-Q : 212
gi|1508073 : A  F TLR H YPV SDVFKAF G---NGQ  SC---SENIQ : 207
gi|1508074 : A AL TLR H YNV SDV EYF   --KGH  AC---PAI-L : 217
gi|5979947 : A  L TLR H YPV SDV EHF   --KGH  ASCSSSSI-E : 203
gi|1736791 : A AL TLR H YNV SDV EYF   --KGH  AC---PAI-L : 217
```

FIGURE 1M

```
gi|7381253  : ASALTLRHYNVSDVEYF--KGHAC---PAI-L : 217
gi|4480448  : AFFLLRHRYNVPVVDNF--ADGEFC---STG-Q : 376
gi|3252840  : AFFLLRHRYNVPAIFDNF--ANGKIC---STG-Q : 386
gi|3252838  : AFFLLRHRYNVPAIFDNF--ANGKIC---STG-Q : 351
gi|1508073  : AFFLLRHRYNVPAIFDNF--ANGKIC---STG-Q : 385
gi|2855836  : ALLTLRHYNVSDVNNF--NGRFS---SAG-Q : 440
gi|1508074  : ALLTLRHYNVSDVNNF--NGRFS---SAG-Q : 440
gi|3576443  : AILLRHRYPVSDVEQFE--KIGHLC---CTT-Q : 190
gi|3778921  : ALLTLRTHYDVSDVNNF--NGRFS---SAG-Q : 440
gi|4253916  : ALLTLRTHYDVSDVNNF--NGRFS---SAG-Q : 440
gi|1457179  : ALLTLRTHYDVSDVNNF--NGRFS---SAG-Q : 440
gi|1586560  : ALILRHYNVSDVENF--KGDFC---FAG-Q : 444
gi|3820148  : ALLTLRTHYDVSDVNNF--NGRFS---SAG-Q : 440
gi|3826010  : ALLTLRTHYDVSDVNNF--NGRFS---SAG-Q : 440
gi|9965484  : ALLTLRTHYDVSDVNNF--NGRFS---SAG-Q : 440
gi|5980027  : ALILRHYNVSDVKTF--NGEFC---FLG-Q : 422
gi|7754686  : ALILRHYNVSDVKTF--NGEFC---FLG-Q : 439
gi|4480452  : ALILRHYNVSDVKTF--NGEFC---FLG-Q : 431
gi|2889448  : AAFTLRHYSVCSDVFKIFQ--KGEAC---SAD-Q : 157
gi|1508073  : ALILRHYNVSDVKTF--NGEFC---FLG-Q : 426
gi|6251118  : ALILRHYNVSDVKTF--NGEFC---FLG-Q : 441
gi|5979947  : AFLLRHRYNVPAVFENF--SNGHVC---SGA-Q : 391
gi|5979947  : AFLLRHRYHVPVVFKKF--ADGELS---SIG-Q : 381
              A  g  r LR HgY Vs  6l F       G f

500           *      520        *
gi|2961462  : EEEGAEAYNKHV-RCLSLSRNI----LFPGEKMEEAK : 202
gi|4480457  : EE-------KFV-RCLTLREI----SFPGEKMDEAK : 190
gi|6251118  : EEGRGD---KQV-RSLSLLREI----SFPGEKMEEAK : 189
gi|4480454  : TE-------GEI-KTLLRLI----FPGEKMEEAE : 239
gi|4480455  : TE-------GEI-RSALLRLI----FPGEKMDDAE : 242
gi|2132215  : TE-------GEI-RSALLRLI----FPGEKMDDAE : 242
gi|2132215  : TE-------GEI-RSFLLRLI----FPGEKMEEAQ : 241
gi|4480458  : TE-------GEI-RSFLLRLI----FPGEKMEEAQ : 241
gi|1736792  : TE-------GEI-RSLLRLI----FPGEKMEEAE : 240
gi|7381249  : KE-------RDI-RTLLRFI----FPGEKMEEAE : 238
gi|2889448  : TE-------DQI-RTLLRLI----FPGEKMDEAE : 242
gi|5979946  : TE-------RQI-RSLLRLI----FPGEKMEFAQ : 238
gi|2929303  : TE-------RQI-SSLLRLI----FPGEKMEEAE : 240
gi|4480453  : TE-------EFI-RSLLRLI----FPGEKMEEAE : 234
gi|2411485  : IE-------GEI-RGLLRLV----FPGEKMDEAE : 233
gi|3458266  : TE-------EFI-RSLLRLI----FPGEKMEEAE : 240
gi|7381251  : TE-------EEI-KSLLRLI----FPGEKMEEAE : 243
gi|2889448  : TE-------EDI-RIVLRLIAFPVFPGEKMEEAE : 240
gi|4480460  : TE-------GDI-KGLLRYI----FPGEKMEKAQ : 191
gi|1736792  : TD-------EEI-RGLLRLI----FPGEKMDEAE : 241
gi|2889448  : TE-------GEI-RDLLRLI----FPGEKMEAAE : 241
gi|1508073  : TD-------EEI-RGLLRLI----FPGEKMDEAE : 236
gi|1508074  : TE-------GQITRSLLRLV----FPGEKMEEAE : 247
```

FIGURE 1N

```
gi|5979947 : TG-------GEI-RS L  L R  LI----  FPNEK MDEAQ : 232
gi|1736791 : TE-------GQITRS L  L R  LV----  FPGEK MEEAE : 247
gi|7381253 : TE-------GQITRS L  L R  LV----  FPGEK MEEAE : 247
gi|4480448 : FN-------KDV-AS LSL R  QL----  FPEES LDEAK : 405
gi|3252840 : FN-------KDV-AS L  L R  QL----  FPGEN LDEAK : 415
gi|3252838 : FN-------KDV-AS L  L R  QL----  FPGEN LDEAK : 380
gi|1508073 : FN-------KDV-AS L  L R  QL----  FPGEN LDEAK : 414
gi|2855836 : TH-------VEL-RS V  L R  DL----  FPDERAMDDAR : 469
gi|1508074 : TH-------VEL-RS V  L R  DL----  FPDERAMDDAR : 469
gi|3576443 : LE-------EFI-KS L  L R  LI----  FPNEK MDEAK : 219
gi|3778921 : TH-------VEL-RS V  L R  DL----  FPDEGAMDDAR : 469
gi|4253916 : TH-------VEL-RS V  L R  DL----  FPDEGAMDDAR : 469
gi|1457179 : TH-------VEL-RS V  L R  DL----  FPDEGAMDDAR : 469
gi|1586560 : TQ-------IGV-TDNL I  RC QV---- CFPGEK MEEAK : 473
gi|3820148 : TH-------VEL-RS V  L R  DL----  FPDEGAMDDAR : 469
gi|3826010 : TH-------VEL-RS V  L R  DL----  FPDEGAMDDAR : 469
gi|9965484 : TH-------VEL-RS VIL R  DL----  FPDEGAMDDAR : 469
gi|5980027 : TQ-------RGV-TD L  VNRC HV----  FPGET MEEAK : 451
gi|7754686 : TQ-------RGV-TD L  VNRC HV----  FPGET MQEAK : 468
gi|4480452 : TQ-------RGV-TD L  VNRC HV----  FPGET MEEAK : 460
gi|2889448 : TE-------GEI-KG L  LLR  LI----  FPGER LQFAE : 186
gi|1508073 : TQ-------RGV-TD L  VNRC HV----SFPGET MEEAK : 455
gi|6251118 : TQ-------RGV-TD L  VNRC HV----SFPGET MEEAK : 470
gi|5979947 : FN-------KDV-AS L  L R  QL----  FPGEN LDEAK : 420
gi|5979947 : FN-------KDV-AS L  L R  CEL---  FPGEN LDEAK : 410
                                6     6n6 Ras 6   aFP E  6  A

540         *        560           *
gi|2961462 : A TTN L KV A--GR-EATHVDES LGEVK ALE PW CS : 240
gi|4480457 : A TTE LTKV T--GV-DVTDVNQS LREVK ALE PW CS : 228
gi|6251118 : A TRE LNQV A--GHGDVTDVDQS LREVK ALE PW CS : 228
gi|4480454 : I STI L E L------KIPVCS- SREIA VLE GW MN : 273
gi|4480455 : I SSR L E Q------ETPDCS- SQEIA ALE GW TN : 276
gi|2132215 : I SSR L E Q------KIPDCS- SQEIA ALE GW TN : 276
gi|2132215 : I SSR L E Q------KIPVSS- SREIGDVLE GW TN : 275
gi|4480458 : I SSR L E Q------KIPVSG- SREIGDVLE GW TN : 275
gi|1736792 : I STR L E KV-----KIPVSA- SQEIK VME GW TN : 274
gi|7381249 : I SSR L E Q------KIPVSS- SQEID TLE GW TN : 272
gi|2889448 : S SAK L E Q------KIPVSS-FSREIGDVLE GW TY : 276
gi|5979946 : I SAT L E Q------TIPLSG- SQEIQ ALF RW SN : 272
gi|2929303 : I SAT L E Q------TIPVSS- SQEIQ VLQ RW SN : 274
gi|4480453 : I SAK LEE Q------KISVSS- SQEIRDVLE GW TY : 268
gi|2411485 : T STK L E Q------KIPASSI SLEIRDVLE GW TN : 268
gi|3458266 : I SAK LEES Q-----KISVSS- SQEIRDVLE GW TY : 274
gi|7381251 : I SKI L E Q------NIAVSS- SREIE VLEDGWQTN : 277
gi|2889448 : S SEK L ET Q-----KIPDCS- SREIGDVLEHGW TN : 274
gi|4480460 : T AAT L E Q------KIQVSS- SREIE VLF GWLTN : 225
gi|1736792 : I STK L E Q------KIPVSS- SREIGDVLE GW TY : 275
gi|2889448 : I STM L D Q------KIPPSG- SQEIE LLE GW TN : 275
```

FIGURE 1O

```
gi|1508073  : I  STK  L E  Q------KIPVSS- SREIGDVL  GW  TY : 270
gi|1508074  : I  SAS  L EV Q------KIPVSN- SGEIE VL  GW  TN : 281
gi|5979947  : I  STT  L E VQ------KIPVSS- SRQIE VM  GWDTN : 266
gi|1736791  : I  SAS  L KV Q------KIPVSN- SGEIE VL  GW  TN : 281
gi|7381253  : I  SAS  L EV Q------KIPVSS-FSREIE VL  GW  TN : 281
gi|4480448  : S  STQ  L E  EKSETFSSWNHRQS SEEIK ALKTSW  AS : 446
gi|3252840  : S  ATK  L E  EKSETSSAWNNKQN SQEIK ALKTSW  AS : 456
gi|3252838  : S  ATK  L E  EKSETSSAWNNKQN SQEIK ALKTSW  AS : 421
gi|1508073  : S  ATK  L E  EKSETSSAWNNKQN SQEIK ALKTSW  AS : 455
gi|2855836  : K  AEP  L E  A-----TKISTNTK FKEIE VVE PW  MS : 505
gi|1508074  : K  AEP  L E  A-----TKISTNTK FKEIE VVE PW  MS : 505
gi|3576443  : A  STM  L QVFQ-----KSHILGTH LKEIT NLE GWRTN : 255
gi|3778921  : K  AEP  L D  A-----TKISTNTK YKEIE VVE PW  MS : 505
gi|4253916  : K  AEP  L D  A-----TKISTNTK YKEIE VVE PW  MS : 505
gi|1457179  : K  AEP  L D  A-----TKISTNTK YKEIE VVE PW  MS : 505
gi|1586560  : T  TTNHL QN  AKNNAFDKWAVKKD PGEVE AIK PW  RS : 514
gi|3820148  : K  AEP  L D  A-----TKISTNTK FKEIE VVE PW  MS : 505
gi|3826010  : K  AEP  L D  A-----TKISTNTK FKEIE VVE PW  MS : 505
gi|9965484  : K  AEP  L D  A-----TKISTNTK FKEIE VVE PW  MS : 505
gi|5980027  : LCTER  L N  EDGGASDKWALKKN RGEVE ALK PW  RS : 492
gi|7754686  : LCTER  L N  EDVGAFDKWALKKN RGEVE ALK PW  RS : 509
gi|4480452  : TCTER  L N  EDVGAFDKWALKKN RGEVE ALK PW  RS : 501
gi|2889448  : I  ATT  L E  P------KIQGSR- SQEIE VL  GWLTD : 220
gi|1508073  : LCTER  L N  ENVDAFDKWAFKKN RGEVE ALK PW  KS : 496
gi|6251118  : LCTER  L N  ENVDAFDKWAFKKN RGEVE ALK PW  KS : 511
gi|5979947  : S  TSK  L E  EKRETYSAWNNKQS SEEIK ALENSW  AS : 461
gi|5979947  : G  TAK  L E  EKTETFSSWNIKRN SQEIK ALKTSW  AS : 451
                f    yL  a                26    6    Wh

580          *         600         *
gi|2961462  : QRWE   S  ET  GQIDSELKSNL-------SK M  L  KL : 274
gi|4480457  :  RWE   S  EICGQ DSWLKSIM-------NK VL  L  KL : 262
gi|6251118  :  RWE   S  ET  GH HSWLKSNI-------NQ M KL  KL : 262
gi|4480454  :  R E   N  DV GQ  PIYLRS---------TQ  L  L  KL : 305
gi|4480455  :  R E   N  DV GHPSSPWLKKN-KTQY DGE LL  L  KL : 316
gi|2132215  :  R E   N  DV GHPSSPWLKKN-KTQY DGE LL  L  KL : 316
gi|2132215  :  RWE   N  DV GQ TNTPFNKN-KMQY NTE IL  L  KL : 315
gi|4480458  :  RWE   N  DV GQ TNTSFNKN-KMQY NTE IL  IVKL : 315
gi|1736792  :  R E   N  DTLEK TSAWLNKN------AGK LL  L  KL : 309
gi|7381249  :  R ET  N  DV GHPTSPWLKKK-RTQY DSE LL  L  KL : 312
gi|2889448  :  R E   N  DV GQ -----TEN-SKSY KTE IL  L  KL : 311
gi|5979946  :  R EV  S  DILAE -----TIN-EMSYPKVE IL  L  KL : 307
gi|2929303  :  R E   T  DILQE -----TKN-QMLD NTK VL  L  KL : 309
gi|4480453  :  R E   NH DV GQ -----TQN-SKSC NTD IL  L  KL : 303
gi|2411485  :  R E   N  DV GQH --------TKNKNAAE IL  L  KL : 300
gi|3458266  :  R E   NH DV GQ -----TQN-SKSC NTE IL  L  KL : 309
gi|7381251  :  R ET  N  DVLGE -----DRD-ETLY NME IL  I  KL : 312
gi|2889448  :  R E   N  DV GQ -----TKN-MEPNRKTE IL  L  KL : 309
gi|4480460  : F R E   N  DV GEEI----CPYFKKPC MVD IL  L  KL : 262
```

FIGURE 1P

```
gi|1736792 : .RE.N..QV.GQ-----TEN-TKSY.KSK.IL.L.KL : 310
gi|2889448 : .R.ET.M..DV.GE-----TTF-ETPY.IRE.LL.L.KL : 310
gi|1508073 : .RE.N..HV.GQ-----TEN-TKSY.KSK.IL.L.KL : 305
gi|1508074 : .RE.N..EV.EQSGYE--SLN-EMPY.NMK.IL.L.KL : 319
gi|5979947 : .RE..H..HVLGQ.ITYNDN---EMPYTNVE.IL.L.KL : 304
gi|1736791 : .RE.N..EV.EQSGYE--SLN-EMPY.NMK.IL.L.KL : 319
gi|7381253 : .RE.N..DV.GQ.SYE--SSN-EMPY.NTQ.IIKL.KL : 319
gi|4480448 : .RE..R.CQV.RQ.YAHLAKSVYKLPK.NNE.IL.L.KL : 487
gi|3252840 : .RE..R.CQV.RP.YARIAKCVYKLPY.NNE.FL.LGKL : 497
gi|3252838 : .RE..R.CQV.RP.YARIAKCVYKLPY.NNE.FL.LGKL : 462
gi|1508073 : .RE..R.CQV.RP.YARIAKCVYKLPY.NNE.FL.LGKL : 496
gi|2855836 : .RE..S.DS.DD.YVWQRKTLYRMPS.SNS.CL.L.KL : 546
gi|1508074 : .RE..S.DS.DD.YVWQRKTLYRMPS.SNS.CL.LAKL : 546
gi|3576443 : .RE.N..DI.GE.SSWLMDMD-------NKNI.Y.KL : 289
gi|3778921 : .RE..S.DS.DD.YVWQRKTLYRMPS.SNS.CL.L.KL : 546
gi|4253916 : .RE..S.DS.DD.YVWQRKTLYRMPS.SNS.CL.L.KL : 546
gi|1457179 : .RE..S.DS.DD.YVWQRKTLYRMPS.SNS.CL.L.KL : 546
gi|1586560 : .RE..S.EQ.GS.DVWLGKTVYKMLY.SNE.YL.L.KL : 555
gi|3820148 : .RE..GS.DS.DD.YVWQRKTLYRMPS.SNS.CL.L.KL : 546
gi|3826010 : .RE..S.DS.DD.YVWERKTLYRMPS.SNS.CL.L.KL : 546
gi|9965484 : .RSE..S.DS.DD.YVWERKTLYRMPS.SNS.CL.L.KL : 546
gi|5980027 : .RE..S.EN.GP.DVWLGKTMYMMPN.SNE.YL.L.KL : 533
gi|7754686 : .RE..S.EH.GP.DVWLGKTMYMMPY.SNL.YL.L.KL : 550
gi|4480452 : .RE..S.EH.GP.DVWLGKTMYMMPY.SNE.YL.L.KL : 542
gi|2889448 : .R.ET.N..EV.LAEEI----TPYFKKPC.AVE.LIKL.KI : 257
gi|1508073 : .RE..S.EN.GP.DVWLGKTVYMMPY.SNE.YL.L.KL : 537
gi|6251118 : .RE..S.EN.GP.DVWLGKTVYMMPY.SNE.YL.L.KL : 552
gi|5979947 : .RE..R.CQV.RS.YTYLAKSVYKLPK.NNE.IL.L.KL : 502
gi|5979947 : .RE..R.CQV.RP.YARLDKSVYKLHH.NNE.IL.L.KL : 492
              pR Ea                             6 6aK6

620        *        640        *
gi|2961462 : DF..LQCTHQK..QI.S..AD.SIAS.NFYRKCYVE..FW : 315
gi|4480457 : DF..LQWAHHR..QL.SS..SQ.DIAQQNFYRK.HVEF.LW : 303
gi|6251118 : DF..LQCKHHK..QF.T..D..ISQ.NFYRK.HVEY.SW : 303
gi|4480454 : EF..FQ..QQE..KH.S..D..FSQ.AFARH.HVEY.TL : 346
gi|4480455 : EF..FH..QQE..QY.S..D..LPK.AFSRH.HVEY.TL : 357
gi|2132215 : EF..FH..QQE..QY.S..D..LPK.AFSRH.HVEY.TL : 357
gi|2132215 : EF..FH..QQR..QC.L..E..LPQ.TFARH.HVEF.TL : 356
gi|4480458 : EF..FH..QQR..QC.L..E..LPQ.TFARH.HVEF.TL : 356
gi|1736792 : EF..FN..QQK..QY.L..E.DLPK.TFARH.HVEF.TL : 350
gi|7381249 : EF..FH..QQK..QY.S..IH..LPE.TFGRH.HVEY.TL : 353
gi|2889448 : EF..FHA.QKR..EY.V..G..SPQ.TFCRH.HVEY.TL : 352
gi|5979946 : EF..FH..QQK..QC.W..E..SPE.TFVRH.YVEY.TL : 348
gi|2929303 : EF..FH..QQN..KS.S..E..FPD.NFIRH.HVEF.TL : 350
gi|4480453 : EF..FH..QKR..EY.V..D..SPQ.TFGRI.HIEY.TL : 344
gi|2411485 : EF..FH..QER..KH.S..D..SPE.TFCRH.HVEY.AL : 341
gi|3458266 : EF..FH..QKR..EY.V..D..SPQ.TFCRH.HVEY.TL : 350
gi|7381251 : EF..FH..QQR..KD.S..D..FSH.TFSRH.HVEF.AL : 353
```

FIGURE 1Q

```
gi|2889448 : E FQ QKT ES L ND SPQ TFTRH HVEY TL : 350
gi|4480460 : E FH QQT KH D FSQ TFTRH HVEF TL : 303
gi|1736792 : E FQ QKR ES V E FPE TFCRH HVEY TI : 351
gi|2889448 : E FH VKR QS DY FPE TFSRH HVEY TL : 351
gi|1508073 : E FQ QKR ES V E FPE TFCRH HVEY TI : 346
gi|1508074 : E FH QLR QS E SSQ TFTRH HVEY TM : 360
gi|5979947 : E FH QQR KH D MPEAT FTRH HVEY AL : 345
gi|1736791 : E FH QLR QS E SSQ TFTRH HVEY TM : 360
gi|7381253 : E FH QQK QY D CSSH TFTRH HVEY TM : 360
gi|4480448 : D IQ HQK KN TS D LPLFT FARE PIEF FL : 528
gi|3252840 : D IQ HQE KN TS D LPLFT FARE PIEF FL : 538
gi|3252838 : D IQ HQE KN TS D LPLFT FARE PIEF FL : 503
gi|1508073 : D IQ HQE KN TS D LPLFT FARE PIEF FL : 537
gi|2855836 : D VQ HQE KL T E MAD NFTRH VAEV F- : 586
gi|1508074 : D VQ HQE KL T E MAD NFTRH VAEV F- : 586
gi|3576443 : D LQ YRP QM S D SLYK DFSRH HIEY LFQ : 330
gi|3778921 : D VQ HQE KL T E MAD NFTRH VAEV F- : 586
gi|4253916 : D VQ HQE KL T E MAD NFTRH VAEV F- : 586
gi|1457179 : D VQ HQE KL T E MAD NFTRH VAEV F- : 586
gi|1586560 : D VQA HQK TQH VS E FND TFTRQ PVEM FS : 596
gi|3820148 : D VQ HQE KL T E MAD NFTRH VAEV F- : 586
gi|3826010 : D VQ HQE KL T E MAD NFTRH VAEV F- : 586
gi|9965484 : D VQ HQE KL T E MAD NFTRH VAEV F- : 586
gi|5980027 : D RVQFFHRQ QD R NS FSQ GFTRE VAEI FS : 574
gi|7754686 : D HVQ HQK RD R S LSE KFTRE VTEI FS : 591
gi|4480452 : D HVQ HQK RD R TS FTE KFTRE VTEI FS : 583
gi|2889448 : E FH QQT KH D FAQ TFTRH HVEF TI : 298
gi|1508073 : D KLQ HQT QD R S FTE NFTRE VTEI FS : 578
gi|6251118 : D KVQ HQT QD R S FTD NFTRE VTEI FS : 593
gi|5979947 : DFQHYPGHPPKRDEECHHLV N EFPL PFGRE PVEC FI : 543
gi|5979947 : D IQ LQE KN TS D LPLFS ARQ PIEF FL : 533
              Fn    s    e   rw  sg   F R  r   E

660       *        680       *
gi|2961462 : MAAAIS EFSGSRVA TKIAI MTM DDL DTH LK : 356
gi|4480457 : VVIGTF EFSTCRIT AKIST MTI DDL DTH LK : 344
gi|6251118 : VVMCIF EFSESRIA AKTAI CTV DDL DTHA H IK : 344
gi|4480454 : ASCIDIY QHSSFRLG AKIAH GTV DDI DT LE : 387
gi|4480455 : GSCIATD KHRAFRLG VKTCH NTV DDI DT IE : 398
gi|2132215 : GSCIATD KHRAFRLG VKTCH NTV DDI DT IE : 398
gi|2132215 : ASCIAT KHSAFRLG AKMCH VTV DDV DT K LE : 397
gi|4480458 : ASCIAC KHSAFRLG AKMCH VTV DDV DT K LE : 397
gi|1736792 : ASCIAID KHSAFRLG AKMCH VTV DDI DT LE : 391
gi|7381249 : SSCIAT KHSAFRLG AKTCH ITV DDI DT IE : 394
gi|2889448 : ASCIAF QHSGFRLG AKACH ITV DDM DT LE : 393
gi|5979946 : VAGIDM QHSAFRIA VKMCH ITI DDM DT LR : 389
gi|2929303 : VSGIDM KHCTFRLS VKMCH ITV DDM DT LR : 391
gi|4480453 : ASCIAF QHSGFRLG AKTCH ITI DDM DT LE : 385
gi|2411485 : ASCIAF QHSGFRLG TKMSH ITV DDM DV LE : 382
```

FIGURE 1R

```
gi|3458266  : ASCIAF  QHSGFRLG AKACH ITI DDM DT      LE : 391
gi|7381251  : ASCIETDRKHSGFRLG AKMCH ITV DDI DT      LE : 394
gi|2889448  : ASCIAF  QHSGFRLG AKACH LTV DDM DL      LK : 391
gi|4480460  : ASCIAI  KHSAFRLG AKVCY GIV DDI DT   K K LE : 344
gi|1736792  : ASCIAF  QHSGFRLG AKTCH ITV DDM DT      LE : 392
gi|2889448  : AACIAND KHSAFRLG GKISH ITI DDI DT    E LK : 392
gi|1508073  : ASCIAF  QHSGFRLG AKTCH ITV DDM DT      LE : 387
gi|1508074  : ASCISM  KHSAFRME VKVCH VTV DDI DT      LQ : 401
gi|5979947  : ASCIAF  QHSGFRFG AKLCH ITV DDM DL      LE : 386
gi|1736791  : ASCISML KHSAFRME VKVCH VTV DDI DT      LQ : 401
gi|7381253  : ASCISM  KHSAFRLG VKTCH LTV DDM DT      LQ : 401
gi|4480448  : IAGGTY  QYAKCRFL TKVAC QTV DDM DT   PS LK : 569
gi|3252840  : VAAGTY  QYAKCRFL TKVAC QTV DDM DT      LK : 579
gi|3252838  : VAAGTY  QYAKCRFL TKVAC QTV DDM DT      LK : 544
gi|1508073  : VAAGTY  QYAKCRFL TKVAC QTV DDM DT      LK : 578
gi|2855836  : -SSATF  EYSATRIA TKIGC QVLFDDMADI A    LK : 626
gi|1508074  : -SSATF  EYSATRIA TKIGC QVLFDDMADI A    LK : 626
gi|3576443  : GCAITG  KHSGFRIDIAKYST ATI DDI DT    E LK : 371
gi|3778921  : -SSATF  EYSATRIA TKIGC QVLFDDMADI A    LK : 626
gi|4253916  : -SSATF  EYSATRIA TKIGC QVLFDDMADI A    LK : 626
gi|1457179  : -SSATF  EYSATRIA TKIGC QVLFDDMADI A    LK : 626
gi|1586560  : VAVSMF  EFAACRIA AKTSC AVI DDI DTH   DLK : 637
gi|3820148  : -SSATF  EYSATRIA TKIGC QVLFDDMADI A    LK : 626
gi|3826010  : -SSATF  EYSATRIA TKIGC QVLFDDMADI A    LK : 626
gi|9965484  : -SSATF  EYSATRIA TKIGC QVLFDDMADI A    LK : 626
gi|5980027  : PASFLF  EFATCRAV TKTSNFTVI DDL DAH   NLK : 615
gi|7754686  : AASFIF  EFATCRDV TKISIFTVI DDL DAH   NLE : 632
gi|4480452  : PASFMF  EFATCRAV TKTSNFTVI DDL DAH   DLK : 624
gi|2889448  : ASCIAM  KHSAFRLG AKLCY GIV DDI DT   K E LE : 339
gi|1508073  : PASFIF  EFSKCREV TKTSNFTVI DDL DAH   DLK : 619
gi|6251118  : PASFIF  EFSKCREV TKTSNFTVI DDL DAH   DLK : 634
gi|5979947  : VAAGTY  QYAKCRFL SKVAC NTV DDM DT      LK : 584
gi|5979947  : ITAGTY  RYAKCRLL TKVAC ETV DDM DT      LK : 574
               ep     R    K     6 DD6yD g       6

700         *         720          *         7
gi|2961462  :   EG RRW VSLVEGL DF-M IAF EFWLKTSN  IA AV : 396
gi|4480457  :   EG KRW LSLVDRL DY-I ITFEFFLNTSN   IA VA : 384
gi|6251118  : M EG RRW LSLTDDL DY-I IAFQFF NT N   IV IV : 384
gi|4480454  :  AA KRWHPSAAEGL EY-M GVYMMF ET N   AR AE : 427
gi|4480455  :  EA RRW PSETESL DY-M GVYMVL EA T   AQ AQ : 438
gi|2132215  :  EA RRW PSETESL DY-M GVYMVL EA T   AQ AQ : 438
gi|2132215  :  AA KRW LSETERL EY-M GLYVVL ET N   AQ AE : 437
gi|4480458  :  AA KRW LSETERL EY-M GLYVVL ET N   AQ AE : 437
gi|1736792  :  SA KRW SSEIEHL EY-M CVYMVV ET N   TR AE : 431
gi|7381249  :  NEA RRW PSEKERL EY-M EIYMAL EA TD AR AE : 434
gi|2889448  :  SA KRW PSATECL EY-M GVYMTV NT N   SQ AD : 433
gi|5979946  :  AA KRW RSPTECL QY-M GVYMVL DT N   AC AL : 429
gi|2929303  :  AA KRW PSTTECL EY-M GVYTVL ET N   AQ AQ : 431
```

FIGURE 1S

```
gi|4480453 :      AA KRW PSAADCL EY-M VMYMTV DT N  CQ AE : 425
gi|2411485 :      AT KRW PSAMECL EY-M GVYMMV HT N  ARV AE : 422
gi|3458266 :      AA KRW PSAADCL EY-M GVYLIL DT N  TSR AE : 431
gi|7381251 :      AAFKRW PSATDLL EY-M GLYMVV ET N  AR  AD : 434
gi|2889448 :      AA KRW PSATDCL QY-M GIYMMV NT N  SA  AQ : 431
gi|4480460 :      AA KRW PSTTECL EY-M GVYMAF NC N  AL  AE : 384
gi|1736792 :      AT KRW PSSIDCL EY-M GVYIAV DT N  AR  AE : 432
gi|2889448 :    L AAFKRW PSSIECL DY-M GVYMAV DN N  AR  AQ : 432
gi|1508073 :      AT KRW PSSIDCL EY-M GVYIAV DT N  AR  AE : 427
gi|1508074 :      DA KRW LSTTRWL EY-M GVYMDL QC N  VE  AQ : 441
gi|5979947 :      AA KRW PSATDCL EY-M GVYTMV DT N  AG  AQ : 426
gi|1736791 :      DA KRW LSTTRWL EY-M GVYMDL QC N  VE  AE : 441
gi|7381253 :      TAFKRW LSETKCL EY-M AVYMDL QC N  AQ  AE : 441
gi|4480448 :      EA RRW LSFTENL DY-M LCYKIY DI H  AW  VE : 609
gi|3252840 :      EA RRW LSFTENL DY-M LCYQIY DI H  AW  AE : 619
gi|3252838 :      EA RRW LSFTENL DY-M LCYQIY DI H  AW  AE : 584
gi|1508073 :      EA RRW VSFTENL DY-M LCYQIY DI H  AW  AE : 618
gi|2855836 :  S   EG KRW TSLLHEI EC-MQTCFKVW KL E  NNDVV : 666
gi|1508074 :  S   EG KRW TSLLHEI EC-MQTCFKVW KL E  NNDVV : 666
gi|3576443 :  H  EVFKRW SSPPDYL EY-M IAYSAL DG N KSAQ AV : 411
gi|3778921 :  S   EG KRW TSLLHEI EC-MQTCFKVW KL E  NNDVV : 666
gi|4253916 :  S   EG KRW TSLLHEI EC-MQTCFKVW KL E  NNDVV : 666
gi|1457179 :  S   EG KRW TSLLHEI EC-MQTCFKVW KL E  NNDVV : 666
gi|1586560 :      EA RRW ISVLDSVRDNQL VCFLGL NT N GFGKDGL : 678
gi|3820148 :  S   EG KRW TSLLHEI EC-MQTCFKVW KL E  NNDVV : 666
gi|3826010 :  S   EG KRW TSLLHEI EC-MQTCFKVW KL E  NNDVV : 666
gi|9965484 :  S   EG KRW TSLLHEI EC-MQTCFKVW KL E  NNDVV : 666
gi|5980027 :      ES KRW LSLVDQM QD-M ICFKGF NTFN AE  GR : 655
gi|7754686 :      EG KRW LSLVDRM QD-M ICFTVL NT N AV  GR : 672
gi|4480452 :      DS KKW LSLVDRM QD-M ICFMGF NTFN AE  GR : 664
gi|2889448 :      AA KRW TSTTECL EY-M GVYMAF DC N  AR  AE : 379
gi|1508073 :      ES KRW LSLVDQM KQ-M ICFVGF NTFND AK  GR : 659
gi|6251118 :      ES KRW LSLVDQM QQ-M ICFVGF NTFND AK  GR : 674
gi|5979947 :      EA RRW LSLTENL DY-M LCYKIF DI H  VL  AE : 624
gi|5979947 :      QA RRW PSLTENL DY-M RCYKIF DI H  AAW AE : 614
                  f    44W   S      6p   6k  5        e

40          *         760       *         78
gi|2961462 :  AQ Q  MAAYI KNA  RYLEA LQD EW ATGHVP  D  Y : 437
gi|4480457 :  TQE   MSAYI K-T  RYLEA LQ  EW AARHVP  D  Y : 424
gi|6251118 :  RQ    MTTIV D-C  KRYIES LQ  EW ATGHIP  N  Y : 424
gi|4480454 :  SQ   T NYA  Q-AL AYIDS MK  KW SSG LP  E  Y : 467
gi|4480455 :  TQ   T NYA  K-A  IYLDS TQ  KW ASG LP  Q  Y : 478
gi|2132215 :  TQ   T NYA  K-A  IYLDS TQ  KW ATG LP  Q  Y : 478
gi|2132215 :  TQ   T NYV  K-A  AYFDS MK  EW STG LP  E  Y : 477
gi|4480458 :  TQ   T NYV  K-A  AYFDS MK  EW STG LP  E  Y : 477
gi|1736792 :  TQ   T NYV  K-A  AYFDS MF  KW SNG LPM E  Y : 471
gi|7381249 :  TQ   T NYA  K-A  VYLDS TQ  KW ASG LP  E  Y : 474
gi|2889448 :  AQ   T NYC  Q-A  EYIDA MQ  KW ASGEVP  E  Y : 473
```

FIGURE 1T

```
gi|5979946 :  SQ W T NYA Q-A DYIDS LK  EW STG LP  E Y : 469
gi|2929303 :  SQ  T SYV Q-AL AYIGA HK  EW SSG LP  D Y : 471
gi|4480453 :  AQ  T DYA Q-A DYLDS MQ  KW ATG LP  E Y : 465
gi|2411485 :  AQ  T NYA Q-A ACFDS MQ  KW ATG LP  E Y : 462
gi|3458266 :  AQ  T DYA R-A DDYLDS MQ  KW ATG LP  A Y : 471
gi|7381251 :  SQ  ET NDA R-A AYLDS MK  EW SSG LP  E Y : 474
gi|2889448 :  AQ  T NYA Q-A DCLDSHMQ  KW ATG LP  E Y : 471
gi|4480460 :  TQ  M NYA K-A ALFDA LE  KW SSG LP  E Y : 424
gi|1736792 :  EAQ  T TYA E-A AYIDS MQ  RW ATG LP  D Y : 472
gi|2889448 :  IQ W T SYA K-S AFIGA IQ  KW SSG LP  D Y : 472
gi|1508073 :  EAQ  T TYA E-A AYIDS MQ  RW ATG LP  D Y : 467
gi|1508074 :  TQ  M NYIQN-G ALFDT IQ  KW SSS LP  E Y : 481
gi|5979947 :  NAQ  T NYA E-A ACLDS LQ  KW ATG LP  E Y : 466
gi|1736791 :  TQ  M NYIQN-A ALFDT MQ  KW SSS LP  E Y : 481
gi|7381253 :  TQ  T NYI N-A SHFDS MH  KW SSG LP  E Y : 481
gi|4480448 :  EQ  EL SFF K-G DYLLG YE  EW AAE VP  LD Y : 649
gi|3252840 :  EQ  EL SFF K-G DYLLG YE  EW AAE VP  LD Y : 659
gi|3252838 :  EQ  EL SFF K-G DYLLG YE  EW AAE VP  LD Y : 624
gi|1508073 :  EQ  EL SFF K-G DYLLG YE  EW AAE VP  LD Y : 658
gi|2855836 :  VQ  M AHI K-P LYFNC VQ  REW EAG IP  E Y : 706
gi|1508074 :  VQ  M AHI K-P LYFNC VQ  REW EAG IP  E Y : 706
gi|3576443 :  QIQ  T HNA N-A DDYLDAVMQ  KWNSIGHMPNLK  F : 451
gi|3778921 :  VQ  M AHI K-P LYFNC VQ  REW EAG IP  E Y : 706
gi|4253916 :  VQ  M AHI K-P LYFNC VQ  REW EAG IP  E Y : 706
gi|1457179 :  VQ  M AHI K-P LYFNC VQ  REW EAG IP  E Y : 706
gi|1586560 :  EQ  V GYL K-V GLIAS TK  EW SAAK VP  N Y : 718
gi|3820148 :  VQ  M AHI K-P LYFNC VQ  REW EAG IP  E Y : 706
gi|3826010 :  VQ  M AHI K-P LYFNC VQ  REW DAG IP  E Y : 706
gi|9965484 :  VQ  M AHI K-P LYFNC VQ  REW DAG IP  E Y : 706
gi|5980027 :  RQ  V SYIQK-V VQLEA TK  EW SAVR VP  D Y : 695
gi|7754686 :  RQ  V GYI N-VL ILLAAHTK  EW SAAR VP  D Y : 712
gi|4480452 :  RQ  V GYI N-V IQLEA TK  EW SAAR VP  D Y : 704
gi|2889448 :  TQ W T DYA K-T ALIDA ME  KW SSG VP  QKY : 419
gi|1508073 :  ERQ  V GYIQN-V KVQLEA TK  EW SEAK VP  N Y : 699
gi|6251118 :  ERQ  V GYIQN-V KVQLEA TK  EW SEAK VP  N Y : 714
gi|5979947 :  EQ  EL TFF K-G EYIMG YF  EW ACE LP  LE Y : 664
gi|5979947 :  EQ  EL SFL K-A DFVLS HE  EW SAE VPG D Y : 654
              k Qgr          e       ea W     6P    e5

0         *        800        *       820
gi|2961462 :  IN  GTPNTGMCVLN IP  L -GEHLPID IEQ IFL  R-- : 475
gi|4480457 :  MK  GIS SGMCILN YS  L -GQLLPDD IEQ IHS  K-- : 462
gi|6251118 :  IK  GMA SGMCILN NP  L -DKLLPDN IEQ IHS  K-- : 462
gi|4480454 :  LD  GK  FGYRIAT QP  T -GIPFPHH LQEIDF  R-- : 505
gi|4480455 :  FE  GK  SAYRAAA TP  T -DVPLPEY LKGIDF  R-- : 516
gi|2132215 :  FE  GK  SAYRAAA TP  T -DVPLPEY LKGIDF  R-- : 516
gi|2132215 :  XE  GK  SAYRVAA QP  T -DVQLPDD LKGIDF  R-- : 515
gi|4480458 :  CE  GK  SAYRVAA QP  T -DVQLPDD LKGIDF  R-- : 515
gi|1736792 :  HE  GK  SAYRVAT QP  T -NAWLPDY LKGIDF  R-- : 509
```

FIGURE 1U

```
gi|7381249  : LE AK  SGHRAAA TP  T -DVPLPDD LKG IDF  R-- : 512
gi|2889448  : YE GK  SGHRVSA QP  TT-DIPFPEH LKE VDI  Q-- : 511
gi|5979946  : LE GK  SAHRVAT QP  T -DIPFPLH LQE IDF  K-- : 507
gi|2929303  : FE GK  SGHRIAT QPTFM-DIPFPHH LQE IDF  K-- : 509
gi|4480453  : YE GK  SGHRVAA QP  T -DIPFPPH LKE VDF  K-- : 503
gi|2411485  : LE GK  SAHRPCA QP  T -DIPFPDH LKE VDF  K-- : 500
gi|3458266  : YE GK  SGHRTSA QP  T -DIPFPPH LKE VDF  K-- : 509
gi|7381251  : METSK  FGYRIFA QP  T -DVPLTHH LQE IDF  LR  : 512
gi|2889448  : LE GK  SAHRVSA QP  T -DIPFPPH LKE VDF  N-- : 509
gi|4480460  : LE GK  FGYRAAT QP  T -DIPLPLH LQQ IDF  R-- : 462
gi|1736792  : YE GK  CGHRISA QP  T -DIPFPDH LKE VDF  K-- : 510
gi|2889448  : LE GK  FGSRITT EP  T -GFPLPPR LQE IDF  K-- : 510
gi|1508073  : YE GK  CGHRISA QP  T -DIPFPDH LKE VDF  K-- : 505
gi|1508074  : LK AK  SGSRIAT QP  T -DVPLPDY LQE IDY  R-- : 519
gi|5979947  : YE GK  SAHRVCT QP  T -DIPFPDH LKE VDF  K-- : 504
gi|1736791  : LK AK  SGSRIAT QP  T -DVPLPDY LQE IDY  R-- : 519
gi|7381253  : LK GK  SGSRTAT QP  T -DVPLPNY LQE IDY  R-- : 519
gi|4480448  : IK GIT IGQRILL SG  I EGQLLSQEA LEK VDY  GR-R : 689
gi|3252840  : IK GIT IGQRILL SG  I DGQLLSQEA LEK VDY  GR-R : 699
gi|3252838  : IK GIT IGQRILL SG  I DGQLLSQEA LEK VDY  GR-R : 664
gi|1508073  : IK GIT IGQRILL SG  I DGQLLSQEA LEK VDY  GR-R : 698
gi|2855836  : LKTYA  VGLGPCT QP  L -GELVKDD VEK VHY  N-- : 744
gi|1508074  : LKTYA  VGLGPCT QP  L -GELVKDD VEK VHY  N-- : 744
gi|3576443  : LE GR  SGTRVIT QA  R ---EALQESE LQK IDH  K-- : 488
gi|3778921  : LKTYA  VGLGPCT QP  L -GELVKDD VEK VHY  N-- : 744
gi|4253916  : LKTYA  VGLGPCT QP  L -GELVKDD VEK VHY  N-- : 744
gi|1457179  : LKTYA  VGLGPCT QP  L -GELVKDD VEK VHY  N-- : 744
gi|1586560  : VE AK  IALATVV NS FFT-GELLPDY LQQ VDLR  K-- : 756
gi|3820148  : LKTYA  VGLGPCT QP  L -GELVKDD VEK VHY  N-- : 744
gi|3826010  : LKTYA  VGLGPCTPQP  L -GELVKDD VEK VHY  N-- : 744
gi|9965484  : LKTYA  VGLGPCT QP  L -GELVKDD VEK VHY  N-- : 744
gi|5980027  : IG AS  IALGTVV ISA FT-GEILTDD LSK IGRD  R-- : 733
gi|7754686  : IE AS  ISLGTLV IS  FT-GEILTDD LSK IGRG  R-- : 750
gi|4480452  : ID AS  IALGTVV ISA FT-GEILTDD LSK IGRG  R-- : 742
gi|2889448  : LD GK  FGYRAAT QP  T -DIPLPLH LQE IDF  S-- : 457
gi|1508073  : IE AS  IALGTVV ISA FT-GEVLTDE LSK IDRE  R-- : 737
gi|6251118  : IE AS  IALGTVV ISA FT-GEVLTDE LSK IDRE  R-- : 752
gi|5979947  : IR GI  IGQRILV SG  L EGQILSQEA LEQ LDY  GR-R : 704
gi|5979947  : IK GIT IGQRVLL SG  V DGQLLSQKA LEK IDY  ERSR : 695
                n    s          l        6   6   ps

*       840         *       860
gi|2961462  : -FHH IELASRLVDDA DFQ E DHGDL-SCIECYL HE : 514
gi|4480457  : -IHE VELTARLVDD  DFETK VGG L SGIECYV  NE : 502
gi|6251118  : -ILD LELTGRIADDL DFEDE E G M SSLQCYM ENE : 502
gi|4480454  : -LND AGSILRLKGDIHSYQ E S  G ESSCISCYM NE : 545
gi|4480455  : -FND ASSFLRLRGD  CYK D A  G E SCISCYM NG : 556
gi|2132215  : -FND ASSFLRLRGD  CYK D A  G E SCISCYM NG : 556
gi|2132215  : -FND ASSFLRLRGD  CYX D A  G E SCISCYM HG : 555
```

FIGURE 1V

```
                       *           840           *           860
gi|4480458 : -FND ASSFLRLRGD  CYE D A G E  SCI SCYM   N G : 555
gi|1736792 : -FND ASSFLRLRGD  CYK D D G E  SCI SCYM   N G : 549
gi|7381249 : -FND ASSFLRLRGD  CYK D D G E  SSI SCYM   N G : 552
gi|2889448 : -LND ASAILRLRGD  CYQ D A G E  SCI SCYM   N G : 551
gi|5979946 : -FNDSASSILRLRGD  CYQ DMA G E  SSI SCYM   H N G : 547
gi|2929303 : -FNDFACSILRLRGD  CYQ D A G E  SCI SCYM   N G : 549
gi|4480453 : -LSD ACAILRLRGD  CYK D A G E  SSI SCYM   N G : 543
gi|2411485 : -LND ICIILRLRGD  CYK D A G E  SSI SCYM   N G : 540
gi|3458266 : -LND ASAILRLRGD  CYK D A G E  SSI SCYM   N G : 549
gi|7381251 : -FND ICSILRLKND  CYK D A G E  SCI SCYM   EN G : 552
gi|2889448 : -LND ACAMLRLRGD  CYQ D A G ETSCI SCYM   N G : 549
gi|4480460 : -FND ASSILRLRGDICGYQ E S G E  SSI SCYM   N G : 502
gi|1736792 : -LND ACAILRLRGD  CYK D A G E  SSI SCYM   N G : 550
gi|2889448 : -FND ICAILRLKGD QCYK D A G E  SAV SCYM   H G : 550
gi|1508073 : -LND ACAILRLRGD  CYK D A G E  SSI SCYM   N G : 545
gi|1508074 : -FNE ASSILRLRGD  CYK D A G E  SAI SCYM   H G : 559
gi|5979947 : -LND ACAVLRLRGD  CYQ D A G E  SSI SCYM   N G : 544
gi|1736791 : -FNE ASSILRLRGD  CYK D A G E  SAI SCYM   H G : 559
gi|7381253 : -FND ASSLLRLRGD  CYK D A G E  SAI SCYM   H G : 559
gi|4480448 : VLTE NSLISRLADD  TYK E A G L  SSIECYM   H G : 730
gi|3252840 : VLTE NSLISRLADD  TYK E A G L  SSIECYM   H E : 740
gi|3252838 : VLTE NSLISRLADD  TYK E A G L  SSIECYM   H E : 705
gi|1508073 : VLTE NSLISRLADD  TYK E A G L  SSIECYM   H E : 739
gi|2855836 : -MFE VSLSWRLTND  TYQ E A G Q  SGIACYM   N G : 784
gi|1508074 : -MFE VSLSWRLTND  TYQ E V G Q  SGIACYM   N G : 784
gi|3576443 : -FNY FGLTLRLRGD  TFK EAN G  VTSSIACYL   EH E : 528
gi|3778921 : -MFE VSLSWRLTND  TYQ E A G Q  SGIACYM   N G : 784
gi|4253916 : -MFE VSLSWRLTND  TYQ E A G Q  SGIACYM   N G : 784
gi|1457179 : -MFE VSLSWRLTND  TYQ E A G Q  SGIACYM   N G : 784
gi|1586560 : -FLH VSLTGRLIND  TYQ E N G  LVSSVQCYM   EN E : 796
gi|3820148 : -MFE VSLSWRLTND  TYQ E A G Q  SGIACYM   N G : 784
gi|3826010 : -MFE VSLSWRLTND  TYQ E A G Q  SGIACYM   N G : 784
gi|9965484 : -MFE VSLSWRLTND  TYQ E A G Q  SGIACYM   NLG : 784
gi|5980027 : -FLY MGLTGRLVND  TYQ E GQG V  SAVQCYM   H E : 773
gi|7754686 : -FLQ MGLTGRLVND  TYE E GQG V  SAVQCYM   EH E : 790
gi|4480452 : -FLQ MGLTGRLVND  TYE E GQG V  SAVQCYM   H E : 782
gi|2889448 : -FND ASSILRLRGDICGYQ E S G Q  SSI SCYM   N G : 497
gi|1508073 : -FLQ MGLTGRLVND  TYQ E GQG V  SAIQCYM   H K : 777
gi|6251118 : -FLQ MGLTGRLVND  TYQ E GQG V  SAIQCYM   H K : 792
gi|5979947 : VLTE NSIITRLADDIHTYK E A G L  SSIECYM   EH G : 745
gi|5979947 : VLMEQICLISRLADD QSYK E A G L  SGIECYM   H E : 736
                  l    R6 D   5 a   rG  aS 6 CY6   d p

*           880           *           900
gi|2961462 : S V DA N VNGLLGNC L  NWKF  KQDS--- CISCK : 552
gi|4480457 : C L DASN LNGLLDLT   NW F  HDS---- ALCFK : 539
gi|6251118 : S V NA N IKGILNRS E FNW F  QDS---- MCCK : 539
gi|4480454 : A  DA TY INAMVNRL   NW L  PDNN--- ITSK : 583
gi|4480455 : S   DA N INSMINEI   NW L  PDSN--- MPAR : 594
```

FIGURE 1W

```
gi|2132215 : S G DA N INSMINEI    NW L  PDSN---  MPAR  : 594
gi|2132215 : S   DA N INAMINDI    NW F  PDSN---  MPAR  : 593
gi|4480458 : S   DA N INAMINDI    NW F  PDSN---  MPAR  : 593
gi|1736792 : S   DA N INAMVNDI    NW L  SNDN---  MLAK  : 587
gi|7381249 : L   DA N INAMINDI    NW L  PDSN---  MTAR  : 590
gi|2889448 : T   DA N LNAMISDV  G NW L  PNSS---  ISAK  : 589
gi|5979946 : S   DA N INGMIEDI    NW L  KDIN---  ISCK  : 585
gi|2929303 : S   DA N INNMIEET  K NW L  PDNN---  ISSK  : 587
gi|4480453 : A   DA D INAMISDV  G NW L  PNSS---  ISSK  : 581
gi|2411485 : L   DA N INFMIRDA    NW L  PDNS---  ITSK  : 578
gi|3458266 : A   DA D INAMISDV  G NW L  NPNSS--  ISSK  : 587
gi|7381251 : S   DA N INAMVNNL    NW L  QDGT---AH IACK : 590
gi|2889448 : A   DA N LNVMISGV    NW L  PNSS---  ISSK  : 587
gi|4480460 : S   DA S INAMISDN  N NW L  PNSN---  ISSK  : 540
gi|1736792 : V   DA D INAMISDV  G NW L  PDIN---  ISAK  : 588
gi|2889448 : I   DA NQVNAMVDNLT   NW L  PDSG---  ISYK  : 588
gi|1508073 : V   DA D INAMISDV  G NW L  PDIN---  ISAK  : 583
gi|1508074 : S   DA N INAMISDA    NW L  PDSK---S ISSK  : 597
gi|5979947 : S   DA N INAMLSDV    NW L  PDS----  ISAK  : 581
gi|1736791 : SI  DA N INAMISDA    NW L  PDSK---S ISSK  : 597
gi|7381253 : S   DA N INVMISDA    NW L  PDSK---S ISSK  : 597
gi|4480448 : CQ  EA N IYGILEPA    TR F  ADH----  FPCK  : 767
gi|3252840 : C   EA D IYSILEPA    TR F  PDD----  FACK  : 777
gi|3252838 : C   EA D IYSILEPA    TR F  PDD----  FACK  : 742
gi|1508073 : C   EA D IYSILEPA    TR F  PDD----  FACK  : 776
gi|2855836 : A   DA K ICRVVDRA    AS F YF PSND--- MGCKS : 822
gi|1508074 : A   DA K ICRVVDRA    AS F YF PSND--- MGCKS : 822
gi|3576443 : S  KDA KYLQFMLDEN    NL Y  NDG----  CIKD  : 565
gi|3778921 : A   DA K ICRVVDRA    AS F YF PSND--- MGCKS : 822
gi|4253916 : A   DA K ICRVVDRA    AS F YF PSND--- MGCKS : 822
gi|1457179 : A   DA K ICRVVDRA    AS F YF PSND--- MGCKS : 822
gi|1586560 : C   EA S VYGIIDNA    NW LANPASN---A  LCVR  : 834
gi|3820148 : A   DA K ICRVVDRA    AS F YF PSND--- MGCKS : 822
gi|3826010 : A   DA K ICRVVDRA    AS F YF PSND--- MGCKS : 822
gi|9965484 : A   DA K ICRVVDRA    AS F YF PSND--- MGCKS : 822
gi|5980027 : I   EA K VYTIMDNA  D NR F  NNRD---  DTCR  : 810
gi|7754686 : I   EA K VYTVMENA  D NR F  NNRD---  DSCR  : 827
gi|4480452 : I   EA K VYTVMENA  D NR F  NNRE---  DSCR  : 819
gi|2889448 : S   DA S VNAMIGDK  P FNW F  PSK----A ISSK  : 534
gi|1508073 : I   EA Q VYSVMENA  E NR F  NNK-----  DIYK  : 813
gi|6251118 : I   EA Q VYSVMENA  E NR F  NNK-----  DIYK  : 828
gi|5979947 : S   VA NYMYSLLEPA    TW F  PEDSTVH  FQCK  : 786
gi|5979947 : C   EA N IYGIMEVTA   TK Y  VDDDD--  FACK  : 775
              e A  h6 66         e     e        p   4

*         920         *         940
gi|2961462 : YS HVLA SIQFMYNQGD   SS-NKVIKDQ QKV  V VP : 592
gi|4480457 : FA NV-A GLRLIYKYRD  D S-NQ MKTH FKI  D LT : 578
gi|6251118 : FT NI-G GLQFIYKYRD LY S-DK VKDQ FKI  H QVP : 578
```

FIGURE 1X

```
gi|4480454 : HA DI-L AFYHLYKDRD  S A-RN IRNL MTT  EHVP : 622
gi|4480455 : HA DI-T ALHHLYKYRD  S A-TK TKSL SRM  EVP  : 633
gi|2132215 : HA DI-T ALHHLYKYRD  S A-TK TKSL SRM  EVP  : 633
gi|2132215 : HA DI-T ALHHLYIYRD  S A-SK TKNL EKA  EAVL : 632
gi|4480458 : HA DI-T ALHHLYIYRD  S A-NK TKNL EKT  ESML : 632
gi|1736792 : HA DI-T ALHHLYIYRD  S A-NK TKKL MET  ESML : 626
gi|7381249 : HA EI-T AFHQLYKYRD  S A-TQ TKSL RRT  EVP  : 629
gi|2889448 : HA DI-S AFHCGYKYRD  S A-NI TKSL KRT  D VT : 628
gi|5979946 : HA EI-S GFHHFYKDRD  T S-NI TKDL MKT  EVP  : 624
gi|2929303 : HA DI-N GLHHFYNYRD  T A-SN TKNL IKT  EVP  : 626
gi|4480453 : HV DI-S AFHYGYKYRD  S A-NI TKSL KRT  D VT : 620
gi|2411485 : HA DI-S VWHHGYRYRD  SFA-NV TKSL MRT  EVP  : 617
gi|3458266 : HV DI-S AFHYGYKYRD  S A-NI TKSL RRT  D VT : 626
gi|7381251 : HA DI-L GSLHGYKYRD  S A-NK TKNW RRT  ESVP : 629
gi|2889448 : IN DI-T AFHYGYKYRD  S S-SV TKSL MRT  E VP : 626
gi|4480460 : HA DI-L AFYHLYKYRD  S A-KI TKNL MRT  EVP  : 579
gi|1736792 : HA DI-A AFHYGYKYRD  S A-NV TKSL TRT  ESVP : 627
gi|2889448 : VA DI-C VFHYGYKYRD  S A-SI IKNL TRT  ETVP : 627
gi|1508073 : HA DI-A AFHYGYKYRD  S A-NV TKSL TRT  ESVP : 622
gi|1508074 : HA DI-T AFHHVYKYRD  T S-NN TKNL MKT  E LA : 636
gi|5979947 : HA DV-S AFHYGYKYRD  S A-NI IKNF AIS  EV-  : 619
gi|1736791 : HA DI-T AFHHVYKYRD  T S-NN TKNL MKT  E LA : 636
gi|7381253 : HA DI-T AFHHLYKYRD  T A-SS TKNL MKT  E VA : 636
gi|4480448 : ML DE-T VTMVIFKDGD  G S-KL VKDH KEC  E LP : 806
gi|3252840 : ML EE-T VTMVIFKDGD  G S-KL VKDH KEC  E LP : 816
gi|3252838 : ML EE-T VTMVIFKDGD  G S-KL VKDH KEC  E LP : 781
gi|1508073 : ML EE-TGVTMVIFKDGD  G S-KL VKDH KEC  E LP : 815
gi|2855836 : FI NL-RLCVQIFYKFID  G A-NE IKDY RKVY D IQ : 861
gi|1508074 : FI NL-RLCVQIFYKFID  G A-NE IKDY RKVY D IQ : 861
gi|3576443 : FA DM-S CFEVFYKERD  S S-TKDMKNH ERI  E VE : 604
gi|3778921 : FI NL-RLCVQIFYKFID  G A-NE IKDY RKVY D IQ : 861
gi|4253916 : FI NL-RLCVQIFYKFID  G A-NE IKDY RKVY D IQ : 861
gi|1457179 : FI NL-RLCVQIFYKFID  G A-NE IKDY RKVY D IQ : 861
gi|1586560 : LL NT-A VMQLFYMYRD  G S-DK MKDH SRT  FD VA : 873
gi|3820148 : FI NL-RLCVQIFYKFID  G A-NE IKDY RKVY D IQ : 861
gi|3826010 : FI NL-RLCVQIFYKFID  G A-NE IKDY RKVY D IQ : 861
gi|9965484 : FI NL-RLCVQIFYKFID  G A-NE IKDY RKVY D IQ : 861
gi|5980027 : LV ET-A IMQLFYMDGD  LT SHNM IKEH KNC  FQ VA : 850
gi|7754686 : LV ET-A IMQLFYMEGD  LT SHEM IKEH KNC  FQ VA : 867
gi|4480452 : LV ET-A IMQLFYMDGD  LT SHET IKEH KNC  FQ VA : 859
gi|2889448 : YA DI-L AFYHLYKYRD  S A-KI TKKL MRT  D VP : 573
gi|1508073 : LV ET-A IMQLFYMQGD  LT SHDM IKEH KNC  FQ VA : 853
gi|6251118 : LV ET-A IMQLFYMQGD  LT SHDM IKEH KNC  FQ VA : 868
gi|5979947 : MLMEE-T VTMVIFKEGD  G S-KTKIKDY KDC  E LP : 825
gi|5979947 : ML EE-T VTMVIFKDGDRLSNS-KL MKDHFKEC  E LP : 814
                         5   Dg      e   4       p6 gi|2961462 :  T-- : 593
```

FIGURE 1Y

```
gi|4480457 : --- :  -
gi|6251118 : MEE : 581
gi|4480454 : L-- : 623
gi|4480455 : L-- : 634
gi|2132215 : L-- : 634
gi|2132215 : F-- : 633
gi|4480458 : F-- : 633
gi|1736792 : F-- : 627
gi|7381249 : L-- : 630
gi|2889448 : L-- : 629
gi|5979946 : L-- : 625
gi|2929303 : M-- : 627
gi|4480453 : L-- : 621
gi|2411485 : L-- : 618
gi|3458266 : L-- : 627
gi|7381251 : L-- : 630
gi|2889448 : L-- : 627
gi|4480460 : M-- : 580
gi|1736792 : L-- : 628
gi|2889448 : L-- : 628
gi|1508073 : L-- : 623
gi|1508074 : L-- : 637
gi|5979947 : --- :  -
gi|1736791 : L-- : 637
gi|7381253 : L-- : 637
gi|4480448 : L-- : 807
gi|3252840 : L-- : 817
gi|3252838 : L-- : 782
gi|1508073 : L-- : 816
gi|2855836 : V-- : 862
gi|1508074 : V-- : 862
gi|3576443 : M-- : 605
gi|3778921 : V-- : 862
gi|4253916 : V-- : 862
gi|1457179 : V-- : 862
gi|1586560 : --- :  -
gi|3820148 : V-- : 862
gi|3826010 : V-- : 862
gi|9965484 : V-- : 862
gi|5980027 : --- :  -
gi|7754686 : --- :  -
gi|4480452 : --- :  -
gi|2889448 : M-- : 574
gi|1508073 : --- :  -
gi|6251118 : --- :  -
gi|5979947 : L-- : 826
gi|5979947 : L-- : 815
```

FIGURE 2A

```
                        *        20         *        40
Yeast       : PVLTNKTVISGSKVKSLSSAQSSSSGPSSSSEEDDSRDIES :  41
gi|1113282  : ---------------------------------------- :   -
gi|5457796  : ---------------------------------------- :   -
gi|1889403  : ---------------------------------------- :   -
gi|5715917  : ---------------------------------------- :   -
gi|1988670  : ---------------------------------------- :   -
gi|1816067  : ---------------------------------------- :   -
gi|5105561  : ---------------------------------------- :   -
gi|1591421  : ---------------------------------------- :   -
gi|6821049  : ---------------------------------------- :   -
gi|2090469  : ---------------------------------------- :   -
gi|6015941  : ---------------------------------------- :   -
gi|6856776  : ---------------------------------------- :   -
gi|1991708  : ---------------------------------------- :   -
gi|2621639  : ---------------------------------------- :   -
gi|6813399  : ---------------------------------------- :   -
gi|4504721  : ---------------------------------------- :   -
gi|7655771  : ---------------------------------------- :   -
gi|3141549  : ---------------------------------------- :   -
gi|1579077  : ---------------------------------------- :   -
gi|5537994  : ---------------------------------------- :   -
gi|7870341  : ---------------------------------------- :   -
gi|1146450  : ---------------------------------------- :   -
```

FIGURE 2B

```
                              *         60           *         80
Yeast        : LDKKIRPLEELEALLSSGNTKQLKNKEAALVIHKLPLYA  :  82
gi|1113282   : ----------------MGGGNLNIEETIEVANEIKFYQ   :  24
gi|5457796   : --------------------MKTLNVEDIEVANEIKLHQ  :  22
gi|1889403   : -----------------------MEIEEIEVAREIKFHQ  :  19
gi|5715917   : -----------------------MNFEEVEVASFIKLHQ  :  19
gi|1988670   : ----------------------MDEKKIEEVSVVKEIKFHE :  22
gi|1816067   : ------------------------------MFLMEVKLHE :  10
gi|5105561   : -------------MGSSSGQKPRRLEDVDIASSLSHSR   :  28
gi|1591421   : ---------------------MENYNDIEMLNEIKPYQ   :  20
gi|6821049   : -------------MASKTETTMKEDEIEVVSEMPLRK    :  27
gi|2090469   : -------------MFTEAYELTEEEKLLQVLDDIAFRK   :  28
gi|6015941   : ---------------------MKIDEVELVKEISFHE    :  19
gi|6856776   : -------------------MQETIDNVDVVKQIQFHE    :  21
gi|1991708   : -MRKRIKRSTGDFMFLNDYELGEEEKLLQVLDDIAFRK   :  40
gi|2621639   : ------------------------MSMDDIMERIKLYE   :  16
gi|6813399   : -------------MFLQDYELSEEEKVLQILDDVALRK   :  28
gi|4504721   : -----------------MENNVNIDEVELLKKEIKVYQ   :  23
gi|7655771   : ---------------------MDTDAVDAVRDELRLHE   :  19
gi|3141549   : ---------------------MTDAASADVREDLRLHE   :  20
gi|1579077   : ---------------------MPDDASDADVQADLRLYE  :  21
gi|5537994   : ---------------------MTDSVVAAEVRDELRLYE  :  22
gi|7870341   : ------------------------MDEYIRLRDTLKLYA :  17
gi|1146450   : ---------------------MTDSDATAAEVRDELRLYE :  22
                                              6  g  6
```

FIGURE 2C

```
                         *         100          *         120
Yeast       : EKKL-GDTTRVAVRRKALSILAEAPVLASDRLPYKNYLY :  122
gi|1113282  : EKYVNGDKRLTEIRRKALKRLGIKL---HHIGYYSIIP :   62
gi|5457796  : EKYVNGDKRLTEIRRKALRKLGISL---KHIGHYSIIP :   60
gi|1889403  : ENYVNGDKRLTEIRRRALKKLGIQL---KHIGHYSIIP :   57
gi|5715917  : EKYTNGDKKLTEIRRKALKKLGIKL---ENIGHYSIIP :   57
gi|1988670  : EKYTDGDSEVTEVRRRALRLTGAKL---EHLGKYTIIA :   60
gi|1816067  : FEKVY-GDANKAEARRQYLKVTGVKL---ENIGRTIIL :   47
gi|5105561  : EKEL-GNANEALVRRLYLRLTGASL---SSVASTILIF :   65
gi|1591421  : DKMF--GSKITEIRRKFIKKVGIEF---KHICNYSIIE :   56
gi|6821049  : DAYT--DTDTVRVRKCAIKMNGVKF---EHIQNYTIIA :   63
gi|2090469  : EEFA--DPLTVKIRRLAIEYGKLEF---EHIQNFSLIV :   64
gi|6015941  : DNLL--EANAMVARRLALKIVGVGL---PSIGSTVIIY :   55
gi|6856776  : DNLL--EANAMVARRLAIKLTGAKL---PSIGSTIIIY :   57
gi|1991708  : EEFA--EPLTVKIRRLAIEYAKLEF---EHIQNFSLIV :   76
gi|2621639  : ERHV--PVDEVRIRREFIRTCGVKL---EHVSNYSIIM :   52
gi|6813399  : EEFA--DPETSVKLRRLAIEFAKLEF---EHIQNFSLIV :   64
gi|4504721  : DSKF--GERNVIARRKYVKLSNVET---RHIQEYTLLE :   59
gi|7655771  : EAHA--DADTAAAARRIVADAADTSL---ETVGEYAFPA :   55
gi|3141549  : EAHA--DADTAEARRLLVSQSGASL---DAVGNYGFPA :   56
gi|1579077  : DDET--DADTAAAARRAVLRETDADT---DALGAFAFIA :   57
gi|5537994  : EDHA--EPDVAAAARRHLLAEETDTDL---SAVGDYTFIA :   58
gi|7870341  : EKEL--APADVSIRRKFIEETGVPL---DRIGDCTISL :   53
gi|1146450  : EDHA--DPDTAAAARRHLLAEETGADL---SAVGDYTFIA :   58
                         a  R4  6            6   d
```

FIGURE 2D

```
                         *         140           *         160
Yeast       : DRVFGACCEN  GY PLPVG IG LVI GT----S HIPMA :  159
gi|1113282  : NELIGR  EN  GV IPMG AG LKI GEY K E  IPLA :  103
gi|5457796  : NELIGR  EN  GV IPMG AG LKI GEY K E  IPLA :  101
gi|1889403  : NEVIGR  EN  GV IPMG AG LKI GEY K E  IPLA :   98
gi|5715917  : NQVIGK  EN  GV IPMG AG LKI GEY K E  IPLA :   98
gi|1988670  : NRAMDK  EN  GA VPVG AG LVH GEY E E  VPLA :  101
gi|1816067  : NTVVGR  EN  GA IPVG AG LVR GDY N Y  VPLA :   88
gi|5105561  : QELYGR  ENP GA VPVG AG LRI GDY R D  IPLA :  106
gi|1591421  : EMAMKK  EN  GA IPLGFAG LKI GEY K E  IPLA :   97
gi|6821049  : EAATKR  EN  GT IPLG AGAIMV GEY S E  MLPLA :  104
gi|2090469  : ESVTKR  EN  GA IPLG AGLLKV GEY A E  IPLA :  105
gi|6015941  : SEIKNK  AEN GA IPLG VG IRV GDY K D  VPMA :   96
gi|6856776  : AEIRNK  AEN GA VPLG IG LKI GEY K D  VPLA :   98
gi|1991708  : EIVTKR  EN  GA IPLGTAGLLKV GEY DAE  IPLA :  117
gi|2621639  : ERASRR  ENP GV IPLG AG LRV GEH D E  VPLA :   93
gi|6813399  : EAASKR  EN  GA IPLG AGLLKV GEY NSE  IPLA :  105
gi|4504721  : KLAMQK  EN  GA IPLGFAG ISI GKY Q E  NVPLA :  100
gi|7655771  : DDA-EP  EN  GAA VPMG VG LAV GDAID EP LPLA :   95
gi|3141549  : EAA-ESA EN  GS VPMG AG VSV GGSVA EK LPLA :   96
gi|1579077  : DQAADTA EN  TGGA LPLG AG VALSGGA D E LPMA :   98
gi|5537994  : ADA-ES  EN  GAA VPMG VG LPV GGA E DHHLPLA :   98
gi|7870341  : DAVVKK  CEN GT VPLG AG VRIKGEY D TM LPLA :   94
gi|1146450  : ADA-ES  EN  GA VPMG VG LPV GGA E DHHLPLA :   98
                       n EN   G   q6P6G Gp6 6 G  a g  y6P6A
```

FIGURE 2E

```
                       *         180           *         200
Yeast        : TTEGCLVAAAMRGCKAINAGGATTVLTKSGMSRGPSVSFP : 200
gi|1113282   : TTEGSLVASSSRGCSALSEAGGVVTTLIDSKMSRSPSISCP : 144
gi|5457796   : TTEGSLVASSSRGCSALSEAGGVVTTLIDSKMSRSPSISCP : 142
gi|1889403   : TTEGSLVASSSRGCSALSEAGGVYTTLIDSKMSRSPSLSCP : 139
gi|5715917   : TTEGSLVASSSRGCSALSAAGGVKTTLIDSKMSRSPSLSCP : 139
gi|1988670   : TTEGSLVASSSRGCSTISDSGGAHVSIVRSGMSRSPSFSLP : 142
gi|1816067   : TTEGSLVASSSRGAKFVSESGGARVSVLKSGMARSPSFSVP : 129
gi|5105561   : TTEGSLVASSSRGAKAISLSGGARASVIKSGMSRSPSLWTP : 147
gi|1591421   : TTEGSLVASSSRGCSIISKCGGATVSVIDSKMSRSPCLSTK : 138
gi|6821049   : TTEGSLVASSSRGCTVISASGGSNVSIFQSLMSRSPSFSLE : 145
gi|2090469   : TTEGSLVASSSRGCSVISRSGGANVSVFESEMSRSPSFSFE : 146
gi|6015941   : TTEGSLIASSSRGIKAVSLSGGVRASVLKSEMSRSPSFSFD : 137
gi|6856776   : TTEGSLIASSSRGAKAVSLSGGTRVSIFYSGMSRSPSFSLD : 139
gi|1991708   : TTEGSLVASSSRGCSVISKSGGANVSVFESEMSRSPSFSLE : 158
gi|2621639   : TSEGSLVASSSRGCSVISRAGGATVSVTGSSMSRSPSISTG : 134
gi|6813399   : TTEGSLVAGSSRGCSVISKSGGANVSVFESEMSRSPSFSLE : 146
gi|4504721   : TTEGSLVASSSRGCSIISKCGGATVSVIDSKMSRSPSISTN : 141
gi|7655771   : TTEGSLVASSSRGCASMSAAGGATASVLKSAMSRSPSFSVA : 136
gi|3141549   : TTEGSLLASSSRGCSVINSAGGATASVLKSGMSRSPSFSVA : 137
gi|1579077   : TTEGSLVASSSRGCSAISAAGGANASVTKTGMSRSPSFSVA : 139
gi|5537994   : TSEGSLLASSSRGVSTISRNAGGATASVLKSGMSRSPSFSVE : 139
gi|7870341   : TTEGSLIASSSRGCSLISAAGGADVSILKSGMSRSPSFAAD : 135
gi|1146450   : TSEGSLLASSSRGVSTIRNAGGATASVLKSGMSRSPSFSVE : 139
               T3EGaL6As nRG   6t  GG    6     MtRaP
```

FIGURE 2F

```
                       *         220           *         240
Yeast       : T KRSGACKIW DSEEGQNA IKKAFNS- SRFAR LQH IQT- : 239
gi|1113282  : NARR REVAKW E--ENLDY LQEK VSKV TRH KLRGVK - : 182
gi|5457796  : NARR REVAEW K--ENLNY LQEK VAKV TRH KLRDVK - : 180
gi|1889403  : NARR REVAEW K--NNLDY LQEK VSKV TRH KLRGVK - : 177
gi|5715917  : DARR REVAEW K--NNLDY LQEK VSKV TRH KLRGVR - : 177
gi|1988670  : SARK LEFCEW R--KHFDD IKEV ES- TRH ELLDIQE- : 179
gi|1816067  : S ID VELVEW T--GHFEE IKKV ES- TRF KLKDIQH- : 166
gi|5105561  : S YE HRLAMW E--DRIED LRSVVAG-VTRH RLQHIY - : 184
gi|1591421  : S VD IKVRDW R--ENFER IKEV ES- TRH KLIKIE I : 176
gi|6821049  : N NKVKEFVDW KREETFTNMKEK GE- TRF ELLSVD - : 184
gi|2090469  : S ER RKFYDW KSPETFEQMKQA EK- TRF KLLSVK - : 185
gi|6015941  : S EQIPNFLKF E--ENLEK IRNI NS- SHH KLKSIT - : 174
gi|6856776  : S RDVAEFLEW D--KNKEK LEQV NS- TSH KLSKIE - : 176
gi|1991708  : S DR KKFYEW KRPEIFEQMKEV EK- TRF KLVSVK - : 197
gi|2621639  : S VE LQIREW Y--ENMDA LREE ES- TRH KLVKID I : 172
gi|6813399  : S SR KEFYEW KCPEIFEKMKVV EK- TRF KLLSVR - : 185
gi|4504721  : S VD LKIKEW L--DNFAK IKEI ES- TRH KLIQIS I : 179
gi|7655771  : G AE SETAAW R--DNVES LASA EA- TSH ELRDVT - : 173
gi|3141549  : D AE EALVSWTR--DNFAA LKEA EE- TNH ELLDVT - : 174
gi|1579077  : D TEGAEVAQWAD--DNTDA LAAA ES- TSH ELTDVT - : 176
gi|5537994  : D AE GEVSAW R--EHVDV LADA ES- TSH ELQDVT - : 176
gi|7870341  : S VH KAVCDW H--AHEGE IRAE ES- TRF KLTGIEM- : 172
gi|1146450  : D AK GEVSAW R--EHVDV LADA ES- TSH ELQDVT - : 176
                       a         5             6     a    t3  g L  6 p
```

FIGURE 2G

```
              *         260         *         280
Yeast      : C AGDLLF R RTT TGD MGMNM SKGVEYSLKQMVE YGW : 280
gi|1113282 : F VGNNLY R E ETGD MGMNM T   EEIMKV E FP- : 222
gi|5457796 : F VGNNLY R E ETGD MGMNM T   EEIMKV E FP- : 220
gi|1889403 : F VGRNLY R E ETGD MGMNM T   EEIMKV E FP- : 217
gi|5715917 : F VGNNLY R E ETGD MGMNM T   EEIMKV E FP- : 217
gi|1988670 : F VGRHVF R E DTKD MGMNM T   EEAVNWI EKP- : 219
gi|1816067 : F VGNYVW RLV STGD MGMNM T   EAVAKFI ENFP- : 206
gi|5105561 : Y TGNLVW RLS STGD MGMNM T S DRICRYI ENYD- : 224
gi|1591421 : L VGRNLYPR V KTGD MGMNM T   EKACNFI G LKK : 217
gi|6821049 : F TGNTVF R A DTKD MGMNM T   DAVLNFI SED G- : 224
gi|2090469 : F TGTYIY R S DTKD MGMNM T   DAVMHLI D FG- : 225
gi|6015941 : F LGNNVW R S ETGD MGMNM T   VEKVCEFI ENFP- : 214
gi|6856776 : L LGNNVW R V STGD MGMNM A   EKLCEFI K FG- : 216
gi|1991708 : F TGTYVY R S DTKD MGMNM T   DAVMHLI D FG- : 237
gi|2621639 : I AGSYVYPR V TTGD SMGMNM T   ERALELL TR TG- : 212
gi|6813399 : F TGTYVY R S DTKD MGMNM T   DAVMHLI D FG- : 225
gi|4504721 : L VGRNVYPR T KTGD MGMNM T   EKACSFI S LKK : 220
gi|7655771 : Y VGDNVF R A DTKD MGMNM A   EAACEVV A TP- : 213
gi|3141549 : Y VGNSVY R R DTKD MGMNM A   EAVCGVV A TA- : 214
gi|1579077 : Y VGDNVY R R DTKD MGMNM A   EAASEIV D TP- : 216
gi|5537994 : Y VGDSVF R S DTKD MGMNM A   EAACDVV T TP- : 216
gi|7870341 : TTAGTSVF RLS VTGD MGMNM T   AKAADLI SR TG- : 212
gi|1146450 : Y VGDSVF R S DTKD MGMNM A   EAACDVV S TP- : 216
              G  65 Rf   T DaMGMNM 3ia       6   e
```

FIGURE 2H

```
                          *         300          *        320
Yeast       : ED--MEVVSVSVNYCTDKKVAAIVWIEGRGKVVVAEATIPG : 319
gi|1113282  : -D--VRYLAVSVNVCVDKKVNAVVFILGRGKVVIAEAVVPR : 260
gi|5457796  : -D--VRYLAVSVNVCVDKKVNAVVFILGRGKVVVAEAIVPR : 258
gi|1889403  : -D--VKYLAVSVNVCVDKKVNALVFILGRGKVIIAEAVVPR : 255
gi|5715917  : -D--VKYLAVSVNVCVDKKVNAMVFINGRGKVVIAEAVIPR : 255
gi|1988670  : -D--AKCVSASVNVCVDKKVSWLVNVLGRGRVVVAEVEVPR : 257
gi|1816067  : -K--AKLIAVSVNVCVDKKANAVVFILGRGKVVVAEAVIKK : 244
gi|5105561  : GD--AKCIAVSVNVCTDKKVAAIVKILGRGKYVVAEAVIKG : 263
gi|1591421  : EGIFVKTVAVSVNACVDKKVSGMVLINGRGKVIVAEVFLTE : 258
gi|6821049  : ----VYPISVSVNVCTDKKVAAIVNILGRGKVVAADVTIPK : 261
gi|2090469  : ----AHPVTVSVNVCTDKKVASISAILGRGKVVVAEVTIPQ : 262
gi|6015941  : -S--ADCLAVSVNVCSDKKQTNVVSLFGRGKVVVAEALIKK : 252
gi|6856776  : -K--ATCLAVSVNVCSDKKQSMIVALHGRGKVVVAEALIPD : 254
gi|1991708  : ----AHPITVSSNVCTDKKVASISTILGRGKVVVAEVTIPE : 274
gi|2621639  : ----AHVIAVSVNVCTDKKVAAVVLIEGRGKVITAEITVPG : 249
gi|6813399  : ----AHPVTVSVNVCIDKKVASISTILGRGKVVVAEVTIPK : 262
gi|4504721  : EGIIIDTVAVSVNVCVDKKVAAIVLIEGRGKVVVAEVFLKE : 261
gi|7655771  : ----AELVAVSVNVCSDKKVAAVVSVEGRGRVVAADVVLPG : 250
gi|3141549  : ----ASLVAVSVNVCSDKKVAAIVAVEGRGRVVTADVRIPR : 251
gi|1579077  : ----AELVAVSVNVCTDKKVAAIVAVEGRGRVVTADVTIPQ : 253
gi|5537994  : ----ADLVAVSVNVCSDKKVAAIVAVEGRGRVVAADVLIPH : 253
gi|7870341  : ----ARLIAVSVNWCTDKKVAAVVVVMGRGKVVSAGVLLSQ : 249
gi|1146450  : ----ADLVAVSVNVCSDKKVAAIVAVEGRGRVVAADVLIPH : 253
                  6  SgN C DKKp  6n 6 GRG4 6 A    6
```

FIGURE 2I

```
              *         340         *         360
Yeast      : D VRKV K DVSA V  NIAKN VG AM  SVG FNA A N : 360
gi|1113282 : K VEKK K  PEL A  NYFKN VG AQ  S-Y FNA F N : 300
gi|5457796 : E VEKK K  PEL A  NYFKN VG AQ  S-Y FNA FGN : 298
gi|1889403 : E VKKK K  PEL A  NYLKN VG AQ  S-Y FNA F N : 295
gi|5715917 : K VEEK K  PEL A  NYRKN VG AQ  S-Y FNA FGN : 295
gi|1988670 : D VEEK K  PEA A  NYRKN VG AA  N-I FNA H N : 297
gi|1816067 : E LE-R GI PED HN NVRKN IG AL HS-Y FNA F N : 283
gi|5105561 : E VKNV K  PQN NL NVTKN LG AA  S-HS FNA F N : 303
gi|1591421 : KE VNKY K  SQA A  NRLKNYIG AISNS-M FNA Y N : 298
gi|6821049 : E VEKK K  PKM E  NYRKN LG AR  A-L FNA A N : 301
gi|2090469 : E VKET KC PES F  NYSKN LG AR  A-M FNA A N : 302
gi|6015941 : D IRNI H  NAQL HD NLRKNWLG AR  SLSQ FNA F N : 293
gi|6856776 : S VKSA K  DKHL H  NLRKNWLGGAR  NIFQYNA F N : 295
gi|1991708 : E VKET KC PES F  NYSKN LG AR  A-M FNA A N : 314
gi|2621639 : E VESV K  PEA V  NTAKN IG AA  S-M FNA Y N : 289
gi|6813399 : E VKET KC PES F  NYSKN LG AR  A-L FNA A N : 302
gi|4504721 : EY VEKY K  SKA E  NTYKN IG AISSS-L FNAQY N : 301
gi|7655771 : S VEEYFG  PAA A  ANTRKN VG AK  S-L FNA A N : 290
gi|3141549 : E VEER H  PERGR ANTRKN VG AK AS-L FNA V N : 291
gi|1579077 : D VEERFD  PAA E  ANTRKN IG AK  S-L FNA A N : 293
gi|5537994 : EQ VEDR D  SDA V  ANTRKN VG AK  A-L FNA A N : 293
gi|7870341 : E ISKV K  DAAS L  NTRKN VG AR  S-F FNA A N : 289
gi|1146450 : EQ VEER D  SDA V  ANTRKN VG AK  A-L FNA T N : 293
             6    l   t        N  KN16G A  ag   g5NAh aN
```

FIGURE 2J

```
                     *         380           *         400         *
Yeast       : VTA FLALGQDPAQN  SSNC TLMKEV-D DIRI V M : 400
gi|1113282  : VGA FLA GQDEAQ T  AHG TIA VTPD DL I  I M : 341
gi|5457796  : VGA FLA GQDEAQ T  SHG TIA VTPE DL I  I M : 339
gi|1889403  : VGA FLA GQDEAQ T  AHG TLA VTED DL I  I M : 336
gi|5715917  : VGA FLA GQDEAQ T  SHG TLA VTPE DL I  I M : 336
gi|1988670  : VAA FIA GQDEAHA D STGY TM VTED DL A  V I : 338
gi|1816067  : IAA FIA GQDVAQ   SSMG TST ARED-L I  VFL : 323
gi|5105561  : IAA FIA GQDAAQ   SSMGYTWT VRGED-L I V L : 343
gi|1591421  : IGA FLA GQDEAH   SLG TMA VEDD-L F  V L : 338
gi|6821049  : IAA YLACGQDAAH   SSA TTM VNEN DL C  V L : 342
gi|2090469  : IAA YLACGQDAAH   STA TSM LTKYEEIHC V L : 343
gi|6015941  : VTA FIA GQDVAQ   SSSGYTWT VRGED-L I V L : 333
gi|6856776  : IAA FLA GQDIAQ   SSMGYTWT VREN-L I I N : 335
gi|1991708  : IAA YLACGQDAAH   STA TSM LTKY EIHC V L : 355
gi|2621639  : IGA FLA GQDEAH   SLG TIA ERK- DL FAVNL : 329
gi|6813399  : IAA YLACGQDAAH   STA TSM LTKYEEIQC V L : 343
gi|4504721  : VGA FLA GQDEAH   SMG TTA CTGD-L F  V L : 341
gi|7655771  : TVAAAFLA GQDIAQ   ANA TTADVR-D DL A  I A : 330
gi|3141549  : VAA FLA GQDEAQ   ANA TTA VQ-D DL V V IA : 331
gi|1579077  : VAA FLA GQDAAQ   ANA TTV ARDDA-L A VNLA : 333
gi|5537994  : VAAAFLALGQDMAQ   SNA TTVDARED-L A  V IA : 333
gi|7870341  : IAA FIACGQDPAH   SLC TTVDPAHE-V V  V L : 329
gi|1146450  : VAAAFLALGQDIAQ   NNA TTVDARED-L A  V I : 333
               6 A 56A GQD A   veg  T e    g 6y s6 6p
```

FIGURE 2K

```
                     420          *         440          *
Yeast       : SIEV IG G V EP GAMLDL GRGPHATAP T RQL  : 441
gi|1113282  : SLEI VG G R P REALEI GAGG- PP I KKF    : 381
gi|5457796  : SLEI VG G R P REALSI GAGG- PP V KKF    : 379
gi|1889403  : SLEI VG G R PP REALEI GAGG- PP M KKF   : 376
gi|5715917  : SLEI VG G R P REALSI GAGG- PP T KKF    : 376
gi|1988670  : SLNV VG G G E RECLEI GAGG- PP V KEF    : 378
gi|1816067  : SLEV VG G G P REALEL GAGS- PP V LKF    : 363
gi|5105561  : SLEV VG G R P RELLAL GAGG- PP S LKL    : 383
gi|1591421  : DVPI VG G R E KECLEM GCYGD-N-----K LKF : 373
gi|6821049  : SIQV VG G G A RDCLNL GAGA- EVP H SKKL  : 382
gi|2090469  : ALPV VG G G G RDCLNI GAGA- TP I SRKF   : 383
gi|6015941  : SLEV VG G R P KEALSI GYGS- PP S KKL    : 373
gi|6856776  : SLEV VG G R P REALSI GLGS- PP S RKF    : 375
gi|1991708  : ALPV VG G G G RDCLNI GAGA- EP I SLKF   : 395
gi|2621639  : DVPLA VG G G E ASECLDI GRGG-  -----RVHAF: 364
gi|6813399  : SLPV VG G S G G RDCLNI GAGA- VP I SKKF : 383
gi|4504721  : DLPVA IG G R E RECLEI GCAGA-E-----K VKF: 376
gi|7655771  : SLEV VG G K P AEALDV GRGG- PA S DAL    : 370
gi|3141549  : SLEV VG G K P SEGLDI GSGG- PA S DAL    : 371
gi|1579077  : SLEV VG G T P REALDV GRGG- PA A DAL    : 373
gi|5537994  : SLEV VG G G P SEALDV GYSGG- PA S DAL   : 373
gi|7870341  : ALPI VG G S E AECLRM GSGS- PP SH RKL   : 369
gi|1146450  : FLEV NVGRG-RFPEAFGGLEVGGDNGG PA S EALG : 373
              6 6gt6GgG   q  L 6 Gv G  g   g na   a
```

FIGURE 2L

```
              460          *         480          *
Yeast      : R  CA L GE SL CAA  AG  VQS MTHN KPAEPTKPN : 482
gi|1113282 :    GA L GELSL AA   AK  AR  HKM  R-------- : 413
gi|5457796 :    GA L GELSL AA   AK  AR  HKM  R-------- : 411
gi|1889403 :    GA L GELSL AA   AK  AR  HKM  R-------- : 408
gi|5715917 :    GA L GELSL AA   AK  AK  HKE  R-------- : 408
gi|1988670 :    AA L GELSL AA   AG  GK  HRL  R-------- : 410
gi|1816067 :    AA L GEINL IA   RNE AS  HKK  RGAR----- : 398
gi|5105561 :    SA L GEINL SA   AGQ AR  HEL  RGGLKIS-- : 421
gi|1591421 :    GAA L GELSL GA  AG  GK  HQE  R-------- : 405
gi|6821049 :    AA L GEISL GAQ  AG  AK  HAE  R-------- : 414
gi|2090469 :    SA L GEISL GAQ  AG  AR  HAQ  RGKF----- : 418
gi|6015941 :    ST LSGEINL AA   SNKE GK HAK RAMKV----- : 409
gi|6856776 :    SA L GEINL SA   NKE GK  HAK RGMKV----- : 411
gi|1991708 :    SA L GEISL GAQ  AG  AR  HAQ  RGKF----- : 430
gi|2621639 :    GGA L GELSL GA  AG  AR  HSE  RG------- : 397
gi|6813399 :    SA L GEVNL GAQ  AG  AR  HAQ  RGKF----- : 418
gi|4504721 :  AGAA L GELSL GA   AG  AK  HSE  R-------- : 408
gi|7655771 : A  TAALGGELSL GA   SN  AS  HEE  R-------- : 402
gi|3141549 : C  VGSL GELSL SA   SR  SS  HAE  R-------- : 403
gi|1579077 :    VGA L GEINL AA   SRR SA  HAD  R-------- : 405
gi|5537994 :    AGA L GELSL AA  SSR SS  HAD  R-------- : 405
gi|7870341 :    SG L GELSL GA   AQ  AR  HST  R-------- : 401
gi|1146450 :    GGA L GELSL AA   SSR SS  HAE  R-------- : 405
             e   a   vLaGE6 L    A   a   hL  aH   lgR
```

FIGURE 2M

```
                       500                 *
Yeast        : NLDATDINRLKDGSVTCIKS : 502
gi|1113282   : -------------------- : -
gi|5457796   : -------------------- : -
gi|1889403   : -------------------- : -
gi|5715917   : -------------------- : -
gi|1988670   : -------------------- : -
gi|1816067   : -------------------- : -
gi|5105561   : -------------------- : -
gi|1591421   : -------------------- : -
gi|6821049   : -------------------- : -
gi|2090469   : -------------------- : -
gi|6015941   : -------------------- : -
gi|6856776   : -------------------- : -
gi|1991708   : -------------------- : -
gi|2621639   : -------------------- : -
gi|6813399   : -------------------- : -
gi|4504721   : -------------------- : -
gi|7655771   : -------------------- : -
gi|3141549   : -------------------- : -
gi|1579077   : -------------------- : -
gi|5537994   : -------------------- : -
gi|7870341   : -------------------- : -
gi|1146450   : -------------------- : -
```

Figure 3A-D
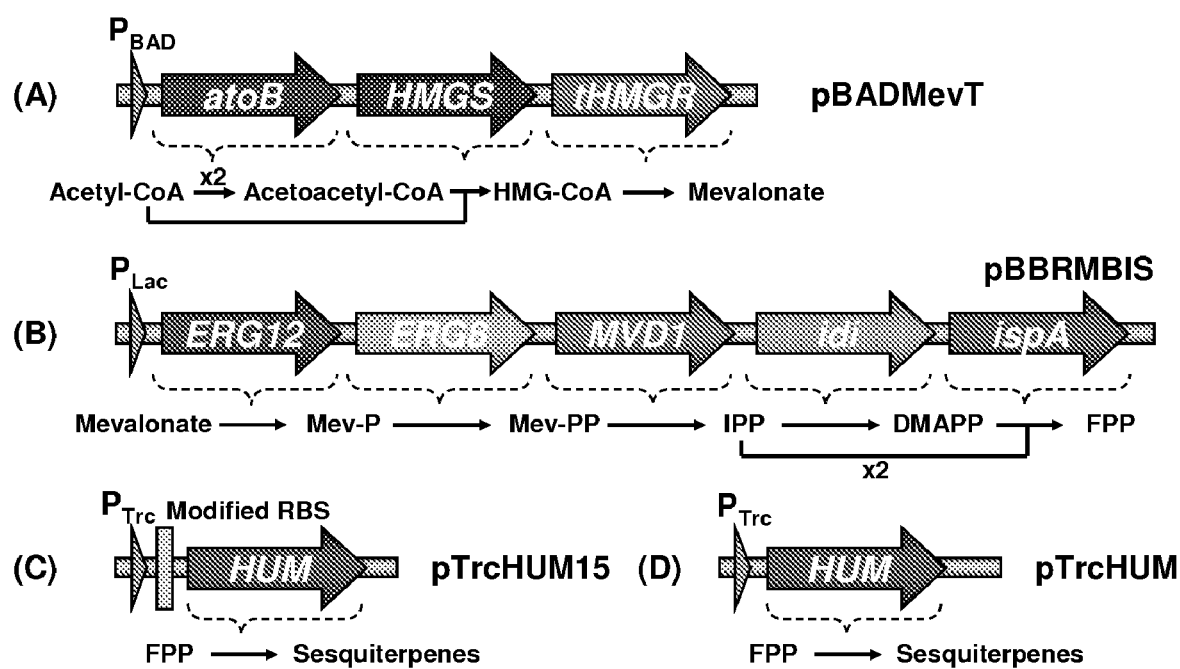

Figures 4A-E
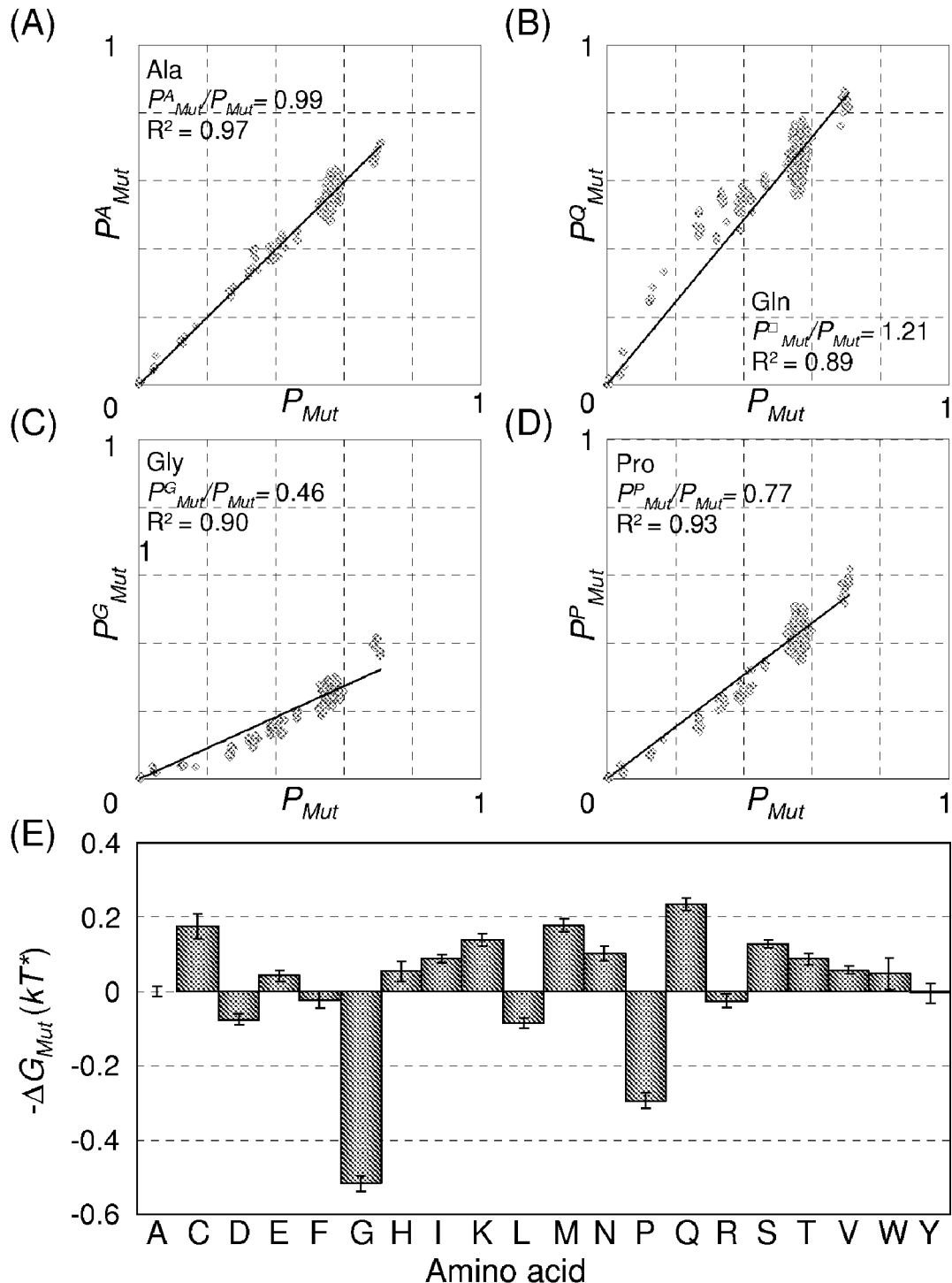

Figures 5A-D
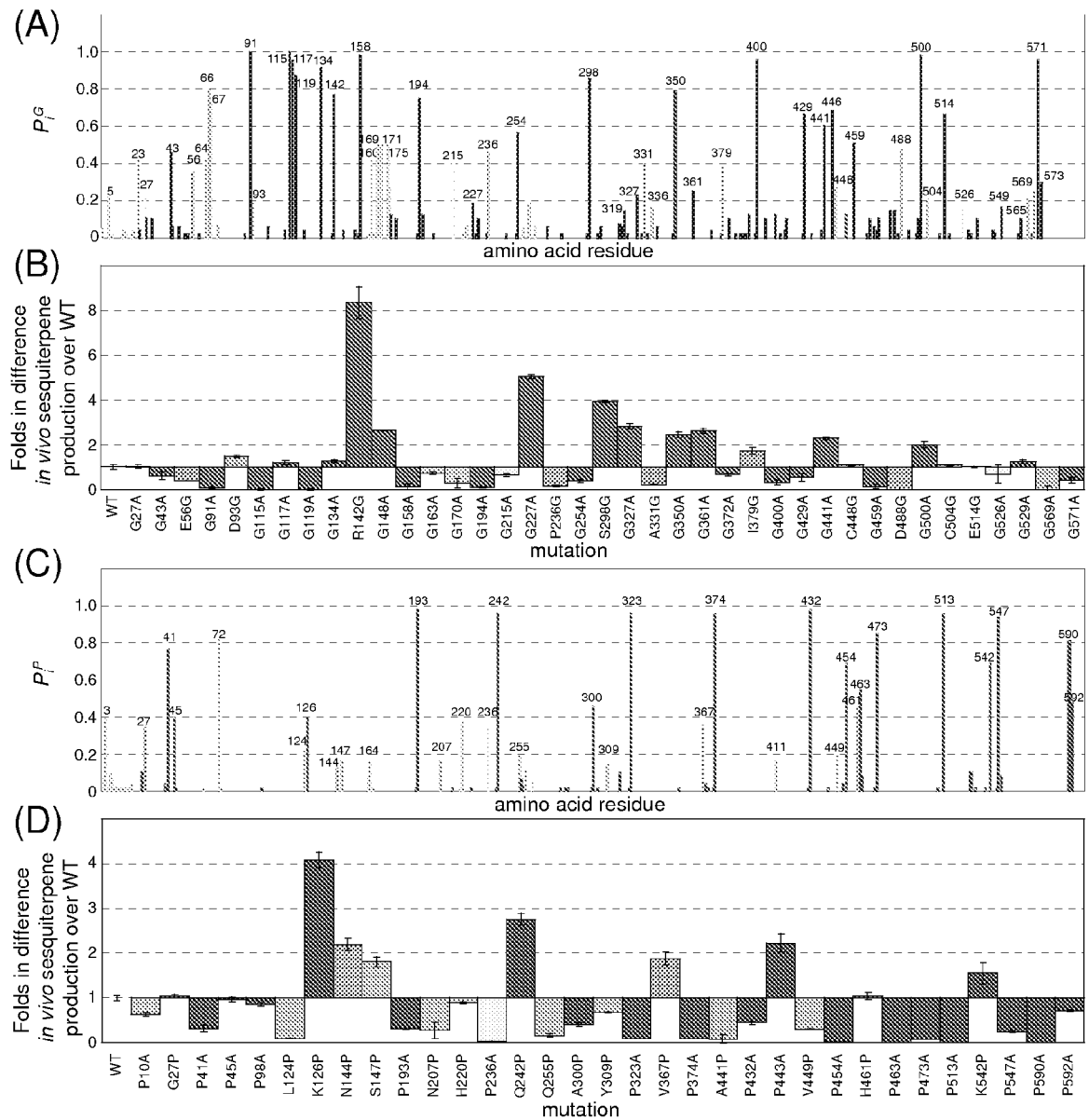

Figures 6A-D
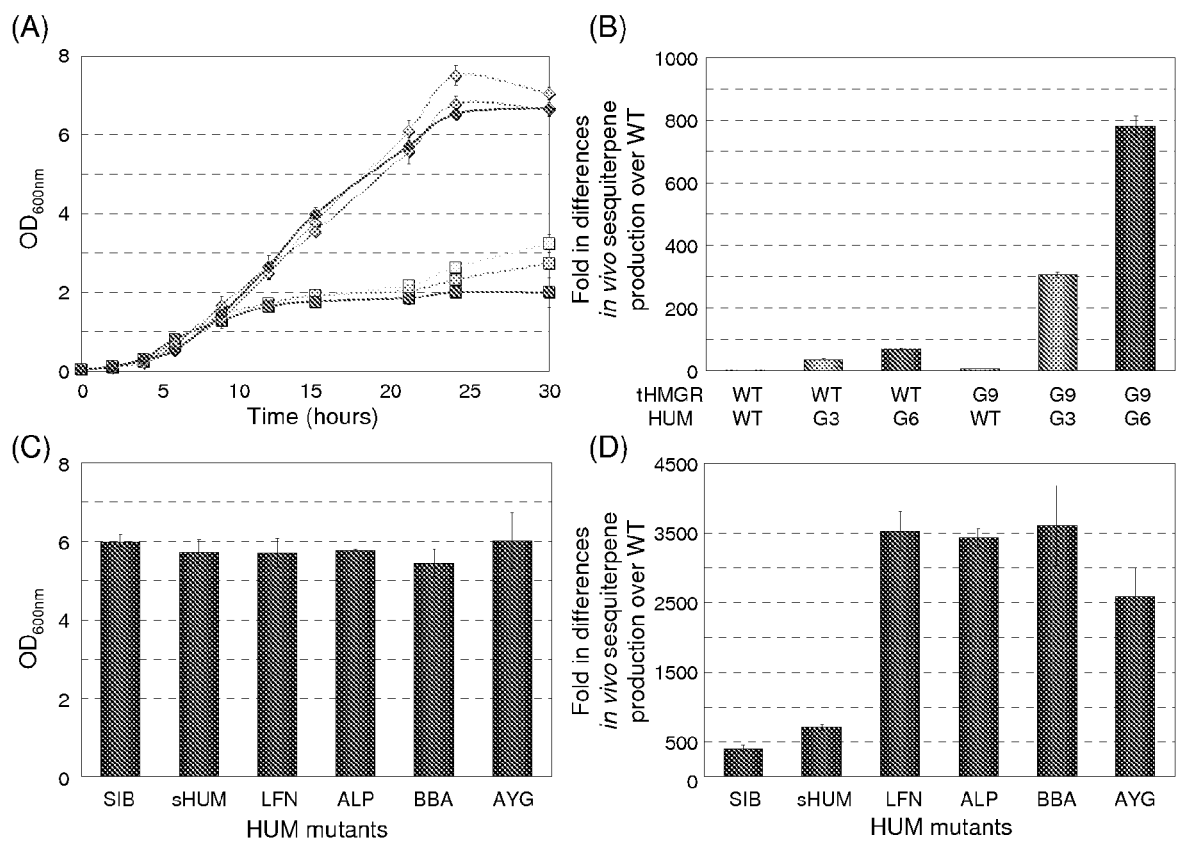

Figures 7A-D
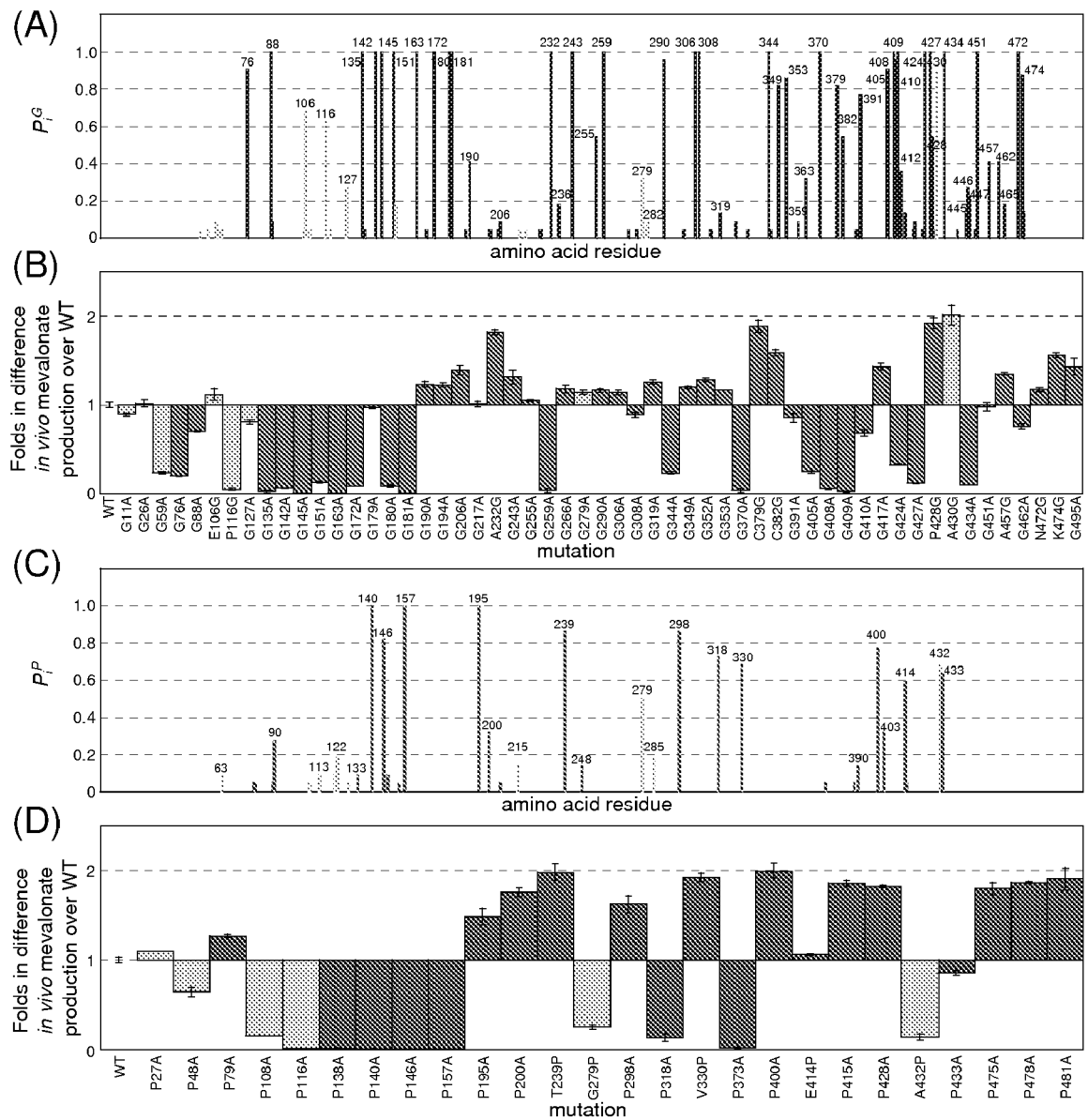

Figures 9A-D
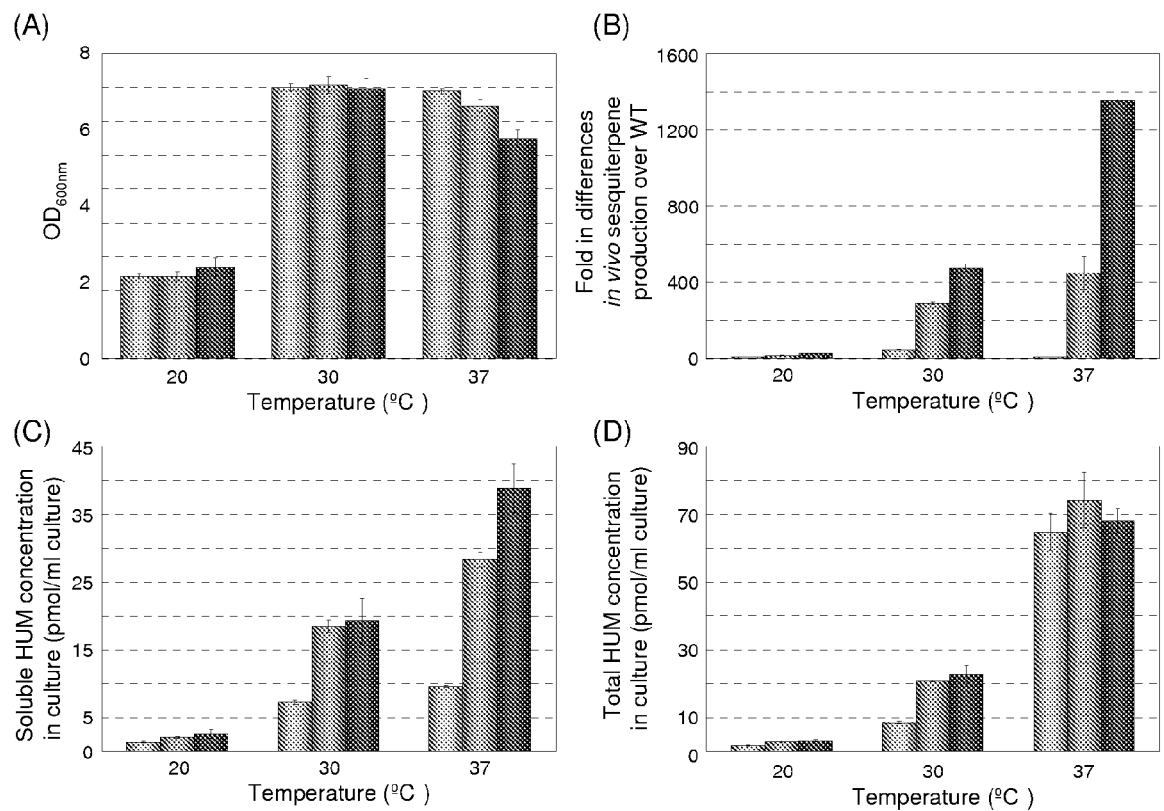

Figure 10A
γ-humulene synthase (*Abies grandis*)
GenBank Accession No. AAC05728

```
  1 maqisesvsp stdlkstess itsnrhgnmw eddriqslns pygapayger seklieeikl
 61 lflsdmddsc ndsdrdlikr leivdtvecl gidrhfqpei klaldyvyrc wnergigegs
121 rdslkkdlna talgfralrl hrynvssgvl enfrddngqf fcgstveeeg aeaynkhvrc
181 mslsrasni lfpgekvmee akafttnylk kvlagreath vdesllgevk yalefpwhcs
241 vqrwearsfi eifggidsel ksnlskkmle lakldfnilq cthqkelqii srwfadssia
301 slnfyrkcyv efyfwmaaai sepefsgsrv aftkiailmt mlddlydthg tldqlkifte
361 gvrrwdvslv eglpdfmkia fefwlktsne liaeavkagg qdmaayirkn aweryleayl
421 qdaewiatgh vptfdeylnn gtpntgmcvl nliplllmge hlpidileqi flpsrfhhli
481 elasrlvdda rdfqaekdhg dlsciecylk dhpestveda lnhvngllgn cllemnwkfl
541 kkgdsvplsc kkysfhvlar sigfmynqgd gfsisnkvik dqvqkvlivp vpi (SEQ ID NO:1)
```

Figure 10B
γ-humulene synthase (*Abies grandis*)
GenBank Accession No. U92267

```
   1 atggctcaga tttctgaatc tgtatcaccc tctaccgatt tgaagagcac cgaatcttcc
  61 attacctcta atcgacatgg aaatatgtgg gaggacgatc gcatacagtc tctcaactca
 121 ccttatgggg cacctgcata tcaagaacgc agcgaaaagc ttattgaaga gatcaaactt
 181 ttattttttga gtgacatgga cgatagctgc aatgatagcg atcgtgattt aatcaaacgt
 241 cttgagatcg ttgatactgt cgagtgtctg ggaattgatc gacatttttca acctgagata
 301 aaattagctc tggattacgt ttacagatgt tggaacgaaa gaggcatcgg agaggatca
 361 agagattccc tcaagaaaga tctgaacgct acagctttgg gattccgggc tctccgactc
 421 catcgatata acgtatcctc aggtgtcttg gagaatttca gagatgataa cgggcagttc
 481 ttctgcggtt ctacagttga agaagaagga gcagaagcat ataataaaca cgtaagatgc
 541 atgctgtcat tatcgcgagc ttcaaacatt ttatttccgg gcgaaaaagt gatggaagag
 601 gcgaaggcat tcacaacaaa aaagtttttag caggacggga ggctacccac
 661 gtcgatgaaa gccttttttggg agaggtgaag tacgcattgg agtttccatg gcattgcagt
 721 gtgcagagat gggaggcaag gagctttatc gaaatatttg gacaaattga ttcagagctt
 781 aagtcgaatt tgagcaaaaa aatgttagag ttggcgaaat tggcttcaa tattctgcaa
 841 tgcacacatc agaaagaact gcagattatc tcaaggtggt tcgcagactc aagtatagca
 901 tccctgaatt tctatcggaa atgttacgtc gaatttttact tttggatggc tgcagccatc
 961 tccgagccgg agtttttctgg aagcagagtt gccttcacaa aaattgctat actgatgaca
1021 atgctagatg accttgtacga tactcacgga accttggacc aactcaaaat ctttacagag
1081 ggagtgagac gatgggatgt ttcgttggta gaggcctcc cagacttcat gaaaattgca
1141 ttcgagttct ggttaaagac atctaatgaa ttgattgctg aagctgttaa agcgcaaggg
1201 caagatatgc cggcctacac aagaaaaaat gcatgggagc gatacccttga agcttatctg
1261 caagatgcgg aatggatagc cactggacat gtccccacct ttgatgagta cttgaataat
1321 ggcacaccaa acactgggat gtgtgtattg aatttgattc cgcttctgtt aatgggtgaa
1381 catttaccaa tcgacattct ggagcaaata ttcttgccct ccaggttcca ccatctcatt
1441 gaattggctt ccaggctcgt cgatgacgcg agagatttcc aggcggagaa ggatcatggg
1501 gattatcgt gtattgagtg ttatttaaaa gatcatcctg agtctacagt agaagatgct
1561 ttaaatcatg ttaatggcct ccttgcaat tgccttctgg aaatgaattg gaagttctta
1621 aagaagcagg acagtgtgcc actctcgtgt aagaagtaca gcttccatgt attggcacga
1681 agcatccaat tcatgtacaa tcaaggcgat ggcttctcca tttcgaacaa agtgatcaag
1741 gatcaagtgc agaaagttct tattgtcccc gtgcctattt ga (SEQ ID NO:72)
```

Figure 10C
Variant γ-humulene synthase
HUM-G3

```
  1  maqisesvsp stdlkstess itsnrhgnmw eddriqslns pygapayger seklieeikl
 61  lflsdmddsc ndsdrdlikr leivdtvecl gidrhfqpei klaldyvyrc wnergigegs
121  rdslkpdlna talgfralrl hgynvssgvl enfrddngqf fcgstveeeg aeaynkhvrc
181  mslsrasni  lfpgekvmee akafttnylk kvlagreath vdesllaevk yalefpwhcs
241  vqrwearsfi eifgqidsel ksnlskkmle lakldfnilq cthqkelqii srwfadssia
301  slnfyrkcyv efyfwmaaai sepefsgsrv aftkiailmt mlddlydthg tldqlkifte
361  gvrrwdvslv eglpdfmkia fefwlktsne liaeavkagg qdmaayirkn aweryleayl
421  qdaewiatgh vptfdeylnn gtpntgmcvl nlipillmge hlpidileqi flpsrfhhli
481  elasrlvdda rdfqaekdhg dlsciecylk dhpestveda lnhvngllgn cllemnwkfl
541  kkqdsvplsc kkysfhvlar sigfmynqgd gfsisnkvik dqvqkvlivp vpi (SEQ ID NO:73)
```

Figure 10D
Variant γ-humulene synthase
HUM-G6

```
  1 maqisesvsp stdlkstess itsnrhgnmw eddriqslns pygapaygqer seklieeikl
 61 lflsdmddsc ndsdrdlikr leivdtvecl gidrhfqpei klaldyvyrc wnergigegs
121 rdslkpdlna talgfralrl hgynvssavl enfrddnggf fcgstveeeg aeaynkhvrc
181 mislsrasni lfpgekvmee akafttnylk kvlagreath vdesllaevk yalefpwhcs
241 vqrwearsfi eifgqidsel ksnlskkmle lakldfnilq cthqkelqii srwfadssia
301 slnfyrkcyv efyfwmaaai sepefsasrv aftkiailmt mlddlydthg tldqlkifte
361 avrrwdvslv eglpdfmkia fefwlktsne liaeavkagg qdmaayirkn aweryleayl
421 qdaewiatgh vptfdeylnn gtpntgmcvl nliplllmge hlpidileqi flpsrfhhli
481 elasrlvdda rdfqaekdhg dlsciecylk dhpestveda lnhvngllgn cllemnwkfl
541 kkqdsvplsc kkysfhvlar slqfmynggd gfsisnkvik dqvqkvlivp vpi (SEQ ID NO:74)
```

Figure 11A
Truncated HMGR

```
  1  PVLTNKTVIS  GSKVKSLSSA  QSSSSGPSSS  SEEDDSRDIE  SLDKKIRPLE
 51  ELEAALLSSGN  TKQLKNKEVA  ALVIHGKLPL  YALEKKLGDT  TRAVAVRRKA
101  LSILAEAPVL  ASDRLPYKNY  DYDRVFGACC  ENVIGYMPLP  VGVIGPLVID
151  GTSYHIPMAT  TEGCLVASAM  RGCKAINAGG  GATTVLTKDG  MTRGPVVRFP
201  TLKRSGACKI  WLDSEEGQNA  IKKAFNSTSR  FARLQHIQTC  LAGDLLFMRF
251  RTTGDAMGM  NMISKGVEYS  LKQMVEEYGW  EDMEVVSVSG  NYCTDKKPAA
301  INWIEGRGKS  VVAEATIPGD  VVRKVLKSDV  SALVELNIAK  NLVGSAMAGS
351  VGGFNAHAAN  LVTAVFLALG  QDPAQNVESS  NCITLMKEVD  GDLRISVSMP
401  SIEVGTIGGG  TVLEPQGAML  DLLGVRGPHA  TAPGTNARQL  ARIVACAVLA
451  GELSLCAALA  AGHLVQSHMT  HNRKPAEPTK  PNNLDATDIN  RLKDGSVTCI
501  KS (SEQ ID NO:49)
```

Figure 11B
Variant tHMGR

```
  1 PVLTNKTVIS GSKVKSLSSA QSSSSGPSSS SEEDDSRDIE SLDKKIRPLE
 51 ELEALLSSGN TKQLKNKEVA ALVIHGKLPL YALEKKLGDT TRAVAVRRKA
101 LSILAEAPVL ASDRLPYKNY DYDRVFGACC ENVIGYMPLP VGVIGPLVID
151 GTSYHIPMAT TEGCLVASAM RGCKAINAGG GATTVLTKDG MTRGPVVRFP
201 TLKRSAACKI WLDSEEGQNA IKKAFNSTSR FARLQHIQTC LAGDLLFMRF
251 RTTTGDAMGM NMISKGVEYS LKQMVEEYGW EDMEVVSVSG NYCTDKKPAA
301 INWIEGRGKS VVAAEATIPAD VVRKVLKSDV SALVELNIAK NLVGSAMAGS
351 VAGFNAHAAN LVTAVFLALG QDPAQNVESS NCITLMKEVD GDLRISVSMP
401 SIEVGTIGGG TVLEPQAAML DLLGVRGPHA TAPGTNARQL ARIVACAVLA
451 GELSLCAALA AGHLVQSHMT HNRKPAEPTK PNNLDATDIN RLKDASVTCI
501 KS (SEQ ID NO:75)
```

Figure 11C
Variant tHMGR

```
  1 PVLTNKTVIS GSKVVKSLSSA QSSSSGPSSS SEEDDSRDIE SLDKKIRPLE
 51 ELEALLSSGN TKQLKNKEVA ALVIHGKLPL YALEKKLGDT TRAVAVRRKA
101 LSILAEAPVL ASDRLPYKNY DYDRVFGACC ENVIGYMPLP VGVIGPLVID
151 GTSYHIPMAT TEGCLVASAM RGCKAINAGG GATTVLTKDG MTRGPVVRFA
201 TLKRSAACKI WLDSEEGQNA IKKAFNSTSR FARLQHIQPC LAGDLLFMRF
251 RTTTGDAMGM NMISKGVEYS LKQMVEEYGW EDMEVVSVSG NYCTDKKPAA
301 INWIEGRGKS VVAAEATIPAD VVRKVLKSDV SALVELNIAK NLVGSAMAGS
351 VAGFNAHAAN LVTAVFLALG QDPAQNVESS NCITLMKEVD GDLRISVSMP
401 SIEVGTIGGG TVLEPQAAML DLLGVRGGHA TAPGTNARQL ARIVACAVLA
451 GELSLCAALA AGHLVQSHMT HNRGPAEPTK PNNLDATDIN RLKDASVTCI
501 KS (SEQ ID NO:76)
```

Figure 12A

| name | gene | aa | sample | A | C | D | E | F | G | H | I |
|---|---|---|---|---|---|---|---|---|---|---|---|
| long-chain-fatty-acid-[acyl-carrier-protein] ligase/acyl-[acyl-carrier-protein]-phospholipid O-acyltransferase | aas | 719 | 70 | 1.081 | 1.5197 | 0.949 | 1.0009 | 0.8803 | 0.5791 | 1.1451 | 1.1043 |
| acetyl CoA carboxylase, biotin carboxylase subunit | accC | 449 | 995 | 0.9482 | 1.2465 | 1.1038 | 0.8319 | 0.8495 | 0.4834 | 1.0259 | 1.0866 |
| pyruvate dehydrogenase | aceE | 887 | 205 | 1.1253 | 1.4071 | 0.9186 | 1.0551 | 0.7418 | 0.5476 | 1.202 | 1.187 |
| dihydrolipoamide acetyltransferase | aceF | 630 | 234 | 0.8998 | | 0.8742 | 1.0507 | 1.0242 | 0.6425 | 1.0395 | 1.0834 |
| aconitate hydrase A | acnA | 891 | 500 | 0.9943 | 0.8939 | 1.0418 | 1.1414 | 0.9065 | 0.5819 | 1.0516 | 1.0543 |
| aconitate hydrase B | acnB | 865 | 150 | 1.003 | 0.8028 | 0.9407 | 1.2691 | 0.6624 | 0.4608 | 1.3226 | 1.1473 |
| acetyl-CoA synthetase | acs | 652 | 906 | 1.0271 | 1.2258 | 0.8293 | 1.0117 | 1.1476 | 0.6038 | 1.091 | 1.1442 |
| adenosine deaminase | add | 333 | 289 | 0.9447 | 1.0337 | 0.9692 | 0.885 | 0.9579 | 0.744 | 0.8 | 1.0508 |
| Mn-dependent adenine deaminase (cryptic) | ade | 588 | 98 | 0.9931 | 1.2324 | 0.9342 | 1.0315 | 0.9848 | 0.5321 | 0.8286 | 0.9574 |
| arginine decarboxylase; inducible by acid, catabolic | adiA | 756 | 197 | 0.9796 | 1.2632 | 0.9157 | 1.1152 | 0.8576 | 0.6402 | 0.9491 | 1.0839 |
| adenylate kinase | ack | 214 | 788 | 1.1442 | 1.3185 | 0.7628 | 1.1112 | 1.0468 | 0.4586 | 1.2129 | 1.1852 |
| alanyl-tRNA synthetase | alaS | 876 | 539 | 1.0774 | 0.8493 | 0.9432 | 1.0596 | 0.6332 | 0.5899 | 0.8272 | 1.1446 |
| aldehyde dehydrogenase | aldH | 495 | 999 | 0.9616 | 1.2903 | 0.9444 | 0.9901 | 0.7828 | 0.5363 | 1.332 | 1.1076 |
| alanine racemase | alr | 356 | 518 | 0.9391 | | 0.945 | 1.1193 | 1.0733 | 0.6015 | 1.0413 | 1.2024 |
| cytoplasmic asparaginase I | ansA | 388 | 311 | 1.0294 | | 0.922 | 1.1184 | 1.0161 | 0.6413 | 1.089 | 1.038 |
| periplasmic L-asparaginase II | ansB | 348 | 328 | 0.9968 | 1.4789 | 0.9793 | 1.1963 | 1.0394 | 0.6063 | 1.0663 | 1.0115 |
| membrane-bound ATP synthasebeta-subunit | aptD | 460 | 1000 | 0.9567 | 2.9564 | 0.7847 | 1.2054 | 0.7189 | 0.5904 | 0.8899 | 1.0245 |
| acetylornithine delta-aminotransferase | argD | 406 | 978 | 0.9546 | 1.0737 | 0.933 | 0.9692 | 0.9778 | 0.5819 | 0.9033 | 1.1663 |
| argininosuccinate synthetase | argG | 447 | 445 | 1.0293 | 1.347 | 0.9077 | 0.953 | 1.0032 | 0.5936 | 1.1638 | 1.1807 |
| argininosuccinate lyase | argH | 457 | 585 | 1.0227 | 1.5375 | 0.7601 | 1.0379 | 1.0512 | 0.6816 | 0.8452 | 1.2782 |
| arginine tRNA synthetase | argS | 577 | 607 | 1.0001 | 1.2709 | 0.8706 | 0.9932 | 0.9517 | 0.6601 | 0.935 | 1.1415 |
| 3-enolpyruvylshikimate-5-phosphate synthetase | aroA | 427 | 729 | 0.8565 | 1.3192 | 0.8662 | 1.1123 | 1.0256 | 0.7119 | 1.2574 | 1.0641 |
| 3-dehydroquinate synthase | aroB | 362 | 449 | 1.056 | 1.4244 | 0.9636 | 1.0094 | 1.0651 | 0.5121 | 0.9446 | 1.1707 |
| chorismate synthase | aroC | 361 | 467 | 0.9253 | | 0.776 | 1.0756 | 1.2174 | 0.4078 | 1.0665 | 1.0835 |
| 3-deoxy-D-arabinoheptulosonate-7-phosphate synthase (DAHP synthetase), tyrosine-repressible | aroF | 356 | 420 | 1.1516 | | 0.9828 | 1.2037 | | 0.4526 | 0.9025 | 1.147 |
| 3-deoxy-D-arabinoheptulosonate-7-phosphate synthase (DAHP synthetase), phenylalanine repressible) | aroG | 350 | 419 | 1.0278 | 1.1741 | 0.9388 | 1.2507 | 1.0332 | 0.5996 | 0.9669 | 0.9934 |
| 3-deoxy-D-arabinoheptulosonate-7-phosphate synthase (DAHP synthetase), tryptophan-repressible | aroH | 348 | 419 | 0.9895 | 1.081 | 1.02 | 1.1263 | 1.0883 | 0.5161 | 0.9981 | 1.0051 |
| asparagine synthetase B | asnB | 554 | 276 | 1.0479 | 1.1087 | 0.8574 | 0.9482 | 0.8766 | 0.5867 | 0.9971 | 1.0629 |
| asparagine tRNA synthetase | asnS | 466 | 430 | 1.0992 | 1.4377 | 1.0079 | 0.8339 | 0.7625 | 0.6726 | 0.9184 | 1.2346 |
| aspartate ammonia-lyase (aspartase) | aspA | 493 | 599 | 1.0209 | 1.2673 | 0.8962 | 0.9691 | 1.1772 | 0.629 | 1.4609 | 1.1101 |
| aspartate aminotransferase | aspC | 396 | 496 | 1.0949 | 1.1484 | 1.0152 | 1.1316 | 0.795 | 0.5963 | 0.8698 | 1.1923 |
| aspartate tRNA synthetase | aspS | 590 | 452 | 1.1056 | 1.0197 | 0.8646 | 1.025 | 0.7211 | 0.6526 | 1.0332 | 1.213 |
| acetyl-CoA acetyltransferase | atoB | 394 | 996 | 0.8316 | | 0.9749 | 0.9373 | 1.1787 | 0.5015 | 1.338 | 1.0733 |
| membrane-bound ATP synthase, F1 sector, alpha-subunit | atpA | 513 | 959 | 1.0156 | | 1.0244 | 1.0584 | 0.9568 | 0.4786 | 1.682 | 1.0573 |
| valine--pyruvate transaminase | avtA | 417 | 314 | 1.0149 | | 1.0464 | 1.0109 | 0.9589 | 0.6969 | 1.1653 | 1.0323 |
| 6-phospho-beta-glucosidase A | bglA | 479 | 868 | 0.9859 | 1.1772 | 0.8472 | 0.6601 | 1.0192 | 0.6605 | 1.0387 | 1.0106 |
| carbamoyl phosphate synthetase, Small subunit | carA | 382 | 649 | 1.1692 | 1.3391 | 0.7767 | 1.1225 | 0.8768 | 0.5018 | 1.0374 | 1.0218 |
| carbamoyl phosphate synthase, Large subunit | carB | 1073 | 598 | 0.9611 | 1.1525 | 0.9436 | 0.8888 | 0.9464 | 0.5434 | 1.3525 | 1.0985 |
| phospho-beta-glucosidase | celF | 450 | 165 | 0.9476 | 1.1486 | 0.9725 | 0.9532 | 1.1555 | 0.6122 | 1.1663 | 1.0329 |
| citrate lyase beta chain | citE | 307 | 297 | 0.9071 | 0.8248 | 0.7523 | 0.9838 | 1.1051 | 0.6772 | 1.3719 | 1.0999 |
| cytidine monophosphate (CMP) kinase | cmk | 227 | 361 | 0.9149 | 1.4245 | 0.6904 | 1.1952 | 1.0406 | 0.6078 | 1.5898 | 1.1057 |
| 2',3'-cyclic nucleotide 2'-phosphodiesterase/3'-nucleotidase bifunctional periplasmic precursor protein | cpdB | 647 | 368 | 0.9967 | 1.3161 | 0.8902 | 1.0431 | 0.9741 | 0.6494 | 0.6601 | 1.0514 |
| adenylate cyclase | cyaA | 848 | 80 | 1.1481 | 1.0686 | 0.9896 | 1.0216 | 0.7622 | 0.8026 | 1.3147 | 1.2611 |
| cysteine tRNA synthetase | cysS | 461 | 547 | 1.1067 | 0.835 | 0.8343 | 1.1099 | 0.9792 | 0.6496 | 0.7511 | 0.9808 |
| succinyl-diaminopimelate desuccinylase | dapE | 375 | 556 | 1.0205 | 1.2384 | 0.8837 | 0.9353 | 0.9358 | 0.6187 | 0.8645 | 1.1696 |

Figure 12B

| name | gene | aa | sample | A | C | D | E | F | G | H | I |
|---|---|---|---|---|---|---|---|---|---|---|---|
| thymidine phosphorylase | deoA | 440 | 214 | 0.9036 | 1.4258 | 0.9235 | 1.0966 | 1.0773 | 0.5546 | 1.0216 | 1.0564 |
| phosphopentomutase | deoB | 407 | 179 | 1.0334 | 1.1976 | 0.6541 | 1.0984 | 0.8662 | 0.6392 | 0.8585 | 1.0252 |
| deoxyribose-phosphate aldolase | deoC | 259 | 243 | 0.8642 | 0.812 | 0.945 | 0.9739 | 0.9786 | 0.6167 | 1.4131 | 1.139 |
| purine-nucleoside phosphorylase | deoD | 306 | 307 | 0.8538 | 1.3396 | 0.8827 | 0.8894 | 0.9284 | 0.6234 | 1.1588 | 0.9952 |
| DNA polymerase IV | dgt | 505 | 176 | 0.996 | 1.1942 | 0.8176 | 0.9396 | 0.9549 | 0.7949 | 0.9772 | 0.9445 |
| DNA polymerase IV | dinB | 351 | 512 | 0.9313 | 1.1401 | 0.8281 | 1.0306 | 0.8879 | 0.6322 | 1.2761 | 1.062 |
| DNA polymerase III, alpha subunit | dnaE | 1160 | 519 | 1.006 | 1.294 | 0.9236 | 1.0501 | 0.8248 | 0.6876 | 1.0822 | 1.0336 |
| DNA polymerase III, epsilon subunit | dnaQ | 243 | 206 | 0.9306 | | 0.8582 | 0.9996 | 0.8133 | 0.7053 | 0.6087 | 1.0271 |
| DNA polymerase III, tau and gamma subunits; DNA elongation factor III | dnaX | 643 | 133 | 0.9573 | | 1.0107 | 1.0557 | 0.7306 | 0.7951 | 0.961 | 0.0509 |
| D-serine deaminase (dehydratase) | dsdA | 442 | 79 | 1.1024 | 0.8465 | 0.8533 | 1.1662 | 0.8878 | 0.4902 | 1.2052 | 1.1271 |
| 2-keto-3-deoxygluconate 6-phosphate aldolase | eda | 213 | 250 | 0.9194 | 1.2057 | 1.2754 | 1.0634 | 0.7975 | 0.4228 | | 1.1747 |
| 6-phosphogluconate dehydratase | edd | 603 | 557 | 0.9227 | 0.9783 | 0.9564 | 1.0008 | 1.161 | 0.6466 | 1.0893 | 1.1308 |
| enolase | eno | 432 | 746 | 0.711 | | 0.8059 | 0.8603 | 1.5813 | 0.5768 | 1.039 | 0.9614 |
| 3-oxoacyl-[acyl-carrier-protein] synthase I | fabB | 406 | 956 | 0.9454 | 1.127 | 0.905 | 0.9702 | 1.0015 | 0.5308 | 1.0219 | 1.0442 |
| 3-oxoacyl-[acyl-carrier-protein] synthase II | fabF | 413 | 962 | 0.9668 | 1.2243 | 0.9092 | 1.0361 | 0.8437 | 0.5173 | 0.9966 | 1.1624 |
| 3-ketoacyl-CoA thiolase; (thiolase I, acetyl-CoA transferase), in complex with FadB catalyzes | fadA | 387 | 997 | 0.7937 | 0.8799 | 1.0268 | 0.9205 | 0.9476 | 0.5775 | 1.3069 | 1.1275 |
| 4-enzyme protein: 3-hydroxyacyl-CoA dehydrogenase; 3-hydroxybutyryl-CoA epimerase; delta(3)-cis-delta(2)-trans-enoyl-CoA isomerase; enoyl-CoA hydratase | fadB | 729 | 418 | 0.9826 | 1.2532 | 0.954 | 0.9256 | 0.8619 | 0.568 | 1.2236 | 1.0849 |
| acyl-CoA synthase | fadD | 561 | 903 | 1.1094 | 1.2253 | 0.8874 | 0.9159 | 1.0806 | 0.5657 | | 1.1872 |
| fructose-bisphosphate aldolase, class II | fbaA | 359 | 367 | 0.917 | 1.1525 | 0.8697 | 0.8757 | 1.1445 | 0.6638 | 0.7672 | 1.0787 |
| fructose-1,6-bisphosphatase | fbp | 332 | 330 | 1.1108 | 1.504 | 0.8965 | 0.9551 | 1.0643 | 0.5265 | 1.1971 | 1.111 |
| methionyl-tRNA formyltransferase | fmt | 315 | 569 | 1.0291 | 1.3301 | 0.8893 | 1.2783 | 1.0932 | 0.5708 | 1.0995 | 1.1144 |
| fumarate reductase, anaerobic, catalytic and NAD/flavoprotein subunit | frdA | 602 | 974 | 0.9345 | 1.366 | 0.8168 | 0.9712 | 1.1894 | 0.5579 | 0.9487 | 1.2017 |
| fumarase A (fumarate hydratase class I) | fumA | 548 | 176 | 0.9742 | 0.7424 | 0.9572 | 1.0505 | 1.3319 | 0.5596 | 1.006 | 1.1649 |
| fumarase C (fumarate hydratase Class II) | fumC | 467 | 594 | 0.9624 | 1.3506 | 0.9122 | 1.0947 | 0.999 | 0.5181 | 1.32 | 1.1503 |
| 4-aminobutyrate aminotransferase | gabT | 426 | 968 | 0.9791 | 1.1216 | 0.9416 | 0.924 | 1.1496 | 0.5812 | 0.9184 | 1.0686 |
| glutamate decarboxylase A, isozyme, PLP-dependent | gadA | 466 | 152 | 0.9889 | 1.1865 | 0.9451 | 1.1478 | 0.9249 | 0.5872 | 1.1057 | 1.1981 |
| glutamate decarboxylase isozyme | gadB | 466 | 143 | 0.9836 | 1.183 | 0.9476 | 1.1493 | 0.9247 | 0.5845 | 1.1078 | 1.2061 |
| galactose-1-epimerase | galM | 346 | 298 | 1.0506 | 1.4377 | 0.935 | 1.2011 | 0.8846 | 0.6169 | 0.8595 | 1.0949 |
| glyceraldehyde-3-phosphate dehydrogenase | gapA | 331 | 919 | 0.0197 | 1.0632 | 1.0167 | 1.2483 | 0.8648 | 0.5435 | 1.1894 | 1.3244 |
| glycine cleavage complex protein P, glycine decarboxylase, PLP-dependent | gcvP | 957 | 304 | 1.0385 | 0.9472 | 1.083 | 1.071 | 1.0257 | 0.4713 | 0.7929 | 1.0886 |
| aminomethyltransferase | gcvT | 364 | 714 | 0.9781 | | 0.8968 | 0.962 | 1.2016 | 0.5831 | 1.0907 | 1.1196 |
| glutamate dehydrogenase | gdhA | 447 | 465 | 0.9323 | 1.2676 | 0.9533 | 0.9369 | 1.2016 | 0.5528 | | 1.3397 |
| glucokinase | glk | 321 | 158 | 1.0409 | 1.1419 | 1.0307 | 1.0798 | 0.8659 | 0.5185 | 1.1902 | 1.1097 |
| glutamine synthetase | glnA | 496 | 605 | 0.9864 | | 0.9147 | 0.9021 | 0.9133 | 0.6989 | 0.9755 | 1.1356 |
| glutamine tRNA synthetase | glnS | 554 | 339 | 1.2148 | 1.1311 | 0.8582 | 1.0895 | 0.8259 | 0.6958 | 0.9511 | 1.0299 |
| citrate synthase | gltA | 427 | 621 | 0.9573 | 1.3095 | 0.9804 | 0.9913 | 0.9316 | 0.5767 | 0.8733 | 1.091 |
| glutamate synthase, large subunit | gltB | 1517 | 359 | 0.9931 | 1.1141 | 0.9554 | 1.0542 | 1 | 0.4556 | 1.1495 | 1.1359 |
| glutamate synthase, small subunit | gltD | 472 | 617 | 0.9065 | 0.4007 | 0.983 | 1.0332 | 0.9859 | 0.5525 | 1.4327 | 1.055 |
| glutamate tRNA synthetase, catalytic subunit | gltX | 471 | 478 | 1.0379 | | 0.8851 | 1.0574 | 0.9379 | 0.6953 | 1.0522 | 1.0306 |
| serine hydroxymethyltransferase | glyA | 417 | 716 | 0.9135 | 1.4951 | 0.9745 | 1.0845 | 1.3461 | 0.5481 | 0.7489 | 1.2472 |
| glycine tRNA synthetase, beta subunit | glyS | 689 | 350 | 1.0078 | 1.4633 | 0.9336 | 1.0112 | 0.7477 | 0.7001 | 1.2829 | 1.1186 |
| guanylate kinase | gmk | 107 | 691 | 1.0988 | | 0.9895 | 0.9626 | 0.8764 | 0.5034 | 1.2299 | 0.9773 |
| 6-phosphogluconate dehydrogenase | gnd | 468 | 473 | 1.0425 | 0.9133 | 0.996 | 1.2256 | 1.0037 | 0.4898 | 0.7879 | 0.8348 |
| phosphoglyceromutase 1 | gpmA | 250 | 508 | 1.0737 | | 1.0842 | 0.9298 | 1.1911 | 0.6003 | 0.8476 | 1.2302 |

Figure 12C

| name | gene | aa | sample | A | C | D | E | F | G | H | I |
|---|---|---|---|---|---|---|---|---|---|---|---|
| bifunctional GMP synthase/glutamine amidotransferase protein | guaA | 525 | 429 | 1.1926 | 0.9777 | 1.076 | 0.9974 | 0.9761 | 0.535 | 1.0158 | 1.105 |
| IMP dehydrogenase | guaB | 488 | 453 | 0.9734 | 1.3823 | 0.9025 | 1.1375 | 1.2214 | 0.4472 | 1.0999 | 1.0702 |
| GMP reductase | guaC | 347 | 192 | 0.8853 | 0.9698 | 0.9054 | 1.0156 | 1.1304 | 0.4787 | 1.164 | 1.1641 |
| guanine deaminase | guaD | 439 | 351 | 0.9757 | | 0.9002 | 0.9923 | 1.1143 | 0.6538 | | 1.1467 |
| bifunctional: histidinol-phosphatase (N-terminal); imidazoleglycerol-phosphate dehydratase (C-terminal) | hisB | 356 | 104 | 1.2173 | 1.1413 | 0.7692 | 1.3283 | 0.6626 | 0.6061 | 0.4931 | 1.0083 |
| histidinol-phosphate aminotransferase | hisC | 356 | 787 | 0.9789 | 1.2018 | 1.031 | 0.9524 | 1.1376 | 0.8002 | 1.3935 | 1.0853 |
| histidinol dehydrogenase | hisD | 434 | 478 | 0.9091 | 1.4476 | 0.9831 | 1.0453 | 0.9541 | 0.5434 | | 1.0645 |
| histidine tRNA synthetase | hisS | 424 | 611 | 1.0893 | 1.3177 | 0.9166 | 0.9036 | 0.9678 | 0.644 | 1.2448 | 1.2007 |
| isocitrate dehydrogenase | icdA | 416 | 848 | 0.913 | 1.3535 | 0.8363 | 0.9603 | 1.1515 | 0.7043 | 0.9471 | 0.976 |
| isoleucine tRNA synthetase | ileS | 938 | 887 | 1.0745 | 0.941 | 0.8719 | 1.0336 | 0.9362 | 0.701 | 0.949 | 1.1488 |
| acetolactate synthase I, valine-sensitive, large subunit | ilvB | 562 | 973 | 0.9534 | 1.3574 | 0.8955 | 1.0966 | 1.0696 | 0.4989 | 1.0406 | 1.0607 |
| ketol-acid reductoisomerase | ilvC | 491 | 82 | 1.148 | 1.0199 | 1.0455 | 1.1005 | 0.7994 | 0.6135 | 0.841 | 1.1051 |
| dihydroxy-acid dehydratase | ilvD | 616 | 748 | 0.9203 | 1.0038 | 0.9293 | 1.0229 | 1.1628 | 0.5908 | 0.9962 | 1.0281 |
| branched-chain amino acid aminotransferase | ilvE | 309 | 870 | 0.9867 | 1.3957 | 1.0645 | 0.8923 | 0.9571 | 0.666 | 1.0679 | 1.0535 |
| acetohydroxy acid synthase II | ilvG | 548 | 978 | 0.883 | 1.3038 | 0.8552 | 1.1984 | 0.9626 | 0.467 | 1.1167 | 1.1866 |
| acetolactate synthase III, valine sensitive, large subunit | ilvI | 604 | 977 | 0.9234 | 1.5065 | 0.8234 | 1.1349 | 1.0588 | 0.492 | 1.0615 | 1.1378 |
| 2-amino-3-ketobutyrate coenzyme A ligase | kbl | 398 | 930 | 0.9646 | 1.2536 | 0.9466 | 1.0884 | 1.0955 | 0.5944 | 0.9231 | 1.0158 |
| ketodeoxygluconokinase | kdgK | 382 | 139 | 0.9747 | 1.2452 | 0.8146 | 1.0056 | 0.9318 | 0.6435 | 1.2917 | 1.0688 |
| 3-isopropylmalate dehydrogenase | leuB | 364 | 931 | 0.928 | 1.4985 | 0.8041 | 1.0005 | 1.0659 | 0.6695 | 1.4396 | 1.0398 |
| 3-isopropylmalate isomerase (dehydratase) subunit | leuC | 466 | 837 | 0.9834 | 0.6907 | 0.9191 | 0.9776 | 1.0045 | 0.6476 | 0.8819 | 1.1614 |
| leucine tRNA synthetase | leuS | 860 | 734 | 1.0645 | 1.3085 | 0.9117 | 1.0394 | 1.0396 | 0.6938 | 0.9136 | 1.1149 |
| dihydrolipoamide dehydrogenase | lpdA | 474 | 988 | 0.9461 | 0.9262 | 0.9912 | 0.9507 | 1.2508 | 0.5798 | 1.134 | 1.055 |
| L-allo-threonine aldolase, PLP-dependent | ltaE | 333 | 251 | 0.9171 | 1.1414 | 0.8137 | 1.0741 | 1.1848 | 0.5945 | 0.6622 | 1.2072 |
| diaminopimelate decarboxylase | lysA | 420 | 655 | 1.0012 | 1.0652 | 0.9365 | 0.9903 | 1.1447 | 0.5991 | 1.1094 | 0.0971 |
| aspartate kinase III | lysC | 449 | 638 | 0.9162 | 1.334 | 0.9446 | 1.024 | 0.927 | 0.6609 | 1.0831 | 1.041 |
| lysine tRNA synthetase, constitutive | lysS | 505 | 599 | 1.0967 | | 0.9387 | 0.8789 | 0.7589 | 0.6403 | 1.1851 | 1.0543 |
| lysine tRNA synthetase, inducible; heat shock protein | lysU | 505 | 600 | 1.1073 | | 0.9195 | 0.8928 | 0.7742 | 0.6238 | 1.1614 | 1.058 |
| bifunctional: PLP-dependent beta-cystathionase; repressor of maltose regulon through interaction with MalT | malY | 390 | 680 | 0.9756 | 1.1464 | 0.862 | 1.0142 | 1.0479 | 0.8267 | 1.0618 | 1.0298 |
| malate dehydrogenase | mdh | 312 | 752 | 0.9523 | 1.241 | 0.9228 | 1.0305 | 1.0895 | 0.6687 | 0.8103 | 1.0773 |
| cystathionine gamma-synthase | metB | 386 | 980 | 1.0537 | 1.5326 | 0.7582 | 1.0171 | 0.9846 | 0.6638 | 1.0579 | 1.1308 |
| cystathionine beta-lyase | metC | 395 | 973 | 1.0238 | 1.3386 | 0.7522 | 0.953 | 1.0396 | 0.6897 | 0.9936 | 1.1639 |
| 5-methyltetrahydropteroyltriglutamate- homocysteine S-methyltransferase | metE | 735 | 286 | 1.2042 | 0.9076 | 1.0071 | 1.0149 | 0.7876 | 0.6386 | 1.0027 | 1.0955 |
| methionine tRNA synthetase | metG | 677 | 438 | 1.0574 | 0.9373 | 0.8596 | 1.1173 | 0.9317 | 0.7243 | 0.8504 | 1.0144 |
| B12-dependent methionine synthase | metH | 1227 | 218 | 0.9923 | 1.0095 | 0.9444 | 1.0747 | 0.9308 | 0.5497 | 1.1302 | 1.0121 |
| methionine adenosyltransferase 1 | metK | 384 | 659 | 0.9106 | 1.2519 | 0.8422 | 1.2629 | 0.8363 | 0.4017 | 1.1095 | 1.0887 |
| aspartokinase II and homoserine dehydrogenase II | metL | 810 | 173 | 0.9473 | 1.3338 | 0.9057 | 1.07 | 0.9936 | 0.669 | 1.0879 | 1.0941 |
| UDP-N-acetylmuramoylalanyl-D-glutamate 2,6-diaminopimelate ligase | murE | 495 | 529 | 0.9527 | 1.2988 | 0.8213 | 1.1179 | 1.0224 | 0.6503 | 1.0332 | 1.1996 |
| L-aspartate oxidase | nadB | 504 | 900 | 0.8748 | 1.3273 | 0.8556 | 0.9621 | 1.0908 | 0.571 | 0.9318 | 1.117 |
| nucleoside diphosphate kinase | ndk | 143 | 659 | 1.0716 | | 1.2933 | 1.8336 | 0.6713 | 0.7817 | 0.9612 | 1.1007 |
| ribonucleoside diphosphate reductase 1, alpha subunit | nrdA | 761 | 427 | 0.9794 | 0.8124 | 0.9333 | 0.9506 | 1.0618 | 0.7038 | 1.1882 | 0.9954 |
| anaerobic ribonucleoside triphosphate reductase | nrdD | 712 | 194 | 0.997 | 0.7792 | 0.9311 | 1.0274 | 0.9492 | 0.642 | 1.0255 | 1.0749 |
| ribonucleoside-diphosphate reductase 2, alpha subunit | nrdE | 714 | 575 | 0.9649 | 0.6749 | 0.9251 | 1.0369 | 0.9576 | 0.7076 | 1.169 | 0.9907 |
| NADH dehydrogenase I chain C, D | nuoC,nuoD | 600 | 130 | 1.1411 | 1.3164 | 0.839 | 0.8295 | 1.1475 | 0.6624 | 0.9327 | 1.0949 |
| NADH dehydrogenase I chain F | nuoF | 445 | 464 | 1.0354 | 0.6875 | 1.1295 | 0.8764 | 1.0356 | 0.4962 | 1.3363 | 1.1613 |
| NADH dehydrogenase I chain L | nuoL | 613 | 332 | 0.9029 | 1.4474 | 0.9005 | 1.2343 | 0.9481 | 0.7792 | 0.8565 | 1.2056 |
| NADH dehydrogenase I chain M | nuoM | 509 | 872 | 0.9508 | 1.5042 | 0.9181 | 0.9761 | 0.9558 | 0.8192 | 0.7363 | 1.1354 |

Figure 12D

| name | gene | aa | sample | A | C | D | E | F | G | H | I |
|---|---|---|---|---|---|---|---|---|---|---|---|
| NADH dehydrogenase I chain N | nuoN | 425 | 905 | 1.0328 | | 1.162 | 0.9384 | 0.9823 | 0.8434 | 0.9225 | 1.192 |
| phosphoenolpyruvate carboxykinase | pckA | 540 | 212 | 1.1038 | 0.9449 | 1.1192 | 1.019 | 0.7315 | 0.5561 | 1.0837 | 1.0315 |
| aminoacyl-histidine dipeptidase (peptidase D) | pepD | 485 | 127 | 1.0074 | 0.915 | 1.0296 | 1.0098 | 1.23081 | 0.567 | 0.8662 | 1.0309 |
| 6-phosphofructokinase I | pfkA | 320 | 459 | 0.9919 | 1.3758 | 0.8699 | 1.0341 | 1.2703 | 0.459 | 1.1212 | 1.0496 |
| Glucose 6-phosphate isomerase | pgi | 549 | 509 | 1.0935 | | 1.0728 | 1.091 | 0.7799 | 0.4854 | 0.8761 | 0.8689 |
| phosphoglycerate kinase | pgk | 387 | 674 | 0.9596 | 1.5581 | 0.8998 | 1.116 | 0.869 | 0.4418 | 1.0006 | 1.1474 |
| phosphoglucomutase | pgm | 546 | 569 | 0.999 | 1.2903 | 0.8126 | 0.9331 | 1.0362 | 0.6751 | 1.1034 | 1.0695 |
| phenylalanine tRNA synthetase, beta-subunit | pheT | 795 | 455 | 1.0359 | 0.989 | 0.9299 | 0.9923 | 0.9815 | 0.5999 | 1.092 | 1.0723 |
| polynucleotide phosphorylase | pnp | 734 | 401 | 0.9894 | | 0.9979 | 1.0992 | 0.8066 | 0.591 | 0.91 | 0.9521 |
| DNA polymerase I, 3' --> 5' polymerase, 5' --> 3' and 3' --> 5' exonuclease | polA | 928 | 414 | 0.9652 | | 0.8905 | 1.0457 | 0.8996 | 0.706 | 1.0798 | 1.0616 |
| DNA polymerase II | polB | 783 | 240 | 1.0298 | 1.2564 | 0.8481 | 0.9587 | 1.0441 | 0.6688 | 1.1878 | 1.0105 |
| proline tRNA synthetase | proS | 572 | 343 | 1.045 | | 0.9826 | 0.8219 | 0.9527 | 0.4893 | 0.897 | 1.1504 |
| phosphoribosylpyrophosphate synthetase | prsA | 315 | 664 | 0.8353 | 1.3942 | 0.7488 | 1.1182 | 0.8 | 0.7549 | 1.0067 | 1.0701 |
| adenylosuccinate synthetase | purA | 432 | 486 | 1.1895 | 1.463 | 0.951 | 0.9669 | 1.3344 | 0.3861 | 0.9318 | 1.1803 |
| adenylosuccinate lyase | purB | 456 | 268 | 0.9654 | 1.3551 | 0.9311 | 0.9733 | 1.073 | 0.7461 | 0.9265 | 1.1262 |
| phosphoribosylaminoimidazole-succinocarboxamide synthase | purC | 237 | 343 | 1.0915 | | 0.817 | 0.9474 | 1.031 | 0.6118 | | 1.336 |
| phosphoribosylglycinamide synthetase | purD | 429 | 478 | 0.9321 | 1.6438 | 1.0304 | 1.034 | 0.8436 | 0.4786 | 1.2289 | 1.115 |
| phosphoribosylaminoimidazole carboxylase | purE | 169 | 401 | 0.7468 | | 1.0253 | 1.6952 | 1.8301 | 0.5021 | 1.1803 | 0.9975 |
| amidophosphoribosyltransferase | purF | 505 | 425 | 0.9725 | 1.13 | 0.9006 | 1.1543 | 1.0208 | 0.5664 | 1.1034 | 1.0561 |
| bifunctional phosphoribosylaminoimidazolecarboxamide formyltransferase/IMP cyclohydrolase | purH | 529 | 413 | 0.9346 | 1.371 | 0.9458 | 1.1777 | 0.705 | 0.6141 | 0.6876 | 1.0146 |
| phosphoribosylaminoimidazole carboxylase | purK | 355 | 450 | 1.0533 | 1.3455 | 1.0795 | 0.8961 | 0.985 | 0.6209 | 0.7028 | 1.1066 |
| phosphoribosylformyl-glycineamide synthetase | purL | 1295 | 224 | 1.0285 | 0.8572 | 1.0188 | 1.0009 | 0.9495 | 0.5587 | 1.0378 | 1.1197 |
| phosphoribosylformylglycinamidine cyclo-ligase | purM | 345 | 463 | 1.1265 | 1.0564 | 0.9136 | 1.2357 | 0.7996 | 0.4861 | 1.105 | 1.1877 |
| phosphoribosylglycinamide formyltransferase | purN | 212 | 142 | 1.0588 | | 0.916 | 1.2145 | 1.0293 | 0.5489 | 0.8148 | 1.0391 |
| multifunctional: proline dehydrogenase (in membrane); pyrroline-5-carboxylate dehydrogenase (in membrane); transcriptional repressor of proline synthesis (in cytoplasm) | putA | 1320 | 99 | 0.9049 | 0.8815 | 1.126 | 1.0221 | 0.8606 | 0.5353 | 1.1763 | 0.9973 |
| pyruvate kinase | pykA | 480 | 636 | 0.9412 | | 0.7561 | 0.9575 | 1.1412 | 0.6328 | 1.1549 | 1.0307 |
| pyruvate kinase | pykF | 470 | 667 | 1.0177 | | 0.7623 | 1.0209 | 1.1237 | 0.5668 | 1.2376 | 0.9949 |
| aspartate carbamoyltransferase, catalytic subunit | pyrB | 311 | 901 | 0.9964 | | 0.8875 | 0.9169 | 0.9182 | 0.822 | 0.9364 | 1.1708 |
| dihydro-orotase | pyrC | 348 | 190 | 1.0258 | 0.9005 | 1.1087 | 1.0992 | 0.9823 | 0.6883 | 0.7597 | 1.144 |
| dihydro-orotate dehydrogenase | pyrD | 336 | 476 | 1.0548 | 1.4572 | 1.0773 | 1.1169 | 1.0923 | 0.4985 | 1.3061 | 1.0016 |
| orotate phosphoribosyltransferase | pyrE | 213 | 307 | 1.0376 | 1.387 | 0.8563 | 1.0003 | 0.7751 | 0.5513 | 1.1709 | 1.1634 |
| orotidine 5'-phosphate decarboxylase | pyrF | 245 | 338 | 1.0162 | 1.1651 | 0.8324 | 1.2147 | 1.0459 | 0.5188 | 1.0012 | 1.1045 |
| CTP synthetase | pyrG | 545 | 490 | 1.1955 | 1.1137 | 1.0255 | 0.9037 | 0.9121 | 0.5188 | 0.7093 | 1.0669 |
| ribokinase | rbsK | 309 | 930 | 0.8591 | 1.3589 | 0.8533 | 0.9558 | 1.0356 | 0.6273 | 1.2879 | 1.1189 |
| ribulose-phosphate 3-epimerase | rpe | 225 | 485 | 0.9355 | 1.6715 | 0.8076 | 1.2642 | 0.873 | 0.4536 | 0.5364 | 1.1246 |
| ribosephosphate isomerase | rpiA | 219 | 346 | 1.0261 | 1.4593 | 0.7862 | 1.1105 | 0.992 | 0.5244 | 1.5427 | 0.9398 |
| RNA polymerase, alpha subunit | rpoA | 329 | 520 | 1.0417 | 1.0666 | 1.0187 | 0.9547 | 1.2374 | 0.5683 | 1.1732 | 1.0553 |
| RNA polymerase, beta subunit | rpoB | 1342 | 294 | 1.1105 | 1.1142 | 0.9345 | 1.0418 | 0.8195 | 0.4446 | 1.0248 | 1.1543 |
| RNA polymerase, beta prime subunit | rpoC | 1407 | 275 | 1.0642 | 0.5492 | 1.0162 | 1.1117 | 0.8257 | 0.4737 | 1.0479 | 1.1298 |
| L-serine deaminase | sdaA | 454 | 285 | 0.9001 | 0.6545 | 1.1715 | 1.0672 | 0.8978 | 0.5038 | 1.1488 | 1.2004 |
| L-serine deaminase 2 | sdaB | 455 | 285 | 0.8623 | 0.8621 | 1.1576 | 1.0836 | 0.9339 | 0.5275 | 1.1525 | 1.1605 |
| succinate dehydrogenase, catalytic and NAD/flavoprotein subunit | sdhA | 588 | 807 | 0.9473 | 1.3677 | 0.8807 | 0.9777 | 1.0079 | 0.5418 | 0.9048 | 1.1848 |
| 3-phosphoserine phosphatase | serB | 322 | 44 | 0.8717 | 0.9188 | 0.8849 | 1.2473 | 1.2777 | 0.4802 | 1.4325 | 1.0071 |

Figure 12E

| name | gene | aa | sample | A | C | D | E | F | G | H | I |
|---|---|---|---|---|---|---|---|---|---|---|---|
| serine tRNA synthetase; also charges selenocystein tRNA with serine | serS | 430 | 582 | 1.1218 | 1.0075 | 0.9424 | 0.9626 | 0.82 | 0.7017 | 0.9795 | 1.2181 |
| arginine decarboxylase, PLP-binding, biosynthetic | speA | 658 | 183 | 1.1065 | 0.9673 | 0.9367 | 0.9808 | 0.9292 | 0.544 | 1.036 | 1.1936 |
| ornithine decarboxylase isozyme | speC | 731 | 210 | 0.9949 | 1.2778 | 0.9529 | 1.1264 | 0.8308 | 0.5839 | 0.947 | 1.1398 |
| ornithine decarboxylase isozyme, inducible | speF | 732 | 221 | 0.967 | 1.2597 | 0.9837 | 1.0641 | 0.832 | 0.5932 | 0.9135 | 1.1559 |
| 2-oxoglutarate decarboxylase | sucA | 933 | 384 | 1.0913 | 1.0071 | 1.0091 | 0.9238 | 1.0002 | 0.6617 | 0.831 | 1.1692 |
| succinyl-CoA synthetase, beta subunit | sucB | 405 | 948 | 1.0157 | | 0.8714 | 1.0081 | 0.9212 | 0.6936 | 1.0746 | 1.0382 |
| succinyl-CoA synthetase, alpha subunit | sucC | 388 | 461 | 1.022 | 1.1092 | 0.8629 | 1.0212 | 1.0508 | 0.5271 | 1.3394 | 1.0537 |
| transaldolase | sucD | 289 | 518 | 1.0198 | 1.2982 | 1.0087 | 1.0291 | 1.1612 | 0.422 | 1.0674 | 0.9131 |
| L-threonine 3-dehydrogenase | talA | 316 | 235 | 0.9281 | 0.7735 | 0.8632 | 1.1641 | 0.8075 | 0.66 | 1.7993 | 0.937 |
| bifunctional aspartokinase I/homeserine dehydrogenase I | tdh | 341 | 272 | 0.9842 | | 0.8681 | 1.0278 | 1.1456 | 0.5607 | 0.9236 | 1.1104 |
| homoserine kinase | thrA | 820 | 173 | 0.9638 | 1.2972 | 0.9417 | 1.0667 | 0.8996 | 0.5798 | 1.2157 | 1.1036 |
| threonine synthase | thrB | 310 | 369 | 0.9339 | 1.224 | 0.8567 | 1.044 | 1.0663 | 0.6911 | 1.1168 | 1.2459 |
| threonine tRNA synthetase | thrC | 428 | 337 | 0.93 | 1.2038 | 0.9596 | 1.1734 | 0.7971 | 0.7282 | 1.0466 | 1.0985 |
| transketolase | thrS | 642 | 541 | 1.0815 | 1.0738 | 0.9476 | 0.9472 | 0.951 | 0.6061 | 0.8779 | 1.0484 |
| transketolase | tktA | 663 | 616 | 1.0148 | 1.4499 | 0.9609 | 1.028 | 0.9632 | 0.5321 | 0.8615 | 1.1577 |
| triosephosphate isomerase | tktB | 667 | 620 | 0.9958 | 1.4221 | 0.9363 | 1.0517 | 0.9916 | 0.6004 | 0.991 | 1.1315 |
| tryptophan synthase, beta protein | tpiA | 255 | 623 | 1.0092 | 1.1444 | 1.1479 | 0.9318 | 1.2228 | 0.4922 | 1.1854 | 1.0439 |
| bifunctional indole-3-glycerol phosphate synthase/phosphoribosylanthranilate isomerase | trpB | 397 | 687 | 0.8866 | 1.1589 | 0.9849 | 1.0141 | 1.0436 | 0.4268 | 1.0537 | 1.1639 |
| | trpC | 453 | 132 | 0.9643 | 0.9628 | 0.9345 | 1.1308 | 0.8197 | 0.5666 | 1.4799 | 1.0263 |
| anthranilate synthase component I | trpE | 520 | 214 | 0.9645 | 1.1431 | 0.8927 | 0.982 | 0.9342 | 0.6319 | 1.1586 | 1.0821 |
| thioredoxin reductase | trxB | 321 | 879 | 0.7713 | | 1.0638 | 1.077 | 0.9612 | 0.5204 | 1.2116 | 1.0459 |
| copper amine oxidase (tyramine oxidase) | tynA | 757 | 117 | 1.1525 | | 0.8901 | 1.0829 | 0.9295 | 0.7246 | 0.947 | 1.0071 |
| bifunctional: chorismate mutase T (N-terminal); prephenate dehydrogenase (C-terminal) | tyrA | 373 | 71 | 1.1999 | 1.2121 | 0.8726 | 1.1757 | 0.7236 | 0.5722 | 1.0758 | 0.9216 |
| tyrosine aminotransferase, tyrosine repressible | tyrB | 397 | 67 | 1.2033 | 1.2059 | 0.876 | 1.1807 | 0.7246 | 0.5668 | 1.0629 | 0.9196 |
| tyrosine tRNA synthetase | tyrS | 424 | 995 | 1.1357 | 1.4864 | 0.8576 | 1.0639 | 0.9525 | 0.6301 | 0.885 | 1.1293 |
| uridine/cytidine kinase | udk | 231 | 316 | 0.9613 | 1.4655 | 0.7443 | 1.0771 | 1.1271 | 0.5674 | 0.9311 | 0.8923 |
| uridine phosphorylase | udp | 253 | 292 | 0.8936 | 1.3364 | 0.9035 | 0.8362 | 0.8975 | 0.6229 | 0.8512 | 1.0651 |
| UDP-sugar hydrolase (5'-nucleotidase) | ushA | 550 | 546 | 0.9688 | 1.2694 | 0.9197 | 1.033 | 0.9271 | 0.6786 | 0.9245 | 0.9797 |
| valine tRNA synthetase | valS | 951 | 809 | 1.0813 | 1.1952 | 0.8653 | 1.0009 | 0.8831 | 0.7462 | 1.004 | 1.0219 |
| bifunctional fatty acid oxidation complex protein : putative enoyl-CoA hydratase/isomerase (N-terminal); putative NAD(P)-binding dehydrogenase (C-terminal) | yfcX | 714 | 450 | 1.0089 | 1.1531 | 0.9585 | 0.9959 | 0.7533 | 0.5921 | 1.2498 | 1.0167 |
| glucose-6-phosphate 1-dehydrogenase | zwf | 491 | 522 | 1.1375 | 1.3847 | 1.0044 | 0.9745 | 0.8617 | 0.6112 | 1.1787 | 1.1109 |
| name | gene | aa | sample | K | L | M | N | P | Q | R | S |
| long-chain-fatty-acid-[acyl-carrier-protein] ligase/acyl-[acyl-carrier-protein]-phospholipid O-acyltransferase | aas | 719 | 70 | 0.0192 | 0.9016 | 1.1737 | 1.1431 | 0.6646 | 1.4207 | 0.9998 | 1.1355 |
| acetyl CoA carboxylase, biotin carboxylase subunit | accC | 449 | 995 | 1.2093 | 1.1857 | 1.1631 | 1.1552 | 0.6479 | 1.107 | 0.885 | 1.3071 |
| pyruvate dehydrogenase | aceE | 887 | 205 | 1.383 | 0.8862 | 1.3444 | 1.1427 | 0.6593 | 1.2204 | 0.9311 | 1.1939 |
| dihydrolipoamide acetyltransferase | aceF | 630 | 234 | 1.0044 | 0.9807 | 1.2603 | 1.1366 | 0.6868 | 1.3516 | 0.8512 | 1.2275 |
| aconitate hydrase A | acnA | 891 | 500 | 1.2869 | 0.8341 | 1.1672 | 0.9848 | 0.757 | 1.4677 | 0.9245 | 1.037 |
| aconitate hydrase B | acnB | 865 | 150 | 1.4348 | 0.7554 | 1.036 | 1.2185 | 0.6582 | 1.71 | 0.763 | 1.061 |
| acetyl-CoA synthetase | acs | 652 | 906 | 1.1161 | 0.9628 | 1.2046 | 1.2208 | 0.7402 | 1.3721 | 0.8891 | 1.0797 |
| adenosine deaminase | add | 333 | 289 | 1.2559 | 0.8754 | 1.3188 | 1.0156 | 0.7498 | 1.2606 | 1.0244 | 1.1272 |
| Mn-dependent adenine deaminase (cryptic) | ade | 588 | 98 | 1.239 | 0.9753 | 0.9887 | 1.1058 | 0.7539 | 1.3412 | 1.1485 | 1.1043 |
| arginine decarboxylase; inducible by acid, catabolic | adiA | 756 | 197 | 1.0731 | 0.9431 | 1.1695 | 0.0441 | 0.576 | 1.3624 | 1.1317 | 1.1098 |
| adenylate kinase | adk | 214 | 788 | 1.0814 | 0.9506 | 1.2483 | 1.3893 | 0.8076 | 1.1427 | 0.6387 | |
| alanyl-tRNA synthetase | alaS | 876 | 539 | 1.209 | 0.8521 | 1.096 | 1.1254 | 0.9809 | 1.2146 | 0.842 | 1.2332 |
| aldehyde dehydrogenase | aldH | 495 | 999 | 1.0344 | 0.9212 | 1.563 | 0.9531 | 0.6366 | 1.4579 | 1.0791 | 1.2372 |

Figure 12F

| name | gene | aa | sample | A | C | D | E | F | G | H | I |
|---|---|---|---|---|---|---|---|---|---|---|---|
| alanine racemase | alr | 356 | 518 | 1.1613 | 0.858 | 1.0169 | 1.0735 | 0.8778 | 1.3189 | 0.977 | 1.1321 |
| cytoplasmic asparaginase I | ansA | 388 | 311 | 1.0261 | 0.9265 | 1.0363 | 1.0253 | 0.8866 | 1.2221 | 1.2544 | 1.0851 |
| periplasmic L-asparaginase II | ansB | 348 | 328 | 1.0927 | 0.9117 | 1.0966 | 1.0413 | 0.8716 | 1.2732 | 1.0691 | 1.1347 |
| membrane-bound ATP synthasebeta-subunit | aptD | 460 | 1000 | 1.5548 | 0.7953 | 1.3944 | 1.8248 | 0.3457 | 1.4654 | 1.3756 | 0.8799 |
| acetylornithine delta-aminotransferase | argD | 406 | 978 | 1.1362 | 0.9144 | 1.4492 | 1.121 | 0.7427 | 1.1314 | 0.9573 | 1.2198 |
| argininosuccinate synthetase | argG | 447 | 445 | 1.1241 | 0.9458 | 1.2944 | 0.8494 | 1.0045 | 1.1794 | 0.9769 | 0.9657 |
| argininosuccinate lyase | argH | 457 | 585 | 1.0587 | 0.8359 | 1.1558 | 1.0766 | 0.7848 | 1.219 | 0.9822 | 1.0919 |
| arginine tRNA synthetase | argS | 577 | 607 | 1.0712 | 0.866 | 1.1294 | 1.0457 | 0.9758 | 1.1308 | 0.9335 | 1.1726 |
| 3-enolpyruvylshikimate-5-phosphate synthetase | aroA | 427 | 729 | 1.1483 | 0.8479 | 0.9998 | 1.1539 | 0.894 | | 0.9654 | 1.0664 |
| 3-dehydroquinate synthase | aroB | 362 | 449 | 0.8329 | 0.9267 | 1.2373 | 1.0874 | 0.889 | 1.2943 | 1.014 | 1.3013 |
| chorismate synthase | aroC | 361 | 467 | 1.1752 | 1.1094 | 1.4048 | 1.0612 | 0.8784 | 1.3942 | 0.8409 | 1.0092 |
| 3-deoxy-D-arabinoheptulosonate-7-phosphate synthase (DAHP synthetase), tyrosine-repressible | aroF | 356 | 420 | 1.1666 | 0.9105 | 1.2148 | 1.1091 | 0.6499 | 1.3003 | 0.8681 | 1.0658 |
| 3-deoxy-D-arabinoheptulosonate-7-phosphate synthase (DAHP synthetase), phenylalanine repressible) | aroG | 350 | 419 | 1.3217 | 0.7818 | 1.2583 | 1.2847 | 0.6884 | 1.2468 | 0.7511 | 1.0824 |
| 3-deoxy-D-arabinoheptulosonate-7-phosphate synthase (DAHP synthetase), tryptophan-repressible | aroH | 348 | 419 | 1.1588 | 0.794 | 1.2886 | 1.1352 | 0.7605 | 1.1656 | 0.9302 | 1.0829 |
| asparagine synthetase B | asnB | 554 | 276 | 1.1051 | 0.859 | 1.1453 | 1.1384 | 0.773 | 1.3311 | 0.909 | 0.9773 |
| asparagine tRNA synthetase | asnS | 466 | 430 | 1.1818 | 0.9371 | 1.2044 | 1.2504 | 0.7806 | 1.1751 | 0.8184 | 1.1495 |
| aspartate ammonia-lyase (aspartase) | aspA | 493 | 599 | 1.0266 | 0.993 | 1.3098 | 0.7631 | 0.5908 | 1.1906 | 1.0749 | 1.1135 |
| aspartate aminotransferase | aspC | 396 | 496 | 1.2253 | 0.8903 | 1.1018 | 1.1415 | 0.8931 | 1.0277 | 0.8807 | 1.1729 |
| aspartate tRNA synthetase | aspS | 590 | 452 | 1.1833 | 0.9239 | 1.2731 | 1.4118 | 0.5733 | 1.0692 | 0.676 | 1.3355 |
| acetyl-CoA acetyltransferase | atoB | 394 | 996 | 1.3433 | 1.005 | 1.134 | 0.9646 | 0.8092 | 1.2995 | 0.9626 | 1.2807 |
| membrane-bound ATP synthase, F1 sector, alpha-subunit | atpA | 513 | 959 | 1.298 | 0.8122 | 1.4448 | 1.436 | 0.6397 | 0.8224 | 0.9375 | 1.2021 |
| valine--pyruvate transaminase | avtA | 417 | 314 | 1.063 | 0.9436 | 1.2309 | 1.053 | 0.7112 | 1.1847 | 1.0237 | 1.0877 |
| 6-phospho-beta-glucosidase A | bglA | 479 | 868 | 1.0731 | 1.0313 | 1.3136 | 1.0565 | 0.7276 | 1.2136 | 0.9486 | 1.1284 |
| carbamoyl phosphate synthetase, Small subunit | carA | 382 | 649 | 1.1911 | 0.9109 | 1.2903 | 0.9753 | 0.6066 | 1.1114 | 0.0815 | 1.2516 |
| carbamoyl phosphate synthase, Large subunit | carB | 1073 | 598 | 1.1805 | 0.0311 | 1.1997 | 1.0581 | 0.7598 | 1.1998 | 0.9798 | 1.0892 |
| phospho-beta-glucosidase | celF | 450 | 165 | 1.1219 | 0.9221 | 1.2132 | 0.9417 | 0.7189 | 1.2467 | 1.0064 | 1.2098 |
| citrate lyase beta chain | citE | 307 | 297 | 1.1833 | 1.0052 | 1.1955 | 1.1697 | 0.8092 | 1.2117 | 0.9165 | 1.1822 |
| cytidine monophosphate (CMP) kinase | cmk | 227 | 361 | 0.9451 | 0.9172 | 1.5461 | 0.7215 | 0.7984 | 0.6486 | 1.2124 | 1.1927 |
| 2',3'-cyclic nucleotide 2'-phosphodiesterase/3'-nucleotidase bifunctional periplasmic precursor protein | cpdB | 647 | 368 | 1.0616 | 0.9332 | 1.2968 | 0.9049 | 0.8094 | 1.1252 | 1.0732 | 1.1694 |
| adenylate cyclase | cyaA | 848 | 80 | 1.0433 | 0.7144 | 1.3358 | 1.158 | 0.8269 | 1.1371 | 0.9452 | 1.1335 |
| cysteine tRNA synthetase | cysS | 461 | 547 | 1.0576 | 0.8632 | 1.2361 | 1.079 | 0.8374 | 1.4293 | 0.8766 | 1.0818 |
| succinyl-diaminopimelate desuccinylase | dapE | 375 | 556 | 1.1508 | 0.9691 | 1.1978 | 1.0308 | 0.7329 | 1.2531 | 1.0022 | 1.1585 |
| thymidine phosphorylase | deoA | 440 | 214 | 1.0742 | 0.8934 | 1.0649 | 1.374 | 0.9109 | 1.1784 | 1.1516 | 1.1431 |
| phosphopentomutase | deoB | 407 | 179 | 1.303 | 0.8902 | 1.4706 | 1.2046 | 0.9113 | 1.4507 | 0.7785 | 1.2238 |
| deoxyribose-phosphate aldolase | deoC | 259 | 243 | 0.9962 | 0.9149 | 1.2418 | 1.3081 | 0.925 | 1.5053 | 1.1889 | 1.1272 |
| purine-nucleoside phosphorylase | deoD | 306 | 307 | 1.1943 | 1.114 | 1.0476 | 1.3757 | | | 0.993 | 1.0107 |
| deoxyguanosinetriphosphate triphosphohydrolase | dgt | 505 | 176 | 1.0021 | 0.8874 | 1.0852 | 1.0017 | 0.9613 | 1.038 | 0.8478 | 1.1153 |
| DNA polymerase IV | dinB | 351 | 512 | 0.9407 | 0.9145 | 1.1651 | 1.2601 | 0.7679 | 1.3673 | 1.0812 | 1.04 |
| DNA polymerase III, alpha subunit | dnaE | 1160 | 519 | 1.1265 | 0.8336 | 1.1386 | 1.1873 | 0.8131 | 1.1883 | 0.9718 | 1.2027 |
| DNA polymerase III, epsilon subunit | dnaQ | 243 | 206 | 1.3688 | 0.8841 | 1.4482 | 1.0565 | 0.8753 | 1.4518 | 0.9275 | 1.3927 |
| DNA polymerase III, tau and gamma subunits; DNA elongation factor III | dnaX | 643 | 133 | 1.0011 | 0.781 | 1.1768 | 1.1819 | 0.7839 | 1.1606 | 0.9263 | 1.213 |
| D-serine deaminase (dehydratase) | dsdA | 442 | 79 | 1.29 | 0.8289 | 1.2231 | 1.2331 | 0.6417 | 1.7144 | 1.2275 | 1.0189 |
| 2-keto-3-deoxygluconate 6-phosphate aldolase | eda | 213 | 250 | 1.2122 | 1.0988 | 1.42 | 1.2797 | 0.6119 | 1.3457 | 1.2218 | 1.1903 |
| 6-phosphogluconate dehydratase | edd | 603 | 557 | 1.1211 | 0.9523 | 1.1506 | 1.081 | 0.7458 | 1.3411 | 1.0099 | 0.9972 |
| enolase | eno | 432 | 746 | 1.1006 | 0.9875 | 1.3481 | 0.8175 | 0.74724 | 1.0755 | 0.8366 | 1.044 |
| 3-oxoacyl-[acyl-carrier-protein] synthase I | fabB | 406 | 956 | 1.1876 | 1.129 | 1.1543 | 0.9368 | 1.0467 | 1.4175 | 0.9481 | 1.0306 |

Figure 12G

| name | gene | aa | sample | A | C | D | E | F | G | H | I |
|---|---|---|---|---|---|---|---|---|---|---|---|
| 3-oxoacyl-[acyl-carrier-protein] synthase II | fabF | 413 | 962 | 1.2176 | 1.0492 | 1.245 | 1.0596 | 0.7937 | 1.473 | 0.9595 | 1.0756 |
| 3-ketoacyl-CoA thiolase; (thiolase I, acetyl-CoA transferase), in complex with FadB catalyzes | fadA | 387 | 997 | 1.3858 | 1.0034 | 1.1189 | 1.0469 | 0.6712 | 1.2663 | 0.881 | 1.1065 |
| 4-enzyme protein: 3-hydroxyacyl-CoA dehydrogenase; 3-hydroxybutyryl-CoA epimerase; delta(3)-cis-delta(2)-trans-enoyl-CoA isomerase; enoyl-CoA hydratase | fadB | 729 | 418 | 1.0554 | 0.9747 | 1.1377 | 1.0953 | 0.7067 | 1.3447 | 1.0313 | 1.2361 |
| acyl-CoA synthase | fadD | 561 | 903 | 1.0022 | 0.9648 | 1.1981 | 1.0352 | 0.7591 | 1.2625 | 1.0873 | 1.222 |
| fructose-bisphosphate aldolase, class II | fbaA | 359 | 367 | 0.8543 | 1.0304 | 1.101 | 0.9071 | 0.7381 | 1.164 | 1.2173 | 1.0081 |
| fructose-1,6-bisphosphatase | fbp | 332 | 330 | 1.2356 | 0.8091 | 1.3863 | 1.0044 | 0.7715 | 1.0179 | 1.0773 | 1.0984 |
| methionyl-tRNA formyltransferase | fmt | 315 | 569 | 1.105 | 0.8401 | 1.1457 | 1.2909 | 0.6971 | 1.1515 | 0.9627 | 1.2632 |
| fumarate reductase, anaerobic, catalytic and NAD/flavoprotein subunit | frdA | 602 | 974 | 1.2309 | 0.8894 | 1.1674 | 1.1069 | 0.8321 | 1.2899 | 0.8564 | 1.1453 |
| fumarase A (fumarate hydratase class I) | fumA | 548 | 176 | 1.0647 | 0.9501 | 1.153 | 1.0108 | 0.6993 | 1.1018 | 1.0369 | 1.1565 |
| fumarase C (fumarate hydratase Class II) | fumC | 467 | 594 | 1.1214 | 0.919 | 1.1439 | 0.7528 | 0.5629 | 1.1729 | 1.1211 | 1.0918 |
| 4-aminobutyrate aminotransferase | gabT | 426 | 968 | 1.1556 | 0.963 | 1.3434 | 1.2113 | 0.7015 | 1.068 | 0.8764 | 1.3707 |
| glutamate decarboxylase A, isozyme, PLP-dependent | gadA | 466 | 152 | 1.0395 | 0.9073 | 1.1992 | 1.0751 | 0.8346 | 1.2407 | 0.9392 | 1.0567 |
| glutamate decarboxylase isozyme | gadB | 466 | 143 | 1.037 | 0.9108 | 1.2031 | 1.0714 | 0.8345 | 1.2409 | 0.932 | 1.0522 |
| galactose-1-epimerase | galM | 346 | 298 | 1.2704 | 0.8869 | 1.3219 | 0.8433 | 0.7923 | 1.2446 | 0.0728 | 1.2405 |
| glyceraldehyde-3-phosphate dehydrogenase | gapA | 331 | 919 | 1.0087 | 1.1059 | 1.21 | 0.889 | 0.6361 | 1.7274 | 0.87 | 1.112 |
| glycine cleavage complex protein P, glycine decarboxylase, PLP-dependent | gcvP | 957 | 304 | 1.3833 | 0.882 | 1.0089 | 1.0226 | 0.5451 | 1.3289 | 0.9032 | 1.2628 |
| aminomethyltransferase | gcvT | 364 | 714 | 1.1965 | 0.9159 | 1.1028 | 1.1531 | 0.7671 | 1.2419 | 1.0746 | 1.1155 |
| glutamate dehydrogenase | gdhA | 447 | 465 | 0.9672 | 1.0702 | 1.1672 | 0.9605 | 0.5857 | 1.2297 | 0.9564 | 1.1048 |
| glucokinase | glk | 321 | 158 | 1.3263 | 0.8165 | 1.3838 | 1.0059 | 0.8412 | 1.4004 | 1.0609 | 1.1777 |
| glutamine synthetase | glnA | 496 | 605 | 1.0955 | 1.0121 | 1.1408 | 1 | 0.6275 | 1.3115 | 0.868 | 1.0264 |
| glutamine tRNA synthetase | glnS | 554 | 339 | 1.1162 | 0.8924 | 1.1269 | 1.1516 | 0.7516 | 1.427 | 0.7046 | 1.1338 |
| citrate synthase | gltA | 427 | 621 | 1.2211 | 0.909 | 0.9956 | 1.0388 | 0.7017 | 1.3428 | 0.9281 | 1.1726 |
| glutamate synthase, large subunit | gltB | 1517 | 359 | 1.2157 | 0.8926 | 1.207 | 1.0393 | 0.765 | 1.2142 | 1.0082 | 1.0362 |
| glutamate synthase, small subunit | gltD | 472 | 617 | 1.1818 | 0.9397 | 1.3253 | 1.2471 | 0.8011 | 1.3575 | 0.9492 | 1.3309 |
| glutamate tRNA synthetase, catalytic subunit | gltX | 471 | 478 | 1.1639 | 0.9219 | 1.2486 | 1.185 | 0.7922 | 1.2476 | 0.7502 | 1.137 |
| serine hydroxymethyltransferase | glyA | 417 | 716 | 1.0924 | 1.0239 | 1.4638 | 0.9016 | 0.5852 | 1.268 | 1.121 | 1.0766 |
| glycine tRNA synthetase, beta subunit | glyS | 689 | 350 | 1.1097 | 0.7867 | 0.9835 | 1.2283 | 0.7081 | 1.2853 | 0.8195 | 1.3954 |
| guanylate kinase | gmk | 107 | 691 | 1.3199 | 0.8834 | 1.2923 | 1.0387 | 0.6509 | 1.2584 | 0.9001 | 1.0032 |
| 6-phosphogluconate dehydrogenase | gnd | 468 | 473 | 1.2219 | 0.8752 | 1.024 | 1.0809 | 0.728 | 1.3494 | 0.8305 | 1.2903 |
| phosphoglyceromutase 1 | gpmA | 250 | 508 | 1.1394 | 0.8603 | 1.5159 | 0.9538 | 0.7714 | 1.2967 | 0.7863 | 0.9873 |
| bifunctional GMP synthase/glutamine amidotransferase protein | guaA | 525 | 429 | 1.3453 | 0.8703 | 1.1777 | 1.4312 | 0.5574 | 1.1253 | 0.8625 | 1.1064 |
| IMP dehydrogeanse | guaB | 488 | 453 | 1.1267 | 0.6654 | 1.0067 | 1.3433 | 0.5682 | 1.3383 | 1.1472 | 1.1016 |
| GMP reductase | guaC | 347 | 192 | 1.1444 | 1.0003 | 0.9698 | 1.0669 | 0.738 | 1.2537 | 1.1634 | 1.0744 |
| guanine deaminase | guaD | 439 | 351 | 1.1724 | 0.8946 | 1.1944 | 1.1225 | 0.7522 | 1.2212 | 1.0446 | 1.1116 |
| bifunctional: histidinol-phosphatase (N-terminal); imidazoleglycerol-phosphate dehydratase (C-terminal) | hisB | 356 | 104 | 1.2093 | 0.6953 | 0.9482 | 1.3894 | 0.6554 | 1.3346 | 1.1033 | 1.2137 |
| histidinol-phosphate aminotransferase | hisC | 356 | 787 | 1.124 | 0.8612 | 1.2568 | 0.9598 | 0.7647 | 1.2163 | 0.8462 | 1.1436 |
| histidinol dehydrogenase | hisD | 434 | 478 | 1.1964 | 0.8563 | 1.2398 | 1.0986 | 0.683 | 1.1215 | 1.2233 | 1.1986 |
| histidine tRNA synthetase | hisS | 424 | 611 | 1.1593 | 0.8654 | 1.2348 | 1.1966 | 0.8218 | 1.0701 | 0.7777 | 1.3165 |
| isocitrate dehydrogenase | icdA | 416 | 848 | 1.1251 | 1.0209 | 1.0994 | 0.84 | 0.7074 | 1.2269 | 0.8249 | 1.1071 |
| isoleucine tRNA synthetase | ileS | 938 | 887 | 1.0683 | 0.9691 | 1.2051 | 1.0993 | 0.7242 | 1.2269 | 0.9153 | 1.0746 |
| acetolactate synthase I, valine-sensitive, large subunit | ilvB | 562 | 973 | 1.1625 | 1.001 | 1.0793 | 1.0893 | 0.6683 | 1.0767 | 1.0768 | 1.2297 |
| ketol-acid reductoisomerase | ilvC | 491 | 82 | 1.271 | 0.7355 | 0.7487 | 1.0859 | 0.8674 | 1.4395 | 0.9144 | 1.2021 |
| dihydroxy-acid dehydratase | ilvD | 616 | 748 | 1.1578 | 0.9224 | 1.0211 | 1.0958 | 0.7159 | 1.45 | 0.9923 | 1.0704 |
| branched-chain amino acid aminotransferase | ilvE | 309 | 870 | 1.1559 | 0.9711 | 1.3501 | 0.9901 | 0.8195 | 1.3193 | 0.9531 | 1.1362 |

Figure 12H

| name | gene | aa | sample | A | C | D | E | F | G | H | I |
|---|---|---|---|---|---|---|---|---|---|---|---|
| acetohydroxy acid synthase II | ilvG | 548 | 978 | 1.2774 | 0.978 | 1.1205 | 1.2018 | 0.6686 | 1.0821 | 1.0999 | 1.2522 |
| acetolactate synthase III, valine sensitive, large subunit | ilvI | 604 | 977 | 1.2621 | 1.0014 | 0.9897 | 1.1843 | 0.6222 | 1.0822 | 1.1241 | 1.238 |
| 2-amino-3-ketobutyrate coenzyme A ligase | kbl | 398 | 930 | 1.2021 | 0.8347 | 1.222 | 0.923 | 0.8689 | 1.3665 | 0.9378 | 1.101 |
| ketodeoxygluconokinase | kdgK | 382 | 139 | 1.1064 | 0.9536 | 1.082 | 1.0048 | 1.0102 | 1.2467 | 0.9227 | 1.1109 |
| 3-isopropylmalate dehydrogenase | leuB | 364 | 931 | 1.1604 | 0.8772 | 1.2407 | 0.9801 | 0.6247 | 1.4412 | 0.9198 | 1.0963 |
| 3-isopropylmalate isomerase (dehydratase) subunit | leuC | 466 | 837 | 1.1531 | 1.0233 | 1.1226 | 0.998 | 0.8243 | 1.2734 | 0.995 | 1.027 |
| leucine tRNA synthetase | leuS | 860 | 734 | 1.0706 | 0.9315 | 1.1007 | 1.0786 | 0.6171 | 1.1026 | 0.9103 | 1.1246 |
| dihydrolipoamide dehydrogenase | lpdA | 474 | 988 | 1.0696 | 0.9301 | 1.3723 | 1.2182 | 0.6202 | 1.4434 | 1.1026 | 1.2534 |
| L-allo-threonine aldolase, PLP-dependent | ltaE | 333 | 251 | 1.1499 | 0.9164 | 1.1596 | 0.9153 | 0.9971 | 1.3062 | 1.0237 | 1.1535 |
| diaminopimelate decarboxylase | lysA | 420 | 655 | 1.0155 | 0.9081 | 1.1909 | 1.0436 | 0.8376 | 1.272 | 0.9105 | 1.0016 |
| aspartate kinase III | lysC | 449 | 638 | 1.2172 | 0.9063 | 1.2221 | 1.145 | 0.9397 | 1.3205 | 1.0973 | 1.0136 |
| lysine tRNA synthetase, constitutive | lysS | 505 | 599 | 1.2123 | 0.9489 | 1.1903 | 1.1267 | 0.5723 | 1.1799 | 0.7734 | 1.2917 |
| lysine tRNA synthetase, inducible; heat shock protein | lysU | 505 | 600 | 1.1951 | 0.9418 | 1.1915 | 1.1217 | 0.5723 | 1.2128 | 0.7842 | 1.2955 |
| bifunctional: PLP-dependent beta-cystathionase; repressor of maltose regulon through interaction with MalT | malY | 390 | 680 | 1.0724 | 0.9235 | 1.2404 | 1.0434 | 0.7397 | 1.2118 | 1.0422 | 1.0427 |
| malate dehydrogenase | mdh | 312 | 752 | 0.9729 | 0.9145 | 1.2241 | 0.9814 | 0.7992 | 1.2661 | 0.9055 | 1.192 |
| cystathionine gamma-synthase | metB | 386 | 980 | 1.1994 | 0.8855 | 1.0757 | 0.9701 | 0.7907 | 1.2861 | 0.9716 | 1.0518 |
| cystathionine beta-lyase | metC | 395 | 973 | 1.0727 | 0.8466 | 1.3037 | 1.1742 | 0.966 | 1.2854 | 0.9323 | 1.0953 |
| 5-methyltetrahydropteroyltriglutamate- homocysteine S-methyltransferase | metE | 735 | 286 | 1.2869 | 0.8085 | 0.9266 | 1.3178 | 0.6184 | 1.2509 | 0.8847 | 1.1884 |
| methionine tRNA synthetase | metG | 677 | 438 | 1.0479 | 0.8969 | 1.147 | 1.0258 | 0.7594 | 1.3063 | 0.8992 | 1.1224 |
| B12-dependent methionine synthase | metH | 1227 | 218 | 1.23 | 0.8744 | 0.9412 | 1.0555 | 0.6697 | 1.4037 | 1.0891 | 1.1338 |
| methionine adenosyltransferase 1 | metK | 384 | 659 | 1.1916 | 1.1061 | 1.3821 | 1.6557 | 0.6316 | 1.0917 | 0.9337 | 1.1368 |
| aspartokinase II and homoserine dehydrogenase II | metL | 810 | 173 | 1.2131 | 0.893 | 1.3967 | 1.1861 | 0.8438 | 1.251 | 1.0031 | 1.0515 |
| UDP-N-acetylmuramoylalanyl-D-glutamate 2,6-diaminopimelate ligase | murE | 495 | 529 | 1.0928 | 0.9322 | 1.1391 | 0.9388 | 0.9601 | 1.2342 | 0.9841 | 1.1724 |
| L-aspartate oxidase | nadB | 504 | 900 | 1.2523 | 0.898 | 1.2184 | 1.0778 | 0.8976 | 1.2364 | 0.9503 | 1.168 |
| nucleoside diphosphate kinase | ndk | 143 | 659 | 1.0554 | 1.2845 | 1.2077 | 1.1036 | 0.5445 | 1.6989 | 0.902 | 0.9581 |
| ribonucleoside diphosphate reductase 1, alpha subunit | nrdA | 761 | 427 | 1.0445 | 0.8793 | 1.254 | 1.0805 | 0.8126 | 1.1042 | 0.9419 | 1.0232 |
| anaerobic ribonucleoside triphosphate reductase | nrdD | 712 | 194 | 1.1051 | 0.875 | 1.2495 | 0.9701 | 0.7249 | 1.2522 | 0.9288 | 1.2074 |
| ribonucleoside-diphosphate reductase 2, alpha subunit | nrdE | 714 | 575 | 1.0704 | 0.9092 | 1.2135 | 0.9696 | 0.773 | 1.1816 | 0.9988 | 0.9537 |
| NADH dehydrogenase I chain C, D | nuoC, nuoD | 600 | 130 | 1.1193 | 1.0084 | 1.2558 | 1.2008 | 0.7661 | 1.266 | 0.6437 | 1.1223 |
| NADH dehydrogenase I chain F | nuoF | 445 | 464 | 1.0663 | 1.0684 | 1.321 | 1.1401 | 0.6316 | 1.4997 | 1.1088 | 1.2501 |
| NADH dehydrogenase I chain L | nuoL | 613 | 332 | 0.8753 | 0.8844 | 1.0364 | 1.295 | 0.8066 | 1.026 | 0.9217 | 1.1167 |
| NADH dehydrogenase I chain M | nuoM | 509 | 872 | 0.9365 | 0.8549 | 1.1588 | 1.2998 | 0.6602 | 1.2189 | 0.7779 | 1.1293 |
| NADH dehydrogenase I chain N | nuoN | 425 | 905 | 0.7048 | 0.8381 | 1.3344 | 1.1807 | 0.6916 | 1.1267 | 0.9279 | 0.9769 |
| phosphoenolpyruvate carboxykinase | pckA | 540 | 212 | 1.2289 | 0.7936 | 1.31 | 0.9231 | 0.6978 | 1.6605 | 1.0356 | 1.0761 |
| aminoacyl-histidine dipeptidase (peptidase D) | pepD | 485 | 127 | 1.1853 | 0.8688 | 1.1049 | 1.0025 | 0.6857 | 1.3985 | 0.9419 | 1.0232 |
| 6-phosphofructokinase I | pfkA | 320 | 459 | 1.2325 | 0.9461 | 1.2077 | 1.0876 | 0.8588 | 1.2522 | 0.8834 | 1.1118 |
| Glucose 6-phosphate isomerase | pgi | 549 | 509 | 1.194 | 0.8502 | 1.2141 | 0.946 | 0.8219 | 1.0237 | 1.2288 | 1.1397 |
| phosphoglycerate kinase | pgk | 387 | 674 | 1.0985 | 0.9024 | 1.6074 | 1.2421 | 0.6868 | 1.5564 | 0.8091 | 1.0217 |
| phosphoglucomutase | pgm | 546 | 569 | 0.9884 | 1.0174 | 1.2604 | 1.0607 | 0.9058 | 1.226 | 1.0295 | 1.0117 |
| phenylalanine tRNA synthetase, beta-subunit | pheT | 795 | 455 | 1.2034 | 0.8784 | 1.1316 | 1.1977 | 0.8058 | 1.3359 | 0.9252 | 1.1236 |
| polynucleotide phosphorylase | pnp | 734 | 401 | 1.2823 | 0.8868 | 1.1675 | 1.4335 | 0.7051 | 1.2624 | 0.8294 | 1.0564 |
| DNA polymerase I, 3 --> 5' polymerase, 5' --> 3' and 3' --> 5' exonuclease | polA | 928 | 414 | 1.1239 | 0.8363 | 1.1165 | 1.0904 | 0.9047 | 1.1536 | 0.9368 | 1.0906 |
| DNA polymerase II | polB | 783 | 240 | 0.9831 | 0.8473 | 1.2287 | 1.0896 | 0.8803 | 1.1949 | 1.0176 | 1.0476 |
| proline tRNA synthetase | proS | 572 | 343 | 1.1998 | 1.0263 | 1.0707 | 1.2016 | 0.7358 | 1.3111 | 0.673 | 1.176 |
| phosphoribosylpyrophosphate synthetase | prsA | 315 | 664 | 1.2865 | 0.9773 | 1.1622 | 1.1867 | 0.8197 | 1.0065 | 0.8656 | 1.1569 |
| adenylosuccinate synthetase | purA | 432 | 486 | 1.2105 | 0.9657 | 1.65673 | 1.184 | 0.615 | 1.3503 | 0.9665 | 1.2234 |
| adenylosuccinate lyase | purB | 456 | 268 | 1.0512 | 0.9337 | 1.1558 | 1.0165 | 0.818 | 1.2092 | 0.9467 | 1.0407 |

Figure 12I

| name | gene | aa | sample | A | C | D | E | F | G | H | I |
|---|---|---|---|---|---|---|---|---|---|---|---|
| phosphoribosylaminoimidazole-succinocarboxamide synthase | purC | 237 | 343 | 0.7803 | 0.8926 | 1.2591 | 1.0957 | 0.6969 | 1.4559 | 0.9657 | 1.0702 |
| phosphoribosylglycinamide synthetase | purD | 429 | 478 | 1.1859 | 1.0715 | 1.0685 | 1.2425 | 0.637 | 1.3381 | 0.9896 | 1.3304 |
| phosphoribosylaminoimidazole carboxylase | purE | 169 | 401 | 1.8799 | 0.9663 | 0.6506 | 1.4853 | 0.3701 | 1.348 | 1.2978 | 0.8626 |
| amidophosphoribosyltransferase | purF | 505 | 425 | 1.2139 | 0.9147 | 1.2643 | 1.1247 | 0.6332 | 1.1461 | 0.8817 | 1.1437 |
| bifunctional phosphoribosylaminoimidazolecarboxamide formyltransferase/IMP cyclohydrolase | purH | 529 | 413 | 1.0533 | 1.1193 | 1.233 | 0.9289 | 0.7211 | 1.2822 | 0.9353 | 1.1107 |
| phosphoribosylaminoimidazole carboxylase | purK | 355 | 450 | 0.9078 | 0.9125 | 1.0411 | 1.0388 | 0.8745 | 1.0938 | 0.9201 | 1.1131 |
| phosphoribosylformyl-glycineamide synthetase | purL | 1295 | 224 | 1.1922 | 0.8739 | 1.233 | 1.0012 | 0.7602 | 1.2523 | 0.9217 | 1.1058 |
| phosphoribosylformylglycinamidine cyclo-ligase | purM | 345 | 463 | 1.2675 | 0.8896 | 0.9689 | 1.06 | 0.9419 | 1.6042 | 1.1282 | 1.1954 |
| phosphoribosylglycinamide formyltransferase | purN | 212 | 142 | 1.5429 | 0.7905 | 1.186 | 0.944 | 0.7669 | 1.1518 | 1.0614 | 1.0271 |
| multifunctional: proline dehydrogenase (in membrane); pyrroline-5-carboxylate dehydrogenase (in membrane); transcriptional repressor of proline synthesis (in cytoplasm) | putA | 1320 | 99 | 1.1806 | 0.7942 | 1.0689 | 1.0298 | 0.7804 | 1.318 | 0.986 | 1.2496 |
| pyruvate kinase | pykA | 480 | 636 | 1.1285 | 1.0649 | 1.0955 | 1.0986 | 0.9299 | 1.2568 | 0.9265 | 1.12 |
| pyruvate kinase | pykF | 470 | 667 | 1.1181 | 0.9985 | 0.9834 | 1.062 | 0.7689 | 1.2412 | 1.0667 | 1.203 |
| aspartate carbamoyltransferase, catalytic subunit | pyrB | 311 | 901 | 1.0672 | 0.8768 | 1.3171 | 1.1235 | 0.7148 | 1.0788 | 0.8624 | 1.0497 |
| dihydro-orotase | pyrC | 348 | 190 | 1.155 | 0.8326 | 0.9274 | 1.1286 | 0.5745 | 1.6238 | 1.0943 | 1.2276 |
| dihydro-orotate dehydrogenase | pyrD | 336 | 476 | 1.0723 | 1.0145 | 1.3286 | 0.6985 | 0.6651 | 1.202 | 1.1128 | 1.0262 |
| orotate phosphoribosyltransferase | pyrE | 213 | 307 | 1.0563 | 0.9646 | 1.5228 | 1.2108 | 0.8487 | 1.3265 | 0.9298 | 1.0952 |
| orotidine 5'-phosphate decarboxylase | pyrF | 245 | 338 | 1.0934 | 0.9515 | 1.1406 | 1.0939 | 0.6619 | 1.2111 | 1.0603 | 1.1659 |
| CTP synthetase | pyrG | 545 | 490 | 1.2756 | 0.9865 | 1.4154 | 1.3004 | 0.6167 | 1.1522 | 0.9833 | 1.1196 |
| ribokinase | rbsK | 309 | 930 | 1.248 | 0.945 | 1.371 | 1.0146 | 0.8482 | 1.2127 | 1.1266 | 1.2388 |
| ribulose-phosphate 3-epimerase | rpe | 225 | 485 | 1.2694 | 1.0556 | 0.8874 | 1.1431 | 0.7772 | 1.2542 | 1.115 | 1.1671 |
| ribosephosphate isomerase | rpiA | 219 | 346 | 0.926 | 0.9896 | 1.4399 | 1.1444 | 0.7975 | 1.4806 | 1.1586 | 1.1026 |
| RNA polymerase, alpha subunit | rpoA | 329 | 520 | 1.0991 | 0.6874 | 1.3704 | 1.0546 | 0.8417 | 1.3959 | 1.0145 | 1.2073 |
| RNA polymerase, beta subunit | rpoB | 1342 | 294 | 1.1286 | 0.8824 | 1.2302 | 1.157 | 0.6157 | 1.2123 | 0.8742 | 1.1705 |
| RNA polymerase, beta prime subunit | rpoC | 1407 | 275 | 1.119 | 0.8274 | 1.0644 | 1.0962 | 0.5868 | 1.2535 | 0.8331 | 1.3063 |
| L-serine deaminase 1 | sdaA | 454 | 285 | 1.3542 | 0.9574 | 1.0447 | 1.0637 | 0.6857 | 1.4179 | 1.2904 | 1.0058 |
| L-serine deaminase 2 | sdaB | 455 | 285 | 1.3753 | 0.8843 | 1.0141 | 1.0282 | 0.7012 | 1.5271 | 1.2516 | 1.0757 |
| succinate dehydrogenase, catalytic and NAD/flavoprotein subunit | sdhA | 588 | 807 | 1.3011 | 0.8982 | 1.1138 | 1.1001 | 0.8115 | 1.1646 | 0.826 | 1.2071 |
| 3-phosphoserine phosphatase | serB | 322 | 44 | 1.1604 | 0.6902 | 0.9758 | 1.3532 | 0.8987 | 1.5211 | 1.2144 | 1.3208 |
| serine tRNA synthetase; also charges selenocystein tRNA with serine | serS | 430 | 582 | 1.2173 | 0.8726 | 1.2368 | 1.034 | 0.6024 | 1.0936 | 0.8261 | 1.193 |
| arginine decarboxylase, PLP-binding, biosynthetic | speA | 658 | 183 | 1.0948 | 0.8217 | 1.4984 | 1.0909 | 0.7188 | 1.1856 | 1.1523 | 1.0794 |
| ornithine decarboxylase isozyme | speC | 731 | 210 | 1.0421 | 0.9443 | 1.2938 | 1.0381 | 0.5834 | 1.2143 | 1.0749 | 1.1365 |
| ornithine decarboxylase isozyme, inducible | speF | 732 | 173 | 1.0665 | 0.9761 | 1.196 | 1.044 | 0.624 | 1.1971 | 1.105 | 1.0788 |
| 2-oxoglutarate decarboxylase | sucA | 933 | 369 | 1.1833 | 0.8315 | 1.2915 | 1.138 | 0.7141 | 1.1392 | 0.871 | 1.1474 |
| 2-oxoglutarate dehydrogenase | sucB | 405 | 948 | 1.029 | 0.8525 | 1.1472 | 1.0581 | 0.7355 | 1.2996 | 0.8991 | 1.1846 |
| succinyl-CoA synthetase, beta subunit | sucC | 388 | 461 | 1.1801 | 0.957 | 1.1619 | 0.9466 | 0.8474 | 1.2613 | 1.0467 | 1.3158 |
| succinyl-CoA synthetase, alpha subunit | sucD | 289 | 518 | 1.1524 | 1.2338 | 1.3486 | 1.4025 | 0.6064 | 1.3617 | 1.3607 | 1.1407 |
| transaldolase | talA | 316 | 235 | 1.2257 | 0.656 | 1.106 | 1.2767 | 0.893 | 1.5272 | 1.0843 | 1.1481 |
| L-threonine 3-dehydrogenase | tdh | 341 | 272 | 1.0573 | 1.0608 | 1.2267 | 1.1764 | 0.8245 | 1.3555 | 1.0709 | 1.2357 |
| bifunctional aspartokinase I/homoserine dehydrogenase I | thrA | 820 | 173 | 1.1572 | 0.8942 | 1.2868 | 1.1535 | 0.8342 | 1.2854 | 1.0561 | 1.0049 |
| homoserine kinase | thrB | 310 | 369 | 1.2357 | 0.9004 | 1.2705 | 0.8654 | 0.5911 | 1.2591 | 1.094 | 0.9615 |
| threonine synthase | thrC | 428 | 337 | 1.0758 | 0.9037 | 1.1951 | 0.8356 | 0.672 | 1.1154 | 1.1203 | 1.0642 |
| threonine tRNA synthetase | thrS | 642 | 541 | 1.1513 | 0.8847 | 1.1737 | 1.3361 | 0.6201 | 1.1954 | 0.8063 | 1.3216 |
| transketolase | tktA | 663 | 616 | 1.28 | 0.9267 | 1.199 | 1.138 | 0.6276 | 1.3179 | 0.8501 | 1.0669 |

Figure 12J

| name | gene | aa | sample | A | C | D | E | F | G | H | I |
|---|---|---|---|---|---|---|---|---|---|---|---|
| transketolase | tktB | 667 | 620 | 1.3208 | 0.8184 | 1.2496 | 1.136 | 0.6799 | 1.2937 | 0.8292 | 1.0148 |
| triosephosphate isomerase | tpiA | 255 | 623 | 1.1687 | 1.0863 | 1.3717 | 1.0676 | 0.7387 | 1.029 | 0.9325 | 1.039 |
| tryptophan synthase, beta protein | trpB | 397 | 687 | 1.1133 | 0.943 | 1.3244 | 1.1411 | 0.7972 | 1.0444 | 1.1049 | 1.2069 |
| bifunctional indole-3-glycerol phosphate synthase/phosphoribosylanthranilate isomerase | trpC | 453 | 132 | 1.0694 | 0.6822 | 0.9123 | 1.1123 | 0.9874 | 1.315 | 1.0474 | 0.9541 |
| anthranilate synthase component I | trpE | 520 | 214 | 1.133 | 0.9437 | 0.9955 | 1.1702 | 0.7371 | 1.279 | 0.954 | 1.0265 |
| thioredoxin reductase | trxB | 321 | 879 | | 0.9539 | 1.3274 | 1.1262 | 0.7879 | | 0.9774 | 1.2742 |
| copper amine oxidase (tyramine oxidase) | tynA | 757 | 117 | 1.0641 | 1.0305 | 1.2111 | 0.9821 | 0.7043 | 1.2883 | 0.9585 | 1.1907 |
| bifunctional: chorismate mutase T (N-terminal); prephenate dehydrogenase (C-terminal) | tyrA | 373 | 71 | 1.4694 | 0.6277 | 0.8422 | 1.736 | 0.6137 | 1.4207 | 0.9217 | 1.3395 |
| tyrosine aminotransferase, tyrosine repressible | tyrB | 397 | 67 | 1.4599 | 0.6302 | 0.8376 | 1.7222 | 0.618 | 1.4217 | 0.9256 | 1.3432 |
| tyrosine tRNA synthetase | tyrS | 424 | 514 | 1.106 | 0.8294 | 1.3345 | 1.0759 | 0.7912 | 1.023 | 0.9915 | 1.1452 |
| uridine/cytidine kinase | udk | 231 | 316 | 1.0709 | 0.9872 | 1.4437 | 1.1625 | 0.5965 | 1.2172 | 0.7883 | 1.163 |
| uridine phosphorylase | udp | 253 | 292 | 1.2183 | 1.1223 | 1.1408 | 1.278 | 0.7278 | 1.1995 | 0.9019 | 1.013 |
| UDP-sugar hydrolase (5'-nucleotidase) | ushA | 550 | 546 | 1.0436 | 0.9392 | 1.1211 | 0.9605 | 0.877 | 1.1063 | 1.0927 | 1.1457 |
| valine tRNA synthetase | valS | 951 | 809 | 1.0862 | 0.931 | 1.1422 | 1.0746 | 0.7021 | 1.2027 | 0.8901 | 1.1309 |
| bifunctional fatty acid oxidation complex protein : putative enoyl-CoA hydratase/isomerase (N-terminal); putative NAD(P)-binding dehydrogenase (C-terminal) | ylcX | 714 | 450 | 1.0861 | 0.9288 | 1.1703 | 1.1203 | 0.767 | 1.3527 | 1.0462 | 1.2363 |
| glucose-6-phosphate 1-dehydrogenase | zwf | 491 | 522 | 1.0173 | 0.8292 | 1.2671 | 1.0838 | 0.7861 | 1.1067 | 0.8284 | 1.3573 |

| name | gene | aa | sample | T | V | W | Y |
|---|---|---|---|---|---|---|---|
| | aas | 719 | 70 | 1.0207 | 1.108 | 1.0072 | 0.8478 |
| long-chain-fatty-acid-[acyl-carrier-protein] ligase/acyl-[acyl-carrier-protein]-phospholipid O-acyltransferase | accC | 449 | 995 | 1.2033 | 1.2123 | | 0.8835 |
| acetyl CoA carboxylase, biotin carboxylase subunit | aceE | 887 | 205 | 1.1097 | 1.0783 | 0.6584 | 0.6462 |
| pyruvate dehydrogenase | aceF | 630 | 234 | 1.2191 | 0.9277 | 1.1573 | 1.3183 |
| dihydrolipoamide acetyltransferase | acnA | 891 | 500 | 1.0378 | 1.0082 | 0.9632 | 0.8419 |
| aconitate hydrase A | acnB | 865 | 150 | 1.1517 | 1.1442 | 0.4934 | 0.9067 |
| aconitate hydrase B | acs | 652 | 906 | 1.0212 | 1.0638 | 0.846 | 1.0134 |
| acetyl-CoA synthetase | acd | 333 | 289 | 1.1382 | 1.107 | 1.3007 | 1.132 |
| adenosine deaminase | ade | 588 | 98 | 1.1313 | 1.0125 | 1.3986 | 1.1882 |
| Mn-dependent adenine deaminase (cryptic) | adiA | 756 | 197 | 1.1454 | 1.0697 | 0.926 | 0.8065 |
| arginine decarboxylase; inducible by acid, catabolic | adk | 214 | 788 | 1.0365 | 1.0474 | | 0.7788 |
| adenylate kinase | aIaS | 876 | 539 | 1.0562 | 1.0165 | 0.7712 | 0.903 |
| alanyl-tRNA synthetase | aldH | 495 | 999 | 1.1246 | 1.1075 | 0.8338 | 1.2375 |
| aldehyde dehydrogenase | alr | 356 | 518 | 1.2326 | 0.9105 | 1.2707 | 0.6851 |
| alanine racemase | ansA | 338 | 311 | 0.922 | 0.9981 | | 1.0598 |
| cytoplasmic asparaginase I | ansB | 348 | 328 | 0.9677 | 0.9244 | | 1.1034 |
| periplasmic L-asparaginase II | aptD | 460 | 1000 | 1.0603 | 0.7715 | | 0.822 |
| membrane-bound ATP synthase beta-subunit | argD | 406 | 978 | 1.1779 | 1.1346 | | 1.0449 |
| acetylornithine delta-aminotransferase | argG | 447 | 445 | 1.0236 | 1.11 | 0.8051 | 0.9928 |
| argininosuccinate synthetase | argH | 457 | 585 | 1.1389 | 1.1126 | 1.3004 | 1.1047 |
| argininosuccinate lyase | argS | 577 | 607 | 1.1716 | 1.0869 | | 0.7712 |
| arginine tRNA synthetase | aroA | 427 | 729 | 1.0812 | 1.1241 | 1.3244 | 1.1436 |
| 3-enolpyruvylshikimate-5-phosphate synthetase | aroB | 362 | 449 | 1.1151 | 0.9589 | 1.2691 | 0.9896 |
| 3-dehydroquinate synthase | aroC | 361 | 467 | 1.0695 | 1.1684 | | 1.1443 |
| chorismate synthase | | | | | | | |
| 3-deoxy-D-arabinoheptulosonate-7-phosphate synthase (DAHP synthetase), tyrosine-repressible | aroF | 356 | 420 | 0.9465 | 1.2061 | | |

Figure 12K

| name | gene | aa | sample | A | C | D | E | F | G | H | I |
|---|---|---|---|---|---|---|---|---|---|---|---|
| 3-deoxy-D-arabinoheptulosonate-7-phosphate synthase (DAHP synthase), phenylalanine repressible) | aroG | | | 350 | 419 | | 1.0192 | 1.2127 | | | 0.9409 |
| 3-deoxy-D-arabinoheptulosonate-7-phosphate synthase (DAHP synthase), tryptophan-repressible | aroH | | | 348 | 419 | | 1.1187 | 1.353 | | | 0.9528 |
| asparagine synthetase B | asnB | | | 554 | 276 | | 1.2027 | 1.0441 | | 1.13 | 0.9222 |
| asparagine tRNA synthetase | asnS | | | 466 | 430 | | 1.0798 | 0.9834 | | 0.9126 | 1.3867 |
| aspartate ammonia-lyase (aspartase) | aspA | | | 493 | 599 | | 0.908 | 1.0202 | | | |
| aspartate aminotransferase | aspC | | | 396 | 496 | | 1.2668 | 1.0578 | | | |
| aspartate tRNA synthetase | aspS | | | 590 | 452 | | 1.2222 | 1.1222 | | 0.8524 | 0.8203 |
| acetyl-CoA acetyltransferase | atoB | | | 394 | 996 | | 1.1589 | 1.0666 | | | 1.4137 |
| membrane-bound ATP synthase, F1 sector, alpha-subunit | atpA | | | 513 | 959 | | 0.9104 | 1.0577 | | | 1.027 |
| valine–pyruvate transaminase | avtA | | | 417 | 314 | | 1.0734 | 1.0489 | | 1.037 | 0.8669 |
| 6-phospho-beta-glucosidase A | bglA | | | 479 | 868 | | 1.1681 | 1.0691 | | 0.6552 | 0.791 |
| carbamoyl phosphate synthetase, Small subunit | carA | | | 382 | 649 | | 0.9049 | 1.1312 | | 1.4706 | 1.1251 |
| carbamoyl phosphate synthase, Large subunit | carB | | | 1073 | 598 | | 0.9696 | 1.0759 | | 1.2427 | 0.9722 |
| phospho-beta-glucosidase | celF | | | 450 | 165 | | 1.0628 | 1.0744 | | 1.1156 | 1.0237 |
| citrate lyase beta chain | citE | | | 307 | 297 | | 1.2879 | 0.9728 | | | 1.214 |
| cytidine monophosphate (CMP) kinase | cmk | | | 227 | 361 | | 1.0364 | | | | |
| 2',3'-cyclic nucleotide 2'-phosphodiesterase/3'-nucleotidase bifunctional periplasmic precursor protein | cpdB | | | 647 | 368 | | 1.0785 | 1.0219 | | 0.987 | 1.0017 |
| adenylate cyclase | cyaA | | | 848 | 80 | | 1.2333 | 1.0757 | | 0.7113 | 0.7327 |
| cysteine tRNA synthetase | cysS | | | 461 | 547 | | 1.1462 | 1.122 | | | 0.8743 |
| succinyl-diaminopimelate desuccinylase | dapE | | | 375 | 556 | | 1.0669 | 1.023 | | 0.9806 | 1.1612 |
| thymidine phosphorylase | deoA | | | 440 | 214 | | 1.0439 | 1.0658 | | 1.3272 | 1.3636 |
| phosphopentomutase | deoB | | | 407 | 179 | | 0.8381 | 1.1682 | | 1.2195 | 1.0003 |
| deoxyribose-phosphate aldolase | deoC | | | 259 | 243 | | 0.8104 | 1.0695 | | | 1.3258 |
| purine-nucleoside phosphorylase | deoD | | | 306 | 307 | | 1.1635 | 1.0303 | | | 1.0769 |
| deoxyguanosinetriphosphate triphosphohydrolase | dgt | | | 505 | 176 | | 0.9344 | 0.9967 | | 1.1108 | 0.9611 |
| DNA polymerase IV | dinB | | | 351 | 512 | | 1.0389 | 1.0559 | | 1.3779 | 0.9419 |
| DNA polymerase III, alpha subunit | dnaE | | | 1160 | 519 | | 1.0678 | 1.0371 | | 1.2302 | 0.9151 |
| DNA polymerase III, epsilon subunit | dnaQ | | | 243 | 206 | | 0.9835 | 1.0666 | | | 0.9652 |
| DNA polymerase III, tau and gamma subunits; DNA elongation factor III | dnaX | | | 643 | 133 | | 1.0479 | 1.0859 | | 0.9911 | 0.8266 |
| D-serine deaminase (dehydratase) | dsdA | | | 442 | 79 | | 1.0974 | 0.8408 | | 0.6977 | 0.8733 |
| 2-keto-3-deoxygluconate 6-phosphate aldolase | eda | | | 213 | 250 | | 0.9528 | 1.064 | | 1.0317 | 1.2981 |
| 6-phosphogluconate dehydratase | edd | | | 603 | 557 | | 1.1005 | 0.9896 | | 1.2941 | 1.295 |
| enolase | eno | | | 432 | 746 | | 1.0955 | 1.0936 | | 1.2941 | 1.0582 |
| 3-oxoacyl-[acyl-carrier-protein] synthase I | fabB | | | 406 | 956 | | 1.1081 | 1.1305 | | 1.482 | 1.0565 |
| 3-oxoacyl-[acyl-carrier-protein] synthase II | fabF | | | 413 | 962 | | 1.1317 | 1.1419 | | | 1.1336 |
| 3-ketoacyl-CoA thiolase; (thiolase I, acetyl-CoA transferase), in complex with FadB catalyzes | fadA | | | 387 | 997 | | 1.0417 | 1.2858 | | 1.6553 | 1.6709 |
| 4-enzyme protein: 3-hydroxyacyl-CoA dehydrogenase; 3-hydroxybutyryl-CoA epimerase; delta(3)-cis-delta(2)-trans-enoyl-CoA isomerase; enoyl-CoA hydratase | fadB | | | 729 | 418 | | 1.2302 | 1.0568 | | 1.3921 | 0.9946 |
| acyl-CoA synthase | fadD | | | 561 | 903 | | 0.9156 | 1.0174 | | | 0.9758 |
| fructose-bisphosphate aldolase, class II | fbaA | | | 359 | 367 | | 1.1408 | 1.0516 | | 1.2771 | 1.0406 |
| fructose-1,6-bisphosphatase | fbp | | | 332 | 330 | | 1.1805 | 1.0867 | | | 0.711 |
| methionyl-tRNA formyltransferase | fmt | | | 315 | 569 | | 0.9792 | 1.0113 | | 0.9107 | 1.1722 |
| fumarate reductase, anaerobic, catalytic and NAD/flavoprotein subunit | frdA | | | 602 | 974 | | 0.9791 | 1.0596 | | 1.3603 | 1.1395 |
| fumarase A (fumarate hydratase class I) | fumA | | | 548 | 176 | | 1.0813 | 1.1249 | | 1.2069 | 1.023 |
| fumarase C (fumarate hydratase Class II) | fumC | | | 467 | 594 | | 1.036 | 1.1538 | | 1.149 | 1.4616 |
| 4-aminobutyrate aminotransferase | gabT | | | 426 | 968 | | 1.0383 | 1.0706 | | | 1.127 |

Figure 12L

| name | gene | aa sample | A | C | D | E | F | G | H | I |
|---|---|---|---|---|---|---|---|---|---|---|
| glutamate decarboxylase A, isozyme, PLP-dependent | gadA | | 466 | 152 | | 1.0107 | 1.0845 | | | 0.9862 |
| glutamate decarboxylase isozyme | gadB | | 466 | 143 | | 1.0094 | 1.088 | | 0.6615 | 0.9909 |
| galactose-1-epimerase | galM | | 346 | 298 | | 1.0709 | 1.1126 | | 1.0462 | 0.7019 |
| glyceraldehyde-3-phosphate dehydrogenase | gapA | | 331 | 919 | | 1.0311 | 0.9666 | | | 0.6268 |
| glycine cleavage complex protein P, glycine decarboxylase, PLP-dependent | gcvP | | 957 | 304 | | 1.1251 | 1.224 | | | 0.6789 |
| aminomethyltransferase | gcvT | | 364 | 714 | | 1.1278 | 1.0113 | | | 0.9441 |
| glutamate dehydrogenase | gchA | | 447 | 465 | | 1.0939 | 0.9875 | | 1.0635 | 1.2658 |
| glucokinase | glk | | 321 | 158 | | 1.0788 | 1.1357 | | 0.8699 | 0.9735 |
| glutamine synthetase | glnA | | 496 | 605 | | 1.1859 | 1.2036 | | 1.3606 | 0.92 |
| glutamine tRNA synthetase | glnS | | 554 | 339 | | 1.1007 | 1.0933 | | 0.7179 | 0.8334 |
| citrate synthase | gltA | | 427 | 621 | | 1.123 | 1.1672 | | 0.9138 | 0.9928 |
| glutamate synthase, large subunit | gltB | | 1517 | 359 | | 1.1758 | 1.1333 | | 0.8766 | 0.9429 |
| glutamate synthase, small subunit | gltD | | 472 | 617 | | 1.1334 | 0.9254 | | 1.2567 | 1.2513 |
| glutamate tRNA synthetase, catalytic subunit | gltX | | 471 | 478 | | 1.0177 | 1.1316 | | 0.7698 | 0.819 |
| serine hydroxymethyltransferase | glyA | | 417 | 716 | | 0.8503 | 1.1108 | | | 0.7695 |
| glycine tRNA synthetase, beta subunit | glyS | | 689 | 350 | | 1.3041 | 0.9901 | | 1.1435 | 1.0154 |
| guanylate kinase | gmk | | 107 | 691 | | 1.0398 | 1.1547 | | 1.4142 | 0.8538 |
| 6-phosphogluconate dehydrogenase | gnd | | 468 | 473 | | 1.2994 | 1.1263 | | 0.6247 | 0.9205 |
| phosphoglyceromutase 1 | gpmA | | 250 | 508 | | 1.0339 | 1.1 | | 0.78 | 0.95 |
| bifunctional GMP synthase/glutamine amidotransferase protein | guaA | | 525 | 429 | | 1.3222 | 0.8705 | | 0.9977 | 0.9363 |
| IMP dehydrogenase | guaB | | 488 | 453 | | 0.9808 | 0.9781 | | | 1.1421 |
| GMP reductase | guaC | | 347 | 192 | | 1.0207 | 1.047 | | 1.4383 | 1.147 |
| guanine deaminase | guaD | | 439 | 351 | | 0.9176 | 1.0443 | | 1.0827 | 1.1547 |
| bifunctional: histidinol-phosphatase (N-terminal); imidazoleglycerol-phosphate dehydratase (C-terminal) | hisB | | 356 | 104 | | 1.0858 | 1.2021 | | 1.0288 | 1.5428 |
| histidinol-phosphate aminotransferase | hisC | | 356 | 787 | | 1.054 | 1.0087 | | 1.2908 | 0.8542 |
| histidinol dehydrogenase | hisD | | 434 | 478 | | 1.2662 | 0.9844 | | | 1.0681 |
| histidine tRNA synthetase | hisS | | 424 | 611 | | 1.1258 | 1.0096 | | 1.275 | 0.7946 |
| isocitrate dehydrogenase | icdA | | 416 | 848 | | 1.1193 | 1.0719 | | 1.2165 | 1.0696 |
| isoleucine tRNA synthetase | ileS | | 938 | 887 | | 1.0504 | 1.0463 | | 0.5668 | 0.9627 |
| acetolactate synthase I, valine-sensitive, large subunit | ilvB | | 562 | 973 | | 1.1083 | 1.0742 | | 0.956 | 1.2476 |
| ketol-acid reductoisomerase | ilvC | | 491 | 82 | | 1.1941 | 1.0311 | | 0.7771 | 1.015 |
| dihydroxy-acid dehydratase | ilvD | | 616 | 748 | | 1.1123 | 1.0281 | | 1.2884 | 1.2198 |
| branched-chain amino acid aminotransferase | ilvE | | 309 | 870 | | 1.0404 | 1.0275 | | 0.9544 | 0.864 |
| acetohydroxy acid synthase II | ilvG | | 548 | 978 | | 0.9845 | 1.0562 | | 0.9822 | 1.2093 |
| acetolactate synthase III, valine sensitive, large subunit | ilvI | | 604 | 977 | | 1.1637 | 0.9512 | | 1.0754 | 1.1041 |
| 2-amino-3-ketobutyrate coenzyme A ligase | kbl | | 398 | 930 | | 1.1997 | 1.1395 | | | 0.9777 |
| ketodeoxygluconokinase | kdgK | | 382 | 139 | | 1.0943 | 0.9949 | | 0.9668 | 1.0858 |
| 3-isopropylmalate dehydrogenase | leuB | | 364 | 931 | | 1.1424 | 1.1206 | | | 1.025 |
| 3-isopropylmalate isomerase (dehydratase) subunit | leuC | | 466 | 837 | | 0.9768 | 1.0619 | | 1.1994 | 1.179 |
| leucine tRNA synthetase | leuS | | 860 | 734 | | 1.0137 | 1.0132 | | 0.5527 | 0.8706 |
| dihydrolipoamide dehydrogenase | lpdA | | 474 | 988 | | 1.1021 | 1.0099 | | 1.3239 | 1.1821 |
| L-allo-threonine aldolase, PLP-dependent | ltaE | | 333 | 251 | | 0.9797 | 1.1009 | | 1.4795 | 1.2039 |
| diaminopimelate decarboxylase | lysA | | 420 | 655 | | 1.1651 | 0.9771 | | 1.3575 | 0.9321 |
| aspartate kinase III | lysC | | 449 | 638 | | 0.9167 | 0.9109 | | | 1.1912 |
| lysine tRNA synthetase, constitutive | lysS | | 505 | 599 | | 1.0854 | 1.248 | | | 0.9379 |

Figure 12M

| name | gene | aa | sample | A | C | D | E | F | G | H | I |
|---|---|---|---|---|---|---|---|---|---|---|---|
| lysine tRNA synthetase, inducible; heat shock protein | lysU | | | 505 | 600 | | 1.0667 | 1.2583 | | | 0.8734 |
| bifunctional: PLP-dependent beta-cystathionase; repressor of maltose regulon through interaction with MalT | malY | | | 390 | 680 | | 1.074 | 0.9822 | | 1.0608 | 1.0235 |
| malate dehydrogenase | mdh | | | 312 | 752 | | 1.1566 | 0.9894 | | | 1.1735 |
| cystathionine gamma-synthase | metB | | | 386 | 980 | | 1.0785 | 1.0861 | | | 0.979 |
| cystathionine beta-lyase | metC | | | 395 | 973 | | 0.9785 | 1.068 | | | 0.959 |
| 5-methyltetrahydropteroyltriglutamate- homocysteine S-methyltransferase | metE | | | 735 | 286 | | 1.0332 | 1.0646 | | 0.7411 | 0.6261 |
| methionine tRNA synthetase | metG | | | 677 | 438 | | 1.0946 | 1.0946 | | 0.7608 | 0.8804 |
| B12-dependent methionine synthase | metH | | | 1227 | 218 | | 1.1183 | 1.0176 | | 1.1553 | 0.8519 |
| methionine adenosyltransferase 1 | metK | | | 384 | 659 | | 0.9519 | 1.0057 | | 1.252 | 0.8357 |
| aspartokinase II and homoserine dehydrogenase II | metL | | | 810 | 173 | | 1.0599 | 0.9166 | | 1.1565 | 0.8921 |
| UDP-N-acetylmuramoylalanyl-D-glutamate 2,6-diaminopimelate ligase | murE | | | 495 | 529 | | 0.889 | 1.0506 | | 1.3226 | 0.9485 |
| L-aspartate oxidase | nadB | | | 504 | 900 | | 0.9784 | 0.0581 | | 1.2578 | 1.0967 |
| nucleoside diphosphate kinase | ndk | | | 143 | 659 | | 0.9316 | 1.0526 | | | 1.0014 |
| ribonucleoside diphosphate reductase 1, alpha subunit | nrdA | | | 761 | 427 | | 1.1169 | 1.1549 | | 0.9448 | 0.8903 |
| anaerobic ribonucleoside triphosphate reductase | nrdD | | | 712 | 194 | | 1.1395 | 1.1113 | | 1.0853 | 0.8622 |
| ribonucleoside-diphosphate reductase 2, alpha subunit | nrdE | | | 714 | 575 | | 1.109 | 1.0938 | | 1.0514 | 0.9173 |
| NADH dehydrogenase I chain C, D | nuoC, nuoD | | | 600 | 130 | | 1.1797 | 1.0966 | | 1.0256 | 0.9644 |
| NADH dehydrogenase I chain F | nuoF | | | 445 | 464 | | 1.0008 | 1.2927 | | 1.0495 | 0.9986 |
| NADH dehydrogenase I chain L | nuoL | | | 613 | 332 | | 1.0718 | 1.0649 | | 1.079 | 0.7775 |
| NADH dehydrogenase I chain M | nuoM | | | 509 | 872 | | 1.1666 | 1.2073 | | 0.9606 | 0.8924 |
| NADH dehydrogenase I chain N | nuoN | | | 425 | 905 | | 1.2917 | 1.1508 | | 1.0294 | 0.7748 |
| phosphoenolpyruvate carboxykinase | pckA | | | 540 | 212 | | 0.9581 | 1.1808 | | 0.8513 | 0.989 |
| aminoacyl-histidine dipeptidase (peptidase D) | pepD | | | 485 | 127 | | 1.242 | 1.1585 | | 0.6962 | 1.0597 |
| 6-phosphofructokinase I | pfkA | | | 320 | 459 | | 0.9426 | 1.052 | | | 1.3068 |
| Glucose 6-phosphate isomerase | pgi | | | 549 | 509 | | 1.0024 | 1.1448 | | | 1.0015 |
| phosphoglycerate kinase | pgk | | | 387 | 674 | | 1.0466 | 1.0467 | | | 1.5757 |
| phosphoglucomutase | pgm | | | 546 | 569 | | 0.9557 | 1.0238 | | 1.0834 | 1.1265 |
| phenylalanine tRNA synthetase, beta-subunit | pheT | | | 795 | 455 | | 1.2 | 0.9874 | | 0.8382 | 1.0138 |
| polynucleotide phosphorylase | pnp | | | 734 | 401 | | 1.1708 | 1.0219 | | 1.6657 | 0.9672 |
| DNA polymerase I, 3' --> 5' polymerase, 5' --> 3' and 3' --> 5' exonuclease | polA | | | 928 | 414 | | 0.9806 | 1.0993 | | 1.2066 | 0.8418 |
| DNA polymerase II | polB | | | 783 | 240 | | 1.0978 | 0.9707 | | 1.1132 | 0.8001 |
| proline tRNA synthetase | proS | | | 572 | 343 | | 1.1881 | 1.1881 | | | 0.7647 |
| phosphoribosylpyrophosphate synthetase | prsA | | | 315 | 664 | | 1.0487 | 1.0518 | | | 1.152 |
| adenylosuccinate synthetase | purA | | | 432 | 486 | | 0.9934 | 1.032 | | 0.5944 | 0.8936 |
| adenylosuccinate lyase | purB | | | 456 | 268 | | 0.9753 | 1.0534 | | 0.9711 | 1.053 |
| phosphoribosylaminoimidazole-succinocarboxamide synthase | purC | | | 237 | 343 | | 1.2277 | 1.0821 | | | 1.0579 |
| phosphoribosylglycinamide synthetase | purD | | | 429 | 478 | | 1.1519 | 1.0114 | | 1.2025 | 0.7719 |
| phosphoribosylaminoimidazole carboxylase | purE | | | 169 | 401 | | 0.9567 | 0.8035 | | | |
| phosphoribosylaminoimidazole carboxylase amidophosphoribosyltransferase | purF | | | 505 | 425 | | 1.1314 | 1.0115 | | | 0.7827 |
| bifunctional phosphoribosylaminoimidazolecarboxamide formyltransferase/IMP cyclohydrolase | purH | | | 529 | 413 | | 1.0536 | 0.9815 | | 1.3591 | 0.7973 |
| phosphoribosylaminoimidazole carboxylase | purK | | | 355 | 450 | | 1.1058 | 1.1061 | | 1.2152 | 0.971 |
| phosphoribosylformyl-glycineamide synthetase | purL | | | 1295 | 224 | | 1.2081 | 1.0739 | | 0.8958 | 1.0867 |
| phosphoribosylformylglycinamidine cyclo-ligase | purM | | | 345 | 463 | | 0.9535 | 0.982 | | 1.1587 | 0.6393 |
| phosphoribosylglycinamide formyltransferase | purN | | | 212 | 142 | | 1.4345 | 0.8639 | | | 1.0835 |

Figure 12N

| name | gene | aa | sample | A | C | D | E | F | G | H | I |
|---|---|---|---|---|---|---|---|---|---|---|---|
| multifunctional: proline dehydrogenase (in membrane); pyrroline-5-carboxylate dehydrogenase (in membrane); transcriptional repressor of proline synthesis (in cytoplasm) | putA | | | 1320 | | 99 | 1.1132 | 0.9992 | | 0.6853 | 0.7335 |
| pyruvate kinase | pykA | | | 480 | | 636 | 1.0123 | 0.9913 | | | 1.1638 |
| pyruvate kinase | pykF | | | 470 | | 667 | 1.0155 | 0.9775 | | | 1.1348 |
| aspartate carbamoyltransferase, catalytic subunit | pyrB | | | 311 | | 901 | 0.9626 | 1.0146 | | | 1.2081 |
| dihydro-orotase | pyrC | | | 348 | | 190 | 0.987 | 1.1224 | | | 0.8157 |
| dihydro-orotate dehydrogenase | pyrD | | | 336 | | 476 | 1.0037 | 1.1905 | | | 1.029 |
| orotate phosphoribosyltransferase | pyrE | | | 213 | | 307 | 1.1013 | 1.0614 | | | 0.8797 |
| orotidine 5′-phosphate decarboxylase | pyrF | | | 245 | | 338 | 0.8996 | 1.0517 | | | 1.2789 |
| CTP synthetase | pyrG | | | 545 | | 490 | 0.9546 | 1.0188 | | 1.0015 | 0.7674 |
| ribokinase | rbsK | | | 309 | | 930 | 1.0488 | 1.014 | | | |
| ribulose-phosphate 3-epimerase | rpe | | | 225 | | 485 | 1.1336 | 1.0232 | | | 1.4412 |
| ribosephosphate isomerase | rpiA | | | 219 | | 346 | 1.0622 | 0.954 | | | 1.3997 |
| RNA polymerase, alpha subunit | rpoA | | | 329 | | 520 | 1.0378 | 1.0289 | | | 0.9457 |
| RNA polymerase, beta subunit | rpoB | | | 1342 | | 294 | 1.0785 | 1.0251 | | | 0.933 |
| RNA polymerase, beta prime subunit | rpoC | | | 1407 | | 275 | 1.1248 | 1.0992 | | 0.6714 | 0.8814 |
| L-serine deaminase | sdaA | | | 454 | | 285 | 0.9929 | 0.9941 | | | 0.9948 |
| L-serine deaminase 2 | sdaB | | | 455 | | 285 | 1.294 | 0.9844 | | | 0.8578 |
| succinate dehydrogenase, catalytic and NAD/flavoprotein subunit | sdhA | | | 588 | | 807 | 1.0131 | 1.1458 | | 1.2729 | 1.1645 |
| 3-phosphoserine phosphatase | serB | | | 322 | | 44 | 1.2343 | 0.9559 | | | 1.2364 |
| serine tRNA synthetase; also charges selenocystein tRNA with serine | serS | | | 430 | | 582 | 1.1034 | 1.0698 | | 0.9736 | 0.9749 |
| arginine decarboxylase, PLP-binding, biosynthetic | speA | | | 658 | | 183 | 1.2715 | 1.0239 | | 0.9116 | 0.728 |
| ornithine decarboxylase isozyme | speC | | | 731 | | 210 | 1.1536 | 1.0918 | | 0.941 | 0.8313 |
| ornithine decarboxylase isozyme, inducible | speF | | | 732 | | 221 | 1.131 | 1.0872 | | 0.976 | 0.846 |
| 2-oxoglutarate decarboxylase | sucA | | | 933 | | 384 | 1.2305 | 0.955 | | 0.6928 | 0.8483 |
| 2-oxoglutarate dehydrogenase | sucB | | | 405 | | 948 | 1.0543 | 1.0891 | | | 1.1054 |
| succinyl-CoA synthetase, beta subunit | sucC | | | 388 | | 461 | 1.2065 | 0.9338 | | 1.4923 | 1.0544 |
| succinyl-CoA synthetase, alpha subunit | sucD | | | 289 | | 518 | 1.0515 | 1.01 | | | 1.2683 |
| transaldolase | talA | | | 316 | | 235 | 0.9379 | 1.0182 | | 0.6201 | 0.6845 |
| L-threonine 3-dehydrogenase | tdh | | | 341 | | 272 | 1.1633 | 0.9911 | | | 1.1471 |
| bifunctional aspartokinase I/homeserine dehydrogenase I | thrA | | | 820 | | 173 | 1.1521 | 0.9344 | | 0.982 | 0.8744 |
| homoserine kinase | thrB | | | 310 | | 369 | 1.0905 | 1.043 | | 1.234 | 1.1242 |
| threonine synthase | thrC | | | 428 | | 337 | 0.969 | 1.1083 | | 1.3755 | 1.0552 |
| threonine tRNA synthetase | thrS | | | 642 | | 541 | 1.2749 | 1.211 | | 0.6817 | 0.7962 |
| transketolase | tktA | | | 663 | | 616 | 1.0894 | 1.146 | | 0.8354 | 0.9618 |
| transketolase | tktB | | | 667 | | 620 | 1.1027 | 1.1761 | | 0.7999 | 1.0006 |
| triosephosphate isomerase | tpiA | | | 255 | | 623 | 1.0252 | 1.1151 | | | |
| tryptophan synthase, beta protein | trpB | | | 397 | | 687 | 1.3102 | 1.0409 | | | 1.1434 |
| bifunctional indole-3-glycerol phosphate synthase/phosphoribosylanthranilate isomerase | trpC | | | 453 | | 132 | 1.3054 | 0.9988 | | | 0.9759 |
| anthranilate synthase component I | trpE | | | 520 | | 214 | 1.2135 | 0.9685 | | | 0.8819 |
| thioredoxin reductase | trxB | | | 321 | | 879 | 1.0648 | 1.0136 | | | 1.0182 |
| copper amine oxidase (tyramine oxidase) | tynA | | | 757 | | 117 | 1.0792 | 0.9613 | | 0.817 | 0.8703 |
| bifunctional: chorismate mutase T (N-terminal); prephenate dehydrogenase (C-terminal) | tyrA | | | 373 | | 71 | 1.7362 | 1.0117 | | | 0.6519 |
| tyrosine aminotransferase, tyrosine repressible | tyrB | | | 397 | | 67 | 1.7058 | 1.0061 | | | 0.6592 |
| tyrosine tRNA synthetase | tyrS | | | 424 | | 514 | 1.0218 | 1.1232 | | | 0.9862 |
| uridine/cytidine kinase | udk | | | 231 | | 316 | 1.2382 | 1.1004 | | | 0.849 |

Figure 12O

| name | gene | aa sample | A | C | D | E | F | G | H | I |
|---|---|---|---|---|---|---|---|---|---|---|
| uridine phosphorylase | udp | | 253 | 292 | | 1.1291 | 0.9631 | | | 1.1866 |
| UDP-sugar hydrolase (5'-nucleotidase) | ushA | | 550 | 546 | | 1.0231 | 1.0674 | | 1.1867 | 1.0219 |
| valine tRNA synthetase | valS | | 951 | 809 | | 1.0203 | 1.0309 | | | 1.0121 |
| bifunctional fatty acid oxidation complex protein : putative enoyl-CoA hydratase/isomerase (N-terminal); putative NAD(P)-binding dehydrogenase (C-terminal) | yfcX | | 714 | 450 | | 1.1381 | 1.0348 | | 1.5523 | 0.8853 |
| glucose-6-phosphate 1-dehydrogenase | zwf | | 491 | 522 | | 1.242 | 1.0351 | | 0.7148 | 0.724 |

Figure 13A

| Mutation | Forward Primer (5'→3') | Reverse Primer (5'→3') |
|---|---|---|
| G27A | ACCAGCAACCGCCACGCTAACATGTGGGAAGAT<br>SEQ ID NO:85 | ATCTTCCCACATGTTAGCGTGGCGGTTGCTGGT<br>SEQ ID NO:86 |
| G43A | TTAAACAGCCCATATGCCGCACCCGCTTATCAG<br>SEQ ID NO:87 | CTGATAAGCGGGTGCGGCATATGGGCTGTTTAA<br>SEQ ID NO:88 |
| G91A | ACGGTTGAGTGTCTGGCCATTGATCGTCATTTC<br>SEQ ID NO:89 | GAAATGACGATCAATGGCCAGACACTCAACCGT<br>SEQ ID NO:90 |
| G115A | TGCTGGAATGAGCGTGCCATCGGAGAAGGTAGC<br>SEQ ID NO:91 | GCTACCTTCTCCGATGGCACGCTCATTCCAGCA<br>SEQ ID NO:92 |
| G117A | AATGAGCGTGGCATCGCAGAAGGTAGCCGTGAT<br>SEQ ID NO:93 | ATCACGGCTACCTTCTGCGATGCCACGCTCATT<br>SEQ ID NO:94 |
| G119A | CGTGGCATCGGAGAAGCTAGCCGTGATAGCTTA<br>SEQ ID NO:95 | TAAGCTATCACGGCTAGCTTCTCCGATGCCACG<br>SEQ ID NO:96 |
| G134A | AATGCGACCGCCTTGCCCTTTCGGGCTTTACGC<br>SEQ ID NO:97 | GCGTAAAGCCCGAAAGGCCAAGGCGGTCGCATT<br>SEQ ID NO:98 |
| G148A | TATAATGTAAGCTCAGCAGTGCTGGAGAACTTC<br>SEQ ID NO:99 | GAAGTTCTCCAGCACTGCTGAGCTTACATTATA<br>SEQ ID NO:100 |
| G158A | TTCCGTGATGACAATGCTCAATTCTTTTGCGGT<br>SEQ ID NO:101 | ACCGCAAAAGAATTGAGCATTGTCATCACGGAA<br>SEQ ID NO:102 |
| G163A | GGTCAATTCTTTTGCGCTTCTACTGTGGAGGAG<br>SEQ ID NO:103 | CTCCTCCACAGTAGAAGCGCAAAAGAATTGACC<br>SEQ ID NO:104 |
| G170A | ACTGTGGAGGAGGAAGCCGCGGAGGCCTACAAT<br>SEQ ID NO:105 | ATTGTAGGCCTCCGCGGCTTCCTCCTCCACAGT<br>SEQ ID NO:106 |
| G194A | AATATTTTATTCCCGGCCGAGAAAGTGATGGAA<br>SEQ ID NO:107 | TTCCATCACTTTCTCGGCCGGGAATAAAATATT<br>SEQ ID NO:108 |
| G215A | AAGAAAGTCCTGGCCGGCTCGTGAAGCAACTCAT<br>SEQ ID NO:109 | ATGAGTTGCTTCACGAGCCGCCAGGACTTTCTT<br>SEQ ID NO:110 |
| G227A | GACGAGAGTCTCCTTGCAGAGGTCAAGTATGCA<br>SEQ ID NO:111 | TGCATACTTGACCTCTGCAAGGAGACTCTCGTC<br>SEQ ID NO:112 |
| G254A | TTTATCGAAATTTTCGCTCAGATTGATAGTGAA<br>SEQ ID NO:113 | TTCACTATCAATCTGAGCGAAAATTTCGATAAA<br>SEQ ID NO:114 |
| G327A | GAACCAGAATTTAGTGCCTCTCGCGTGGCATTC<br>SEQ ID NO:115 | GAATGCCACGCGAGAGGCACTAAATTCTGGTTC<br>SEQ ID NO:116 |
| G350A | TTATACGACACGCATGCGACGCTGGATCAATTG<br>SEQ ID NO:117 | CAATTGATCCAGCGTCGCATGCGTGTCGTATAA<br>SEQ ID NO:118 |
| G361A | AAAATATTTACCGAAGCTGTGCGCAGGTGGGAC<br>SEQ ID NO:119 | GTCCCACCTGCGCACAGCTTCGGTAAATATTTT<br>SEQ ID NO:120 |
| G372A | GTGTCGCTGGTGGAGGCCCTGCCGGATTTCATG<br>SEQ ID NO:121 | CATGAAATCCGGCAGGGCCTCCACCAGCGACAC<br>SEQ ID NO:122 |
| G400A | GCGGTTAAGGCCCAAGCCCAGGATATGGCGGCC<br>SEQ ID NO:123 | GGCCGCCATATCCTGGGCTTGGGCCTTAACCGC<br>SEQ ID NO:124 |
| G429A | GAATGGATCGCCACCGCTCACGTTCCGACATTC<br>SEQ ID NO:125 | GAATGTCGGAACGTGAGCGGTGGCGATCCATTC<br>SEQ ID NO:126 |
| G441A | GAATATCTGAACAATGCCACCCCCAACACCGGT<br>SEQ ID NO:127 | ACCGGTGTTGGGGGTGGCATTGTTCAGATATTC<br>SEQ ID NO:128 |
| G459A | CCGTTGCTGCTTATGGCCGAACACTTGCCGATC<br>SEQ ID NO:129 | GATCGGCAAGTGTTCGGCCATAAGCAGCAACGG<br>SEQ ID NO:130 |
| G500A | GCCCGAAAAAGATCATGCTGATTTATCCTGCATC<br>SEQ ID NO:131 | GATGCAGGATAAATCAGCATGATCTTTTTCGGC<br>SEQ ID NO:132 |
| G526A | CTGAATCACGTCAACGCCCTGCTGGGGAATTGT<br>SEQ ID NO:133 | ACAATTCCCCAGCAGGGCGTTGACGTGATTCAG<br>SEQ ID NO:134 |
| G529A | GTCAACGGCCTGCTGGCGAATTGTTTGCTGGAA<br>SEQ ID NO:135 | TTCCAGCAAACAATTCGCCAGCAGGCCGTTGAC<br>SEQ ID NO:136 |
| G569A | TTTATGTATAACCAGGCGGACGGGTTTTCGATT<br>SEQ ID NO:137 | AATCGAAAACCCGTCCGCCTGGTTATACATAAA<br>SEQ ID NO:138 |
| G571A | TATAACCAGGGGGACGCGTTTTCGATTTCGAAC<br>SEQ ID NO:139 | GTTCGAAATCGAAAACGCGTCCCCCTGGTTATA<br>SEQ ID NO:140 |
| E56G | AGCGAAAAATTGATTGGAGAAATTAAGCTCCTG<br>SEQ ID NO:141 | CAGGAGCTTAATTTCTCCAATCAATTTTTCGCT<br>SEQ ID NO:142 |
| D93G | GAGTGTCTGGGCATTGGTCGTCATTTCCAACCT<br>SEQ ID NO:143 | AGGTTGGAAATGACGACCAATGCCCAGACACTC<br>SEQ ID NO:144 |
| R142G | GCTTTACGCTTACACGGTTATAATGTAAGCTCA<br>SEQ ID NO:145 | TGAGCTTACATTATAACCGTGTAAGCGTAAAGC<br>SEQ ID NO:146 |
| P236G | TATGCACTAGAATTTGGGTGGCATTGTTCCGTG<br>SEQ ID NO:147 | CACGGAACAATGCCACCCAAATTCTAGTGCATA<br>SEQ ID NO:148 |
| S298G | TGGTTCGCCGATTCAGGTATCGCAAGTCTG<br>SEQ ID NO:149 | CAGACTTGCGATACCTGAATCGGCGAACCA<br>SEQ ID NO:150 |
| A331G | AGTGGCTCTCGCGTGGGATTCACTAAAATTGCG<br>SEQ ID NO:151 | CGCAATTTTAGTGAATCCCACGCGAGAGCCACT<br>SEQ ID NO:152 |
| I379G | CCGGATTTCATGAAAGGTGCCTTTGAGTTCTGG<br>SEQ ID NO:153 | CCAGAACTCAAAGGCACCTTTCATGAAATCCGG<br>SEQ ID NO:154 |
| C448G | CCCAACACCGGTATGGGTGTACTTAATCTGATC<br>SEQ ID NO:155 | GATCAGATTAAGTACACCCATACCGGTGTTGGG<br>SEQ ID NO:156 |
| D488G | GCTAGCCCGACTGGTCGGTGATGCGAGAGATTTT<br>SEQ ID NO:157 | AAAATCTCTCGCATCACCGACCAGTCGGCTAGC<br>SEQ ID NO:158 |

Figure 13B

| Mutation | Forward Primer (5'→3') | Reverse Primer (5'→3') |
|---|---|---|
| C504G | CATGGTGATTTATCCGGCATCGAATGCTACCTG<br>SEQ ID NO:159 | CAGGTAGCATTCGATGCCGGATAAATCACCATG<br>SEQ ID NO:160 |
| E514G | CTGAAAGACCATCCGGGATCAACAGTTGAAGAC<br>SEQ ID NO:161 | GTCTTCAACTGTTGATCCCGGATGGTCTTTCAG<br>SEQ ID NO:162 |
| P10A | AGCGAATCAGTGTCTGCAAGCACCGACCTTAAA<br>SEQ ID NO:163 | TTTAAGGTCGGTGCTTGCAGACACTGATTCGCT<br>SEQ ID NO:164 |
| P41A | CAGAGCTTAAACAGCGCATATGGCGCACCCGCT<br>SEQ ID NO:165 | AGCGGGTGCGCCATATGCGCTGTTTAAGCTCTG<br>SEQ ID NO:166 |
| P45A | AGCCCATATGGCGCAGCCGCTTATCAGGAACGT<br>SEQ ID NO:167 | ACGTTCCTGATAAGCGGCTGCGCCATATGGGCT<br>SEQ ID NO:168 |
| P98A | GATCGTCATTTCCAAGCTGAAATTAAGCTGGCG<br>SEQ ID NO:169 | CGCCAGCTTAATTTCAGCTTGGAAATGACGATC<br>SEQ ID NO:170 |
| P193A | TCCAATATTTTATTCGCGGGCGAGAAAGTGATG<br>SEQ ID NO:171 | CATCACTTTCTCGCCCGCGAATAAAATATTGGA<br>SEQ ID NO:172 |
| P236A | TATGCACTAGAATTTGCGTGGCATTGTTCCGTG<br>SEQ ID NO:173 | CACGGAACAATGCCACGCAAATTCTAGTGCATA<br>SEQ ID NO:174 |
| P323A | GCGGCAATTTCAGAAGCAGAATTTAGTGGCTCT<br>SEQ ID NO:175 | AGAGCCACTAAATTCTGCTTCTGAAATTGCCGC<br>SEQ ID NO:176 |
| P374A | CTGGTGGAGGGCCTGGCGGATTTCATGAAAATT<br>SEQ ID NO:177 | AATTTTCATGAAATCCGCCAGGCCCTCCACCAG<br>SEQ ID NO:178 |
| P432A | GCCACCGGTCACGTTGCGACATTCGATGAATAT<br>SEQ ID NO:179 | ATATTCATCGAATGTCGCAACGTGACCGGTGCC<br>SEQ ID NO:180 |
| P443A | CTGAACAATGGCACCGCCAACACCGGTATGTGT<br>SEQ ID NO:181 | ACACATACCGGTGTTGGCGGTGCCATTGTTCAG<br>SEQ ID NO:182 |
| P454A | GTACTTAATCTGATCGCGTTGCTGCTTATGGGC<br>SEQ ID NO:183 | GCCCATAAGCAGCAACGCGATCAGATTAAGTAC<br>SEQ ID NO:184 |
| P463A | ATGGGCGAACACTTGGCGATCGATATTCTTGAA<br>SEQ ID NO:185 | TTCAAGAATATCGATCGCCAAGTGTTCGCCCAT<br>SEQ ID NO:186 |
| P473A | GAACAGATCTTTCTGGCGAGCCGGTTCCACCAT<br>SEQ ID NO:187 | ATGGTGGAACCGGCTCGCCAGAAAGATCTGTTC<br>SEQ ID NO:188 |
| P513A | TACCTGAAAGACCATGCGGAATCAACAGTTGAA<br>SEQ ID NO:189 | TTCAACTGTTGATTCCGCATGGTCTTTCAGGTA<br>SEQ ID NO:190 |
| P547A | AAACAGGACTCGGTAGCTCTGTCGTGTAAAAAA<br>SEQ ID NO:191 | TTTTTTACACGACAGAGCTACCGAGTCCTGTTT<br>SEQ ID NO:192 |
| P590A | None | GCTCTAGATTATATAGGAACCGCAACGATTAGAACTTT<br>SEQ ID NO:193 |
| P592A | None | GCTCTAGATTATATAGCAACCGGAACGATTAG<br>SEQ ID NO:194 |
| G27P | ACCAGCAACCGCCACCCGAACATGTGGGAAGAT<br>SEQ ID NO:195 | ATCTTCCCACATGTTCGGGTGGCGGTTGCTGGT<br>SEQ ID NO:196 |
| L124P | GGTAGCCGTGATAGCCCAAAAAAGGACCTGAAT<br>SEQ ID NO:197 | ATTCAGGTCCTTTTTTGGGCTATCACGGCTACC<br>SEQ ID NO:198 |
| K126P | CGTGATAGCTTAAAACCGGACCTGAATGCGACC<br>SEQ ID NO:199 | GGTCGCATTCAGGTCCGGTTTTAAGCTATCACG<br>SEQ ID NO:200 |
| N144P | CGCTTACACCGTTATCCTGTAAGCTCAGGAGTG<br>SEQ ID NO:201 | CACTCCTGAGCTTACAGGATAACGGTGTAAGCG<br>SEQ ID NO:202 |
| S147P | CGTTATAATGTAAGCCCAGGAGTGCTGGAGAAC<br>SEQ ID NO:203 | GTTCTCCAGCACTCCTGGGCTTACATTATAACG<br>SEQ ID NO:204 |
| N207P | AAGGCGTTTACGACCCCTATCTTAAGAAAGTC<br>SEQ ID NO:205 | GACTTTCTTAAGATAGGGGGTCGTAAACGCCTT<br>SEQ ID NO:206 |
| N220P | GGTCGTGAAGCAACTCCTGTCGACGAGAGTCTC<br>SEQ ID NO:207 | GAGACTCTCGTCGACAGGAGTTGCTTCACGACC<br>SEQ ID NO:208 |
| Q242P | TGGCATTGTTCCGTGCCGCGCTGGGAGGCACGT<br>SEQ ID NO:209 | ACGTGCCTCCCAGCGCGGCACGGAACAATGCCA<br>SEQ ID NO:210 |
| Q255P | ATCGAAATTTTCGGTCCGATTGATAGTGAACTG<br>SEQ ID NO:211 | CAGTTCACTATCAATCGGACCGAAAATTTCGAT<br>SEQ ID NO:212 |
| A300P | GCCGATTCAAGTATCCCAAGTCTGAACTTTTAC<br>SEQ ID NO:213 | GTAAAAGTTCAGACTTGGGATACTTGAATCGGC<br>SEQ ID NO:214 |
| S298G | TGGTTCGCCGATTCAGGTATCGCAAGTCTG<br>SEQ ID NO:215 | CAGACTTGCGATACCTGAATCGGCGAACCA<br>SEQ ID NO:216 |
| A331G | AGTGGCTCTCGCGTGGGATTCACTAAAATTGCG<br>SEQ ID NO:217 | CGCAATTTTAGTGAATCCCACGCGAGAGCCACT<br>SEQ ID NO:218 |
| I379G | CCGGATTTCATGAAAGGTGCCTTTGAGTTCTGG<br>SEQ ID NO:219 | CCAGAACTCAAAGGCACCTTTCATGAAATCCGG<br>SEQ ID NO:220 |
| C448G | CCCAACACCGGTATGGGTGTACTTAATCTGATC<br>SEQ ID NO:221 | GATCAGATTAAGTACACCCATACCGGTGTTGGG<br>SEQ ID NO:222 |
| D488G | GCTAGCCGACTGGTCGGTGATGCGAGAGATTTT<br>SEQ ID NO:223 | AAAATCTCTCGCATCACCGACCAGTCGGCTAGC<br>SEQ ID NO:224 |
| C504G | CATGGTGATTTATCCGGCATCGAATGCTACCTG<br>SEQ ID NO:225 | CAGGTAGCATTCGATGCCGGATAAATCACCATG<br>SEQ ID NO:226 |
| E514G | CTGAAAGACCATCCGGGATCAACAGTTGAAGAC<br>SEQ ID NO:227 | GTCTTCAACTGTTGATCCCGGATGGTCTTTCAG<br>SEQ ID NO:228 |

Figure 13C

| Mutation | Forward Primer (5'→3') | Reverse Primer (5'→3') |
|---|---|---|
| P10A | AGCGAATCAGTGTCTGCAAGCACCGACCTTAAA<br>SEQ ID NO:229 | TTTAAGGTCGGTGCTTGCAGACACTGATTCGCT<br>SEQ ID NO:230 |
| P41A | CAGAGCTTAAACAGCGCATATGGCGCACCCGCT<br>SEQ ID NO:231 | AGCGGGTGCGCCATATGCGCTGTTTAAGCTCTG<br>SEQ ID NO:232 |
| P45A | AGCCCATATGGCGCAGCCGCTTATCAGGAACGT<br>SEQ ID NO:233 | ACGTTCCTGATAAGCGGCTGCGCCATATGGGCT<br>SEQ ID NO:234 |
| P98A | GATCGTCATTTCCAAGCTGAAATTAAGCTGGCG<br>SEQ ID NO:235 | CGCCAGCTTAATTTCAGCTTGGAAATGACGATC<br>SEQ ID NO:236 |
| P193A | TCCAATATTTTATTCGCGGGCGAGAAAGTGATG3<br>SEQ ID NO:237 | CATCACTTTCTCGCCCGCGAATAAAATATTGGA<br>SEQ ID NO:238 |
| P236A | TATGCACTAGAATTTGCGTGGCATTGTTCCGTG<br>SEQ ID NO:239 | CACGGAACAATGCCACGCAAATTCTAGTGCATA<br>SEQ ID NO:240 |
| P323A | GCGGCAATTTCAGAAGCAGAATTTAGTGGCTCT<br>SEQ ID NO:241 | AGAGCCACTAAATTCTGCTTCTGAAATTGCCGC<br>SEQ ID NO:242 |
| P374A | CTGGTGGAGGGCCTGGCGGATTTCATGAAAATT<br>SEQ ID NO:243 | AATTTTCATGAAATCCGCCAGGCCCTCCACCAG<br>SEQ ID NO:244 |
| P432A | GCCACCGGTCACGTTGCGACATTCGATGAATAT<br>SEQ ID NO:245 | ATATTCATCGAATGTCGCAACGTGACCGGTGGC<br>SEQ ID NO:246 |
| P443A | CTGAACAATGGCACCGCCAACACCGGTATGTGT<br>SEQ ID NO:247 | ACACATACCGGTGTTGGCGGTGCCATTGTTCAG<br>SEQ ID NO:248 |
| P454A | GTACTTAATCTGATCGCGTTGCTGCTTATGGGC<br>SEQ ID NO:249 | GCCCATAAGCAGCAACGCGATCAGATTAAGTAC<br>SEQ ID NO:250 |
| P463A | ATGGGCGAACACTTGGCGATCGATATTCTTGAA<br>SEQ ID NO:251 | TTCAAGAATATCGATCGCCAAGTGTTCGCCCAT<br>SEQ ID NO:252 |
| P473A | GAACAGATCTTTCTGGCGAGCCGGTTCCACCAT<br>SEQ ID NO:253 | ATGGTGGAACCGGCTCGCCAGAAAGATCTGTTC<br>SEQ ID NO:254 |
| P513A | TACCTGAAAGACCATGCGGAATCAACAGTTGAA<br>SEQ ID NO:255 | TTCAACTGTTGATTCCGCATGGTCTTTCAGGTA<br>SEQ ID NO:256 |
| P547A | AAACAGGACTCGGTAGCTCTGTCGTGTAAAAAA<br>SEQ ID NO:257 | TTTTTTACACGACAGAGCTACCGAGTCCTGTTT<br>SEQ ID NO:258 |
| P590A | None | GCTCTAGATTATATAGGAACCGCAACGATTAGAACTTT<br>SEQ ID NO:259 |
| P592A | None | GCTCTAGATTATATAGCAACCGGAACGATTAG<br>SEQ ID NO:260 |
| G27P | ACCAGCAACCGCCACCCGAACATGTGGAAGAT<br>SEQ ID NO:261 | ATCTTCCCACATGTTCGGGTGGCGGTTGCTGGT<br>SEQ ID NO:262 |
| L124P | GGTAGCCGTGATAGCCCAAAAAAGGACCTGAAT<br>SEQ ID NO:263 | ATTCAGGTCCTTTTTTGGGCTATCACGGCTACC<br>SEQ ID NO:264 |
| K126P | CGTGATAGCTTAAAACCGGACCTGAATGCGACC<br>SEQ ID NO:265 | GGTCGCATTCAGGTCCGGTTTTAAGCTATCACG<br>SEQ ID NO:266 |
| N144P | CGCTTACACCGTTATCCTGTAAGCTCAGGAGTG<br>SEQ ID NO:267 | CACTCCTGAGCTTACAGGATAACGGTGTAAGCG<br>SEQ ID NO:268 |
| S147P | CGTTATAATGTAAGCCCAGGAGTGCTGGAGAAC<br>SEQ ID NO:269 | GTTCTCCAGCACTCCTGGGCTTACATTATAACG<br>SEQ ID NO:270 |
| N207P | AAGGCGTTTACGACCCCTATCTTAAGAAAGTC<br>SEQ ID NO:271 | GACTTTCTTAAGATAGGGGTCGTAAACGCCTT<br>SEQ ID NO:272 |
| N220P | GGTCGTGAAGCAACTCCTGTCGACGAGAGTCTC<br>SEQ ID NO:273 | GAGACTCTCGTCGACAGGAGTTGCTTCACGACC<br>SEQ ID NO:274 |
| Q242P | TGGCATTGTTCCGTGCCGCGCTGGGAGGCACGT<br>SEQ ID NO:275 | ACGTGCCTCCCAGCGCGGCACGGAACAATGCCA<br>SEQ ID NO:276 |
| Q255P | ATCGAAATTTTCGGTCCGATTGATAGTGAACTG<br>SEQ ID NO:277 | CAGTTCACTATCAATCGGACCGAAAATTTCGAT<br>SEQ ID NO:278 |
| A300P | GCCGATTCAAGTATCCCAAGTCTGAACTTTTAC<br>SEQ ID NO:279 | GTAAAAGTTCAGACTTGGGATACTTGAATCGGC<br>SEQ ID NO:280 |
| Y309P | TTTTACCGTAAATGCCCTGTGGAATTTTACTTC<br>SEQ ID NO:281 | GAAGTAAAATTCCACAGGGCATTTACGGTAAAA<br>SEQ ID NO:282 |
| V367P | GTGCGCAGGTGGGACCCGTCGCTGGTGGAGGGC<br>SEQ ID NO:283 | GCCCTCCACCAGCGACGGGTCCCACCTGCGCAC<br>SEQ ID NO:284 |
| A411P | TATATCCGCAAAAACCCTTGGGAACGCTATCTG<br>SEQ ID NO:285 | CAGATAGCGTTCCCAAGGGTTTTTGCGGATATA<br>SEQ ID NO:286 |
| V449P | AACACCGGTATGTGTCCACTTAATCTGATCCCG<br>SEQ ID NO:287 | CGGGATCAGATTAAGTGGACACATACCGGTGTT<br>SEQ ID NO:288 |
| H461P | CTGCTTATGGGCGAACCCTTGCCGATCGATATT<br>SEQ ID NO:289 | AATATCGATCGGCAAGGGTTCGCCCATAAGCAG<br>SEQ ID NO:290 |
| K542P | TGGAAATTTCTGAAACCACAGGACTCGGTACCT<br>SEQ ID NO:291 | AGGTACCGAGTCCTGTGGTTTCAGAAATTTCCA<br>SEQ ID NO:292 |

Figure 14A

| Mutation | Forward Primer (5'→3') | Reverse Primer (5'→3') |
|---|---|---|
| G11A | AACAAAACCGTCATTAGCGCCAGCAAGGTGAAGTCTCTG<br>SEQ ID NO:293 | CAGAGACTTCACCTTGCTGGCGCTAATGACGGTTTTGTT<br>SEQ ID NO:294 |
| G26A | GCCCAAAGCTCTAGCAGCGCCCCGTCTAGCAGCAGCGAG<br>SEQ ID NO:295 | CTCGCTGCTGCTAGACGGGGCGCTGCTAGAGCTTTGGGC<br>SEQ ID NO:296 |
| G59A | GAGGCCCTGCTGAGCAGCGCCAACACCAAGCAGCTGAAG<br>SEQ ID NO:297 | CTTCAGCTGCTTGGTGTTGGCGCTGCTCAGCAGGGCCTC<br>SEQ ID NO:298 |
| G76A | GCAGCGCTGGTGATCCACGCTAAGCTGCCACTGTATGCG<br>SEQ ID NO:299 | CGCATACAGTGGCAGCTTAGCGTGGATCACCAGCGCTGC<br>SEQ ID NO:300 |
| G88A | GCGCTGGAAAAGAAACTGGCCGATACGACGCGTGCGGTC<br>SEQ ID NO:301 | GACCGCACGCGTCGTATCGGCCAGTTTCTTTTCCAGCGC<br>SEQ ID NO:302 |
| G127A | GACTACGACCGCGTGTTTGCCGCGTGCTGCGAGAATGTC<br>SEQ ID NO:303 | GACATTCTCGCAGCACGCGGCAAACACGCGGTCGTAGTC<br>SEQ ID NO:304 |
| G135A | TGCTGCGAGAATGTCATTGCCTACATGCCGTTACCGGTT<br>SEQ ID NO:305 | AACCGGTAACGGCATGTAGGCAATGACATTCTCGCAGCA<br>SEQ ID NO:306 |
| G142A | TACATGCCGTTACCGGTTGCTGTGATCGGCCCCGCTGGTC<br>SEQ ID NO:307 | GACCAGCGGGCCGATCACAGCAACCGGTAACGGCATGTA<br>SEQ ID NO:308 |
| G145A | TTACCGGTTGGTGTGATCGCCCCGCTGGTCATTGATGCC<br>SEQ ID NO:309 | GCCATCAATGACCAGCGGGGCGATCACACCAACCGGTAA<br>SEQ ID NO:310 |
| G151A | GGCCCGCTGGTCATTGATGCCACGAGCTATCACATTCCA<br>SEQ ID NO:311 | TGGAATGTGATAGCTCGTGGCATCAATGACCAGCGGGCC<br>SEQ ID NO:312 |
| G163A | CCAATGGCGACCACGGAAGCTTGCTTAGTCGCCAGCGCC<br>SEQ ID NO:313 | GGCGCTGGCGACTAAGCAAGCTTCCGTGGTCGCCATTGG<br>SEQ ID NO:314 |
| G172A | GTCGCCAGCGCCATGCGTGCCTGTAAGGCGATTAACGCC<br>SEQ ID NO:315 | GGCGTTAATCGCCTTACAGGCACGCATGGCGCTGGCGAC<br>SEQ ID NO:316 |
| G179A | TGTAAGGCGATTAACGCCGCCGGTGGCGCGACGACCGTG<br>SEQ ID NO:317 | CACGGTCGTCGCGCCACCGGCGGCGTTAATCGCCTTACA<br>SEQ ID NO:318 |
| G180A | AAGGCGATTAACGCCGGCGCTGGCGCGACGACCGTGTTA<br>SEQ ID NO:319 | TAACACGGTCGTCGCGCCAGCGCCGGCGTTAATCGCCTT<br>SEQ ID NO:320 |
| G181A | GCGATTAACGCCGGCGGTGCCGCGACGACCGTGTTAACC<br>SEQ ID NO:321 | GGTTAACACGGTCGTCGCGGCACCGCCGGCGTTAATCGC<br>SEQ ID NO:322 |
| G190A | GTGTTAACCAAGGATGCCATGACGCGCGGTCCG<br>SEQ ID NO:323 | CGGACCGCGCGTCATGGCATCCTTGGTTAACAC<br>SEQ ID NO:324 |
| G194A | AAGGATGGTATGACGCGCGCTCCGGTCGTCCGCTTCCCA<br>SEQ ID NO:325 | TGGGAAGCGGACGACCGGAGCGCGCGTCATACCATCCTT<br>SEQ ID NO:326 |
| G190A/G194A | GTGTTAACCAAGGATGCCATGACGCGCGCGTCCGGTCGTCCGCTTC<br>SEQ ID NO:327 | GAAGCGGACGACCGGAGCGCGCGTCATGGCATCCTTGGTTAACAC<br>SEQ ID NO:328 |
| G206A | CCAACGCTGAAGCGCAGCGCCGCGTGTAAGATTTGGCTG<br>SEQ ID NO:329 | CAGCCAAATCTTACACGCGGCGCTGCGCTTCAGCGTTGG<br>SEQ ID NO:330 |
| G217A | TGGCTGGATTCTGAGGACGCCCAAAACGCGATCAAGAAA<br>SEQ ID NO:331 | TTTCTTGATCGCGTTTTGGGCCTCCTCAGAATCCAGCCA<br>SEQ ID NO:332 |
| G243A | ATCCAGACCTGCCTGGCCGCCGACCTGCTGTTCATGCCC<br>SEQ ID NO:333 | GCGCATGAACAGCAGGTCGGCGGCCAGGCAGGTCTGGAT<br>SEQ ID NO:334 |
| G255A | CGCTTCCGCACCACCACGGCCGATGCGATGGGCATGAAC<br>SEQ ID NO:335 | GTTCATGCCCATCGCATCGGCCGTGGTGGTGCGGAAGCG<br>SEQ ID NO:336 |
| G259A | ACCACGGGCGATGCGATGGCCATGAACATGATCAGCAAG<br>SEQ ID NO:337 | CTTGCTGATCATGTTCATGGCCATCGCATCGCCCGTGGT<br>SEQ ID NO:338 |
| G266A | ATGAACATGATCAGCAAGGCCGTCGAATATAGCCTGAAA<br>SEQ ID NO:339 | TTTCAGGCTATATTCGACGGCCTTGCTGATCATGTTCAT<br>SEQ ID NO:340 |
| G279A | CAAATGGTGGAAGAATATGCCTGGGAGGACATGGAGGTT<br>SEQ ID NO:341 | AACCTCCATGTCCTCCCAGGCATATTCTTCCACCATTTG<br>SEQ ID NO:342 |
| G290A | GAGGTTGTCTCTGTGAGCGCCAACTATTGCACCGACAAG<br>SEQ ID NO:343 | CTTGTCGGTGCAATAGTTGGCGCTCACAGAGACAACCTC<br>SEQ ID NO:344 |
| G306A | GCCATTAACTGGATTGAGGCTCGCGGCAAAAGCGTCGTG<br>SEQ ID NO:345 | CACGACGCTTTTGCCGCGAGCCTCAATCCAGTTAATGGC<br>SEQ ID NO:346 |
| G308A | AACTGGATTGAGGGTCGCGCCAAAAGCGTCGTGGCAGAA<br>SEQ ID NO:347 | TTCTGCCACGACGCTTTTGGCGCGACCCTCAATCCAGTT<br>SEQ ID NO:348 |
| G319A | GCAGAAGCGACCATCCCAGCCGACGTGGTCCGTAAGGTT<br>SEQ ID NO:349 | AACCTTACGGACCACGTCGGCTGGGATGGTCGCTTCTGC<br>SEQ ID NO:350 |
| G344A | ATCGCGAAAAACCTGGTCGCCAGCGCGATGGCGGGCAGC<br>SEQ ID NO:351 | GCTGCCCGCCATCGCGCTGGCGACCAGGTTTTTCGCGAT<br>SEQ ID NO:352 |
| G349A | GTCGGCAGCGCGATGGCGGCCAGCGTGGGTGGCTTTAAC<br>SEQ ID NO:353 | GTTAAAGCCACCCACGCTGGCCGCCATCGCGCTGCCGAC<br>SEQ ID NO:354 |
| G349A/G352A/G353A | GGCAGCGCGATGGCGGCCAGCGTGGCTGCCTTTAACGCACATGCA<br>SEQ ID NO:355 | TGCATGTGCGTTAAAGGCAGCCACGCTGGCCGCCATCGCGCTGCC<br>SEQ ID NO:356 |
| G349A/G352A | GGCAGCGCGATGGCGGCCAGCGTGGCTGGCTTAACGCACATGCA<br>SEQ ID NO:357 | TGCATGTGCGTTAAAGCCAGCCACGCTGGCCGCCATCGCGCTGCC<br>SEQ ID NO:358 |
| G349A/G353A | GGCAGCGCGATGGCGGCCAGCGTGGGTGCCTTTAACGCACATGCA<br>SEQ ID NO:359 | TGCATGTGCGTTAAAGGCACCCACGCTGGCCGCCATCGCGCTGCC<br>SEQ ID NO:360 |
| G352A/G353A | GGCAGCGCGATGGCGGGCAGCGTGGCTGCCTTTAACGCACATGCA<br>SEQ ID NO:361 | TGCATGTGCGTTAAAGGCAGCCACGCTGCCCGCCATCGCGCTGCC<br>SEQ ID NO:362 |
| G352A | GCGATGGCGGGCAGCGTGGCTGCCTTTAACGCACATGCA<br>SEQ ID NO:363 | TGCATGTGCGTTAAAGCCAGCCACGCTGCCCGCCATCGC<br>SEQ ID NO:364 |

Figure 14B

| Mutation | Forward Primer (5'→3') | Reverse Primer (5'→3') |
|---|---|---|
| G353A | ATGGCGGGCAGCGTGGGTGCCTTTAACGCACATGCAGCG<br>SEQ ID NO:365 | CGCTGCATGTGCGTTAAAGGCACCCACGCTGCCCGCCAT<br>SEQ ID NO:366 |
| G370A | GCGGTTTTCTTAGCCTTAGCTCAGGACCCAGCCCAAAAT<br>SEQ ID NO:367 | ATTTTGGGCTGGGTCCTGAGCTAAGGCTAAGAAAACCGC<br>SEQ ID NO:368 |
| G391A | TTAATGAAAGAGGTTGACGCTGACCTGCGCATCAGCGTT<br>SEQ ID NO:369 | AACGCTGATGCGCAGGTCAGCGTCAACCTCTTTCATTAA<br>SEQ ID NO:370 |
| G405A | ATGCCGTCTATCGAGGTCGCCACGATCGGCGGCGGCACC<br>SEQ ID NO:371 | GGTGCCGCCGCCGATCGTGGCGACCTCGATAGACGGCAT<br>SEQ ID NO:372 |
| G408A | ATCGAGGTCGGCACGATCGCCGGCGGCACCGTTTTAGAA<br>SEQ ID NO:373 | TTCTAAAACGGTGCCGCCGGCGATCGTGCCGACCTCGAT<br>SEQ ID NO:374 |
| G409A | GAGGTCGGCACGATCGGCGCCGGCACCGTTTTAGAACCG<br>SEQ ID NO:375 | CGGTTCTAAAACGGTGCCGGCGCCGATCGTGCCGACCTC<br>SEQ ID NO:376 |
| G410A | GTCGGCACGATCGGCGGCGCCACCGTTTTAGAACCGCAA<br>SEQ ID NO:377 | TTGCGGTTCTAAAACGGTGGCGCCGCCGATCGTGCCGAC<br>SEQ ID NO:378 |
| G417A | ACCGTTTTAGAACCGCAAGCTGCGATGCTGGATCTGCTG<br>SEQ ID NO:379 | CAGCAGATCCAGCATCGCAGCTTGCGGTTCTAAAACGGT<br>SEQ ID NO:380 |
| G424A | GCGATGCTGGATCTGCTGGCCGTGCGCGGCCCACATGCA<br>SEQ ID NO:381 | TGCATGTGGGCCGCGCACGGCCAGCAGATCCAGCATCGC<br>SEQ ID NO:382 |
| G427A | GATCTGCTGGGCGTGCGCGCCCCACATGCAACGGCCCCA<br>SEQ ID NO:383 | TGGGGCCGTTGCATGTGGGGCGCGCACGCCCAGCAGATC<br>SEQ ID NO:384 |
| G434A | CCACATGCAACGGCCCCAGCCACCAATGCCCGCCAACTG<br>SEQ ID NO:385 | CAGTTGGCGGGCATTGGTGGCTGGGGCCGTTGCATGTGG<br>SEQ ID NO:386 |
| G451A | GCCTGCGCGGTTCTCGCGGCTGAGCTGAGCCTGTGCGCC<br>SEQ ID NO:387 | GGCGCACAGGCTCAGCTCAGCCGCCAGAACCGCGCAGGC<br>SEQ ID NO:388 |
| G462A | TGCGCCGCATTAGCCGCGGCCCATTTAGTTCAATCTCAC<br>SEQ ID NO:389 | GTGAGATTGAACTAAATGGGCCGCGGCTAATGCGGCGCA<br>SEQ ID NO:390 |
| G495A | ATTAACCGTCTGAAGGATGCCAGCGTCACGTGCATTAAA<br>SEQ ID NO:391 | TTTAATGCACGTGACGCTGGCATCCTTCAGACGGTTAAT<br>SEQ ID NO:392 |
| A93G | GGCGATACGACGCGTGGGGTCGCGGTGCGTCGC<br>SEQ ID NO:393 | GCGACGCACCGCGACCCCACGCGTCGTATCGCC<br>SEQ ID NO:394 |
| A232G | TCTACGAGCCGTTTCGGGCGTTTACAGCATATC<br>SEQ ID NO:395 | GATATGCTGTAAACGCCCGAAACGGCTCGTAGA<br>SEQ ID NO:396 |
| T363G | GCAGCGAATCTCGTTGGGGCGGTTTTCTTAGCC<br>SEQ ID NO:397 | GGCTAAGAAAACCGCCCCAACCAGATTCGCTGC<br>SEQ ID NO:398 |
| E378G | CCAGCCCAAAATGTCGGGAGCAGCAACTGCATT<br>SEQ ID NO:399 | AATGCAGTTGCTGCTCCCGACATTTTGGGCTGG<br>SEQ ID NO:400 |
| C379G | GCCCAAAATGTCGAGGGCAGCAACTGCATTACC<br>SEQ ID NO:401 | GGTAATGCAGTTGCTGCCCTCGACATTTTGGGC<br>SEQ ID NO:402 |
| C382G | GTCGAGAGCAGCAACGGCATTACCTTAATGAAA<br>SEQ ID NO:403 | TTTCATTAAGGTAATGCCGTTGCTGCTCTCGAC<br>SEQ ID NO:404 |
| P428G | CTGGGCGTGCGCGGCGGACATGCAACGGCCCCA<br>SEQ ID NO:405 | TGGGGCCGTTGCATGTCCGCCGCGCACGCCCAG<br>SEQ ID NO:406 |
| A430G | GTGCGCGGCCCACATGGAACGGCCCCAGGCACC<br>SEQ ID NO:407 | GGTGCCTGGGGCCGTTCCATGTGGGCCGCGCAC<br>SEQ ID NO:408 |
| C446G | GCCCGTATCGTGGCCGGCGCGGTTCTGGCGGGT<br>SEQ ID NO:409 | ACCCGCCAGAACCGCGCCGGCCACGATACGGGC<br>SEQ ID NO:410 |
| N472G | AACCGCAAGCCGGCAGGACCAACCAAGCCAAAT<br>SEQ ID NO:411 | ATTTGGCTTGGTTGGTCCTGCCGGCTTGCGGTT<br>SEQ ID NO:412 |
| E106G | TTAAGCATCTTAGCGGGGCCCCCGGTGTTAGCC<br>SEQ ID NO:413 | GGCTAACACCGGGGCCCCCGCTAAGATGCTTAA<br>SEQ ID NO:414 |
| P116G | GCCAGCGACCGCCTGGGGTACAAGAACTACGAC<br>SEQ ID NO:415 | GTCGTAGTTCTTGTACCCCAGGCGGTCGCTGGC<br>SEQ ID NO:416 |
| D392G | AAAGAGGTTGACGGTGGCCTGCGCATCAGCGTT<br>SEQ ID NO:417 | AACGCTGATGCGCAGGCCACCGTCAACCTCTTT<br>SEQ ID NO:418 |
| V412G | ATCGGCGGCGGCACCGGTTTAGAACCGCAAGGT<br>SEQ ID NO:419 | ACCTTGCGGTTCTAAACCGGTGCCGCCGCCGAT<br>SEQ ID NO:420 |
| A447G | CGTATCGTGGCCTGCGGGGTTCTGGCGGGTGAG<br>SEQ ID NO:421 | CTCACCCGCCAGAACCCCGCAGGCCACGATACG<br>SEQ ID NO:422 |
| A457G | GAGCTGAGCCTGTGCGGCGCATTAGCCGCGGGC<br>SEQ ID NO:423 | GCCCGCGGCTAATGCGCCGCACAGGCTCAGCTC<br>SEQ ID NO:424 |
| N472G | TCTCACATGACCCACGGCCGCAAGCCGGCAGAA<br>SEQ ID NO:425 | TTCTGCCGGCTTGCGGCCGTGGGTCATGTGAGA<br>SEQ ID NO:426 |
| K474G | ATGACCCACAACCGCGGGCCGGCAGAACCAACC<br>SEQ ID NO:427 | GGTTGGTTCTGCCGGCCCGCGGTTGTGGGTCAT<br>SEQ ID NO:428 |
| 378G/379G | CCAGCCCAAAATGTCGGGGGCAGCAACTGCATTACC<br>SEQ ID NO:429 | GGTAATGCAGTTGCTGCCCCCGACATTTTGGGCTGG<br>SEQ ID NO:430 |
| 378G/382G | CCAGCCCAAAATGTCGGGAGCAGCAACGGCATTACCTTAATGAAA<br>SEQ ID NO:431 | TTTCATTAAGGTAATGCCGTTGCTGCTCCCGACATTTTGGGCTGG<br>SEQ ID NO:432 |
| 379G/382G | GCCCAAAATGTCGAGGGCAGCAACGGCATTACCTTAATGAAA<br>SEQ ID NO:433 | TTTCATTAAGGTAATGCCGTTGCTGCCCTCGACATTTTGGGC<br>SEQ ID NO:434 |
| 378G/379G/382G | CCAGCCCAAAATGTCGGGGGCAGCAACGGCATTACCTTAATGAAA<br>SEQ ID NO:435 | TTTCATTAAGGTAATGCCGTTGCTGCCCCCGACATTTTGGGCTGG<br>SEQ ID NO:436 |

Figure 14C

| Mutation | Forward Primer (5'→3') | Reverse Primer (5'→3') |
|---|---|---|
| 428G/430G | CTGGGCGTGCGCGGCGGACATGGAACGGCCCCAGGCACC<br>SEQ ID NO:437 | GGTGCCTGGGGCCGTTCCATGTCCGCCGCGCACGCCCAG<br>SEQ ID NO:438 |
| 446G/447G | GCCCGTATCGTGGCCGGCGGGGTTCTGCGGGTGAG<br>SEQ ID NO:439 | CTCACCCGCCAGAACCCCGCCGGCCACGATACGGGC<br>SEQ ID NO:440 |
| 412G/417A | ATCGGCGGCGGCACCGGTTTAGAACCGCAAGCT<br>SEQ ID NO:441 | AGCTTGCGGTTCTAAACCGGTGCCGCCGCCGAT<br>SEQ ID NO:442 |
| 472G/474G | TCTCACATGACCCACGGCCGCGGGCCGGCAGAACCAACC<br>SEQ ID NO:443 | GGTTGGTTCTGCCGGCCCGCGGCCGTGGGTCATGTGAGA<br>SEQ ID NO:444 |
| P27A | AGCTCTAGCAGCGGCGCGTCTAGCAGCAGCGAG<br>SEQ ID NO:445 | CTCGCTGCTGCTAGACGCGCCGCTGCTAGAGCT<br>SEQ ID NO:446 |
| P48A | GACAAGAAGATCCGCGCGCTGGAGGAGTTAGAG<br>SEQ ID NO:447 | CTCTAACTCCTCCAGCGCGCGGATCTTCTTGTC<br>SEQ ID NO:448 |
| P79A | ATCCACGGTAAGCTGGCACTGTATGCGCTGGAA<br>SEQ ID NO:449 | TTCCAGCGCATACAGTGCCAGCTTACCGTGGAT<br>SEQ ID NO:450 |
| P108A | ATCTTAGCGGAGGCCGCGGTGTTAGCCAGCGAC<br>SEQ ID NO:451 | GTCGCTGGCTAACACCGCGGCCTCCGCTAAGAT<br>SEQ ID NO:452 |
| P116A | GCCAGCGACCGCCTGGCGTACAAGAACTACGAC<br>SEQ ID NO:453 | GTCGTAGTTCTTGTACGCCAGGCGGTCGCTGGC<br>SEQ ID NO:454 |
| P138A | GTCATTGGCTACATGGCGTTACCGGTTGGTGTG<br>SEQ ID NO:455 | CACACCAACCGGTAACGCCATGTAGCCAATGAC<br>SEQ ID NO:456 |
| P140A | GGCTACATGCCGTTAGCGGTTGGTGTGATCGGC<br>SEQ ID NO:457 | GCCGATCACACCAACCGCTAACGGCATGTAGCC<br>SEQ ID NO:458 |
| P146A | GTTGGTGTGATCGGCGCGCTGGTCATTGATGGC<br>SEQ ID NO:459 | GCCATCAATGACCAGCGCGCCGATCACACCAAC<br>SEQ ID NO:460 |
| P157A | ACGAGCTATCACATTGCAATGGCGACCACGGAA<br>SEQ ID NO:461 | TTCCGTGGTCGCCATTGCAATGTGATAGCTCGT<br>SEQ ID NO:462 |
| P195A | GGTATGACGCGCGGTGCGGTCGTCCGCTTCCCA<br>SEQ ID NO:463 | TGGGAAGCGGACGACCGCACCGCGCGTCATACC<br>SEQ ID NO:464 |
| P195A/P200A | GGATGGTATGACGCGCGGTGCGGTCGTCCGCTTCGCAACGCTGAA<br>SEQ ID NO:465 | GCTGCGCTTCAGCGTTGCGAAGCGGACGACCGCACCGCGCG<br>SEQ ID NO:466 |
| P200A | CGGTCCGGTCGTCCGCTTCGCAACGCTG<br>SEQ ID NO:467 | CCGCTGCGCTTCAGCGTTGCGAAGCGGA<br>SEQ ID NO:468 |
| P298A | CTATTGCAGCGACAAGAAGGCGGCAGCC<br>SEQ ID NO:469 | ATCCAGTTAATGGCTGCCGCCTTCTTGT<br>SEQ ID NO:470 |
| P318A | GCAGAAGCGACCATCGCAGGCGACGTGGTCCGT<br>SEQ ID NO:471 | ACGGACCACGTCGCCTGCGATGGTCGCTTCTGC<br>SEQ ID NO:472 |
| P373A | GCCTTAGGTCAGGACGCAGCCCAAAATGTCGAG<br>SEQ ID NO:473 | CTCGACATTTTGGGCTGCGTCCTGACCTAAGGC<br>SEQ ID NO:474 |
| P400A | ATCAGCGTTTCTATGGCGTCTATCGAGGTCGGC<br>SEQ ID NO:475 | GCCGACCTCGATAGACGCCATAGAAACGCTGAT<br>SEQ ID NO:476 |
| P415A | GGCACCGTTTTAGAAGCGCAAGGTGCGATGCTG<br>SEQ ID NO:477 | CAGCATCGCACCTTGCGCTTCTAAAACGGTGCC<br>SEQ ID NO:478 |
| P415A/A416G | GGCACCGTTTTAGAAGCGCAAGGTGCGATGCTG<br>SEQ ID NO:479 | CAGCATCGCACCTTGCGCTTCTAAAACGGTGCC<br>SEQ ID NO:480 |
| P428A | CTGGGCGTGCGCGGCGCACATGCAACGGCCCCA<br>SEQ ID NO:481 | TGGGGCCGTTGCATGTGCGCCGCGCACGCCCAG<br>SEQ ID NO:482 |
| P433A | CCACATGCAACGGCCGCAGGCACCAATGCCCGC<br>SEQ ID NO:483 | GCGGGCATTGGTGCCTGCGGCCGTTGCATGTGG<br>SEQ ID NO:484 |
| P475A | ACCCACAACCGCAAGGCGGCAGAACCAACCAAG<br>SEQ ID NO:485 | CTTGGTTGGTTCTGCCGCCTTGCGGTTGTGGGT<br>SEQ ID NO:486 |
| P478A | CGCAAGCCGGCAGAAGCAACCAAGCCAAATAAC<br>SEQ ID NO:487 | GTTATTTGGCTTGGTTGCTTCTGCCGGCTTGCG<br>SEQ ID NO:488 |
| P481A | GCAGAACCAACCAAGGCAAATAACCTGGACGCA<br>SEQ ID NO:489 | TGCGTCCAGGTTATTTGCCTTGGTTGGTTCTGC<br>SEQ ID NO:490 |
| I46P | TCTCTGGACAAGAAGCCCCGCCCGCTGGAGGAG<br>SEQ ID NO:491 | CTCCTCCAGCGGGCGGGGCTTCTTGTCCAGAGA<br>SEQ ID NO:492 |
| D43P/I46P | CCGTGACATTGAGTCTCTGCCCAAGAAGCCACGCCCGCT<br>SEQ ID NO:493 | AGTCTCTGCCCAAGAAGCCACGCCCGCTGGAGGAG<br>SEQ ID NO:494 |
| T90P | AAGAAACTGGCGATCCGACGCGTGCCGTCGCG<br>SEQ ID NO:495 | CGCGACCGCACGCGTCGGATCGCCCAGTTTCTT<br>SEQ ID NO:496 |
| A105P | GCCTTAAGCATCTTACCGGAGGCCCCGGTGTTA<br>SEQ ID NO:497 | TAACACCGGGGCCTCCGGTAAGATGCTTAAGGC<br>SEQ ID NO:498 |
| E106P | AGCCTTAAGCATCTTAGCGCCGGCCCCG<br>SEQ ID NO:499 | CTGGCTAACACCGGGGCCGGCGCTAAGA<br>SEQ ID NO:500 |
| E215P | ATTTGCTGGATTCTCCGGAGGGCCAAAACGCG<br>SEQ ID NO:501 | CGCGTTTTGGCCCTCCGGAGAATCCAGCCAAAT<br>SEQ ID NO:502 |
| T239P | TTACAGCATATCCAGCCCTGCCTGGCCGGCGAC<br>SEQ ID NO:503 | GTCGCCGGCCAGGCAGGGCTGGATATGCTGTAA<br>SEQ ID NO:504 |
| G279P | ATGGTGGAAGAATATCCCTGGGAGGACATGGAG<br>SEQ ID NO:505 | CTCCATGTCCTCCCAGGGATATTCTTCCACCAT<br>SEQ ID NO:506 |
| E281P | GAAGAATATGGCTGGCCGGACATGGAGGTTGTC<br>SEQ ID NO:507 | GACAACCTCCATGTCCGGCCAGCCATATTCTTC<br>SEQ ID NO:508 |

Figure 14D

| Mutation | Forward Primer (5'→3') | Reverse Primer (5'→3') |
|---|---|---|
| V285P | TGGGAGGACATGGAGCCTGTCTCTGTGAGCGGC<br>SEQ ID NO:509 | GCCGCTCACAGAGACAGGCTCCATGTCCTCCCA<br>SEQ ID NO:510 |
| V330P | GTTCTGAAGAGCGACCCCAGCGCCCTGGTTGAG<br>SEQ ID NO:511 | CTCAACCAGGGCGCTGGGGTCGCTCTTCAGAAC<br>SEQ ID NO:512 |
| E388P | ATTACCTTAATGAAACCGGTTGACGGTGACCTG<br>SEQ ID NO:513 | CAGGTCACCGTCAACCGGTTTCATTAAGGTAAT<br>SEQ ID NO:514 |
| E403P | CGTTTCTATGCCGTCTATCCCGGTCGGC<br>SEQ ID NO:515 | CCGCCGATCGTGCCGACCGGGATAGACG<br>SEQ ID NO:516 |
| E414P | GGCGGCACCGTTTTACCACCGCAAGGTGCGATG<br>SEQ ID NO:517 | CATCGCACCTTGCGGTGGTAAAACGGTGCCGCC<br>SEQ ID NO:518 |
| A430P | GTGCGCGGCCCACATCCAACGGCCCCAGGCACC<br>SEQ ID NO:519 | GGTGCCTGGGGCCGTTGGATGTGGGCCGCGCAC<br>SEQ ID NO:520 |
| A432P | GGCCCACATGCAACGCCCCCAGGCACCAATGCC<br>SEQ ID NO:521 | GGCATTGGTGCCTGGGGGCGTTGCATGTGGGCC<br>SEQ ID NO:522 |

# METHODS OF GENERATING PROTEIN VARIANTS

CROSS-REFERENCE

This application claims the benefit of U.S. Provisional Patent Application No. 60/918,417, filed Mar. 16, 2007, which application is incorporated herein by reference in its entirety.

GOVERNMENT GRANT SUPPORT

This invention was made with government support under Grant Number 2001-52104-11228 awarded by the U.S. Department of Agriculture, CSREES. The government has certain rights in the invention.

BACKGROUND

The in vivo enzyme properties attributable to their intracellular activity and concentration are important determinants of the efficiencies of metabolic pathways. It is well known that many enzymes are able to catalyze very specific chemical reactions with surprising accuracy and efficiency. These enzymes, each catalyzing different but a series of chemical reactions, often cooperate to act and minimize the unnecessary accumulation of metabolic intermediates, and thus form highly integrated metabolic pathways. It is thought that the evolution of enzymes and metabolic pathways are driven in large part by the recruitment of enzymes from other metabolic pathways; enzymes with promiscuous function initially shared by a few distinctive pathways may divergently and cooperatively evolve through gene duplications and subsequent functional specialization depending on the importance of each metabolite, resulting in a mosaic or patchwork of homologous enzymes in two distinct pathways[8]. Since natural evolution is known to be a highly accomplished designer for in vivo enzyme properties and the efficiencies of metabolic pathways, understanding the mechanisms for molecular evolution might allow for the development of a methodology to redesign efficiencies of constructed synthetic metabolic pathways.

In molecular evolution, the fixation probability of mutations is simply determined by their fitness effects: deleterious (opposed by purifying selection and likely discarded from a population), neutral or nearly neutral (genetic drift), or advantageous (supposed by positive selection and likely fixed to a population)[9]. However, detailed mechanisms for the molecular basis of adaptations of enzymes and pathways are still largely unclear, as the fitness effects are highly dependent on genotypic and/or phenotypic backgrounds of host organisms. Additionally, impacted by changes in the environment, the fitness effects could also vary even in a population in the same environment due to biological noise[10,11]. Since it is assumed that the large diversity in protein sequences with orthologous relations are created based on the contributions of mutations to fitness effects, it is thought that changes that are kept to a minimum during the course of evolution may be very essential to maintain in vivo enzyme functions.

Directed evolution, modifying a parent protein such that the modified protein exhibits a desirable property, can be achieved by mutagenizing one or more parent proteins and screening the mutants to identify those having a desired property. A variety of directed evolution methods are currently available for generating protein variants that exhibit altered function, compared to a parent polypeptide. However, currently available methods involve generation of tens of thousands to a million or more mutants, which must be screened to find a few critical mutations. Thus, application of currently available methods is limited by inefficiency of screening the enormous number of mutants that are generated.

There is a need in the art for efficient methods of designing and generating protein variants that exhibit altered properties, without the need for generating and screening large numbers of variants.

LITERATURE

WO 06/133013; Martin et al. (2003) *Nat. Biotech.* 21(7):796-802; U.S. Pat. No. 7,172,886.

SUMMARY OF THE INVENTION

The present invention provides methods of designing and generating polypeptide variants that have altered properties compared to a parent polypeptide. The present invention further provides a computer program product for carrying out the design of a variant polypeptide. The present invention further provides nucleic acids encoding enzyme variants, as well as vectors and host cells comprising the nucleic acids. The present invention further provides variant enzymes; methods of producing the variant enzymes; and methods of producing compounds using the enzymes.

BRIEF DESCRIPTION OF THE DRAWINGS

FIGS. 1A-Y present an alignment of amino acid sequences (SEQ ID NOs:1-48) of sesquiterpene synthases, monoterpene synthases, and diterpene synthases.

FIGS. 2A-M present an alignment of amino acid sequences (SEQ ID NOs:49-71) of a truncated form of yeast HMGR, and various archaeal HMGR.

FIGS. 3A-D present a schematic depiction of constructs used for production of terpenoids.

FIGS. 4A-E depict an evolutionary study of the relative stability of each amino acid.

FIGS. 5A-D depict the relevance between evolutionary relations and the fitness effects of Gly and Pro distribution in gamma-humulene synthase (HUM).

FIGS. 6A-D depict co-integration of designed HUM and tHMGR into a synthetic biological system for production of terpenoids and resulting sesquiterpene production.

FIGS. 7A-D depict the relevance between evolutionary relations and functional consequences of Gly and Pro distributions in tHMGR.

FIGS. 9A-D depict the effect of Gly and Pro mutations at various temperatures.

FIGS. 10 A, C, and D depict the amino acid sequences of γ-humulene synthase and variant γ-humulene synthases; and FIG. 10B depicts the nucleotide sequence encoding the γ-humulene synthase depicted in FIG. 10A.

FIGS. 11A-C depict the amino acid sequences of a truncated HMGR (tHMGR) and variant tHMGR.

FIGS. 12A-O provide a list of exemplary proteins analyzed using a subject method.

FIGS. 13A-C provide the primer sequences used for site directed mutagenesis of humulene synthase (HUM).

FIGS. 14A-D provide the primer sequences used for site directed mutagenesis of tHMGR.

DEFINITIONS

Figures 8A, 8B:
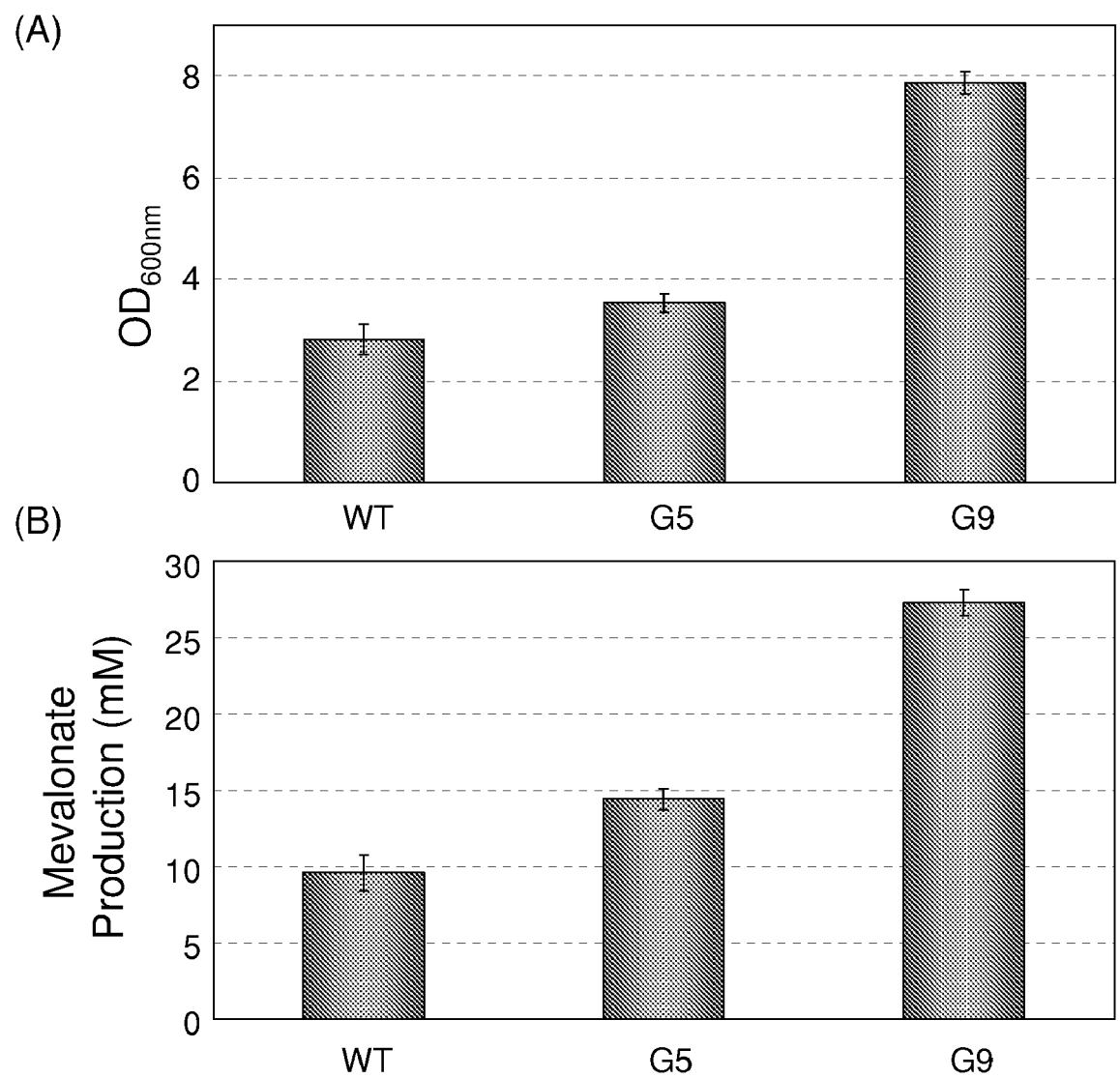
FIGS. 8A and 8B depict integration of redesigned tHMGR and resulting mevalonate production.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, serine-threonine, phenylalanine-tyrosine, lysine-arginine, alanine-valine, aspartate-glutamate, and asparagine-glutamine.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

By "construct" is meant a recombinant nucleic acid, generally recombinant DNA, which has been generated for the purpose of the expression of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

Expression cassettes may be prepared comprising a transcription initiation or transcriptional control region(s) (e.g., a promoter), the coding region for the protein of interest, and a transcriptional termination region. Transcriptional control regions include those that provide for over-expression of the protein of interest in the genetically modified host cell; those that provide for inducible expression, such that when an inducing agent is added to the culture medium, transcription of the coding region of the protein of interest is induced or increased to a higher level than prior to induction.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

The terms "isoprenoid," "isoprenoid compound," "terpene," "terpene compound," "terpenoid," and "terpenoid compound" are used interchangeably herein. Isoprenoid compounds are made up various numbers of so-called isoprene (C5) units. The number of C-atoms present in the isoprenoids is typically evenly divisible by five (e.g., C5, C10, C15, C20, C25, C30 and C40). Irregular isoprenoids and polyterpenes have been reported, and are also included in the definition of "isoprenoid." Isoprenoid compounds include, but are not limited to, monoterpenes, sesquiterpenes, diterpenes, triterpenes, and polyterpenes.

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" or "isoprenoid synthase" refers to any enzyme that enzymatically modifies IPP, DMAPP, or a polyprenyl pyrophosphate, such that a terpenoid compound is produced. The term "terpene synthase" includes enzymes that catalyze the conversion of a prenyl diphosphate into an isoprenoid.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'-4 condensation of isopentenyl diphosphate with allylic primer substrates, resulting in the formation of prenyl diphosphates of various chain lengths.

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and farnesyl pyrophosphate" are interchangeable; etc.

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate.

The term "1-deoxy-D-xylulose 5-diphosphate pathway" or "DXP pathway" is used herein to refer to the pathway that converts glyceraldehyde-3-phosphate and pyruvate to IPP and DMAPP through a DXP pathway intermediate.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an enzyme variant" includes a plurality of such variants and reference to "the algorithm" includes reference to one or more algorithms and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides methods of designing and generating polypeptide variants that have altered properties compared to a parent polypeptide. The present invention further provides a computer program product for carrying out the design of a variant polypeptide. The present invention further provides nucleic acids encoding enzyme variants, as well as vectors and host cells comprising the nucleic acids. The present invention further provides variant enzymes; methods of producing the variant enzymes; and methods of producing compounds using the enzymes.

Methods of Designing and Generating Polypeptide Variants

The present invention provides methods of designing and generating polypeptide variants that have altered properties (e.g., altered functional and/or physical properties) compared to a parent polypeptide. The methods generally involve: a) identifying one or more conserved amino acid residues in a family of polypeptides, where the parent polypeptide is a member of the family of polypeptides; b) calculating a conservation probability $P_i^X$ for an amino acid (X) (where X corresponds to the identified, conserved amino acid residue) at an amino acid position (i) for a parent polypeptide; and c) where the conservation probability for the amino acid sequence at the amino acid position is above a threshold value, modifying the amino acid sequence of the parent polypeptide to include amino acid X at position i; or where the conservation probability for an amino acid is below the threshold value, modifying the amino acid sequence of the parent polypeptide to include an amino acid other than amino acid X at the amino acid position, thereby generating a polypeptide variant with altered functional and/or physical properties. Conserved amino acid residues can be identified using a method as described in Example 1, below.

The conservation probability is calculated by aligning amino acid sequences of polypeptide members of a polypeptide family, e.g., polypeptides sharing a function, e.g., an enzymatic activity or similar enzymatic activities; etc., to generate a multiple sequence alignment (MSA). $P_1^X$ is calculated as follows:

$$P_i^X = \frac{N_i^X}{N_i}$$

where $N_i^X$ and $N_i$ denote the number of amino acid X (e.g., Gly or Pro) and the total number of aligned amino acids at position i in each column of a multiple sequence alignment, respectively.

For example, in some embodiments, the conservation probabilities for glycine (Gly) and proline (Pro) for a given polypeptide are calculated. The conservation probability for Gly ($P_i^G$) and Pro ($P_i^P$) at column i in a given MSA is calculated based on the composition of Gly and Pro at column i as follows:

$$P_i^X = \frac{N_i^X}{N_i}$$

where $N_i^X$ and $N_i$ denote the number of amino acid X (Gly or Pro) and the total number of aligned amino acids at position i in each column of MSA, respectively. The fitness effects contributed by mutations of these residues are predicted dependent on the value of $P_i$; when $P_i^X \leq 0$, the mutation to amino acid X likely shows neutral, nearly neutral, or positive fitness effects, and when $P_i^X \leq 0$ the mutations to amino acid X likely shows neutral, nearly neutral, or negative fitness effects. $P_i^X=0.4$ can be used as a threshold; and the $P_i^X$ compared; and the fitness effects resulting from single mutations evaluated.

As an example, where the $P_i^G$ value is greater than 0.4 and the amino acid at position i is other than Gly, the amino acid sequence of the parent polypeptide is modified to include a Gly at position i. As another example, where the $P_i^G$ value is less than 0.4, and the amino acid at position i is a Gly, the amino acid sequence of the parent polypeptide is modified to include an amino acid other than Gly at position i. As another example, where the $P_i^P$ value is less than 0.4 and the amino acid at position i is other than Pro, the amino acid sequence of the parent polypeptide is modified to include a Pro at position i. As another example, where the Pip value is less than 0.4 and the amino acid at position i is a Pro, the amino acid sequence of the parent polypeptide is modified to include an amino acid other than Pro at position i. In some embodiments, where the conservation probability for a Pro or a Gly at a position i is below a threshold (e.g., below 0.4), the Pro or the Gly at position i is substituted with an Ala.

Using a subject method, polypeptide variants can be generated based on a wide variety of parent polypeptides, where parent polypeptides include, but are not limited to, enzymes, antibodies, transcription factors, receptors for ligands, polypeptide ligands for receptors, signal proteins, a fluorescent protein, a carrier protein, a small molecule binding protein, a large molecule binding protein, and the like. A "parent" polypeptide is any polypeptide that serves as a reference for generating a variant polypeptide, where a variant polypeptide comprises one or more amino acid substitutions compared to the amino acid sequence of the parent polypeptide. A "parent" polypeptide is in some embodiments a wild-type polypeptide, e.g., a polypeptide found in nature.

As noted above, a subject method for generating a protein variant provides for generating a protein variant that has one or more altered properties compared to a parent polypeptide. As used herein, the term "altered property(ies)" refers to one or more characteristics present in a parent polypeptide that is altered in a variant of the parent polypeptide. Altered properties (e.g., altered functional and/or physical properties) exhibited by a variant polypeptide include, but are not limited to, increased enzymatic activity; increased substrate affinity; increased ligand binding affinity; increased solubility (e.g., increased solubility in the cytosol of a prokaryotic host cell; etc.); increased stability (e.g., increased in vivo and/or in vitro half life); and the like, where the one or more functional and/or physical properties are altered compared to a parent polypeptide.

Altered properties include altered intracellular properties, e.g., increased intracellular solubility in a host cell (e.g., increased solubility in the cytosol or cytoplasm of a host cell); reduced likelihood that a variant protein produced by a prokaryotic host cell will be sequestered in an inclusion body; improved folding (e.g., increased degree of native folding; e.g., an increased proportion of protein that exhibits native folding) such that activity of the polypeptide is maintained; and the like. For example, where a variant polypeptide is produced recombinantly in a host cell (e.g., a prokaryotic host cell), the variant polypeptide will exhibit one or more of: a) increased solubility in the cytosol or cytoplasm of the host cell, compared to the solubility of the parent polypeptide when produced recombinantly in the host cell; increased proportion of the recombinantly produced variant that is soluble in the cytosol compared to the proportion of the parent polypeptide that is soluble in the cytosol when produced recombinantly in the host cell; reduced proportion of the recombinantly produced variant that is insoluble, e.g., sequestered in an inclusion body compared to the proportion of the parent polypeptide that is insoluble when produced recombinantly in the host cell; reduced proportion of the recombinantly produced variant that is present in an aggregate (e.g., an insoluble aggregate) compared to the proportion of the parent polypeptide that is present in an aggregate when produced recombinantly in the host cell; and increased native folding, e.g., the proportion of recombinantly produced variant protein that exhibits native folding is increased, compared to the proportion of the parent polypeptide that exhibits native folding when produced recombinantly in the host cell.

In some embodiments, the parent polypeptide is an enzyme; and the variant enzyme exhibits enhanced enzymatic activity level compared to the parent polypeptide. For example, in some embodiments, the variant enzyme exhibits an at least about 5%, at least about 10%, at least about 25%, at least about 50%, at least about 75%, at least about 10% (or two-fold), at least about 2.5-fold, at least about 5-fold, at least about 7.5-fold, at least about 10-fold, at least about 25-fold, at least about 50-fold, or at least about 100-fold, or greater than 100-fold, higher enzymatic activity level compared to the parent polypeptide. In some embodiments, e.g., where the enzyme is produced recombinantly in a host cell (e.g., a prokaryotic host cell), a property such as increased solubility, improved folding, and the like, can result in increased enzymatic activity level, compared to the activity level of a parent polypeptide produced recombinantly in the host cell.

In some embodiments, the parent polypeptide is an enzyme that is part of a biosynthetic pathway (a "biosynthetic pathway enzyme") having and end product and/or intermediate products, and the variant polypeptide provides for increased production of the intermediate and/or end product when integrated into the biosynthetic pathway. For example, in some embodiments, the variant biosynthetic pathway enzyme, when integrated into a biosynthetic pathway, provides for production of an intermediate and/or an end product at a level that is at least about 5%, at least about 10%, at least about 25%, at least about 50%, at least about 75%, at least about 10% (or two-fold), at least about 2.5-fold, at least about 5-fold, at least about 7.5-fold, at least about 10-fold, at least about 25-fold, at least about 50-fold, or at least about 100-fold, or greater than 100-fold, higher than the level produced by the parent biosynthetic pathway enzyme when integrated into the biosynthetic pathway.

In some embodiments, the parent polypeptide is an antibody, where "antibody" includes single chain antibodies, monoclonal antibodies, antibody fragments that retain antigen-binding (e.g., Fv, $F(ab')_2$ and Fab fragments), and the like. In some embodiments, the parent antibody binds specifically to an antigen (or epitope); and the variant antibody binds with altered (greater or less) affinity to the antigen (or epitope). The term "specific binding," in the context of antibody binding to an antigen, is a term well understood in the art and refers to binding of an antibody to the antigen to which the antibody was raised, but not other, unrelated antigens. Specific binding typically refers to binding with an affinity of at least about $10^{-6}$ M, at least about $10^{-7}$ M, at least about $10^{-8}$ M, or at least about $10^{-9}$ M, or greater.

In some embodiments, the parent polypeptide is a receptor, e.g., a cell surface receptor, a nuclear receptor, a cytoplasmic receptor, etc., that binds to a ligand; and the variant polypeptide is a receptor that binds to the ligand with altered affinity.

In some embodiments, the parent polypeptide is a fluorescent protein. Fluorescent proteins are proteins that, following excitation at a first wavelength of light, will emit light at a second wavelength. For example, the excitation spectra of fluorescent proteins typically ranges from about 300 to 700, while the emission spectra of typically ranges from about 400 to 800. Fluorescent proteins are known in the art, and include green fluorescent proteins (GFP) from *Aequoria victoria*; derivatives of GFP that are known in the art; and any of a variety of fluorescent proteins from Anthozoan species, as described in, e.g., Matz et al. (1999) Nature Biotechnol. 17:969-973. In some embodiments, following excitation at an excitation wavelength of light, the parent fluorescent protein emits light at a first emission wavelength, and the variant polypeptide emits light at second emission wavelength.

Functions or properties that may be altered include, but are not limited to, enzymatic activity (where the parent polypeptide and the corresponding variant polypeptide are enzymes), where enzymatic activity includes specific activity, substrate specificity, and product profile (where "product profile" refers to the product(s) generated using a given substrate); antigen-binding properties (where the parent polypeptide and the corresponding variant polypeptide are antibodies or antigen-binding fragments of antibodies), where antigen-binding properties include antigen specificity, antigen binding affinity, etc.; ligand binding properties (e.g., where the parent polypeptide and the corresponding variant polypeptide are ligand receptors), where ligand binding properties include ligand specificity, ligand affinity, etc.; substrate binding properties, e.g., where the parent polypeptide and the corresponding variant polypeptide are transcription factors, the function being altered is in some embodiments specificity for a particular nucleotide sequence; protein stability; protein solubility; fluorescent properties (e.g., where the parent polypeptide is a fluorescent protein); signal transduction properties (e.g., where the parent polypeptide is a signal transduction protein such as a receptor); binding specificity and/or affinity to a small molecule; binding specificity and/or affinity to a large molecule; and the like.

Computer Program Product and Computational Analysis System

The present invention provides a computer program product for carrying out a subject method for designing a variant polypeptide. The present invention also includes an algorithm for performing the subject methods, where the algorithm is recorded on a computer readable medium. The present invention further provides computational analysis systems that include a subject computer program product. The present invention further provides a kit for identifying a polypeptide variant.

One or more aspects of the above methodology may be in the form of computer readable media having programming stored thereon for implementing the subject methods. In other words, the subject methodology may be provided in the form of programming (a computer program product) or an algorithm recorded onto a computer readable medium. The computer readable media may be, for example, in the form of a computer disk or CD (compact disc), a floppy disc, a magnetic "hard card", a server, or any other computer readable media capable of containing data or the like, stored electronically, magnetically, optically or by other means. Accordingly, stored programming embodying steps for carrying-out the subject methods may be transferred to a computer such as a personal computer (PC), (i.e., accessible by a researcher or the like), by physical transfer of a CD, floppy disk, or like medium, or may be transferred using a computer network, server, or other interface connection, e.g., the Internet.

In some embodiments, a subject computer-readable medium has recorded thereon a program (a computer program product) that: a) identifies one or more conserved amino acid residues in a family of polypeptides, wherein the parent polypeptide is a member of the family of polypeptides; b) assigns a conservation probability to an amino acid (e.g., a Gly; a Pro; etc.) at an amino acid position of a parent polypeptide, where the amino acid is at a position corresponding to the position of an identified conserved amino acid; and c) based on the conservation probability, identifies at least one amino acid sequence modification that provides for a variant polypeptide that exhibits one or more altered properties as compared to the parent polypeptide.

The present invention provides a computational analysis system comprising a subject computer-readable medium or a subject computer program product. In one embodiment of the subject invention, a system of the invention may include a single computer or the like with a stored algorithm capable of carrying out a subject method, i.e., a computational analysis system. In certain embodiments, the system is further characterized in that it provides a user interface, where the user interface presents to a user the option of selecting among one or more different, including multiple different, inputs, e.g., various parameter values for the algorithm, as described above, such as an omega value, etc. Computational systems that may be readily modified to become systems of the subject invention include those described in U.S. Pat. No. 6,251,588; the disclosure of which is herein incorporated by reference.

The present invention provides a kit for generating a polypeptide variant exhibiting one or more altered properties as compared to a parent polypeptide. A subject kit comprises a computer readable medium, as described above, which computer readable medium has an algorithm stored or recorded thereon, as described above; and instructions for using the algorithm to identify candidate mutant sequences, where a polypeptide comprising such a mutant sequence exhibits one or more altered properties as compared to a parent polypeptide.

Polypeptide Variants

The present invention provides polypeptide variants that exhibit one or more altered properties compared to a parent polypeptide. As noted above, a subject method for generating a protein variant provides for generating a protein variant that has one or more altered properties compared to a parent polypeptide. As used herein, the term "altered property(ies)" refers to one or more characteristics present in a parent polypeptide that is altered in a variant of the parent polypeptide. Altered properties (e.g., altered functional and/or physical properties) exhibited by a variant polypeptide include, but are not limited to, increased enzymatic activity; increased substrate affinity; increased ligand binding affinity; increased solubility (e.g., increased solubility in the cytosol of a prokaryotic host cell; etc.); increased stability (e.g., increased in vivo and/or in vitro half life); and the like, where the one or more functional and/or physical properties are altered compared to a parent polypeptide.

Altered properties include altered intracellular properties, e.g., increased intracellular solubility in a host cell (e.g., increased solubility in the cytosol or cytoplasm of a host cell); reduced likelihood that a variant protein produced by a prokaryotic host cell will be sequestered in an inclusion body; improved folding (e.g., increased degree of native folding; e.g., an increased proportion of protein that exhibits native folding) such that activity of the polypeptide is maintained; and the like. For example, where a variant polypeptide is produced recombinantly in a host cell (e.g., a prokaryotic host cell), the variant polypeptide will exhibit one or more of: a) increased solubility in the cytosol or cytoplasm of the host cell, compared to the solubility of the parent polypeptide when produced recombinantly in the host cell; increased proportion of the recombinantly produced variant that is soluble in the cytosol compared to the proportion of the parent polypeptide that is soluble in the cytosol when produced recombinantly in the host cell; reduced proportion of the recombinantly produced variant that is insoluble, e.g., sequestered in an inclusion body compared to the proportion of the parent polypeptide that is insoluble when produced recombinantly in the host cell; reduced proportion of the recombinantly produced variant that is present in an aggregate (e.g., an insoluble aggregate) compared to the proportion of the parent polypeptide that is present in an aggregate when produced recombinantly in the host cell; and increased native folding, e.g., the proportion of recombinantly produced variant protein that exhibits native folding is increased, compared to the proportion of the parent polypeptide that exhibits native folding when produced recombinantly in the host cell.

In addition to altered properties such as increased intracellular solubility, increased native folding, etc., a subject variant protein can have one or more additional altered features, including, but not limited to, altered substrate specificity, and the like.

The present invention provides variant biosynthetic pathway enzymes. In some embodiments, a subject variant biosynthetic pathway enzyme is a variant isoprenoid synthase (also referred to herein as a variant terpene cyclase). In other embodiments, a subject variant biosynthetic pathway enzyme is a variant mevalonate biosynthetic pathway enzyme.

A subject variant terpene cyclase catalyzes an enzymatic reaction, using a polyprenyl diphosphate as substrate. Polyprenyl diphosphate substrates that can serve as substrate for a subject variant terpene cyclase include, but are not limited to, geranyl diphosphate (GPP), farnesyl diphosphate (FPP), geranylgeranyl diphosphate (GGPP), hexaprenyl diphosphate (HexPP), heptaprenyl diphosphate (HepPP), octaprenyl diphosphate (OPP), solanesyl diphosphate (SPP), decaprenyl diphosphate (DPP), nonaprenyl diphosphate (NPP), and undecaprenyl diphosphate (UPP) In some embodiments, the substrate of a subject variant terpene cyclase is GPP. In other embodiments, the substrate of a subject variant terpene cyclase is FPP. In other embodiments, the substrate of a subject variant terpene cyclase is GGPP.

Variant Sesquiterpene Synthases

In some embodiments, a subject variant terpene cyclase is a sesquiterpene synthase. The present invention provides variant sesquiterpene synthases; and methods of producing the variant sesquiterpene synthases. The present invention further provides compositions comprising a subject variant sesquiterpene synthases. The present invention further provides methods of producing an isoprenoid compound, the method involving culturing a genetically modified host cell in a suitable medium, where the genetically modified host cell comprises a nucleic acid comprising a nucleotide sequence encoding a subject variant sesquiterpene synthase.

In some embodiments, a subject variant sesquiterpene synthase, when integrated into a biosynthetic pathway (e.g., a mevalonate pathway) provides for production of a sesquiterpene at a level that is at least about 5%, at least about 10%, at least about 25%, at least about 50%, at least about 75%, at least about 10% (or two-fold), at least about 2.5-fold, at least about 5-fold, at least about 7.5-fold, at least about 10-fold, at least about 25-fold, at least about 50-fold, or at least about 100-fold, or greater than 100-fold, higher than the level produced by a parent sesquiterpene synthase when integrated into the same biosynthetic pathway.

For example, in some embodiments, a subject variant sesquiterpene synthase comprises at least one amino acid substitution compared to the amino acid sequence set forth in FIG. 10A (GenBank Accession No. AAC05728; SEQ ID NO:1). In some embodiments, a subject variant sesquiterpene synthase comprises from one amino acid substitution to about 50 amino acid substitutions compared to the amino acid sequence set forth in FIG. 10A and in SEQ ID NO:1; e.g., in some embodiments, a subject variant sesquiterpene synthase comprises one, two, three, four, five, six, seven, eight, nine, or 10 amino acid substitutions, from about 10 amino acid substitutions to about 12 amino acid substitutions, from about 12 amino acid substitutions to about 15 amino acid substitutions, from about 15 amino acid substitutions to about 20 amino acid substitutions, from about 20 amino acid substitutions to about 25 amino acid substitutions, or from about 25 amino acid substitutions to about 50 amino acid substitutions compared to the amino acid sequence set forth in FIG. 10A.

In some embodiments, a subject variant sesquiterpene synthase comprises at least the amino acid substitutions K126P, R142G, and G227A, compared to the amino acid sequence set forth in FIG. 10A and in SEQ ID NO:1, or a variant thereof. In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; and comprising the amino acid substitutions K126P, R142G, and G227A.

In some embodiments, a subject variant sesquiterpene synthase comprises at least the amino acid substitutions K126P, R142G, G148A, G227A, G327A, and G361A compared to the amino acid sequence set forth in FIG. 10A, or a variant thereof. In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; and comprising the amino acid substitutions amino acid substitutions K126P, R142G, G148A, G227A, G327A, and G361A.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, and G227A, and further comprises amino acid substitutions as set forth in Table 1.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, G148A, G227A, G327A, and G361A, and further comprises amino acid substitutions as set forth in Table 1.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, and G227A, and further comprises the amino acid substitutions F312Q, M339A, and M447F.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, and G227A, and further comprises the amino acid substitutions M339N, S484C, and M565I.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, and G227A, and further comprises the amino acid substitutions A317N, A336S, S484C, and I562V.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, and G227A, and further comprises the amino acid substitutions A336C, T445C, S484C, I562L, and M565L.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, and G227A, and further comprises the amino acid substitutions A336V, M447H, and I562T.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, and G227A, and further comprises the amino acid substitutions S484A and Y566F.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, G148A, G227A, G327A, and G361A, and further comprises the amino acid substitutions F312Q, M339A, and M447F.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, G148A, G227A, G327A, and G361A, and further comprises the amino acid substitutions M339N, S484C, and M565I.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, G148A, G227A, G327A, and G361A, and further comprises the amino acid substitutions A317N, A336S, S484C, and I562V.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, G148A, G227A, G327A, and G361A, and further comprises the amino acid substitutions A336C, T445C, S484C, I562L, and M565L.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, G148A, G227A, G327A, and G361A, and further comprises the amino acid substitutions A336V, M447H, and I562T.

In some embodiments, a subject variant sesquiterpene synthase comprises an amino acid sequence having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, G148A, G227A, G327A, and G361A, and further comprises the amino acid substitutions S484A and Y566F.

Amino acid sequences of exemplary variant sesquiterpene synthases are depicted in FIGS. 10C and 10D.

Variant Mevalonate Biosynthetic Pathway Enzyme

In some embodiments, a subject variant enzyme is a variant mevalonate biosynthetic pathway enzyme, e.g., a variant of an enzyme selected from an acetoacetyl-CoA thiolase, a hydroxymethyl glutaryl-CoA synthase (HMGS), a hydroxymethyl glutaryl-CoA reductase (HMGR), a mevalonate kinase (MK), a phosphomevalonate kinase (PMK), a mevalonate pyrophosphate decarboxylase (MPD), and an isopentenyl pyrophosphate (IPP) isomerase.

In some embodiments, a subject variant mevalonate biosynthetic pathway enzyme, when integrated into a mevalonate pathway, provides for production of a sesquiterpene at a level that is at least about 5%, at least about 10%, at least about 25%, at least about 50%, at least about 75%, at least about 10% (or two-fold), at least about 2.5-fold, at least about 5-fold, at least about 7.5-fold, at least about 10-fold, at least about 25-fold, at least about 50-fold, or at least about 100-fold, or greater than 100-fold, higher than the level produced by a parent mevalonate biosynthetic pathway enzyme integrated into a mevalonate pathway.

As one non-limiting example, a subject variant enzyme is a variant HMGR. In some embodiments, a subject variant HMGR comprises one or more amino acid substitutions compared to the amino acid sequence set forth in FIG. 11A and in SEQ ID NO:49.

In some embodiments, a subject variant HMGR comprises from one amino acid substitution to about 50 amino acid substitutions compared to the amino acid sequence set forth in FIG. 11A and in SEQ ID NO:49; e.g., in some embodiments, a subject variant sesquiterpene synthase comprises one, two, three, four, five, six, seven, eight, nine, or 10 amino acid substitutions, from about 10 amino acid substitutions to about 12 amino acid substitutions, from about 12 amino acid substitutions to about 15 amino acid substitutions, from about 15 amino acid substitutions to about 20 amino acid substitutions, from about 20 amino acid substitutions to about 25 amino acid substitutions, or from about 25 amino acid substitutions to about 50 amino acid substitutions compared to the amino acid sequence set forth in FIG. 11A.

In some embodiments, a subject variant HMGR comprises at least the amino acid substitutions G206A, G319A, G352A, G417A, and G495A, compared to the amino acid sequence set forth in FIG. 10A, or a variant thereof. In some embodiments, a subject variant HMGR comprises an amino acid sequence having at least about 75%, at least about 80%, at least about 85%, at least about 90%, at least about 95%, at least about 98%, or at least about 99% amino acid sequence identity to the amino acid sequence set forth in FIG. 11A; where the variant HMGR comprises the amino acid substitutions G206A, G319A, G352A, G417A, and G495A.

In some embodiments, a subject variant HMGR comprises at least the amino acid substitutions P200A, G206A, T239P, G319A, G352A, G417A, P428G, K474G, and G495A, compared to the amino acid sequence set forth in FIG. 11A, or a variant thereof. In some embodiments, a subject variant HMGR comprises an amino acid sequence having at least about 75%, at least about 80%, at least about 85%, at least about 90%, at least about 95%, at least about 98%, or at least about 99% amino acid sequence identity to the amino acid sequence set forth in FIG. 11A; where the variant HMGR comprises the amino acid substitutions P200A, G206A, T239P, G319A, G352A, G417A, P428G, K474G, and G495A.

Amino acid sequences of exemplary variant HMGR are depicted in FIGS. 11B and 11C.

Production of a Subject Variant Enzyme

A subject variant enzyme is readily generated using well-established methods. A subject variant enzyme can be produced synthetically, or can be produced recombinantly, i.e., a subject variant enzyme-coding region can be inserted into an expression vector, and the coding region transcribed and translated, either in a living cell or in an in vitro transcription/translation system. One may employ solid phase peptide synthesis techniques, where such techniques are known to those of skill in the art. See Jones, The Chemical Synthesis of Peptides (Clarendon Press, Oxford)(1994). Generally, in such methods a peptide is produced through the sequential additional of activated monomeric units to a solid phase bound growing peptide chain.

A subject variant enzyme can be produced recombinantly, e.g., a subject variant enzyme-coding region can be inserted into an expression vector, and the coding region transcribed and translated, either in a living cell or in an in vitro transcription/translation system. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to the subject gene, or may be derived from exogenous sources. Expression vectors generally have convenient restriction sites located near the promoter sequence to provide for the insertion of nucleic acid sequences encoding heterologous proteins. A selectable marker operative in the expression host may be present.

A subject variant enzyme may be produced in prokaryotes or eukaryotes in accordance with conventional ways, depending upon the purpose for expression. For large scale production of the variant terpene cyclase, a unicellular organism, such as E. coli, B. subtilis, S. cerevisiae, insect cells in combination with baculovirus vectors, or cells of a higher organism such as vertebrates, particularly mammals, e.g. COS 7 cells, may be used as the expression host cells. In some situations, it is desirable to produce the variant enzyme in eukaryotic cells, where the protein will benefit from native folding and post-translational modifications. In other situations, it is desirable to produce the variant enzyme in a prokaryotic cell, e.g., for production of an isoprenoid compound generated by action of the enzyme on a substrate in a mevalonate pathway or in an isoprenoid biosynthetic pathway.

With the availability of a subject enzyme in large amounts, e.g., by employing an expression host, the variant enzyme may be isolated and purified in accordance with conventional ways. A lysate may be prepared of the expression host, and the lysate purified using high performance liquid chromatography, size exclusion chromatography, gel electrophoresis, affinity chromatography, or other purification technique.

The present invention further provides compositions comprising a subject variant enzyme. Compositions comprising a subject variant enzyme will in many embodiments include one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

Nucleic Acids, Vectors, and Host Cells

The present invention provides nucleic acids encoding a subject polypeptide variant (e.g., a subject variant biosynthetic pathway enzyme, a subject variant mevalonate pathway enzyme, a subject variant isoprenoid biosynthetic pathway enzyme), as well as recombinant vectors and recombinant host cells comprising the nucleic acids or recombinant vectors. In many embodiments, a subject nucleic acid is isolated, and is can be synthetic. In some embodiments, a subject nucleic acid is pure, e.g., at least about 50% pure, at least about 60% pure, at least about 70% pure, at least about 80% pure, at least about 90%, or at least about 95% or more pure. In many embodiments, a subject host cell is isolated. In some embodiments, a subject host cell is part of a multicellular organism. In other embodiments, a subject host cell is in vitro and is cultured as a unicellular entity.

A subject nucleic acid comprises a nucleotide sequence encoding a subject variant enzyme. A subject recombinant vector comprises a subject nucleic acid. In many embodiments, a subject recombinant vector comprises a subject nucleic acid operably linked to one or more control elements, such as a promoter, a transcription terminator, and the like. A subject recombinant vector in some embodiments provides for amplification of the copy number of a subject nucleic acid. A subject recombinant vector is in some embodiments an expression vector that provides for synthesis of a subject variant terpene cyclase in a host cell, e.g., a prokaryotic host cell or a eukaryotic host cell.

Nucleic Acids Encoding Variant Sesquiterpene Synthase

In some embodiments, a subject nucleic acid comprises a nucleotide sequence that encodes a polypeptide comprising an amino acid sequence encoding a subject variant sesquiterpene synthase and having at least about 75%, at least about 80%, at least about 85%, at least about 90%, at least about 95%, at least about 98%, or at least about 99% amino acid sequence identity to the amino acid sequence set forth in FIG.

10A and in SEQ ID NO:1; where the variant sesquiterpene synthase comprises the amino acid substitutions K126P, R142G, and G227A.

In some embodiments, a subject nucleic acid comprises a nucleotide sequence that encodes a polypeptide comprising an amino acid sequence encoding a subject variant sesquiterpene synthase and having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions amino acid substitutions K126P, R142G, G148A, G227A, G327A, and G361A.

In some embodiments, a subject nucleic acid comprises a nucleotide sequence that encodes a polypeptide comprising an amino acid sequence encoding a subject variant sesquiterpene synthase and having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions K126P, R142G, and G227A; and where the variant sesquiterpene synthase further comprises one or more additional amino acid sequences as set forth in Table 1, as described above.

In some embodiments, a subject nucleic acid comprises a nucleotide sequence that encodes a polypeptide comprising an amino acid sequence encoding a subject variant sesquiterpene synthase and having at least about 75%, at least about 80%, at least about 85%, at least about 90%, at least about 95%, at least about 98%, or at least about 99% amino acid sequence identity to the amino acid sequence set forth in FIG. 10A; where the variant sesquiterpene synthase comprises the amino acid substitutions amino acid substitutions K126P, R142G, G148A, G227A, G327A, and G361A; and where the variant sesquiterpene synthase further comprises one or more additional amino acid sequences as set forth in Table 1, as described above.

Nucleic Acids Encoding Variant HMGR

In some embodiments, a subject nucleic acid comprises a nucleotide sequence that encodes a polypeptide comprising an amino acid sequence encoding a subject variant HMGR and having at least about 75%, at least about 80%, at least about 85%, at least about 90%, at least about 95%, at least about 98%, or at least about 99% amino acid sequence identity to the amino acid sequence set forth in FIG. 11A and in SEQ ID NO:49; where the variant HMGR comprises the amino acid substitutions G206A, G319A, G352A, G417A, and G495A.

In some embodiments, a subject nucleic acid comprises a nucleotide sequence that encodes a polypeptide comprising an amino acid sequence encoding a subject variant HMGR and having at least about 75%, at least about 80%, at least about 85%, at least about 90%, at least about 95%, at least about 98%, or at least about 99% amino acid sequence identity to the amino acid sequence set forth in FIG. 11A; where the variant HMGR comprises the amino acid substitutions P200A, G206A, T239P, G319A, G352A, G417A, P428G, K474G, and G495A.

Expression Vectors

In some embodiments, a subject nucleic acid is an expression vector that includes a nucleic acid comprising a nucleotide sequence that encodes a subject variant enzyme. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as E. coli and yeast). Thus, for example, a nucleic acid encoding a subject variant terpene cyclase is included in any one of a variety of expression vectors for expressing the variant terpene cyclase. Such vectors include chromosomal, nonchromosomal and synthetic DNA sequences.

Numerous suitable expression vectors are known to those of skill in the art, and many are commercially available. The following vectors are provided by way of example; for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXT1, pSG5 (Stratagene), pSVK3, pBPV, pMSG, and pSVLSV40 (Pharmacia). However, any other plasmid or other vector may be used so long as it is compatible with the host cell.

The variant enzyme-encoding nucleotide sequence in the expression vector is operably linked to an appropriate expression control sequence(s) (promoter) to direct synthesis of the encoded variant enzyme. Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035-7056); and the like.

Non-limiting examples of suitable eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

In addition, the expression vectors will in many embodiments contain one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as E. coli.

Generally, recombinant expression vectors will include origins of replication and selectable markers permitting transformation of the host cell, e.g., the ampicillin resistance gene of E. coli, the S. cerevisiae TRP1 gene, etc.; and a promoter derived from a highly-expressed gene to direct transcription of the variant terpene cyclase-encoding sequence. Such promoters can be derived from operons encoding glycolytic enzymes such as 3-phosphoglycerate kinase (PGK), α-factor, acid phosphatase, or heat shock proteins, among others.

In many embodiments, a subject nucleic acid includes a nucleotide sequence encoding a subject variant enzyme, where the nucleotide sequence encoding the variant enzyme is operably linked to an inducible promoter. Inducible promoters are well known in the art. Suitable inducible promoters include, but are not limited to, the pL of bacteriophage λ; Placo; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) J. Bacteriol. 177:4121-4130); a xylose-inducible promoter, e.g., Pxyl (see, e.g., Kim et al. (1996) Gene 181: 71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., C1857-repressed lambda-based expression vectors; see, e.g., Hoffmann et al. (1999) FEMS Microbiol Lett. 177(2):327-34); and the like.

In many embodiments, a subject nucleic acid includes a nucleotide sequence encoding a subject variant enzyme, where the nucleotide sequence encoding the variant enzyme is operably linked to a constitutive promoter. Suitable constitutive promoters for use in prokaryotic cells are known in the art and include, but are not limited to, a sigma70 promoter, e.g., a consensus sigma70 promoter.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

The present invention provides genetically modified host cells, where a subject genetically modified host cell comprises a subject nucleic acid or a subject recombinant vector. Genetically modified host cells are in many embodiments unicellular organisms, or are grown in culture as single cells. In some embodiments, the host cell is a eukaryotic cell. Suitable eukaryotic host cells include, but are not limited to, yeast cells, insect cells, plant cells, fungal cells, and algal cells. Suitable eukaryotic host cells include, but are not limited to, Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Neurospora crassa, Chlamydomonas reinhardtii, and the like.

In other embodiments, the genetically modified host cell is a prokaryotic cell. Suitable prokaryotic cells include, but are not limited to, any of a variety of laboratory strains of Escherichia coli, Lactobacillus sp., Salmonella sp., Shigella sp., and the like. See, e.g., Carrier et al. (1992) J. Immunol. 148:1176-1181; U.S. Pat. No. 6,447,784; and Sizemore et al. (1995) Science 270:299-302. Examples of Salmonella strains which can be employed in the present invention include, but are not limited to, Salmonella typhi and S. typhimurium. Suitable Shigella strains include, but are not limited to, Shigella flexneri, Shigella sonnei, and Shigella disenteriae. Typically, the laboratory strain is one that is non-pathogenic. Non-limiting examples of other suitable bacteria include, but are not limited to, Pseudomonas pudita, Pseudomonas aeruginosa, Pseudomonas mevalonii, Rhodobacter sphaeroides, Rhodobacter capsulatus, Rhodospirillum rubrum, Rhodococcus sp., and the like.

To generate a genetically modified host cell, a subject nucleic acid or a subject recombinant vector is introduced stably or transiently into a host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

The present invention further provides compositions comprising a subject genetically modified host cell. A subject composition comprises a subject genetically modified host cell; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

A subject genetically modified host cell is useful for producing isoprenoid or isoprenoid precursor compound, as described below. For the production of an isoprenoid or isoprenoid precursor compound, a host cell is one that produces, or has been genetically modified to produce, one or more enzymes in a mevalonate pathway and/or an isoprenoid biosynthetic pathway. In some embodiments, the host cell is one that produces a substrate of a subject variant sesquiterpene synthase via a mevalonate pathway. In other embodiments, the host cell is one that produces a substrate of a subject variant sesquiterpene synthase via a DXP pathway. In some embodiments, the host cell is one that produces one or more mevalonate pathway enzymes.

In some embodiments, a genetically modified host cell is a host cell that comprises an endogenous mevalonate pathway. In other embodiments, a genetically modified host cell is a host cell that does not normally produce mevalonate or IPP via a mevalonate pathway, but has been genetically modified with one or more nucleic acids comprising nucleotide sequences encoding one or more mevalonate pathway enzymes. See, e.g., U.S. Patent Publication No. 2004/005678; U.S. Patent Publication No. 2003/0148479; Martin et al. (2003) *Nat. Biotech.* 21(7):796-802.

In some embodiments, a suitable host cell is a host cell that does not normally produce mevalonate or IPP via a mevalonate pathway, but has been genetically modified to produce mevalonate, or IPP, via a mevalonate pathway, e.g., has been genetically modified with one or more nucleic acids comprising nucleotide sequences encoding acetoacetyl-CoA thiolase; hydroxymethylglutaryl-CoA (HMG-CoA) synthase; and a subject variant HMGR. In some embodiments, a suitable host cell is a host cell that does not normally produce mevalonate or IPP via a mevalonate pathway, but has been genetically modified to produce mevalonate, or IPP, via a mevalonate pathway, e.g., has been genetically modified with one or more nucleic acids comprising nucleotide sequences encoding acetoacetyl-CoA thiolase; HMG-CoA synthase; HMG-CoA reductase; mevalonate kinase; phosphomevalonate kinase; and mevalonate pyrophosphate decarboxylase. In some embodiments, a suitable host cell is a host cell that does not normally produce mevalonate or IPP via a mevalonate pathway, but has been genetically modified to produce mevalonate, or IPP, via a mevalonate pathway, e.g., has been genetically modified with one or more nucleic acids comprising nucleotide sequences encoding mevalonate kinase; phosphomevalonate kinase; and mevalonate pyrophosphate decarboxylase. In some of these embodiments, the host cell has been further genetically modified with a nucleic acid comprising a nucleotide sequence encoding a polyprenyl diphosphate synthase, e.g., FPP synthase, GPP synthase, GGPP synthase, and the like. In some embodiments, the DXP pathway of the host cell has been functionally disabled.

The present invention further provides compositions comprising a subject nucleic acid. Compositions comprising a subject nucleic acid will in many embodiments include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino) ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a nuclease inhibitor; and the like.

The present invention further provides compositions comprising a subject genetically modified host cell. A subject composition comprises a subject genetically modified host cell; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

Methods of Producing Isoprenoid Compounds

The present invention provides methods of producing an isoprenoid or isoprenoid precursor compound in a host cell. The methods generally involve culturing a subject genetically modified host cell in a suitable culture medium under conditions that promote synthesis of an isoprenoid compound or isoprenoid precursor compound, where the isoprenoid compound is generated by action of a subject variant enzyme(s), which enzyme is produced in the genetically modified host cell, on a substrate present in the host cell. In some embodiments, a subject method further comprises isolating the isoprenoid compound from the cell and/or from the culture medium.

In some embodiments, the isoprenoid or isoprenoid compound is produced in a subject genetically modified host cell at a level that is at least about 2-fold, at least about 5-fold, at least about 10-fold, at least about 25-fold, at least about 50-fold, at least about 100-fold, at least about 500-fold, at least about 1000-fold, at least about 2000-fold, at least about 3000-fold, at least about 4000-fold, at least about 5000-fold, or at least about 10,000-fold, or more, higher than the level of the isoprenoid or isoprenoid precursor compound produced in a host cell that produces the isoprenoid or isoprenoid precursor compound via the same biosynthetic pathway having integrated therein a parent isoprenoid biosynthetic pathway enzyme and/or a parent mevalonate pathway enzyme.

In some embodiments, a subject genetically modified host cell is cultured in a suitable medium (e.g., Luria-Bertoni broth, optionally supplemented with one or more additional agents, such as an inducer (e.g., where the variant terpene cyclase is under the control of an inducible promoter), etc.); and the culture medium is overlaid with an organic solvent, e.g. dodecane, forming an organic layer. The isoprenoid compound produced by the genetically modified host cell partitions into the organic layer, from which it can be purified. In some embodiments, where the variant terpene cyclase-encoding nucleotide sequence is operably linked to an inducible promoter, an inducer is added to the culture medium; and, after a suitable time, the isoprenoid compound is isolated from the organic layer overlaid on the culture medium.

In some embodiments, the isoprenoid compound will be separated from other products which may be present in the organic layer. Separation of the isoprenoid compound from other products that may be present in the organic layer is readily achieved using, e.g., standard chromatographic techniques.

In some embodiments, the isoprenoid compound is pure, e.g., at least about 40% pure, at least about 50% pure, at least about 60% pure, at least about 70% pure, at least about 80% pure, at least about 90% pure, at least about 95% pure, at least about 98%, or more than 98% pure, where "pure" in the context of an isoprenoid compound refers to an isoprenoid compound that is free from other isoprenoid compounds, contaminants, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s);

Example 1

Design and Generation of Variant Enzymes

Redesigning in vivo enzyme properties and thereby efficiencies of metabolic pathways based on their evolutionary relations allows us to test our current understandings for the molecular basis of adaptation, and has many important practical applications in synthetic biology[1-5]. Here, we demonstrate a strategy to redesign functionalities of enzymes using evolutionary relations as the sole guide. An analysis of over 10,000 sequences in 209 different enzyme families involved in central metabolism indicated that Gly and Pro were significantly more immutable; hence each enzyme family may have a preference for Gly and Pro distributions in its primary sequence. To investigate how these residues contribute to the evolution of enzymes and metabolic pathways, and thereby formulate redesign methodology, Gly and Pro distributions in several enzymes catalyzing the rate-limiting-steps (γ-humulene synthase (HUM)[1,6] specific mutant variants of HUM[1], and truncated hydroxy-3-methylglutaryl-CoA reductase (tHMGR)[7]) in a previously constructed synthetic metabolic pathway for mass-production of terpenoids[3] were probed. Approximately 80-90% of the fitness effects for those substitutions were accurately predicted, and multiple substitutions significantly improved the in vivo properties of these enzymes. Co-integration of these enzymes into the system dramatically improved host (E. coli) viability (3-4-fold) and the specific sesquiterpene production (~3,500-fold). Creation of these enzymes demonstrated that fitness effects contributed by the appropriate Gly and Pro distributions are important for in vivo properties of enzymes, may have been evolutionary acquired and maintained, and are therefore essential for the construction of novel metabolic pathways both in nature and a laboratory.

Methods

Analysis of amino acid composition changes in proteins across multiple species. To examine the relative importance of each of twenty different amino acids (X: Ala, Cys, Asp . . . ), we examined the average free energy difference for each amino acid in 209 different protein families against mutations (gain and loss by substitutions, deletions, and insertions) ($-\Delta G_{Mut}^X$). These protein families are all involved in central metabolism, including: glycolysis, citric acid cycle, pentose phosphate pathway, oxidative phosphorylation, fatty acid metabolism, amino acid metabolism, and nucleic acid metabolism (FIGS. 12A-O). Because of their essential roles in maintaining the viability of every organism, if any of these proteins had suboptimal in vivo functions, that enzyme would be a major bottleneck in the particular metabolic pathway and cause a severe competitive growth disadvantage for the host organisms. Consequently, these proteins are expected to have better in vivo properties across multiple species in order to maintain the efficiencies of biological systems and viabilities of organisms. In this analysis, we compared protein sequences derived from E. coli to their orthologous counterparts derived from other organisms, because our primary objective was to redesign heterologous enzymes adaptable to expression in E. coli.

In each protein family (F), orthologous protein sequences (O) were searched using the basic local alignment search tool for proteins (BLASTP: on the world wide web at www(dot)ncbi(dot)nih(dot)gov). In pair-wise alignment between a particular E. coli protein sequence and its orthologous protein sequence derived from a particular species, the probability of mutations ($P_{Mut,O,F}^X$) for each amino acid (X) was calculated based on the composition of each mutated amino acid between the two sequences. The pair-wise alignments used herein covered more than eighty-percent and less than hundred twenty-percent of the corresponding E. coli protein sequences. If proteins evolved without any constraint, the $P_{Mut,O,F}^X$ should be identical to that for all amino acids ($P_{Mut,O,F}$). $P_{Mut,O,F}^X$ was then plotted against $P_{Mut,O,F}^X$. Interestingly, in many cases, $P_{Mut,O,F}^X$ and $P_{Mut,O,F}$ were linearly correlated. On average, 490 (S.D. 265) plots (pair-wise sequence alignments) were made for each protein family. $P_{Mut,F}^X/P_{Mut,F}$ is defined as the slope for the linear regression of the data in the plot. The free energy of each amino acid X for the mutations in each protein family F ($-\Delta G_{Mut,F}^X$) was then calculated according to Boltzmann statistics as follows:

$$\frac{P_{Mut,F}^X}{P_{Mut,F}} = \exp\left(\frac{-\Delta G_{Mut,F}^X}{kT^*}\right)$$

where kT* denotes an arbitrary constant. In this analysis, we calculated $\Delta G_{Mut,F}^X$ only when the $R^2$ of the $P_{Mut,F}^X/P_{MUt,F}$ plot was greater than 0.5.

Design methodology to improve in vivo properties of enzymes using MSA as a guide. To predict where to distribute Gly, Pro, and Xaa (Xaa denotes any amino acid residues other than Gly and Pro), we first created an MSA for both γ-humulene synthase (HUM) and truncated hydroxymethyl glutaryl-CoA reductase (tHMGR) using MUSCLE (on the internet at phylogenomics(dot)berkeley(dot)edu/cgi-bin/muscle/inpu_muscle(dot)py). The primary sequence of HUM from *Abies grandis* was aligned with other mono-, sesqui-, and diterpene synthases derived from gymnosperms (MSA 1; FIGS. 1A-Y). Although many sesquiterpene synthases have been isolated from angiosperms, mono- and diterpene synthases from gymnosperms are more closely correlated to HUM at the primary sequence level. The primary sequence of tHMGR derived from yeast was aligned with other orthologous sequences derived from archaeal species, as the archaeal HMGR is produced in a soluble form as opposed to the membrane bound form found in most eukaryotes (MSA 2; FIGS. 2A-M). The conservation probability for Gly ($P_i^G$) and Pro ($P_i^P$) at column i in a given MSA was calculated based on the composition of Gly and Pro at column i as follows:

$$P_i^X = \frac{N_i^X}{N_i}$$

where $N_i^X$ and $N_i$ denote the number of amino acid X (Gly or Pro) and the total number of aligned amino acids at position i in each column of MSA, respectively. The fitness effects contributed by these mutations were predicted dependent on the value of $P_i$; when $P_i^X \geq 0$, the mutation to amino acid X likely shows neutral, nearly neutral, or positive fitness effects, and when $P_i^X \geq 0$, the mutations to amino acid X likely shows neutral, nearly neutral, or negative fitness effects. We used $P_i^X=0.4$ as a threshold and compared $P_i^X$ and the fitness effects resulting from single mutations.

Reagents and equipments. All enzymes and chemicals were purchased from New England Biolabs and Sigma-Aldrich Co, respectively, unless otherwise stated. An HP6890 gas chromatograph equipped with a 5973 mass selective detector (Hewlett Packard) or flame ionization detector, a CyclosilB capillary column (30 m×250 μm i.d.×0.25 μm thickness, Agilent Technologies) or DB5-MS capillary column (30 m×250 μm i.d.×0.25 μm thickness, Agilent Technologies), and a CombiPAL auto sample-injector (LEAP Technologies) were used for analysis. An LS6500 multi-purpose scintillation counter (Beckman coulter) was used for enzyme kinetics.

Strains and Plasmids. *Escherichia coli* strain DH10B and DH1 was used for both mevalonate and sesquiterpene productions, and BL21(DE3) was used for protein over-expression and purification. Plasmids pBADMevT[1,2] and their mutant variants were used for mevalonate production. A plasmid pBBRMBIS[1] was used for FPP production. Plasmids pTrcHUM[3], pTrcHUM15, and their mutant variants were used for sesquiterpene productions (FIG. 3). Plasmids pTrcSHUM15 and its mutant variants were used for quantification of protein concentrations in vivo. Plasmids pETHUM[3] and its mutant variants were used for protein over-expression and purification.

FIGS. 3A-D. Synthetic biological system for mass-production of terpenoids. The plasmids contained in our system are shown. (A) pBADMevT, an artificial operon of atoB (acetoacetyl-CoA synthase from *E. coli*), HMGS (HMG-CoA synthase from yeast), and tHMGR (HMG-CoA reductase I from yeast with its membraning-spanning region truncated) under control of $P_{BAD}$. (B) pBBRMBIS, an artificial operon of ERG12 (mevalonate kinase (MK) from yeast), ERG8 (phosphomevalonate kinase (PMK) from yeast), MVD (mevalonate diphosphate decarboxylase from yeast), idi (isopentenyldiphosphate (IPP) isomerase from *E. coli*), and ispA (farnesyldiphosphate (FPP) synthase from *E. coli*) under control of $P_{Lac}$. (C) pTrcHUM15, containing modified ribosome-binding-site (mRBS). (D) pTrcHUM.

Since reduced expression of HUM slightly improved sesquiterpene production, an extra seven base pairs were introduced between the ribosome-binding-site (RBS) and the start codon at the NcoI site of pTrcHUM. The RBS region were amplified by polymerase chain reaction (PCR): 98° C. for 30 sec, 55° C. for 30 sec, and 72° C. for 30 sec, repeated 30 times. The reaction mixture contained 1× Phusion buffer, 2 mM dNTP, 0.5 μM forward (5'-GCGCGTTGGTGCGGATATC-3'; SEQ ID NO:77) and reverse (5'-CATGCCATGGAGCTTATTCTGTTTCCTGTGTGAAATTG-3'; SEQ ID NO:78) primers, 2.5 U Phusion DNA polymerase (Finezyme), and 50 ng pTrcHUM as a template in a total volume of 100 μl. The amplified fragments were then digested with EcoRV/NcoI and inserted into the corresponding site of pTrcHUM to form pTrcHUM15.

pTrcSHUM15 was constructed based on pTrcHUM15 backbone. S-tag was fused to the N-terminal of HUM. The RBS region in pTrcHUM15 was amplified by PCR: 98° C. for 30 sec, 55° C. for 30 sec, and 72° C. for 30 sec, repeated for 30 times. The reaction mixture contained 1× Phusion buffer, 2 mM dNTP, 0.5 μM forward (5'-GCGCGTTGGTGCGGATATC-3'; SEQ ID NO:79) and reverse (5'-GCAGCAGCGGTTTCTTTCATGGAGCTTATTCTGTTTC-3'; SEQ ID NO:80) primers, 2.5 U Phusion DNA polymerase (Finezyme), and 50 ng pTrcHUM15 as a template in total volume of 100 μl. The S-tag was amplified by PCR: 98° C. for 30 sec, 55° C. for 30 sec, and 72° C. for 30 sec, repeated for 30 times. The reaction mixture contained 1× Phusion buffer, 2 mM dNTP, 0.5 μM forward (5'-GAAACAGAATAAGCTCCATGAAAGAAACCGCTGCTGC-3'; SEQ ID NO:81) and reverse (5'-CATGCCATGGAACCGCGTGGC-3'; SEQ ID NO:82) primers, 2.5 U Phusion DNA polymerase (Finezyme), and 50 ng pET29 (Novagen) as a template in a total volume of 100 μl. These two amplified fragments were spliced by over-lap PCR: 98° C. for 30 sec, 55° C. for 30 sec, and 72° C. for 30 sec, repeated for 30 times. The reaction mixture contained 1× Phusion buffer, 2 mM dNTP, 0.5 μM forward (5'-GCGCGTTGGTGCGGATATC-3'; SEQ ID NO:83) and reverse (5'-CATGCCATGGAACCGCGTGGC-3'; SEQ ID NO:84) primers, 2.5 U Phusion DNA polymerase (Finezyme), and the abovementioned fragments as a template in a total volume of 100 μl. The spliced fragment was then digested with EcoRV/NcoI and inserted into the corresponding site of pTrcHUM to form pTrcSHUM15.

GC-FID and GC-MS analysis for in vivo sesquiterpene production. To screen the single mutation library, a single colony harboring pTrcHUM (wild type HUM or its mutant variants) and pBBRMBIS was inoculated into Luria Bertani (LB) medium containing 50 μg/ml carbenicillin ($Cb^{50}$) and 50 μg/ml kanamycin ($Km^{50}$) and grown overnight at 37° C. An aliquot (50 μl) of this seed culture was inoculated into fresh LB medium (5 ml) containing 10 mM D/L-mevalonate, $Cb^{50}$, and $Km^{50}$, overlaid with 500 μl dodecane, and grown for 24 hours at 37° C. An aliquot of dodecane (50 μl) was diluted into 200 μl of ethyl acetate, and the mixture was analyzed by GC-MS or GC-FID using a GC oven temperature program of 80° C. for 1 min, then ramping 30° C./min to 110° C., 5° C./min to 160° C., and 130° C./min to 250° C. for CyclosilB capillary column analysis and of 80° C. for 3 min, then ramping 5° C./min to 160° C., and 120° C./min to 300° C. for DB-5MS capillary column analysis. Camphor was used as an internal standard. Sesquiterpenes were identified from their mass spectra and GC retention times by comparison to available authentic standards and spectra in libraries previously reported in the literature.

As for the final sesquiterpene production assay, a bacterial system containing three plasmids was used[1]. A single colony harboring pTrcHUM15 or pTrcSHUM15 (wild type HUM or its mutant variants), pBBRMBIS, and pBADMevT (wild type tHMGR[4] or its mutant variants) was inoculated into LB medium containing $Cb^{50}$, $Km^{50}$, and chloramphenicol ($Cm^{50}$) and grown for overnight at 37° C. An aliquot of this seed culture was inoculated into fresh modified m9 medium (pH 7, M9 salt, 75 mM MOPS, 3% glycerol, 5 g/L yeast extract, 2 mM $MgSO_4$, 1 mg/L thiamine, 10 μM $FeSO_4$, 0.01 mM $CaCl_2$, and micronutrient) (50 ml) to the final $OD_{600nm}$ of 0.05 containing $Cb^{50}$, $Km^{50}$, and $Cm^{50}$, overlaid with 10 ml of dodecane. Two hours after the inoculation, isopropyl-β-D-thiogalactopyranosid (IPTG) and (+)-L-arabinose were added to the final concentrations of 1 mM and 13.3 mM, respectively. Sesquiterpene production was analyzed as mentioned above.

GC-MS analysis for in vivo mevalonate production. As for screening the single mutation library, a single colony harboring pBADMevT (wild type tHMGR or its mutant variants) was inoculated into LB medium containing $Cm^{50}$ and grown overnight at 37° C. An aliquot (50 μl) of this seed culture was inoculated into fresh LB medium (5 ml) containing $Cm^{50}$ and 13.3 mM (+)-L-arabinose, and grown for 24 hours at 37° C. An aliquot of culture (560 μl) was mixed with 140 μl of 0.5 M HCl to dehydrate the mevalonate to form mevalonolactone, and 700 μl of ethyl acetate was then added to the sample. The mixture was vortexed for 5 minutes, and the ethyl acetate was analyzed by GC-MS using a GC oven temperature program of 90° C. for 1 min, then ramping 30° C./min to 250° C. for CyclosilB capillary column analysis. Mevalonolactone was identified from its mass spectra and retention time by comparison to an authentic standard.

As for the final mevalonate production assay, a single colony harboring pBADMevT (wild type tHMGR or its mutant variants) was inoculated into LB medium containing Cm$^{50}$ and grown overnight at 37° C. An aliquot (500 µl) of this seed culture was inoculated into fresh modified m9 medium (50 ml, see above formulation) containing Cm$^{50}$. Two hours after the inoculation (+)-L-arabinose was added to the final concentration of 13.3 mM. Mevalonate production was analyzed as mentioned above.

Site directed mutagenesis of HUM by overlap PCR. Site directed mutagenesis for HUM was carried out using over-lap PCR (FIGS. 13A-C provide the primer sequences used for site directed mutagenesis of HUM).

DNA fragments encoding the N- and C-terminus of the mutation were amplified by PCR: 98° C. for 30 sec, 55° C. for 30 sec, and 72° C. for 30 sec, repeated 30 times. The reaction mixture contained 1× Phusion buffer, 2 mM dNTP, 0.5 µM forward and reverse primers, 2.5 U Phusion DNA polymerase (Finezyme), and 50 ng pTrcHUM in 100 µl as a template for γ-humulene synthase. Amplified DNA was gel purified using a gel purification kit (Qiagen) or treated with DpnI and purified using a PCR purification kit (Qiagen). These two amplified DNA fragments were spliced via over-lap PCR: 98° C. for 30 sec, 55° C. for 30 sec, and 72° C. for 30 sec, repeated for 30 times. The reaction mixture contained 1× Phusion buffer, 2 mM dNTP, 0.5 µM forward and reverse primers, 2.5 U Phusion DNA polymerase (Finezyme), and 50 ng of the abovementioned DNA fragments as a template in a total volume of 100 µl. The fully amplified HUM fragment was digested with NcoI/XbaI and cloned into the corresponding site in pTrcHUM.

Site directed mutagenesis of tHMGR by overlap PCR. Site directed mutagenesis for tHMGR was carried out using over-lap PCR (FIGS. 14A-D provide the primer sequences used for site directed mutagenesis of tHMGR).

DNA fragments encoding the N- and C-terminus of the mutation were amplified by PCR: 98° C. for 30 sec, 55° C. for 30 sec, and 72° C. for 30 sec, repeated for 30 times. The reaction mixture contained 1× Phusion buffer, 2 mM dNTP, 0.5 µM forward and reverse primers, 2.5 U Phusion DNA polymerase (Finezyme), and 50 ng pBADMevT as a template for tHMGR in a total volume of 100 µl. The amplified DNA fragment was gel purified using a gel purification kit (Qiagen) or treated with DpnI and purified using a PCR purification kit (Qiagen). These two amplified DNA fragments were spliced via over-lap PCR: 98° C. for 30 sec, 55° C. for 30 sec, and 72° C. for 30 sec, repeated for 30 times. The reaction mixture contained 1× Phusion buffer, 2 mM dNTP, 0.5 µM forward and reverse primers, 2.5 U Phusion DNA polymerase (Finezyme), and 50 ng abovementioned DNA fragments as a template in a total volume of 100 µl. The fully amplified HMGR fragment was digested with SpeI/HindIII and inserted into the corresponding site of pBADMevT.

Quantification of in vivo HUM concentrations. A single colony harboring pTrcSHUM15 (wild type or its mutant variant), pBBRMBIS, and pBADMevT was inoculated into LB medium containing Cb$^{50}$, Km$^{50}$, and Cm$^{50}$ was grown overnight at 37° C. An aliquot of this seed culture was inoculated into fresh modified m9 medium (50 ml, see above formulation) containing Cb$^{50}$, Km$^{50}$, and Cm$^{50}$ to the final OD$_{600nm}$ of 0.05 and was grown at 37° C. Two hours after the inoculation, IPTG and (+)-L-arabinose was added to the final concentrations of 1 mM and 13.3 mM, respectively. The cultures were then grown at 20° C., 30° C., and 37° C. An aliquot of culture (1 ml) was taken and centrifuged at 14,000×g. The resulting pellet was resuspended into Bugbuster containing recommended amount of Lysonase (Novagen) to the final OD$_{600nm}$ of 20, and it was incubated for half an hour at room temperature. This lysis solution was centrifuged for 10 min at 14,000×g. 24 µl of whole lysis solution (both soluble and insoluble fractions) and supernatant of lysis solution (soluble fraction) were mixed with 75 µl of 8 M guanidium hydrochloride and 1 µl of 4 M dithiothreitol. These solutions were incubated for another hour at room temperature. The concentration of HUM was determined by FRET Works S-tag assay kit following the recommended protocols (Novagen). In vivo sesquiterpene production from each culture was measured as described above.

Protein expression and purification of HUM. Wild type HUM and its variants were cloned into pET29 and transformed into BL21 (DE3). Each transformant was inoculated into LB medium (5 ml) containing Km$^{50}$ and was grown overnight at 30° C. An aliquot (2 ml) of this seed culture was inoculated into fresh terrific broth (TB) medium containing Km$^{50}$ (500 ml), and the culture was grown at 30° C. When the culture reached OD$_{600nm}$ of 0.6-0.8, 0.1 mM of IPTG was added, and it was grown at 20° C. for another 16 hours. Cells were harvested by centrifugation at 6,000×g for 15 min. The pellet was suspended in 50 ml of BugBuster (Novagen) containing 20 U DNaseI and bacterial protease inhibitor cocktail II (Novagen), and was incubated for an hour at 4° C. The solution was then centrifuged at 20,000×g for 30 min, and then filtered through a 0.45-µm filter. S-tag™ Thrombin purification kit (Novagen) was used for the purification following the protocol recommended by Novagen. All purifications were done at half scale. The eluted protein solution was dialyzed twice (PIERCE, MW 3,000 Da) against 1 L of buffer containing 10 mM Tes (pH 7.0), 10 mM MgCl$_2$, 1 mM DTT and 5% glycerol overnight. The protein concentration was measured using the Bradford method. We obtained approximately 3 ml of 25-500 µg/ml of protein solution with about 95% purity (confirmed by SDS-PAGE gel).

Enzyme kinetics. The kinetics studies of HUM and its variants were carried out following a slightly modified protocol from that previously reported by Little et. al. Kinetics for each enzyme was measured in a 40 µl reaction containing 0.15-0.4 µM enzyme, in buffer described in the previous section and overlaid with dodecane. The concentration of FPP was varied from 0.229 to 58.6 µM with a fixed ratio of [$^3$H]FPP. Seven to nine different concentrations of FPP were used for each enzyme (n=3). The reaction mixture was incubated for 20 minutes at 31° C. To stop the reaction, 40 µL of a solution containing 4 M NaOH and 1 M EDTA was added and mixed. To extract sesquiterpene products, the reaction mixture was vortexed for 2 min, and 400 µL of dodecane was taken from the solution and mixed with 15 mL of scintillation fluid. Radioactivity was measured by scintillation counting. $k_{cat}$, $K_m$ and $k_{cat}/K_m$ were calculated using Enzyme Kinetics!Pro (ChemSW).

Results

In this analysis, we primarily considered enzymes involved in central metabolism. Because of their essential roles in maintaining the viability of host organisms and their practical applications to many different industries[12], the in vivo properties of these enzymes and the efficiencies of these metabolic pathways are expected to be very high. Since our objective is to redesign in vivo enzyme properties adaptable to an E. coli environment, protein sequences derived from E. coli were compared to each of their orthologous counterparts derived from other organisms. We analyzed over 10,000 protein sequences in 209 different protein families involved in central metabolism across multiple species (see Methods section for detail) spanning a wide range of different lifestyles and environments (FIGS. 12A-O). The probability of mutations to each amino acid between two sequences was plotted against that for all amino acids. The plots for Ala, Gln, Gly, and Pro of the glutamate synthase large subunit are shown as examples (FIG. 4A-D, respectively). The stability of each amino acid (X) to mutations ($-\Delta G_{Mut}^{X}$) was then calculated (FIG. 4E). It clearly shows that Gly and Pro are significantly more immutable compared to other amino acids; hence, it is likely that each protein family has its own preference in Gly and Pro distributions in its primary sequence, and satisfaction of this preference might be very important for in vivo enzyme function.

FIGS. 4A-E. Evolutionary study of the relative stability for each amino acid. A relative stability ($-\Delta G_{Mut}^{X}$; kT* denotes arbitrary unit) for each amino acid to mutations (gain and loss by substitutions, insertions, and deletions) was calculated by comparing E. coli proteins involved in central metabolism and each of their orthologous counterparts. A probability of mutation to each amino acid ($P_{Mut}^{X}$) is plotted against that for all amino acids ($P_{Mut}$); plots for alanine ($P_{Mut}^{A}/P_{Mut}=1$)(A), glutamine ($P_{Mut}^{Q}/P_{Mut}>1$)(B), glycine ($P_{Mut}^{G}/P_{Mut}<1$)(C), and proline ($P_{Mut}^{P}/P_{Mut}<1$)(D) using the glutamate synthase large subunit protein family are shown. The average of the relative stability for each amino acid to mutations obtained from analyses of 209 different protein families is shown (E: Mean±S.E.) (N=4042; ANOVA: P=0, F=234.43, d.f.=19). The result clearly indicates that Gly and Pro were significantly more immutable during the course of evolution.

To investigate the contributions of Gly and Pro distributions to in vivo enzyme properties, we chose HUM as a model enzyme. HUM is a sesquiterpene synthase from *Abies grandis* that is known to produce 52 different sesquiterpenes from a sole substrate, farnesyl diphosphate, through wide varieties of cyclization mechanisms[6]. We previously explored the evolvability of this enzyme, and successfully constructed, based on the theory of divergent molecular evolution, several specific sesquiterpene synthases that produce a single product[13]. However, integration of HUM and its specific mutant variants into our synthetic biological system[3] resulted in very poor sesquiterpene production (approximately 1 mg/L). Thus, redesigning HUM should allow us to explore the mechanisms of divergent molecular evolution even further. In addition, it will allow us to redesign any terpene synthase useful for the mass production of single terpenes that have found use as drugs, flavors, fragrances, neutraceuticals and in many other applications.

First, multiple sequence alignment (MSA) for HUM was constructed (see Methods section for detail). Since few sesquiterpene synthases derived from gymnosperms have been discovered, mono- and diterpene synthases derived from gymnosperms were also used for MSA construction (MSA 1; FIGS. 1A-Y). Although a number of sesquiterpene synthases have been cloned from angiosperms, mono- and diterpene synthases derived from gymnosperms are more closely related to HUM[14]. The probability of conservation for both Gly ($P_{i}^{G}$) and Pro ($P_{i}^{P}$) at ith residue of HUM was calculated (FIGS. 5A and C). Substitutions involving Gly and Pro were then introduced to HUM according to the calculated profile, and the fitness effects of these mutations were monitored by the level of in vivo sesquiterpene production (FIGS. 5B and D). Although MSA was constructed primarily from various terpene synthases sharing neither substrate specificity nor product selectivity, approximately 80-90% of the fitness effects for these mutations were accurately predicted ($P_i$=0.4 as a threshold); the exceptions were the residues predominantly conserved in mono- and diterpene synthases (green and purple bars in FIG. 5A-D respectively). In particular, mutations that most significantly affected the in vivo enzyme functions (R142G and G227A) were accurately predicted. Although saturation mutagenesis was carried out on G148, G227, G327, and G361, Ala substitution was appeared to be the best in terms of in vivo sesquiterpene production and steady state kinetics.

FIGS. 5A-D. Relevance between evolutionary relations and the fitness effects of Gly and Pro distributions in HUM. Distributions for Gly (A) and Pro (C) were predicted based on an MSA constructed using the primary sequences of mono-, sesqui-, and diterpene synthases derived from gymnosperms as a guide. According to this profile, Gly→Ala, Xaa→Gly, Pro→Ala, and Xaa→Pro substitutions were introduced into HUM, and fitness effects for these substitutions were monitored by in vivo sesquiterpene production (B: Gly→Ala and Xaa→Gly, D: Pro→Ala, and Xaa→Pro; Mean±S.D. of triplicate measurements is shown). The results show that 80-90% of fitness effects were well predicted from the value of $P_i$ ($P_i$=0.4 as a threshold; see Methods section) except for the residues unaligned (orange), aligned only in monoterpene synthases (green), and aligned only in diterpene synthases (purple). The sequences aligned only in sesquiterpene synthases are shown in light blue.

Mutations that improved the in vivo properties of HUM were subsequently recombined. The effects of many of selected mutations were cumulative. As a result, we obtained the HUM-G6 mutant containing the changes K126P/R142G/G148A/G227A/G327A/G361A, resulting in significantly higher sesquiterpene production (~80-fold) (FIG. 6A, 6B, and FIG. 3). Interestingly, none of the single mutations to HUM-G6 predicted as false negative (G350A, G441A, and G500A) improved sesquiterpene production further. Some single mutations that demonstrated positive fitness effect as they were predicted to HUM-G6 (Q242P, S298G, and P443A) did not improve sesquiterpene production either. Overall, all of the mutations introduced into HUM-G6 were well predicted using the methodology formulated herein. Interestingly, product selectivity for HUM-G6 was comparable to that of the HUM (Table 1), even though the enzymes are known to be very plastic (single mutations have been known to significantly alter product selectivity[1]).

TABLE 1

Product selectivity of HUM and its mutant variants

| Name[*1] | Mutations | Products[*2*3] | | | | | |
|---|---|---|---|---|---|---|---|
| | | 1 | 2 | 3 | 4 | 5 | 6 |
| WT | None | 8.3 | 7.2 | 14.9 | 26.1 | 34.0 | 9.5 |
| G3 | K126P, 142G, G227A | 7.2 | 6.3 | 16.5 | 27.9 | 31.7 | 10.4 |
| G6 | K126P, 142G, G148A, G227A, G327A G361A | 7.1 | 6.8 | 15.2 | 27.4 | 32.8 | 10.7 |
| SIB | K126P, 142G, G148A, G227A, G327A G361A F312Q, M339A, M447F | 0.2 | 2.8 | 2.2 | 80.1 | 13.8 | 0.9 |
| HUM | K126P, 142G, G148A, G227A, G327A G361A M339N, S484C, M565I | 5.6 | 11.7 | 5.9 | 0.7 | 75.6 | 0.6 |

TABLE 1-continued

Product selectivity of HUM and its mutant variants

| Name*[1] | Mutations | Products*[2]*[3] | | | | | |
|---|---|---|---|---|---|---|---|
| | | 1 | 2 | 3 | 4 | 5 | 6 |
| LFN | K126P, 142G, G148A, G227A, G327A G361A A317N*[4], A336S, S484C, I562V | 12.8 | 3.4 | 62.1 | 1.6 | 11.9 | 8.1 |
| ALP | K126P, 142G, G148A, G227A, G327A, G361A A336C, T445C, S484C, I562L, M565L | 60.2 | 4.6 | 13.7 | 0.4 | 14.6 | 6.5 |
| BBA | K126P, 142G, G148A, G227A, G327A, G361A A336V, M447H, I562T | 1.6 | 0.2 | 3.9 | 0.5 | 4.7 | 89.1 |
| AYG | K126P, 142G, G148A, G227A, G327A, G361A S484A, Y566F | 14.6 | 27.5 | 0.5 | 0.6 | 47.1 | 9.6 |

*[1]WT: wild type γ-humulene synthase, G3: third generation of mutant γ-humulene synthase, G6: sixth generation of mutant γ-humulene synthase, SIB: sibirene synthase, HUM: new γ-humulene synthase, LFN: longifolene synthase, ALP: α-longipinene synthase, BBA: β-bisabolene synthase, AYG: α-ylangene synthase
*[2]1: α-longipinene, 2: α-ylangene, 3: longifolene 4: sibirene, 5: γ-humulene, 6: β-bisabolene
*[3]All product distributions were represented for 1-6 as 100%; these are corresponding to more than 85-95% and to 75% of total products in mutants and wild type (including G3 and G6), respectively.
*[4]A317N occurred during recombination, and improved in vivo terpene production without a change in product distribution In addition, both $k_{cat}$ and $K_m$ decreased in HUM-G6, resulting in a similar $k_{cat}/K_m$ to that of HUM (Table 2).

TABLE 2

Steady state kinetics for HUM and some of its mutant variants.

| Enzymes | $k_{cat}$ ($10^{-3} s^{-1}$) | $K_m$ (μM) | $k_{cat}/K_m$ ($10^3 M^{-1} s^{-1}$) |
|---|---|---|---|
| WT | 12.00 ± 0.34 | 2.01 ± 0.17 | 5.96 |
| G3 | 7.62 ± 0.21 | 4.66 ± 0.39 | 1.64 |
| G6 | 1.71 ± 0.17 | 0.69 ± 0.13 | 2.47 |

Using the same methodology, we also redesigned the in vivo properties of tHMGR (ERG12) (FIGS. 7A-D; and FIGS. 8A and 8B), which has been identified as another enzyme catalyzing a rate-limiting-step in our synthetic biological system[15]. Integration of pBADMevT containing tHMGR-G9 (P200A/G206A/T239P/G319A/G352A/G417A/P428G/ $K_{474}G$/G495A) improved both growth (~3-fold) and mevalonate production (~3-fold). Co-integration of both tHMGR-G9 and HUM-G6 into the system dramatically improved growth (3-4-fold) and sesquiterpene production (800-fold) (FIGS. 6A and B), such that the production reached approximately 1 g/L 48 hours after inoculation. The same mutations were also introduced to specific mutant variants of HUM previously constructed in our laboratory[1], and the specific terpene productivities were also dramatically improved (400-3500-fold: FIGS. 6C and D). Since these enzymes are divergently evolved from HUM and these predictions were made based on other terpene synthases as guides, these results implied that appropriate Gly and Pro distributions are essential for proper enzyme function in vivo. Additionally, similar mutations may improve the in vivo properties of other terpene synthases including mono-, sesqui-, and diterpene synthases.

FIGS. 6A-D. Co-integration of redesigned HUM and tHMGR into a synthetic biological system for mass-production of terpenoids and the resulting in vivo sesquiterpene production. *Escherichia coli* DH1 harboring pBADMevT (containing tHMGR-WT, tHMGR-G3 (G206A/G319A/ G352A/G417A/G495A), or tHMGR-G6 (P200A/G206A/ T239P/G319A/G352A/G417A/P428G/$K_{474}$G/G495A)), pBBRMBIS, and pTrcHUM (containing HUM-WT, HUM-G3 (K126P/R142G/G227A), or HUM-G6 (K126P/R142G/ G148A/G227A/G327A/G361A)) was used for in vivo sesquiterpene production. The growth curve (A) and sesquiterpene production at 24 hours after inoculation (B) are shown. HUM-WT, HUM-G3, and HUM-G6 co-integrated with tHMGR are shown in light blue, medium blue, and blue, respectively, and those with tHMGR-G9 are shown in orange, light green, and green, respectively. The strain containing tHMGR-G9 grew 3-fold higher and produced 3-fold more mevalonate (FIGS. 8A and 8B), resulting in synergistic improvement in overall sesquiterpene production. The mutations in HUM-G6 were also applied to specific mutant variants of HUM previously constructed in our laboratory (SIB, sibirene synthase; sHUM, specific γ-humulene synthase; LFN, longifolene synthase; ALP, α-longipinene synthase; BBA, β-bisabolene synthase; and AYG, α-ylangene synthase). The resulting specific terpene production was also dramatically improved in each case (400-3500-fold). All data represent mean±S.D. of triplicate measurements.

FIGS. 7A-D. Relevance between evolutionary relations and functional consequences of Gly and Pro distributes in tHMGR. Proper distributes of Gly (A) and Pro (C) for tHMGR were predicted based on an MSA constructed using the primary sequences of HMGR derived from archaea as a guide (sharing 30-40% sequence identity). HMGR derived from archaea is produced in a soluble form rather than membrane bound form as is generally found in eukaryotes; thus, it is more appropriate to use an MSA derived from archaea. According to this profile, Gly→Ala, Xaa→Gly, Pro→Ala, and Xaa→Pro substitutions were introduced into tHMGR, and functional consequences for these substitutions were monitored by in vivo mevalonate production (B: Gly→Ala and Xaa→Gly, D: Pro→Ala, and Xaa→Pro). The results show that 80-90% of mutations were well predicted from these profiles with $P_i$=0.4 as a threshold except for the unaligned residues (orange).

FIGS. 8A and 8B Integration of redesigned tHMGR to *E. coli* and resulting mevalonate production. The growth (A) and mevalonate production (B) for strains harboring pBADMevT containing tHMGR-WT (wild type HMGR1 of its membrane binding domain truncated), tHMGR-G5 (G206A/G319A/ G352A/G417A/G495A) and tHMGR-G9 (P200A/G206A/ T239P/G319A/G352A/G417A/P428G/K474G/G495A) were measured. Interestingly, both growth level and mevalonate production improved approximately 2.5-3-fold, and the increase in growth level accounts for the increase in mevalonate production. We previously proposed that accumulation of HMG-CoA inhibits cell growth[5]. Thus, improvement of the in vivo properties of tHMGR allowed *E. coli* to alleviate the toxicity derived from HMG-CoA. Three days after inoculation, both growth and mevalonate production from strains harboring pBADMevT containing any tHMGR variant reached an almost identical level of mevalonate (approximately 10 in $OD_{600nm}$ and 40 mM in mevalonate production).

To understand how Gly and Pro redistributions contributed to this enormous improvement in sesquiterpene production, sesquiterpene production from S-tagged versions of HUM, HUM-G3 (K126P/R142G/G227A), and HUM-G6 were examined at different temperatures (FIGS. 9A and 9B). Interestingly, in vivo sesquiterpene production from S-tagged HUM-G6 increased approximately two-fold over the non-S-tagged HUM-G6 (~1350-fold). HUM showed the highest sesquiterpene production at 30° C. In contrast, HUM-G6 showed the highest production at 37° C. The differences in sesquiterpene production between HUM and HUM-G6 increased with temperature (3.3-fold at 20° C., 10-fold at 30° C., and 220-fold at 37° C.: FIG. 9B), suggesting that HUM does not fold properly at higher temperatures, and Gly and Pro redistributions made HUM more adaptable in the E. coli growth environment. Quantification of in vivo enzyme concentrations in both the soluble fraction and crude lysate revealed that increases in sesquiterpene production were primarily attributable to increases in overall protein production at the lower temperature, and large increases in sesquiterpene production at higher temperatures were due to increased solubility (or foldability) (FIGS. 9C and 9D).

FIGS. 9A-D. Investigation of the effects for Gly and Pro mutations at different temperatures. S-tagged HUM-WT (orange), HUM-G3 (light green), and HUM-G6 (green) were co-integrated with tHMGR-G9 into the synthetic biological system for mass-production of terpenoids to see the temperature effects of accumulated Gly and Pro mutations. The growth (A), fold increases in sesquiterpene production over that of the strain harboring tHMGR-WT and HUM-WT (B), soluble enzyme concentration (C), and total enzyme concentration (D) at 24 hours after inoculation are shown. Interestingly, sesquiterpene productivity of HUM-G6 was improved almost 2-fold with an N-terminal S-tag (~1.350-fold). The higher the temperature becomes, the more HUM proteins were produced. At 37° C., HUM-G6 in the soluble fraction was significantly higher than that of HUM-WT. Thus, Gly and Pro redistributions likely improved foldability of HUM-G6. All data represent mean±S.D. of triplicate measurements.

Although we were unable to quantify the free energies of folding and unfolding for the effects of those mutations (due to irreversibility of HUM folding), several studies have considered the physicochemical roles of Gly and Pro in protein structure[16,17]. Substitutions of Gly→Xaa and Xaa→Pro (Xaa denotes any amino acids other than Gly and Pro) could reduce the conformational entropy of unfolding, and thereby stabilize the native states of proteins by ~1 kcal/mol (entropic stabilization)[18]. In addition, substitutions of Gly→Ala (or Xaa) can reduce the conformational complexity (accessible conformations during protein folding) by approximately 3.4-fold, and hence the protein can fold to its native state faster[19]. However, substitutions of Xaa→Gly and Pro→Xaa at some local positions are known to be favorable, because the more rigid or bulky residues at some positions can introduce unfavorable kinetic barriers to their folding and/or strain energy to their native states; for example, Gly is more favorable at the C-terminal cap of α-helices[20]. Thus, Gly and Pro redistributions for both HUM and tHMGR might be similarly affected.

More recently, it has been proposed that amino acid substitutions were asymmetric rather than symmetric as was often assumed 2. All amino acids with declining frequencies were thought to be incorporated into the genetic code at earlier stages in evolution, and vice versa $(R=0.55)^{21,22}$. Interestingly, Gly and Pro were shown to be among the strong 'loosers'. Thought to over-represent primordial protein sequences and to be gradually diluted upon recruitment of new amino acids, Gly and Pro might have been longer exposed to natural selection and have had higher chance to be properly distributed, resulting in higher immutability. Although the general tendency is likely affected by the genetic drift of each amino acid depending on codon biases and degree of differences in chemical properties from other amino acids, the stability of amino acids to mutations was relatively well correlated to both a rate of recent gain and loss of amino acids $(R=0.60)^{21}$, and the consensus order of amino acid recruitment into the genetic code $(R=0.59)^{22}$. In addition to the unique physicochemical roles of Gly and Pro in protein structure, this may explain why these two residues are relatively more conserved in proteins that are evolutionary related. Therefore, it is reasonable to consider the proper distributions of these amino acids to redesign protein function.

On the basis of the evolutionary relationship, we successfully redesigned the enzymes of a heterologous metabolic pathway to improve its efficiency. Although the methodology developed herein focused only on Gly and Pro, the results showed that it was very powerful and effective, and might be generally applied to improve the function of any other proteins. In addition, the methodology required neither the structural information nor the high-throughput screening generally required for conventional protein engineering strategies: rational design[23], computational design[24], and directed evolution[25,26]. These results also provide evidence that proper Gly and Pro distributions are very important for enzyme function and therefore metabolic pathways. Since proper distributions of these residues can largely be predicted from their evolutionary relations, it is likely that there exists proper distributions innate to each protein scaffold, and this can be achieved mainly as a result of adaptation in earlier stages of evolution.

REFERENCES

1. Yoshikuni, Y., Ferrin, T. E. & Keasling, J. D. Designed divergent evolution of enzyme function. Nature 440, 1078-82 (2006).
2. Ro, D. K. et al. Production of the antimalarial drug precursor artemisinic acid in engineered yeast. Nature 440, 940-3 (2006).
3. Martin, V. J., Pitera, D. J., Withers, S. T., Newman, J. D. & Keasling, J. D. Engineering a mevalonate pathway in Escherichia coli for production of terpenoids. Nat Biotechnol 21, 796-802 (2003).
4. Sprinzak, D. & Elowitz, M. B. Reconstruction of genetic circuits. Nature 438, 443-8 (2005).
5. Endy, D. Foundations for engineering biology. Nature 438, 449-53 (2005).
6. Steele, C. L., Crock, J., Bohlmann, J. & Croteau, R. Sesquiterpene synthases from grand fir (Abies grandis). Comparison of constitutive and wound-induced activities, and cDNA isolation, characterization, and bacterial expression of delta-selinene synthase and gamma-humulene synthase. J Biol Chem 273, 2078-89 (1998).
7. Donald, K. A., Hampton, R. Y. & Fritz, I. B. Effects of overproduction of the catalytic domain of 3-hydroxy-3-methylglutaryl coenzyme A reductase on squalene synthesis in Saccharomyces cerevisiae. Appl Environ Microbiol 63, 3341-4 (1997).
8. Schmidt, S., Sunyaev, S., Bork, P. & Dandekar, T. Metabolites: a helping hand for pathway evolution? Trends Biochem Sci 28, 336-41 (2003).

9. Pal, C., Papp, B. & Lercher, M. J. An integrated view of protein evolution. *Nat Rev Genet.* 7, 337-48 (2006).
10. Newman, J. R. et al. Single-cell proteomic analysis of *S. cerevisiae* reveals the architecture of biological noise. *Nature* 441, 840-6 (2006).
11. Austin, D. W. et al. Gene network shaping of inherent noise spectra. *Nature* 439, 608-11 (2006).
12. Glazer, A. N. & Nikaido, H. *Microbioal biotechnology: fundamentals of applied microbiology* (W. H. Freeman and Company, New York, N.Y., USA, 1995).
13. Yoshikuni, Y., Ferrin, T. E. & Keasling, J. D. Designed divergent evolution of enzyme function. *Nature* (2006).
14. Bohlmann, J., Meyer-Gauen, G. & Croteau, R. Plant terpenoid synthases: molecular biology and phylogenetic analysis. *Proc Natl Acad Sci USA* 95, 4126-33 (1998).
15. Pitera, D. J. in *Chemical Engineering* 273 (University of California, Berkeley, Berkeley, 2006).
16. Dobson, C. M. Protein folding and misfolding. *Nature* 426, 884-90 (2003).
17. Dill, K. A. & Chan, H. S. From Levinthal to pathways to funnels. *Nat Struct Biol* 4, 10-9 (1997).
18. Matthews, B. W., Nicholson, H. & Becktel, W. J. Enhanced protein thermostability from site-directed mutations that decrease the entropy of unfolding. *Proc Natl Acad Sci USA* 84, 6663-7 (1987).
19. Burton, R. E., Huang, G. S., Daugherty, M. A., Calderone, T. L. & Oas, T. G. The energy landscape of a fast-folding protein mapped by Ala->Gly substitutions. *Nat Struct Biol* 4, 305-10 (1997).
20. Bang, D. et al. Dissecting the energetics of protein alpha-helix C-cap termination through chemical protein synthesis. *Nat Chem Biol* 2, 139-43 (2006).
21. Jordan, I. K. et al. A universal trend of amino acid gain and loss in protein evolution. *Nature* 433, 633-8 (2005).
22. Trifonov, E. N. The triplet code from first principles. *J Biomol Struct Dyn* 22, 1-11 (2004).
23. Eijsink, V. G. et al. Rational engineering of enzyme stability. *J Biotechnol* 113, 105-20 (2004).
24. Korkegian, A., Black, M. E., Baker, D. & Stoddard, B. L. Computational thermostabilization of an enzyme. *Science* 308, 857-60 (2005).
25. Roodveldt, C., Aharoni, A. & Tawfik, D. S. Directed evolution of proteins for heterologous expression and stability. *Curr Opin Struct Biol* 15, 50-6 (2005).
26. Aharoni, A. et al. Directed evolution of mammalian paraoxonases PON1 and PON3 for bacterial expression and catalytic specialization. *Proc Natl Acad Sci USA* 101, 482-7 (2004).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

<160> NUMBER OF SEQ ID NOS: 522

<210> SEQ ID NO 1
<211> LENGTH: 593
<212> TYPE: PRT
<213> ORGANISM: Abies grandis

<400> SEQUENCE: 1

```
Met Ala Gln Ile Ser Glu Ser Val Ser Pro Ser Thr Asp Leu Lys Ser
1               5                   10                  15

Thr Glu Ser Ser Ile Thr Ser Asn Arg His Gly Asn Met Trp Glu Asp
            20                  25                  30

Asp Arg Ile Gln Ser Leu Asn Ser Pro Tyr Gly Ala Pro Ala Tyr Gln
        35                  40                  45

Glu Arg Ser Glu Lys Leu Ile Glu Ile Lys Leu Leu Phe Leu Ser
    50                  55                  60

Asp Met Asp Asp Ser Cys Asn Asp Ser Asp Arg Asp Leu Ile Lys Arg
65                  70                  75                  80

Leu Glu Ile Val Asp Thr Val Glu Cys Leu Gly Ile Asp Arg His Phe
                85                  90                  95

Gln Pro Glu Ile Lys Leu Ala Leu Asp Tyr Val Tyr Arg Cys Trp Asn
            100                 105                 110

Glu Arg Gly Ile Gly Glu Gly Ser Arg Asp Ser Leu Lys Lys Asp Leu
        115                 120                 125

Asn Ala Thr Ala Leu Gly Phe Arg Ala Leu Arg Leu His Arg Tyr Asn
    130                 135                 140

Val Ser Ser Gly Val Leu Glu Asn Phe Arg Asp Asp Asn Gly Gln Phe
145                 150                 155                 160

Phe Cys Gly Ser Thr Val Glu Glu Glu Gly Ala Glu Ala Tyr Asn Lys
```

```
                    165                 170                 175
His Val Arg Cys Met Leu Ser Leu Ser Arg Ala Ser Asn Ile Leu Phe
                180                 185                 190

Pro Gly Glu Lys Val Met Glu Glu Ala Lys Ala Phe Thr Thr Asn Tyr
            195                 200                 205

Leu Lys Lys Val Leu Ala Gly Arg Glu Ala Thr His Val Asp Glu Ser
        210                 215                 220

Leu Leu Gly Glu Val Lys Tyr Ala Leu Glu Phe Pro Trp His Cys Ser
225                 230                 235                 240

Val Gln Arg Trp Glu Ala Arg Ser Phe Ile Glu Ile Phe Gly Gln Ile
                245                 250                 255

Asp Ser Glu Leu Lys Ser Asn Leu Ser Lys Met Leu Glu Leu Ala
                260                 265                 270

Lys Leu Asp Phe Asn Ile Leu Gln Cys Thr His Gln Lys Glu Leu Gln
            275                 280                 285

Ile Ile Ser Arg Trp Phe Ala Asp Ser Ser Ile Ala Ser Leu Asn Phe
        290                 295                 300

Tyr Arg Lys Cys Tyr Val Glu Phe Tyr Phe Trp Met Ala Ala Ala Ile
305                 310                 315                 320

Ser Glu Pro Glu Phe Ser Gly Ser Arg Val Ala Phe Thr Lys Ile Ala
                325                 330                 335

Ile Leu Met Thr Met Leu Asp Asp Leu Tyr Asp Thr His Gly Thr Leu
            340                 345                 350

Asp Gln Leu Lys Ile Phe Thr Glu Gly Val Arg Arg Trp Asp Val Ser
        355                 360                 365

Leu Val Glu Gly Leu Pro Asp Phe Met Lys Ile Ala Phe Glu Phe Trp
370                 375                 380

Leu Lys Thr Ser Asn Glu Leu Ile Ala Glu Ala Val Lys Ala Gln Gly
                385                 390                 395                 400

Gln Asp Met Ala Ala Tyr Ile Arg Lys Asn Ala Trp Glu Arg Tyr Leu
            405                 410                 415

Glu Ala Tyr Leu Gln Asp Ala Glu Trp Ile Ala Thr Gly His Val Pro
        420                 425                 430

Thr Phe Asp Glu Tyr Leu Asn Asn Gly Thr Pro Asn Thr Gly Met Cys
    435                 440                 445

Val Leu Asn Leu Ile Pro Leu Leu Met Gly Glu His Leu Pro Ile
450                 455                 460

Asp Ile Leu Glu Gln Ile Phe Leu Pro Ser Arg Phe His His Leu Ile
465                 470                 475                 480

Glu Leu Ala Ser Arg Leu Val Asp Asp Ala Arg Asp Phe Gln Ala Glu
                485                 490                 495

Lys Asp His Gly Asp Leu Ser Cys Ile Glu Cys Tyr Leu Lys Asp His
            500                 505                 510

Pro Glu Ser Thr Val Glu Asp Ala Leu Asn His Val Asn Gly Leu Leu
        515                 520                 525

Gly Asn Cys Leu Leu Glu Met Asn Trp Lys Phe Leu Lys Lys Gln Asp
    530                 535                 540

Ser Val Pro Leu Ser Cys Lys Lys Tyr Ser Phe His Val Leu Ala Arg
545                 550                 555                 560

Ser Ile Gln Phe Met Tyr Asn Gln Gly Asp Gly Phe Ser Ile Ser Asn
                565                 570                 575

Lys Val Ile Lys Asp Gln Val Gln Lys Val Leu Ile Val Pro Val Pro
            580                 585                 590
```

Ile

<210> SEQ ID NO 2
<211> LENGTH: 578
<212> TYPE: PRT
<213> ORGANISM: Picea abies

<400> SEQUENCE: 2

```
Met Ala Gln Ile Ser Lys Cys Ser Ser Leu Ser Ala Glu Leu Asn Glu
 1               5                  10                  15

Ser Ser Ile Ile Ser His His Gly Asn Leu Trp Asp Asp Phe
            20                  25                  30

Ile Gln Ser Leu Lys Ser Ser Asn Gly Ala Pro Gln Tyr His Glu Arg
                35                  40                  45

Ala Ala Lys Leu Val Glu Glu Ile Lys Asn Leu Val Ser Glu Met
        50                  55                  60

Lys Asp Cys Asn Asp Asp Leu Ile Arg Arg Leu Gln Met Val Asp Ile
 65                  70                  75                  80

Phe Glu Cys Leu Gly Ile Asp Arg His Phe Gln His Glu Ile Gln Val
                85                  90                  95

Ala Leu Asp Tyr Val Tyr Arg Tyr Trp Asn Gln Leu Glu Gly Ile Gly
            100                 105                 110

Ile Gly Ser Arg Asp Ser Leu Ile Lys Asp Phe Asn Ala Thr Ala Leu
            115                 120                 125

Gly Phe Arg Ala Leu Arg Leu His Arg Tyr Asn Val Ser Ser Asp Val
        130                 135                 140

Leu Glu Asn Phe Lys Asn Glu Asn Gly Gln Phe Phe Cys Ser Ser Thr
145                 150                 155                 160

Val Glu Glu Lys Glu Val Arg Cys Met Leu Thr Leu Phe Arg Ala Ser
                165                 170                 175

Glu Ile Ser Phe Pro Gly Glu Lys Val Met Asp Glu Ala Lys Ala Phe
            180                 185                 190

Thr Thr Glu Tyr Leu Thr Lys Val Leu Thr Gly Val Asp Val Thr Asp
        195                 200                 205

Val Asn Gln Ser Leu Leu Arg Glu Val Lys Tyr Ala Leu Glu Phe Pro
210                 215                 220

Trp His Cys Ser Leu Pro Arg Trp Glu Ala Arg Ser Phe Ile Glu Ile
225                 230                 235                 240

Cys Gly Gln Asn Asp Ser Trp Leu Lys Ser Ile Met Asn Lys Arg Val
                245                 250                 255

Leu Glu Leu Ala Lys Leu Asp Phe Asn Ile Leu Gln Trp Ala His His
            260                 265                 270

Arg Glu Leu Gln Leu Leu Ser Ser Trp Trp Ser Gln Ser Asp Ile Ala
        275                 280                 285

Gln Gln Asn Phe Tyr Arg Lys Arg His Val Glu Phe Tyr Leu Trp Val
    290                 295                 300

Val Ile Gly Thr Phe Glu Pro Glu Phe Ser Thr Cys Arg Ile Thr Phe
305                 310                 315                 320

Ala Lys Ile Ser Thr Leu Met Thr Ile Leu Asp Asp Leu Tyr Asp Thr
                325                 330                 335

His Gly Thr Leu Glu Gln Leu Lys Ile Phe Thr Glu Gly Val Lys Arg
            340                 345                 350

Trp Asp Leu Ser Leu Val Asp Arg Leu Pro Asp Tyr Ile Lys Ile Thr
        355                 360                 365

Phe Glu Phe Phe Leu Asn Thr Ser Asn Glu Leu Ile Ala Glu Val Ala
```

```
              370              375              380
    Lys Thr Gln Glu Arg Asp Met Ser Ala Tyr Ile Arg Lys Thr Trp Glu
    385              390              395              400

Arg Tyr Leu Glu Ala Tyr Leu Gln Glu Ala Glu Trp Ile Ala Ala Arg
                    405              410              415

His Val Pro Thr Phe Asp Glu Tyr Met Lys Asn Gly Ile Ser Ser Ser
                420              425              430

Gly Met Cys Ile Leu Asn Leu Tyr Ser Leu Leu Met Gly Gln Leu
                435              440              445

Leu Pro Asp Asp Val Leu Glu Gln Ile His Ser Pro Ser Lys Ile His
    450              455              460

Glu Leu Val Glu Leu Thr Ala Arg Leu Val Asp Asp Ser Lys Asp Phe
    465              470              475              480

Glu Thr Lys Lys Val Gly Gly Glu Leu Ala Ser Gly Ile Glu Cys Tyr
                    485              490              495

Val Lys Asp Asn Pro Glu Cys Thr Leu Glu Asp Ala Ser Asn His Leu
                500              505              510

Asn Gly Leu Leu Asp Leu Thr Val Lys Glu Leu Asn Trp Glu Phe Val
                515              520              525

Arg His Asp Ser Val Ala Leu Cys Phe Lys Lys Phe Ala Phe Asn Val
                530              535              540

Ala Arg Gly Leu Arg Leu Ile Tyr Lys Tyr Arg Asp Gly Phe Asp Val
    545              550              555              560

Ser Asn Gln Glu Met Lys Thr His Ile Phe Lys Ile Leu Ile Asp Pro
                565              570              575

Leu Thr

<210> SEQ ID NO 3
<211> LENGTH: 581
<212> TYPE: PRT
<213> ORGANISM: Abies grandis

<400> SEQUENCE: 3

Met Ala Glu Ile Ser Glu Ser Ser Ile Pro Arg Arg Thr Gly Asn His
    1               5                   10                  15

His Gly Asn Val Trp Asp Asp Leu Ile His Ser Leu Asn Ser Pro
                20                  25                  30

Tyr Gly Ala Pro Ala Tyr Tyr Glu Leu Leu Gln Lys Leu Ile Gln Glu
                35                  40                  45

Ile Lys His Leu Leu Leu Thr Glu Met Glu Met Asp Asp Gly Asp His
    50                  55                  60

Asp Leu Ile Lys Arg Leu Gln Ile Val Asp Thr Leu Glu Cys Leu Gly
    65                  70                  75                  80

Ile Asp Arg His Phe Glu His Glu Ile Gln Thr Ala Ala Leu Asp Tyr
                    85                  90                  95

Val Tyr Arg Trp Trp Asn Glu Lys Gly Ile Gly Glu Gly Ser Arg Asp
                    100             105                 110

Ser Phe Ser Lys Asp Leu Asn Ala Thr Ala Leu Gly Phe Arg Ala Leu
                115                 120                 125

Arg Leu His Arg Tyr Asn Val Ser Ser Val Leu Lys Asn Phe Lys
    130                 135                 140

Asp Glu Asn Gly Lys Phe Phe Cys Asn Phe Thr Gly Glu Glu Gly Arg
    145                 150                 155                 160

Gly Asp Lys Gln Val Arg Ser Met Leu Ser Leu Leu Arg Ala Ser Glu
                165                 170                 175
```

```
Ile Ser Phe Pro Gly Glu Lys Val Met Glu Ala Lys Ala Phe Thr
            180                 185                 190

Arg Glu Tyr Leu Asn Gln Val Leu Ala Gly His Gly Asp Val Thr Asp
        195                 200                 205

Val Asp Gln Ser Leu Leu Arg Glu Val Lys Tyr Ala Leu Glu Phe Pro
210                 215                 220

Trp His Cys Ser Val Pro Arg Trp Glu Arg Ser Phe Leu Glu Ile
225                 230                 235                 240

Tyr Gly His Asn His Ser Trp Leu Lys Ser Asn Ile Asn Gln Lys Met
                245                 250                 255

Leu Lys Leu Ala Lys Leu Asp Phe Asn Ile Leu Gln Cys Lys His His
            260                 265                 270

Lys Glu Ile Gln Phe Ile Thr Arg Trp Arg Asp Ser Gly Ile Ser
        275                 280                 285

Gln Leu Asn Phe Tyr Arg Lys Arg His Val Glu Tyr Tyr Ser Trp Val
        290                 295                 300

Val Met Cys Ile Phe Glu Pro Glu Phe Ser Glu Ser Arg Ile Ala Phe
305                 310                 315                 320

Ala Lys Thr Ala Ile Leu Cys Thr Val Leu Asp Asp Leu Tyr Asp Thr
                325                 330                 335

His Ala Thr Leu His Glu Ile Lys Ile Met Thr Glu Gly Val Arg Arg
            340                 345                 350

Trp Asp Leu Ser Leu Thr Asp Leu Pro Asp Tyr Ile Lys Ile Ala
        355                 360                 365

Phe Gln Phe Phe Asn Thr Val Asn Glu Leu Ile Val Glu Ile Val
370                 375                 380

Lys Arg Gln Gly Arg Asp Met Thr Thr Ile Val Lys Asp Cys Trp Lys
385                 390                 395                 400

Arg Tyr Ile Glu Ser Tyr Leu Gln Glu Ala Glu Trp Ile Ala Thr Gly
                405                 410                 415

His Ile Pro Thr Phe Asn Glu Tyr Ile Lys Asn Gly Met Ala Ser Ser
            420                 425                 430

Gly Met Cys Ile Leu Asn Leu Asn Pro Leu Leu Leu Asp Lys Leu
        435                 440                 445

Leu Pro Asp Asn Ile Leu Glu Gln Ile His Ser Pro Ser Lys Ile Leu
        450                 455                 460

Asp Leu Leu Glu Leu Thr Gly Arg Ile Ala Asp Asp Leu Lys Asp Phe
465                 470                 475                 480

Glu Asp Glu Lys Glu Arg Gly Glu Met Ala Ser Ser Leu Gln Cys Tyr
                485                 490                 495

Met Lys Glu Asn Pro Glu Ser Thr Val Glu Asn Ala Leu Asn His Ile
            500                 505                 510

Lys Gly Ile Leu Asn Arg Ser Leu Glu Glu Phe Asn Trp Glu Phe Met
        515                 520                 525

Lys Gln Asp Ser Val Pro Met Cys Cys Lys Lys Phe Thr Phe Asn Ile
530                 535                 540

Gly Arg Gly Leu Gln Phe Ile Tyr Lys Tyr Arg Asp Gly Leu Tyr Ile
545                 550                 555                 560

Ser Asp Lys Glu Val Lys Asp Gln Ile Phe Lys Ile Leu Val His Gln
                565                 570                 575

Val Pro Met Glu Glu
            580
```

<210> SEQ ID NO 4
<211> LENGTH: 623
<212> TYPE: PRT
<213> ORGANISM: Picea abies

<400> SEQUENCE: 4

```
Met Ala Leu Leu Ser Ile Ala Pro Leu Thr Ser Thr Trp Cys Val Asp
  1               5                  10                  15

Lys Ser Leu Val Gly Ser Ser Glu Ala Lys Ala Leu Leu Arg Lys Ile
             20                  25                  30

Pro Thr Leu Glu Met Cys Arg Leu Thr Lys Ser Val Thr Pro Ser Ile
         35                  40                  45

Ser Met Cys Leu Thr Thr Thr Val Ser Asp Asp Gly Val Gln Arg Arg
 50                  55                  60

Ile Ala Asp His His Pro Asn Leu Trp Asp Asp Asn Phe Ile Gln Ser
 65                  70                  75                  80

Leu Ser Thr Pro Tyr Gly Ala Thr Ala Tyr His Glu Arg Ala Gln Lys
             85                  90                  95

Leu Ile Gly Glu Val Lys Val Ile Ile Asn Ser Ile Leu Val Glu Asp
        100                 105                 110

Gly Glu Leu Ile Thr Pro Pro Asn Asp Leu Leu Gln Arg Leu Ser Ile
        115                 120                 125

Val Asp Ser Ile Glu Arg Leu Gly Ile Asp Arg His Phe Lys Asn Glu
130                 135                 140

Ile Lys Ser Ala Leu Asp Tyr Val Tyr Ser Tyr Trp Ser Glu Lys Gly
145                 150                 155                 160

Ile Gly Cys Gly Arg Asp Ser Val Val Asn Asp Leu Asn Thr Thr Ala
                165                 170                 175

Leu Gly Leu Arg Thr Leu Arg Leu His Gly Tyr Pro Val Ser Ser Asp
            180                 185                 190

Val Leu Glu Gln Phe Lys Asp Gln Asn Gly Gln Phe Ala Cys Ser Ala
        195                 200                 205

Ile Gln Thr Glu Gly Glu Ile Lys Thr Val Leu Asn Leu Phe Arg Ala
    210                 215                 220

Ser Leu Ile Ala Phe Pro Gly Glu Lys Val Met Glu Glu Ala Glu Ile
225                 230                 235                 240

Phe Ser Thr Ile Tyr Leu Lys Glu Ala Leu Leu Lys Ile Pro Val Cys
                245                 250                 255

Ser Leu Ser Arg Glu Ile Ala Tyr Val Leu Glu Tyr Gly Trp His Met
            260                 265                 270

Asn Leu Pro Arg Leu Glu Ala Arg Asn Tyr Ile Asp Val Phe Gly Gln
        275                 280                 285

Asp Pro Ile Tyr Leu Arg Ser Thr Gln Lys Leu Ile Glu Leu Ala Lys
    290                 295                 300

Leu Glu Phe Asn Ile Phe Gln Ser Leu Gln Gln Glu Leu Lys His
305                 310                 315                 320

Val Ser Arg Trp Trp Lys Asp Ser Gly Phe Ser Gln Met Ala Phe Ala
                325                 330                 335

Arg His Arg His Val Glu Tyr Tyr Thr Leu Ala Ser Cys Ile Asp Ile
            340                 345                 350

Tyr Pro Gln His Ser Ser Phe Arg Leu Gly Phe Ala Lys Ile Ala His
        355                 360                 365

Leu Gly Thr Val Leu Asp Asp Ile Tyr Asp Thr Phe Gly Thr Met Asp
    370                 375                 380

Glu Leu Glu Leu Phe Thr Ala Ala Val Lys Arg Trp His Pro Ser Ala
```

```
385                 390                 395                 400
Ala Glu Gly Leu Pro Glu Tyr Met Lys Gly Val Tyr Met Met Phe Tyr
                405                 410                 415

Glu Thr Val Asn Glu Met Ala Arg Glu Ala Glu Lys Ser Gln Gly Arg
            420                 425                 430

Asp Thr Leu Asn Tyr Ala Arg Gln Ala Leu Glu Ala Tyr Ile Asp Ser
        435                 440                 445

Tyr Met Lys Glu Ala Lys Trp Ile Ser Ser Gly Phe Leu Pro Thr Phe
    450                 455                 460

Glu Glu Tyr Leu Asp Asn Gly Lys Val Ser Phe Gly Tyr Arg Ile Ala
465                 470                 475                 480

Thr Leu Gln Pro Ile Leu Thr Leu Gly Ile Pro Phe Pro His His Ile
                485                 490                 495

Leu Gln Glu Ile Asp Phe Pro Ser Arg Leu Asn Asp Leu Ala Gly Ser
            500                 505                 510

Ile Leu Arg Leu Lys Gly Asp Ile His Ser Tyr Gln Ala Glu Arg Ser
        515                 520                 525

Arg Gly Glu Glu Ser Ser Cys Ile Ser Cys Tyr Met Lys Asp Asn Pro
    530                 535                 540

Glu Ala Thr Glu Glu Asp Ala Val Thr Tyr Ile Asn Ala Met Val Asn
545                 550                 555                 560

Arg Leu Leu Lys Glu Leu Asn Trp Glu Leu Lys Pro Asp Asn Asn
                565                 570                 575

Val Pro Ile Thr Ser Lys Lys His Ala Phe Asp Ile Leu Arg Ala Phe
            580                 585                 590

Tyr His Leu Tyr Lys Asp Arg Asp Gly Phe Ser Val Ala Arg Asn Glu
        595                 600                 605

Ile Arg Asn Leu Val Met Thr Thr Val Ile Glu His Val Pro Leu
    610                 615                 620

<210> SEQ ID NO 5
<211> LENGTH: 634
<212> TYPE: PRT
<213> ORGANISM: Picea abies

<400> SEQUENCE: 5

Met Ser Pro Val Ser Val Ile Pro Leu Ala Tyr Lys Leu Cys Leu Pro
1               5                   10                  15

Arg Ser Leu Met Ser Ser Ser Arg Glu Val Lys Pro Leu His Ile Thr
            20                  25                  30

Ile Pro Asn Leu Gly Met Cys Arg Arg Gly Lys Ser Met Ala Pro Ala
        35                  40                  45

Ser Thr Ser Met Ile Leu Thr Ala Ala Val Ser Asp Asp Asp Arg Val
    50                  55                  60

Gln Arg Arg Arg Gly Asn Tyr His Ser Asn Leu Trp Asp Asp Asp Phe
65                  70                  75                  80

Ile Gln Ser Leu Ser Thr Pro Tyr Gly Glu Pro Ser Tyr Arg Glu Arg
                85                  90                  95

Ala Glu Arg Leu Lys Gly Glu Ile Lys Lys Met Phe Arg Ser Met Ser
            100                 105                 110

Lys Asp Asp Gly Glu Leu Ile Thr Pro Leu Asn Asp Leu Ile Gln Arg
        115                 120                 125

Leu Trp Met Val Asp Ser Val Gln Arg Leu Gly Ile Asp Arg His Phe
    130                 135                 140

Lys Asn Glu Ile Lys Ser Ala Leu Asp Tyr Val Tyr Ser Tyr Trp Asn
```

-continued

```
            145                 150                 155                 160
Glu Lys Gly Ile Gly Cys Gly Arg Asp Ser Val Val Ala Asp Leu Asn
                165                 170                 175
Ser Thr Ala Leu Gly Phe Arg Thr Leu Arg Leu His Gly Tyr Asn Val
                180                 185                 190
Ser Ser Glu Val Leu Lys Val Phe Glu Asp Gln Asn Gly Gln Phe Ala
            195                 200                 205
Cys Ser Pro Ser Lys Thr Glu Gly Glu Ile Arg Ser Ala Leu Asn Leu
        210                 215                 220
Tyr Arg Ala Ser Leu Ile Ala Phe Pro Gly Glu Lys Val Met Asp Asp
225                 230                 235                 240
Ala Glu Ile Phe Ser Ser Arg Tyr Leu Lys Glu Ala Val Gln Glu Ile
                245                 250                 255
Pro Asp Cys Ser Leu Ser Gln Glu Ile Ala Tyr Ala Leu Glu Tyr Gly
                260                 265                 270
Trp His Thr Asn Met Pro Arg Leu Glu Ala Arg Asn Tyr Met Asp Val
            275                 280                 285
Phe Gly His Pro Ser Ser Pro Trp Leu Lys Lys Asn Lys Thr Gln Tyr
        290                 295                 300
Met Asp Gly Glu Lys Leu Leu Glu Leu Ala Lys Leu Glu Phe Asn Ile
305                 310                 315                 320
Phe His Ser Leu Gln Gln Glu Leu Gln Tyr Ile Ser Arg Trp Trp
                325                 330                 335
Lys Asp Ser Gly Leu Pro Lys Leu Ala Phe Ser Arg His Arg His Val
            340                 345                 350
Glu Tyr Tyr Thr Leu Gly Ser Cys Ile Ala Thr Asp Pro Lys His Arg
        355                 360                 365
Ala Phe Arg Leu Gly Phe Val Lys Thr Cys His Leu Asn Thr Val Leu
    370                 375                 380
Asp Asp Ile Tyr Asp Thr Phe Gly Thr Met Asp Glu Ile Glu Leu Phe
385                 390                 395                 400
Thr Glu Ala Val Arg Arg Trp Asp Pro Ser Glu Thr Glu Ser Leu Pro
                405                 410                 415
Asp Tyr Met Lys Gly Val Tyr Met Val Leu Tyr Glu Ala Leu Thr Glu
            420                 425                 430
Met Ala Gln Glu Ala Gln Lys Thr Gln Gly Arg Asp Thr Leu Asn Tyr
        435                 440                 445
Ala Arg Lys Ala Trp Glu Ile Tyr Leu Asp Ser Tyr Ile Gln Glu Ala
    450                 455                 460
Lys Trp Ile Ala Ser Gly Tyr Leu Pro Thr Phe Gln Glu Tyr Phe Glu
465                 470                 475                 480
Asn Gly Lys Ile Ser Ser Ala Tyr Arg Ala Ala Leu Thr Pro Ile
                485                 490                 495
Leu Thr Leu Asp Val Pro Leu Pro Glu Tyr Ile Leu Lys Gly Ile Asp
            500                 505                 510
Phe Pro Ser Arg Phe Asn Asp Leu Ala Ser Ser Phe Leu Arg Leu Arg
        515                 520                 525
Gly Asp Thr Arg Cys Tyr Lys Ala Asp Arg Ala Arg Gly Glu Glu Ala
    530                 535                 540
Ser Cys Ile Ser Cys Tyr Met Lys Asp Asn Pro Gly Ser Thr Glu Glu
545                 550                 555                 560
Asp Ala Leu Asn His Ile Asn Ser Met Ile Asn Glu Ile Ile Lys Glu
            565                 570                 575
```

```
Leu Asn Trp Glu Leu Leu Arg Pro Asp Ser Asn Ile Pro Met Pro Ala
                580                 585                 590

Arg Lys His Ala Phe Asp Ile Thr Arg Ala Leu His His Leu Tyr Lys
            595                 600                 605

Tyr Arg Asp Gly Phe Ser Val Ala Thr Lys Glu Thr Lys Ser Leu Val
        610                 615                 620

Ser Arg Met Val Leu Glu Pro Val Pro Leu
625                 630

<210> SEQ ID NO 6
<211> LENGTH: 634
<212> TYPE: PRT
<213> ORGANISM: Picea abies

<400> SEQUENCE: 6

Met Ser Pro Val Ser Val Ile Pro Leu Ala Tyr Lys Leu Cys Leu Pro
1               5                   10                  15

Arg Ser Leu Met Ser Ser Arg Glu Val Lys Pro Leu His Ile Thr
            20                  25                  30

Ile Pro Asn Leu Gly Met Cys Arg Arg Gly Lys Ser Met Ala Pro Ala
            35                  40                  45

Ser Thr Ser Met Ile Leu Thr Ala Ala Val Ser Asp Asp Arg Val
    50                  55                  60

Gln Arg Arg Gly Asn Tyr His Ser Asn Leu Trp Asp Asp Phe
65              70                  75                  80

Ile Gln Ser Leu Ser Thr Pro Tyr Gly Glu Pro Ser Tyr Arg Glu Arg
                85                  90                  95

Ala Glu Thr Leu Lys Gly Glu Ile Lys Lys Met Phe Arg Ser Ile Ser
            100                 105                 110

Lys Asp Asp Gly Glu Leu Ile Thr Pro Leu Asn Asp Leu Ile Gln Arg
        115                 120                 125

Leu Trp Met Val Asp Ser Val Glu Arg Leu Gly Ile Asp Arg His Phe
    130                 135                 140

Lys Asn Glu Ile Lys Ser Ala Leu Asp Tyr Val Tyr Ser Tyr Trp Asn
145                 150                 155                 160

Glu Lys Gly Ile Gly Cys Gly Arg Asp Ser Val Val Ala Asp Leu Asn
                165                 170                 175

Ser Thr Ala Leu Gly Phe Arg Thr Leu Arg Leu His Gly Tyr Thr Val
            180                 185                 190

Ser Ser Glu Val Leu Lys Val Phe Glu Asp Gln Asn Gly Gln Phe Ala
        195                 200                 205

Cys Ser Pro Ser Lys Thr Glu Gly Glu Ile Arg Ser Ala Leu Asn Leu
    210                 215                 220

Tyr Arg Ala Ser Leu Ile Ala Phe Pro Gly Glu Lys Val Met Asp Asp
225                 230                 235                 240

Ala Glu Ile Phe Ser Ser Arg Tyr Leu Lys Glu Ala Val Gln Lys Ile
                245                 250                 255

Pro Asp Cys Ser Leu Ser Gln Glu Ile Ala Tyr Ala Leu Glu Tyr Gly
            260                 265                 270

Trp His Thr Asn Met Pro Arg Leu Glu Ala Arg Asn Tyr Met Asp Val
        275                 280                 285

Phe Gly His Pro Ser Ser Pro Trp Leu Lys Lys Asn Lys Thr Gln Tyr
    290                 295                 300

Met Asp Gly Glu Lys Leu Leu Glu Leu Ala Lys Leu Glu Phe Asn Ile
305                 310                 315                 320
```

```
Phe His Ser Leu Gln Gln Glu Glu Leu Gln Tyr Ile Ser Arg Trp Trp
                325                 330                 335
Lys Asp Ser Gly Leu Pro Lys Leu Ala Phe Ser Arg His Arg His Val
            340                 345                 350
Glu Tyr Tyr Thr Leu Gly Ser Cys Ile Ala Thr Asp Pro Lys His Arg
        355                 360                 365
Ala Phe Arg Leu Gly Phe Val Lys Thr Cys His Leu Asn Thr Val Leu
    370                 375                 380
Asp Asp Ile Tyr Asp Thr Phe Gly Thr Met Asp Glu Ile Glu Leu Phe
385                 390                 395                 400
Thr Glu Ala Val Arg Arg Trp Asp Pro Ser Thr Glu Ser Leu Pro
                405                 410                 415
Asp Tyr Met Lys Gly Val Tyr Met Val Leu Tyr Glu Ala Leu Thr Glu
            420                 425                 430
Met Ala Gln Glu Ala Gln Lys Thr Gln Gly Arg Asp Thr Leu Asn Tyr
        435                 440                 445
Ala Arg Lys Ala Trp Glu Ile Tyr Leu Asp Ser Tyr Ile Gln Glu Ala
    450                 455                 460
Lys Trp Ile Ala Thr Gly Tyr Leu Pro Thr Phe Gln Glu Tyr Phe Glu
465                 470                 475                 480
Asn Gly Lys Ile Ser Ser Ala Tyr Arg Ala Ala Ala Leu Thr Pro Ile
                485                 490                 495
Leu Thr Leu Asp Val Pro Leu Pro Glu Tyr Ile Leu Lys Gly Ile Asp
            500                 505                 510
Phe Pro Ser Arg Phe Asn Asp Leu Ala Ser Ser Phe Leu Arg Leu Arg
        515                 520                 525
Gly Asp Thr Arg Cys Tyr Lys Ala Asp Arg Ala Arg Gly Glu Glu Ala
    530                 535                 540
Ser Cys Ile Ser Cys Tyr Met Lys Asp Asn Pro Gly Ser Thr Gly Glu
545                 550                 555                 560
Asp Ala Leu Asn His Ile Asn Ser Met Ile Asn Glu Ile Ile Lys Glu
                565                 570                 575
Leu Asn Trp Glu Leu Leu Arg Pro Asp Ser Asn Ile Pro Met Pro Ala
            580                 585                 590
Arg Lys His Ala Phe Asp Ile Thr Arg Ala Leu His His Leu Tyr Lys
        595                 600                 605
Tyr Arg Asp Gly Phe Ser Val Ala Thr Lys Glu Thr Lys Ser Leu Val
    610                 615                 620
Ser Arg Met Val Leu Glu Pro Val Pro Leu
625                 630

<210> SEQ ID NO 7
<211> LENGTH: 633
<212> TYPE: PRT
<213> ORGANISM: Picea abies
<220> FEATURE:
<221> NAME/KEY: VARIANT
<222> LOCATION: 182, 478, 534
<223> OTHER INFORMATION: Xaa = Any Amino Acid

<400> SEQUENCE: 7

Met Ser Pro Val Ser Val Val Pro Leu Ala Cys Lys Leu Cys Leu Cys
1               5                   10                  15
Arg Ser Met Thr Ser Ser Thr Asp Glu Leu Lys Pro Leu Pro Thr Thr
            20                  25                  30
Ile Pro Thr Arg Gly Met Cys Gly Arg Arg Met Ser Val Thr Pro Ser
        35                  40                  45
```

Met Ser Met Ser Leu Asn Thr Val Val Ser Asp Asn Asp Ala Val Gln
            50                  55                  60

Arg Arg Ile Gly Asp Tyr His Ser Asn Leu Trp Asn Asp Asp Phe Ile
 65                  70                  75                  80

Gln Ser Leu Thr Thr Pro Tyr Gly Ala Pro Ser Tyr Ile Glu Arg Ala
                85                  90                  95

Asp Gly Leu Ile Ser Glu Val Lys Glu Met Phe Asn Arg Met Cys Met
                100                 105                 110

Glu Asp Gly Glu Leu Met Ser Pro Leu Asn Asp Leu Ile Gln Arg Leu
                115                 120                 125

Trp Thr Val Asp Ser Val Glu Arg Leu Gly Ile Asp Arg His Phe Lys
            130                 135                 140

Asn Glu Ile Lys Ala Ser Leu Asp Tyr Val Tyr Ser Tyr Trp Asn Glu
145                 150                 155                 160

Lys Gly Ile Gly Cys Gly Arg Thr Ser Val Val Thr Asp Leu Asn Ser
                165                 170                 175

Thr Ala Leu Gly Ala Xaa Ile Leu Arg Leu His Gly Tyr Thr Val Ser
                180                 185                 190

Ser Glu Val Leu Lys Val Phe Glu Glu Asn Gly Gln Phe Ala Cys
                195                 200                 205

Ser Pro Ser Gln Thr Glu Gly Glu Ile Arg Ser Phe Leu Asn Leu Tyr
210                 215                 220

Arg Ala Ser Leu Ile Ala Phe Pro Gly Glu Lys Val Met Glu Glu Ala
225                 230                 235                 240

Gln Ile Phe Ser Ser Arg Tyr Leu Lys Glu Ala Val Gln Lys Ile Pro
                245                 250                 255

Val Ser Ser Leu Ser Arg Glu Ile Gly Asp Val Leu Glu Tyr Gly Trp
                260                 265                 270

His Thr Asn Leu Pro Arg Trp Glu Ala Arg Asn Tyr Met Asp Val Phe
            275                 280                 285

Gly Gln Asp Thr Asn Thr Pro Phe Asn Lys Asn Lys Met Gln Tyr Met
290                 295                 300

Asn Thr Glu Lys Ile Leu Gln Leu Ala Lys Leu Glu Phe Asn Ile Phe
305                 310                 315                 320

His Ser Leu Gln Gln Arg Glu Leu Gln Cys Leu Leu Arg Trp Trp Lys
                325                 330                 335

Glu Ser Gly Leu Pro Gln Leu Thr Phe Ala Arg His Arg His Val Glu
                340                 345                 350

Phe Tyr Thr Leu Ala Ser Cys Ile Ala Thr Glu Pro Lys His Ser Ala
            355                 360                 365

Phe Arg Leu Gly Phe Ala Lys Met Cys His Leu Val Thr Val Leu Asp
            370                 375                 380

Asp Val Tyr Asp Thr Phe Gly Lys Met Asp Glu Leu Glu Leu Phe Thr
385                 390                 395                 400

Ala Ala Val Lys Arg Trp Asp Leu Ser Glu Thr Glu Arg Leu Pro Glu
                405                 410                 415

Tyr Met Lys Gly Leu Tyr Val Val Leu Phe Glu Thr Val Asn Glu Leu
                420                 425                 430

Ala Gln Glu Ala Glu Lys Thr Gln Gly Arg Asn Thr Leu Asn Tyr Val
            435                 440                 445

Arg Lys Ala Trp Glu Ala Tyr Phe Asp Ser Tyr Met Lys Glu Ala Glu
450                 455                 460

Trp Ile Ser Thr Gly Tyr Leu Pro Thr Phe Glu Glu Tyr Xaa Glu Asn

```
            465                 470                 475                 480
Gly Lys Val Ser Ser Ala Tyr Arg Val Ala Leu Gln Pro Ile Leu
                    485                 490                 495

Thr Leu Asp Val Gln Leu Pro Asp Ile Leu Lys Gly Ile Asp Phe
                500                 505                 510

Pro Ser Arg Phe Asn Asp Leu Ala Ser Ser Phe Leu Arg Leu Arg Gly
            515                 520                 525

Asp Thr Arg Cys Tyr Xaa Ala Asp Arg Ala Arg Gly Glu Glu Ala Ser
            530                 535                 540

Cys Ile Ser Cys Tyr Met Lys Asp His Pro Gly Ser Thr Glu Asp
545                 550                 555                 560

Ala Val Asn His Ile Asn Ala Met Ile Asn Asp Ile Ile Arg Glu Leu
                565                 570                 575

Asn Trp Glu Phe Leu Lys Pro Asp Ser Asn Ile Pro Met Pro Ala Arg
                580                 585                 590

Lys His Ala Phe Asp Ile Thr Arg Ala Leu His Leu Tyr Ile Tyr
            595                 600                 605

Arg Asp Gly Phe Ser Val Ala Ser Lys Glu Thr Lys Asn Leu Val Glu
            610                 615                 620

Lys Ala Leu Leu Glu Ala Val Leu Phe
625                 630

<210> SEQ ID NO 8
<211> LENGTH: 633
<212> TYPE: PRT
<213> ORGANISM: Picea abies

<400> SEQUENCE: 8

Met Ser Pro Val Ser Val Pro Leu Ala Cys Lys Leu Cys Leu Cys
 1               5                  10                  15

Arg Ser Met Thr Ser Ser Thr Asp Glu Leu Lys Pro Leu Pro Thr Thr
                20                  25                  30

Ile Pro Thr Arg Gly Met Cys Gly Arg Arg Met Ser Val Thr Pro Ser
                35                  40                  45

Met Ser Met Ser Leu Asn Thr Val Val Ser Asp Asn Asp Ala Val Gln
50                  55                  60

Arg Arg Ile Gly Asp Tyr His Ser Asn Leu Trp Asn Asp Asp Phe Ile
65                  70                  75                  80

Gln Ser Leu Thr Thr Pro Tyr Gly Ala Pro Ser Tyr Ile Glu Arg Ala
                85                  90                  95

Asp Arg Leu Ile Ser Glu Val Lys Glu Met Phe Asn Arg Met Cys Met
            100                 105                 110

Glu Asp Gly Glu Leu Met Ser Pro Leu Asn Asp Leu Ile Gln Arg Leu
            115                 120                 125

Trp Thr Val Asp Ser Val Glu Arg Leu Gly Ile Asp Arg His Phe Lys
130                 135                 140

Asn Glu Ile Lys Ala Ser Leu Asp Tyr Val Tyr Ser Tyr Trp Asn Glu
145                 150                 155                 160

Lys Gly Ile Gly Cys Gly Arg Gln Ser Val Val Thr Asp Leu Asn Ser
            165                 170                 175

Thr Ala Leu Gly Leu Arg Ile Leu Arg Gln His Gly Tyr Thr Val Ser
            180                 185                 190

Ser Glu Val Leu Lys Val Phe Glu Glu Asn Gly Gln Phe Ala Cys
            195                 200                 205

Ser Pro Ser Gln Thr Glu Gly Glu Ile Arg Ser Phe Leu Asn Leu Tyr
```

-continued

```
            210                 215                 220
Arg Ala Ser Leu Ile Ala Phe Pro Gly Glu Lys Val Met Glu Ala
225                 230                 235                 240

Gln Ile Phe Ser Ser Arg Tyr Leu Lys Glu Ala Val Gln Lys Ile Pro
                245                 250                 255

Val Ser Gly Leu Ser Arg Glu Ile Gly Asp Val Leu Glu Tyr Gly Trp
                260                 265                 270

His Thr Asn Leu Pro Arg Trp Glu Ala Arg Asn Tyr Met Asp Val Phe
                275                 280                 285

Gly Gln Asp Thr Asn Thr Ser Phe Asn Lys Asn Lys Met Gln Tyr Met
290                 295                 300

Asn Thr Glu Lys Ile Leu Gln Leu Val Lys Leu Glu Phe Asn Ile Phe
305                 310                 315                 320

His Ser Leu Gln Gln Arg Glu Leu Gln Cys Leu Leu Arg Trp Trp Lys
                325                 330                 335

Glu Ser Gly Leu Pro Gln Leu Thr Phe Ala Arg His Arg His Val Glu
                340                 345                 350

Phe Tyr Thr Leu Ala Ser Cys Ile Ala Cys Glu Pro Lys His Ser Ala
                355                 360                 365

Phe Arg Leu Gly Phe Ala Lys Met Cys His Leu Val Thr Val Leu Asp
370                 375                 380

Asp Val Tyr Asp Thr Phe Gly Lys Met Asp Glu Leu Glu Leu Phe Thr
385                 390                 395                 400

Ala Ala Val Lys Arg Trp Asp Leu Ser Glu Thr Glu Arg Leu Pro Glu
                405                 410                 415

Tyr Met Lys Gly Leu Tyr Val Val Phe Glu Thr Val Asn Glu Leu
                420                 425                 430

Ala Gln Glu Ala Glu Lys Thr Gln Gly Arg Asn Thr Leu Asn Tyr Val
                435                 440                 445

Arg Lys Ala Trp Glu Ala Tyr Phe Asp Ser Tyr Met Lys Glu Ala Glu
                450                 455                 460

Trp Ile Ser Thr Gly Tyr Leu Pro Thr Phe Glu Glu Tyr Cys Glu Asn
465                 470                 475                 480

Gly Lys Val Ser Ser Ala Tyr Arg Val Ala Ala Leu Gln Pro Ile Leu
                485                 490                 495

Thr Leu Asp Val Gln Leu Pro Asp Asp Ile Leu Lys Gly Ile Asp Phe
                500                 505                 510

Pro Ser Arg Phe Asn Asp Leu Ala Ser Ser Phe Leu Arg Leu Arg Gly
                515                 520                 525

Asp Thr Arg Cys Tyr Glu Ala Asp Arg Ala Arg Gly Glu Glu Ala Ser
                530                 535                 540

Cys Ile Ser Cys Tyr Met Lys Asp Asn Pro Gly Ser Thr Glu Glu Asp
545                 550                 555                 560

Ala Leu Asn His Ile Asn Ala Met Ile Asn Asp Ile Ile Arg Glu Leu
                565                 570                 575

Asn Trp Glu Phe Leu Lys Pro Asp Ser Asn Ile Pro Met Pro Ala Arg
                580                 585                 590

Lys His Ala Phe Asp Ile Thr Arg Ala Leu His His Leu Tyr Ile Tyr
                595                 600                 605

Arg Asp Gly Phe Ser Val Ala Asn Lys Glu Thr Lys Asn Leu Val Glu
                610                 615                 620

Lys Thr Leu Leu Glu Ser Met Leu Phe
625                 630
```

<210> SEQ ID NO 9
<211> LENGTH: 627
<212> TYPE: PRT
<213> ORGANISM: Abies grandis

<400> SEQUENCE: 9

Met Ala Leu Val Ser Ile Ser Pro Leu Ala Ser Lys Ser Cys Leu Arg
1               5                   10                  15

Lys Ser Leu Ile Ser Ser Ile His Glu His Lys Pro Pro Tyr Arg Thr
            20                  25                  30

Ile Pro Asn Leu Gly Met Arg Arg Gly Lys Ser Val Thr Pro Ser
        35                  40                  45

Met Ser Ile Ser Leu Ala Thr Ala Ala Pro Asp Asp Gly Val Gln Arg
    50                  55                  60

Arg Ile Gly Asp Tyr His Ser Asn Ile Trp Asp Asp Phe Ile Gln
65                  70                  75                  80

Ser Leu Ser Thr Pro Tyr Gly Glu Pro Ser Tyr Gln Glu Arg Ala Glu
                85                  90                  95

Arg Leu Ile Val Glu Val Lys Lys Ile Phe Asn Ser Met Tyr Leu Asp
            100                 105                 110

Asp Gly Arg Leu Met Ser Ser Phe Asn Asp Leu Met Gln Arg Leu Trp
        115                 120                 125

Ile Val Asp Ser Val Glu Arg Leu Gly Ile Ala Arg His Phe Lys Asn
130                 135                 140

Glu Ile Thr Ser Ala Leu Asp Tyr Val Phe Arg Tyr Trp Glu Glu Asn
145                 150                 155                 160

Gly Ile Gly Cys Gly Arg Asp Ser Ile Val Thr Asp Leu Asn Ser Thr
                165                 170                 175

Ala Leu Gly Phe Arg Thr Leu Arg Leu His Gly Tyr Thr Val Ser Pro
            180                 185                 190

Glu Val Leu Lys Ala Phe Gln Asp Gln Asn Gly Gln Phe Val Cys Ser
        195                 200                 205

Pro Gly Gln Thr Glu Gly Glu Ile Arg Ser Val Leu Asn Leu Tyr Arg
    210                 215                 220

Ala Ser Leu Ile Ala Phe Pro Gly Glu Lys Val Met Glu Glu Ala Glu
225                 230                 235                 240

Ile Phe Ser Thr Arg Tyr Leu Lys Glu Ala Leu Gln Lys Ile Pro Val
                245                 250                 255

Ser Ala Leu Ser Gln Glu Ile Lys Phe Val Met Glu Tyr Gly Trp His
            260                 265                 270

Thr Asn Leu Pro Arg Leu Glu Ala Arg Asn Tyr Ile Asp Thr Leu Glu
        275                 280                 285

Lys Asp Thr Ser Ala Trp Leu Asn Lys Asn Ala Gly Lys Lys Leu Leu
    290                 295                 300

Glu Leu Ala Lys Leu Glu Phe Asn Ile Phe Asn Ser Leu Gln Gln Lys
305                 310                 315                 320

Glu Leu Gln Tyr Leu Leu Arg Trp Trp Lys Glu Ser Asp Leu Pro Lys
                325                 330                 335

Leu Thr Phe Ala Arg His Arg His Val Glu Phe Tyr Thr Leu Ala Ser
            340                 345                 350

Cys Ile Ala Ile Asp Pro Lys His Ser Ala Phe Arg Leu Gly Phe Ala
        355                 360                 365

Lys Met Cys His Leu Val Thr Val Leu Asp Asp Ile Tyr Asp Thr Phe
    370                 375                 380

```
Gly Thr Ile Asp Glu Leu Glu Leu Phe Thr Ser Ala Ile Lys Arg Trp
385                 390                 395                 400

Asn Ser Ser Glu Ile Glu His Leu Pro Glu Tyr Met Lys Cys Val Tyr
            405                 410                 415

Met Val Val Phe Glu Thr Val Asn Glu Leu Thr Arg Glu Ala Glu Lys
        420                 425                 430

Thr Gln Gly Arg Asn Thr Leu Asn Tyr Val Arg Lys Ala Trp Glu Ala
    435                 440                 445

Tyr Phe Asp Ser Tyr Met Glu Glu Ala Lys Trp Ile Ser Asn Gly Tyr
450                 455                 460

Leu Pro Met Phe Glu Glu Tyr His Glu Asn Gly Lys Val Ser Ser Ala
465                 470                 475                 480

Tyr Arg Val Ala Thr Leu Gln Pro Ile Leu Thr Leu Asn Ala Trp Leu
            485                 490                 495

Pro Asp Tyr Ile Leu Lys Gly Ile Asp Phe Pro Ser Arg Phe Asn Asp
        500                 505                 510

Leu Ala Ser Ser Phe Leu Arg Leu Arg Gly Asp Thr Arg Cys Tyr Lys
    515                 520                 525

Ala Asp Arg Asp Arg Gly Glu Glu Ala Ser Cys Ile Ser Cys Tyr Met
530                 535                 540

Lys Asp Asn Pro Gly Ser Thr Glu Glu Asp Ala Leu Asn His Ile Asn
545                 550                 555                 560

Ala Met Val Asn Asp Ile Ile Lys Glu Leu Asn Trp Glu Leu Leu Arg
            565                 570                 575

Ser Asn Asp Asn Ile Pro Met Leu Ala Lys His Ala Phe Asp Ile
        580                 585                 590

Thr Arg Ala Leu His His Leu Tyr Ile Tyr Arg Asp Gly Phe Ser Val
    595                 600                 605

Ala Asn Lys Glu Thr Lys Lys Leu Val Met Glu Thr Leu Leu Glu Ser
        610                 615                 620

Met Leu Phe
625

<210> SEQ ID NO 10
<211> LENGTH: 630
<212> TYPE: PRT
<213> ORGANISM: Abies grandis

<400> SEQUENCE: 10

Met Ala Leu Val Ser Ser Ala Pro Lys Ser Cys Leu His Lys Ser Leu
1               5                   10                  15

Ile Arg Ser Thr His His Glu Leu Lys Pro Leu Arg Arg Thr Ile Pro
            20                  25                  30

Thr Leu Gly Met Cys Arg Arg Gly Lys Ser Phe Thr Pro Ser Val Ser
        35                  40                  45

Met Ser Leu Thr Thr Ala Val Ser Asp Asp Gly Leu Gln Arg Arg Ile
    50                  55                  60

Gly Asp Tyr His Ser Asn Leu Trp Asp Asp Phe Ile Gln Ser Leu
65                  70                  75                  80

Ser Thr Pro Tyr Gly Glu Pro Ser Tyr Arg Glu Arg Ala Glu Lys Leu
            85                  90                  95

Ile Gly Glu Val Lys Glu Met Phe Asn Ser Met Pro Ser Glu Asp Gly
        100                 105                 110

Glu Ser Met Ser Pro Leu Asn Asp Leu Ile Glu Arg Leu Trp Met Val
    115                 120                 125
```

```
Asp Ser Val Glu Arg Leu Gly Ile Asp Arg His Phe Lys Lys Glu Ile
130                 135                 140

Lys Ser Ala Leu Asp Tyr Val Tyr Ser Tyr Trp Asn Glu Lys Gly Ile
145                 150                 155                 160

Gly Cys Gly Arg Asp Ser Val Phe Pro Asp Val Asn Ser Thr Ala Ser
                165                 170                 175

Gly Phe Arg Thr Leu Arg Leu His Gly Tyr Ser Val Ser Ser Glu Val
                180                 185                 190

Leu Lys Val Phe Gln Asp Gln Asn Gly Gln Phe Ala Phe Ser Pro Ser
                195                 200                 205

Thr Lys Glu Arg Asp Ile Arg Thr Val Leu Asn Leu Tyr Arg Ala Ser
210                 215                 220

Phe Ile Ala Phe Pro Gly Glu Lys Val Met Glu Glu Ala Glu Ile Phe
225                 230                 235                 240

Ser Ser Arg Tyr Leu Lys Glu Ala Val Gln Lys Ile Pro Val Ser Ser
                245                 250                 255

Leu Ser Gln Glu Ile Asp Tyr Thr Leu Glu Tyr Gly Trp His Thr Asn
                260                 265                 270

Met Pro Arg Leu Glu Thr Arg Asn Tyr Leu Asp Val Phe Gly His Pro
                275                 280                 285

Thr Ser Pro Trp Leu Lys Lys Lys Arg Thr Gln Tyr Leu Asp Ser Glu
290                 295                 300

Lys Leu Leu Glu Leu Ala Lys Leu Glu Phe Asn Ile Phe His Ser Leu
305                 310                 315                 320

Gln Gln Lys Glu Leu Gln Tyr Leu Ser Arg Trp Trp Ile His Ser Gly
                325                 330                 335

Leu Pro Glu Leu Thr Phe Gly Arg His Arg His Val Glu Tyr Tyr Thr
                340                 345                 350

Leu Ser Ser Cys Ile Ala Thr Glu Pro Lys His Ser Ala Phe Arg Leu
                355                 360                 365

Gly Phe Ala Lys Thr Cys His Leu Ile Thr Val Leu Asp Asp Ile Tyr
                370                 375                 380

Asp Thr Phe Gly Thr Met Asp Glu Ile Glu Leu Phe Asn Glu Ala Val
385                 390                 395                 400

Arg Arg Trp Asn Pro Ser Glu Lys Glu Arg Leu Pro Glu Tyr Met Lys
                405                 410                 415

Glu Ile Tyr Met Ala Leu Tyr Glu Ala Leu Thr Asp Met Ala Arg Glu
                420                 425                 430

Ala Glu Lys Thr Gln Gly Arg Asp Thr Leu Asn Tyr Ala Arg Lys Ala
                435                 440                 445

Trp Glu Val Tyr Leu Asp Ser Tyr Thr Gln Glu Ala Lys Trp Ile Ala
450                 455                 460

Ser Gly Tyr Leu Pro Thr Phe Glu Glu Tyr Leu Glu Asn Ala Lys Val
465                 470                 475                 480

Ser Ser Gly His Arg Ala Ala Ala Leu Thr Pro Leu Leu Thr Leu Asp
                485                 490                 495

Val Pro Leu Pro Asp Asp Val Leu Lys Gly Ile Asp Phe Pro Ser Arg
                500                 505                 510

Phe Asn Asp Leu Ala Ser Ser Phe Leu Arg Leu Arg Gly Asp Thr Arg
                515                 520                 525

Cys Tyr Lys Ala Asp Arg Asp Arg Gly Glu Glu Ala Ser Ser Ile Ser
530                 535                 540

Cys Tyr Met Lys Asp Asn Pro Gly Leu Thr Glu Glu Asp Ala Leu Asn
545                 550                 555                 560
```

His Ile Asn Ala Met Ile Asn Asp Ile Ile Lys Glu Leu Asn Trp Glu
                565                 570                 575

Leu Leu Lys Pro Asp Ser Asn Ile Pro Met Thr Ala Arg Lys His Ala
            580                 585                 590

Tyr Glu Ile Thr Arg Ala Phe His Gln Leu Tyr Lys Tyr Arg Asp Gly
        595                 600                 605

Phe Ser Val Ala Thr Gln Glu Thr Lys Ser Leu Val Arg Arg Thr Val
    610                 615                 620

Leu Glu Pro Val Pro Leu
625             630

<210> SEQ ID NO 11
<211> LENGTH: 629
<212> TYPE: PRT
<213> ORGANISM: Pinus taeda

<400> SEQUENCE: 11

Met Ser Pro Val Ser Val Ile Ser Leu Pro Ser Asp Leu Cys Leu Pro
 1               5                  10                  15

Thr Ser Phe Ile Asp Arg Ser Gly Arg Glu Leu Ile Pro Leu His Ile
            20                  25                  30

Thr Ile Pro Asn Val Ala Met Arg Arg Gln Gly Lys Leu Met Thr Arg
        35                  40                  45

Ala Ser Met Ser Met Asn Leu Arg Thr Ala Val Ser Asp Asp Ala Val
    50                  55                  60

Ile Arg Arg Arg Gly Asp Phe His Ser Asn Leu Trp Asp Asp Asp Leu
65                  70                  75                  80

Ile Gln Ser Leu Ser Ser Pro Tyr Gly Glu Pro Ser Tyr Arg Glu Arg
                85                  90                  95

Ala Glu Arg Leu Ile Gly Glu Val Lys Asn Ser Phe Asn Ser Met Ser
            100                 105                 110

Asn Glu Asp Gly Glu Ser Ile Thr Pro Leu Asp Asp Leu Ile Gln Arg
        115                 120                 125

Leu Trp Met Val Asp Ser Val Glu Arg Leu Gly Ile Asp Arg His Phe
    130                 135                 140

Lys Lys Glu Ile Lys Ser Ala Leu Asp His Val Tyr Arg Tyr Trp Ser
145                 150                 155                 160

Glu Lys Gly Ile Gly Cys Gly Arg Glu Ser Val Val Thr Asp Leu Asn
                165                 170                 175

Ser Thr Ala Leu Gly Leu Arg Thr Leu Arg Leu His Gly Tyr Asp Val
            180                 185                 190

Ser Ala Asp Val Leu Asn His Phe Lys Asn Gln Ser Gly Gln Phe Ala
        195                 200                 205

Cys Thr Leu Lys Gln Thr Glu Asp Gln Ile Arg Thr Val Leu Asn Leu
    210                 215                 220

Tyr Arg Ala Ser Leu Ile Ala Phe Pro Gly Glu Lys Val Met Asp Glu
225                 230                 235                 240

Ala Glu Ser Phe Ser Ala Lys Tyr Leu Lys Glu Ala Leu Gln Lys Ile
                245                 250                 255

Pro Val Ser Ser Phe Ser Arg Glu Ile Gly Asp Val Leu Glu Tyr Gly
            260                 265                 270

Trp His Thr Tyr Leu Pro Arg Leu Glu Ala Arg Asn Tyr Ile Asp Val
        275                 280                 285

Phe Gly Gln Asp Thr Glu Asn Ser Lys Ser Tyr Met Lys Thr Glu Lys
    290                 295                 300

Leu Leu Glu Leu Ala Lys Leu Glu Phe Asn Ile Phe His Ala Leu Gln
305                 310                 315                 320

Lys Arg Glu Leu Glu Tyr Leu Val Arg Trp Trp Lys Gly Ser Gly Ser
                325                 330                 335

Pro Gln Met Thr Phe Cys Arg His Arg His Val Glu Tyr Tyr Thr Leu
            340                 345                 350

Ala Ser Cys Ile Ala Phe Glu Pro Gln His Ser Gly Phe Arg Leu Gly
        355                 360                 365

Phe Ala Lys Ala Cys His Ile Ile Thr Val Leu Asp Asp Met Tyr Asp
    370                 375                 380

Thr Phe Gly Thr Leu Asp Glu Leu Glu Leu Phe Thr Ser Ala Ile Lys
385                 390                 395                 400

Arg Trp Asp Pro Ser Ala Thr Glu Cys Leu Pro Glu Tyr Met Lys Gly
                405                 410                 415

Val Tyr Met Ile Val Tyr Asn Thr Val Asn Glu Met Ser Gln Glu Ala
            420                 425                 430

Asp Lys Ala Gln Gly Arg Asp Thr Leu Asn Tyr Cys Arg Gln Ala Trp
        435                 440                 445

Glu Glu Tyr Ile Asp Ala Tyr Met Gln Glu Ala Lys Trp Ile Ala Ser
    450                 455                 460

Gly Glu Val Pro Thr Phe Glu Glu Tyr Tyr Glu Asn Gly Lys Val Ser
465                 470                 475                 480

Ser Gly His Arg Val Ser Ala Leu Gln Pro Ile Leu Thr Thr Asp Ile
                485                 490                 495

Pro Phe Pro Glu His Val Leu Lys Glu Val Asp Ile Pro Ser Gln Leu
            500                 505                 510

Asn Asp Leu Ala Ser Ala Ile Leu Arg Leu Arg Gly Asp Thr Arg Cys
        515                 520                 525

Tyr Gln Ala Asp Arg Ala Arg Gly Glu Glu Ala Ser Cys Ile Ser Cys
    530                 535                 540

Tyr Met Lys Asp Asn Pro Gly Thr Thr Glu Glu Asp Ala Leu Asn His
545                 550                 555                 560

Leu Asn Ala Met Ile Ser Asp Val Ile Lys Gly Leu Asn Trp Glu Leu
                565                 570                 575

Leu Lys Pro Asn Ser Ser Val Pro Ile Ser Ala Lys Lys His Ala Phe
            580                 585                 590

Asp Ile Ser Arg Ala Phe His Cys Gly Tyr Lys Tyr Arg Asp Gly Tyr
        595                 600                 605

Ser Val Ala Asn Ile Glu Thr Lys Ser Leu Val Lys Arg Thr Val Ile
    610                 615                 620

Asp Pro Val Thr Leu
625

<210> SEQ ID NO 12
<211> LENGTH: 625
<212> TYPE: PRT
<213> ORGANISM: Pseudotsuga menziesii

<400> SEQUENCE: 12

Met Ser Leu Ile Ser Met Ala Pro Leu Ala Pro Lys Ser Cys Leu His
1               5                   10                  15

Lys Pro Phe Ile Gly Ser Thr His Glu Pro Lys Val Phe Cys Arg Lys
            20                  25                  30

Ile Pro Thr Pro Thr Leu Val Met Cys Arg Arg Ala Lys Ser Val Thr
        35                  40                  45

Ser Ser Met Gly Thr Ser Leu Asp Ala Gly His Val Gln Arg Ile
50                  55                  60

Gly Asp Tyr His Ser Asn Ile Trp Asp Asn Phe Ile Gln Ser Leu
65                  70                  75                  80

Ser Ser Pro Tyr Glu Glu Ser Ser Tyr Gly Asp Arg Ala Glu Thr Leu
            85                  90                  95

Ile Gly Glu Val Lys Glu Ile Phe Asn Ser Leu Ser Met Thr Gly Val
            100                 105                 110

Val Ser Pro Leu Asn Asp Leu Leu Gln Arg Leu Leu Met Val Asp Asn
            115                 120                 125

Val Glu Arg Leu Gly Ile Glu Arg His Phe Gln Asn Glu Ile Lys Ser
            130                 135                 140

Ala Leu Gln Tyr Val Tyr Ser Tyr Trp Ser Glu Asn Gly Ile Gly Cys
145                 150                 155                 160

Gly Lys Asp Ser Val Ser Thr Asp Leu Asn Thr Thr Ala Leu Gly Phe
            165                 170                 175

Arg Ile Leu Arg Leu His Gly Tyr Thr Val Phe Ser Asp Val Leu Glu
            180                 185                 190

Gln Phe Lys Asp Gln Lys Gly Gln Phe Ala Ser Ala Trp Ser Ala Asn
            195                 200                 205

His Thr Glu Arg Gln Ile Arg Ser Val Leu Asn Leu Phe Arg Ala Ser
210                 215                 220

Leu Ile Ala Phe Pro Gly Glu Lys Val Met Glu Glu Ala Gln Ile Phe
225                 230                 235                 240

Ser Ala Thr Tyr Leu Lys Glu Ala Leu Gln Thr Ile Pro Leu Ser Gly
            245                 250                 255

Leu Ser Gln Glu Ile Gln Tyr Ala Leu Glu Tyr Arg Trp His Ser Asn
            260                 265                 270

Leu Pro Arg Leu Glu Val Arg Ser Tyr Ile Asp Ile Leu Ala Glu Asn
            275                 280                 285

Thr Ile Asn Glu Met Ser Tyr Pro Lys Val Glu Lys Leu Leu Glu Leu
            290                 295                 300

Ala Lys Leu Glu Phe Asn Ile Phe His Ser Leu Gln Gln Lys Glu Leu
305                 310                 315                 320

Gln Cys Ile Trp Arg Trp Trp Lys Glu Ser Gly Ser Pro Glu Leu Thr
            325                 330                 335

Phe Val Arg His Arg Tyr Val Glu Tyr Tyr Thr Leu Val Ala Gly Ile
            340                 345                 350

Asp Met Glu Pro Gln His Ser Ala Phe Arg Ile Ala Tyr Val Lys Met
            355                 360                 365

Cys His Leu Ile Thr Ile Leu Asp Asp Met Tyr Asp Thr Phe Gly Thr
370                 375                 380

Ile Asp Glu Leu Arg Leu Phe Thr Ala Ala Val Lys Arg Trp Asp Arg
385                 390                 395                 400

Ser Pro Thr Glu Cys Leu Pro Gln Tyr Met Lys Gly Val Tyr Met Val
            405                 410                 415

Leu Tyr Asp Thr Val Asn Glu Met Ala Cys Glu Ala Leu Lys Ser Gln
            420                 425                 430

Gly Trp Asp Thr Leu Asn Tyr Ala Arg Gln Ala Phe Glu Asp Tyr Ile
            435                 440                 445

Asp Ser Tyr Leu Lys Glu Ala Glu Trp Ile Ser Thr Gly Tyr Leu Pro
450                 455                 460

Thr Phe Glu Glu Tyr Leu Glu Asn Gly Lys Val Ser Ser Ala His Arg

```
                    465                 470                 475                 480
Val Ala Thr Leu Gln Pro Ile Leu Thr Leu Asp Ile Pro Phe Pro Leu
                485                 490                 495

His Ile Ile Gln Glu Ile Asp Phe Pro Ser Lys Phe Asn Asp Ser Ala
                500                 505                 510

Ser Ser Ile Leu Arg Leu Arg Gly Asp Thr Arg Cys Tyr Gln Ala Asp
                515                 520                 525

Met Ala Arg Gly Glu Glu Ala Ser Ser Ile Ser Cys Tyr Met His Asp
                530                 535                 540

Asn Pro Gly Ser Thr Glu Glu Asp Ala Leu Asn His Ile Asn Gly Met
545                 550                 555                 560

Ile Glu Asp Ile Ile Lys Glu Leu Asn Trp Glu Leu Leu Arg Lys Asp
                565                 570                 575

Ile Asn Val Pro Ile Ser Cys Lys Lys His Ala Phe Glu Ile Ser Arg
                580                 585                 590

Gly Phe His His Phe Tyr Lys Asp Arg Asp Gly Tyr Thr Val Ser Asn
                595                 600                 605

Ile Glu Thr Lys Asp Leu Val Met Lys Thr Val Leu Glu Pro Val Pro
                610                 615                 620

Leu
625

<210> SEQ ID NO 13
<211> LENGTH: 627
<212> TYPE: PRT
<213> ORGANISM: Picea abies

<400> SEQUENCE: 13

Met Ser Val Ile Ser Ile Leu Pro Leu Ala Ser Lys Ser Cys Leu Tyr
  1               5                  10                  15

Lys Ser Leu Met Ser Ser Thr His Glu Leu Lys Ala Leu Cys Arg Pro
                 20                  25                  30

Ile Ala Thr Leu Gly Met Cys Arg Arg Gly Lys Ser Val Met Ala Ser
                 35                  40                  45

Lys Ser Thr Ser Leu Thr Thr Ala Val Ser Asp Asp Gly Val Gln Arg
 50                  55                  60

Arg Ile Gly Asp His His Ser Asn Leu Trp Asp Asp Asn Phe Ile Gln
 65                  70                  75                  80

Ser Leu Ser Ser Pro Tyr Gly Ala Ser Ser Tyr Gly Glu Arg Ala Glu
                 85                  90                  95

Arg Leu Ile Gly Glu Val Lys Glu Ile Phe Asn Ser Leu Ser Arg Thr
                100                 105                 110

Asp Gly Glu Leu Val Ser His Val Asp Asp Leu Leu Gln His Leu Ser
                115                 120                 125

Met Val Asp Asn Val Glu Arg Leu Gly Ile Asp Arg His Phe Gln Thr
                130                 135                 140

Glu Ile Lys Val Ser Leu Asp Tyr Val Tyr Ser Tyr Trp Ser Glu Lys
145                 150                 155                 160

Gly Ile Gly Ser Gly Arg Asp Ile Val Cys Thr Asp Leu Asn Thr Thr
                165                 170                 175

Ala Leu Gly Phe Arg Ile Leu Arg Leu His Gly Tyr Thr Val Phe Pro
                180                 185                 190

Asp Val Phe Glu His Phe Lys Asp Gln Met Gly Arg Ile Ala Cys Ser
                195                 200                 205

Asp Asn His Thr Glu Arg Gln Ile Ser Ser Ile Leu Asn Leu Phe Arg
```

```
                210                 215                 220
Ala Ser Leu Ile Ala Phe Pro Gly Glu Lys Val Met Glu Ala Glu
225                 230                 235                 240

Ile Phe Ser Ala Thr Tyr Leu Lys Glu Ala Leu Gln Thr Ile Pro Val
                245                 250                 255

Ser Ser Leu Ser Gln Glu Ile Gln Tyr Val Leu Gln Tyr Arg Trp His
                260                 265                 270

Ser Asn Leu Pro Arg Leu Glu Ala Arg Thr Tyr Ile Asp Ile Leu Gln
                275                 280                 285

Glu Asn Thr Lys Asn Gln Met Leu Asp Val Asn Thr Lys Lys Val Leu
290                 295                 300

Glu Leu Ala Lys Leu Glu Phe Asn Ile Phe His Ser Leu Gln Gln Asn
305                 310                 315                 320

Glu Leu Lys Ser Val Ser Arg Trp Trp Lys Glu Ser Gly Phe Pro Asp
                325                 330                 335

Leu Asn Phe Ile Arg His Arg His Val Glu Phe Tyr Thr Leu Val Ser
                340                 345                 350

Gly Ile Asp Met Glu Pro Lys His Cys Thr Phe Arg Leu Ser Phe Val
                355                 360                 365

Lys Met Cys His Leu Ile Thr Val Leu Asp Asp Met Tyr Asp Thr Phe
370                 375                 380

Gly Thr Ile Asp Glu Leu Arg Leu Phe Thr Ala Ala Val Lys Arg Trp
385                 390                 395                 400

Asp Pro Ser Thr Thr Glu Cys Leu Pro Glu Tyr Met Lys Gly Val Tyr
                405                 410                 415

Thr Val Leu Tyr Glu Thr Val Asn Glu Met Ala Gln Glu Ala Gln Lys
                420                 425                 430

Ser Gln Gly Arg Asp Thr Leu Ser Tyr Val Arg Gln Ala Leu Glu Ala
                435                 440                 445

Tyr Ile Gly Ala Tyr His Lys Glu Ala Glu Trp Ile Ser Ser Gly Tyr
                450                 455                 460

Leu Pro Thr Phe Asp Glu Tyr Phe Glu Asn Gly Lys Val Ser Ser Gly
465                 470                 475                 480

His Arg Ile Ala Thr Leu Gln Pro Thr Phe Met Leu Asp Ile Pro Phe
                485                 490                 495

Pro His His Val Leu Gln Glu Ile Asp Phe Pro Ser Lys Phe Asn Asp
                500                 505                 510

Phe Ala Cys Ser Ile Leu Arg Leu Arg Gly Asp Thr Arg Cys Tyr Gln
                515                 520                 525

Ala Asp Arg Ala Arg Gly Glu Glu Ala Ser Cys Ile Ser Cys Tyr Met
530                 535                 540

Lys Asp Asn Pro Gly Ser Thr Gln Glu Asp Ala Leu Asn His Ile Asn
545                 550                 555                 560

Asn Met Ile Glu Glu Thr Ile Lys Lys Leu Asn Trp Glu Leu Leu Lys
                565                 570                 575

Pro Asp Asn Asn Val Pro Ile Ser Ser Lys Lys His Ala Phe Asp Ile
                580                 585                 590

Asn Arg Gly Leu His His Phe Tyr Asn Tyr Arg Asp Gly Tyr Thr Val
                595                 600                 605

Ala Ser Asn Glu Thr Lys Asn Leu Val Ile Lys Thr Val Leu Glu Pro
                610                 615                 620

Val Pro Met
625
```

<210> SEQ ID NO 14
<211> LENGTH: 621
<212> TYPE: PRT
<213> ORGANISM: Picea abies

<400> SEQUENCE: 14

```
Pro Arg Ala Ala Gly Lys Ser Cys Leu His Lys Ser Leu Ser Ser Ser
 1               5                  10                  15

Ala His Glu Leu Lys Thr Ile Cys Arg Thr Ile Pro Thr Leu Gly Met
            20                  25                  30

Ser Arg Arg Gly Lys Ser Ala Thr Pro Ser Met Ser Met Ser Leu Thr
        35                  40                  45

Thr Thr Val Ser Asp Asp Gly Val Gln Arg Arg Met Gly Asp Phe His
 50                  55                  60

Ser Asn Leu Trp Asn Asp Asp Phe Ile Gln Ser Leu Ser Thr Ser Tyr
 65                  70                  75                  80

Gly Glu Pro Ser Tyr Arg Glu Arg Ala Glu Arg Leu Ile Gly Glu Val
                85                  90                  95

Lys Lys Met Phe Asn Ser Met Ser Ser Glu Asp Gly Glu Leu Ile Ser
            100                 105                 110

Pro His Asn Asp Leu Ile Gln Arg Val Trp Met Val Asp Ser Val Glu
        115                 120                 125

Arg Leu Gly Ile Glu Arg His Phe Lys Asn Glu Ile Lys Ser Ala Leu
130                 135                 140

Asp Tyr Val Tyr Ser Tyr Trp Ser Glu Lys Gly Ile Gly Cys Gly Arg
145                 150                 155                 160

Glu Ser Val Val Ala Asp Leu Asn Ser Thr Ala Leu Gly Leu Arg Thr
                165                 170                 175

Leu Arg Leu His Gly Tyr Ala Val Ser Ala Asp Val Leu Asn Leu Phe
            180                 185                 190

Lys Asp Gln Asn Gly Gln Phe Ala Cys Ser Pro Ser Thr Gln Thr Glu
        195                 200                 205

Glu Ile Arg Ser Val Leu Asn Leu Tyr Arg Ala Ser Leu Ile Ala Phe
210                 215                 220

Pro Gly Glu Lys Val Met Glu Glu Ala Glu Ile Phe Ser Ala Lys Tyr
225                 230                 235                 240

Leu Glu Glu Ala Leu Gln Lys Ile Ser Val Ser Ser Leu Ser Gln Glu
                245                 250                 255

Ile Arg Asp Val Leu Glu Tyr Gly Trp His Thr Tyr Leu Pro Arg Met
            260                 265                 270

Glu Ala Arg Asn His Ile Asp Val Phe Gly Gln Asp Thr Gln Asn Ser
        275                 280                 285

Lys Ser Cys Ile Asn Thr Asp Lys Leu Leu Glu Leu Ala Lys Leu Glu
290                 295                 300

Phe Asn Ile Phe His Ser Leu Gln Lys Arg Glu Leu Glu Tyr Leu Val
305                 310                 315                 320

Arg Trp Trp Lys Asp Ser Gly Ser Pro Gln Met Thr Phe Gly Arg His
                325                 330                 335

Arg His Ile Glu Tyr Tyr Thr Leu Ala Ser Cys Ile Ala Phe Glu Pro
            340                 345                 350

Gln His Ser Gly Phe Arg Leu Gly Phe Ala Lys Thr Cys His Ile Ile
        355                 360                 365

Thr Ile Leu Asp Asp Met Tyr Asp Thr Phe Gly Thr Val Asp Glu Leu
370                 375                 380
```

```
Glu Leu Phe Thr Ala Ala Met Lys Arg Trp Asp Pro Ser Ala Ala Asp
385                 390                 395                 400

Cys Leu Pro Glu Tyr Met Lys Val Met Tyr Met Ile Val Tyr Asp Thr
                405                 410                 415

Val Asn Glu Met Cys Gln Glu Ala Glu Lys Ala Gln Gly Arg Asp Thr
            420                 425                 430

Leu Asp Tyr Ala Arg Gln Ala Trp Glu Asp Tyr Leu Asp Ser Tyr Met
        435                 440                 445

Gln Glu Ala Lys Trp Ile Ala Thr Gly Tyr Leu Pro Thr Phe Glu Glu
    450                 455                 460

Tyr Tyr Glu Asn Gly Lys Val Ser Ser Gly His Arg Val Ala Ala Leu
465                 470                 475                 480

Gln Pro Ile Leu Thr Met Asp Ile Pro Phe Pro Pro His Ile Leu Lys
                485                 490                 495

Glu Val Asp Phe Pro Ser Lys Leu Ser Asp Leu Ala Cys Ala Ile Leu
            500                 505                 510

Arg Leu Arg Gly Asp Thr Arg Cys Tyr Lys Ala Asp Arg Ala Arg Gly
        515                 520                 525

Glu Glu Ala Ser Ser Ile Ser Cys Tyr Met Lys Asp Asn Pro Gly Ala
    530                 535                 540

Thr Glu Glu Asp Ala Leu Asp His Ile Asn Ala Met Ile Ser Asp Val
545                 550                 555                 560

Ile Arg Gly Leu Asn Trp Glu Leu Leu Lys Pro Asn Ser Ser Val Pro
                565                 570                 575

Ile Ser Ser Lys Lys His Val Phe Asp Ile Ser Arg Ala Phe His Tyr
            580                 585                 590

Gly Tyr Lys Tyr Arg Asp Gly Tyr Ser Val Ala Asn Ile Glu Thr Lys
        595                 600                 605

Ser Leu Val Lys Arg Thr Val Ile Asp Pro Val Thr Leu
    610                 615                 620

<210> SEQ ID NO 15
<211> LENGTH: 618
<212> TYPE: PRT
<213> ORGANISM: Abies grandis

<400> SEQUENCE: 15

Met Ala Leu Leu Ser Ile Thr Pro Leu Val Ser Arg Ser Cys Leu Ser
1               5                   10                  15

Ser Ser His Glu Ile Lys Ala Leu Arg Arg Thr Ile Pro Thr Leu Gly
            20                  25                  30

Ile Cys Arg Pro Gly Lys Ser Val Ala His Ser Ile Asn Met Cys Leu
        35                  40                  45

Thr Ser Val Ala Ser Thr Asp Ser Val Gln Arg Arg Val Gly Asn Tyr
    50                  55                  60

His Ser Asn Leu Trp Asp Asp Phe Ile Gln Ser Leu Ile Ser Thr
65                  70                  75                  80

Pro Tyr Gly Ala Pro Asp Tyr Arg Glu Arg Ala Asp Arg Leu Ile Gly
                85                  90                  95

Glu Val Lys Asp Ile Met Phe Asn Phe Lys Ser Leu Glu Asp Gly Gly
            100                 105                 110

Asn Asp Leu Leu Gln Arg Leu Leu Val Asp Asp Val Glu Arg Leu
        115                 120                 125

Gly Ile Asp Arg His Phe Lys Lys Glu Ile Lys Thr Ala Leu Asp Tyr
    130                 135                 140
```

-continued

Val Asn Ser Tyr Trp Asn Glu Lys Gly Ile Gly Cys Gly Arg Glu Ser
145                 150                 155                 160

Val Val Thr Asp Leu Asn Ser Thr Ala Leu Gly Leu Arg Thr Leu Arg
            165                 170                 175

Leu His Gly Tyr Thr Val Ser Ser Asp Val Leu Asn Val Phe Lys Asp
            180                 185                 190

Lys Asn Gly Gln Phe Ser Ser Thr Ala Asn Ile Gln Ile Glu Gly Glu
        195                 200                 205

Ile Arg Gly Val Leu Asn Leu Phe Arg Ala Ser Leu Val Ala Phe Pro
210                 215                 220

Gly Glu Lys Val Met Asp Glu Ala Glu Thr Phe Ser Thr Lys Tyr Leu
225                 230                 235                 240

Arg Glu Ala Leu Gln Lys Ile Pro Ala Ser Ser Ile Leu Ser Leu Glu
                245                 250                 255

Ile Arg Asp Val Leu Glu Tyr Gly Trp His Thr Asn Leu Pro Arg Leu
            260                 265                 270

Glu Ala Arg Asn Tyr Met Asp Val Phe Gly Gln His Thr Lys Asn Lys
        275                 280                 285

Asn Ala Ala Glu Lys Leu Leu Glu Leu Ala Lys Leu Glu Phe Asn Ile
290                 295                 300

Phe His Ser Leu Gln Glu Arg Glu Leu Lys His Val Ser Arg Trp Trp
305                 310                 315                 320

Lys Asp Ser Gly Ser Pro Glu Met Thr Phe Cys Arg His Arg His Val
                325                 330                 335

Glu Tyr Tyr Ala Leu Ala Ser Cys Ile Ala Phe Glu Pro Gln His Ser
            340                 345                 350

Gly Phe Arg Leu Gly Phe Thr Lys Met Ser His Leu Ile Thr Val Leu
        355                 360                 365

Asp Asp Met Tyr Asp Val Phe Gly Thr Val Asp Glu Leu Glu Leu Phe
370                 375                 380

Thr Ala Thr Ile Lys Arg Trp Asp Pro Ser Ala Met Glu Cys Leu Pro
385                 390                 395                 400

Glu Tyr Met Lys Gly Val Tyr Met Met Val Tyr His Thr Val Asn Glu
                405                 410                 415

Met Ala Arg Val Ala Glu Lys Ala Gln Gly Arg Asp Thr Leu Asn Tyr
            420                 425                 430

Ala Arg Gln Ala Trp Glu Ala Cys Phe Asp Ser Tyr Met Gln Glu Ala
        435                 440                 445

Lys Trp Ile Ala Thr Gly Tyr Leu Pro Thr Phe Glu Glu Tyr Leu Glu
450                 455                 460

Asn Gly Lys Val Ser Ser Ala His Arg Pro Cys Ala Leu Gln Pro Ile
465                 470                 475                 480

Leu Thr Leu Asp Ile Pro Phe Pro Asp His Ile Leu Lys Glu Val Asp
                485                 490                 495

Phe Pro Ser Lys Leu Asn Asp Leu Ile Cys Ile Ile Leu Arg Leu Arg
            500                 505                 510

Gly Asp Thr Arg Cys Tyr Lys Ala Asp Arg Ala Arg Gly Glu Glu Ala
        515                 520                 525

Ser Ser Ile Ser Cys Tyr Met Lys Asp Asn Pro Gly Leu Thr Glu Glu
530                 535                 540

Asp Ala Leu Asn His Ile Asn Phe Met Ile Arg Asp Ala Ile Arg Glu
545                 550                 555                 560

Leu Asn Trp Glu Leu Leu Lys Pro Asp Asn Ser Val Pro Ile Thr Ser
                565                 570                 575

```
Lys Lys His Ala Phe Asp Ile Ser Arg Val Trp His His Gly Tyr Arg
            580                 585                 590

Tyr Arg Asp Gly Tyr Ser Phe Ala Asn Val Glu Thr Lys Ser Leu Val
            595                 600                 605

Met Arg Thr Val Ile Glu Pro Val Pro Leu
            610                 615

<210> SEQ ID NO 16
<211> LENGTH: 627
<212> TYPE: PRT
<213> ORGANISM: Picea sitchensis

<400> SEQUENCE: 16

Met Ala Leu Val Ser Val Ala Pro Met Ala Ser Arg Ser Cys Leu His
  1               5                  10                  15

Lys Ser Leu Ser Ser Ser Ala His Glu Leu Lys Thr Ile Cys Arg Thr
             20                  25                  30

Ile Pro Thr Leu Gly Met Ser Arg Arg Gly Lys Ser Ala Thr Pro Ser
         35                  40                  45

Met Ser Met Ser Leu Thr Thr Thr Val Ser Asp Asp Gly Val Gln Arg
     50                  55                  60

Arg Met Gly Asp Phe His Ser Asn Leu Trp Asn Asp Asp Phe Ile Gln
 65                  70                  75                  80

Ser Leu Ser Thr Ser Tyr Gly Glu Pro Ser Tyr Arg Glu Arg Ala Glu
                 85                  90                  95

Arg Leu Ile Gly Glu Val Lys Lys Met Phe Asn Ser Met Ser Ser Glu
            100                 105                 110

Asp Gly Glu Leu Ile Ser Pro His Asn Asp Leu Ile Gln Arg Val Trp
        115                 120                 125

Met Val Asp Ser Val Glu Arg Leu Gly Ile Glu Arg His Phe Lys Asn
    130                 135                 140

Glu Ile Lys Ser Ala Leu Asp Tyr Val Tyr Ser Tyr Trp Ser Glu Lys
145                 150                 155                 160

Gly Ile Gly Cys Gly Arg Glu Ser Val Val Ala Asp Leu Asn Ser Thr
                165                 170                 175

Ala Leu Gly Phe Arg Thr Leu Arg Leu His Gly Tyr Ala Val Ser Ala
            180                 185                 190

Asp Val Leu Asn Leu Phe Lys Asp Gln Asn Gly Gln Phe Ala Cys Ser
        195                 200                 205

Pro Ser Gln Thr Glu Glu Ile Arg Ser Val Leu Asn Leu Tyr Arg
    210                 215                 220

Ala Ser Leu Ile Ala Phe Pro Gly Glu Lys Val Met Glu Glu Ala Glu
225                 230                 235                 240

Ile Phe Ser Ala Lys Tyr Leu Glu Glu Ser Leu Gln Lys Ile Ser Val
                245                 250                 255

Ser Ser Leu Ser Gln Glu Ile Arg Asp Val Leu Glu Tyr Gly Trp His
            260                 265                 270

Thr Tyr Leu Pro Arg Met Glu Ala Arg Asn His Ile Asp Val Phe Gly
        275                 280                 285

Gln Asp Thr Gln Asn Ser Lys Ser Cys Ile Asn Thr Glu Lys Leu Leu
    290                 295                 300

Glu Leu Ala Lys Leu Glu Phe Asn Ile Phe His Ser Leu Gln Lys Arg
305                 310                 315                 320

Glu Leu Glu Tyr Leu Val Arg Trp Trp Lys Asp Ser Gly Ser Pro Gln
                325                 330                 335
```

```
Met Thr Phe Cys Arg His Arg His Val Glu Tyr Tyr Thr Leu Ala Ser
            340                 345                 350

Cys Ile Ala Phe Glu Pro Gln His Ser Gly Phe Arg Leu Gly Phe Ala
            355                 360                 365

Lys Ala Cys His Ile Ile Thr Ile Leu Asp Asp Met Tyr Asp Thr Phe
            370                 375                 380

Gly Thr Val Asp Glu Leu Glu Leu Phe Thr Ala Ala Met Lys Arg Trp
385                 390                 395                 400

Asp Pro Ser Ala Ala Asp Cys Leu Pro Glu Tyr Met Lys Gly Val Tyr
            405                 410                 415

Leu Ile Leu Tyr Asp Thr Val Asn Glu Thr Ser Arg Glu Ala Glu Lys
            420                 425                 430

Ala Gln Gly Arg Asp Thr Leu Asp Tyr Ala Arg Arg Ala Trp Asp Asp
            435                 440                 445

Tyr Leu Asp Ser Tyr Met Gln Glu Ala Lys Trp Ile Ala Thr Gly Tyr
            450                 455                 460

Leu Pro Thr Phe Ala Glu Tyr Tyr Glu Asn Gly Lys Val Ser Ser Gly
465                 470                 475                 480

His Arg Thr Ser Ala Leu Gln Pro Ile Leu Thr Met Asp Ile Pro Phe
            485                 490                 495

Pro Pro His Ile Leu Lys Glu Val Asp Phe Pro Ser Lys Leu Asn Asp
            500                 505                 510

Leu Ala Ser Ala Ile Leu Arg Leu Arg Gly Asp Thr Arg Cys Tyr Lys
            515                 520                 525

Ala Asp Arg Ala Arg Gly Glu Glu Ala Ser Ser Ile Ser Cys Tyr Met
            530                 535                 540

Lys Asp Asn Pro Gly Ala Thr Glu Glu Asp Ala Leu Asp His Ile Asn
545                 550                 555                 560

Ala Met Ile Ser Asp Val Ile Arg Gly Leu Asn Trp Glu Leu Leu Asn
            565                 570                 575

Pro Asn Ser Ser Val Pro Ile Ser Ser Lys Lys His Val Phe Asp Ile
            580                 585                 590

Ser Arg Ala Phe His Tyr Gly Tyr Lys Tyr Arg Asp Gly Tyr Ser Val
            595                 600                 605

Ala Asn Ile Glu Thr Lys Ser Leu Val Arg Arg Thr Val Ile Asp Pro
            610                 615                 620

Val Thr Leu
625

<210> SEQ ID NO 17
<211> LENGTH: 630
<212> TYPE: PRT
<213> ORGANISM: Abies grandis

<400> SEQUENCE: 17

Met Ala Leu Val Ser Ile Leu Pro Leu Ser Ser Lys Ser Val Leu His
1               5                   10                  15

Lys Ser Trp Ile Val Ser Thr Tyr Glu His Lys Ala Ile Ser Arg Thr
                20                  25                  30

Ile Pro Asn Leu Gly Leu Arg Gly Arg Gly Lys Ser Val Thr His Ser
            35                  40                  45

Leu Arg Met Ser Leu Ser Thr Ala Val Ser Asp Asp His Gly Val Gln
        50                  55                  60

Arg Arg Ile Val Glu Phe His Ser Asn Leu Trp Asp Asp Asp Phe Ile
65              70                  75                  80
```

```
Gln Ser Leu Ser Thr Pro Tyr Gly Ala Pro Ser Tyr Arg Glu Arg Ala
                85                  90                  95

Asp Arg Leu Ile Val Glu Val Lys Gly Ile Phe Thr Ser Ile Ser Ala
            100                 105                 110

Glu Asp Gly Glu Leu Ile Thr Pro Leu Asn Asp Leu Ile Gln Arg Leu
            115                 120                 125

Leu Met Val Asp Asn Val Glu Arg Leu Gly Ile Asp Arg His Phe Lys
    130                 135                 140

Asn Glu Ile Lys Ala Ala Leu Asp Tyr Val Tyr Ser Tyr Trp Asn Glu
145                 150                 155                 160

Lys Gly Ile Gly Ser Gly Ser Asp Ser Gly Val Ala Asp Leu Asn Ser
                165                 170                 175

Thr Ala Leu Gly Phe Arg Ile Leu Arg Leu His Gly Tyr Ser Val Ser
            180                 185                 190

Ser Asp Val Leu Glu His Phe Lys Glu Glu Lys Glu Lys Gly Gln Phe
            195                 200                 205

Val Cys Ser Ala Ile Gln Thr Glu Glu Glu Ile Lys Ser Val Leu Asn
    210                 215                 220

Leu Phe Arg Ala Ser Leu Ile Ala Phe Pro Gly Glu Lys Val Met Glu
225                 230                 235                 240

Glu Ala Glu Ile Phe Ser Lys Ile Tyr Leu Lys Glu Ala Leu Gln Asn
                245                 250                 255

Ile Ala Val Ser Ser Leu Ser Arg Glu Ile Glu Tyr Val Leu Glu Asp
            260                 265                 270

Gly Trp Gln Thr Asn Met Pro Arg Leu Glu Thr Arg Asn Tyr Ile Asp
            275                 280                 285

Val Leu Gly Glu Asn Asp Arg Asp Glu Thr Leu Tyr Met Asn Met Glu
    290                 295                 300

Lys Leu Leu Glu Ile Ala Lys Leu Glu Phe Asn Ile Phe His Ser Leu
305                 310                 315                 320

Gln Gln Arg Glu Leu Lys Asp Leu Ser Arg Trp Trp Lys Asp Ser Gly
                325                 330                 335

Phe Ser His Leu Thr Phe Ser Arg His Arg His Val Glu Phe Tyr Ala
            340                 345                 350

Leu Ala Ser Cys Ile Glu Thr Asp Arg Lys His Ser Gly Phe Arg Leu
            355                 360                 365

Gly Phe Ala Lys Met Cys His Leu Ile Thr Val Leu Asp Asp Ile Tyr
    370                 375                 380

Asp Thr Phe Gly Thr Met Glu Glu Leu Glu Leu Phe Thr Ala Ala Phe
385                 390                 395                 400

Lys Arg Trp Asp Pro Ser Ala Thr Asp Leu Leu Pro Glu Tyr Met Lys
                405                 410                 415

Gly Leu Tyr Met Val Val Tyr Glu Thr Val Asn Glu Ile Ala Arg Glu
            420                 425                 430

Ala Asp Lys Ser Gln Gly Arg Glu Thr Leu Asn Asp Ala Arg Arg Ala
            435                 440                 445

Trp Glu Ala Tyr Leu Asp Ser Tyr Met Lys Glu Ala Glu Trp Ile Ser
    450                 455                 460

Ser Gly Tyr Leu Pro Thr Phe Glu Glu Tyr Met Glu Thr Ser Lys Val
465                 470                 475                 480

Ser Phe Gly Tyr Arg Ile Phe Ala Leu Gln Pro Ile Leu Thr Met Asp
                485                 490                 495

Val Pro Leu Thr His His Ile Leu Gln Glu Ile Asp Phe Pro Leu Arg
```

```
                      500             505             510
Phe Asn Asp Leu Ile Cys Ser Ile Leu Arg Leu Lys Asn Asp Thr Arg
            515                 520                 525

Cys Tyr Lys Ala Asp Arg Ala Arg Gly Glu Glu Ala Ser Cys Ile Ser
        530                 535                 540

Cys Tyr Met Lys Glu Asn Pro Gly Ser Thr Glu Glu Asp Ala Ile Asn
545                 550                 555                 560

His Ile Asn Ala Met Val Asn Asn Leu Ile Lys Glu Val Asn Trp Glu
                565                 570                 575

Leu Leu Arg Gln Asp Gly Thr Ala His Ile Ala Cys Lys Lys His Ala
            580                 585                 590

Phe Asp Ile Leu Lys Gly Ser Leu His Gly Tyr Lys Tyr Arg Asp Gly
        595                 600                 605

Phe Ser Val Ala Asn Lys Glu Thr Lys Asn Trp Val Arg Arg Thr Val
    610                 615                 620

Leu Glu Ser Val Pro Leu
625                 630

<210> SEQ ID NO 18
<211> LENGTH: 627
<212> TYPE: PRT
<213> ORGANISM: Pinus taeda

<400> SEQUENCE: 18

Met Asp Leu Ile Ser Val Leu Pro Ser Ala Ser Lys Ser Cys Val Cys
1               5                   10                  15

Leu His Lys Pro Leu Ser Ser Thr His Lys Leu Lys Pro Phe Cys
            20                  25                  30

Lys Thr Ile Arg Ile Leu Val Met Pro Arg Arg Trp Glu Phe Ala Arg
        35                  40                  45

Pro Ser Met Ser Leu Ser Thr Val Ala Ser Glu Asp Asp Ile Gln Arg
    50                  55                  60

Arg Thr Gly Gly Tyr Leu Ser Asn Leu Trp Asn Asp Val Ile Gln
65                  70                  75                  80

Phe Leu Ser Thr Pro Tyr Gly Glu Leu Ala Tyr Arg Glu Arg Ala Glu
                85                  90                  95

Arg Leu Ile Asp Glu Val Arg Ile Phe Ser Ser Met Ser Leu Glu
            100                 105                 110

Asp Gly Glu Phe Ser Asp Leu Ile Gln Arg Leu Trp Met Val Asp Asn
        115                 120                 125

Val Glu Arg Leu Gly Ile Asp Arg His Phe Lys Asn Glu Ile Lys Ser
    130                 135                 140

Ala Leu Asp Tyr Val Tyr Ser Tyr Trp Ser Glu Lys Gly Ile Gly Cys
145                 150                 155                 160

Gly Thr Lys Ser Ile Ile Thr Asn Leu Asn Ser Thr Ala Leu Gly Phe
                165                 170                 175

Arg Thr Leu Arg Leu His Gly Tyr Pro Val Ser Ala Asp Val Leu Lys
            180                 185                 190

His Phe Arg Asn Gln Ile Gly Gln Phe Val Ser Cys Pro Ser Glu Thr
        195                 200                 205

Glu Glu Asp Ile Arg Ile Met Val Asn Leu Tyr Arg Ala Ser Leu Ile
    210                 215                 220

Ala Phe Pro Val Ala Phe Pro Gly Glu Lys Val Met Glu Glu Ala Glu
225                 230                 235                 240

Ser Phe Ser Glu Lys Tyr Leu Lys Glu Thr Leu Gln Lys Ile Pro Asp
```

```
                245                 250                 255
Cys Ser Leu Ser Arg Glu Ile Gly Asp Val Leu Glu His Gly Trp His
            260                 265                 270

Thr Asn Leu Pro Arg Leu Glu Ala Arg Asn Tyr Ile Asp Val Phe Gly
            275                 280                 285

Gln Asp Thr Lys Asn Met Glu Pro Asn Arg Lys Thr Glu Lys Leu Leu
290                 295                 300

Glu Leu Ala Lys Leu Glu Phe Asn Ile Phe Gln Ser Ile Gln Lys Thr
305                 310                 315                 320

Glu Leu Glu Ser Leu Leu Arg Trp Trp Asn Asp Ser Gly Ser Pro Gln
            325                 330                 335

Ile Thr Phe Thr Arg His Arg His Val Glu Tyr Tyr Thr Leu Ala Ser
            340                 345                 350

Cys Ile Ala Phe Glu Pro Gln His Ser Gly Phe Arg Leu Gly Phe Ala
            355                 360                 365

Lys Ala Cys His Ile Leu Thr Val Leu Asp Asp Met Tyr Asp Leu Phe
            370                 375                 380

Gly Thr Val Asp Glu Leu Lys Leu Phe Thr Ala Ala Ile Lys Arg Trp
385                 390                 395                 400

Asp Pro Ser Ala Thr Asp Cys Leu Pro Gln Tyr Met Lys Gly Ile Tyr
                    405                 410                 415

Met Met Val Tyr Asn Thr Val Asn Glu Met Ser Ala Glu Ala Gln Lys
                420                 425                 430

Ala Gln Gly Arg Asp Thr Leu Asn Tyr Ala Arg Gln Ala Trp Glu Asp
            435                 440                 445

Cys Leu Asp Ser His Met Gln Glu Ala Lys Trp Ile Ala Thr Gly Phe
            450                 455                 460

Leu Pro Thr Phe Glu Glu Tyr Leu Glu Asn Gly Lys Val Ser Ser Ala
465                 470                 475                 480

His Arg Val Ser Ala Leu Gln Pro Met Leu Thr Met Asp Ile Pro Phe
                485                 490                 495

Pro Pro His Ile Leu Lys Glu Val Asp Phe Pro Ser Asn Leu Asn Asp
            500                 505                 510

Leu Ala Cys Ala Met Leu Arg Leu Arg Gly Asp Thr Arg Cys Tyr Gln
            515                 520                 525

Ala Asp Arg Ala Arg Gly Glu Glu Thr Ser Cys Ile Ser Cys Tyr Met
            530                 535                 540

Lys Asp Asn Pro Gly Ala Thr Glu Glu Asp Ala Leu Asn His Leu Asn
545                 550                 555                 560

Val Met Ile Ser Gly Val Ile Lys Glu Leu Asn Trp Glu Leu Leu Lys
                565                 570                 575

Pro Asn Ser Ser Val Pro Ile Ser Ser Lys Lys Ile Asn Phe Asp Ile
                580                 585                 590

Thr Arg Ala Phe His Tyr Gly Tyr Lys Tyr Arg Asp Gly Tyr Ser Val
            595                 600                 605

Ser Ser Val Glu Thr Lys Ser Leu Val Met Arg Thr Leu Leu Glu Pro
610                 615                 620

Val Pro Leu
625

<210> SEQ ID NO 19
<211> LENGTH: 580
<212> TYPE: PRT
<213> ORGANISM: Picea abies
```

<400> SEQUENCE: 19

| | | | | | | | | | | | | | | |
|---|---|---|---|---|---|---|---|---|---|---|---|---|---|---|
|Met|Asp|Leu|Ala|Val|Glu|Ile|Ala|Met|Asp|Leu|Ala|Val|Asp|Val|
|1| | | |5| | | | |10| | | | |15|
|Glu|Arg|Arg|Val|Gly|Asp|Tyr|His|Ser|Asn|Leu|Trp|Asp|Asp|Phe|
| | | | |20| | | | |25| | | | |30|
|Ile|Gln|Ser|Leu|Ser|Thr|Pro|Tyr|Gly|Ala|Ser|Ser|Tyr|Arg|Glu|Arg|
| | | | |35| | | | |40| | | | |45|
|Ala|Glu|Arg|Leu|Val|Gly|Glu|Val|Lys|Glu|Met|Phe|Thr|Ser|Ile|Ser|
| |50| | | | |55| | | | |60| | | |
|Ile|Glu|Asp|Gly|Glu|Leu|Thr|Ser|Asp|Leu|Leu|Gln|Arg|Leu|Trp|Met|
|65| | | | |70| | | | |75| | | | |80|
|Val|Asp|Asn|Val|Glu|Arg|Leu|Gly|Ile|Ser|Arg|His|Phe|Glu|Asn|Glu|
| | | | |85| | | | |90| | | | |95| |
|Ile|Lys|Ala|Ala|Ile|Asp|Tyr|Val|Tyr|Ser|Tyr|Trp|Ser|Asp|Lys|Gly|
| | | | |100| | | | |105| | | | |110| |
|Ile|Val|Arg|Gly|Arg|Asp|Ser|Ala|Val|Pro|Asp|Leu|Asn|Ser|Ile|Ala|
| | | | |115| | | | |120| | | | |125| |
|Leu|Gly|Phe|Arg|Thr|Leu|Arg|Leu|His|Gly|Tyr|Thr|Val|Ser|Ser|Asp|
| |130| | | | |135| | | | |140| | | |
|Val|Phe|Lys|Val|Phe|Gln|Asp|Arg|Lys|Gly|Glu|Phe|Ala|Cys|Ser|Ala|
|145| | | | |150| | | | |155| | | | |160|
|Ile|Pro|Thr|Glu|Gly|Asp|Ile|Lys|Gly|Val|Leu|Asn|Leu|Leu|Arg|Ala|
| | | | |165| | | | |170| | | | |175| |
|Ser|Tyr|Ile|Ala|Phe|Pro|Gly|Glu|Lys|Val|Met|Glu|Lys|Ala|Gln|Thr|
| | | | |180| | | | |185| | | | |190| |
|Phe|Ala|Ala|Thr|Tyr|Leu|Lys|Glu|Ala|Leu|Gln|Lys|Ile|Gln|Val|Ser|
| | | |195| | | | |200| | | | |205| | |
|Ser|Leu|Ser|Arg|Glu|Ile|Glu|Tyr|Val|Leu|Glu|Tyr|Gly|Trp|Leu|Thr|
| |210| | | | |215| | | | |220| | | |
|Asn|Phe|Pro|Arg|Leu|Glu|Ala|Arg|Asn|Tyr|Ile|Asp|Val|Phe|Gly|Glu|
|225| | | | |230| | | | |235| | | | |240|
|Glu|Ile|Cys|Pro|Tyr|Phe|Lys|Lys|Pro|Cys|Ile|Met|Val|Asp|Lys|Leu|
| | | | |245| | | | |250| | | | |255| |
|Leu|Glu|Leu|Ala|Lys|Leu|Glu|Phe|Asn|Leu|Phe|His|Ser|Leu|Gln|Gln|
| | | | |260| | | | |265| | | | |270| |
|Thr|Glu|Leu|Lys|His|Val|Ser|Arg|Trp|Trp|Lys|Asp|Ser|Gly|Phe|Ser|
| | | |275| | | | |280| | | | |285| | |
|Gln|Leu|Thr|Phe|Thr|Arg|His|Arg|His|Val|Glu|Phe|Tyr|Thr|Leu|Ala|
| |290| | | | |295| | | | |300| | | |
|Ser|Cys|Ile|Ala|Ile|Glu|Pro|Lys|His|Ser|Ala|Phe|Arg|Leu|Gly|Phe|
|305| | | | |310| | | | |315| | | | |320|
|Ala|Lys|Val|Cys|Tyr|Leu|Gly|Ile|Val|Leu|Asp|Asp|Ile|Tyr|Asp|Thr|
| | | | |325| | | | |330| | | | |335| |
|Phe|Gly|Lys|Met|Lys|Glu|Leu|Glu|Leu|Phe|Thr|Ala|Ala|Ile|Lys|Arg|
| | | |340| | | | |345| | | | |350| | |
|Trp|Asp|Pro|Ser|Thr|Thr|Glu|Cys|Leu|Pro|Glu|Tyr|Met|Lys|Gly|Val|
| | |355| | | | |360| | | | |365| | | |
|Tyr|Met|Ala|Phe|Tyr|Asn|Cys|Val|Asn|Glu|Leu|Ala|Leu|Gln|Ala|Glu|
| |370| | | | |375| | | | |380| | | |
|Lys|Thr|Gln|Gly|Arg|Asp|Met|Leu|Asn|Tyr|Ala|Arg|Lys|Ala|Trp|Glu|
|385| | | | |390| | | | |395| | | | |400|
|Ala|Leu|Phe|Asp|Ala|Phe|Leu|Glu|Glu|Ala|Lys|Trp|Ile|Ser|Ser|Gly|
| | | | |405| | | | |410| | | | |415| |

```
Tyr Leu Pro Thr Phe Glu Glu Tyr Leu Glu Asn Gly Lys Val Ser Phe
            420                 425                 430

Gly Tyr Arg Ala Ala Thr Leu Gln Pro Ile Leu Thr Leu Asp Ile Pro
        435                 440                 445

Leu Pro Leu His Ile Leu Gln Gln Ile Asp Phe Pro Ser Arg Phe Asn
    450                 455                 460

Asp Leu Ala Ser Ser Ile Leu Arg Leu Arg Gly Asp Ile Cys Gly Tyr
465                 470                 475                 480

Gln Ala Glu Arg Ser Arg Gly Glu Glu Ala Ser Ile Ser Cys Tyr
                485                 490                 495

Met Lys Asp Asn Pro Gly Ser Thr Glu Glu Asp Ala Leu Ser His Ile
                500                 505                 510

Asn Ala Met Ile Ser Asp Asn Ile Asn Glu Leu Asn Trp Glu Leu Leu
        515                 520                 525

Lys Pro Asn Ser Asn Val Pro Ile Ser Ser Lys His Ala Phe Asp
    530                 535                 540

Ile Leu Arg Ala Phe Tyr His Leu Tyr Lys Tyr Arg Asp Gly Phe Ser
545                 550                 555                 560

Ile Ala Lys Ile Glu Thr Lys Asn Leu Val Met Arg Thr Val Leu Glu
                565                 570                 575

Pro Val Pro Met
            580

<210> SEQ ID NO 20
<211> LENGTH: 628
<212> TYPE: PRT
<213> ORGANISM: Aggpin1

<400> SEQUENCE: 20

Met Ala Leu Val Ser Thr Ala Pro Leu Ala Ser Lys Ser Cys Leu His
 1               5                  10                  15

Lys Ser Leu Ile Ser Ser Thr His Glu Leu Lys Ala Leu Ser Arg Thr
            20                  25                  30

Ile Pro Ala Leu Gly Met Ser Arg Arg Gly Lys Ser Ile Thr Pro Ser
        35                  40                  45

Ile Ser Met Ser Ser Thr Thr Val Val Thr Asp Gly Val Arg Arg
 50                  55                  60

Arg Met Gly Asp Phe His Ser Asn Leu Trp Asp Asp Val Ile Gln
65                  70                  75                  80

Ser Leu Pro Thr Ala Tyr Glu Glu Lys Ser Tyr Leu Glu Arg Ala Glu
                85                  90                  95

Lys Leu Ile Gly Glu Val Lys Asn Met Phe Asn Ser Met Ser Leu Glu
            100                 105                 110

Asp Gly Glu Leu Met Ser Pro Leu Asn Asp Leu Ile Gln Arg Leu Trp
        115                 120                 125

Ile Val Asp Ser Leu Glu Arg Leu Gly Ile His Arg His Phe Lys Asp
    130                 135                 140

Glu Ile Lys Ser Ala Leu Asp Tyr Val Tyr Ser Tyr Trp Gly Glu Asn
145                 150                 155                 160

Gly Ile Gly Cys Gly Arg Glu Ser Val Val Thr Asp Leu Asn Ser Thr
                165                 170                 175

Ala Leu Gly Leu Arg Thr Leu Arg Leu His Gly Tyr Pro Val Ser Ser
            180                 185                 190

Asp Val Phe Lys Ala Phe Lys Gly Gln Asn Gly Gln Phe Ser Cys Ser
        195                 200                 205
```

-continued

Glu Asn Ile Gln Thr Asp Glu Glu Ile Arg Gly Val Leu Asn Leu Phe
      210                 215                 220

Arg Ala Ser Leu Ile Ala Phe Pro Gly Glu Lys Ile Met Asp Glu Ala
225                 230                 235                 240

Glu Ile Phe Ser Thr Lys Tyr Leu Lys Glu Ala Leu Gln Lys Ile Pro
                245                 250                 255

Val Ser Ser Leu Ser Arg Glu Ile Gly Asp Val Leu Glu Tyr Gly Trp
                260                 265                 270

His Thr Tyr Leu Pro Arg Leu Glu Ala Arg Asn Tyr Ile Gln Val Phe
            275                 280                 285

Gly Gln Asp Thr Glu Asn Thr Lys Ser Tyr Val Lys Ser Lys Lys Leu
290                 295                 300

Leu Glu Leu Ala Lys Leu Glu Phe Asn Ile Phe Gln Ser Leu Gln Lys
305                 310                 315                 320

Arg Glu Leu Glu Ser Leu Val Arg Trp Trp Lys Glu Ser Gly Phe Pro
                325                 330                 335

Glu Met Thr Phe Cys Arg His Arg His Val Glu Tyr Tyr Thr Leu Ala
                340                 345                 350

Ser Cys Ile Ala Phe Glu Pro Gln His Ser Gly Phe Arg Leu Gly Phe
            355                 360                 365

Ala Lys Thr Cys His Leu Ile Thr Val Leu Asp Asp Met Tyr Asp Thr
370                 375                 380

Phe Gly Thr Val Asp Glu Leu Glu Leu Phe Thr Ala Thr Met Lys Arg
385                 390                 395                 400

Trp Asp Pro Ser Ser Ile Asp Cys Leu Pro Glu Tyr Met Lys Gly Val
                405                 410                 415

Tyr Ile Ala Val Tyr Asp Thr Val Asn Glu Met Ala Arg Glu Ala Glu
                420                 425                 430

Glu Ala Gln Gly Arg Asp Thr Leu Thr Tyr Ala Arg Glu Ala Trp Glu
            435                 440                 445

Ala Tyr Ile Asp Ser Tyr Met Gln Glu Ala Arg Trp Ile Ala Thr Gly
450                 455                 460

Tyr Leu Pro Ser Phe Asp Glu Tyr Tyr Glu Asn Gly Lys Val Ser Cys
465                 470                 475                 480

Gly His Arg Ile Ser Ala Leu Gln Pro Ile Leu Thr Met Asp Ile Pro
                485                 490                 495

Phe Pro Asp His Ile Leu Lys Glu Val Asp Phe Pro Ser Lys Leu Asn
                500                 505                 510

Asp Leu Ala Cys Ala Ile Leu Arg Leu Arg Gly Asp Thr Arg Cys Tyr
            515                 520                 525

Lys Ala Asp Arg Ala Arg Gly Glu Glu Ala Ser Ser Ile Ser Cys Tyr
530                 535                 540

Met Lys Asp Asn Pro Gly Val Ser Glu Glu Asp Ala Leu Asp His Ile
545                 550                 555                 560

Asn Ala Met Ile Ser Asp Val Ile Lys Gly Leu Asn Trp Glu Leu Leu
                565                 570                 575

Lys Pro Asp Ile Asn Val Pro Ile Ser Ala Lys Lys His Ala Phe Asp
                580                 585                 590

Ile Ala Arg Ala Phe His Tyr Gly Tyr Lys Tyr Arg Asp Gly Tyr Ser
            595                 600                 605

Val Ala Asn Val Glu Thr Lys Ser Leu Val Thr Arg Thr Leu Leu Glu
610                 615                 620

Ser Val Pro Leu
625

<210> SEQ ID NO 21
<211> LENGTH: 628
<212> TYPE: PRT
<213> ORGANISM: Pinus taeda

<400> SEQUENCE: 21

```
Met Ala Leu Val Ser Ala Val Pro Leu Asn Ser Lys Leu Cys Leu Arg
 1               5                  10                  15
Arg Thr Leu Phe Gly Phe Ser His Glu Leu Lys Ala Ile His Ser Thr
            20                  25                  30
Val Pro Asn Leu Gly Met Cys Arg Gly Lys Ser Ile Ala Pro Ser
        35                  40                  45
Met Ser Met Ser Ser Thr Thr Ser Val Ser Asn Glu Asp Gly Val Pro
 50                  55                  60
Arg Arg Ile Ala Gly His His Ser Asn Leu Trp Asp Asp Ser Ile
 65                  70                  75                  80
Ala Ser Leu Ser Thr Ser Tyr Glu Ala Pro Ser Tyr Arg Lys Arg Ala
                85                  90                  95
Asp Lys Leu Ile Gly Glu Val Lys Asn Ile Phe Asp Leu Met Ser Val
            100                 105                 110
Glu Asp Gly Val Phe Thr Ser Pro Leu Ser Asp Leu His His Arg Leu
        115                 120                 125
Trp Met Val Asp Ser Val Glu Arg Leu Gly Ile Asp Arg His Phe Lys
130                 135                 140
Asp Glu Ile Asn Ser Ala Leu Asp His Val Tyr Ser Tyr Trp Thr Glu
145                 150                 155                 160
Lys Gly Ile Gly Arg Gly Arg Glu Ser Gly Val Thr Asp Leu Asn Ser
                165                 170                 175
Thr Ala Leu Gly Leu Arg Thr Leu Arg Leu His Gly Tyr Thr Val Ser
            180                 185                 190
Ser His Val Leu Asp His Phe Lys Asn Glu Lys Gly Gln Phe Thr Cys
        195                 200                 205
Ser Ala Ile Gln Thr Glu Gly Glu Ile Arg Asp Val Leu Asn Leu Phe
    210                 215                 220
Arg Ala Ser Leu Ile Ala Phe Pro Gly Glu Lys Ile Met Glu Ala Ala
225                 230                 235                 240
Glu Ile Phe Ser Thr Met Tyr Leu Lys Asp Ala Leu Gln Lys Ile Pro
                245                 250                 255
Pro Ser Gly Leu Ser Gln Glu Ile Glu Tyr Leu Leu Glu Phe Gly Trp
            260                 265                 270
His Thr Asn Leu Pro Arg Met Glu Thr Arg Met Tyr Ile Asp Val Phe
        275                 280                 285
Gly Glu Asp Thr Thr Phe Glu Thr Pro Tyr Leu Ile Arg Glu Lys Leu
    290                 295                 300
Leu Glu Leu Ala Lys Leu Glu Phe Asn Ile Phe His Ser Leu Val Lys
305                 310                 315                 320
Arg Glu Leu Gln Ser Leu Ser Arg Trp Trp Lys Asp Tyr Gly Phe Pro
                325                 330                 335
Glu Ile Thr Phe Ser Arg His Arg His Val Glu Tyr Tyr Thr Leu Ala
            340                 345                 350
Ala Cys Ile Ala Asn Asp Pro Lys His Ser Ala Phe Arg Leu Gly Phe
        355                 360                 365
Gly Lys Ile Ser His Met Ile Thr Ile Leu Asp Asp Ile Tyr Asp Thr
    370                 375                 380
```

```
Phe Gly Thr Met Glu Glu Leu Lys Leu Leu Thr Ala Ala Phe Lys Arg
385                 390                 395                 400

Trp Asp Pro Ser Ser Ile Glu Cys Leu Pro Asp Tyr Met Lys Gly Val
                405                 410                 415

Tyr Met Ala Val Tyr Asp Asn Ile Asn Glu Met Ala Arg Glu Ala Gln
            420                 425                 430

Lys Ile Gln Gly Trp Asp Thr Val Ser Tyr Ala Arg Lys Ser Trp Glu
        435                 440                 445

Ala Phe Ile Gly Ala Tyr Ile Gln Glu Ala Lys Trp Ile Ser Ser Gly
    450                 455                 460

Tyr Leu Pro Thr Phe Asp Glu Tyr Leu Glu Asn Gly Lys Val Ser Phe
465                 470                 475                 480

Gly Ser Arg Ile Thr Thr Leu Glu Pro Met Leu Thr Leu Gly Phe Pro
                485                 490                 495

Leu Pro Pro Arg Ile Leu Gln Glu Ile Asp Phe Pro Ser Lys Phe Asn
            500                 505                 510

Asp Leu Ile Cys Ala Ile Leu Arg Leu Lys Gly Asp Thr Gln Cys Tyr
        515                 520                 525

Lys Ala Asp Arg Ala Arg Gly Glu Glu Ala Ser Ala Val Ser Cys Tyr
    530                 535                 540

Met Lys Asp His Pro Gly Ile Thr Glu Glu Asp Ala Val Asn Gln Val
545                 550                 555                 560

Asn Ala Met Val Asp Asn Leu Thr Lys Glu Leu Asn Trp Glu Leu Leu
                565                 570                 575

Arg Pro Asp Ser Gly Val Pro Ile Ser Tyr Lys Lys Val Ala Phe Asp
            580                 585                 590

Ile Cys Arg Val Phe His Tyr Gly Tyr Lys Tyr Arg Asp Gly Phe Ser
        595                 600                 605

Val Ala Ser Ile Glu Ile Lys Asn Leu Val Thr Arg Thr Val Val Glu
    610                 615                 620

Thr Val Pro Leu
625

<210> SEQ ID NO 22
<211> LENGTH: 623
<212> TYPE: PRT
<213> ORGANISM: Abies grandis

<400> SEQUENCE: 22

Thr Ala Pro Leu Ala Ser Lys Ser Cys Leu His Lys Ser Leu Ile Ser
  1               5                  10                  15

Ser Thr His Glu Leu Lys Ala Leu Ser Arg Thr Ile Pro Ala Leu Gly
             20                  25                  30

Met Ser Arg Arg Gly Lys Ser Ile Thr Pro Ser Ile Ser Met Ser Ser
         35                  40                  45

Thr Thr Val Val Thr Asp Asp Gly Val Arg Arg Met Gly Asp Phe
     50                  55                  60

His Ser Asn Leu Trp Asp Asp Val Ile Gln Ser Leu Pro Thr Ala
 65                  70                  75                  80

Tyr Glu Glu Lys Ser Tyr Leu Glu Arg Ala Glu Lys Leu Ile Gly Glu
                 85                  90                  95

Val Glu Asn Met Phe Asn Ser Met Ser Leu Glu Asp Gly Glu Leu Met
            100                 105                 110

Ser Pro Leu Asn Asp Leu Ile Gln Arg Leu Trp Ile Val Asp Ser Leu
        115                 120                 125
```

```
Gly Arg Leu Gly Ile His Arg His Phe Lys Asp Glu Ile Lys Ser Ala
    130                 135                 140

Leu Asp Tyr Val Tyr Ser Tyr Trp Gly Glu Asn Gly Ile Gly Cys Gly
145                 150                 155                 160

Arg Glu Ser Ala Val Thr Asp Leu Asn Ser Thr Ala Leu Gly Phe Arg
                165                 170                 175

Thr Leu Arg Leu His Gly Tyr Pro Val Ser Ser Asp Val Phe Lys Ala
            180                 185                 190

Phe Lys Gly Gln Asn Gly Gln Phe Ser Cys Ser Glu Asn Ile Gln Thr
        195                 200                 205

Asp Glu Glu Ile Arg Gly Val Leu Asn Leu Phe Arg Ala Ser Leu Ile
    210                 215                 220

Ala Phe Pro Gly Glu Lys Ile Met Asp Glu Ala Glu Ile Phe Ser Thr
225                 230                 235                 240

Lys Tyr Leu Lys Glu Ala Leu Gln Lys Ile Pro Val Ser Ser Leu Ser
                245                 250                 255

Arg Glu Ile Gly Asp Val Leu Glu Tyr Gly Trp His Thr Tyr Leu Pro
            260                 265                 270

Arg Leu Glu Ala Arg Asn Tyr Ile His Val Phe Gly Gln Asp Thr Glu
        275                 280                 285

Asn Thr Lys Ser Tyr Val Lys Ser Lys Leu Leu Glu Leu Ala Lys
    290                 295                 300

Leu Glu Phe Asn Ile Phe Gln Ser Leu Gln Lys Arg Glu Leu Glu Ser
305                 310                 315                 320

Leu Val Arg Trp Trp Lys Glu Ser Gly Phe Pro Glu Met Thr Phe Cys
                325                 330                 335

Arg His Arg His Val Glu Tyr Tyr Thr Leu Ala Ser Cys Ile Ala Phe
            340                 345                 350

Glu Pro Gln His Ser Gly Phe Arg Leu Gly Phe Ala Lys Thr Cys His
        355                 360                 365

Leu Ile Thr Val Leu Asp Asp Met Tyr Asp Thr Phe Gly Thr Val Asp
    370                 375                 380

Glu Leu Glu Leu Phe Thr Ala Thr Met Lys Arg Trp Asp Pro Ser Ser
385                 390                 395                 400

Ile Asp Cys Leu Pro Glu Tyr Met Lys Gly Val Tyr Ile Ala Val Tyr
                405                 410                 415

Asp Thr Val Asn Glu Met Ala Arg Glu Ala Glu Glu Ala Gln Gly Arg
            420                 425                 430

Asp Thr Leu Thr Tyr Ala Arg Glu Ala Trp Glu Ala Tyr Ile Asp Ser
        435                 440                 445

Tyr Met Gln Glu Ala Arg Trp Ile Ala Thr Gly Tyr Leu Pro Ser Phe
    450                 455                 460

Asp Glu Tyr Tyr Glu Asn Gly Lys Val Ser Cys Gly His Arg Ile Ser
465                 470                 475                 480

Ala Leu Gln Pro Ile Leu Thr Met Asp Ile Pro Phe Pro Asp His Ile
                485                 490                 495

Leu Lys Glu Val Asp Phe Pro Ser Lys Leu Asn Asp Leu Ala Cys Ala
            500                 505                 510

Ile Leu Arg Leu Arg Gly Asp Thr Arg Cys Tyr Lys Ala Asp Arg Ala
        515                 520                 525

Arg Gly Glu Glu Ala Ser Ser Ile Ser Cys Tyr Met Lys Asp Asn Pro
    530                 535                 540

Gly Val Ser Glu Glu Asp Ala Leu Asp His Ile Asn Ala Met Ile Ser
```

```
                545                 550                 555                 560
Asp Val Ile Lys Gly Leu Asn Trp Glu Leu Leu Lys Pro Asp Ile Asn
                565                 570                 575
Val Pro Ile Ser Ala Lys Lys His Ala Phe Asp Ile Ala Arg Ala Phe
                580                 585                 590
His Tyr Gly Tyr Lys Tyr Arg Asp Gly Tyr Ser Val Ala Asn Val Glu
                595                 600                 605
Thr Lys Ser Leu Val Thr Arg Thr Leu Leu Glu Ser Val Pro Leu
                610                 615                 620

<210> SEQ ID NO 23
<211> LENGTH: 637
<212> TYPE: PRT
<213> ORGANISM: Abies grandis

<400> SEQUENCE: 23

Met Ala Leu Leu Ser Ile Val Ser Leu Gln Val Pro Lys Ser Cys Gly
  1               5                  10                  15
Gln Lys Ser Leu Ile Ser Ser Ser Asn Val Gln Lys Ala Leu Cys Ile
                 20                  25                  30
Ser Thr Ala Val Pro Thr Leu Arg Met Arg Arg Gln Lys Ala Leu
             35                  40                  45
Val Ile Asn Met Lys Leu Thr Thr Val Ser His Arg Asp Asp Asn Asp
 50                  55                  60
Gly Gly Val Leu Gln Arg Arg Ile Ala Asp His His Pro Asn Leu Trp
 65                  70                  75                  80
Glu Asp Asp Phe Ile Gln Ser Leu Ser Ser Pro Tyr Gly Gly Ser Ser
                 85                  90                  95
Tyr Ser Glu Arg Ala Glu Thr Leu Val Glu Val Lys Glu Met Phe
                100                 105                 110
Asn Ser Ile Pro Asn Asn Arg Glu Leu Phe Gly Ser Gln Asn Asp Leu
                115                 120                 125
Leu Thr Arg Leu Trp Met Val Asp Ser Ile Glu Arg Leu Gly Ile Asp
            130                 135                 140
Arg His Phe Gln Asn Glu Ile Arg Val Ala Leu Asp Tyr Val Tyr Ser
145                 150                 155                 160
Tyr Trp Lys Glu Lys Glu Gly Ile Gly Cys Gly Arg Asp Ser Thr Phe
                165                 170                 175
Pro Asp Leu Asn Ser Thr Ala Leu Ala Leu Arg Thr Leu Arg Leu His
            180                 185                 190
Gly Tyr Asn Val Ser Ser Asp Val Leu Glu Tyr Phe Lys Asp Gln Lys
            195                 200                 205
Gly His Phe Ala Cys Pro Ala Ile Leu Thr Glu Gly Gln Ile Thr Arg
        210                 215                 220
Ser Val Leu Asn Leu Tyr Arg Ala Ser Leu Val Ala Phe Pro Gly Glu
225                 230                 235                 240
Lys Val Met Glu Glu Ala Glu Ile Phe Ser Ala Ser Tyr Leu Lys Glu
                245                 250                 255
Val Leu Gln Lys Ile Pro Val Ser Asn Leu Ser Gly Glu Ile Glu Tyr
            260                 265                 270
Val Leu Glu Tyr Gly Trp His Thr Asn Leu Pro Arg Leu Glu Ala Arg
            275                 280                 285
Asn Tyr Ile Glu Val Tyr Glu Gln Ser Gly Tyr Glu Ser Leu Asn Glu
        290                 295                 300
Met Pro Tyr Met Asn Met Lys Lys Leu Leu Gln Leu Ala Lys Leu Glu
```

```
                305                 310                 315                 320
Phe Asn Ile Phe His Ser Leu Gln Leu Arg Glu Leu Gln Ser Ile Ser
                    325                 330                 335

Arg Trp Trp Lys Glu Ser Gly Ser Ser Gln Leu Thr Phe Thr Arg His
                340                 345                 350

Arg His Val Glu Tyr Tyr Thr Met Ala Ser Cys Ile Ser Met Glu Pro
            355                 360                 365

Lys His Ser Ala Phe Arg Met Glu Phe Val Lys Val Cys His Leu Val
        370                 375                 380

Thr Val Leu Asp Asp Ile Tyr Asp Thr Phe Gly Thr Met Asn Glu Leu
385                 390                 395                 400

Gln Leu Phe Thr Asp Ala Ile Lys Arg Trp Asp Leu Ser Thr Thr Arg
                405                 410                 415

Trp Leu Pro Glu Tyr Met Lys Gly Val Tyr Met Asp Leu Tyr Gln Cys
                420                 425                 430

Ile Asn Glu Met Val Glu Ala Gln Lys Thr Gln Gly Arg Asp Met
            435                 440                 445

Leu Asn Tyr Ile Gln Asn Gly Trp Glu Ala Leu Phe Asp Thr Phe Ile
        450                 455                 460

Gln Glu Ala Lys Trp Ile Ser Ser Tyr Leu Pro Thr Phe Glu Glu
465                 470                 475                 480

Tyr Leu Lys Asn Ala Lys Val Ser Ser Gly Ser Arg Ile Ala Thr Leu
                485                 490                 495

Gln Pro Ile Leu Thr Leu Asp Val Pro Leu Pro Asp Tyr Ile Leu Gln
                500                 505                 510

Glu Ile Asp Tyr Pro Ser Arg Phe Asn Glu Leu Ala Ser Ser Ile Leu
            515                 520                 525

Arg Leu Arg Gly Asp Thr Arg Cys Tyr Lys Ala Asp Arg Ala Arg Gly
        530                 535                 540

Glu Glu Ala Ser Ala Ile Ser Cys Tyr Met Lys Asp His Pro Gly Ser
545                 550                 555                 560

Thr Glu Glu Asp Ala Leu Asn His Ile Asn Ala Met Ile Ser Asp Ala
                565                 570                 575

Ile Arg Glu Leu Asn Trp Glu Leu Leu Arg Pro Asp Ser Lys Ser Pro
                580                 585                 590

Ile Ser Ser Lys Lys His Ala Phe Asp Ile Thr Arg Ala Phe His His
            595                 600                 605

Val Tyr Lys Tyr Arg Asp Gly Tyr Thr Val Ser Asn Asn Glu Thr Lys
        610                 615                 620

Asn Leu Val Met Lys Thr Val Leu Glu Pro Leu Ala Leu
625                 630                 635

<210> SEQ ID NO 24
<211> LENGTH: 619
<212> TYPE: PRT
<213> ORGANISM: Pseudotsuga menziesii

<400> SEQUENCE: 24

Met Ser Ser Ile Phe His Glu His Lys Pro Leu Arg Lys Thr Ile Pro
1               5                   10                  15

Thr Leu Ile Gly Lys Cys Ser Ser Ser Arg Arg Ser Val Thr Pro
                20                  25                  30

Ala Ser Ile Thr Ser Met Thr Met Glu Thr Ala Val Ser Asp Asp Gly
            35                  40                  45

Val Gln Arg Arg Val Gly Asn Tyr His Ser Asn Leu Trp Asp Asp Asp
```

```
              50                  55                  60
Phe Ile Asn Ser Leu Ile Ser Thr Pro Tyr Glu Ala Pro Ser Tyr Arg
 65                  70                  75                  80

Glu Arg Gly Glu Thr Leu Ile Gly Val Lys Glu Ile Phe Asn Ser
                 85                  90                  95

Ile Ser Val Glu Asp Ala Gly Glu Leu Ile Thr Pro Leu Asn Asp Leu
                100                 105                 110

Ile Gln Arg Leu Trp Met Val Asp Ser Val Arg Leu Gly Ile Asp
                115                 120                 125

Arg His Phe Lys Asp Glu Ile Lys Ser Ala Leu Asp Tyr Val Tyr Ser
130                 135                 140

His Trp Arg Glu Glu Gly Ile Gly Cys Gly Arg Glu Ser Val Ala Thr
145                 150                 155                 160

Asp Leu Asn Ser Thr Ala Leu Gly Leu Arg Thr Leu Arg Leu His Gly
                165                 170                 175

Tyr Pro Val Ser Ser Asp Val Leu Glu His Phe Lys Asp Gln Lys Gly
                180                 185                 190

His Phe Ala Ser Cys Ser Ser Ser Ile Glu Thr Gly Gly Glu Ile
                195                 200                 205

Arg Ser Val Leu Asn Leu Phe Arg Ala Ser Leu Ile Ala Phe Pro Asn
210                 215                 220

Glu Lys Val Met Asp Glu Ala Gln Ile Phe Ser Thr Thr Tyr Leu Lys
225                 230                 235                 240

Glu Ala Val Gln Lys Ile Pro Val Ser Ser Leu Ser Arg Gln Ile Glu
                245                 250                 255

Tyr Val Met Glu Tyr Gly Trp Asp Thr Asn Leu Pro Arg Leu Glu Ala
                260                 265                 270

Arg His Tyr Ile His Val Leu Gly Gln Asp Ile Thr Tyr Asn Asp Asn
                275                 280                 285

Glu Met Pro Tyr Thr Asn Val Glu Lys Leu Leu Glu Leu Ala Lys Leu
                290                 295                 300

Glu Phe Asn Met Phe His Ser Leu Gln Gln Arg Glu Leu Lys His Leu
305                 310                 315                 320

Ser Arg Trp Trp Lys Asp Ser Gly Met Pro Glu Ala Thr Phe Thr Arg
                325                 330                 335

His Arg His Val Glu Tyr Tyr Ala Leu Ala Ser Cys Ile Ala Phe Glu
                340                 345                 350

Pro Gln His Ser Gly Phe Arg Phe Gly Phe Ala Lys Leu Cys His Ile
                355                 360                 365

Ile Thr Val Leu Asp Asp Met Tyr Asp Leu Phe Gly Thr Ile Asp Glu
                370                 375                 380

Leu Glu Leu Phe Thr Ala Ala Ile Lys Arg Trp Asp Pro Ser Ala Thr
385                 390                 395                 400

Asp Cys Leu Pro Glu Tyr Met Lys Gly Val Tyr Thr Met Val Tyr Asp
                405                 410                 415

Thr Ile Asn Glu Met Ala Gly Glu Ala Gln Asn Ala Gln Gly Arg Asp
                420                 425                 430

Thr Leu Asn Tyr Ala Arg Glu Ala Trp Glu Ala Cys Leu Asp Ser Tyr
                435                 440                 445

Leu Gln Glu Ala Lys Trp Ile Ala Thr Gly Tyr Leu Pro Ser Phe Glu
                450                 455                 460

Glu Tyr Tyr Glu Asn Gly Lys Val Ser Ser Ala His Arg Val Cys Thr
465                 470                 475                 480
```

```
Leu Gln Pro Ile Leu Thr Leu Asp Ile Pro Phe Pro Asp His Ile Leu
                485                 490                 495

Lys Glu Val Asp Phe Pro Ser Lys Leu Asn Asp Leu Ala Cys Ala Val
            500                 505                 510

Leu Arg Leu Arg Gly Asp Thr Arg Cys Tyr Gln Ala Asp Arg Ala Arg
        515                 520                 525

Gly Glu Glu Ala Ser Ser Ile Ser Cys Tyr Met Lys Asp Asn Pro Gly
    530                 535                 540

Ser Thr Glu Glu Asp Ala Leu Asn His Ile Asn Ala Met Leu Ser Asp
545                 550                 555                 560

Val Ile Lys Glu Leu Asn Trp Glu Leu Leu Lys Pro Asp Ser Val Pro
                565                 570                 575

Ile Ser Ala Lys Lys His Ala Tyr Asp Val Ser Arg Ala Phe His Tyr
            580                 585                 590

Gly Tyr Lys Tyr Arg Asp Gly Tyr Ser Val Ala Asn Ile Glu Ile Lys
        595                 600                 605

Asn Phe Val Ala Ile Ser Val Leu Glu Pro Val
    610                 615

<210> SEQ ID NO 25
<211> LENGTH: 637
<212> TYPE: PRT
<213> ORGANISM: Abies grandis

<400> SEQUENCE: 25

Met Ala Leu Leu Ser Ile Val Ser Leu Gln Val Pro Lys Ser Cys Gly
  1               5                  10                  15

Leu Lys Ser Leu Ile Ser Ser Asn Val Gln Lys Ala Leu Cys Ile
                 20                  25                  30

Ser Thr Ala Val Pro Thr Leu Arg Met Arg Arg Arg Gln Lys Ala Leu
             35                  40                  45

Val Ile Asn Met Lys Leu Thr Thr Val Ser His Arg Asp Asp Asn Gly
         50                  55                  60

Gly Gly Val Leu Gln Arg Arg Ile Ala Asp His His Pro Asn Leu Trp
65                  70                  75                  80

Glu Asp Asp Phe Ile Gln Ser Leu Ser Ser Pro Tyr Gly Gly Ser Ser
                 85                  90                  95

Tyr Ser Glu Arg Ala Glu Thr Val Val Glu Glu Val Lys Glu Met Phe
            100                 105                 110

Asn Ser Ile Pro Asn Asn Arg Glu Leu Phe Gly Ser Gln Asn Asp Leu
        115                 120                 125

Leu Thr Arg Leu Trp Met Val Asp Ser Ile Glu Arg Leu Gly Ile Asp
    130                 135                 140

Arg His Phe Gln Asn Glu Ile Arg Val Ala Leu Asp Tyr Val Tyr Ser
145                 150                 155                 160

Tyr Trp Lys Glu Lys Glu Gly Ile Gly Cys Gly Arg Asp Ser Thr Phe
                165                 170                 175

Pro Asp Leu Asn Ser Thr Ala Leu Ala Leu Arg Thr Leu Arg Leu His
            180                 185                 190

Gly Tyr Asn Val Ser Ser Asp Val Leu Glu Tyr Phe Lys Asp Glu Lys
        195                 200                 205

Gly His Phe Ala Cys Pro Ala Ile Leu Thr Glu Gly Gln Ile Thr Arg
    210                 215                 220

Ser Val Leu Asn Leu Tyr Arg Ala Ser Leu Val Ala Phe Pro Gly Glu
225                 230                 235                 240
```

```
Lys Val Met Glu Glu Ala Glu Ile Phe Ser Ala Ser Tyr Leu Lys Lys
                245                 250                 255

Val Leu Gln Lys Ile Pro Val Ser Asn Leu Ser Gly Glu Ile Glu Tyr
            260                 265                 270

Val Leu Glu Tyr Gly Trp His Thr Asn Leu Pro Arg Leu Glu Ala Arg
        275                 280                 285

Asn Tyr Ile Glu Val Tyr Glu Gln Ser Gly Tyr Glu Ser Leu Asn Glu
    290                 295                 300

Met Pro Tyr Met Asn Met Lys Lys Leu Leu Gln Leu Ala Lys Leu Glu
305                 310                 315                 320

Phe Asn Ile Phe His Ser Leu Gln Leu Arg Glu Leu Gln Ser Ile Ser
                325                 330                 335

Arg Trp Trp Lys Glu Ser Gly Ser Ser Gln Leu Thr Phe Thr Arg His
            340                 345                 350

Arg His Val Glu Tyr Tyr Thr Met Ala Ser Cys Ile Ser Met Leu Pro
        355                 360                 365

Lys His Ser Ala Phe Arg Met Glu Phe Val Lys Val Cys His Leu Val
    370                 375                 380

Thr Val Leu Asp Asp Ile Tyr Asp Thr Phe Gly Thr Met Asn Glu Leu
385                 390                 395                 400

Gln Leu Phe Thr Asp Ala Ile Lys Arg Trp Asp Leu Ser Thr Thr Arg
                405                 410                 415

Trp Leu Pro Glu Tyr Met Lys Gly Val Tyr Met Asp Leu Tyr Gln Cys
            420                 425                 430

Ile Asn Glu Met Val Glu Glu Ala Glu Lys Thr Gln Gly Arg Asp Met
        435                 440                 445

Leu Asn Tyr Ile Gln Asn Ala Trp Glu Ala Leu Phe Asp Thr Phe Met
    450                 455                 460

Gln Glu Ala Lys Trp Ile Ser Ser Ser Tyr Leu Pro Thr Phe Glu Glu
465                 470                 475                 480

Tyr Leu Lys Asn Ala Lys Val Ser Ser Gly Ser Arg Ile Ala Thr Leu
                485                 490                 495

Gln Pro Ile Leu Thr Leu Asp Val Pro Leu Pro Asp Tyr Ile Leu Gln
            500                 505                 510

Glu Ile Asp Tyr Pro Ser Arg Phe Asn Glu Leu Ala Ser Ser Ile Leu
        515                 520                 525

Arg Leu Arg Gly Asp Thr Arg Cys Tyr Lys Ala Asp Arg Ala Arg Gly
    530                 535                 540

Glu Glu Ala Ser Ala Ile Ser Cys Tyr Met Lys Asp His Pro Gly Ser
545                 550                 555                 560

Ile Glu Glu Asp Ala Leu Asn His Ile Asn Ala Met Ile Ser Asp Ala
                565                 570                 575

Ile Arg Glu Leu Asn Trp Glu Leu Leu Arg Pro Asp Ser Lys Ser Pro
            580                 585                 590

Ile Ser Ser Lys Lys His Ala Phe Asp Ile Thr Arg Ala Phe His His
        595                 600                 605

Val Tyr Lys Tyr Arg Asp Gly Tyr Thr Val Ser Asn Asn Glu Thr Lys
    610                 615                 620

Asn Leu Val Met Lys Thr Val Leu Glu Pro Leu Ala Leu
625                 630                 635

<210> SEQ ID NO 26
<211> LENGTH: 637
<212> TYPE: PRT
<213> ORGANISM: Abies grandis
```

<400> SEQUENCE: 26

```
Met Ala Leu Leu Ser Ile Val Ser Leu Gln Val Pro Lys Ser Cys Gly
1               5                   10                  15
Leu Lys Ser Leu Ile Ser Ser Ser Asn Val Gln Lys Ala Leu Cys Ile
            20                  25                  30
Ser Thr Ala Val Pro Thr Leu Arg Met Arg Arg Gln Lys Ala Leu
        35                  40                  45
Val Ile Asn Met Lys Leu Thr Thr Val Ser His Arg Asp Asp Asn Gly
50                  55                  60
Gly Gly Val Leu Gln Arg Arg Ile Ala Asp His His Pro Asn Leu Trp
65                  70                  75                  80
Glu Asp Asp Phe Ile Gln Ser Leu Ser Ser Pro Tyr Gly Gly Ser Ser
                85                  90                  95
Tyr Ser Glu Arg Ala Val Thr Val Val Glu Glu Val Lys Glu Met Phe
            100                 105                 110
Asn Ser Ile Pro Asn Asn Arg Glu Leu Phe Gly Ser Gln Asn Asp Leu
        115                 120                 125
Leu Thr Arg Leu Trp Met Val Asp Ser Ile Glu Arg Leu Gly Ile Asp
130                 135                 140
Arg His Phe Gln Asn Glu Ile Arg Val Ala Leu Asp Tyr Val Tyr Ser
145                 150                 155                 160
Tyr Trp Lys Glu Lys Glu Gly Ile Gly Cys Gly Arg Asp Ser Thr Phe
                165                 170                 175
Pro Asp Leu Asn Ser Thr Ala Leu Ala Leu Arg Thr Leu Arg Leu His
            180                 185                 190
Gly Tyr Asn Val Ser Ser Asp Val Leu Glu Tyr Phe Lys Asp Gln Lys
        195                 200                 205
Gly His Phe Ala Cys Pro Ala Ile Leu Thr Glu Gly Gln Ile Thr Arg
210                 215                 220
Ser Val Leu Asn Leu Tyr Arg Ala Ser Leu Val Ala Phe Pro Gly Glu
225                 230                 235                 240
Lys Val Met Glu Glu Ala Glu Ile Phe Ser Ala Ser Tyr Leu Lys Glu
                245                 250                 255
Val Leu Gln Lys Ile Pro Val Ser Ser Phe Ser Arg Glu Ile Glu Tyr
            260                 265                 270
Val Leu Glu Tyr Gly Trp His Thr Asn Leu Pro Arg Leu Glu Ala Arg
        275                 280                 285
Asn Tyr Ile Asp Val Tyr Gly Gln Asp Ser Tyr Glu Ser Ser Asn Glu
290                 295                 300
Met Pro Tyr Val Asn Thr Gln Lys Leu Leu Lys Leu Ala Lys Leu Glu
305                 310                 315                 320
Phe Asn Ile Phe His Ser Leu Gln Gln Lys Glu Leu Gln Tyr Ile Ser
                325                 330                 335
Arg Trp Trp Lys Asp Ser Cys Ser Ser His Leu Thr Phe Thr Arg His
            340                 345                 350
Arg His Val Glu Tyr Tyr Thr Met Ala Ser Cys Ile Ser Met Glu Pro
        355                 360                 365
Lys His Ser Ala Phe Arg Leu Gly Phe Val Lys Thr Cys His Leu Leu
370                 375                 380
Thr Val Leu Asp Asp Met Tyr Asp Thr Phe Gly Thr Leu Asp Glu Leu
385                 390                 395                 400
Gln Leu Phe Thr Thr Ala Phe Lys Arg Trp Asp Leu Ser Glu Thr Lys
                405                 410                 415
```

```
Cys Leu Pro Glu Tyr Met Lys Ala Val Tyr Met Asp Leu Tyr Gln Cys
            420                 425                 430

Leu Asn Glu Leu Ala Gln Ala Glu Lys Thr Gln Gly Arg Asp Thr
        435                 440                 445

Leu Asn Tyr Ile Arg Asn Ala Tyr Glu Ser His Phe Asp Ser Phe Met
450                 455                 460

His Glu Ala Lys Trp Ile Ser Ser Gly Tyr Leu Pro Thr Phe Glu Glu
465                 470                 475                 480

Tyr Leu Lys Asn Gly Lys Val Ser Ser Gly Ser Arg Thr Ala Thr Leu
                485                 490                 495

Gln Pro Ile Leu Thr Leu Asp Val Pro Leu Pro Asn Tyr Ile Leu Gln
            500                 505                 510

Glu Ile Asp Tyr Pro Ser Arg Phe Asn Asp Leu Ala Ser Ser Leu Leu
        515                 520                 525

Arg Leu Arg Gly Asp Thr Arg Cys Tyr Lys Ala Asp Arg Ala Arg Gly
530                 535                 540

Glu Glu Ala Ser Ala Ile Ser Cys Tyr Met Lys Asp His Pro Gly Ser
545                 550                 555                 560

Thr Glu Glu Asp Ala Leu Asn His Ile Asn Val Met Ile Ser Asp Ala
                565                 570                 575

Ile Arg Glu Leu Asn Trp Glu Leu Leu Arg Pro Asp Ser Lys Ser Pro
        580                 585                 590

Ile Ser Ser Lys Lys His Ala Phe Asp Ile Thr Arg Ala Phe His His
        595                 600                 605

Leu Tyr Lys Tyr Arg Asp Gly Tyr Thr Val Ala Ser Ser Glu Thr Lys
610                 615                 620

Asn Leu Val Met Lys Thr Val Leu Glu Pro Val Ala Leu
625                 630                 635

<210> SEQ ID NO 27
<211> LENGTH: 807
<212> TYPE: PRT
<213> ORGANISM: Picea abies

<400> SEQUENCE: 27

Met Thr Ser Val Ser Val Glu Ser Gly Thr Val Ser Cys Leu Ser Ser
1               5                   10                  15

Asn Asn Leu Ile Arg Arg Thr Ala Asn Pro His Pro Asn Ile Trp Gly
            20                  25                  30

Tyr Asp Phe Val His Ser Leu Lys Ser Pro Tyr Thr His Asp Ser Ser
        35                  40                  45

Tyr Arg Glu Arg Ala Glu Thr Leu Ile Ser Glu Ile Lys Val Met Leu
    50                  55                  60

Gly Gly Gly Glu Leu Met Met Thr Pro Ser Ala Tyr Asp Thr Ala Trp
65                  70                  75                  80

Val Ala Arg Val Pro Ser Ile Asp Gly Ser Ala Cys Pro Gln Phe Pro
                85                  90                  95

Gln Thr Val Glu Trp Ile Leu Lys Asn Gln Leu Lys Asp Gly Ser Trp
            100                 105                 110

Gly Thr Glu Ser His Phe Leu Leu Ser Asp Arg Leu Leu Ala Thr Leu
        115                 120                 125

Ser Cys Val Leu Ala Leu Leu Lys Trp Lys Val Ala Asp Val Gln Val
    130                 135                 140

Glu Gln Gly Ile Glu Phe Ile Lys Arg Asn Leu Gln Ala Ile Lys Asp
145                 150                 155                 160
```

Glu Arg Asp Gln Asp Ser Leu Val Thr Asp Phe Glu Ile Ile Phe Pro
                165                 170                 175

Ser Leu Leu Lys Glu Ala Gln Ser Leu Asn Leu Gly Leu Pro Tyr Asp
                180                 185                 190

Leu Pro Tyr Ile Arg Leu Leu Gln Thr Lys Arg Gln Glu Arg Leu Ala
                195                 200                 205

Asn Leu Ser Met Asp Lys Ile His Gly Gly Thr Leu Leu Ser Ser Leu
210                 215                 220

Glu Gly Ile Gln Asp Ile Val Glu Trp Glu Thr Ile Met Asp Val Gln
225                 230                 235                 240

Ser Gln Asp Gly Ser Phe Leu Ser Ser Pro Ala Ser Thr Ala Cys Val
                245                 250                 255

Phe Met His Thr Gly Asp Met Lys Cys Leu Asp Phe Leu Asn Asn Val
                260                 265                 270

Leu Thr Lys Phe Gly Ser Ser Val Pro Cys Leu Tyr Pro Val Asp Leu
                275                 280                 285

Leu Glu Arg Leu Leu Ile Val Asp Asn Val Glu Arg Leu Gly Ile Asp
                290                 295                 300

Arg His Phe Glu Lys Glu Ile Lys Glu Ala Leu Asp Tyr Val Tyr Arg
305                 310                 315                 320

His Trp Asn Asp Arg Gly Ile Gly Trp Gly Arg Leu Ser Pro Ile Ala
                325                 330                 335

Asp Leu Glu Thr Thr Ala Leu Gly Phe Arg Leu Leu Arg Leu His Arg
                340                 345                 350

Tyr Asn Val Ser Pro Val Val Leu Asp Asn Phe Lys Asp Ala Asp Gly
                355                 360                 365

Glu Phe Phe Cys Ser Thr Gly Gln Phe Asn Lys Asp Val Ala Ser Met
                370                 375                 380

Leu Ser Leu Tyr Arg Ala Ser Gln Leu Ala Phe Pro Glu Glu Ser Ile
385                 390                 395                 400

Leu Asp Glu Ala Lys Ser Phe Ser Thr Gln Tyr Leu Arg Glu Ala Leu
                405                 410                 415

Glu Lys Ser Glu Thr Phe Ser Ser Trp Asn His Arg Gln Ser Leu Ser
                420                 425                 430

Glu Glu Ile Lys Tyr Ala Leu Lys Thr Ser Trp His Ala Ser Val Pro
                435                 440                 445

Arg Val Glu Ala Lys Arg Tyr Cys Gln Val Tyr Arg Gln Asp Tyr Ala
                450                 455                 460

His Leu Ala Lys Ser Val Tyr Lys Leu Pro Lys Val Asn Asn Glu Lys
465                 470                 475                 480

Ile Leu Glu Leu Ala Lys Leu Asp Phe Asn Ile Ile Gln Ser Ile His
                485                 490                 495

Gln Lys Glu Met Lys Asn Val Thr Ser Trp Phe Arg Asp Ser Gly Leu
                500                 505                 510

Pro Leu Phe Thr Phe Ala Arg Glu Arg Pro Leu Glu Phe Tyr Phe Leu
                515                 520                 525

Ile Ala Gly Gly Thr Tyr Glu Pro Gln Tyr Ala Lys Cys Arg Phe Leu
                530                 535                 540

Phe Thr Lys Val Ala Cys Leu Gln Thr Val Leu Asp Asp Met Tyr Asp
545                 550                 555                 560

Thr Tyr Gly Thr Pro Ser Glu Leu Lys Leu Phe Thr Glu Ala Val Arg
                565                 570                 575

Arg Trp Asp Leu Ser Phe Thr Glu Asn Leu Pro Asp Tyr Met Lys Leu

```
                    580                 585                 590
Cys Tyr Lys Ile Tyr Tyr Asp Ile Val His Glu Val Ala Trp Glu Val
                595                 600                 605

Glu Lys Glu Gln Gly Arg Glu Leu Val Ser Phe Phe Arg Lys Gly Trp
            610                 615                 620

Glu Asp Tyr Leu Leu Gly Tyr Tyr Glu Glu Ala Glu Trp Leu Ala Ala
625                 630                 635                 640

Glu Tyr Val Pro Thr Leu Asp Glu Tyr Ile Lys Asn Gly Ile Thr Ser
                645                 650                 655

Ile Gly Gln Arg Ile Leu Leu Leu Ser Gly Val Leu Ile Met Glu Gly
                660                 665                 670

Gln Leu Leu Ser Gln Glu Ala Leu Glu Lys Val Asp Tyr Pro Gly Arg
            675                 680                 685

Arg Val Leu Thr Glu Leu Asn Ser Leu Ile Ser Arg Leu Ala Asp Asp
        690                 695                 700

Thr Lys Thr Tyr Lys Ala Glu Lys Ala Arg Gly Glu Leu Ala Ser Ser
705                 710                 715                 720

Ile Glu Cys Tyr Met Lys Asp His Pro Gly Cys Gln Glu Glu Glu Ala
                725                 730                 735

Leu Asn His Ile Tyr Gly Ile Leu Glu Pro Ala Val Lys Glu Leu Thr
            740                 745                 750

Arg Glu Phe Leu Lys Ala Asp His Val Pro Phe Pro Cys Lys Lys Met
        755                 760                 765

Leu Phe Asp Glu Thr Arg Val Thr Met Val Ile Phe Lys Asp Gly Asp
    770                 775                 780

Gly Phe Gly Ile Ser Lys Leu Glu Val Lys Asp His Ile Lys Glu Cys
785                 790                 795                 800

Leu Ile Glu Pro Leu Pro Leu
                805

<210> SEQ ID NO 28
<211> LENGTH: 817
<212> TYPE: PRT
<213> ORGANISM: Abies grandis

<400> SEQUENCE: 28

Met Ala Gly Val Ser Ala Val Ser Lys Val Ser Ser Leu Val Cys Asp
1               5                   10                  15

Leu Ser Ser Thr Ser Gly Leu Ile Arg Arg Thr Ala Asn Pro His Pro
            20                  25                  30

Asn Val Trp Gly Tyr Asp Leu Val His Ser Leu Lys Ser Pro Tyr Ile
        35                  40                  45

Asp Ser Ser Tyr Arg Glu Arg Ala Glu Val Leu Val Ser Glu Ile Lys
    50                  55                  60

Ala Met Leu Asn Pro Ala Ile Thr Gly Asp Gly Glu Ser Met Ile Thr
65                  70                  75                  80

Pro Ser Ala Tyr Asp Thr Ala Trp Val Ala Arg Val Pro Ala Ile Asp
                85                  90                  95

Gly Ser Ala Arg Pro Gln Phe Pro Gln Thr Val Asp Trp Ile Leu Lys
            100                 105                 110

Asn Gln Leu Lys Asp Gly Ser Trp Gly Ile Gln Ser His Phe Leu Leu
        115                 120                 125

Ser Asp Arg Leu Leu Ala Thr Leu Ser Cys Val Leu Val Leu Leu Lys
    130                 135                 140

Trp Asn Val Gly Asp Leu Gln Val Glu Gln Gly Ile Glu Phe Ile Lys
```

-continued

```
            145                 150                 155                 160
Ser Asn Leu Glu Leu Val Lys Asp Glu Thr Asp Gln Asp Ser Leu Val
                165                 170                 175

Thr Asp Phe Glu Ile Ile Phe Pro Ser Leu Leu Arg Glu Ala Gln Ser
            180                 185                 190

Leu Arg Leu Gly Leu Pro Tyr Asp Leu Pro Tyr Ile His Leu Leu Gln
        195                 200                 205

Thr Lys Arg Gln Glu Arg Leu Ala Lys Leu Ser Arg Glu Glu Ile Tyr
    210                 215                 220

Ala Val Pro Ser Pro Leu Leu Tyr Ser Leu Glu Gly Ile Gln Asp Ile
225                 230                 235                 240

Val Glu Trp Glu Arg Ile Met Glu Val Gln Ser Gln Asp Gly Ser Phe
            245                 250                 255

Leu Ser Ser Pro Ala Ser Thr Ala Cys Val Phe Met His Thr Gly Asp
        260                 265                 270

Ala Lys Cys Leu Glu Phe Leu Asn Ser Val Met Ile Lys Phe Gly Asn
    275                 280                 285

Phe Val Pro Cys Leu Tyr Pro Val Asp Leu Leu Glu Arg Leu Leu Ile
290                 295                 300

Val Asp Asn Ile Val Arg Leu Gly Ile Tyr Arg His Phe Glu Lys Glu
305                 310                 315                 320

Ile Lys Glu Ala Leu Asp Tyr Val Tyr Arg His Trp Asn Glu Arg Gly
            325                 330                 335

Ile Gly Trp Gly Arg Leu Asn Pro Ile Ala Asp Leu Glu Thr Thr Ala
        340                 345                 350

Leu Gly Phe Arg Leu Leu Arg Leu His Arg Tyr Asn Val Ser Pro Ala
    355                 360                 365

Ile Phe Asp Asn Phe Lys Asp Ala Asn Gly Lys Phe Ile Cys Ser Thr
370                 375                 380

Gly Gln Phe Asn Lys Asp Val Ala Ser Met Leu Asn Leu Tyr Arg Ala
385                 390                 395                 400

Ser Gln Leu Ala Phe Pro Gly Glu Asn Ile Leu Asp Glu Ala Lys Ser
            405                 410                 415

Phe Ala Thr Lys Tyr Leu Arg Glu Ala Leu Glu Lys Ser Glu Thr Ser
        420                 425                 430

Ser Ala Trp Asn Asn Lys Gln Asn Leu Ser Gln Glu Ile Lys Tyr Ala
    435                 440                 445

Leu Lys Thr Ser Trp His Ala Ser Val Pro Arg Val Glu Ala Lys Arg
    450                 455                 460

Tyr Cys Gln Val Tyr Arg Pro Asp Tyr Ala Arg Ile Ala Lys Cys Val
465                 470                 475                 480

Tyr Lys Leu Pro Tyr Val Asn Asn Glu Lys Phe Leu Glu Leu Gly Lys
            485                 490                 495

Leu Asp Phe Asn Ile Ile Gln Ser Ile His Gln Glu Glu Met Lys Asn
        500                 505                 510

Val Thr Ser Trp Phe Arg Asp Ser Gly Leu Pro Leu Phe Thr Phe Ala
    515                 520                 525

Arg Glu Arg Pro Leu Glu Phe Tyr Phe Leu Val Ala Ala Gly Thr Tyr
    530                 535                 540

Glu Pro Gln Tyr Ala Lys Cys Arg Phe Leu Phe Thr Lys Val Ala Cys
545                 550                 555                 560

Leu Gln Thr Val Leu Asp Asp Met Tyr Asp Thr Tyr Gly Thr Leu Asp
            565                 570                 575
```

```
Glu Leu Lys Leu Phe Thr Glu Ala Val Arg Arg Trp Asp Leu Ser Phe
            580                 585                 590

Thr Glu Asn Leu Pro Asp Tyr Met Lys Leu Cys Tyr Gln Ile Tyr Tyr
            595                 600                 605

Asp Ile Val His Glu Val Ala Trp Glu Ala Lys Glu Gln Gly Arg
            610                 615                 620

Glu Leu Val Ser Phe Phe Arg Lys Gly Trp Glu Asp Tyr Leu Leu Gly
625                 630                 635                 640

Tyr Tyr Glu Glu Ala Glu Trp Leu Ala Ala Glu Tyr Val Pro Thr Leu
                645                 650                 655

Asp Glu Tyr Ile Lys Asn Gly Ile Thr Ser Ile Gly Asn Arg Ile Leu
            660                 665                 670

Leu Leu Ser Gly Val Leu Ile Met Asp Gly Gln Leu Leu Ser Gln Glu
            675                 680                 685

Ala Leu Glu Lys Val Asp Tyr Pro Gly Arg Arg Val Leu Thr Glu Leu
            690                 695                 700

Asn Ser Leu Ile Ser Arg Leu Ala Asp Asp Thr Lys Thr Tyr Lys Ala
705                 710                 715                 720

Glu Lys Ala Arg Gly Glu Leu Ala Ser Ser Ile Glu Cys Tyr Met Lys
                725                 730                 735

Asp His Pro Glu Cys Thr Glu Glu Ala Leu Asp His Ile Tyr Ser
            740                 745                 750

Ile Leu Glu Pro Ala Val Lys Glu Leu Thr Arg Glu Phe Leu Lys Pro
            755                 760                 765

Asp Asp Val Pro Phe Ala Cys Lys Lys Met Leu Phe Glu Glu Thr Arg
            770                 775                 780

Val Thr Met Val Ile Phe Lys Asp Gly Asp Gly Phe Gly Val Ser Lys
785                 790                 795                 800

Leu Glu Val Lys Asp His Ile Lys Glu Cys Leu Ile Glu Pro Leu Pro
                805                 810                 815

Leu

<210> SEQ ID NO 29
<211> LENGTH: 782
<212> TYPE: PRT
<213> ORGANISM: Abies grandis

<400> SEQUENCE: 29

Gly Tyr Asp Leu Val His Ser Leu Lys Ser Pro Tyr Ile Asp Ser Ser
1               5                   10                  15

Tyr Arg Glu Arg Ala Glu Val Leu Val Ser Glu Ile Lys Val Met Leu
                20                  25                  30

Asn Pro Ala Ile Thr Gly Asp Gly Glu Ser Met Ile Thr Pro Ser Ala
            35                  40                  45

Tyr Asp Thr Ala Trp Val Ala Arg Val Pro Ala Ile Asp Gly Ser Ala
        50                  55                  60

Arg Pro Gln Phe Pro Gln Thr Val Asp Trp Ile Leu Lys Asn Gln Leu
65                  70                  75                  80

Lys Asp Gly Ser Trp Gly Ile Gln Ser His Phe Leu Leu Ser Asp Arg
                85                  90                  95

Leu Leu Ala Thr Leu Ser Cys Val Leu Val Leu Lys Trp Asn Val
            100                 105                 110

Gly Asp Leu Gln Val Glu Gln Gly Ile Glu Phe Ile Lys Ser Asn Leu
        115                 120                 125

Glu Leu Val Lys Asp Glu Thr Asp Gln Asp Ser Leu Val Thr Asp Phe
```

-continued

```
            130                 135                 140
Glu Ile Ile Phe Pro Ser Leu Leu Arg Glu Ala Gln Ser Leu Arg Leu
145                 150                 155                 160

Gly Leu Pro Tyr Asp Leu Pro Tyr Ile His Leu Leu Gln Thr Lys Arg
                165                 170                 175

Gln Glu Arg Leu Ala Lys Leu Ser Arg Glu Ile Tyr Ala Val Pro
                180                 185                 190

Ser Pro Leu Leu Tyr Ser Leu Glu Gly Ile Gln Asp Ile Val Glu Trp
                195                 200                 205

Glu Arg Ile Met Glu Val Gln Ser Gln Asp Gly Ser Phe Leu Ser Ser
210                 215                 220

Pro Ala Ser Thr Ala Cys Val Phe Met His Thr Gly Asp Ala Lys Cys
225                 230                 235                 240

Leu Glu Phe Leu Asn Ser Val Met Ile Lys Phe Gly Asn Phe Val Pro
                245                 250                 255

Cys Leu Tyr Pro Val Asp Leu Leu Glu Arg Leu Leu Ile Val Asp Asn
                260                 265                 270

Ile Val Arg Leu Gly Ile Tyr Arg His Phe Glu Lys Glu Ile Lys Glu
            275                 280                 285

Ala Leu Asp Tyr Val Tyr Arg His Trp Asn Glu Arg Gly Ile Gly Trp
290                 295                 300

Gly Arg Leu Asn Pro Ile Ala Asp Leu Glu Thr Thr Ala Leu Gly Phe
305                 310                 315                 320

Arg Leu Leu Arg Leu His Arg Tyr Asn Val Ser Pro Ala Ile Phe Asp
                325                 330                 335

Asn Phe Lys Asp Ala Asn Gly Lys Phe Ile Cys Ser Thr Gly Gln Phe
                340                 345                 350

Asn Lys Asp Val Ala Ser Met Leu Asn Leu Tyr Arg Ala Ser Gln Leu
            355                 360                 365

Ala Phe Pro Gly Glu Asn Ile Leu Asp Glu Ala Lys Ser Phe Ala Thr
                370                 375                 380

Lys Tyr Leu Arg Glu Ala Leu Glu Lys Ser Glu Thr Ser Ser Ala Trp
385                 390                 395                 400

Asn Asn Lys Gln Asn Leu Ser Gln Glu Ile Lys Tyr Ala Leu Lys Thr
                405                 410                 415

Ser Trp His Ala Ser Val Pro Arg Val Glu Ala Lys Arg Tyr Cys Gln
                420                 425                 430

Val Tyr Arg Pro Asp Tyr Ala Arg Ile Ala Lys Cys Val Tyr Lys Leu
            435                 440                 445

Pro Tyr Val Asn Asn Glu Lys Phe Leu Glu Leu Gly Lys Leu Asp Phe
450                 455                 460

Asn Ile Ile Gln Ser Ile His Gln Glu Glu Met Lys Asn Val Thr Ser
465                 470                 475                 480

Trp Phe Arg Asp Ser Gly Leu Pro Leu Phe Thr Phe Ala Arg Glu Arg
                485                 490                 495

Pro Leu Glu Phe Tyr Phe Leu Val Ala Ala Gly Thr Tyr Glu Pro Gln
                500                 505                 510

Tyr Ala Lys Cys Arg Phe Leu Phe Thr Lys Val Ala Cys Leu Gln Thr
            515                 520                 525

Val Leu Asp Asp Met Tyr Asp Thr Tyr Gly Thr Leu Asp Glu Leu Lys
            530                 535                 540

Leu Phe Thr Glu Ala Val Arg Arg Trp Asp Leu Ser Phe Thr Glu Asn
545                 550                 555                 560
```

```
Leu Pro Asp Tyr Met Lys Leu Cys Tyr Gln Ile Tyr Asp Ile Val
                565                 570                 575

His Glu Val Ala Trp Glu Ala Glu Lys Glu Gln Gly Arg Glu Leu Val
            580                 585                 590

Ser Phe Phe Arg Lys Gly Trp Glu Asp Tyr Leu Leu Gly Tyr Tyr Glu
            595                 600                 605

Glu Ala Glu Trp Leu Ala Ala Glu Tyr Val Pro Thr Leu Asp Glu Tyr
            610                 615                 620

Ile Lys Asn Gly Ile Thr Ser Ile Gly Gln Arg Ile Leu Leu Leu Ser
625                 630                 635                 640

Gly Val Leu Ile Met Asp Gly Gln Leu Leu Ser Gln Glu Ala Leu Glu
                645                 650                 655

Lys Val Asp Tyr Pro Gly Arg Arg Val Leu Thr Glu Leu Asn Ser Leu
            660                 665                 670

Ile Ser Arg Leu Ala Asp Asp Thr Lys Thr Tyr Lys Ala Glu Lys Ala
            675                 680                 685

Arg Gly Glu Leu Ala Ser Ser Ile Glu Cys Tyr Met Lys Asp His Pro
            690                 695                 700

Glu Cys Thr Glu Glu Ala Leu Asp His Ile Tyr Ser Ile Leu Glu
705                 710                 715                 720

Pro Ala Val Lys Glu Leu Thr Arg Glu Phe Leu Lys Pro Asp Asp Val
                725                 730                 735

Pro Phe Ala Cys Lys Lys Met Leu Phe Glu Glu Thr Arg Val Thr Met
            740                 745                 750

Val Ile Phe Lys Asp Gly Asp Gly Phe Gly Val Ser Lys Leu Glu Val
            755                 760                 765

Lys Asp His Ile Lys Glu Cys Leu Ile Glu Pro Leu Pro Leu
            770                 775                 780

<210> SEQ ID NO 30
<211> LENGTH: 816
<212> TYPE: PRT
<213> ORGANISM: Abies grandis

<400> SEQUENCE: 30

Ala Gly Val Ser Ala Val Ser Lys Val Ser Ser Leu Val Cys Asp Leu
1               5                   10                  15

Ser Ser Thr Ser Gly Leu Ile Arg Arg Thr Ala Asn Pro His Pro Asn
            20                  25                  30

Val Trp Gly Tyr Asp Leu Val His Ser Leu Lys Ser Pro Tyr Ile Asp
        35                  40                  45

Ser Ser Tyr Arg Glu Arg Ala Glu Val Leu Val Ser Glu Ile Lys Val
    50                  55                  60

Met Leu Asn Pro Ala Ile Thr Gly Asp Gly Glu Ser Met Ile Thr Pro
65              70                  75                  80

Ser Ala Tyr Asp Thr Ala Trp Val Ala Arg Val Pro Ala Ile Asp Gly
                85                  90                  95

Ser Ala Arg Pro Gln Phe Pro Gln Thr Val Asp Trp Ile Leu Lys Asn
            100                 105                 110

Gln Leu Lys Asp Gly Ser Trp Gly Ile Gln Ser His Phe Leu Leu Ser
        115                 120                 125

Asp Arg Leu Leu Ala Thr Leu Ser Cys Val Leu Val Leu Leu Lys Trp
    130                 135                 140

Asn Val Gly Asp Leu Gln Val Glu Gln Gly Ile Glu Phe Ile Lys Ser
145                 150                 155                 160
```

```
Asn Leu Glu Leu Val Lys Asp Glu Thr Asp Gln Asp Ser Leu Val Thr
                165                 170                 175
Asp Phe Glu Ile Ile Phe Pro Ser Leu Leu Arg Glu Ala Gln Ser Leu
            180                 185                 190
Arg Leu Gly Leu Pro Tyr Asp Leu Pro Tyr Ile His Leu Leu Gln Thr
        195                 200                 205
Lys Arg Gln Glu Arg Leu Ala Lys Leu Ser Arg Glu Glu Ile Tyr Ala
210                 215                 220
Val Pro Ser Pro Leu Leu Tyr Ser Leu Glu Gly Ile Gln Asp Ile Val
225                 230                 235                 240
Glu Trp Glu Arg Ile Met Glu Val Gln Ser Gln Asp Gly Ser Phe Leu
                245                 250                 255
Ser Ser Pro Ala Ser Thr Ala Cys Val Phe Met His Thr Gly Asp Ala
            260                 265                 270
Lys Cys Leu Glu Phe Leu Asn Ser Val Met Ile Lys Phe Gly Asn Phe
        275                 280                 285
Val Pro Cys Leu Tyr Pro Val Asp Leu Leu Glu Arg Leu Leu Ile Val
290                 295                 300
Asp Asn Ile Val Arg Leu Gly Ile Tyr Arg His Phe Glu Lys Glu Ile
305                 310                 315                 320
Lys Glu Ala Leu Asp Tyr Val Tyr Arg His Trp Asn Glu Arg Gly Ile
                325                 330                 335
Gly Trp Gly Arg Leu Asn Pro Ile Ala Asp Leu Glu Thr Thr Ala Leu
            340                 345                 350
Gly Phe Arg Leu Leu Arg Leu His Arg Tyr Asn Val Ser Pro Ala Ile
        355                 360                 365
Phe Asp Asn Phe Lys Asp Ala Asn Gly Lys Phe Ile Cys Ser Thr Gly
370                 375                 380
Gln Phe Asn Lys Asp Val Ala Ser Met Leu Asn Leu Tyr Arg Ala Ser
385                 390                 395                 400
Gln Leu Ala Phe Pro Gly Glu Asn Ile Leu Asp Glu Ala Lys Ser Phe
                405                 410                 415
Ala Thr Lys Tyr Leu Arg Glu Ala Leu Glu Lys Ser Gly Thr Ser Ser
            420                 425                 430
Ala Trp Asn Asn Lys Gln Asn Leu Ser Gln Glu Ile Lys Tyr Ala Leu
        435                 440                 445
Lys Thr Ser Trp His Ala Ser Val Pro Arg Val Glu Ala Lys Arg Tyr
450                 455                 460
Cys Gln Val Tyr Arg Pro Asp Tyr Ala Arg Ile Ala Lys Cys Val Tyr
465                 470                 475                 480
Lys Leu Pro Tyr Val Asn Asn Glu Lys Phe Leu Glu Leu Gly Lys Leu
                485                 490                 495
Asp Phe Asn Ile Ile Gln Ser Ile His Gln Glu Glu Met Lys Asn Val
            500                 505                 510
Thr Ser Trp Phe Arg Asp Ser Gly Leu Pro Leu Phe Thr Phe Ala Arg
        515                 520                 525
Glu Arg Pro Leu Glu Phe Tyr Phe Leu Val Ala Ala Gly Thr Tyr Glu
530                 535                 540
Pro Gln Tyr Ala Lys Cys Arg Phe Leu Phe Thr Lys Val Ala Cys Leu
545                 550                 555                 560
Gln Thr Val Leu Asp Asp Met Tyr Asp Thr Tyr Gly Thr Leu Asp Glu
                565                 570                 575
Leu Lys Leu Phe Thr Glu Ala Val Arg Arg Trp Asp Val Ser Phe Thr
            580                 585                 590
```

```
Glu Asn Leu Pro Asp Tyr Met Lys Leu Cys Tyr Gln Ile Tyr Tyr Asp
            595                 600                 605

Ile Val His Glu Val Ala Trp Glu Ala Glu Lys Glu Gln Gly Arg Glu
    610                 615                 620

Leu Val Ser Phe Phe Arg Lys Gly Trp Glu Asp Tyr Leu Leu Gly Tyr
625                 630                 635                 640

Tyr Glu Glu Ala Glu Trp Leu Ala Ala Glu Tyr Val Pro Ser Leu Asp
                645                 650                 655

Glu Tyr Ile Lys Asn Gly Ile Thr Ser Ile Gly Gln Arg Ile Leu Leu
            660                 665                 670

Leu Ser Gly Val Leu Ile Met Asp Gly Gln Leu Leu Ser Gln Glu Ala
        675                 680                 685

Leu Glu Lys Val Asp Tyr Pro Gly Arg Arg Val Leu Thr Glu Leu Asn
    690                 695                 700

Ser Leu Ile Ser Arg Leu Ala Asp Asp Thr Lys Thr Tyr Lys Ala Glu
705                 710                 715                 720

Lys Ala Arg Gly Glu Leu Ala Ser Ser Ile Glu Cys Tyr Met Lys Asp
                725                 730                 735

His Pro Glu Cys Thr Glu Glu Glu Ala Leu Asp His Ile Tyr Ser Ile
            740                 745                 750

Leu Glu Pro Ala Val Lys Glu Leu Thr Arg Glu Phe Leu Lys Pro Asp
        755                 760                 765

Asp Val Pro Phe Ala Cys Lys Lys Met Leu Phe Glu Glu Thr Gly Val
    770                 775                 780

Thr Met Val Ile Phe Lys Asp Gly Asp Gly Phe Gly Val Ser Lys Leu
785                 790                 795                 800

Glu Val Lys Asp His Ile Lys Glu Cys Leu Ile Glu Pro Leu Pro Leu
                805                 810                 815

<210> SEQ ID NO 31
<211> LENGTH: 862
<212> TYPE: PRT
<213> ORGANISM: Taxus brevifolia

<400> SEQUENCE: 31

Met Ala Gln Leu Ser Phe Asn Ala Ala Leu Lys Met Asn Ala Leu Gly
1               5                   10                  15

Asn Lys Ala Ile His Asp Pro Thr Asn Cys Arg Ala Lys Ser Glu Arg
            20                  25                  30

Gln Met Met Trp Val Cys Ser Arg Ser Gly Arg Thr Arg Val Lys Met
        35                  40                  45

Ser Arg Gly Ser Gly Gly Pro Gly Pro Val Val Met Met Ser Ser Ser
    50                  55                  60

Thr Gly Thr Ser Lys Val Val Ser Glu Thr Ser Ser Thr Ile Val Asp
65                  70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Tyr
            100                 105                 110

Gln Glu Arg Ala Asp Glu Leu Val Val Lys Ile Lys Asp Met Phe Asn
        115                 120                 125

Ala Leu Gly Asp Gly Asp Ile Ser Pro Ser Ala Tyr Asp Thr Ala Trp
    130                 135                 140

Val Ala Arg Leu Ala Thr Ile Ser Ser Asp Gly Ser Glu Lys Pro Arg
145                 150                 155                 160
```

```
Phe Pro Gln Ala Leu Asn Trp Val Phe Asn Asn Gln Leu Gln Asp Gly
                165                 170                 175
Ser Trp Gly Ile Glu Ser His Phe Ser Leu Cys Asp Arg Leu Leu Asn
            180                 185                 190
Thr Thr Asn Ser Val Ile Ala Leu Ser Val Trp Lys Thr Gly His Ser
        195                 200                 205
Gln Val Gln Gln Gly Ala Glu Phe Ile Ala Glu Asn Leu Arg Leu Leu
    210                 215                 220
Asn Glu Glu Asp Glu Leu Ser Pro Asp Phe Gln Ile Ile Phe Pro Ala
225                 230                 235                 240
Leu Leu Gln Lys Ala Lys Ala Leu Gly Ile Asn Leu Pro Tyr Asp Leu
                245                 250                 255
Pro Phe Ile Lys Tyr Leu Ser Thr Thr Arg Glu Ala Arg Leu Thr Asp
            260                 265                 270
Val Ser Ala Ala Ala Asp Asn Ile Pro Ala Asn Met Leu Asn Ala Leu
        275                 280                 285
Glu Gly Leu Glu Glu Val Ile Asp Trp Asn Lys Ile Met Arg Phe Gln
    290                 295                 300
Ser Lys Asp Gly Ser Phe Leu Ser Ser Pro Ala Ser Thr Ala Cys Val
305                 310                 315                 320
Leu Met Asn Thr Gly Asp Glu Lys Cys Phe Thr Phe Leu Asn Asn Leu
                325                 330                 335
Leu Asp Lys Phe Gly Gly Cys Val Pro Cys Met Tyr Ser Ile Asp Leu
            340                 345                 350
Leu Glu Arg Leu Ser Leu Val Asp Asn Ile Glu His Leu Gly Ile Gly
        355                 360                 365
Arg His Phe Lys Gln Glu Ile Lys Gly Ala Leu Asp Tyr Val Tyr Arg
    370                 375                 380
His Trp Ser Glu Arg Gly Ile Gly Trp Gly Arg Asp Ser Leu Val Pro
385                 390                 395                 400
Asp Leu Asn Thr Thr Ala Leu Gly Leu Arg Thr Leu Arg Met His Gly
                405                 410                 415
Tyr Asn Val Ser Ser Asp Val Leu Asn Asn Phe Lys Asp Glu Asn Gly
            420                 425                 430
Arg Phe Phe Ser Ser Ala Gly Gln Thr His Val Glu Leu Arg Ser Val
        435                 440                 445
Val Asn Leu Phe Arg Ala Ser Asp Leu Ala Phe Pro Asp Glu Arg Ala
    450                 455                 460
Met Asp Asp Ala Arg Lys Phe Ala Glu Pro Tyr Leu Arg Glu Ala Leu
465                 470                 475                 480
Ala Thr Lys Ile Ser Thr Asn Thr Lys Leu Phe Lys Glu Ile Glu Tyr
                485                 490                 495
Val Val Glu Tyr Pro Trp His Met Ser Ile Pro Arg Leu Glu Ala Arg
            500                 505                 510
Ser Tyr Ile Asp Ser Tyr Asp Asp Asn Tyr Val Trp Gln Arg Lys Thr
        515                 520                 525
Leu Tyr Arg Met Pro Ser Leu Ser Asn Ser Lys Cys Leu Glu Leu Ala
    530                 535                 540
Lys Leu Asp Phe Asn Ile Val Gln Ser Leu His Gln Glu Glu Leu Lys
545                 550                 555                 560
Leu Leu Thr Arg Trp Trp Lys Glu Ser Gly Met Ala Asp Ile Asn Phe
                565                 570                 575
Thr Arg His Arg Val Ala Glu Val Tyr Phe Ser Ser Ala Thr Phe Glu
```

```
                      580                 585                 590
Pro Glu Tyr Ser Ala Thr Arg Ile Ala Phe Thr Lys Ile Gly Cys Leu
            595                 600                 605

Gln Val Leu Phe Asp Asp Met Ala Asp Ile Phe Ala Thr Leu Asp Glu
        610                 615                 620

Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
            645                 650                 655

Leu Met Glu Glu Val Asn Asn Asp Val Val Lys Val Gln Gly Arg Asp
        660                 665                 670

Met Leu Ala His Ile Arg Lys Pro Trp Glu Leu Tyr Phe Asn Cys Tyr
            675                 680                 685

Val Gln Glu Arg Glu Trp Leu Glu Ala Gly Tyr Ile Pro Thr Phe Glu
        690                 695                 700

Glu Tyr Leu Lys Thr Tyr Ala Ile Ser Val Gly Leu Gly Pro Cys Thr
705                 710                 715                 720

Leu Gln Pro Ile Leu Leu Met Gly Glu Leu Val Lys Asp Asp Val Val
            725                 730                 735

Glu Lys Val His Tyr Pro Ser Asn Met Phe Glu Leu Val Ser Leu Ser
        740                 745                 750

Trp Arg Leu Thr Asn Asp Thr Lys Thr Tyr Gln Ala Glu Lys Ala Arg
            755                 760                 765

Gly Gln Gln Ala Ser Gly Ile Ala Cys Tyr Met Lys Asp Asn Pro Gly
        770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
            805                 810                 815

Pro Met Gly Cys Lys Ser Phe Ile Phe Asn Leu Arg Leu Cys Val Gln
        820                 825                 830

Ile Phe Tyr Lys Phe Ile Asp Gly Tyr Gly Ile Ala Asn Glu Glu Ile
            835                 840                 845

Lys Asp Tyr Ile Arg Lys Val Tyr Ile Asp Pro Ile Gln Val
850                 855                 860

<210> SEQ ID NO 32
<211> LENGTH: 862
<212> TYPE: PRT
<213> ORGANISM: Taxus brevifolia

<400> SEQUENCE: 32

Met Ala Gln Leu Ser Phe Asn Ala Ala Leu Lys Met Asn Ala Leu Gly
 1               5                  10                  15

Asn Lys Ala Ile His Asp Pro Thr Asn Cys Arg Ala Lys Ser Glu Arg
            20                  25                  30

Gln Met Met Trp Val Cys Ser Arg Ser Gly Arg Thr Arg Val Lys Met
        35                  40                  45

Ser Arg Gly Ser Gly Gly Pro Gly Pro Val Val Met Met Ser Ser Ser
    50                  55                  60

Thr Gly Thr Ser Lys Val Val Ser Glu Thr Ser Ser Thr Ile Val Asp
65                  70                  75                  80

Asp Ile Pro Arg Leu Ser Ala Asn Tyr His Gly Asp Leu Trp His His
            85                  90                  95

Asn Val Ile Gln Thr Leu Glu Thr Pro Phe Arg Glu Ser Ser Thr Tyr
```

-continued

```
                100                 105                 110
Gln Glu Arg Ala Asp Glu Leu Val Val Lys Ile Lys Asp Met Phe Asn
            115                 120                 125
Ala Leu Gly Asp Gly Asp Ile Ser Pro Ser Ala Tyr Asp Thr Ala Trp
        130                 135                 140
Val Ala Arg Val Ala Thr Ile Ser Ser Asp Gly Ser Glu Lys Pro Arg
145                 150                 155                 160
Phe Pro Gln Ala Leu Asn Trp Val Phe Asn Asn Gln Leu Gln Asp Gly
                165                 170                 175
Ser Trp Gly Ile Glu Ser His Phe Ser Leu Cys Asp Arg Leu Leu Asn
            180                 185                 190
Thr Thr Asn Ser Val Ile Ala Leu Ser Val Trp Lys Thr Gly His Ser
        195                 200                 205
Gln Val Gln Gln Gly Ala Glu Phe Ile Ala Glu Asn Leu Arg Leu Leu
    210                 215                 220
Asn Glu Glu Asp Glu Leu Ser Pro Asp Phe Gln Ile Ile Phe Pro Ala
225                 230                 235                 240
Leu Leu Gln Lys Ala Lys Ala Leu Gly Ile Asn Leu Pro Tyr Asp Leu
                245                 250                 255
Pro Phe Ile Lys Tyr Leu Ser Thr Thr Arg Glu Ala Arg Leu Thr Asp
            260                 265                 270
Val Ser Ala Ala Ala Asp Asn Ile Pro Ala Asn Met Leu Asn Ala Leu
        275                 280                 285
Glu Gly Leu Glu Glu Val Ile Asp Trp Asn Lys Ile Met Arg Phe Gln
    290                 295                 300
Ser Lys Asp Gly Ser Phe Leu Ser Ser Pro Ala Ser Thr Ala Cys Val
305                 310                 315                 320
Leu Met Asn Thr Gly Asp Glu Lys Cys Phe Thr Phe Leu Asn Asn Leu
                325                 330                 335
Leu Asp Lys Phe Gly Gly Cys Val Pro Cys Met Tyr Ser Ile Asp Leu
            340                 345                 350
Leu Glu Arg Leu Ser Leu Val Asp Asn Ile Glu His Leu Gly Ile Gly
        355                 360                 365
Arg His Phe Lys Gln Glu Ile Lys Gly Ala Leu Asp Tyr Val Tyr Arg
    370                 375                 380
His Trp Ser Glu Arg Gly Ile Gly Trp Gly Arg Asp Ser Leu Val Pro
385                 390                 395                 400
Asp Leu Asn Thr Thr Ala Leu Gly Leu Arg Thr Leu Arg Met His Gly
                405                 410                 415
Tyr Asn Val Ser Ser Asp Val Leu Asn Asn Phe Lys Asp Glu Asn Gly
            420                 425                 430
Arg Phe Phe Ser Ser Ala Gly Gln Thr His Val Glu Leu Arg Ser Val
        435                 440                 445
Val Asn Leu Phe Arg Ala Ser Asp Leu Ala Phe Pro Asp Glu Arg Ala
    450                 455                 460
Met Asp Asp Ala Arg Lys Phe Ala Glu Pro Tyr Leu Arg Glu Ala Leu
465                 470                 475                 480
Ala Thr Lys Ile Ser Thr Asn Thr Lys Leu Phe Lys Glu Ile Glu Tyr
                485                 490                 495
Val Val Glu Tyr Pro Trp His Met Ser Ile Pro Arg Leu Glu Ala Arg
            500                 505                 510
Ser Tyr Ile Asp Ser Tyr Asp Asp Asn Tyr Val Trp Gln Arg Lys Thr
        515                 520                 525
```

```
Leu Tyr Arg Met Pro Ser Leu Ser Asn Ser Lys Cys Leu Glu Leu Ala
        530                 535                 540

Lys Leu Asp Phe Asn Ile Val Gln Ser Leu His Gln Glu Glu Leu Lys
545                 550                 555                 560

Leu Leu Thr Arg Trp Trp Lys Glu Ser Gly Met Ala Asp Ile Asn Phe
                565                 570                 575

Thr Arg His Arg Val Ala Glu Val Tyr Phe Ser Ser Ala Thr Phe Glu
            580                 585                 590

Pro Glu Tyr Ser Ala Thr Arg Ile Ala Phe Thr Lys Ile Gly Cys Leu
        595                 600                 605

Gln Val Leu Phe Asp Asp Met Ala Asp Ile Phe Ala Thr Leu Asp Glu
610                 615                 620

Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
                645                 650                 655

Leu Met Glu Glu Val Asn Asn Asp Val Val Lys Val Gln Gly Arg Asp
            660                 665                 670

Met Leu Ala His Ile Arg Lys Pro Trp Glu Leu Tyr Phe Asn Cys Tyr
        675                 680                 685

Val Gln Glu Arg Glu Trp Leu Glu Ala Gly Tyr Ile Pro Thr Phe Glu
690                 695                 700

Glu Tyr Leu Lys Thr Tyr Ala Ile Ser Val Gly Leu Gly Pro Cys Thr
705                 710                 715                 720

Leu Gln Pro Ile Leu Leu Met Gly Glu Leu Val Lys Asp Asp Val Val
                725                 730                 735

Glu Lys Val His Tyr Pro Ser Asn Met Phe Glu Leu Val Ser Leu Ser
            740                 745                 750

Trp Arg Leu Thr Asn Asp Thr Lys Thr Tyr Gln Ala Glu Lys Val Arg
        755                 760                 765

Gly Gln Gln Ala Ser Gly Ile Ala Cys Tyr Met Lys Asp Asn Pro Gly
770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
                805                 810                 815

Pro Met Gly Cys Lys Ser Phe Ile Phe Asn Leu Arg Leu Cys Val Gln
            820                 825                 830

Ile Phe Tyr Lys Phe Ile Asp Gly Tyr Gly Ile Ala Asn Glu Glu Ile
        835                 840                 845

Lys Asp Tyr Ile Arg Lys Val Tyr Ile Asp Pro Ile Gln Val
850                 855                 860

<210> SEQ ID NO 33
<211> LENGTH: 605
<212> TYPE: PRT
<213> ORGANISM: Chamaecyparis obtusa

<400> SEQUENCE: 33

Met Ala Leu Ile Ser Leu Ser Ser Ala Phe Thr Phe Cys Leu Lys
  1               5                  10                  15

Ser Lys Pro Thr His Leu Ser Lys Pro Ser Lys Ser Phe Pro Thr
                 20                  25                  30

Leu Ala Arg Lys Cys Met Arg Asn Thr Met Ala Met Ala Thr Thr Ser
         35                  40                  45
```

```
Val Glu Ser Val Thr Arg Arg Thr Gly Asn His His Gly Asn Leu Trp
    50              55                  60

Asp Asp Asp Phe Ile Gln Ser Leu Pro Lys Leu Pro Tyr Asp Ala Pro
 65              70                  75                      80

Glu Tyr Arg Glu Arg Ala Asp Arg Leu Val Gly Glu Val Lys Asn Met
                85                  90                  95

Phe Asn Ala Val Arg Ala Ala Asp Ser Ser Gln Asn Ile Leu Arg
            100             105             110

Leu Leu Glu Met Val Asp Lys Val Glu Arg Leu Gly Ile Gly Arg His
            115             120             125

Phe Glu Thr Glu Ile Ala Glu Ala Leu Asp Tyr Val Tyr Arg Phe Trp
        130             135             140

Asn Asp Ile Ser Ser Lys Asp Leu Asn Thr Ala Ala Leu Gly Leu Arg
145             150             155                     160

Ile Leu Arg Leu His Arg Tyr Pro Val Ser Ser Asp Val Leu Glu Gln
                165             170             175

Phe Lys Glu Lys Asp Gly His Phe Leu Cys Cys Thr Thr Gln Leu Glu
            180             185             190

Glu Glu Ile Lys Ser Ile Leu Asn Leu Phe Arg Ala Ser Leu Ile Ala
            195             200             205

Phe Pro Asn Glu Lys Ile Met Asp Glu Ala Lys Ala Phe Ser Thr Met
    210             215             220

Tyr Leu Lys Gln Val Phe Gln Lys Ser His Ile Leu Gly Thr His Leu
225             230             235                     240

Leu Lys Glu Ile Thr Phe Asn Leu Glu Tyr Gly Trp Arg Thr Asn Leu
                245             250             255

Pro Arg Leu Glu Ala Arg Asn Tyr Met Asp Ile Tyr Gly Glu Asn Ser
            260             265             270

Ser Trp Leu Met Asp Met Asp Asn Lys Asn Ile Leu Tyr Leu Ala Lys
            275             280             285

Leu Asp Phe Asn Ile Leu Gln Ser Leu Tyr Arg Pro Glu Leu Gln Met
    290             295             300

Ile Ser Arg Trp Trp Lys Asp Ser Ser Leu Tyr Lys Leu Asp Phe Ser
305             310             315                     320

Arg His Arg His Ile Glu Tyr Leu Phe Gln Gly Cys Ala Ile Thr Gly
                325             330             335

Glu Pro Lys His Ser Gly Phe Arg Ile Asp Ile Ala Lys Tyr Ser Thr
            340             345             350

Leu Ala Thr Ile Ile Asp Asp Ile Tyr Asp Thr Tyr Gly Ser Ile Glu
            355             360             365

Glu Leu Lys His Phe Thr Glu Val Phe Lys Arg Trp Asp Ser Ser Pro
    370             375             380

Pro Asp Tyr Leu Pro Glu Tyr Met Lys Ile Ala Tyr Ser Ala Leu Tyr
385             390             395                     400

Asp Gly Ile Asn Lys Ser Ala Gln Glu Ala Val Gln Ile Gln Gly Arg
                405             410             415

Asp Thr Leu His Asn Ala Arg Asn Ala Trp Asp Tyr Leu Asp Ala
            420             425             430

Val Met Gln Glu Ala Lys Trp Asn Ser Ile Gly His Met Pro Asn Leu
            435             440             445

Lys Glu Phe Leu Glu Asn Gly Arg Val Ser Ser Gly Thr Arg Val Ile
    450             455             460

Thr Leu Gln Ala Leu Leu Arg Leu Glu Ala Leu Gln Glu Ser Glu Leu
465             470             475             480
```

```
Gln Lys Ile Asp His Pro Ser Lys Phe Asn Tyr Leu Phe Gly Leu Thr
                485                 490                 495

Leu Arg Leu Arg Gly Asp Thr Arg Thr Phe Lys Ala Glu Ala Asn Arg
            500                 505                 510

Gly Glu Val Thr Ser Ser Ile Ala Cys Tyr Leu Lys Glu His Pro Glu
        515                 520                 525

Ser Thr Glu Lys Asp Ala Leu Lys Tyr Leu Gln Phe Met Leu Asp Glu
    530                 535                 540

Asn Leu Lys Glu Leu Asn Leu Glu Tyr Leu Lys Asn Asp Gly Val Pro
545                 550                 555                 560

Ile Cys Ile Lys Asp Phe Ala Tyr Asp Met Ser Arg Cys Phe Glu Val
                565                 570                 575

Phe Tyr Lys Glu Arg Asp Gly Phe Ser Ile Ser Thr Lys Asp Met Lys
            580                 585                 590

Asn His Val Glu Arg Ile Leu Ile Glu Pro Val Glu Met
        595                 600                 605

<210> SEQ ID NO 34
<211> LENGTH: 862
<212> TYPE: PRT
<213> ORGANISM: Taxus baccata

<400> SEQUENCE: 34

Met Ala Gln Leu Ser Phe Asn Ala Ala Leu Lys Met Asn Ala Leu Gly
1               5                   10                  15

Asn Lys Ala Ile His Asp Pro Thr Asn Cys Arg Ala Lys Ser Glu Gly
            20                  25                  30

Gln Met Met Trp Val Cys Ser Lys Ser Gly Arg Thr Arg Val Lys Met
        35                  40                  45

Ser Arg Gly Ser Gly Gly Pro Gly Pro Val Val Met Met Ser Ser Ser
    50                  55                  60

Thr Gly Thr Ser Lys Val Val Ser Glu Thr Ser Ser Thr Ile Val Asp
65                  70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Phe
            100                 105                 110

Gln Glu Arg Ala Asp Glu Leu Val Val Lys Ile Lys Asp Met Phe Asn
        115                 120                 125

Ala Leu Gly Asp Gly Asp Ile Ser Pro Ser Ala Tyr Asp Thr Ala Trp
    130                 135                 140

Val Ala Arg Val Ala Thr Val Ser Ser Asp Gly Ser Glu Lys Pro Arg
145                 150                 155                 160

Phe Pro Gln Ala Leu Asn Trp Val Leu Asn Asn Gln Leu Gln Asp Gly
                165                 170                 175

Ser Trp Gly Ile Glu Ser His Phe Ser Leu Cys Asp Arg Leu Leu Asn
            180                 185                 190

Thr Val Asn Ser Val Ile Ala Leu Ser Val Trp Lys Thr Gly His Ser
        195                 200                 205

Gln Val Glu Gln Gly Thr Glu Phe Ile Ala Glu Asn Leu Arg Leu Leu
    210                 215                 220

Asn Glu Glu Asp Glu Leu Ser Pro Asp Phe Glu Ile Ile Phe Pro Ala
225                 230                 235                 240

Leu Leu Gln Lys Ala Lys Ala Leu Gly Ile Asn Leu Pro Tyr Asp Leu
                245                 250                 255
```

```
Pro Phe Ile Lys Ser Leu Ser Thr Thr Arg Glu Ala Arg Leu Thr Asp
            260                 265                 270

Val Ser Ala Ala Asp Asn Ile Pro Ala Asn Met Leu Asn Ala Leu
    275                 280                 285

Glu Gly Leu Glu Val Ile Asp Trp Asn Lys Ile Met Arg Phe Gln
    290                 295                 300

Ser Lys Asp Gly Ser Phe Leu Ser Pro Ala Ser Thr Ala Cys Val
305                 310                 315                 320

Leu Met Asn Thr Gly Asp Glu Lys Cys Phe Thr Leu Asn Asn Leu
                325                 330                 335

Leu Asp Lys Phe Gly Gly Cys Val Pro Cys Met Tyr Ser Ile Asp Leu
                340                 345                 350

Leu Glu Arg Leu Ser Leu Val Asp Asn Ile Glu His Leu Gly Ile Gly
                355                 360                 365

Arg His Phe Lys Gln Glu Ile Lys Val Ala Leu Asp Tyr Val Tyr Arg
        370                 375                 380

His Trp Ser Glu Arg Gly Ile Gly Trp Gly Arg Asp Ser Leu Val Pro
385                 390                 395                 400

Asp Leu Asn Thr Thr Ala Leu Gly Leu Arg Thr Leu Arg Thr His Gly
                405                 410                 415

Tyr Asp Val Ser Ser Asp Val Leu Asn Asn Phe Lys Asp Glu Asn Gly
                420                 425                 430

Arg Phe Phe Ser Ser Ala Gly Gln Thr His Val Glu Leu Arg Ser Val
                435                 440                 445

Val Asn Leu Phe Arg Ala Ser Asp Leu Ala Phe Pro Asp Glu Gly Ala
        450                 455                 460

Met Asp Asp Ala Arg Lys Phe Ala Glu Pro Tyr Leu Arg Asp Ala Leu
465                 470                 475                 480

Ala Thr Lys Ile Ser Thr Asn Thr Lys Leu Tyr Lys Glu Ile Glu Tyr
                485                 490                 495

Val Val Glu Tyr Pro Trp His Met Ser Ile Pro Arg Leu Glu Ala Arg
                500                 505                 510

Ser Tyr Ile Asp Ser Tyr Asp Asp Tyr Val Trp Gln Arg Lys Thr
        515                 520                 525

Leu Tyr Arg Met Pro Ser Leu Ser Asn Ser Lys Cys Leu Glu Leu Ala
        530                 535                 540

Lys Leu Asp Phe Asn Ile Val Gln Ser Leu His Gln Glu Glu Leu Lys
545                 550                 555                 560

Leu Leu Thr Arg Trp Trp Lys Glu Ser Gly Met Ala Asp Ile Asn Phe
                565                 570                 575

Thr Arg His Arg Val Ala Glu Val Tyr Phe Ser Ser Ala Thr Phe Glu
        580                 585                 590

Pro Glu Tyr Ser Ala Thr Arg Ile Ala Phe Thr Lys Ile Gly Cys Leu
        595                 600                 605

Gln Val Leu Phe Asp Asp Met Ala Asp Ile Phe Ala Thr Leu Asp Glu
    610                 615                 620

Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
                645                 650                 655

Leu Met Glu Glu Val Asn Asn Asp Val Val Lys Val Gln Gly Arg Asp
                660                 665                 670

Met Leu Ala His Ile Arg Lys Pro Trp Glu Leu Tyr Phe Asn Cys Tyr
```

```
                    675                 680                 685
Val Gln Glu Arg Glu Trp Leu Glu Ala Gly Tyr Ile Pro Thr Phe Glu
690                 695                 700

Glu Tyr Leu Lys Thr Tyr Ala Ile Ser Val Gly Leu Gly Pro Cys Thr
705                 710                 715                 720

Leu Gln Pro Ile Leu Leu Met Gly Glu Leu Val Lys Asp Asp Val Val
                725                 730                 735

Glu Lys Val His Tyr Pro Ser Asn Met Phe Glu Leu Val Ser Leu Ser
                740                 745                 750

Trp Arg Leu Thr Asn Asp Thr Lys Thr Tyr Gln Ala Glu Lys Ala Arg
            755                 760                 765

Gly Gln Gln Ala Ser Gly Ile Ala Cys Tyr Met Lys Asp Asn Pro Gly
            770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
                805                 810                 815

Pro Met Gly Cys Lys Ser Phe Ile Phe Asn Leu Arg Leu Cys Val Gln
            820                 825                 830

Ile Phe Tyr Lys Phe Ile Asp Gly Tyr Gly Ile Ala Asn Glu Glu Ile
            835                 840                 845

Lys Asp Tyr Ile Arg Lys Val Tyr Ile Asp Pro Ile Gln Val
850                 855                 860

<210> SEQ ID NO 35
<211> LENGTH: 862
<212> TYPE: PRT
<213> ORGANISM: Taxus x media

<400> SEQUENCE: 35

Met Ala Gln Leu Ser Phe Asn Ala Ala Leu Lys Met Asn Ala Leu Gly
1               5                   10                  15

Asn Lys Ala Ile His Asp Pro Thr Asn Cys Arg Ala Lys Ser Glu Gly
                20                  25                  30

Gln Met Met Trp Val Cys Ser Lys Ser Gly Arg Thr Arg Val Lys Met
            35                  40                  45

Ser Arg Gly Ser Gly Gly Pro Gly Pro Val Val Met Met Ser Ser Ser
50                  55                  60

Thr Gly Thr Ser Lys Val Val Ser Glu Thr Ser Ser Thr Ile Val Asp
65                  70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Phe
                100                 105                 110

Gln Glu Arg Ala Asp Glu Leu Val Val Lys Ile Lys Asp Met Phe Asn
            115                 120                 125

Ala Leu Gly Asp Gly Asp Ile Ser Pro Ser Ala Tyr Asp Thr Ala Trp
        130                 135                 140

Val Ala Arg Val Ala Thr Val Ser Ser Asp Gly Ser Glu Lys Pro Arg
145                 150                 155                 160

Phe Pro Gln Ala Leu Asn Trp Val Leu Asn Asn Gln Leu Gln Asp Gly
                165                 170                 175

Ser Trp Gly Ile Glu Ser His Phe Ser Leu Cys Asp Arg Leu Leu Asn
                180                 185                 190

Thr Val Asn Ser Val Ile Ala Leu Ser Val Trp Lys Thr Gly His Ser
```

```
                195                 200                 205
Gln Val Glu Gln Gly Thr Glu Phe Ile Ala Glu Asn Leu Arg Leu Leu
    210                 215                 220

Asn Glu Glu Asp Glu Leu Ser Pro Asp Phe Glu Ile Ile Phe Pro Ala
225                 230                 235                 240

Leu Leu Gln Lys Ala Lys Ala Leu Gly Ile Asn Leu Pro Tyr Asp Leu
                245                 250                 255

Pro Phe Ile Lys Ser Leu Ser Thr Thr Arg Glu Ala Arg Leu Thr Asp
                260                 265                 270

Val Ser Ala Val Ala Asp Asn Ile Pro Ala Asn Met Leu Asn Ala Leu
            275                 280                 285

Glu Gly Leu Glu Glu Val Ile Asp Trp Asn Lys Ile Met Arg Phe Gln
        290                 295                 300

Ser Lys Asp Gly Ser Phe Leu Ser Ser Pro Ala Ser Thr Ala Cys Val
305                 310                 315                 320

Leu Met Asn Thr Gly Asp Glu Lys Cys Phe Thr Leu Leu Asn Asn Leu
                325                 330                 335

Leu Asp Lys Phe Gly Gly Cys Val Pro Cys Met Tyr Ser Ile Asp Leu
                340                 345                 350

Leu Glu Arg Leu Ser Leu Val Asp Asn Ile Glu His Leu Gly Ile Gly
            355                 360                 365

Arg His Phe Lys Gln Glu Ile Lys Val Ala Leu Asp Tyr Val Tyr Arg
        370                 375                 380

His Trp Ser Glu Arg Gly Ile Gly Trp Gly Arg Asp Ser Leu Val Pro
385                 390                 395                 400

Asp Leu Asn Thr Thr Ala Leu Gly Leu Arg Thr Leu Arg Thr His Gly
                405                 410                 415

Tyr Asp Val Ser Ser Asp Val Leu Asn Asn Phe Lys Asp Glu Asn Gly
                420                 425                 430

Arg Phe Phe Ser Ser Ala Gly Gln Thr His Val Glu Leu Arg Ser Val
            435                 440                 445

Val Asn Leu Phe Arg Ala Ser Asp Leu Ala Phe Pro Asp Glu Gly Ala
        450                 455                 460

Met Asp Asp Ala Arg Lys Phe Ala Glu Pro Tyr Leu Arg Asp Ala Leu
465                 470                 475                 480

Ala Thr Lys Ile Ser Thr Asn Thr Lys Leu Tyr Lys Glu Ile Glu Tyr
                485                 490                 495

Val Val Glu Tyr Pro Trp His Met Ser Ile Pro Arg Leu Glu Ala Arg
                500                 505                 510

Ser Tyr Ile Asp Ser Tyr Asp Asp Tyr Val Trp Gln Arg Lys Thr
            515                 520                 525

Leu Tyr Arg Met Pro Ser Leu Ser Asn Ser Lys Cys Leu Glu Leu Ala
        530                 535                 540

Lys Leu Asp Phe Asn Ile Val Gln Ser Leu His Gln Glu Glu Leu Lys
545                 550                 555                 560

Leu Leu Thr Arg Trp Trp Lys Glu Ser Gly Met Ala Asp Ile Asn Phe
                565                 570                 575

Thr Arg His Arg Val Ala Glu Val Tyr Phe Ser Ser Ala Thr Phe Glu
                580                 585                 590

Pro Glu Tyr Ser Ala Thr Arg Ile Ala Phe Thr Lys Ile Gly Cys Leu
            595                 600                 605

Gln Val Leu Phe Asp Asp Met Ala Asp Ile Phe Ala Thr Leu Asp Glu
        610                 615                 620
```

```
Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
            645                 650                 655

Leu Met Glu Glu Val Asn Asn Asp Val Val Lys Val Gln Gly Arg Asp
        660                 665                 670

Met Leu Ala His Ile Arg Lys Pro Trp Glu Leu Tyr Phe Asn Cys Tyr
    675                 680                 685

Val Gln Glu Arg Glu Trp Leu Glu Ala Gly Tyr Ile Pro Thr Phe Glu
690                 695                 700

Glu Tyr Leu Lys Thr Tyr Ala Ile Ser Val Gly Leu Gly Pro Cys Thr
705                 710                 715                 720

Leu Gln Pro Ile Leu Leu Met Gly Glu Leu Val Lys Asp Asp Val Val
            725                 730                 735

Glu Lys Val His Tyr Pro Ser Asn Met Phe Glu Leu Val Ser Leu Ser
        740                 745                 750

Trp Arg Leu Thr Asn Asp Thr Lys Thr Tyr Gln Ala Glu Lys Ala Arg
    755                 760                 765

Gly Gln Gln Ala Ser Gly Ile Ala Cys Tyr Met Lys Asp Asn Pro Gly
770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
            805                 810                 815

Pro Met Gly Cys Lys Ser Phe Ile Phe Asn Leu Arg Leu Cys Val Gln
        820                 825                 830

Ile Phe Tyr Lys Phe Ile Asp Gly Tyr Gly Ile Ala Asn Glu Glu Ile
    835                 840                 845

Lys Asp Tyr Ile Arg Lys Val Tyr Ile Asp Pro Ile Gln Val
850                 855                 860

<210> SEQ ID NO 36
<211> LENGTH: 862
<212> TYPE: PRT
<213> ORGANISM: Taxus baccata

<400> SEQUENCE: 36

Met Ala Gln Leu Ser Phe Asn Ala Ala Leu Lys Met Asn Ala Leu Gly
1               5                   10                  15

Asn Lys Ala Ile His Asp Pro Thr Asn Cys Arg Ala Lys Ser Glu Arg
            20                  25                  30

Gln Met Met Trp Val Cys Ser Arg Ser Gly Arg Thr Arg Val Lys Met
        35                  40                  45

Ser Arg Gly Ser Gly Gly Pro Gly Pro Val Val Met Met Ser Ser Ser
    50                  55                  60

Thr Gly Thr Ser Lys Val Val Ser Glu Thr Ser Thr Ile Val Asp Asp
65                  70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Tyr
            100                 105                 110

Gln Glu Arg Ala Asp Glu Leu Val Val Lys Ile Lys Asp Met Phe Asn
        115                 120                 125

Ala Leu Gly Asp Gly Asp Ile Ser Pro Ser Ala Tyr Asp Thr Ala Trp
    130                 135                 140
```

-continued

```
Val Ala Arg Val Ala Thr Val Ser Ser Asp Gly Ser Glu Lys Pro Arg
145                 150                 155                 160

Phe Pro Gln Ala Leu Asn Trp Val Leu Asn Gln Leu Gln Asp Gly
            165                 170                 175

Ser Trp Gly Ile Glu Ser His Phe Ser Leu Cys Asp Arg Leu Leu Asn
        180                 185                 190

Thr Val Asn Ser Val Ile Ala Leu Ser Val Trp Lys Thr Gly His Ser
        195                 200                 205

Gln Val Glu Gln Gly Ala Glu Phe Ile Ala Glu Asn Leu Arg Leu Leu
    210                 215                 220

Asn Glu Glu Asp Glu Leu Ser Pro Asp Phe Glu Ile Ile Phe Pro Ala
225                 230                 235                 240

Leu Leu Gln Lys Ala Lys Ala Leu Gly Ile Asn Leu Pro Tyr Asp Leu
                245                 250                 255

Pro Phe Ile Lys Ser Leu Ser Thr Thr Arg Glu Ala Arg Leu Thr Asp
            260                 265                 270

Val Ser Ala Ala Ala Asp Asn Ile Pro Ala Asn Met Leu Asn Ala Leu
        275                 280                 285

Glu Gly Leu Glu Glu Val Ile Asp Trp Asn Lys Ile Met Arg Phe Gln
    290                 295                 300

Ser Lys Asp Gly Ser Phe Leu Ser Ser Pro Ala Ser Thr Ala Cys Val
305                 310                 315                 320

Leu Met Asn Thr Gly Asp Glu Lys Cys Phe Thr Leu Leu Asn Asn Leu
                325                 330                 335

Leu Asp Lys Phe Gly Gly Cys Val Pro Cys Met Tyr Ser Ile Asp Leu
            340                 345                 350

Leu Glu Arg Leu Ser Leu Val Asp Asn Ile Glu His Leu Gly Ile Gly
        355                 360                 365

Arg His Phe Lys Gln Glu Ile Lys Val Ala Leu Asp Tyr Val Tyr Arg
    370                 375                 380

His Trp Ser Glu Arg Gly Ile Gly Trp Gly Arg Asp Ser Leu Val Pro
385                 390                 395                 400

Asp Leu Asn Thr Thr Ala Leu Gly Leu Arg Thr Leu Arg Thr His Gly
                405                 410                 415

Tyr Asp Val Ser Ser Asp Val Leu Asn Asn Phe Lys Asp Glu Asn Gly
            420                 425                 430

Arg Phe Phe Ser Ser Ala Gly Gln Thr His Val Glu Leu Arg Ser Val
        435                 440                 445

Val Asn Leu Phe Arg Ala Ser Asp Leu Ala Phe Pro Asp Glu Gly Ala
    450                 455                 460

Met Asp Asp Ala Arg Lys Phe Ala Glu Pro Tyr Leu Arg Asp Ala Leu
465                 470                 475                 480

Ala Thr Lys Ile Ser Thr Asn Thr Lys Leu Tyr Lys Glu Ile Glu Tyr
                485                 490                 495

Val Val Glu Tyr Pro Trp His Met Ser Ile Pro Arg Leu Glu Ala Arg
            500                 505                 510

Ser Tyr Ile Asp Ser Tyr Asp Asp Tyr Val Trp Gln Arg Lys Thr
        515                 520                 525

Leu Tyr Arg Met Pro Ser Leu Ser Asn Ser Lys Cys Leu Glu Leu Ala
    530                 535                 540

Lys Leu Asp Phe Asn Ile Val Gln Ser Leu His Gln Glu Glu Leu Lys
545                 550                 555                 560

Leu Leu Thr Arg Trp Trp Lys Glu Ser Gly Met Ala Asp Ile Asn Phe
                565                 570                 575
```

```
Thr Arg His Arg Val Ala Glu Val Tyr Phe Ser Ser Ala Thr Phe Glu
            580                 585                 590

Pro Glu Tyr Ser Ala Thr Arg Ile Ala Phe Thr Lys Ile Gly Cys Leu
        595                 600                 605

Gln Val Leu Phe Asp Asp Met Ala Asp Ile Phe Ala Thr Leu Asp Glu
    610                 615                 620

Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
                645                 650                 655

Leu Met Glu Glu Val Asn Asn Asp Val Val Lys Val Gln Gly Arg Asp
            660                 665                 670

Met Leu Ala His Ile Arg Lys Pro Trp Glu Leu Tyr Phe Asn Cys Tyr
        675                 680                 685

Val Gln Glu Arg Glu Trp Leu Glu Ala Gly Tyr Ile Pro Thr Phe Glu
    690                 695                 700

Glu Tyr Leu Lys Thr Tyr Ala Ile Ser Val Gly Leu Gly Pro Cys Thr
705                 710                 715                 720

Leu Gln Pro Ile Leu Leu Met Gly Glu Leu Val Lys Asp Asp Val Val
                725                 730                 735

Glu Lys Val His Tyr Pro Ser Asn Met Phe Glu Leu Val Ser Leu Ser
            740                 745                 750

Trp Arg Leu Thr Asn Asp Thr Lys Thr Tyr Gln Ala Glu Lys Ala Arg
        755                 760                 765

Gly Gln Gln Ala Ser Gly Ile Ala Cys Tyr Met Lys Asp Asn Pro Gly
    770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
                805                 810                 815

Pro Met Gly Cys Lys Ser Phe Ile Phe Asn Leu Arg Leu Cys Val Gln
            820                 825                 830

Ile Phe Tyr Lys Phe Ile Asp Gly Tyr Gly Ile Ala Asn Glu Glu Ile
        835                 840                 845

Lys Asp Tyr Ile Arg Lys Val Tyr Ile Asp Pro Ile Gln Val
    850                 855                 860

<210> SEQ ID NO 37
<211> LENGTH: 873
<212> TYPE: PRT
<213> ORGANISM: Ginkgo biloba

<400> SEQUENCE: 37

Met Ala Gly Val Leu Phe Ala Asn Leu Pro Cys Ser Leu Gln Leu Ser
1               5                   10                  15

Pro Lys Val Pro Phe Arg Gln Ser Thr Asn Ile Leu Ile Pro Phe His
            20                  25                  30

Lys Arg Ser Ser Phe Gly Phe Asn Ala Gln His Cys Val Arg Ser His
        35                  40                  45

Leu Arg Leu Arg Trp Asn Cys Val Gly Ile His Ala Ser Ala Ala Glu
    50                  55                  60

Thr Arg Pro Asp Gln Leu Pro Gln Glu Glu Arg Phe Val Ser Arg Leu
65                  70                  75                  80

Asn Ala Asp Tyr His Pro Ala Val Trp Lys Asp Phe Ile Asp Ser
                85                  90                  95
```

```
Leu Thr Ser Pro Asn Ser His Ala Thr Ser Lys Ser Ser Val Asp Glu
            100                 105                 110

Thr Ile Asn Lys Arg Ile Gln Thr Leu Val Lys Glu Ile Gln Cys Met
        115                 120                 125

Phe Gln Ser Met Gly Asp Gly Glu Thr Asn Pro Ser Ala Tyr Asp Thr
    130                 135                 140

Ala Trp Val Ala Arg Ile Pro Ser Ile Asp Gly Ser Ala Pro Gln
145                 150                 155                 160

Phe Pro Gln Thr Leu Gln Trp Ile Leu Asn Asn Gln Leu Pro Asp Gly
            165                 170                 175

Ser Trp Gly Glu Glu Cys Ile Phe Leu Ala Tyr Asp Arg Val Leu Asn
            180                 185                 190

Thr Leu Ala Cys Leu Leu Thr Leu Lys Ile Trp Asn Lys Gly Asp Ile
        195                 200                 205

Gln Val Gln Lys Gly Val Glu Phe Val Arg Lys His Met Glu Glu Met
    210                 215                 220

Lys Asp Glu Ala Asp Asn His Arg Pro Ser Gly Phe Glu Val Val Phe
225                 230                 235                 240

Pro Ala Met Leu Asp Glu Ala Lys Ser Leu Gly Leu Asp Leu Pro Tyr
            245                 250                 255

His Leu Pro Phe Ile Ser Gln Ile His Gln Lys Arg Gln Lys Lys Leu
            260                 265                 270

Gln Lys Ile Pro Leu Asn Val Leu His Asn His Gln Thr Ala Leu Leu
        275                 280                 285

Tyr Ser Leu Glu Gly Leu Gln Asp Val Val Asp Trp Gln Glu Ile Thr
    290                 295                 300

Asn Leu Gln Ser Arg Asp Gly Ser Phe Leu Ser Ser Pro Ala Ser Thr
305                 310                 315                 320

Ala Cys Val Phe Met His Thr Gln Asn Lys Arg Cys Leu His Phe Leu
            325                 330                 335

Asn Phe Val Leu Ser Lys Phe Gly Asp Tyr Val Pro Cys His Tyr Pro
            340                 345                 350

Leu Asp Leu Phe Glu Arg Leu Trp Ala Val Asp Thr Val Glu Arg Leu
        355                 360                 365

Gly Ile Asp Arg Tyr Phe Lys Lys Glu Ile Lys Glu Ser Leu Asp Tyr
    370                 375                 380

Val Tyr Arg Tyr Trp Asp Ala Glu Arg Gly Val Gly Trp Ala Arg Cys
385                 390                 395                 400

Asn Pro Ile Pro Asp Val Asp Asp Thr Ala Met Gly Leu Arg Ile Leu
            405                 410                 415

Arg Leu His Gly Tyr Asn Val Ser Ser Asp Val Leu Glu Asn Phe Arg
            420                 425                 430

Asp Glu Lys Gly Asp Phe Phe Cys Phe Ala Gly Gln Thr Gln Ile Gly
        435                 440                 445

Val Thr Asp Asn Leu Asn Leu Tyr Arg Cys Ser Gln Val Cys Phe Pro
    450                 455                 460

Gly Glu Lys Ile Met Glu Glu Ala Lys Thr Phe Thr Thr Asn His Leu
465                 470                 475                 480

Gln Asn Ala Leu Ala Lys Asn Asn Ala Phe Asp Lys Trp Ala Val Lys
            485                 490                 495

Lys Asp Leu Pro Gly Glu Val Gly Tyr Ala Ile Lys Tyr Pro Trp His
            500                 505                 510

Arg Ser Met Pro Arg Leu Glu Ala Arg Ser Tyr Ile Glu Gln Phe Gly
```

Ser Asn Asp Val Trp Leu Gly Lys Thr Val Tyr Lys Met Leu Tyr Val
                530             535             540

Ser Asn Glu Lys Tyr Leu Glu Leu Ala Lys Leu Asp Phe Asn Met Val
545             550             555             560

Gln Ala Leu His Gln Lys Glu Thr Gln His Ile Val Ser Trp Trp Arg
                565             570             575

Glu Ser Gly Phe Asn Asp Leu Thr Phe Thr Arg Gln Arg Pro Val Glu
                580             585             590

Met Tyr Phe Ser Val Ala Val Ser Met Phe Glu Pro Glu Phe Ala Ala
                595             600             605

Cys Arg Ile Ala Tyr Ala Lys Thr Ser Cys Leu Ala Val Ile Leu Asp
610             615             620

Asp Leu Tyr Asp Thr His Gly Ser Leu Asp Asp Leu Lys Leu Phe Ser
625             630             635             640

Glu Ala Val Arg Arg Trp Asp Ile Ser Val Leu Asp Ser Val Arg Asp
                645             650             655

Asn Gln Leu Lys Val Cys Phe Leu Gly Leu Tyr Asn Thr Val Asn Gly
                660             665             670

Phe Gly Lys Asp Gly Leu Lys Glu Gln Gly Arg Asp Val Leu Gly Tyr
                675             680             685

Leu Arg Lys Val Trp Glu Gly Leu Leu Ala Ser Tyr Thr Lys Glu Ala
690             695             700

Glu Trp Ser Ala Ala Lys Tyr Val Pro Thr Phe Asn Glu Tyr Val Glu
705             710             715             720

Asn Ala Lys Val Ser Ile Ala Leu Ala Thr Val Val Leu Asn Ser Ile
                725             730             735

Phe Phe Thr Gly Glu Leu Leu Pro Asp Tyr Ile Leu Gln Gln Val Asp
                740             745             750

Leu Arg Ser Lys Phe Leu His Leu Val Ser Leu Thr Gly Arg Leu Ile
                755             760             765

Asn Asp Thr Lys Thr Tyr Gln Ala Glu Arg Asn Arg Gly Glu Leu Val
770             775             780

Ser Ser Val Gln Cys Tyr Met Arg Glu Asn Pro Glu Cys Thr Glu Glu
785             790             795             800

Glu Ala Leu Ser His Val Tyr Gly Ile Ile Asp Asn Ala Leu Lys Glu
                805             810             815

Leu Asn Trp Glu Leu Ala Asn Pro Ala Ser Asn Ala Pro Leu Cys Val
                820             825             830

Arg Arg Leu Leu Phe Asn Thr Ala Arg Val Met Gln Leu Phe Tyr Met
                835             840             845

Tyr Arg Asp Gly Phe Gly Ile Ser Asp Lys Glu Met Lys Asp His Val
850             855             860

Ser Arg Thr Leu Phe Asp Pro Val Ala
865             870

<210> SEQ ID NO 38
<211> LENGTH: 862
<212> TYPE: PRT
<213> ORGANISM: Taxus canadensis

<400> SEQUENCE: 38

Met Ala Gln Leu Ser Phe Asn Ala Ala Leu Lys Met Asn Ala Leu Gly
1               5                   10                  15

Asn Lys Ala Ile His Asp Pro Thr Asn Cys Arg Ala Lys Ser Glu Gly

```
                  20                  25                  30
Gln Met Met Trp Val Cys Ser Lys Ser Gly Arg Thr Arg Val Lys Met
             35                  40                  45
Ser Arg Gly Ser Gly Gly Pro Gly Pro Val Val Met Met Ser Ser Ser
 50                  55                  60
Thr Gly Thr Ser Lys Val Val Ser Glu Thr Ser Ser Thr Ile Val Asp
 65                  70                  75                  80
Asp Ile Pro Arg Leu Ser Ala Asn Tyr His Gly Asp Leu Trp His His
                 85                  90                  95
Asn Val Ile Gln Thr Leu Glu Thr Pro Phe Arg Glu Ser Ser Thr Tyr
                100                 105                 110
Gln Glu Arg Ala Asp Glu Leu Val Lys Ile Lys Asp Met Phe Asn
            115                 120                 125
Ala Leu Gly Asp Gly Asp Ile Ser Pro Ser Ala Tyr Asp Thr Ala Trp
            130                 135                 140
Val Ala Arg Val Ala Thr Ile Ser Ser Asp Gly Ser Glu Lys Pro Arg
145                 150                 155                 160
Phe Pro Gln Ala Leu Asn Trp Val Phe Asn Asn Gln Leu Gln Asp Gly
                165                 170                 175
Ser Trp Gly Ile Glu Ser His Phe Ser Leu Cys Asp Arg Leu Leu Asn
                180                 185                 190
Thr Thr Asn Ser Val Ile Ala Leu Ser Val Trp Lys Thr Gly His Ser
                195                 200                 205
Gln Val Glu Gln Gly Thr Glu Phe Ile Ala Glu Asn Leu Arg Leu Leu
            210                 215                 220
Asn Glu Glu Asp Glu Leu Ser Pro Asp Phe Glu Ile Ile Phe Pro Ala
225                 230                 235                 240
Leu Leu Gln Lys Ala Lys Ala Leu Gly Ile Asn Leu Pro Tyr Asp Leu
                245                 250                 255
Pro Phe Ile Lys Ser Leu Ser Thr Thr Arg Glu Ala Arg Leu Thr Asp
                260                 265                 270
Val Ser Ala Ala Ala Asp Asn Ile Pro Ala Asn Met Leu Asn Ala Leu
            275                 280                 285
Glu Gly Leu Glu Glu Val Ile Asp Trp Asn Lys Ile Met Arg Phe Gln
            290                 295                 300
Ser Lys Asp Gly Ser Phe Leu Ser Ser Pro Ala Ser Thr Ala Cys Val
305                 310                 315                 320
Leu Met Asn Ile Gly Asp Glu Lys Cys Phe Thr Phe Leu Asn Asn Leu
                325                 330                 335
Leu Asp Lys Phe Gly Gly Cys Val Pro Cys Met Tyr Ser Ile Asp Leu
                340                 345                 350
Leu Glu Arg Leu Ser Leu Val Asp Asn Ile Glu His Leu Gly Ile Gly
            355                 360                 365
Arg His Phe Lys Gln Glu Ile Lys Gly Ala Leu Asp Tyr Val Tyr Arg
            370                 375                 380
His Trp Ser Glu Arg Gly Ile Gly Trp Gly Arg Asp Ser Leu Val Pro
385                 390                 395                 400
Asp Leu Asn Thr Thr Ala Leu Gly Leu Arg Thr Leu Arg Thr His Gly
                405                 410                 415
Tyr Asp Val Ser Ser Asp Val Leu Asn Asn Phe Lys Asp Glu Asn Gly
                420                 425                 430
Arg Phe Phe Ser Ser Ala Gly Gln Thr His Val Glu Leu Arg Ser Val
            435                 440                 445
```

```
Val Asn Leu Phe Arg Ala Ser Asp Leu Ala Phe Pro Asp Glu Gly Val
    450                 455                 460

Met Asp Asp Ala Arg Lys Phe Ala Glu Pro Tyr Leu Arg Asp Ala Leu
465                 470                 475                 480

Ala Thr Lys Ile Ser Thr Asn Thr Lys Leu Phe Lys Glu Ile Glu Tyr
                485                 490                 495

Val Val Glu Tyr Pro Trp His Met Ser Ile Pro Arg Leu Glu Ala Gly
                500                 505                 510

Ser Tyr Ile Asp Ser Tyr Asp Asp Tyr Val Trp Gln Arg Lys Thr
                515                 520                 525

Leu Tyr Arg Met Pro Ser Leu Ser Asn Ser Lys Cys Leu Glu Leu Ala
                530                 535                 540

Lys Leu Asp Phe Asn Ile Val Gln Ser Leu His Gln Glu Leu Lys
545                 550                 555                 560

Leu Leu Thr Arg Trp Trp Lys Glu Ser Gly Met Ala Asp Ile Asn Phe
                565                 570                 575

Thr Arg His Arg Val Ala Glu Val Tyr Phe Ser Ser Ala Thr Phe Glu
                580                 585                 590

Pro Glu Tyr Ser Ala Thr Arg Ile Ala Phe Thr Lys Ile Gly Cys Leu
                595                 600                 605

Gln Val Leu Phe Asp Asp Met Ala Asp Ile Phe Ala Thr Leu Asp Glu
                610                 615                 620

Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
                645                 650                 655

Leu Met Glu Glu Val Asn Asn Asp Val Val Lys Val Gln Gly Arg Asp
                660                 665                 670

Met Leu Ala His Ile Arg Lys Pro Trp Glu Leu Tyr Phe Asn Cys Tyr
                675                 680                 685

Val Gln Glu Arg Glu Trp Leu Glu Ala Gly Tyr Ile Pro Thr Phe Glu
                690                 695                 700

Glu Tyr Leu Lys Thr Tyr Ala Ile Ser Val Gly Leu Gly Pro Cys Thr
705                 710                 715                 720

Leu Gln Pro Ile Leu Leu Met Gly Glu Leu Val Lys Asp Asp Val Val
                725                 730                 735

Glu Lys Val His Tyr Pro Ser Asn Met Phe Glu Leu Val Ser Leu Ser
                740                 745                 750

Trp Arg Leu Thr Asn Asp Thr Lys Thr Tyr Gln Ala Glu Lys Ala Arg
                755                 760                 765

Gly Gln Gln Ala Ser Gly Ile Ala Cys Tyr Met Lys Asp Asn Pro Gly
                770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
                805                 810                 815

Pro Met Gly Cys Lys Ser Phe Ile Phe Asn Leu Arg Leu Cys Val Gln
                820                 825                 830

Ile Phe Tyr Lys Phe Ile Asp Gly Tyr Gly Ile Ala Asn Glu Glu Ile
                835                 840                 845

Lys Asp Tyr Ile Arg Lys Val Tyr Ile Asp Pro Ile Gln Val
850                 855                 860

<210> SEQ ID NO 39
```

```
<211> LENGTH: 862
<212> TYPE: PRT
<213> ORGANISM: Taxus chinensis var. mairei

<400> SEQUENCE: 39
```

| | | | | | | | | | | | | | | |
|---|---|---|---|---|---|---|---|---|---|---|---|---|---|---|
| Met | Ala | Gln | Leu | Ser | Phe | Asn | Ala | Ala | Leu | Lys | Met | Asn | Ala | Leu | Gly |
| 1 | | | | 5 | | | | | 10 | | | | | 15 | |
| Asn | Lys | Ala | Ile | His | Asp | Pro | Thr | Asn | Cys | Arg | Ala | Lys | Ser | Glu | Gly |
| | | | 20 | | | | | 25 | | | | | 30 | | |
| Gln | Met | Met | Trp | Val | Cys | Ser | Lys | Ser | Gly | Arg | Pro | Arg | Val | Lys | Met |
| | | 35 | | | | | 40 | | | | | 45 | | | |
| Ser | Arg | Gly | Ser | Gly | Gly | Pro | Gly | Pro | Val | Val | Met | Met | Ser | Ser | Ser |
| | 50 | | | | | 55 | | | | | 60 | | | | |
| Thr | Gly | Thr | Ser | Lys | Val | Val | Ser | Glu | Thr | Ser | Ser | Thr | Ile | Val | Asp |
| 65 | | | | | 70 | | | | | 75 | | | | | 80 |
| Asp | Ile | Pro | Arg | Leu | Ser | Ala | Asn | Tyr | His | Gly | Asp | Leu | Trp | His | His |
| | | | | 85 | | | | | 90 | | | | | 95 | |
| Asn | Val | Ile | Gln | Thr | Leu | Glu | Thr | Pro | Phe | Arg | Glu | Ser | Ser | Thr | Tyr |
| | | | 100 | | | | | 105 | | | | | 110 | | |
| Gln | Glu | Arg | Ala | Asp | Glu | Leu | Val | Val | Lys | Ile | Lys | Asp | Met | Phe | Asn |
| | | 115 | | | | | 120 | | | | | 125 | | | |
| Ala | Leu | Gly | Asp | Gly | Asp | Ile | Ser | Pro | Ser | Ala | Tyr | Asp | Thr | Ala | Trp |
| | 130 | | | | | 135 | | | | | 140 | | | | |
| Val | Ala | Arg | Val | Ala | Thr | Ile | Ser | Ser | Asp | Gly | Ser | Glu | Lys | Pro | Arg |
| 145 | | | | | 150 | | | | | 155 | | | | | 160 |
| Phe | Pro | Gln | Ala | Leu | Asn | Trp | Val | Leu | Asn | Asn | Gln | Leu | Gln | Asp | Gly |
| | | | | 165 | | | | | 170 | | | | | 175 | |
| Ser | Trp | Gly | Ile | Glu | Ser | His | Phe | Ser | Leu | Cys | Asp | Arg | Leu | Leu | Asn |
| | | | 180 | | | | | 185 | | | | | 190 | | |
| Thr | Ile | Asn | Ser | Val | Ile | Val | Leu | Ser | Val | Trp | Lys | Thr | Gly | His | Ser |
| | | 195 | | | | | 200 | | | | | 205 | | | |
| Gln | Val | Glu | Gln | Gly | Thr | Glu | Phe | Ile | Ala | Glu | Asn | Leu | Arg | Leu | Leu |
| | 210 | | | | | 215 | | | | | 220 | | | | |
| Asn | Glu | Glu | Asp | Glu | Leu | Ser | Pro | Asp | Phe | Glu | Ile | Ile | Phe | Pro | Ala |
| 225 | | | | | 230 | | | | | 235 | | | | | 240 |
| Leu | Leu | Gln | Lys | Ala | Lys | Ala | Leu | Gly | Ile | Asn | Leu | Pro | Tyr | Asp | Leu |
| | | | | 245 | | | | | 250 | | | | | 255 | |
| Pro | Phe | Ile | Lys | Tyr | Leu | Ser | Thr | Thr | Arg | Glu | Ala | Arg | Leu | Thr | Asp |
| | | | 260 | | | | | 265 | | | | | 270 | | |
| Val | Ser | Ala | Ala | Ala | Asp | Asn | Ile | Pro | Ala | Asn | Met | Leu | Asn | Ala | Leu |
| | | 275 | | | | | 280 | | | | | 285 | | | |
| Glu | Gly | Leu | Glu | Glu | Val | Ile | Asp | Trp | Lys | Lys | Ile | Met | Arg | Phe | Arg |
| | 290 | | | | | 295 | | | | | 300 | | | | |
| Ser | Lys | Asp | Gly | Ser | Phe | Leu | Ser | Ser | Pro | Ala | Ser | Thr | Ala | Cys | Val |
| 305 | | | | | 310 | | | | | 315 | | | | | 320 |
| Leu | Met | Asn | Thr | Gly | Asp | Glu | Lys | Cys | Phe | Thr | Phe | Leu | Asn | Asn | Leu |
| | | | | 325 | | | | | 330 | | | | | 335 | |
| Leu | Asp | Lys | Phe | Gly | Gly | Cys | Val | Pro | Cys | Met | Tyr | Ser | Ile | Asp | Leu |
| | | | 340 | | | | | 345 | | | | | 350 | | |
| Leu | Glu | Arg | Leu | Ser | Leu | Val | Asp | Asn | Ile | Glu | His | Leu | Gly | Ile | Gly |
| | | 355 | | | | | 360 | | | | | 365 | | | |
| Arg | His | Phe | Lys | Gln | Glu | Ile | Lys | Val | Ala | Leu | Asp | Tyr | Val | Tyr | Arg |
| | 370 | | | | | 375 | | | | | 380 | | | | |
| His | Trp | Ser | Glu | Arg | Gly | Ile | Gly | Trp | Gly | Arg | Asp | Cys | Leu | Val | Pro |
| 385 | | | | | 390 | | | | | 395 | | | | | 400 |

```
Asp Leu Asn Thr Thr Ala Leu Gly Leu Arg Thr Leu Arg Thr His Gly
                405                 410                 415

Tyr Asp Val Ser Ser Asp Val Leu Asn Asn Phe Lys Asp Glu Asn Gly
            420                 425                 430

Arg Phe Phe Ser Ser Ala Gly Gln Thr His Val Glu Leu Arg Ser Val
            435                 440                 445

Val Asn Leu Phe Arg Ala Ser Asp Leu Ala Phe Pro Asp Glu Gly Ala
        450                 455                 460

Met Asp Asp Ala Arg Lys Phe Ala Glu Pro Tyr Leu Arg Asp Ala Leu
465                 470                 475                 480

Ala Thr Lys Ile Ser Thr Asn Thr Lys Leu Phe Lys Glu Ile Glu Tyr
                485                 490                 495

Val Val Glu Tyr Pro Trp His Met Ser Ile Pro Arg Leu Glu Ala Arg
            500                 505                 510

Ser Tyr Ile Asp Ser Tyr Asp Asp Tyr Val Trp Glu Arg Lys Thr
        515                 520                 525

Leu Tyr Arg Met Pro Ser Leu Ser Asn Ser Lys Cys Leu Glu Leu Ala
530                 535                 540

Lys Leu Asp Phe Asn Ile Val Gln Ser Leu His Gln Glu Glu Leu Lys
545                 550                 555                 560

Leu Leu Thr Arg Trp Trp Lys Glu Ser Gly Met Ala Asp Ile Asn Phe
                565                 570                 575

Thr Arg His Arg Val Ala Glu Val Tyr Phe Ser Ser Ala Thr Phe Glu
            580                 585                 590

Pro Glu Tyr Ser Ala Thr Arg Ile Ala Phe Thr Lys Ile Gly Cys Leu
            595                 600                 605

Gln Val Leu Phe Asp Asp Met Ala Asp Ile Phe Ala Thr Leu Asp Glu
        610                 615                 620

Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
                645                 650                 655

Leu Met Glu Glu Val Asn Asn Asp Val Val Lys Val Gln Gly Arg Asp
            660                 665                 670

Met Leu Ala His Ile Arg Lys Pro Trp Glu Leu Tyr Phe Asn Cys Tyr
            675                 680                 685

Val Gln Glu Arg Glu Trp Leu Asp Ala Gly Tyr Ile Pro Thr Phe Glu
        690                 695                 700

Glu Tyr Leu Lys Thr Tyr Ala Ile Ser Val Gly Leu Gly Pro Cys Thr
705                 710                 715                 720

Pro Gln Pro Ile Leu Leu Met Gly Glu Leu Val Lys Asp Asp Val Val
                725                 730                 735

Glu Lys Val His Tyr Pro Ser Asn Met Phe Glu Leu Val Ser Leu Ser
            740                 745                 750

Trp Arg Leu Thr Asn Asp Thr Lys Thr Tyr Gln Ala Glu Lys Ala Arg
            755                 760                 765

Gly Gln Gln Ala Ser Gly Ile Ala Cys Tyr Met Lys Asp Asn Pro Gly
        770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
                805                 810                 815

Pro Met Gly Cys Lys Ser Phe Ile Phe Asn Leu Arg Leu Cys Val Gln
```

```
                         820                 825                 830
Ile Phe Tyr Lys Phe Ile Asp Gly Tyr Gly Ile Ala Asn Glu Glu Ile
            835                 840                 845

Lys Asp Tyr Ile Arg Lys Val Tyr Ile Asp Pro Ile Gln Val
    850                 855                 860

<210> SEQ ID NO 40
<211> LENGTH: 862
<212> TYPE: PRT
<213> ORGANISM: Taxus chinensis

<400> SEQUENCE: 40

Met Ala Gln Leu Ser Phe Asn Ala Ala Leu Lys Met Asn Ala Leu Gly
1               5                   10                  15

Asn Lys Ala Ile His Asp Pro Thr Asn Cys Arg Ala Lys Ser Glu Gly
            20                  25                  30

Gln Met Met Trp Val Cys Ser Lys Ser Gly Arg Thr Arg Val Lys Met
        35                  40                  45

Ser Arg Gly Ser Gly Pro Gly Pro Val Val Met Met Ser Ser Ser
    50                  55                  60

Thr Gly Thr Ser Lys Val Val Ser Glu Thr Ser Thr Ile Val Asp
65                  70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Tyr
            100                 105                 110

Gln Glu Arg Ala Asp Glu Leu Val Val Lys Ile Lys Asp Met Phe Asn
        115                 120                 125

Ala Leu Gly Asp Gly Asp Ile Ser Pro Ser Ala Tyr Asp Thr Ala Trp
    130                 135                 140

Val Ala Arg Val Ala Thr Ile Ser Ser Asp Gly Ser Glu Lys Pro Arg
145                 150                 155                 160

Phe Pro Gln Ala Leu Asn Trp Val Phe Asn Asn Gln Leu Gln Asp Gly
                165                 170                 175

Ser Trp Gly Ile Glu Ser His Phe Ser Leu Cys Asp Arg Leu Leu Asn
            180                 185                 190

Thr Thr Asn Ser Val Ile Ala Leu Ser Val Trp Lys Thr Gly His Ser
        195                 200                 205

Gln Val Glu Gln Gly Thr Glu Phe Ile Ala Glu Asn Leu Arg Leu Leu
    210                 215                 220

Asn Glu Glu Asp Glu Leu Ser Pro Asp Phe Glu Ile Ile Phe Pro Ala
225                 230                 235                 240

Leu Leu Gln Lys Ala Lys Ala Leu Gly Ile Asn Leu Pro Tyr Asp Leu
                245                 250                 255

Pro Phe Ile Lys Tyr Leu Ser Thr Thr Arg Glu Ala Arg Leu Thr Asp
            260                 265                 270

Val Ser Ala Ala Ala Asp Asn Ile Pro Ala Asn Met Leu Asn Ala Leu
        275                 280                 285

Glu Gly Leu Glu Glu Val Met Asp Trp Lys Lys Ile Met Arg Phe Gln
    290                 295                 300

Ser Lys Asp Gly Ser Phe Leu Ser Ser Pro Ala Ser Thr Ala Cys Val
305                 310                 315                 320

Leu Met Asn Thr Gly Asp Glu Lys Cys Phe Thr Phe Leu Asn Asn Leu
                325                 330                 335

Leu Val Lys Phe Gly Gly Cys Val Pro Cys Met Tyr Ser Ile Asp Leu
```

```
                    340                 345                 350
Leu Glu Arg Leu Ser Leu Val Asp Asn Ile Glu His Leu Gly Ile Gly
            355                 360                 365

Arg His Phe Lys Gln Glu Ile Lys Val Ala Leu Asp Tyr Val Tyr Arg
    370                 375                 380

His Trp Ser Glu Arg Gly Ile Gly Trp Gly Arg Asp Ser Leu Val Pro
385                 390                 395                 400

Asp Leu Asn Thr Thr Ala Leu Gly Leu Arg Thr Leu Arg Thr His Gly
            405                 410                 415

Tyr Asp Val Ser Ser Asp Val Leu Asn Asn Phe Lys Asp Glu Asn Gly
            420                 425                 430

Arg Phe Phe Ser Ser Ala Gly Gln Thr His Val Glu Leu Arg Ser Val
            435                 440                 445

Val Ile Leu Phe Arg Ala Ser Asp Leu Ala Phe Pro Asp Glu Gly Ala
            450                 455                 460

Met Asp Asp Ala Arg Lys Phe Ala Glu Pro Tyr Leu Arg Asp Ala Leu
465                 470                 475                 480

Ala Thr Lys Ile Ser Thr Asn Thr Lys Leu Phe Lys Glu Ile Glu Tyr
            485                 490                 495

Val Val Glu Tyr Pro Trp His Met Ser Ile Pro Arg Ser Glu Ala Arg
            500                 505                 510

Ser Tyr Ile Asp Ser Tyr Asp Asp Tyr Val Trp Glu Arg Lys Thr
            515                 520                 525

Leu Tyr Arg Met Pro Ser Leu Ser Asn Ser Lys Cys Leu Glu Leu Ala
            530                 535                 540

Lys Leu Asp Phe Asn Ile Val Gln Ser Leu His Gln Glu Glu Leu Lys
545                 550                 555                 560

Leu Leu Thr Arg Trp Trp Lys Glu Ser Gly Met Ala Asp Ile Asn Phe
            565                 570                 575

Thr Arg His Arg Val Ala Glu Val Tyr Phe Ser Ser Ala Thr Phe Glu
            580                 585                 590

Pro Glu Tyr Ser Ala Thr Arg Ile Ala Phe Thr Lys Ile Gly Cys Leu
            595                 600                 605

Gln Val Leu Phe Asp Asp Met Ala Asp Ile Phe Ala Thr Leu Asp Glu
            610                 615                 620

Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
            645                 650                 655

Leu Ile Glu Glu Val Asn Asn Asp Val Val Lys Val Gln Gly Arg Asp
            660                 665                 670

Met Leu Ala His Ile Arg Lys Pro Trp Glu Leu Tyr Phe Asn Cys Tyr
            675                 680                 685

Val Gln Glu Arg Glu Trp Leu Asp Ala Gly Tyr Ile Pro Thr Phe Glu
            690                 695                 700

Glu Tyr Leu Lys Thr Tyr Ala Ile Ser Val Gly Leu Gly Pro Cys Thr
705                 710                 715                 720

Leu Gln Pro Ile Leu Leu Met Gly Glu Leu Val Lys Asp Val Val
            725                 730                 735

Glu Lys Val His Tyr Pro Ser Asn Met Phe Glu Leu Val Ser Leu Ser
            740                 745                 750

Trp Arg Leu Thr Asn Asp Thr Lys Thr Tyr Gln Ala Glu Lys Ala Arg
            755                 760                 765
```

-continued

```
Gly Gln Gln Ala Ser Gly Ile Ala Cys Tyr Met Lys Asp Asn Leu Gly
        770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
                    805                 810                 815

Pro Met Gly Cys Lys Ser Phe Ile Phe Asn Leu Arg Leu Cys Val Gln
                820                 825                 830

Ile Phe Tyr Lys Phe Ile Asp Gly Tyr Gly Ile Ala Asn Glu Glu Ile
            835                 840                 845

Lys Asp Tyr Ile Arg Lys Val Tyr Ile Asp Pro Ile Gln Val
850                 855                 860

<210> SEQ ID NO 41
<211> LENGTH: 850
<212> TYPE: PRT
<213> ORGANISM: Pinus taeda

<400> SEQUENCE: 41

Met Ala Leu Pro Ser Ser Leu Ser Ser Gln Ile His Thr Gly Ala
 1                5                 10                 15

Thr Thr Gln Cys Ile Pro His Phe His Gly Ser Leu Asn Ala Gly Thr
                20                 25                 30

Ser Ala Gly Lys Arg Arg Ser Leu Tyr Leu Arg Trp Gly Lys Gly Pro
            35                 40                 45

Ser Lys Ile Val Ala Cys Ala Gly Gln Asp Pro Phe Ser Val Pro Thr
 50                 55                 60

Leu Val Lys Arg Glu Phe Pro Pro Gly Phe Trp Lys Asp His Val Ile
65                 70                 75                 80

Glu Ser Leu Met Pro Ser Tyr Lys Val Ala Pro Ser Asp Glu Lys Arg
                85                 90                 95

Ile Glu Thr Leu Ile Thr Glu Ile Lys Asn Met Phe Arg Ser Met Gly
            100                 105                 110

Tyr Gly Glu Thr Asn Pro Ser Ala Tyr Asp Thr Ala Trp Val Ala Arg
        115                 120                 125

Ile Pro Ala Val Asp Gly Ser Glu Lys Pro Gln Phe Pro Glu Thr Leu
    130                 135                 140

Glu Trp Ile Leu Gln Asn Gln Leu Lys Asp Gly Ser Trp Gly Glu Glu
145                 150                 155                 160

Phe Tyr Phe Leu Ala Tyr Asp Arg Ile Leu Ala Thr Leu Ala Cys Ile
                165                 170                 175

Ile Thr Leu Thr Ile Trp Gln Thr Gly Asp Thr Gln Val Gln Lys Gly
            180                 185                 190

Ile Glu Phe Phe Lys Thr Gln Ala Gly Lys Ile Glu Glu Glu Ala Asp
        195                 200                 205

Ser His Arg Pro Ser Gly Phe Glu Ile Val Phe Pro Ala Met Leu Lys
    210                 215                 220

Glu Ala Lys Ala Leu Gly Leu Ala Leu Pro Tyr Glu Leu Pro Phe Ile
225                 230                 235                 240

Gln Gln Ile Ile Glu Lys Arg Glu Ala Lys Leu Gln Arg Leu Pro Pro
                245                 250                 255

Asp Leu Leu Tyr Ala Leu Pro Thr Thr Leu Leu Tyr Ser Leu Glu Gly
            260                 265                 270

Leu Gln Glu Ile Val Asp Trp Glu Lys Ile Met Lys Leu Gln Ser Lys
        275                 280                 285
```

```
Asp Gly Ser Phe Leu Ser Ser Pro Ala Ser Thr Ala Ala Val Phe Met
    290                 295                 300

Arg Thr Gly Asn Lys Lys Cys Leu Glu Phe Leu Asn Phe Val Leu Lys
305                 310                 315                 320

Lys Phe Gly Asn His Val Pro Cys His Tyr Pro Leu Asp Leu Phe Glu
                325                 330                 335

Arg Leu Trp Ala Val Asp Thr Val Glu Arg Leu Gly Ile Asp His His
            340                 345                 350

Phe Lys Glu Glu Ile Lys Asp Ala Leu Asp Tyr Val Tyr Ser His Trp
        355                 360                 365

Asp Glu Arg Gly Ile Gly Trp Ala Arg Glu Asn Pro Val Pro Asp Ile
    370                 375                 380

Asp Asp Thr Ala Met Gly Leu Arg Ile Leu Arg Leu His Gly Tyr Asn
385                 390                 395                 400

Val Ser Ser Asp Val Leu Lys Thr Phe Arg Asp Glu Asn Gly Glu Phe
                405                 410                 415

Phe Cys Phe Leu Gly Gln Thr Gln Arg Gly Val Thr Asp Met Leu Asn
            420                 425                 430

Val Asn Arg Cys Ser His Val Ala Phe Pro Gly Glu Thr Ile Met Glu
        435                 440                 445

Glu Ala Lys Leu Cys Thr Glu Arg Tyr Leu Arg Asn Ala Leu Glu Asp
    450                 455                 460

Gly Gly Ala Ser Asp Lys Trp Ala Leu Lys Lys Asn Ile Arg Gly Glu
465                 470                 475                 480

Val Glu Tyr Ala Leu Lys Tyr Pro Trp His Arg Ser Met Pro Arg Leu
                485                 490                 495

Glu Ala Arg Ser Tyr Ile Glu Asn Tyr Gly Pro Asn Asp Val Trp Leu
            500                 505                 510

Gly Lys Thr Met Tyr Met Met Pro Asn Ile Ser Asn Glu Lys Tyr Leu
        515                 520                 525

Glu Leu Ala Lys Leu Asp Phe Asn Arg Val Gln Phe His Arg Gln
    530                 535                 540

Glu Leu Gln Asp Ile Arg Arg Trp Trp Asn Ser Ser Gly Phe Ser Gln
545                 550                 555                 560

Leu Gly Phe Thr Arg Glu Arg Val Ala Glu Ile Tyr Phe Ser Pro Ala
                565                 570                 575

Ser Phe Leu Phe Glu Pro Glu Phe Ala Thr Cys Arg Ala Val Tyr Thr
            580                 585                 590

Lys Thr Ser Asn Phe Thr Val Ile Leu Asp Asp Leu Tyr Asp Ala His
        595                 600                 605

Gly Thr Leu Asp Asn Leu Lys Leu Phe Ser Glu Ser Val Lys Arg Trp
    610                 615                 620

Asp Leu Ser Leu Val Asp Gln Met Pro Gln Asp Met Lys Ile Cys Phe
625                 630                 635                 640

Lys Gly Phe Tyr Asn Thr Phe Asn Glu Ile Ala Glu Glu Gly Arg Lys
                645                 650                 655

Arg Gln Gly Arg Asp Val Leu Ser Tyr Ile Gln Lys Val Trp Glu Val
            660                 665                 670

Gln Leu Glu Ala Tyr Thr Lys Glu Ala Glu Trp Ser Ala Val Arg Tyr
        675                 680                 685

Val Pro Ser Tyr Asp Glu Tyr Ile Gly Asn Ala Ser Val Ser Ile Ala
    690                 695                 700

Leu Gly Thr Val Val Leu Ile Ser Ala Leu Phe Thr Gly Glu Ile Leu
705                 710                 715                 720
```

```
Thr Asp Asp Ile Leu Ser Lys Ile Gly Arg Asp Ser Arg Phe Leu Tyr
            725                 730                 735

Leu Met Gly Leu Thr Gly Arg Leu Val Asn Asp Thr Lys Thr Tyr Gln
            740                 745                 750

Ala Glu Arg Gly Gln Gly Glu Val Ala Ser Ala Val Gln Cys Tyr Met
            755                 760                 765

Lys Asp His Pro Glu Ile Ser Glu Glu Ala Leu Lys His Val Tyr
            770                 775                 780

Thr Ile Met Asp Asn Ala Leu Asp Glu Leu Asn Arg Glu Phe Val Asn
785                 790                 795                 800

Asn Arg Asp Val Pro Asp Thr Cys Arg Arg Leu Val Phe Glu Thr Ala
                805                 810                 815

Arg Ile Met Gln Leu Phe Tyr Met Asp Gly Asp Gly Leu Thr Leu Ser
                820                 825                 830

His Asn Met Glu Ile Lys Glu His Val Lys Asn Cys Leu Phe Gln Pro
                835                 840                 845

Val Ala
    850

<210> SEQ ID NO 42
<211> LENGTH: 867
<212> TYPE: PRT
<213> ORGANISM: Picea abies

<400> SEQUENCE: 42

Met Ala Leu Leu Ser Ser Ser Leu Ser Ser Gln Ile Pro Thr Gly Ser
 1               5                  10                  15

His Pro Leu Thr His Thr Gln Cys Ile Pro His Phe Ser Thr Thr Ile
            20                  25                  30

Asn Ala Gly Ile Ser Ala Gly Lys Pro Arg Ser Phe Tyr Leu Arg Trp
            35                  40                  45

Gly Lys Gly Ser Asn Lys Ile Ile Ala Cys Val Gly Glu Gly Thr Thr
 50                  55                  60

Ser Leu Pro Tyr Gln Ser Ala Glu Lys Thr Asp Ser Leu Ser Ala Pro
65                  70                  75                  80

Thr Leu Val Lys Arg Glu Phe Pro Pro Gly Phe Trp Lys Asp His Val
                85                  90                  95

Ile Asp Ser Leu Thr Ser Ser His Lys Val Ser Ala Ala Glu Glu Lys
            100                 105                 110

Arg Met Glu Thr Leu Ile Ser Glu Ile Lys Asn Ile Phe Arg Ser Met
            115                 120                 125

Gly Tyr Gly Glu Thr Asn Pro Ser Ala Tyr Asp Thr Ala Trp Val Ala
        130                 135                 140

Arg Ile Pro Ala Val Asp Gly Ser Glu His Pro Glu Phe Pro Glu Thr
145                 150                 155                 160

Leu Glu Trp Ile Leu Gln Asn Gln Leu Lys Asp Gly Ser Trp Gly Glu
                165                 170                 175

Gly Phe Tyr Phe Leu Ala Tyr Asp Arg Ile Leu Ala Thr Leu Ala Cys
            180                 185                 190

Ile Ile Thr Leu Thr Leu Trp Arg Thr Gly Glu Thr Gln Ile Arg Lys
            195                 200                 205

Gly Ile Glu Phe Phe Lys Thr Gln Ala Gly Lys Ile Glu Asp Glu Ala
        210                 215                 220

Asp Ser His Arg Pro Ser Gly Phe Glu Ile Val Phe Pro Ala Met Leu
225                 230                 235                 240
```

-continued

```
Lys Glu Ala Lys Val Leu Gly Leu Asp Leu Pro Tyr Glu Leu Pro Phe
                245                 250                 255

Ile Lys Gln Ile Ile Glu Lys Arg Glu Ala Lys Leu Glu Arg Leu Pro
                260                 265                 270

Thr Asn Ile Leu Tyr Ala Leu Pro Thr Thr Leu Leu Tyr Ser Leu Glu
                275                 280                 285

Gly Leu Gln Glu Ile Val Asp Trp Glu Lys Ile Ile Lys Leu Gln Ser
            290                 295                 300

Lys Asp Gly Ser Phe Leu Thr Ser Pro Ala Ser Thr Ala Ala Val Phe
305                 310                 315                 320

Met Arg Thr Gly Asn Lys Lys Cys Leu Glu Phe Leu Asn Phe Val Leu
                325                 330                 335

Lys Lys Phe Gly Asn His Val Pro Cys His Tyr Pro Leu Asp Leu Phe
                340                 345                 350

Glu Arg Leu Trp Ala Val Asp Thr Val Glu Arg Leu Gly Ile Asp His
            355                 360                 365

His Phe Lys Glu Glu Ile Lys Asp Ala Leu Asp Tyr Val Tyr Ser His
        370                 375                 380

Trp Asp Glu Arg Gly Ile Gly Trp Ala Arg Glu Asn Pro Ile Pro Asp
385                 390                 395                 400

Ile Asp Asp Thr Ala Met Gly Leu Arg Ile Leu Arg Leu His Gly Tyr
                405                 410                 415

Asn Val Ser Ser Asp Val Leu Lys Thr Phe Arg Asp Glu Asn Gly Glu
            420                 425                 430

Phe Phe Cys Phe Leu Gly Gln Thr Gln Arg Gly Val Thr Asp Met Leu
        435                 440                 445

Asn Val Asn Arg Cys Ser His Val Ala Phe Pro Gly Glu Thr Ile Met
    450                 455                 460

Gln Glu Ala Lys Leu Cys Thr Glu Arg Tyr Leu Arg Asn Ala Leu Glu
465                 470                 475                 480

Asp Val Gly Ala Phe Asp Lys Trp Ala Leu Lys Lys Asn Ile Arg Gly
                485                 490                 495

Glu Val Glu Tyr Ala Leu Lys Tyr Pro Trp His Arg Ser Met Pro Arg
            500                 505                 510

Leu Glu Ala Arg Ser Tyr Ile Glu His Tyr Gly Pro Asn Asp Val Trp
        515                 520                 525

Leu Gly Lys Thr Met Tyr Met Met Pro Tyr Ile Ser Asn Leu Lys Tyr
    530                 535                 540

Leu Glu Leu Ala Lys Leu Asp Phe Asn His Val Gln Ser Leu His Gln
545                 550                 555                 560

Lys Glu Leu Arg Asp Leu Arg Arg Trp Trp Lys Ser Ser Gly Leu Ser
                565                 570                 575

Glu Leu Lys Phe Thr Arg Glu Arg Val Thr Glu Ile Tyr Phe Ser Ala
            580                 585                 590

Ala Ser Phe Ile Phe Glu Pro Glu Phe Ala Thr Cys Arg Asp Val Tyr
        595                 600                 605

Thr Lys Ile Ser Ile Phe Thr Val Ile Leu Asp Asp Leu Tyr Asp Ala
    610                 615                 620

His Gly Thr Leu Asp Asn Leu Glu Leu Phe Ser Glu Gly Val Lys Arg
625                 630                 635                 640

Trp Asp Leu Ser Leu Val Asp Arg Met Pro Gln Asp Met Lys Ile Cys
                645                 650                 655

Phe Thr Val Leu Tyr Asn Thr Val Asn Glu Ile Ala Val Glu Gly Arg
```

```
                   660                 665                 670
Lys Arg Gln Gly Arg Asp Val Leu Gly Tyr Ile Arg Asn Val Leu Glu
            675                 680                 685

Ile Leu Leu Ala Ala His Thr Lys Glu Ala Glu Trp Ser Ala Ala Arg
            690                 695                 700

Tyr Val Pro Ser Phe Asp Glu Tyr Ile Glu Asn Ala Ser Val Ser Ile
705                 710                 715                 720

Ser Leu Gly Thr Leu Val Leu Ile Ser Val Leu Phe Thr Gly Glu Ile
            725                 730                 735

Leu Thr Asp Asp Val Leu Ser Lys Ile Gly Arg Gly Ser Arg Phe Leu
            740                 745                 750

Gln Leu Met Gly Leu Thr Gly Arg Leu Val Asn Asp Thr Lys Thr Tyr
            755                 760                 765

Glu Ala Glu Arg Gly Gln Gly Glu Val Ala Ser Ala Val Gln Cys Tyr
            770                 775                 780

Met Lys Glu His Pro Glu Ile Ser Glu Glu Ala Leu Lys His Val
785                 790                 795                 800

Tyr Thr Val Met Glu Asn Ala Leu Asp Glu Leu Asn Arg Glu Phe Val
                805                 810                 815

Asn Asn Arg Asp Val Pro Asp Ser Cys Arg Arg Leu Val Phe Glu Thr
                820                 825                 830

Ala Arg Ile Met Gln Leu Phe Tyr Met Glu Gly Asp Gly Leu Thr Leu
            835                 840                 845

Ser His Glu Met Glu Ile Lys Glu His Val Lys Asn Cys Leu Phe Gln
            850                 855                 860

Pro Val Ala
865

<210> SEQ ID NO 43
<211> LENGTH: 859
<212> TYPE: PRT
<213> ORGANISM: Picea abies

<400> SEQUENCE: 43

Met Ala Leu Leu Ser Ser Ser Leu Ser Ser Gln Ile Pro Thr Gly Ala
1               5                   10                  15

His His Leu Thr Leu Asn Ala Tyr Ala Asn Thr Gln Cys Ile Pro His
            20                  25                  30

Phe Phe Ser Thr Leu Asn Ala Gly Thr Ser Ala Gly Lys Arg Ser Ser
        35                  40                  45

Leu Tyr Leu Arg Trp Gly Lys Gly Ser Asn Lys Ile Ile Ala Cys Val
    50                  55                  60

Gly Glu Asp Ser Leu Ser Ala Pro Thr Leu Val Lys Arg Glu Phe Pro
65                  70                  75                  80

Pro Gly Phe Trp Lys Asp His Val Ile Asp Ser Leu Thr Ser Ser His
                85                  90                  95

Lys Val Ala Ala Ser Asp Glu Lys Arg Ile Glu Thr Leu Ile Ser Glu
            100                 105                 110

Ile Lys Asn Met Phe Arg Ser Met Gly Tyr Gly Asp Thr Asn Pro Ser
        115                 120                 125

Ala Tyr Asp Thr Ala Trp Val Ala Arg Ile Pro Ala Val Asp Gly Ser
    130                 135                 140

Glu Gln Pro Glu Phe Pro Glu Thr Leu Glu Trp Ile Leu Gln Asn Gln
145                 150                 155                 160

Leu Lys Asp Gly Ser Trp Gly Glu Gly Phe Tyr Phe Leu Ala Tyr Asp
```

```
                  165                 170                 175
Arg Ile Leu Ala Thr Leu Ala Cys Ile Ile Thr Leu Thr Leu Trp Arg
            180                 185                 190
Thr Gly Glu Ile Gln Val Gln Lys Gly Ile Glu Phe Phe Lys Thr Gln
            195                 200                 205
Ala Gly Lys Ile Glu Asp Glu Ala Asp Ser His Arg Pro Ser Gly Phe
            210                 215                 220
Glu Ile Val Phe Pro Ala Met Leu Lys Glu Ala Lys Val Leu Gly Leu
225                 230                 235                 240
Asp Leu Pro Tyr Glu Leu Pro Phe Ile Lys Gln Ile Ile Glu Lys Arg
                245                 250                 255
Glu Ala Lys Leu Glu Arg Leu Pro Thr Asn Ile Leu Tyr Ala Leu Pro
            260                 265                 270
Thr Thr Leu Leu Tyr Ser Leu Glu Gly Leu Gln Glu Ile Val Asp Trp
            275                 280                 285
Gln Lys Ile Ile Lys Leu Gln Ser Lys Asp Gly Ser Phe Leu Ser Ser
            290                 295                 300
Pro Ala Ser Thr Ala Ala Val Phe Met Arg Thr Gly Asn Lys Lys Cys
305                 310                 315                 320
Leu Glu Phe Leu Asn Phe Val Leu Lys Lys Phe Gly Asn His Val Pro
                325                 330                 335
Cys His Tyr Pro Leu Asp Leu Phe Glu Arg Leu Trp Ala Val Asp Thr
            340                 345                 350
Ile Glu Arg Leu Gly Ile Asp Arg His Phe Lys Glu Glu Ile Lys Asp
            355                 360                 365
Ala Leu Asp Tyr Val Tyr Ser His Trp Asp Glu Arg Gly Ile Gly Trp
            370                 375                 380
Ala Arg Glu Asn Pro Val Pro Asp Ile Asp Asp Thr Ala Met Gly Leu
385                 390                 395                 400
Arg Ile Leu Arg Leu His Gly Tyr Asn Val Ser Ser Asp Val Leu Lys
                405                 410                 415
Thr Phe Arg Asp Glu Asn Gly Glu Phe Phe Cys Phe Leu Gly Gln Thr
            420                 425                 430
Gln Arg Gly Val Thr Asp Met Leu Asn Val Asn Arg Cys Ser His Val
            435                 440                 445
Ala Phe Pro Gly Glu Thr Ile Met Glu Glu Ala Lys Thr Cys Thr Glu
            450                 455                 460
Arg Tyr Leu Arg Asn Ala Leu Glu Asp Val Gly Ala Phe Asp Lys Trp
465                 470                 475                 480
Ala Leu Lys Lys Asn Ile Arg Gly Glu Val Glu Tyr Ala Leu Lys Tyr
                485                 490                 495
Pro Trp His Arg Ser Met Pro Arg Leu Glu Ala Arg Ser Tyr Ile Glu
            500                 505                 510
His Tyr Gly Pro Asn Asp Val Trp Leu Gly Lys Thr Met Tyr Met Met
            515                 520                 525
Pro Tyr Ile Ser Asn Glu Lys Tyr Leu Glu Leu Ala Lys Leu Asp Phe
            530                 535                 540
Asn His Val Gln Ser Leu His Gln Lys Glu Leu Arg Asp Leu Arg Arg
545                 550                 555                 560
Trp Trp Thr Ser Ser Gly Phe Thr Glu Leu Lys Phe Thr Arg Glu Arg
                565                 570                 575
Val Thr Glu Ile Tyr Phe Ser Pro Ala Ser Phe Met Phe Glu Pro Glu
            580                 585                 590
```

Phe Ala Thr Cys Arg Ala Val Tyr Thr Lys Thr Ser Asn Phe Thr Val
        595                 600                 605

Ile Leu Asp Asp Leu Tyr Asp Ala His Gly Thr Leu Asp Asp Leu Lys
610                 615                 620

Leu Phe Ser Asp Ser Val Lys Lys Trp Asp Leu Ser Leu Val Asp Arg
625                 630                 635                 640

Met Pro Gln Asp Met Lys Ile Cys Phe Met Gly Phe Tyr Asn Thr Phe
                645                 650                 655

Asn Glu Ile Ala Glu Glu Gly Arg Lys Arg Gln Gly Arg Asp Val Leu
            660                 665                 670

Gly Tyr Ile Arg Asn Val Trp Glu Ile Gln Leu Glu Ala Tyr Thr Lys
        675                 680                 685

Glu Ala Glu Trp Ser Ala Ala Arg Tyr Val Pro Ser Phe Asp Glu Tyr
690                 695                 700

Ile Asp Asn Ala Ser Val Ser Ile Ala Leu Gly Thr Val Val Leu Ile
705                 710                 715                 720

Ser Ala Leu Phe Thr Gly Glu Ile Leu Thr Asp Val Leu Ser Lys
                725                 730                 735

Ile Gly Arg Gly Ser Arg Phe Leu Gln Leu Met Gly Leu Thr Gly Arg
            740                 745                 750

Leu Val Asn Asp Thr Lys Thr Tyr Glu Ala Glu Arg Gly Gln Gly Glu
        755                 760                 765

Val Ala Ser Ala Val Gln Cys Tyr Met Lys Asp His Pro Glu Ile Ser
770                 775                 780

Glu Glu Glu Ala Leu Lys His Val Tyr Thr Val Met Glu Asn Ala Leu
785                 790                 795                 800

Asp Glu Leu Asn Arg Glu Phe Val Asn Asn Arg Glu Val Pro Asp Ser
                805                 810                 815

Cys Arg Arg Leu Val Phe Glu Thr Ala Arg Ile Met Gln Leu Phe Tyr
            820                 825                 830

Met Asp Gly Asp Gly Leu Thr Leu Ser His Glu Thr Glu Ile Lys Glu
        835                 840                 845

His Val Lys Asn Cys Leu Phe Gln Pro Val Ala
        850                 855

<210> SEQ ID NO 44
<211> LENGTH: 574
<212> TYPE: PRT
<213> ORGANISM: Pinus taeda

<400> SEQUENCE: 44

Met Ser Ser Leu Ala Val Asp Asp Ala Glu Arg Arg Val Gly Asp Tyr
1               5                   10                  15

His Pro Asn Leu Trp Asp Asp Ala Leu Ile Gln Ser Leu Ser Thr Pro
            20                  25                  30

Tyr Gly Ala Ser Pro Tyr Arg Asp Val Ala Glu Lys Leu Ile Gly Glu
        35                  40                  45

Ile Lys Glu Met Phe Ala Ser Ile Ser Ile Glu Asp Gly Asp Glu
    50                  55                  60

Ile Cys Tyr Phe Leu Gln Arg Leu Trp Met Ile Asp Asn Val Glu Arg
65                  70                  75                  80

Leu Gly Ile Ser Arg His Phe Glu Asn Glu Ile Lys Ala Ala Met Glu
                85                  90                  95

Asp Val Tyr Ser Arg His Trp Ser Asp Lys Gly Ile Ala Cys Gly Arg
            100                 105                 110

-continued

```
His Ser Val Val Ala Asp Leu Asn Ser Thr Ala Leu Ala Phe Arg Thr
        115                 120                 125

Leu Arg Leu His Gly Tyr Ser Val Cys Ser Asp Val Phe Lys Ile Phe
    130                 135                 140

Gln Asp Gln Lys Gly Glu Phe Ala Cys Ser Ala Asp Gln Thr Glu Gly
145                 150                 155                 160

Glu Ile Lys Gly Ile Leu Asn Leu Leu Arg Ala Ser Leu Ile Ala Phe
                165                 170                 175

Pro Gly Glu Arg Ile Leu Gln Glu Ala Glu Ile Phe Ala Thr Thr Tyr
                180                 185                 190

Leu Lys Glu Ala Leu Pro Lys Ile Gln Gly Ser Arg Leu Ser Gln Glu
        195                 200                 205

Ile Glu Tyr Val Leu Glu Tyr Gly Trp Leu Thr Asp Leu Pro Arg Leu
210                 215                 220

Glu Thr Arg Asn Tyr Ile Glu Val Leu Ala Glu Ile Thr Pro Tyr
225                 230                 235                 240

Phe Lys Lys Pro Cys Met Ala Val Glu Lys Leu Leu Lys Leu Ala Lys
                245                 250                 255

Ile Glu Phe Asn Leu Phe His Ser Leu Gln Gln Thr Glu Leu Lys His
                260                 265                 270

Leu Ser Arg Trp Trp Lys Asp Ser Gly Phe Ala Gln Leu Thr Phe Thr
    275                 280                 285

Arg His Arg His Val Glu Phe Tyr Thr Leu Ala Ser Cys Ile Ala Met
        290                 295                 300

Glu Pro Lys His Ser Ala Phe Arg Leu Gly Phe Ala Lys Leu Cys Tyr
305                 310                 315                 320

Leu Gly Ile Val Leu Asp Asp Ile Tyr Asp Thr Tyr Gly Lys Met Glu
                325                 330                 335

Glu Leu Glu Leu Phe Thr Ala Ala Ile Lys Arg Trp Asp Thr Ser Thr
                340                 345                 350

Thr Glu Cys Leu Pro Glu Tyr Met Lys Gly Val Tyr Met Ala Phe Tyr
        355                 360                 365

Asp Cys Val Asn Glu Met Ala Arg Gln Ala Glu Lys Thr Gln Gly Trp
370                 375                 380

Asp Thr Leu Asp Tyr Ala Arg Lys Thr Trp Glu Ala Leu Ile Asp Ala
385                 390                 395                 400

Phe Met Glu Glu Ala Lys Trp Ile Ser Ser Gly Tyr Val Pro Thr Phe
                405                 410                 415

Gln Lys Tyr Leu Asp Asn Gly Lys Val Ser Phe Gly Tyr Arg Ala Ala
                420                 425                 430

Thr Leu Gln Pro Ile Leu Thr Leu Asp Ile Pro Leu Pro Leu His Ile
        435                 440                 445

Leu Gln Glu Ile Asp Phe Pro Ser Ser Phe Asn Asp Leu Ala Ser Ser
        450                 455                 460

Ile Leu Arg Leu Arg Gly Asp Ile Cys Gly Tyr Gln Ala Glu Arg Ser
465                 470                 475                 480

Arg Gly Glu Gln Ala Ser Ser Ile Ser Cys Tyr Met Lys Asp Asn Pro
                485                 490                 495

Gly Ser Thr Glu Glu Asp Ala Leu Ser His Val Asn Ala Met Ile Gly
                500                 505                 510

Asp Lys Ile Pro Glu Phe Asn Trp Glu Phe Met Lys Pro Ser Lys Ala
        515                 520                 525

Pro Ile Ser Ser Lys Lys Tyr Ala Phe Asp Ile Leu Arg Ala Phe Tyr
530                 535                 540
```

-continued

His Leu Tyr Lys Tyr Arg Asp Gly Phe Ser Ile Ala Lys Ile Glu Thr
545                 550                 555                 560

Lys Lys Leu Val Met Arg Thr Val Leu Asp Pro Val Pro Met
                565                 570

<210> SEQ ID NO 45
<211> LENGTH: 853
<212> TYPE: PRT
<213> ORGANISM: Abies grandis

<400> SEQUENCE: 45

Ala His His Leu Thr Ala Asn Thr Gln Ser Ile Pro His Phe Ser Thr
1               5                   10                  15

Thr Leu Asn Ala Gly Ser Ser Ala Ser Lys Arg Arg Ser Leu Tyr Leu
            20                  25                  30

Arg Trp Gly Lys Gly Ser Asn Lys Ile Ile Ala Cys Val Gly Glu Gly
        35                  40                  45

Gly Ala Thr Ser Val Pro Tyr Gln Ser Ala Glu Lys Asn Asp Ser Leu
    50                  55                  60

Ser Ser Ser Thr Leu Val Lys Arg Glu Phe Pro Pro Gly Phe Trp Lys
65                  70                  75                  80

Asp Asp Leu Ile Asp Ser Leu Thr Ser Ser His Lys Val Ala Ala Ser
                85                  90                  95

Asp Glu Lys Arg Ile Glu Thr Leu Ile Ser Glu Ile Lys Asn Met Phe
            100                 105                 110

Arg Cys Met Gly Tyr Gly Glu Thr Asn Pro Ser Ala Tyr Asp Thr Ala
        115                 120                 125

Trp Val Ala Arg Ile Pro Ala Val Asp Gly Ser Asp Asn Pro His Phe
    130                 135                 140

Pro Glu Thr Val Glu Trp Ile Leu Gln Asn Gln Leu Lys Asp Gly Ser
145                 150                 155                 160

Trp Gly Glu Gly Phe Tyr Phe Leu Ala Tyr Asp Arg Ile Leu Ala Thr
                165                 170                 175

Leu Ala Cys Ile Ile Thr Leu Thr Leu Trp Arg Thr Gly Glu Thr Gln
            180                 185                 190

Val Gln Lys Gly Ile Glu Ser Phe Arg Thr Gln Ala Gly Lys Met Glu
        195                 200                 205

Asp Glu Ala Asp Ser His Arg Pro Ser Gly Phe Glu Ile Val Phe Pro
    210                 215                 220

Ala Met Leu Lys Glu Ala Lys Ile Leu Gly Leu Asp Leu Pro Tyr Asp
225                 230                 235                 240

Leu Pro Phe Leu Lys Gln Ile Ile Glu Lys Arg Glu Ala Lys Leu Lys
                245                 250                 255

Arg Ile Pro Thr Asp Val Leu Tyr Ala Leu Pro Thr Thr Leu Leu Tyr
            260                 265                 270

Ser Leu Glu Gly Leu Gln Glu Ile Val Glu Trp Glu Lys Ile Met Lys
        275                 280                 285

Leu Gln Ser Lys Asp Gly Ser Phe Leu Ser Ser Pro Ala Ser Thr Ala
    290                 295                 300

Ala Val Phe Met Arg Thr Gly Asn Lys Lys Cys Leu Asp Phe Leu Asn
305                 310                 315                 320

Phe Val Leu Lys Lys Phe Gly Asn His Val Pro Cys His Tyr Pro Leu
                325                 330                 335

Asp Leu Phe Glu Arg Leu Trp Ala Val Asp Thr Val Glu Arg Leu Gly
            340                 345                 350

```
Ile Asp Arg His Phe Lys Glu Glu Ile Lys Glu Ala Leu Asp Tyr Val
            355                 360                 365

Tyr Ser His Trp Asp Glu Arg Gly Ile Gly Trp Ala Arg Glu Asn Pro
        370                 375                 380

Val Pro Asp Ile Asp Asp Thr Ala Met Gly Leu Arg Ile Leu Arg Leu
385                 390                 395                 400

His Gly Tyr Asn Val Ser Ser Asp Val Leu Lys Thr Phe Arg Asp Glu
                405                 410                 415

Asn Gly Glu Phe Phe Cys Phe Leu Gly Gln Thr Gln Arg Gly Val Thr
            420                 425                 430

Asp Met Leu Asn Val Asn Arg Cys Ser His Val Ser Phe Pro Gly Glu
        435                 440                 445

Thr Ile Met Glu Glu Ala Lys Leu Cys Thr Arg Tyr Leu Arg Asn
    450                 455                 460

Ala Leu Glu Asn Val Asp Ala Phe Asp Lys Trp Ala Phe Lys Lys Asn
465                 470                 475                 480

Ile Arg Gly Glu Val Glu Tyr Ala Leu Lys Tyr Pro Trp His Lys Ser
                485                 490                 495

Met Pro Arg Leu Glu Ala Arg Ser Tyr Ile Glu Asn Tyr Gly Pro Asp
            500                 505                 510

Asp Val Trp Leu Gly Lys Thr Val Tyr Met Met Pro Tyr Ile Ser Asn
        515                 520                 525

Glu Lys Tyr Leu Glu Leu Ala Lys Leu Asp Phe Asn Lys Leu Gln Ser
    530                 535                 540

Ile His Gln Thr Glu Leu Gln Asp Leu Arg Arg Trp Trp Lys Ser Ser
545                 550                 555                 560

Gly Phe Thr Glu Leu Asn Phe Thr Arg Glu Arg Val Thr Glu Ile Tyr
                565                 570                 575

Phe Ser Pro Ala Ser Phe Ile Phe Glu Pro Glu Phe Ser Lys Cys Arg
            580                 585                 590

Glu Val Tyr Thr Lys Thr Ser Asn Phe Thr Val Ile Leu Asp Asp Leu
        595                 600                 605

Tyr Asp Ala His Gly Ser Leu Asp Asp Leu Lys Leu Phe Thr Glu Ser
    610                 615                 620

Val Lys Arg Trp Asp Leu Ser Leu Val Asp Gln Met Pro Lys Gln Met
625                 630                 635                 640

Lys Ile Cys Phe Val Gly Phe Tyr Asn Thr Phe Asn Asp Ile Ala Lys
                645                 650                 655

Glu Gly Arg Glu Arg Gln Gly Arg Asp Val Leu Gly Tyr Ile Gln Asn
            660                 665                 670

Val Trp Lys Val Gln Leu Glu Ala Tyr Thr Lys Glu Ala Glu Trp Ser
        675                 680                 685

Glu Ala Lys Tyr Val Pro Ser Phe Asn Glu Tyr Ile Glu Asn Ala Ser
    690                 695                 700

Val Ser Ile Ala Leu Gly Thr Val Leu Ile Ser Ala Leu Phe Thr
705                 710                 715                 720

Gly Glu Val Leu Thr Asp Glu Val Leu Ser Lys Ile Asp Arg Glu Ser
                725                 730                 735

Arg Phe Leu Gln Leu Met Gly Leu Thr Gly Arg Leu Val Asn Asp Thr
            740                 745                 750

Lys Thr Tyr Gln Ala Glu Arg Gly Gln Gly Glu Val Ala Ser Ala Ile
        755                 760                 765

Gln Cys Tyr Met Lys Asp His Pro Lys Ile Ser Glu Glu Glu Ala Leu
```

-continued

```
                770                 775                 780
Gln His Val Tyr Ser Val Met Glu Asn Ala Leu Glu Glu Leu Asn Arg
785                 790                 795                 800

Glu Phe Val Asn Asn Lys Ile Pro Asp Ile Tyr Lys Arg Leu Val Phe
                805                 810                 815

Glu Thr Ala Arg Ile Met Gln Leu Phe Tyr Met Gln Gly Asp Gly Leu
                820                 825                 830

Thr Leu Ser His Asp Met Glu Ile Lys Glu His Val Lys Asn Cys Leu
                835                 840                 845

Phe Gln Pro Val Ala
    850

<210> SEQ ID NO 46
<211> LENGTH: 868
<212> TYPE: PRT
<213> ORGANISM: Abies grandis

<400> SEQUENCE: 46

Met Ala Met Pro Ser Ser Ser Leu Ser Ser Gln Ile Pro Thr Ala Ala
1               5                   10                  15

His His Leu Thr Ala Asn Ala Gln Ser Ile Pro His Phe Ser Thr Thr
                20                  25                  30

Leu Asn Ala Gly Ser Ser Ala Ser Lys Arg Arg Ser Leu Tyr Leu Arg
            35                  40                  45

Trp Gly Lys Gly Ser Asn Lys Ile Ile Ala Cys Val Gly Glu Gly Gly
        50                  55                  60

Ala Thr Ser Val Pro Tyr Gln Ser Ala Glu Lys Asn Asp Ser Leu Ser
65              70                  75                  80

Ser Ser Thr Leu Val Lys Arg Glu Phe Pro Pro Gly Phe Trp Lys Asp
                85                  90                  95

Asp Leu Ile Asp Ser Leu Thr Ser Ser His Lys Val Ala Ala Ser Asp
            100                 105                 110

Glu Lys Arg Ile Glu Thr Leu Ile Ser Glu Ile Lys Asn Met Phe Arg
        115                 120                 125

Cys Met Gly Tyr Gly Glu Thr Asn Pro Ser Ala Tyr Asp Thr Ala Trp
130                 135                 140

Val Ala Arg Ile Pro Ala Val Asp Gly Ser Asp Asn Pro His Phe Pro
145             150                 155                 160

Glu Thr Val Glu Trp Ile Leu Gln Asn Gln Leu Lys Asp Gly Ser Trp
                165                 170                 175

Gly Glu Gly Phe Tyr Phe Leu Ala Tyr Asp Arg Ile Leu Ala Thr Leu
            180                 185                 190

Ala Cys Ile Ile Thr Leu Thr Leu Trp Arg Thr Gly Glu Thr Gln Val
        195                 200                 205

Gln Lys Gly Ile Glu Phe Phe Arg Thr Gln Ala Gly Lys Met Glu Asp
    210                 215                 220

Glu Ala Asp Ser His Arg Pro Ser Gly Phe Glu Ile Val Phe Pro Ala
225                 230                 235                 240

Met Leu Lys Glu Ala Lys Ile Leu Gly Leu Asp Leu Pro Tyr Asp Leu
                245                 250                 255

Pro Phe Leu Lys Gln Ile Glu Lys Arg Glu Ala Lys Leu Lys Arg
            260                 265                 270

Ile Pro Thr Asp Val Leu Tyr Ala Leu Pro Thr Thr Leu Leu Tyr Ser
        275                 280                 285

Leu Glu Gly Leu Gln Glu Ile Val Asp Trp Gln Lys Ile Met Lys Leu
```

-continued

```
            290                 295                 300
Gln Ser Lys Asp Gly Ser Phe Leu Ser Ser Pro Ala Ser Thr Ala Ala
305                 310                 315                 320

Val Phe Met Arg Thr Gly Asn Lys Lys Cys Leu Asp Phe Leu Asn Phe
                325                 330                 335

Val Leu Lys Lys Phe Gly Asn His Val Pro Cys His Tyr Pro Leu Asp
                340                 345                 350

Leu Phe Glu Arg Leu Trp Ala Val Asp Thr Val Glu Arg Leu Gly Ile
                355                 360                 365

Asp Arg His Phe Lys Glu Glu Ile Lys Glu Ala Leu Asp Tyr Val Tyr
        370                 375                 380

Ser His Trp Asp Glu Arg Gly Ile Gly Trp Ala Arg Glu Asn Pro Val
385                 390                 395                 400

Pro Asp Ile Asp Asp Thr Ala Met Gly Leu Arg Ile Leu Arg Leu His
                405                 410                 415

Gly Tyr Asn Val Ser Ser Asp Val Leu Lys Thr Phe Arg Asp Glu Asn
                420                 425                 430

Gly Glu Phe Phe Cys Phe Leu Gly Gln Thr Gln Arg Gly Val Thr Asp
        435                 440                 445

Met Leu Asn Val Asn Arg Cys Ser His Val Ser Phe Pro Gly Glu Thr
450                 455                 460

Ile Met Glu Glu Ala Lys Leu Cys Thr Glu Arg Tyr Leu Arg Asn Ala
465                 470                 475                 480

Leu Glu Asn Val Asp Ala Phe Asp Lys Trp Ala Phe Lys Lys Asn Ile
                485                 490                 495

Arg Gly Glu Val Glu Tyr Ala Leu Lys Tyr Pro Trp His Lys Ser Met
                500                 505                 510

Pro Arg Leu Glu Ala Arg Ser Tyr Ile Glu Asn Tyr Gly Pro Asp Asp
        515                 520                 525

Val Trp Leu Gly Lys Thr Val Tyr Met Met Pro Tyr Ile Ser Asn Glu
                530                 535                 540

Lys Tyr Leu Glu Leu Ala Lys Leu Asp Phe Asn Lys Val Gln Ser Ile
545                 550                 555                 560

His Gln Thr Glu Leu Gln Asp Leu Arg Arg Trp Trp Lys Ser Ser Gly
                565                 570                 575

Phe Thr Asp Leu Asn Phe Thr Arg Glu Arg Val Thr Glu Ile Tyr Phe
                580                 585                 590

Ser Pro Ala Ser Phe Ile Phe Glu Pro Glu Phe Ser Lys Cys Arg Glu
        595                 600                 605

Val Tyr Thr Lys Thr Ser Asn Phe Thr Val Ile Leu Asp Asp Leu Tyr
610                 615                 620

Asp Ala His Gly Ser Leu Asp Asp Leu Lys Leu Phe Thr Glu Ser Val
625                 630                 635                 640

Lys Arg Trp Asp Leu Ser Leu Val Asp Gln Met Pro Gln Gln Met Lys
                645                 650                 655

Ile Cys Phe Val Gly Phe Tyr Asn Thr Phe Asn Asp Ile Ala Lys Glu
                660                 665                 670

Gly Arg Glu Arg Gln Gly Arg Asp Val Leu Gly Tyr Ile Gln Asn Val
        675                 680                 685

Trp Lys Val Gln Leu Glu Ala Tyr Thr Lys Glu Ala Glu Trp Ser Glu
                690                 695                 700

Ala Lys Tyr Val Pro Ser Phe Asn Glu Tyr Ile Glu Asn Ala Ser Val
705                 710                 715                 720
```

```
Ser Ile Ala Leu Gly Thr Val Val Leu Ile Ser Ala Leu Phe Thr Gly
                725                 730                 735

Glu Val Leu Thr Asp Glu Val Leu Ser Lys Ile Asp Arg Glu Ser Arg
                740                 745                 750

Phe Leu Gln Leu Met Gly Leu Thr Gly Arg Leu Val Asn Asp Thr Lys
                755                 760                 765

Thr Tyr Gln Ala Glu Arg Gly Gln Gly Glu Val Ala Ser Ala Ile Gln
            770                 775                 780

Cys Tyr Met Lys Asp His Pro Lys Ile Ser Glu Glu Ala Leu Gln
785                 790                 795                 800

His Val Tyr Ser Val Met Glu Asn Ala Leu Glu Leu Asn Arg Glu
                805                 810                 815

Phe Val Asn Asn Lys Ile Pro Asp Ile Tyr Lys Arg Leu Val Phe Glu
                820                 825                 830

Thr Ala Arg Ile Met Gln Leu Phe Tyr Met Gln Gly Asp Gly Leu Thr
                835                 840                 845

Leu Ser His Asp Met Glu Ile Lys Glu His Val Lys Asn Cys Leu Phe
    850                 855                 860

Gln Pro Val Ala
865

<210> SEQ ID NO 47
<211> LENGTH: 826
<212> TYPE: PRT
<213> ORGANISM: Pseudotsuga menziesii

<400> SEQUENCE: 47

Met Ser Leu Glu Glu Phe Tyr Pro Met Ala Thr Val Tyr Val Pro Ser
  1               5                  10                  15

Ser Thr Leu Pro Cys Ala Leu Ser Thr Ser Ser Ser Ser Ser Ser Leu
                 20                  25                  30

Val Arg Arg Thr Ala Asn Pro His Pro Asn Val Trp Asp Tyr His Phe
             35                  40                  45

Val Gln Ser Leu Gln Ser Pro Tyr Thr Asp Pro Cys Tyr Gly Glu Arg
         50                  55                  60

Val Glu Thr Leu Val Ala Glu Ile Lys Ala Met Leu His Gly Glu Gly
 65                  70                  75                  80

Gly Leu Met Ile Thr Pro Ser Ala Tyr Asp Thr Ala Trp Val Ala Arg
                 85                  90                  95

Val Pro Ser Ile Asp Gly Ser Ala Arg Pro Gln Phe Pro Gln Thr Val
            100                 105                 110

Gln Trp Ile Leu Lys Asn Gln Leu Lys Asp Gly Ser Trp Gly Thr Glu
        115                 120                 125

Ser His Phe Leu Leu Ser Asp Arg Leu Leu Ala Thr Leu Ser Cys Val
    130                 135                 140

Leu Ala Leu Leu Lys Trp Lys Val Gly Asp Leu Gln Val Gln Gln Gly
145                 150                 155                 160

Ile Glu Phe Ile Lys Ser Asn Leu Glu Ala Ile Lys Asp Glu Asn Asp
                165                 170                 175

Glu Asp Ser Leu Val Thr Asp Phe Asp Ile Ile Phe Pro Ser Leu Leu
            180                 185                 190

Arg Glu Ala Gln Tyr Leu Asp Ile Glu Leu Pro Leu Gln Pro Ala Leu
        195                 200                 205

Cys Lys Ser Thr Pro Pro Lys Arg Gln Glu Arg Leu Ala Asn Met Ser
    210                 215                 220
```

```
Arg Glu Glu Ile His Gly Val Pro Ser Pro Leu Leu Tyr Ser Leu Glu
225                 230                 235                 240

Gly Ile Glu Asp Met Val Asp Trp Glu Arg Ile Met Asp Val Arg Ser
            245                 250                 255

Gln Asp Gly Ser Phe Leu Ser Ser Pro Ala Ser Ile Ala Cys Val Phe
        260                 265                 270

Met His Thr Gly Asp Ile Lys Cys Leu Glu Phe Leu Asn Asn Val Leu
    275                 280                 285

Thr Asn Phe Gly Thr Phe Val Pro Cys Leu Tyr Pro Val Asp Leu Leu
290                 295                 300

Glu Arg Leu Leu Ile Val Asp Asn Leu Val Gln Leu Gly Ile Asp Arg
305                 310                 315                 320

His Phe Glu Lys Glu Ile Lys Glu Ala Leu Asp Tyr Val His Arg His
            325                 330                 335

Trp Asn Glu Arg Gly Ile Gly Trp Gly Arg Leu Asn Pro Ile Ala Asp
        340                 345                 350

Leu Glu Ile Thr Ala Leu Gly Phe Arg Leu Leu Arg Leu His Arg Tyr
    355                 360                 365

Asn Val Ser Pro Ala Val Phe Glu Asn Phe Lys Asp Ser Asn Gly His
370                 375                 380

Phe Val Cys Ser Gly Ala Gln Phe Asn Lys Asp Val Ala Ser Met Leu
385                 390                 395                 400

Ser Leu Tyr Arg Ala Ser Gln Leu Ala Phe Pro Gly Glu Asn Ile Leu
            405                 410                 415

Asp Glu Ala Lys Ser Phe Thr Ser Lys Tyr Leu Lys Glu Ala Leu Glu
        420                 425                 430

Lys Arg Glu Thr Tyr Ser Ala Trp Asn Asn Lys Gln Ser Leu Ser Glu
    435                 440                 445

Glu Ile Lys Tyr Ala Leu Glu Asn Ser Trp His Ala Ser Val Pro Arg
450                 455                 460

Val Glu Ala Lys Arg Tyr Cys Gln Val Tyr Arg Ser Asp Tyr Thr Tyr
465                 470                 475                 480

Leu Ala Lys Ser Val Tyr Lys Leu Pro Lys Val Asn Asn Glu Lys Ile
            485                 490                 495

Leu Glu Leu Ala Lys Leu Asp Phe Gln His Tyr Pro Gly His Pro Pro
        500                 505                 510

Lys Arg Asp Glu Glu Cys His His Leu Val Lys Asn Ser Glu Phe Pro
    515                 520                 525

Leu Leu Pro Phe Gly Arg Glu Arg Pro Val Glu Cys Phe Phe Ile Val
530                 535                 540

Ala Ala Gly Thr Tyr Glu Pro Gln Tyr Ala Lys Cys Arg Phe Leu Phe
545                 550                 555                 560

Ser Lys Val Ala Cys Leu Asn Thr Val Leu Asp Asp Met Tyr Asp Thr
            565                 570                 575

Tyr Gly Thr Leu Asp Glu Leu Lys Leu Phe Thr Glu Ala Val Arg Arg
        580                 585                 590

Trp Asp Leu Ser Leu Thr Glu Asn Leu Pro Asp Tyr Met Lys Leu Cys
    595                 600                 605

Tyr Lys Ile Phe Tyr Asp Ile Val His Glu Val Val Leu Glu Ala Glu
610                 615                 620

Lys Glu Gln Gly Arg Glu Leu Leu Thr Phe Phe Arg Lys Gly Trp Glu
625                 630                 635                 640

Glu Tyr Leu Met Gly Tyr Tyr Glu Glu Ala Glu Trp Leu Ala Cys Glu
            645                 650                 655
```

```
Tyr Leu Pro Ser Leu Glu Glu Tyr Ile Arg Asn Gly Ile Ile Ser Ile
            660                 665                 670

Gly Gln Arg Ile Leu Val Val Ser Gly Val Leu Leu Met Glu Gly Gln
        675                 680                 685

Ile Leu Ser Gln Glu Ala Glu Gln Leu Asp Tyr Pro Gly Arg Arg
    690                 695                 700

Val Leu Thr Glu Leu Asn Ser Ile Ile Thr Arg Leu Ala Asp Asp Ile
705                 710                 715                 720

His Thr Tyr Lys Ala Glu Lys Ala Arg Gly Glu Leu Ala Ser Ser Ile
            725                 730                 735

Glu Cys Tyr Met Arg Glu His Pro Gly Ser Thr Glu Glu Val Ala Val
            740                 745                 750

Asn Tyr Met Tyr Ser Leu Leu Glu Pro Ala Val Lys Glu Leu Thr Trp
            755                 760                 765

Glu Phe Leu Lys Pro Glu Asp Ser Thr Val His Ile Pro Phe Gln Cys
    770                 775                 780

Lys Lys Met Leu Met Glu Glu Thr Arg Val Thr Met Val Ile Phe Lys
785                 790                 795                 800

Glu Gly Asp Gly Phe Gly Ile Ser Lys Thr Lys Ile Lys Asp Tyr Ile
            805                 810                 815

Lys Asp Cys Leu Ile Glu Pro Leu Pro Leu
            820                 825

<210> SEQ ID NO 48
<211> LENGTH: 815
<212> TYPE: PRT
<213> ORGANISM: Pseudotsuga menziesii

<400> SEQUENCE: 48

Met Ala Ala Ser Thr Leu Pro Ser Gly Leu Ser Thr Asn Asp Leu Ile
1               5                   10                  15

Arg Arg Thr Ala Asn Pro His Pro Asn Val Trp Gly Tyr Asp Leu Leu
            20                  25                  30

Cys Ser Leu Lys Ser Pro Tyr Ser Arg Asp Ser Ser Tyr Lys Glu Arg
        35                  40                  45

Ala Asp Thr Leu Ile Asn Glu Ile Lys Ala Met Leu Gly Ala Ala Phe
    50                  55                  60

Gly Asp Gly Lys Glu Met Ile Thr Pro Ser Ala Tyr Asp Thr Ala Trp
65              70                  75                  80

Val Ala Arg Ile Pro Ser Ile Asp Gly Ser Gly Ser Ala Arg Pro
            85                  90                  95

Gln Phe Pro Gln Thr Val Asp Trp Ile Leu Lys Asn Gln Leu Lys Asp
            100                 105                 110

Gly Ser Trp Gly Thr Glu Ser His Phe Leu Leu Ser Glu Pro Leu Leu
        115                 120                 125

Ala Thr Ile Ser Cys Val Leu Ala Leu Phe Lys Trp Gln Val Gly Asp
    130                 135                 140

Leu Gln Val Glu Arg Gly Ile Glu Phe Leu Lys Ser Ser Leu Glu Lys
145                 150                 155                 160

Ile Lys Asn Glu Ser Asp Gln Asp Ser Leu Val Thr Asp Phe Glu Ile
            165                 170                 175

Ile Phe Pro Ser Met Leu Arg Glu Ala Gln Ser Leu His Leu Gly Leu
            180                 185                 190

Pro Tyr Asp Leu Pro Tyr Ile Gln Leu Leu Gln Thr Lys Arg Gln Glu
        195                 200                 205
```

```
Arg Leu Ala Asn Leu Ser Arg Glu Lys Ile His Gly Gly Ile Leu Gln
    210                 215                 220

Leu Ser Ser Leu Glu Gly Ile Glu Asp Met Val Gly Trp Glu Arg Leu
225                 230                 235                 240

Met Asp Leu Gln Ser Leu Asp Gly Ser Phe Leu Ser Ser Pro Ala Ser
                    245                 250                 255

Thr Ala Phe Val Phe Ile His Thr Gly Asp Leu Lys Cys Leu Ala Phe
                260                 265                 270

Leu Asn Ser Val Leu Ala Lys Phe Gly Ala Phe Val Pro Cys Leu Tyr
            275                 280                 285

His Val Asp Leu Leu Glu Arg Leu Leu Ile Val Asp Asn Ile Glu Arg
        290                 295                 300

Leu Gly Ile Asp Arg His Phe Glu Lys Glu Ile Asn Glu Ala Leu Asp
305                 310                 315                 320

Tyr Val Tyr Arg Tyr Trp Ser Asn Glu Arg Gly Ile Gly Trp Gly Arg
                325                 330                 335

Met Asn Ala Thr Ala Asp Leu Glu Thr Thr Ala Leu Gly Phe Arg Leu
                340                 345                 350

Leu Arg Leu His Arg Tyr His Val Ser Pro Val Val Phe Lys Lys Phe
            355                 360                 365

Lys Asp Ala Asp Gly Glu Phe Leu Ser Ser Ile Gly Gln Phe Asn Lys
370                 375                 380

Asp Val Ala Ser Met Leu Asn Leu Tyr Arg Ala Cys Glu Leu Ala Phe
385                 390                 395                 400

Pro Gly Glu Asn Ile Leu Asp Glu Ala Lys Gly Phe Thr Ala Lys Tyr
                405                 410                 415

Leu Arg Glu Ala Leu Glu Lys Thr Glu Thr Phe Ser Ser Trp Asn Ile
                420                 425                 430

Lys Arg Asn Leu Ser Gln Glu Ile Lys Tyr Ala Leu Lys Thr Ser Trp
            435                 440                 445

His Ala Ser Ile Pro Arg Val Glu Ala Lys Arg Tyr Cys Gln Val Tyr
        450                 455                 460

Arg Pro Asp Tyr Ala Arg Leu Asp Lys Ser Val Tyr Lys Leu His His
465                 470                 475                 480

Val Asn Asn Glu Lys Ile Leu Glu Leu Ala Lys Leu Asp Phe Asn Ile
                485                 490                 495

Ile Gln Ser Ile Leu Gln Glu Glu Met Lys Asn Val Thr Ser Trp Phe
                500                 505                 510

Arg Asp Ser Gly Leu Pro Leu Phe Ser Phe Ala Arg Gln Arg Pro Leu
            515                 520                 525

Glu Phe Tyr Phe Leu Ile Thr Ala Gly Thr Tyr Glu Pro Arg Tyr Ala
        530                 535                 540

Lys Cys Arg Leu Leu Phe Thr Lys Val Ala Cys Val Glu Thr Val Leu
545                 550                 555                 560

Asp Asp Met Tyr Asp Thr Tyr Gly Thr Leu Asp Glu Leu Lys Leu Phe
                565                 570                 575

Thr Gln Ala Val Arg Arg Trp Asp Pro Ser Leu Thr Glu Asn Leu Pro
                580                 585                 590

Asp Tyr Met Lys Arg Cys Tyr Lys Ile Phe Tyr Asp Ile Val His Glu
            595                 600                 605

Ala Ala Trp Glu Ala Glu Lys Glu Gln Gly Arg Glu Leu Val Ser Phe
        610                 615                 620

Leu Arg Lys Ala Trp Glu Asp Phe Val Leu Ser Tyr His Glu Glu Ala
```

```
                625                 630                 635                 640
Glu Trp Leu Ser Ala Glu Tyr Val Pro Gly Phe Asp Glu Tyr Ile Lys
                    645                 650                 655

Asn Gly Ile Thr Ser Ile Gly Gln Arg Val Leu Leu Ser Gly Leu
                660                 665                 670

Leu Val Met Asp Gly Gln Leu Leu Ser Gln Lys Ala Leu Glu Lys Ile
            675                 680                 685

Asp Tyr Pro Glu Arg Ser Arg Val Leu Met Glu Gln Ile Cys Leu Ile
        690                 695                 700

Ser Arg Leu Ala Asp Asp Thr Gln Ser Tyr Lys Ala Glu Lys Ala Arg
705                 710                 715                 720

Gly Glu Leu Ala Ser Gly Ile Glu Cys Tyr Met Lys Asp His Pro Glu
                725                 730                 735

Cys Thr Glu Glu Glu Ala Leu Asn His Ile Tyr Gly Ile Met Glu Val
                740                 745                 750

Thr Ala Lys Glu Leu Thr Lys Glu Tyr Leu Lys Val Asp Asp Asp Asp
                755                 760                 765

Val Pro Phe Ala Cys Lys Lys Met Leu Phe Glu Glu Thr Arg Val Thr
        770                 775                 780

Met Val Ile Phe Lys Asp Gly Asp Arg Leu Ser Asn Ser Lys Leu Glu
785                 790                 795                 800

Met Lys Asp His Phe Lys Glu Cys Leu Ile Glu Pro Leu Pro Leu
                805                 810                 815

<210> SEQ ID NO 49
<211> LENGTH: 502
<212> TYPE: PRT
<213> ORGANISM: Saccharomyces cerevisiae

<400> SEQUENCE: 49

Pro Val Leu Thr Asn Lys Thr Val Ile Ser Gly Ser Lys Val Lys Ser
  1               5                  10                  15

Leu Ser Ser Ala Gln Ser Ser Ser Gly Pro Ser Ser Ser Ser Glu
            20                  25                  30

Glu Asp Asp Ser Arg Asp Ile Glu Ser Leu Asp Lys Lys Ile Arg Pro
        35                  40                  45

Leu Glu Glu Leu Glu Ala Leu Leu Ser Ser Gly Asn Thr Lys Gln Leu
    50                  55                  60

Lys Asn Lys Glu Val Ala Ala Leu Val Ile His Gly Lys Leu Pro Leu
65                  70                  75                  80

Tyr Ala Leu Glu Lys Lys Leu Gly Asp Thr Thr Arg Ala Val Ala Val
                85                  90                  95

Arg Arg Lys Ala Leu Ser Ile Leu Ala Glu Ala Pro Val Leu Ala Ser
            100                 105                 110

Asp Arg Leu Pro Tyr Lys Asn Tyr Asp Tyr Asp Arg Val Phe Gly Ala
        115                 120                 125

Cys Cys Glu Asn Val Ile Gly Tyr Met Pro Leu Pro Val Gly Val Ile
    130                 135                 140

Gly Pro Leu Val Ile Asp Gly Thr Ser Tyr His Ile Pro Met Ala Thr
145                 150                 155                 160

Thr Glu Gly Cys Leu Val Ala Ser Ala Met Arg Gly Cys Lys Ala Ile
                165                 170                 175

Asn Ala Gly Gly Gly Ala Thr Thr Val Leu Thr Lys Asp Gly Met Thr
            180                 185                 190

Arg Gly Pro Val Val Arg Phe Pro Thr Leu Lys Arg Ser Gly Ala Cys
```

```
              195                 200                 205
Lys Ile Trp Leu Asp Ser Glu Glu Gly Gln Asn Ala Ile Lys Lys Ala
    210                 215                 220
Phe Asn Ser Thr Ser Arg Phe Ala Arg Leu Gln His Ile Gln Thr Cys
225                 230                 235                 240
Leu Ala Gly Asp Leu Leu Phe Met Arg Phe Arg Thr Thr Thr Gly Asp
                245                 250                 255
Ala Met Gly Met Asn Met Ile Ser Lys Gly Val Glu Tyr Ser Leu Lys
                260                 265                 270
Gln Met Val Glu Glu Tyr Gly Trp Glu Asp Met Glu Val Val Ser Val
            275                 280                 285
Ser Gly Asn Tyr Cys Thr Asp Lys Lys Pro Ala Ala Ile Asn Trp Ile
        290                 295                 300
Glu Gly Arg Gly Lys Ser Val Val Ala Glu Ala Thr Ile Pro Gly Asp
305                 310                 315                 320
Val Val Arg Lys Val Leu Lys Ser Asp Val Ser Ala Leu Val Glu Leu
                325                 330                 335
Asn Ile Ala Lys Asn Leu Val Gly Ser Ala Met Ala Gly Ser Val Gly
                340                 345                 350
Gly Phe Asn Ala His Ala Ala Asn Leu Val Thr Ala Val Phe Leu Ala
            355                 360                 365
Leu Gly Gln Asp Pro Ala Gln Asn Val Glu Ser Ser Asn Cys Ile Thr
        370                 375                 380
Leu Met Lys Glu Val Asp Gly Asp Leu Arg Ile Ser Val Ser Met Pro
385                 390                 395                 400
Ser Ile Glu Val Gly Thr Ile Gly Gly Thr Val Leu Glu Pro Gln
                405                 410                 415
Gly Ala Met Leu Asp Leu Leu Gly Val Arg Gly Pro His Ala Thr Ala
                420                 425                 430
Pro Gly Thr Asn Ala Arg Gln Leu Ala Arg Ile Val Ala Cys Ala Val
            435                 440                 445
Leu Ala Gly Glu Leu Ser Leu Cys Ala Ala Leu Ala Ala Gly His Leu
        450                 455                 460
Val Gln Ser His Met Thr His Asn Arg Lys Pro Ala Glu Pro Thr Lys
465                 470                 475                 480
Pro Asn Asn Leu Asp Ala Thr Asp Ile Asn Arg Leu Lys Asp Gly Ser
                485                 490                 495
Val Thr Cys Ile Lys Ser
                500

<210> SEQ ID NO 50
<211> LENGTH: 413
<212> TYPE: PRT
<213> ORGANISM: Pyrococcus horikoshii

<400> SEQUENCE: 50

Met Gly Gly Gly Asn Leu Asn Ile Glu Glu Ile Ile Glu Lys Val Ala
1               5                   10                  15
Asn Gly Glu Ile Lys Phe Tyr Gln Val Glu Lys Tyr Val Asn Gly Asp
                20                  25                  30
Lys Arg Leu Ala Thr Glu Ile Arg Arg Lys Ala Leu Glu Lys Arg Leu
            35                  40                  45
Gly Ile Lys Leu His His Ile Gly Tyr Tyr Ser Ile Asp Pro Asn Glu
        50                  55                  60
Leu Ile Gly Arg Asn Ile Glu Asn Met Ile Gly Val Val Gln Ile Pro
```

```
            65                  70                  75                  80
Met Gly Val Ala Gly Pro Leu Lys Ile Asn Gly Glu Tyr Ala Lys Gly
                    85                  90                  95

Glu Phe Tyr Ile Pro Leu Ala Thr Thr Glu Gly Ala Leu Val Ala Ser
                100                 105                 110

Val Asn Arg Gly Cys Ser Ala Leu Thr Glu Ala Gly Gly Val Val Thr
                115                 120                 125

Thr Leu Ile Asp Asp Lys Met Thr Arg Ala Pro Leu Ile Arg Cys Pro
    130                 135                 140

Asn Ala Arg Arg Ala Arg Glu Val Ala Lys Trp Val Glu Asn Leu
145                 150                 155                 160

Asp Tyr Leu Gln Glu Lys Ala Val Ser Lys Val Thr Arg His Gly Lys
                165                 170                 175

Leu Arg Gly Val Lys Pro Phe Ile Val Gly Asn Asn Leu Tyr Leu Arg
                180                 185                 190

Phe Glu Phe Glu Thr Gly Asp Ala Met Gly Met Asn Met Val Thr Ile
            195                 200                 205

Ala Ser Glu Glu Ile Met Lys Val Ile Glu Glu Phe Pro Asp Val
210                 215                 220

Arg Tyr Leu Ala Leu Ser Gly Asn Leu Cys Val Asp Lys Lys Pro Asn
225                 230                 235                 240

Ala Val Asn Phe Ile Leu Gly Arg Gly Lys Thr Val Ile Ala Glu Ala
                245                 250                 255

Val Val Pro Arg Lys Ile Val Glu Lys Lys Leu Lys Thr Thr Pro Glu
                260                 265                 270

Leu Ile Ala Glu Val Asn Tyr Phe Lys Asn Leu Val Gly Ser Ala Gln
        275                 280                 285

Ala Gly Ser Tyr Gly Phe Asn Ala His Phe Ala Asn Ile Val Gly Ala
    290                 295                 300

Ile Phe Leu Ala Thr Gly Gln Asp Glu Ala Gln Ile Thr Glu Gly Ala
305                 310                 315                 320

His Gly Ile Thr Ile Ala Glu Val Thr Pro Asp Gly Asp Leu Tyr Ile
                325                 330                 335

Ser Ile Thr Met Pro Ser Leu Glu Ile Gly Thr Val Gly Gly Gly Thr
                340                 345                 350

Arg Val Pro Ser Gln Arg Glu Ala Leu Glu Ile Met Gly Val Ala Gly
            355                 360                 365

Gly Gly Asp Pro Pro Gly Ile Asn Ala Lys Lys Phe Ala Glu Ile Val
        370                 375                 380

Ala Gly Ala Val Leu Ala Gly Glu Leu Ser Leu Leu Ala Ala Ile Ala
385                 390                 395                 400

Ala Lys His Leu Ala Arg Ala His Lys Met Leu Gly Arg
                405                 410

<210> SEQ ID NO 51
<211> LENGTH: 411
<212> TYPE: PRT
<213> ORGANISM: Pyrococcus abyssi

<400> SEQUENCE: 51

Met Lys Thr Leu Asn Val Glu Asp Ile Ile Glu Lys Val Ala Asn Gly
1               5                   10                  15

Glu Ile Lys Leu His Gln Val Glu Lys Tyr Val Asn Gly Asp Lys Arg
            20                  25                  30

Leu Ala Thr Glu Ile Arg Arg Lys Ala Leu Glu Arg Lys Leu Gly Ile
```

35                  40                  45
Ser Leu Lys His Ile Gly His Tyr Ser Ile Asp Pro Asn Glu Leu Ile
 50                  55                  60

Gly Arg Asn Ile Glu Asn Met Ile Gly Val Val Gln Ile Pro Met Gly
 65                  70                  75                  80

Val Ala Gly Pro Leu Lys Ile Asn Gly Glu Tyr Ala Lys Gly Glu Phe
                 85                  90                  95

Tyr Ile Pro Leu Ala Thr Thr Glu Gly Ala Leu Val Ala Ser Val Asn
            100                 105                 110

Arg Gly Cys Ser Ala Leu Thr Glu Ala Gly Val Val Thr Thr Ile
        115                 120                 125

Leu Asp Asp Lys Met Thr Arg Ala Pro Leu Ile Arg Cys Pro Asn Ala
130                 135                 140

Arg Arg Ala Arg Glu Val Ala Glu Trp Val Lys Glu Asn Leu Asn Tyr
145                 150                 155                 160

Leu Gln Glu Lys Ala Val Ala Lys Val Thr Arg His Gly Lys Leu Arg
                165                 170                 175

Asp Val Lys Pro Phe Ile Val Gly Asn Asn Leu Tyr Leu Arg Phe Glu
            180                 185                 190

Phe Glu Thr Gly Asp Ala Met Gly Met Asn Met Val Thr Ile Ala Ser
        195                 200                 205

Glu Glu Ile Met Lys Val Ile Glu Glu Phe Pro Asp Val Arg Tyr
210                 215                 220

Leu Ala Leu Ser Gly Asn Leu Cys Val Asp Lys Lys Pro Asn Ala Val
225                 230                 235                 240

Asn Phe Ile Leu Gly Arg Gly Lys Thr Val Val Ala Glu Ala Ile Val
                245                 250                 255

Pro Arg Glu Ile Val Glu Lys Lys Leu Lys Thr Thr Pro Glu Leu Ile
            260                 265                 270

Ala Glu Val Asn Tyr Phe Lys Asn Leu Val Gly Ser Ala Gln Ala Gly
        275                 280                 285

Ser Tyr Gly Phe Asn Ala His Phe Gly Asn Ile Val Gly Ala Ile Phe
290                 295                 300

Leu Ala Thr Gly Gln Asp Glu Ala Gln Ile Thr Glu Gly Ser His Gly
305                 310                 315                 320

Ile Thr Ile Ala Glu Val Thr Pro Glu Gly Asp Leu Tyr Ile Ser Ile
                325                 330                 335

Thr Met Pro Ser Leu Glu Ile Gly Thr Val Gly Gly Gly Thr Arg Val
            340                 345                 350

Pro Thr Gln Arg Glu Ala Leu Ser Ile Met Gly Val Ala Gly Gly Gly
        355                 360                 365

Asp Pro Pro Gly Val Asn Ala Lys Lys Phe Ala Glu Ile Val Ala Gly
370                 375                 380

Ala Val Leu Ala Gly Glu Leu Ser Leu Leu Ala Ala Ile Ala Ala Lys
385                 390                 395                 400

His Leu Ala Arg Ala His Lys Met Leu Gly Arg
                405                 410

<210> SEQ ID NO 52
<211> LENGTH: 408
<212> TYPE: PRT
<213> ORGANISM: Pyrococcus furiosus

<400> SEQUENCE: 52

Met Glu Ile Glu Glu Ile Ile Glu Lys Val Ala Arg Gly Glu Ile Lys

```
                1               5                  10                 15
        Phe His Gln Val Glu Asn Tyr Val Asn Gly Asp Lys Arg Leu Ala Thr
                        20                  25                  30

Glu Ile Arg Arg Ala Leu Glu Lys Lys Leu Gly Ile Gln Leu Lys
                        35                  40                  45

His Ile Gly His Tyr Ser Ile Asp Pro Asn Glu Val Ile Gly Arg Asn
                        50                  55                  60

Ile Glu Asn Met Ile Gly Val Val Gln Ile Pro Met Gly Ile Ala Gly
        65                      70                  75                  80

Pro Leu Lys Ile Asn Gly Glu Tyr Ala Lys Gly Glu Phe Tyr Ile Pro
                        85                  90                  95

Leu Ala Thr Thr Glu Gly Ala Leu Val Ala Ser Val Asn Arg Gly Cys
                        100                 105                 110

Ser Ala Leu Thr Glu Ala Gly Val Tyr Thr Thr Leu Ile Asp Asp
                        115                 120                 125

Lys Met Thr Arg Ala Pro Leu Leu Lys Cys Pro Asn Ala Arg Arg Ala
                        130                 135                 140

Arg Glu Val Ala Glu Trp Val Lys Asn Asn Leu Asp Tyr Leu Gln Glu
        145                     150                 155                 160

Lys Ala Val Ser Lys Val Thr Arg His Gly Lys Leu Arg Gly Val Lys
                        165                 170                 175

Pro Phe Ile Val Gly Arg Asn Leu Tyr Leu Arg Phe Glu Phe Glu Thr
                        180                 185                 190

Gly Asp Ala Met Gly Met Asn Met Val Thr Ile Ala Ser Glu Glu Ile
                        195                 200                 205

Met Lys Val Ile Glu Glu Phe Pro Asp Val Lys Tyr Leu Ala Leu
                        210                 215                 220

Ser Gly Asn Leu Cys Val Asp Lys Lys Pro Asn Ala Leu Asn Phe Ile
        225                     230                 235                 240

Leu Gly Arg Gly Lys Thr Ile Ile Ala Glu Ala Val Val Pro Arg Glu
                        245                 250                 255

Ile Val Lys Lys Lys Leu Lys Thr Thr Pro Glu Leu Ile Ala Glu Val
                        260                 265                 270

Asn Tyr Leu Lys Asn Leu Val Gly Ser Ala Gln Ala Gly Ser Tyr Gly
                        275                 280                 285

Phe Asn Ala His Phe Ala Asn Ile Val Gly Ala Ile Phe Leu Ala Thr
                        290                 295                 300

Gly Gln Asp Glu Ala Gln Ile Thr Glu Gly Ala His Gly Ile Thr Leu
        305                     310                 315                 320

Ala Glu Val Thr Glu Asp Gly Asp Leu Tyr Ile Ser Ile Thr Met Pro
                        325                 330                 335

Ser Leu Glu Ile Gly Thr Val Gly Gly Gly Thr Arg Val Pro Pro Gln
                        340                 345                 350

Arg Glu Ala Leu Glu Ile Met Gly Val Ala Gly Gly Asp Pro Pro
                        355                 360                 365

Gly Met Asn Ala Lys Lys Phe Ala Glu Ile Val Ala Gly Ala Val Leu
        370                     375                 380

Ala Gly Glu Leu Ser Leu Leu Ala Ala Ile Ala Ala Lys His Leu Ala
                        385                 390                 395                 400

Arg Ala His Lys Met Leu Gly Arg
                        405

<210> SEQ ID NO 53
<211> LENGTH: 408
```

```
<212> TYPE: PRT
<213> ORGANISM: Thermococcus kodakarensis

<400> SEQUENCE: 53

Met Asn Phe Glu Glu Leu Val Glu Lys Val Ala Ser Gly Glu Ile Lys
 1               5                  10                  15

Leu His Gln Val Glu Lys Tyr Thr Asn Gly Asp Lys Lys Leu Ala Thr
            20                  25                  30

Glu Ile Arg Arg Lys Ala Leu Glu Lys Leu Gly Ile Lys Leu Glu
        35                  40                  45

Asn Ile Gly His Tyr Ser Ile Asp Pro Asn Gln Val Ile Gly Lys Asn
    50                  55                  60

Ile Glu Asn Met Ile Gly Val Val Gln Ile Pro Met Gly Val Ala Gly
65                  70                  75                  80

Pro Leu Lys Ile Asn Gly Glu Tyr Ala Lys Gly Glu Phe Tyr Ile Pro
                85                  90                  95

Leu Ala Thr Thr Glu Gly Ala Leu Val Ala Ser Val Asn Arg Gly Cys
            100                 105                 110

Ser Ala Leu Thr Ala Ala Gly Val Lys Thr Thr Leu Ile Asp Asp
        115                 120                 125

Lys Met Thr Arg Ala Pro Leu Leu Lys Cys Pro Asp Ala Arg Arg Ala
130                 135                 140

Arg Glu Val Ala Glu Trp Val Lys Asn Asn Leu Asp Tyr Leu Gln Glu
145                 150                 155                 160

Lys Ala Val Ser Lys Val Thr Arg His Gly Lys Leu Arg Gly Val Arg
                165                 170                 175

Pro Phe Ile Val Gly Asn Asn Leu Tyr Leu Arg Phe Glu Phe Glu Thr
            180                 185                 190

Gly Asp Ala Met Gly Met Asn Met Val Thr Ile Ala Ser Glu Glu Ile
        195                 200                 205

Met Lys Val Ile Glu Glu Phe Pro Asp Val Lys Tyr Leu Ala Leu
    210                 215                 220

Ser Gly Asn Leu Cys Val Asp Lys Lys Pro Asn Ala Met Asn Phe Ile
225                 230                 235                 240

Asn Gly Arg Gly Lys Thr Val Ile Ala Glu Ala Val Ile Pro Arg Lys
                245                 250                 255

Ile Val Glu Glu Lys Leu Lys Thr Thr Pro Glu Leu Ile Ala Glu Val
            260                 265                 270

Asn Tyr Arg Lys Asn Leu Val Gly Ser Ala Gln Ala Gly Ser Tyr Gly
        275                 280                 285

Phe Asn Ala His Phe Gly Asn Ile Val Gly Ala Ile Phe Leu Ala Thr
    290                 295                 300

Gly Gln Asp Glu Ala Gln Ile Thr Glu Gly Ser His Gly Ile Thr Leu
305                 310                 315                 320

Ala Glu Val Thr Pro Gly Asp Leu Tyr Ile Ser Ile Thr Met Pro
                325                 330                 335

Ser Leu Glu Ile Gly Thr Val Gly Gly Gly Thr Arg Val Pro Thr Gln
            340                 345                 350

Arg Glu Ala Leu Ser Ile Met Gly Val Ala Gly Gly Asp Pro Pro
        355                 360                 365

Gly Thr Asn Ala Lys Lys Phe Ala Glu Ile Val Ala Gly Ala Val Leu
    370                 375                 380

Ala Gly Glu Leu Ser Leu Leu Ala Ala Ile Ala Ala Lys His Leu Ala
385                 390                 395                 400
```

Lys Ala His Lys Glu Leu Gly Arg
            405

<210> SEQ ID NO 54
<211> LENGTH: 410
<212> TYPE: PRT
<213> ORGANISM: Methanopyrus kandleri

<400> SEQUENCE: 54

Met Asp Glu Lys Lys Ile Glu Glu Leu Val Ser Lys Val Val Lys Gly
 1               5                  10                  15

Glu Ile Lys Phe His Glu Val Gly Lys Tyr Thr Asp Gly Asp Ser Glu
            20                  25                  30

Val Ala Thr Glu Val Arg Arg Ala Leu Glu Arg Leu Thr Gly Ala
        35                  40                  45

Lys Leu Glu His Leu Gly Lys Tyr Thr Ile Asp Ala Asn Arg Ala Met
 50                  55                  60

Asp Lys Asn Ile Glu Asn Met Ile Gly Ala Val Gln Val Pro Val Gly
 65                  70                  75                  80

Ile Ala Gly Pro Leu Leu Val His Gly Glu Tyr Ala Glu Gly Glu Tyr
                85                  90                  95

Tyr Val Pro Leu Ala Thr Thr Glu Gly Ala Leu Val Ala Ser Val Asn
            100                 105                 110

Arg Gly Cys Ser Thr Ile Thr Asp Ser Gly Gly Ala His Val Arg Ile
        115                 120                 125

Val Arg Asp Gly Met Thr Arg Ala Pro Val Phe Lys Leu Pro Ser Ala
130                 135                 140

Arg Lys Ala Leu Glu Phe Cys Glu Trp Val Arg Lys His Phe Asp Asp
145                 150                 155                 160

Ile Lys Glu Val Ala Glu Ser Thr Thr Arg His Gly Glu Leu Leu Asp
                165                 170                 175

Ile Gln Glu Phe Val Val Gly Arg His Val Phe Leu Arg Phe Glu Phe
            180                 185                 190

Asp Thr Lys Asp Ala Met Gly Met Asn Met Val Thr Ile Ala Thr Glu
        195                 200                 205

Glu Ala Val Asn Trp Ile Glu Glu Lys Tyr Pro Asp Ala Lys Cys Val
    210                 215                 220

Ser Ala Ser Gly Asn Val Cys Val Asp Lys Lys Pro Ser Trp Leu Asn
225                 230                 235                 240

Asn Val Leu Gly Arg Gly Arg Thr Val Val Ala Glu Val Glu Val Pro
                245                 250                 255

Arg Asp Ile Val Glu Glu Lys Leu Lys Thr Thr Pro Glu Ala Met Ala
            260                 265                 270

Glu Val Asn Tyr Arg Lys Asn Leu Val Gly Ser Ala Ala Gly Asn
        275                 280                 285

Ile Gly Phe Asn Ala His His Ala Asn Ile Val Ala Ala Ile Phe Ile
    290                 295                 300

Ala Thr Gly Gln Asp Glu Ala His Ala Val Asp Gly Ser Thr Gly Tyr
305                 310                 315                 320

Thr Thr Met Glu Val Thr Glu Asp Gly Asp Leu Tyr Ala Ser Val Thr
                325                 330                 335

Ile Pro Ser Leu Asn Val Gly Thr Val Gly Gly Gly Thr Gly Val Glu
            340                 345                 350

Thr Gln Arg Glu Cys Leu Glu Ile Leu Gly Val Ala Gly Gly Asn
        355                 360                 365

-continued

Pro Pro Gly Val Asn Ala Lys Glu Phe Ala Glu Val Ala Ala Ala
        370                 375                 380

Val Leu Ala Gly Glu Leu Ser Leu Val Ala Leu Ala Ala Gly His
385                 390                 395                 400

Leu Gly Lys Ala His Arg Leu Leu Gly Arg
                405                 410

<210> SEQ ID NO 55
<211> LENGTH: 398
<212> TYPE: PRT
<213> ORGANISM: Pyrobaculum aerophilum

<400> SEQUENCE: 55

Met Phe Leu Met Glu Val Lys Leu His Glu Phe Glu Lys Val Tyr Gly
1               5                   10                  15

Asp Ala Asn Lys Ala Ala Glu Ala Arg Arg Gln Tyr Leu Glu Lys Val
                20                  25                  30

Thr Gly Val Lys Leu Glu Asn Ile Gly Arg Thr Ile Ile Asp Leu Asn
            35                  40                  45

Thr Val Val Gly Arg Asn Ile Glu Asn Val Ile Gly Ala Val Gln Ile
50                  55                  60

Pro Val Gly Val Ala Gly Pro Leu Leu Val Arg Gly Asp Tyr Ala Asn
65                  70                  75                  80

Gly Tyr Phe Tyr Val Pro Leu Ala Thr Thr Glu Gly Ala Leu Val Ala
                85                  90                  95

Ser Val Asn Arg Gly Ala Lys Phe Val Thr Glu Ser Gly Gly Ala Arg
            100                 105                 110

Val Lys Val Leu Lys Asp Gly Met Ala Arg Ala Pro Leu Phe Arg Val
        115                 120                 125

Pro Ser Leu Ile Asp Ala Val Glu Leu Val Glu Trp Val Thr Gly His
130                 135                 140

Phe Glu Glu Leu Lys Lys Val Ala Glu Ser Thr Thr Arg Phe Gly Lys
145                 150                 155                 160

Leu Lys Asp Ile Gln His Phe Ile Val Gly Asn Tyr Val Trp Leu Arg
                165                 170                 175

Leu Val Phe Ser Thr Gly Asp Ala Met Gly Met Asn Met Val Thr Ile
            180                 185                 190

Ala Ser Glu Ala Val Ala Lys Phe Ile Gln Glu Asn Phe Pro Lys Ala
        195                 200                 205

Lys Leu Ile Ala Leu Ser Gly Asn Met Cys Val Asp Lys Lys Ala Asn
210                 215                 220

Ala Val Asn Phe Ile Leu Gly Arg Gly Lys Thr Val Val Ala Glu Ala
225                 230                 235                 240

Val Ile Lys Lys Glu Ile Leu Glu Arg Leu Gly Ile Thr Pro Glu Asp
                245                 250                 255

Val His Asn Val Asn Val Arg Lys Asn Leu Ile Gly Ser Ala Leu Ala
            260                 265                 270

His Ser Tyr Gly Phe Asn Ala His Phe Ala Asn Ile Ile Ala Ala Ile
        275                 280                 285

Phe Ile Ala Thr Gly Gln Asp Val Ala Gln Val Val Glu Ser Ser Met
290                 295                 300

Gly Ile Thr Ser Thr Glu Ala Arg Glu Asp Gly Leu Tyr Ile Ser Val
305                 310                 315                 320

Phe Leu Pro Ser Leu Glu Val Gly Thr Val Gly Gly Gly Thr Gly Leu
                325                 330                 335

```
Pro Thr Gln Arg Glu Ala Leu Glu Leu Leu Gly Val Ala Gly Ser Gly
            340                 345                 350

Asn Pro Pro Gly Val Asn Ala Leu Lys Phe Ala Glu Ile Ile Ala Ala
        355                 360                 365

Ala Val Leu Ala Gly Glu Leu Asn Leu Leu Ile Ala Leu Ala Arg Asn
370                 375                 380

Glu Leu Ala Ser Ala His Lys Lys Leu Gly Arg Gly Ala Arg
385                 390                 395

<210> SEQ ID NO 56
<211> LENGTH: 421
<212> TYPE: PRT
<213> ORGANISM: Aeropyrum pernix

<400> SEQUENCE: 56

Met Gly Ser Ser Gly Gln Lys Pro Arg Leu Glu Asp Leu Val
  1               5                  10                  15

Asp Lys Leu Ala Ser Gly Ser Leu Ser His Ser Arg Leu Glu Lys Glu
             20                  25                  30

Leu Gly Asn Ala Asn Glu Ala Ala Leu Val Arg Arg Leu Tyr Leu Glu
         35                  40                  45

Arg Leu Thr Gly Ala Ser Leu Ser Ser Val Ala Ser Thr Ile Leu Asp
 50                  55                  60

Phe Gln Glu Leu Tyr Gly Arg Asn Ile Glu Asn Pro Ile Gly Ala Val
 65                  70                  75                  80

Gln Val Pro Val Gly Val Ala Gly Pro Leu Arg Ile Asn Gly Asp Tyr
                 85                  90                  95

Ala Arg Gly Asp Phe Tyr Ile Pro Leu Ala Thr Thr Glu Gly Ala Leu
            100                 105                 110

Val Ala Ser Val Asn Arg Gly Ala Lys Ala Ile Thr Leu Ser Gly Gly
            115                 120                 125

Ala Arg Ala Lys Val Ile Lys Asp Gly Met Thr Arg Ala Pro Leu Leu
        130                 135                 140

Trp Thr Pro Ser Val Tyr Glu Ala His Arg Leu Ala Met Trp Val Glu
145                 150                 155                 160

Asp Arg Ile Glu Asp Leu Arg Ser Val Val Ala Gly Val Thr Arg His
                165                 170                 175

Gly Arg Leu Gln His Ile Tyr Pro Tyr Ile Gly Asn Leu Val Trp
            180                 185                 190

Leu Arg Leu Ser Phe Ser Thr Gly Asp Ala Met Gly Met Asn Met Val
        195                 200                 205

Thr Ile Ser Ser Asp Arg Ile Cys Arg Tyr Ile Glu Glu Asn Tyr Asp
210                 215                 220

Gly Asp Ala Lys Cys Ile Ala Leu Ser Gly Asn Met Cys Thr Asp Lys
225                 230                 235                 240

Lys Pro Ala Ala Ile Asn Lys Ile Leu Gly Arg Gly Lys Tyr Val Val
                245                 250                 255

Ala Glu Ala Val Ile Lys Gly Glu Val Val Lys Asn Val Leu Lys Thr
            260                 265                 270

Thr Pro Gln Asn Ile Asn Leu Val Asn Val Thr Lys Asn Leu Leu Gly
        275                 280                 285

Ser Ala Ala Ala Gly Ser His Ser Phe Asn Ala His Phe Ala Asn Ile
        290                 295                 300

Ile Ala Ala Ile Phe Ile Ala Thr Gly Gln Asp Ala Ala Gln Val Val
305                 310                 315                 320
```

```
Glu Ser Ser Met Gly Tyr Thr Trp Thr Glu Val Arg Gly Glu Asp Leu
                325                 330                 335

Tyr Ile Ser Val Thr Leu Pro Ser Leu Glu Val Gly Thr Val Gly Gly
            340                 345                 350

Gly Thr Arg Leu Pro Thr Gln Arg Glu Leu Leu Ala Leu Leu Gly Val
        355                 360                 365

Ala Gly Gly Gly Asn Pro Pro Gly Ser Asn Ala Leu Lys Leu Ala Glu
    370                 375                 380

Ile Ile Ala Ser Ala Val Leu Ala Gly Glu Leu Asn Leu Leu Ser Ala
385                 390                 395                 400

Ile Ala Ala Gly Gln Leu Ala Arg Ala His Glu Leu Leu Gly Arg Gly
                405                 410                 415

Gly Leu Lys Ile Ser
                420

<210> SEQ ID NO 57
<211> LENGTH: 405
<212> TYPE: PRT
<213> ORGANISM: Methanocaldococcus jannaschii

<400> SEQUENCE: 57

Met Glu Asn Tyr Asn Asp Ile Leu Glu Lys Met Leu Asn Gly Glu Ile
1               5                   10                  15

Lys Pro Tyr Gln Leu Asp Lys Met Phe Gly Ser Lys Ile Ala Thr Glu
            20                  25                  30

Ile Arg Arg Lys Phe Ile Glu Lys Val Gly Ile Glu Phe Lys His
        35                  40                  45

Ile Cys Asn Tyr Ser Ile Asp Glu Glu Met Ala Met Lys Lys Asn Ile
    50                  55                  60

Glu Asn Met Ile Gly Ala Ile Gln Ile Pro Leu Gly Phe Ala Gly Pro
65                  70                  75                  80

Leu Lys Ile Asn Gly Glu Tyr Ala Lys Gly Glu Phe Tyr Ile Pro Leu
                85                  90                  95

Ala Thr Thr Glu Gly Ala Leu Val Ala Ser Val Asn Arg Gly Cys Ser
            100                 105                 110

Ile Ile Thr Lys Cys Gly Gly Ala Thr Val Arg Val Ile Asp Asp Lys
        115                 120                 125

Met Thr Arg Ala Pro Cys Leu Lys Thr Lys Ser Val Val Asp Ala Ile
    130                 135                 140

Lys Val Arg Asp Trp Ile Arg Glu Asn Phe Glu Arg Ile Lys Glu Val
145                 150                 155                 160

Ala Glu Ser Thr Thr Arg His Gly Lys Leu Ile Lys Ile Glu Pro Ile
                165                 170                 175

Leu Ile Val Gly Arg Asn Leu Tyr Pro Arg Phe Val Phe Lys Thr Gly
            180                 185                 190

Asp Ala Met Gly Met Asn Met Val Thr Ile Ala Thr Glu Lys Ala Cys
        195                 200                 205

Asn Phe Ile Glu Gly Glu Leu Lys Lys Glu Gly Ile Phe Val Lys Thr
    210                 215                 220

Val Ala Val Ser Gly Asn Ala Cys Val Asp Lys Lys Pro Ser Gly Met
225                 230                 235                 240

Asn Leu Ile Asn Gly Arg Gly Lys Ser Ile Val Ala Glu Val Phe Leu
                245                 250                 255

Thr Glu Lys Glu Val Asn Lys Tyr Leu Lys Thr Thr Ser Gln Ala Ile
            260                 265                 270
```

```
Ala Glu Val Asn Arg Leu Lys Asn Tyr Ile Gly Ser Ala Ile Ser Asn
            275                 280                 285

Ser Met Gly Phe Asn Ala His Tyr Ala Asn Ile Ile Gly Ala Ile Phe
    290                 295                 300

Leu Ala Thr Gly Gln Asp Glu Ala His Ile Val Glu Gly Ser Leu Gly
305                 310                 315                 320

Ile Thr Met Ala Glu Val Glu Asp Asp Gly Leu Tyr Phe Ser Val Thr
                325                 330                 335

Leu Pro Asp Val Pro Ile Gly Thr Val Gly Gly Thr Arg Val Glu
                340                 345                 350

Thr Gln Lys Glu Cys Leu Glu Met Leu Gly Cys Tyr Gly Asp Asn Lys
            355                 360                 365

Ala Leu Lys Phe Ala Glu Ile Val Gly Ala Ala Val Leu Ala Gly Glu
        370                 375                 380

Leu Ser Leu Leu Gly Ala Leu Ala Ala Gly His Leu Gly Lys Ala His
385                 390                 395                 400

Gln Glu Leu Gly Arg
                405

<210> SEQ ID NO 58
<211> LENGTH: 414
<212> TYPE: PRT
<213> ORGANISM: Methanococcoides burtonii

<400> SEQUENCE: 58

Met Ala Ser Lys Thr Glu Thr Thr Met Lys Glu Asp Glu Leu Leu Glu
  1               5                  10                  15

Lys Val Val Ser Gly Glu Met Pro Leu Arg Lys Ile Asp Ala Tyr Thr
                20                  25                  30

Asp Thr Asp Thr Ala Val Arg Val Arg Lys Cys Ala Ile Glu Lys Met
            35                  40                  45

Asn Gly Val Lys Phe Glu His Ile Gln Asn Tyr Thr Ile Asp Ala Glu
        50                  55                  60

Ala Ala Thr Lys Arg Asn Ile Glu Asn Met Ile Gly Thr Ile Gln Ile
65                  70                  75                  80

Pro Leu Gly Val Ala Gly Ala Ile Met Val Asn Gly Glu Tyr Ala Ser
                85                  90                  95

Gly Glu Phe Met Leu Pro Leu Ala Thr Thr Glu Gly Ala Leu Val Ala
                100                 105                 110

Ser Val Asn Arg Gly Cys Thr Val Ile Thr Ala Ser Gly Gly Ser Asn
            115                 120                 125

Val Arg Ile Phe Gln Asp Leu Met Thr Arg Ala Pro Val Phe Lys Leu
        130                 135                 140

Glu Asn Val Asn Lys Val Lys Glu Phe Val Asp Trp Val Lys Arg Glu
145                 150                 155                 160

Glu Thr Phe Thr Asn Met Lys Glu Lys Ala Gly Glu Thr Thr Arg Phe
                165                 170                 175

Gly Glu Leu Leu Ser Val Asp Pro Phe Ile Thr Gly Asn Thr Val Phe
            180                 185                 190

Leu Arg Phe Ala Tyr Asp Thr Lys Asp Ala Met Gly Met Asn Met Val
        195                 200                 205

Thr Ile Ala Thr Asp Ala Val Leu Asn Phe Ile Ser Glu Asp Phe Gly
210                 215                 220

Val Tyr Pro Ile Ser Leu Ser Gly Asn Met Cys Thr Asp Lys Lys Pro
225                 230                 235                 240
```

```
Ala Ala Ile Asn Asn Ile Leu Gly Arg Gly Lys Thr Val Ala Ala Asp
            245                 250                 255

Val Thr Ile Pro Lys Glu Ile Val Glu Lys Lys Leu Lys Thr Thr Pro
        260                 265                 270

Lys Met Met Glu Glu Val Asn Tyr Arg Lys Asn Leu Leu Gly Ser Ala
    275                 280                 285

Arg Ala Gly Ala Leu Gly Phe Asn Ala His Ala Ala Asn Ile Ile Ala
290                 295                 300

Ala Leu Tyr Leu Ala Cys Gly Gln Asp Ala Ala His Val Val Glu Gly
305                 310                 315                 320

Ser Ser Ala Ile Thr Thr Met Glu Val Asn Gly Asn Gly Asp Leu Tyr
                325                 330                 335

Cys Ser Val Thr Leu Pro Ser Ile Gln Val Gly Thr Val Gly Gly Gly
            340                 345                 350

Thr Gly Ile Ala Thr Gln Arg Asp Cys Leu Asn Leu Leu Gly Val Ala
        355                 360                 365

Gly Ala Gly Glu Val Pro Gly His Asn Ser Lys Lys Leu Ala Glu Ile
    370                 375                 380

Ile Ala Ala Ala Val Leu Ala Gly Glu Ile Ser Leu Ile Gly Ala Gln
385                 390                 395                 400

Ala Ala Gly His Leu Ala Lys Ala His Ala Glu Leu Gly Arg
                405                 410

<210> SEQ ID NO 59
<211> LENGTH: 418
<212> TYPE: PRT
<213> ORGANISM: Methanosarcina mazei

<400> SEQUENCE: 59

Met Phe Thr Glu Ala Tyr Glu Leu Thr Glu Glu Lys Leu Leu Leu
1               5                   10                  15

Gln Lys Val Leu Asp Gly Asp Ile Ala Phe Arg Lys Ile Glu Glu Phe
            20                  25                  30

Ala Asp Pro Leu Thr Ala Val Lys Ile Arg Arg Leu Ala Ile Gln Glu
        35                  40                  45

Tyr Gly Lys Leu Glu Phe Glu His Ile Gln Asn Phe Ser Leu Asp Val
    50                  55                  60

Glu Ser Val Thr Lys Arg Asn Ile Glu Asn Met Ile Gly Ala Val Gln
65                  70                  75                  80

Ile Pro Leu Gly Val Ala Gly Leu Leu Lys Val Asn Gly Glu Tyr Ala
                85                  90                  95

Ala Gly Glu Tyr Tyr Ile Pro Leu Ala Thr Thr Glu Gly Ala Leu Val
            100                 105                 110

Ala Ser Val Asn Arg Gly Cys Ser Val Ile Thr Arg Ser Gly Gly Ala
        115                 120                 125

Asn Val Arg Val Phe Glu Asp Glu Met Thr Arg Ala Pro Val Phe Lys
    130                 135                 140

Phe Glu Ser Leu Glu Arg Ala Arg Lys Phe Tyr Asp Trp Val Lys Ser
145                 150                 155                 160

Pro Glu Thr Phe Glu Gln Met Lys Gln Ala Ala Glu Lys Thr Thr Arg
                165                 170                 175

Phe Gly Lys Leu Leu Ser Val Lys Pro Phe Val Thr Gly Thr Tyr Ile
            180                 185                 190

Tyr Leu Arg Phe Ser Tyr Asp Thr Lys Asp Ala Met Gly Met Asn Met
        195                 200                 205
```

```
Val Thr Ile Ala Thr Asp Ala Val Met His Leu Ile Glu Asp Glu Phe
    210             215                 220

Gly Ala His Pro Val Thr Leu Ser Gly Asn Met Cys Thr Asp Lys Lys
225             230                 235                 240

Pro Ala Ser Ile Ser Ala Ile Leu Gly Arg Gly Lys Thr Val Val Ala
                245                 250                 255

Glu Val Thr Ile Pro Gln Glu Ile Val Lys Glu Thr Leu Lys Cys Thr
            260                 265                 270

Pro Glu Ser Met Phe Glu Val Asn Tyr Ser Lys Asn Leu Leu Gly Ser
        275                 280                 285

Ala Arg Ala Gly Ala Met Gly Phe Asn Ala His Ala Ala Asn Ile Ile
    290                 295                 300

Ala Ala Val Tyr Leu Ala Cys Gly Gln Asp Ala Ala His Val Val Glu
305             310                 315                 320

Gly Ser Thr Ala Ile Thr Ser Met Glu Leu Thr Lys Tyr Glu Glu Ile
                325                 330                 335

His Cys Ser Val Thr Leu Pro Ala Leu Pro Val Gly Thr Val Gly Gly
            340                 345                 350

Gly Thr Gly Leu Gly Thr Gln Arg Asp Cys Leu Asn Ile Leu Gly Val
        355                 360                 365

Ala Gly Ala Gly Asp Thr Pro Gly Ile Asn Ser Arg Lys Phe Ala Glu
    370                 375                 380

Ile Val Ala Ser Ala Val Leu Ala Gly Glu Ile Ser Leu Ile Gly Ala
385             390                 395                 400

Gln Ala Ala Gly His Leu Ala Arg Ala His Ala Gln Leu Gly Arg Gly
                405                 410                 415

Lys Phe

<210> SEQ ID NO 60
<211> LENGTH: 409
<212> TYPE: PRT
<213> ORGANISM: Sulfolobus solfataricus

<400> SEQUENCE: 60

Met Lys Ile Asp Glu Val Val Glu Lys Leu Val Lys Gly Glu Ile Ser
1               5                   10                  15

Phe His Glu Val Asp Asn Leu Leu Glu Ala Asn Ala Ala Met Val Ala
            20                  25                  30

Arg Arg Leu Ala Leu Glu Lys Ile Val Gly Val Gly Leu Pro Ser Ile
        35                  40                  45

Gly Ser Thr Val Ile Asp Tyr Ser Glu Ile Lys Asn Lys Asn Ala Glu
    50                  55                  60

Asn Val Ile Gly Ala Ile Gln Ile Pro Leu Gly Ile Val Gly Pro Ile
65                  70                  75                  80

Arg Val Asn Gly Asp Tyr Ala Lys Gly Asp Phe Tyr Val Pro Met Ala
                85                  90                  95

Thr Thr Glu Gly Ala Leu Ile Ala Ser Val Asn Arg Gly Ile Lys Ala
            100                 105                 110

Val Thr Leu Ser Gly Gly Val Arg Ala Lys Val Leu Lys Asp Glu Met
        115                 120                 125

Thr Arg Ala Pro Val Phe Lys Phe Asp Ser Ile Glu Gln Ile Pro Asn
    130                 135                 140

Phe Leu Lys Phe Ile Glu Glu Asn Leu Glu Lys Ile Arg Asn Ile Ala
145                 150                 155                 160

Asn Ser Thr Ser His His Gly Lys Leu Lys Ser Ile Thr Pro Phe Val
```

```
                 165                 170                 175
Leu Gly Asn Asn Val Trp Leu Arg Phe Ser Phe Glu Thr Gly Asp Ala
            180                 185                 190

Met Gly Met Asn Met Val Thr Ile Ala Val Glu Lys Val Cys Glu Phe
            195                 200                 205

Ile Glu Glu Asn Phe Pro Ser Ala Asp Cys Leu Ala Val Ser Gly Asn
            210                 215                 220

Met Cys Ser Asp Lys Lys Gln Thr Asn Val Asn Ser Leu Phe Gly Arg
225                 230                 235                 240

Gly Lys Thr Val Val Ala Glu Ala Leu Ile Lys Lys Asp Val Ile Arg
                245                 250                 255

Asn Ile Leu His Ser Asn Ala Gln Leu Ile His Asp Ile Asn Leu Arg
            260                 265                 270

Lys Asn Trp Leu Gly Thr Ala Arg Ala Gly Ser Leu Ser Gln Phe Asn
            275                 280                 285

Ala His Phe Ala Asn Ile Val Thr Ala Ile Phe Ile Ala Thr Gly Gln
            290                 295                 300

Asp Val Ala Gln Ile Val Glu Ser Ser Ser Gly Tyr Thr Trp Thr Glu
305                 310                 315                 320

Val Arg Gly Glu Asp Leu Tyr Ile Ser Val Thr Leu Pro Ser Leu Glu
                325                 330                 335

Val Gly Thr Val Gly Gly Gly Thr Arg Leu Pro Thr Gln Lys Glu Ala
            340                 345                 350

Leu Ser Ile Met Gly Val Tyr Gly Ser Gly Asn Pro Pro Gly Ser Asn
            355                 360                 365

Ala Lys Lys Leu Ala Glu Ile Ile Ala Ser Thr Val Leu Ser Gly Glu
            370                 375                 380

Leu Asn Leu Leu Ala Ala Leu Ser Asn Lys Glu Leu Gly Lys Ala His
385                 390                 395                 400

Ala Lys Leu Gly Arg Ala Met Lys Val
                405

<210> SEQ ID NO 61
<211> LENGTH: 411
<212> TYPE: PRT
<213> ORGANISM: Sulfolobus acidocaldarius

<400> SEQUENCE: 61

Met Gln Glu Thr Ile Asp Asn Ile Val Asp Lys Val Val Lys Gly Gln
1               5                   10                  15

Ile Gln Phe His Glu Ile Asp Asn Leu Leu Glu Ala Asn Ala Ala Met
            20                  25                  30

Val Ala Arg Arg Leu Ala Ile Glu Lys Leu Thr Gly Ala Lys Leu Pro
        35                  40                  45

Ser Ile Gly Ser Thr Ile Ile Asp Tyr Ala Glu Ile Arg Asn Lys Asn
    50                  55                  60

Ala Glu Asn Val Ile Gly Ala Val Gln Val Pro Leu Gly Ile Ile Gly
65                  70                  75                  80

Pro Leu Lys Ile Asp Gly Glu Tyr Ala Lys Gly Asp Phe Tyr Val Pro
                85                  90                  95

Leu Ala Thr Thr Glu Gly Ala Leu Ile Ala Ser Val Asn Arg Gly Ala
            100                 105                 110

Lys Ala Val Thr Leu Ser Gly Gly Thr Arg Val Lys Ile Phe Tyr Asp
        115                 120                 125

Gly Met Thr Arg Ala Pro Ile Phe Lys Leu Asp Ser Ile Arg Asp Val
```

```
                    130                 135                 140
Ala Glu Phe Leu Glu Trp Val Asp Lys Asn Lys Glu Lys Leu Glu Gln
145                 150                 155                 160

Val Ala Asn Ser Thr Thr Ser His Gly Lys Leu Ser Lys Ile Glu Pro
                165                 170                 175

Leu Ile Leu Gly Asn Asn Val Trp Leu Arg Phe Val Phe Ser Thr Gly
                180                 185                 190

Asp Ala Met Gly Met Asn Met Ala Thr Ile Ala Ser Glu Lys Leu Cys
                195                 200                 205

Glu Phe Ile Glu Lys Glu Phe Gly Lys Ala Thr Cys Leu Ala Val Ser
210                 215                 220

Gly Asn Val Cys Ser Asp Lys Lys Gln Ser Met Ile Asn Ala Leu His
225                 230                 235                 240

Gly Arg Gly Lys Thr Val Val Ala Glu Ala Leu Ile Pro Asp Ser Ile
                245                 250                 255

Val Lys Ser Ala Leu Lys Ser Asp Lys His Leu Ile His Glu Val Asn
                260                 265                 270

Leu Arg Lys Asn Trp Leu Gly Gly Ala Arg Ala Gly Asn Ile Phe Gln
                275                 280                 285

Tyr Asn Ala His Phe Ala Asn Ile Ile Ala Ala Ile Phe Leu Ala Thr
                290                 295                 300

Gly Gln Asp Ile Ala Gln Val Val Glu Ser Ser Met Gly Tyr Thr Trp
305                 310                 315                 320

Thr Glu Val Arg Glu Asn Gly Leu Tyr Ile Ser Ile Thr Leu Asn Ser
                325                 330                 335

Leu Glu Val Gly Thr Val Gly Gly Thr Arg Leu Pro Thr Gln Arg
                340                 345                 350

Glu Ala Leu Ser Ile Met Gly Val Leu Gly Ser Gly Asn Pro Pro Gly
                355                 360                 365

Ser Asn Ala Arg Lys Phe Ala Glu Ile Val Ala Ser Ala Val Leu Ala
                370                 375                 380

Gly Glu Leu Asn Leu Leu Ser Ala Leu Ala Asn Lys Glu Leu Gly Lys
385                 390                 395                 400

Ala His Ala Lys Leu Gly Arg Gly Met Lys Val
                405                 410

<210> SEQ ID NO 62
<211> LENGTH: 430
<212> TYPE: PRT
<213> ORGANISM: Methanosarcina acetivorans

<400> SEQUENCE: 62

Met Arg Lys Arg Ile Lys Arg Ser Thr Gly Asp Phe Met Phe Leu Asn
  1               5                  10                  15

Asp Tyr Glu Leu Gly Glu Glu Glu Lys Leu Leu Leu Gln Lys Val Leu
                 20                  25                  30

Asp Gly Asp Ile Ala Phe Arg Lys Ile Glu Glu Phe Ala Glu Pro Leu
                 35                  40                  45

Thr Ala Val Lys Ile Arg Arg Leu Ala Ile Gln Glu Tyr Ala Lys Leu
 50                  55                  60

Glu Phe Glu His Ile Gln Asn Phe Ser Leu Asp Val Glu Ile Val Thr
 65                  70                  75                  80

Lys Arg Asn Ile Glu Asn Met Ile Gly Ala Val Gln Ile Pro Leu Gly
                 85                  90                  95

Thr Ala Gly Leu Leu Lys Val Asn Gly Glu Tyr Ala Asp Ala Glu Tyr
```

```
            100                 105                 110
Tyr Ile Pro Leu Ala Thr Thr Glu Gly Ala Leu Val Ala Ser Val Asn
        115                 120                 125

Arg Gly Cys Ser Val Ile Thr Lys Ser Gly Ala Asn Val Arg Val
130                 135                 140

Phe Glu Asp Glu Met Thr Arg Ala Pro Val Phe Lys Leu Glu Ser Leu
145                 150                 155                 160

Asp Arg Ala Lys Lys Phe Tyr Glu Trp Val Lys Arg Pro Glu Ile Phe
                165                 170                 175

Glu Gln Met Lys Glu Val Ala Glu Lys Thr Thr Arg Phe Gly Lys Leu
            180                 185                 190

Val Ser Val Lys Pro Phe Val Thr Gly Thr Tyr Val Tyr Leu Arg Phe
        195                 200                 205

Ser Tyr Asp Thr Lys Asp Ala Met Gly Met Asn Met Val Thr Ile Ala
        210                 215                 220

Thr Asp Ala Val Met His Leu Ile Glu Asp Glu Phe Gly Ala His Pro
225                 230                 235                 240

Ile Thr Leu Ser Ser Asn Met Cys Thr Asp Lys Lys Pro Ala Ser Ile
                245                 250                 255

Ser Thr Ile Leu Gly Arg Gly Lys Thr Val Val Ala Glu Val Thr Ile
                260                 265                 270

Pro Glu Glu Ile Val Lys Glu Thr Leu Lys Cys Thr Pro Glu Ser Met
            275                 280                 285

Phe Glu Val Asn Tyr Ser Lys Asn Leu Leu Gly Ser Ala Arg Ala Gly
        290                 295                 300

Ala Met Gly Phe Asn Ala His Ala Ala Asn Val Ile Ala Ala Leu Tyr
305                 310                 315                 320

Leu Ala Cys Gly Gln Asp Ala Ala His Val Val Glu Gly Ser Thr Ala
                325                 330                 335

Ile Thr Ser Met Glu Leu Thr Lys Tyr Gly Ile His Cys Ser Val
                340                 345                 350

Thr Leu Pro Ala Leu Pro Val Gly Thr Val Gly Gly Thr Gly Leu
            355                 360                 365

Gly Thr Gln Arg Asp Cys Leu Asn Ile Leu Gly Val Ala Gly Ala Gly
        370                 375                 380

Asp Glu Pro Gly Ile Asn Ser Leu Lys Phe Ala Glu Ile Val Ala Ser
385                 390                 395                 400

Ala Val Leu Ala Gly Glu Ile Ser Leu Ile Gly Ala Gln Ala Ala Gly
                405                 410                 415

His Leu Ala Arg Ala His Ala Gln Leu Gly Arg Gly Lys Phe
            420                 425                 430

<210> SEQ ID NO 63
<211> LENGTH: 397
<212> TYPE: PRT
<213> ORGANISM: Methanothermobacter thermautotrophicus

<400> SEQUENCE: 63

Met Ser Ile Met Asp Asp Leu Met Glu Gly Arg Ile Lys Leu Tyr Glu
1               5                   10                  15

Ile Glu Arg His Val Pro Val Asp Glu Ala Val Arg Ile Arg Arg Glu
                20                  25                  30

Phe Ile Glu Arg Thr Cys Gly Val Lys Leu Glu His Val Ser Asn Tyr
            35                  40                  45

Ser Ile Asp Met Glu Arg Ala Ser Arg Arg Asn Ile Glu Asn Pro Ile
```

-continued

```
                50                  55                  60
Gly Val Val Gln Ile Pro Leu Gly Val Ala Gly Pro Leu Arg Val Arg
 65                  70                  75                  80

Gly Glu His Ala Asp Gly Glu Tyr Tyr Val Pro Leu Ala Thr Ser Glu
                 85                  90                  95

Gly Ala Leu Val Ala Ser Val Asn Arg Gly Cys Ser Val Ile Thr Arg
            100                 105                 110

Ala Gly Gly Ala Thr Val Arg Val Thr Gly Asp Ser Met Thr Arg Ala
            115                 120                 125

Pro Val Ile Arg Thr Gly Ser Val Val Glu Ala Leu Gln Leu Arg Glu
130                 135                 140

Trp Ile Tyr Glu Asn Met Asp Ala Leu Arg Glu Glu Ala Glu Ser Thr
145                 150                 155                 160

Thr Arg His Gly Lys Leu Val Lys Ile Asp Pro Ile Ile Val Ala Gly
                165                 170                 175

Ser Tyr Val Tyr Pro Arg Phe Val Tyr Thr Thr Gly Asp Ser Met Gly
            180                 185                 190

Met Asn Met Val Thr Ile Ala Thr Glu Arg Ala Leu Glu Leu Leu Thr
            195                 200                 205

Arg Glu Thr Gly Ala His Val Ile Ala Leu Ser Gly Asn Leu Cys Thr
210                 215                 220

Asp Lys Lys Pro Ala Ala Val Asn Leu Ile Glu Gly Arg Gly Lys Ser
225                 230                 235                 240

Ile Thr Ala Glu Ile Thr Val Pro Gly Glu Met Val Glu Ser Val Leu
                245                 250                 255

Lys Thr Thr Pro Glu Ala Val Val Glu Val Asn Thr Ala Lys Asn Leu
            260                 265                 270

Ile Gly Ser Ala Ala Gly Ser Met Gly Phe Asn Ala His Tyr Ala
            275                 280                 285

Asn Ile Ile Gly Ala Ile Phe Leu Ala Thr Gly Gln Asp Glu Ala His
            290                 295                 300

Ile Val Glu Gly Ser Leu Gly Val Thr Ile Ala Glu Glu Arg Lys Gly
305                 310                 315                 320

Asp Leu Tyr Phe Ala Val Asn Leu Pro Asp Val Pro Leu Ala Thr Val
                325                 330                 335

Gly Gly Gly Thr Gly Leu Glu Thr Ala Ser Glu Cys Leu Asp Ile Met
            340                 345                 350

Gly Val Arg Gly Gly Arg Val His Ala Phe Ala Glu Ile Val Gly
            355                 360                 365

Gly Ala Val Leu Ala Gly Glu Leu Ser Leu Met Gly Ala Leu Ala Ala
370                 375                 380

Gly His Leu Ala Arg Ala His Ser Glu Leu Gly Arg Gly
385                 390                 395
```

<210> SEQ ID NO 64
<211> LENGTH: 418
<212> TYPE: PRT
<213> ORGANISM: Methanosarcina barkeri

<400> SEQUENCE: 64

```
Met Phe Leu Gln Asp Tyr Glu Leu Ser Glu Glu Lys Val Leu Leu
  1               5                  10                  15

Gln Lys Ile Leu Asp Gly Asp Val Ala Leu Arg Lys Ile Glu Glu Phe
                 20                  25                  30

Ala Asp Pro Glu Thr Ser Val Lys Leu Arg Arg Leu Ala Ile Gln Glu
```

```
            35                  40                  45
Phe Ala Lys Leu Glu Phe Glu His Ile Gln Asn Phe Ser Leu Asp Val
 50                  55                  60
Glu Ala Ala Ser Lys Arg Asn Ile Glu Asn Met Ile Gly Ala Val Gln
 65                  70                  75                  80
Ile Pro Leu Gly Ile Ala Gly Leu Leu Lys Val Asn Gly Glu Tyr Ala
                 85                  90                  95
Asn Ser Glu Tyr Tyr Ile Pro Leu Ala Thr Thr Glu Gly Ala Leu Val
                100                 105                 110
Ala Gly Val Asn Arg Gly Cys Ser Val Ile Thr Lys Ser Gly Gly Ala
                115                 120                 125
Asn Val Arg Val Phe Glu Asp Glu Met Thr Arg Ala Pro Val Phe Lys
130                 135                 140
Leu Glu Ser Leu Ser Arg Ala Lys Glu Phe Tyr Glu Trp Val Lys Cys
145                 150                 155                 160
Pro Glu Ile Phe Glu Lys Met Lys Val Val Ala Glu Lys Thr Thr Arg
                165                 170                 175
Phe Gly Lys Leu Leu Ser Val Arg Pro Phe Val Thr Gly Thr Tyr Val
                180                 185                 190
Tyr Leu Arg Phe Ser Tyr Asp Thr Lys Asp Ala Met Gly Met Asn Met
                195                 200                 205
Val Thr Ile Ala Thr Asp Ala Val Met His Leu Ile Gln Asp Glu Phe
                210                 215                 220
Gly Ala His Pro Val Thr Leu Ser Gly Asn Met Cys Ile Asp Lys Lys
225                 230                 235                 240
Pro Ala Ser Ile Ser Thr Ile Leu Gly Arg Gly Lys Thr Val Val Ala
                245                 250                 255
Glu Val Thr Ile Pro Lys Glu Ile Val Lys Glu Thr Leu Lys Cys Thr
                260                 265                 270
Pro Glu Ser Met Phe Glu Val Asn Tyr Ser Lys Asn Leu Leu Gly Ser
                275                 280                 285
Ala Arg Ala Gly Ala Leu Gly Phe Asn Ala His Ala Ala Asn Ile Ile
290                 295                 300
Ala Ala Ile Tyr Leu Ala Cys Gly Gln Asp Ala Ala His Val Val Glu
305                 310                 315                 320
Gly Ser Thr Ala Ile Thr Ser Met Glu Leu Thr Lys Tyr Glu Glu Ile
                325                 330                 335
Gln Cys Ser Val Thr Leu Pro Ser Leu Pro Val Gly Thr Val Gly Gly
                340                 345                 350
Gly Ser Gly Leu Gly Thr Gln Arg Asp Cys Leu Asn Ile Leu Gly Val
                355                 360                 365
Ala Gly Ala Gly Asp Val Pro Gly Ile Asn Ser Lys Lys Phe Ala Glu
                370                 375                 380
Ile Val Ala Ser Ala Val Leu Ala Gly Glu Val Asn Leu Ile Gly Ala
385                 390                 395                 400
Gln Ala Ala Gly His Leu Ala Arg Ala His Ala Gln Leu Gly Arg Gly
                405                 410                 415
Lys Phe

<210> SEQ ID NO 65
<211> LENGTH: 408
<212> TYPE: PRT
<213> ORGANISM: Methanococcus maripaludis

<400> SEQUENCE: 65
```

```
Met Glu Asn Asn Val Asn Ile Asp Glu Ile Val Glu Lys Leu Leu Lys
 1               5                  10                  15

Lys Glu Ile Lys Val Tyr Gln Leu Asp Ser Lys Phe Gly Glu Arg Asn
            20                  25                  30

Ala Val Ile Ala Arg Arg Lys Tyr Val Glu Lys Leu Ser Asn Val Glu
        35                  40                  45

Thr Arg His Ile Gln Glu Tyr Thr Leu Asp Glu Lys Leu Ala Met Gln
    50                  55                  60

Lys Asn Ile Glu Asn Met Ile Gly Ala Val Gln Ile Pro Leu Gly Phe
65                  70                  75                  80

Ala Gly Pro Ile Ser Ile Asn Gly Lys Tyr Ala Gln Gly Glu Phe Asn
                85                  90                  95

Val Pro Leu Ala Thr Thr Glu Gly Ala Leu Val Ala Ser Ile Asn Arg
            100                 105                 110

Gly Cys Ser Ile Ile Thr Lys Cys Gly Gly Ala Thr Val Arg Val Ile
        115                 120                 125

Asp Asp Lys Met Thr Arg Ala Pro Ile Ile Lys Thr Asn Ser Val Val
    130                 135                 140

Asp Ala Leu Lys Leu Lys Glu Trp Ile Leu Asp Asn Phe Ala Lys Ile
145                 150                 155                 160

Lys Glu Ile Ala Glu Ser Thr Thr Arg His Gly Lys Leu Ile Gln Ile
                165                 170                 175

Ser Pro Ile Leu Ile Val Gly Arg Asn Val Tyr Pro Arg Phe Thr Phe
            180                 185                 190

Lys Thr Gly Asp Ala Met Gly Met Asn Met Val Thr Ile Ala Thr Glu
        195                 200                 205

Lys Ala Cys Ser Phe Ile Glu Ser Glu Leu Lys Lys Glu Gly Ile Ile
    210                 215                 220

Ile Asp Thr Val Ala Leu Ser Gly Asn Val Cys Val Asp Lys Lys Pro
225                 230                 235                 240

Ala Ala Ile Asn Leu Ile Glu Gly Arg Gly Lys Ser Val Val Ala Glu
                245                 250                 255

Val Phe Leu Lys Glu Glu Tyr Val Glu Lys Tyr Leu Lys Thr Thr Ser
            260                 265                 270

Lys Ala Ile Glu Gln Val Asn Thr Tyr Lys Asn Leu Ile Gly Ser Ala
        275                 280                 285

Ile Ser Ser Ser Leu Gly Phe Asn Ala Gln Tyr Ala Asn Ile Val Gly
    290                 295                 300

Ala Leu Phe Leu Ala Thr Gly Gln Asp Glu Ala His Ile Val Glu Gly
305                 310                 315                 320

Ser Met Gly Ile Thr Thr Ala Glu Cys Thr Gly Asp Gly Leu Tyr Phe
                325                 330                 335

Ser Val Thr Leu Pro Asp Leu Pro Val Ala Thr Ile Gly Gly Gly Thr
            340                 345                 350

Arg Val Glu Thr Gln Arg Glu Cys Leu Glu Ile Leu Gly Cys Ala Gly
        355                 360                 365

Ala Glu Lys Ala Val Lys Phe Ala Glu Ile Ala Gly Ala Ala Val Leu
    370                 375                 380

Ala Gly Glu Leu Ser Leu Ile Gly Ala Leu Ala Ala Gly His Leu Ala
385                 390                 395                 400

Lys Ala His Ser Glu Leu Gly Arg
                405
```

```
<210> SEQ ID NO 66
<211> LENGTH: 402
<212> TYPE: PRT
<213> ORGANISM: Natronomonas pharaonis

<400> SEQUENCE: 66

Met Asp Thr Asp Ala Leu Val Asp Ala Val Arg Asp Gly Glu Leu Arg
 1               5                   10                  15

Leu His Glu Leu Glu Ala His Ala Asp Ala Asp Thr Ala Ala Ala Ala
            20                  25                  30

Arg Arg Arg Ile Val Ala Asp Ala Ala Asp Thr Ser Leu Glu Thr Val
        35                  40                  45

Gly Glu Tyr Ala Phe Pro Ala Asp Ala Glu Pro Asn Ile Glu Asn
    50                  55                  60

Met Val Gly Ala Ala Gln Val Pro Met Gly Val Gly Pro Leu Ala
65                  70                  75                  80

Val Asp Gly Asp Ala Ile Asp Gly Pro Tyr Leu Pro Leu Ala Thr
                85                  90                  95

Thr Glu Gly Ala Leu Val Ala Ser Val Asn Arg Gly Cys Ala Ser Met
            100                 105                 110

Thr Ala Ala Gly Gly Ala Thr Ala Arg Val Leu Lys Asn Ala Met Thr
        115                 120                 125

Arg Ala Pro Val Phe Arg Val Ala Gly Val Ala Glu Ala Ser Glu Thr
    130                 135                 140

Ala Ala Trp Val Arg Asp Asn Val Glu Ser Leu Ala Ser Ala Ala Glu
145                 150                 155                 160

Ala Thr Thr Ser His Gly Glu Leu Arg Asp Val Thr Pro Tyr Val Val
                165                 170                 175

Gly Asp Asn Val Phe Leu Arg Phe Ala Tyr Asp Thr Lys Asp Ala Met
            180                 185                 190

Gly Met Asn Met Ala Thr Ile Ala Thr Glu Ala Ala Cys Glu Val Val
        195                 200                 205

Glu Ala Glu Thr Pro Ala Glu Leu Val Ala Leu Ser Gly Asn Leu Cys
    210                 215                 220

Ser Asp Lys Lys Pro Ala Ala Val Asn Ser Val Glu Gly Arg Gly Arg
225                 230                 235                 240

Thr Val Ala Ala Asp Val Val Leu Pro Gly Ser Val Val Glu Glu Tyr
                245                 250                 255

Phe Gly Thr Thr Pro Ala Ala Ile Ala Glu Ala Asn Thr Arg Lys Asn
            260                 265                 270

Leu Val Gly Ser Ala Lys Ala Gly Ser Leu Gly Phe Asn Ala His Ala
        275                 280                 285

Ala Asn Thr Val Ala Ala Phe Leu Ala Thr Gly Gln Asp Ile Ala
    290                 295                 300

Gln Val Val Glu Gly Ala Asn Ala Ile Thr Thr Ala Asp Val Arg Asp
305                 310                 315                 320

Gly Asp Leu Tyr Ala Ser Leu Thr Leu Ala Ser Leu Glu Val Gly Thr
                325                 330                 335

Val Gly Gly Gly Thr Lys Leu Pro Thr Gln Ala Glu Ala Leu Asp Val
            340                 345                 350

Val Gly Val Arg Gly Gly Asp Pro Ala Gly Ser Asn Ala Asp Ala
        355                 360                 365

Leu Ala Glu Ala Ile Ala Thr Ala Ala Leu Gly Gly Glu Leu Ser Leu
    370                 375                 380

Leu Gly Ala Leu Ala Ser Asn His Leu Ala Ser Ala His Glu Glu Leu
```

```
385                 390                 395                 400

Gly Arg

<210> SEQ ID NO 67
<211> LENGTH: 403
<212> TYPE: PRT
<213> ORGANISM: Artificial Sequence
<220> FEATURE:
<223> OTHER INFORMATION: synthetic construct

<400> SEQUENCE: 67

Met Thr Asp Ala Ala Ser Leu Ala Asp Arg Val Arg Glu Gly Asp Leu
  1               5                  10                  15

Arg Leu His Glu Leu Glu Ala His Ala Asp Ala Asp Thr Ala Ala Glu
             20                  25                  30

Ala Arg Arg Leu Leu Val Glu Ser Gln Ser Gly Ala Ser Leu Asp Ala
         35                  40                  45

Val Gly Asn Tyr Gly Phe Pro Ala Glu Ala Ala Glu Ser Ala Ile Glu
     50                  55                  60

Asn Met Val Gly Ser Ile Gln Val Pro Met Gly Val Ala Gly Pro Val
 65                  70                  75                  80

Ser Val Asp Gly Gly Ser Val Ala Gly Glu Lys Tyr Leu Pro Leu Ala
                 85                  90                  95

Thr Thr Glu Gly Ala Leu Leu Ala Ser Val Asn Arg Gly Cys Ser Val
            100                 105                 110

Ile Asn Ser Ala Gly Gly Ala Thr Ala Arg Val Leu Lys Ser Gly Met
        115                 120                 125

Thr Arg Ala Pro Val Phe Arg Val Ala Asp Val Ala Glu Ala Glu Ala
    130                 135                 140

Leu Val Ser Trp Thr Arg Asp Asn Phe Ala Ala Leu Lys Glu Ala Ala
145                 150                 155                 160

Glu Glu Thr Thr Asn His Gly Glu Leu Leu Asp Val Thr Pro Tyr Val
                165                 170                 175

Val Gly Asn Ser Val Tyr Leu Arg Phe Arg Tyr Asp Thr Lys Asp Ala
            180                 185                 190

Met Gly Met Asn Met Ala Thr Ile Ala Thr Glu Ala Val Cys Gly Val
        195                 200                 205

Val Glu Ala Glu Thr Ala Ala Ser Leu Val Ala Leu Ser Gly Asn Leu
    210                 215                 220

Cys Ser Asp Lys Lys Pro Ala Ala Ile Asn Ala Val Glu Gly Arg Gly
225                 230                 235                 240

Arg Ser Val Thr Ala Asp Val Arg Ile Pro Arg Glu Val Val Glu Glu
                245                 250                 255

Arg Leu His Thr Thr Pro Glu Arg Gly Arg Glu Leu Asn Thr Arg Lys
            260                 265                 270

Asn Leu Val Gly Ser Ala Lys Ala Ala Ser Leu Gly Phe Asn Ala His
        275                 280                 285

Val Ala Asn Val Val Ala Ala Met Phe Leu Ala Thr Gly Gln Asp Glu
    290                 295                 300

Ala Gln Val Val Glu Gly Ala Asn Ala Ile Thr Thr Ala Glu Val Gln
305                 310                 315                 320

Asp Gly Asp Leu Tyr Val Ser Val Ser Ile Ala Ser Leu Glu Val Gly
                325                 330                 335

Thr Val Gly Gly Gly Thr Lys Leu Pro Thr Gln Ser Glu Gly Leu Asp
            340                 345                 350
```

```
Ile Leu Gly Val Ser Gly Gly Asp Pro Ala Gly Ser Asn Ala Asp
        355                 360                 365

Ala Leu Ala Glu Cys Ile Ala Val Gly Ser Leu Ala Gly Glu Leu Ser
370                 375                 380

Leu Leu Ser Ala Leu Ala Ser Arg His Leu Ser Ser Ala His Ala Glu
385                 390                 395                 400

Leu Gly Arg

<210> SEQ ID NO 68
<211> LENGTH: 405
<212> TYPE: PRT
<213> ORGANISM: Halobacterium

<400> SEQUENCE: 68

Met Pro Asp Asp Ala Ser Asp Leu Ala Asp Arg Val Gln Ala Gly Asp
1               5                   10                  15

Leu Arg Leu Tyr Glu Leu Asp Asp Glu Thr Asp Ala Asp Thr Ala Ala
            20                  25                  30

Ala Ala Arg Arg Ala Val Leu Glu Arg Glu Thr Asp Ala Asp Thr Asp
        35                  40                  45

Ala Leu Gly Ala Phe Ala Phe Asp Ala Asp Gln Ala Ala Asp Thr Ala
    50                  55                  60

Val Glu Asn Leu Thr Gly Gly Ala Gln Leu Pro Leu Gly Val Ala Gly
65                  70                  75                  80

Pro Val Ala Leu Ser Gly Gly Ala Ala Asp Gly Glu Tyr Tyr Leu Pro
                85                  90                  95

Met Ala Thr Thr Glu Gly Ala Leu Val Ala Ser Val Asn Arg Gly Cys
            100                 105                 110

Ser Ala Ile Thr Ala Ala Gly Gly Ala Asn Ala Arg Val Thr Lys Thr
        115                 120                 125

Gly Met Thr Arg Ala Pro Val Phe Arg Val Ala Asp Val Thr Glu Gly
    130                 135                 140

Ala Glu Val Ala Gln Trp Ala Asp Asp Asn Thr Asp Ala Leu Ala Ala
145                 150                 155                 160

Ala Ala Glu Ser Thr Thr Ser His Gly Glu Leu Thr Asp Val Thr Pro
                165                 170                 175

Tyr Val Val Gly Asp Asn Val Tyr Leu Arg Phe Arg Tyr Asp Thr Lys
            180                 185                 190

Asp Ala Met Gly Met Asn Met Ala Thr Ile Ala Thr Glu Ala Ala Ser
        195                 200                 205

Glu Leu Val Glu Asp Glu Thr Pro Ala Glu Leu Val Ala Val Ser Gly
    210                 215                 220

Asn Leu Cys Thr Asp Lys Lys Pro Ala Ala Ile Asn Ala Val Glu Gly
225                 230                 235                 240

Arg Gly Arg Thr Val Thr Ala Asp Val Thr Ile Pro Gln Asp Val Val
                245                 250                 255

Glu Glu Arg Phe Asp Thr Thr Pro Ala Ala Ile Glu Glu Ala Asn Thr
            260                 265                 270

Arg Lys Asn Leu Ile Gly Ser Ala Lys Ala Gly Ser Leu Gly Phe Asn
        275                 280                 285

Ala His Ala Ala Asn Val Val Ala Ala Val Phe Leu Ala Thr Gly Gln
    290                 295                 300

Asp Ala Ala Gln Val Val Glu Gly Ala Asn Ala Ile Thr Thr Val Glu
305                 310                 315                 320

Ala Arg Asp Asp Ala Leu Tyr Ala Ser Val Asn Leu Ala Ser Leu Glu
```

```
                   325                 330                 335
Val Gly Thr Val Gly Gly Gly Thr Thr Leu Pro Thr Gln Arg Glu Ala
                340                 345                 350

Leu Asp Val Leu Gly Val Arg Gly Gly Asp Pro Ala Gly Ala Asn
            355                 360                 365

Ala Asp Ala Leu Ala Glu Ile Ile Ala Val Gly Ala Leu Ala Gly Glu
            370                 375                 380

Ile Asn Leu Leu Ala Ala Leu Ala Ser Arg Arg Leu Ser Ala Ala His
385                 390                 395                 400

Ala Asp Leu Gly Arg
            405

<210> SEQ ID NO 69
<211> LENGTH: 405
<212> TYPE: PRT
<213> ORGANISM: Haloarcula marismortui

<400> SEQUENCE: 69

Met Thr Asp Ser Asp Val Val Ala Leu Ala Glu Arg Val Arg Asp Gly
1               5                   10                  15

Glu Leu Arg Leu Tyr Glu Leu Glu Asp His Ala Glu Pro Asp Val Ala
            20                  25                  30

Ala Ala Ala Arg Arg His Leu Leu Ala Glu Thr Asp Thr Asp Leu
            35                  40                  45

Ser Ala Val Gly Asp Tyr Thr Phe Asp Ala Ala Asp Ala Glu Ser Asn
        50                  55                  60

Ile Glu Asn Met Val Gly Ala Ala Gln Val Pro Met Gly Val Val Gly
65                  70                  75                  80

Pro Leu Pro Val Asp Gly Ala Ala Glu Gly Asp His His Leu Pro
                85                  90                  95

Leu Ala Thr Ser Glu Gly Ala Leu Leu Ala Ser Val Asn Arg Gly Val
            100                 105                 110

Ser Thr Ile Arg Asn Ala Gly Gly Ala Thr Ala Arg Val Leu Lys Ser
            115                 120                 125

Gly Met Thr Arg Ala Pro Val Phe Arg Val Glu Asp Val Ala Glu Ala
            130                 135                 140

Gly Glu Val Ser Ala Trp Val Arg Glu His Val Asp Val Leu Ala Asp
145                 150                 155                 160

Ala Ala Glu Ser Thr Thr Ser His Gly Glu Leu Gln Asp Val Thr Pro
                165                 170                 175

Tyr Val Val Gly Asp Ser Val Phe Leu Arg Phe Ser Tyr Asp Thr Lys
            180                 185                 190

Asp Ala Met Gly Met Asn Met Ala Thr Ile Ala Thr Glu Ala Ala Cys
            195                 200                 205

Asp Val Val Glu Thr Glu Thr Pro Ala Asp Leu Val Ala Leu Ser Gly
            210                 215                 220

Asn Leu Cys Ser Asp Lys Lys Pro Ala Ile Asn Ala Val Glu Gly
225                 230                 235                 240

Arg Gly Arg Thr Val Ala Ala Asp Val Leu Ile Pro His Glu Gln Val
                245                 250                 255

Glu Asp Arg Leu Asp Thr Thr Ser Asp Ala Ile Val Glu Ala Asn Thr
            260                 265                 270

Arg Lys Asn Leu Val Gly Ser Ala Lys Ala Gly Ala Leu Gly Phe Asn
            275                 280                 285

Ala His Ala Ala Asn Val Val Ala Ala Ala Phe Leu Ala Leu Gly Gln
```

Asp Met Ala Gln Val Val Glu Gly Ser Asn Ala Ile Thr Thr Val Asp
305                 310                 315                 320

Ala Arg Glu Asp Gly Leu Tyr Ala Ser Val Thr Ile Ala Ser Leu Glu
            325                 330                 335

Val Gly Thr Val Gly Gly Gly Thr Gly Leu Pro Thr Gln Ser Glu Ala
            340                 345                 350

Leu Asp Val Leu Gly Tyr Ser Gly Gly Asp Pro Ala Gly Ser Asn
            355                 360                 365

Ala Asp Ala Leu Ala Glu Val Ile Ala Ala Gly Ala Leu Ala Gly Glu
370                 375                 380

Leu Ser Leu Leu Ala Ala Leu Ser Ser Arg His Leu Ser Ser Ala His
385                 390                 395                 400

Ala Asp Leu Gly Arg
            405

<210> SEQ ID NO 70
<211> LENGTH: 401
<212> TYPE: PRT
<213> ORGANISM: Methanospirillum hungatei

<400> SEQUENCE: 70

Met Asp Glu Tyr Leu Arg Arg Leu Arg Asp Gly Thr Leu Lys Leu Tyr
1               5                   10                  15

Ala Leu Glu Lys Glu Leu Ala Pro Ala Asp Ala Val Ser Ile Arg Arg
            20                  25                  30

Lys Phe Ile Glu Glu Thr Gly Val Pro Leu Asp Arg Ile Gly Asp
            35                  40                  45

Cys Thr Ile Ser Leu Asp Ala Val Val Lys Lys Asn Cys Glu Asn Met
50                  55                  60

Ile Gly Thr Ile Gln Val Pro Leu Gly Val Ala Gly Pro Val Arg Ile
65                  70                  75                  80

Lys Gly Glu Tyr Ala Asp Gly Thr Met Tyr Leu Pro Leu Ala Thr Thr
            85                  90                  95

Glu Gly Ala Leu Ile Ala Ser Val Asn Arg Gly Cys Ser Leu Ile Thr
            100                 105                 110

Ala Ala Gly Gly Ala Asp Val Arg Ile Leu Lys Asp Gly Met Thr Arg
            115                 120                 125

Ala Pro Val Phe Ala Ala Asp Ser Ile Val His Ala Lys Ala Val Cys
130                 135                 140

Asp Trp Ile His Ala His Glu Gly Glu Ile Arg Ala Glu Ala Glu Ser
145                 150                 155                 160

Thr Thr Arg Phe Gly Lys Leu Thr Gly Ile Glu Met Thr Thr Ala Gly
            165                 170                 175

Thr Ser Val Phe Val Arg Leu Ser Phe Val Thr Gly Asp Ala Met Gly
            180                 185                 190

Met Asn Met Val Thr Ile Ala Ser Ala Lys Ala Ala Asp Leu Ile Ser
            195                 200                 205

Arg Glu Thr Gly Ala Arg Leu Ile Ala Leu Ser Gly Asn Trp Cys Thr
210                 215                 220

Asp Lys Lys Pro Ala Ala Val Asn Val Val Met Gly Arg Gly Lys Thr
225                 230                 235                 240

Val Ser Ala Gly Val Leu Leu Ser Gln Glu Leu Ile Ser Lys Val Leu
            245                 250                 255

Lys Thr Asp Ala Ala Ser Leu Leu Glu Val Asn Thr Arg Lys Asn Leu

```
                        260                 265                 270
Val Gly Ser Ala Arg Ala Gly Ser Phe Gly Phe Asn Ala His Ala Ala
                275                 280                 285

Asn Ile Ile Ala Ala Met Phe Ile Ala Cys Gly Gln Asp Pro Ala His
            290                 295                 300

Val Val Glu Gly Ser Leu Cys Ile Thr Thr Val Asp Pro Ala His Glu
305                 310                 315                 320

Gly Val Tyr Val Ser Val Thr Leu Pro Ala Leu Pro Ile Gly Thr Val
                325                 330                 335

Gly Gly Gly Thr Ser Val Glu Thr Gln Ala Glu Cys Leu Arg Met Leu
            340                 345                 350

Gly Val Ser Gly Ser Gly Asp Pro Pro Gly Ser His Ala Arg Lys Leu
            355                 360                 365

Ala Glu Ile Val Ala Ser Gly Val Leu Ala Gly Glu Leu Ser Leu Leu
            370                 375                 380

Gly Ala Leu Ala Ala Gln His Leu Ala Arg Ala His Ser Thr Leu Gly
385                 390                 395                 400

Arg

<210> SEQ ID NO 71
<211> LENGTH: 405
<212> TYPE: PRT
<213> ORGANISM: Haloarcula hispanica

<400> SEQUENCE: 71

Met Thr Asp Ser Asp Ala Thr Ala Leu Ala Glu Arg Val Arg Asp Gly
  1               5                  10                  15

Glu Leu Arg Leu Tyr Glu Leu Glu Asp His Ala Asp Pro Asp Thr Ala
                 20                  25                  30

Ala Ala Ala Arg Arg His Leu Leu Ala Glu Glu Thr Gly Ala Asp Leu
             35                  40                  45

Ser Ala Val Gly Asp Tyr Thr Phe Asp Ala Ala Asp Ala Glu Ser Asn
         50                  55                  60

Ile Glu Asn Met Val Gly Ala Val Gln Val Pro Met Gly Val Val Gly
 65                  70                  75                  80

Pro Leu Pro Val Asp Gly Gly Ala Ala Glu Gly Asp His His Leu Pro
                 85                  90                  95

Leu Ala Thr Ser Glu Gly Ala Leu Leu Ala Ser Val Asn Arg Gly Val
            100                 105                 110

Ser Thr Ile Arg Asn Ala Gly Gly Ala Thr Ala Arg Val Leu Lys Ser
            115                 120                 125

Gly Met Thr Arg Ala Pro Val Phe Arg Val Glu Asp Val Ala Lys Ala
        130                 135                 140

Gly Glu Val Ser Ala Trp Val Arg Glu His Val Asp Val Leu Ala Asp
145                 150                 155                 160

Ala Ala Glu Ser Thr Thr Ser His Gly Glu Leu Gln Asp Val Thr Pro
                165                 170                 175

Tyr Val Val Gly Asp Ser Val Phe Leu Arg Phe Ser Tyr Asp Thr Lys
            180                 185                 190

Asp Ala Met Gly Met Asn Met Ala Thr Ile Ala Thr Glu Ala Ala Cys
        195                 200                 205

Asp Val Val Glu Ser Glu Thr Pro Ala Asp Leu Val Ala Leu Ser Gly
    210                 215                 220

Asn Leu Cys Ser Asp Lys Lys Pro Ala Ala Ile Asn Ala Val Glu Gly
225                 230                 235                 240
```

```
Arg Gly Arg Thr Val Ala Ala Asp Val Leu Ile Pro His Glu Gln Val
                245                 250                 255

Glu Glu Arg Leu Asp Thr Thr Ser Asp Ala Ile Val Glu Ala Asn Thr
            260                 265                 270

Arg Lys Asn Leu Val Gly Ser Ala Lys Ala Gly Ala Leu Gly Phe Asn
        275                 280                 285

Ala His Thr Ala Asn Val Val Ala Ala Ala Phe Leu Ala Leu Gly Gln
    290                 295                 300

Asp Ile Ala Gln Val Val Glu Gly Asn Asn Ala Ile Thr Thr Val Asp
305                 310                 315                 320

Ala Arg Glu Asp Gly Leu Tyr Ala Ser Val Thr Ile Pro Phe Leu Glu
                325                 330                 335

Val Gly Asn Val Gly Arg Gly Arg Phe Pro Glu Ala Phe Gly Gly Leu
            340                 345                 350

Glu Val Gly Gly Asp Asn Gly Gly Gly Asp Pro Ala Gly Ser Asn
        355                 360                 365

Ala Glu Ala Leu Gly Glu Val Ile Ala Gly Gly Ala Leu Ala Gly Glu
    370                 375                 380

Leu Ser Leu Leu Ala Ala Leu Ser Ser Arg His Leu Ser Ser Ala His
385                 390                 395                 400

Ala Glu Leu Gly Arg
            405

<210> SEQ ID NO 72
<211> LENGTH: 1782
<212> TYPE: DNA
<213> ORGANISM: Abies grandis
<220> FEATURE:
<223> OTHER INFORMATION: synthetic DNA

<400> SEQUENCE: 72
atggctcaga tttctgaatc tgtatcaccc tctaccgatt tgaagagcac cgaatcttcc     60
attacctcta atcgacatgg aaatatgtgg gaggacgatc gcatacagtc tctcaactca    120
ccttatgggg cacctgcata tcaagaacgc agcgaaaagc ttattgaaga gatcaaactt    180 ttattttga gtgacatgga cgatagctgc aatgatagcg atcgtgattt aatcaaacgt    240
cttgagatcg ttgatactgt cgagtgtctg ggaattgatc gacattttca acctgagata    300
aaattagctc tggattacgt ttacagatgt tggaacgaaa gaggcatcgg agagggatca    360
agagattccc tcaagaaaga tctgaacgct acagctttgg gattccgggc tctccgactc    420
catcgatata acgtatcctc aggtgtcttg agaaatttca gagatgataa cgggcagttc    480
ttctgcggtt ctacagttga agaagaagga gcagaagcat ataataaaca cgtaagatgc    540
atgctgtcat tatcgcgagc ttcaaacatt ttatttccgg gcgaaaaagt gatggaagag    600
gcgaaggcat tcacaacaaa ttatctaaag aaagttttag caggacggga ggctacccac    660
gtcgatgaaa gccttttggg agaggtgaag tacgcattgg agtttccatg gcattgcagt    720
gtgcagagat gggaggcaag gagctttatc gaaatatttg acaaattga ttcagagctt    780 aagtcgaatt tgagcaaaaa aatgttagag ttggcgaaat ggacttcaa tattctgcaa    840 tgcacacatc agaaagaact gcagattatc tcaaggtggt tcgcagactc aagtatagca    900
tccctgaatt tctatcggaa atgttacgtc gaattttact tttggatggc tgcagccatc    960
tccgagccgg agttttctgg aagcagagtt gccttcacaa aaattgctat actgatgaca   1020
atgctagatg acctgtacga tactcacgga accttggacc aactcaaat ctttacagag   1080
```

```
ggagtgagac gatgggatgt tcgttggta gagggcctcc cagacttcat gaaaattgca    1140
ttcgagttct ggttaaagac atctaatgaa ttgattgctg aagctgttaa agcgcaaggg   1200
caagatatgg cggcctacat aagaaaaaat gcatgggagc gataccttga agcttatctg   1260
caagatgcgg aatggatagc cactggacat gtccccacct tgatgagta cttgaataat    1320
ggcacaccaa acactgggat gtgtgtattg aatttgattc cgcttctgtt aatgggtgaa   1380
catttaccaa tcgacattct ggagcaaata ttcttgccct ccaggttcca ccatctcatt   1440
gaattggctt ccaggctcgt cgatgacgcg agagatttcc aggcggagaa ggatcatggg   1500
gatttatcgt gtattgagtg ttatttaaaa gatcatcctg agtctacagt agaagatgct   1560
ttaaatcatg ttaatggcct ccttggcaat tgccttctgg aaatgaattg aagttctta   1620
aagaagcagg acagtgtgcc actctcgtgt aagaagtaca gcttccatgt attggcacga   1680
agcatccaat tcatgtacaa tcaaggcgat ggcttctcca tttcgaacaa agtgatcaag   1740
gatcaagtgc agaaagttct tattgtcccc gtgcctattt ga                     1782
```

<210> SEQ ID NO 73
<211> LENGTH: 593
<212> TYPE: PRT
<213> ORGANISM: Artificial Sequence
<220> FEATURE:
<223> OTHER INFORMATION: variant gamma-humulene synthase

<400> SEQUENCE: 73

```
Met Ala Gln Ile Ser Glu Ser Val Ser Pro Ser Thr Asp Leu Lys Ser
 1               5                   10                  15

Thr Glu Ser Ser Ile Thr Ser Asn Arg His Gly Asn Met Trp Glu Asp
            20                  25                  30

Asp Arg Ile Gln Ser Leu Asn Ser Pro Tyr Gly Ala Pro Ala Tyr Gln
        35                  40                  45

Glu Arg Ser Glu Lys Leu Ile Glu Glu Ile Lys Leu Leu Phe Leu Ser
    50                  55                  60

Asp Met Asp Asp Ser Cys Asn Asp Ser Asp Arg Asp Leu Ile Lys Arg
65                  70                  75                  80

Leu Glu Ile Val Asp Thr Val Glu Cys Leu Gly Ile Asp Arg His Phe
                85                  90                  95

Gln Pro Glu Ile Lys Leu Ala Leu Asp Tyr Val Tyr Arg Cys Trp Asn
            100                 105                 110

Glu Arg Gly Ile Gly Glu Gly Ser Arg Asp Ser Leu Lys Pro Asp Leu
        115                 120                 125

Asn Ala Thr Ala Leu Gly Phe Arg Ala Leu Arg Leu His Gly Tyr Asn
    130                 135                 140

Val Ser Ser Gly Val Leu Glu Asn Phe Arg Asp Asp Asn Gly Gln Phe
145                 150                 155                 160

Phe Cys Gly Ser Thr Val Glu Glu Gly Ala Glu Ala Tyr Asn Lys
                165                 170                 175

His Val Arg Cys Met Leu Ser Leu Ser Arg Ala Ser Asn Ile Leu Phe
            180                 185                 190

Pro Gly Glu Lys Val Met Glu Glu Ala Lys Ala Phe Thr Thr Asn Tyr
        195                 200                 205

Leu Lys Lys Val Leu Ala Gly Arg Glu Ala Thr His Val Asp Glu Ser
    210                 215                 220

Leu Leu Ala Glu Val Lys Tyr Ala Leu Glu Phe Pro Trp His Cys Ser
225                 230                 235                 240

Val Gln Arg Trp Glu Ala Arg Ser Phe Ile Glu Ile Phe Gly Gln Ile
```

```
                    245                 250                 255
Asp Ser Glu Leu Lys Ser Asn Leu Ser Lys Lys Met Leu Glu Leu Ala
                260                 265                 270

Lys Leu Asp Phe Asn Ile Leu Gln Cys Thr His Gln Lys Glu Leu Gln
            275                 280                 285

Ile Ile Ser Arg Trp Phe Ala Asp Ser Ser Ile Ala Ser Leu Asn Phe
        290                 295                 300

Tyr Arg Lys Cys Tyr Val Glu Phe Tyr Phe Trp Met Ala Ala Ala Ile
305                 310                 315                 320

Ser Glu Pro Glu Phe Ser Gly Ser Arg Val Ala Phe Thr Lys Ile Ala
                325                 330                 335

Ile Leu Met Thr Met Leu Asp Asp Leu Tyr Asp Thr His Gly Thr Leu
            340                 345                 350

Asp Gln Leu Lys Ile Phe Thr Glu Gly Val Arg Arg Trp Asp Val Ser
        355                 360                 365

Leu Val Glu Gly Leu Pro Asp Phe Met Lys Ile Ala Phe Glu Phe Trp
370                 375                 380

Leu Lys Thr Ser Asn Glu Leu Ile Ala Glu Ala Val Lys Ala Gln Gly
385                 390                 395                 400

Gln Asp Met Ala Ala Tyr Ile Arg Lys Asn Ala Trp Glu Arg Tyr Leu
                405                 410                 415

Glu Ala Tyr Leu Gln Asp Ala Glu Trp Ile Ala Thr Gly His Val Pro
            420                 425                 430

Thr Phe Asp Glu Tyr Leu Asn Asn Gly Thr Pro Asn Thr Gly Met Cys
        435                 440                 445

Val Leu Asn Leu Ile Pro Leu Leu Leu Met Gly Glu His Leu Pro Ile
450                 455                 460

Asp Ile Leu Glu Gln Ile Phe Leu Pro Ser Arg Phe His His Leu Ile
465                 470                 475                 480

Glu Leu Ala Ser Arg Leu Val Asp Asp Ala Arg Asp Phe Gln Ala Glu
                485                 490                 495

Lys Asp His Gly Asp Leu Ser Cys Ile Glu Cys Tyr Leu Lys Asp His
            500                 505                 510

Pro Glu Ser Thr Val Glu Asp Ala Leu Asn His Val Asn Gly Leu Leu
        515                 520                 525

Gly Asn Cys Leu Leu Glu Met Asn Trp Lys Phe Leu Lys Lys Gln Asp
530                 535                 540

Ser Val Pro Leu Ser Cys Lys Lys Tyr Ser Phe His Val Leu Ala Arg
545                 550                 555                 560

Ser Ile Gln Phe Met Tyr Asn Gln Gly Asp Gly Phe Ser Ile Ser Asn
                565                 570                 575

Lys Val Ile Lys Asp Gln Val Gln Lys Val Leu Ile Val Pro Val Pro
            580                 585                 590

Ile

<210> SEQ ID NO 74
<211> LENGTH: 593
<212> TYPE: PRT
<213> ORGANISM: Artificial Sequence
<220> FEATURE:
<223> OTHER INFORMATION: variant gamma-humulene synthase

<400> SEQUENCE: 74

Met Ala Gln Ile Ser Glu Ser Val Ser Pro Ser Thr Asp Leu Lys Ser
1               5                   10                  15
```

-continued

```
Thr Glu Ser Ser Ile Thr Ser Asn Arg His Gly Asn Met Trp Glu Asp
         20                  25                  30
Asp Arg Ile Gln Ser Leu Asn Ser Pro Tyr Gly Ala Pro Ala Tyr Gln
             35                  40                  45
Glu Arg Ser Glu Lys Leu Ile Glu Ile Lys Leu Leu Phe Leu Ser
 50                  55                  60
Asp Met Asp Asp Ser Cys Asn Asp Ser Asp Arg Asp Leu Ile Lys Arg
 65                  70                  75                  80
Leu Glu Ile Val Asp Thr Val Glu Cys Leu Gly Ile Asp Arg His Phe
                 85                  90                  95
Gln Pro Glu Ile Lys Leu Ala Leu Asp Tyr Val Tyr Arg Cys Trp Asn
                100                 105                 110
Glu Arg Gly Ile Gly Glu Gly Ser Arg Asp Ser Leu Lys Pro Asp Leu
            115                 120                 125
Asn Ala Thr Ala Leu Gly Phe Arg Ala Leu Arg Leu His Gly Tyr Asn
            130                 135                 140
Val Ser Ser Ala Val Leu Glu Asn Phe Arg Asp Asp Asn Gly Gln Phe
145                 150                 155                 160
Phe Cys Gly Ser Thr Val Glu Glu Gly Ala Glu Ala Tyr Asn Lys
                165                 170                 175
His Val Arg Cys Met Leu Ser Leu Ser Arg Ala Ser Asn Ile Leu Phe
                180                 185                 190
Pro Gly Glu Lys Val Met Glu Ala Lys Ala Phe Thr Thr Asn Tyr
            195                 200                 205
Leu Lys Lys Val Leu Ala Gly Arg Glu Ala Thr His Val Asp Glu Ser
    210                 215                 220
Leu Leu Ala Glu Val Lys Tyr Ala Leu Glu Phe Pro Trp His Cys Ser
225                 230                 235                 240
Val Gln Arg Trp Glu Ala Arg Ser Phe Ile Glu Ile Phe Gly Gln Ile
                245                 250                 255
Asp Ser Glu Leu Lys Ser Asn Leu Ser Lys Lys Met Leu Glu Leu Ala
            260                 265                 270
Lys Leu Asp Phe Asn Ile Leu Gln Cys Thr His Gln Lys Glu Leu Gln
            275                 280                 285
Ile Ile Ser Arg Trp Phe Ala Asp Ser Ser Ile Ala Ser Leu Asn Phe
290                 295                 300
Tyr Arg Lys Cys Tyr Val Glu Phe Tyr Phe Trp Met Ala Ala Ala Ile
305                 310                 315                 320
Ser Glu Pro Glu Phe Ser Ala Ser Arg Val Ala Phe Thr Lys Ile Ala
                325                 330                 335
Ile Leu Met Thr Met Leu Asp Asp Leu Tyr Asp Thr His Gly Thr Leu
            340                 345                 350
Asp Gln Leu Lys Ile Phe Thr Glu Ala Val Arg Arg Trp Asp Val Ser
            355                 360                 365
Leu Val Glu Gly Leu Pro Asp Phe Met Lys Ile Ala Phe Glu Phe Trp
    370                 375                 380
Leu Lys Thr Ser Asn Glu Leu Ile Ala Glu Ala Val Lys Ala Gln Gly
385                 390                 395                 400
Gln Asp Met Ala Ala Tyr Ile Arg Lys Asn Ala Trp Glu Arg Tyr Leu
                405                 410                 415
Glu Ala Tyr Leu Gln Asp Ala Glu Trp Ile Ala Thr Gly His Val Pro
            420                 425                 430
Thr Phe Asp Glu Tyr Leu Asn Asn Gly Thr Pro Asn Thr Gly Met Cys
            435                 440                 445
```

Val Leu Asn Leu Ile Pro Leu Leu Met Gly Glu His Leu Pro Ile
    450                 455                 460

Asp Ile Leu Glu Gln Ile Phe Leu Pro Ser Arg Phe His His Leu Ile
465                 470                 475                 480

Glu Leu Ala Ser Arg Leu Val Asp Asp Ala Arg Asp Phe Gln Ala Glu
                485                 490                 495

Lys Asp His Gly Asp Leu Ser Cys Ile Glu Cys Tyr Leu Lys Asp His
                500                 505                 510

Pro Glu Ser Thr Val Glu Asp Ala Leu Asn His Val Asn Gly Leu Leu
                515                 520                 525

Gly Asn Cys Leu Leu Glu Met Asn Trp Lys Phe Leu Lys Lys Gln Asp
                530                 535                 540

Ser Val Pro Leu Ser Cys Lys Lys Tyr Ser Phe His Val Leu Ala Arg
545                 550                 555                 560

Ser Ile Gln Phe Met Tyr Asn Gln Gly Asp Gly Phe Ser Ile Ser Asn
                565                 570                 575

Lys Val Ile Lys Asp Gln Val Gln Lys Val Leu Ile Val Pro Val Pro
                580                 585                 590

Ile

<210> SEQ ID NO 75
<211> LENGTH: 502
<212> TYPE: PRT
<213> ORGANISM: Artificial Sequence
<220> FEATURE:
<223> OTHER INFORMATION: variant HMGR

<400> SEQUENCE: 75

Pro Val Leu Thr Asn Lys Thr Val Ile Ser Gly Ser Lys Val Lys Ser
1               5                   10                  15

Leu Ser Ser Ala Gln Ser Ser Ser Ser Gly Pro Ser Ser Ser Ser Glu
                20                  25                  30

Glu Asp Asp Ser Arg Asp Ile Glu Ser Leu Asp Lys Lys Ile Arg Pro
            35                  40                  45

Leu Glu Glu Leu Glu Ala Leu Leu Ser Ser Gly Asn Thr Lys Gln Leu
50                  55                  60

Lys Asn Lys Glu Val Ala Ala Leu Val Ile His Gly Lys Leu Pro Leu
65                  70                  75                  80

Tyr Ala Leu Glu Lys Lys Leu Gly Asp Thr Thr Arg Ala Val Ala Val
                85                  90                  95

Arg Arg Lys Ala Leu Ser Ile Leu Ala Glu Ala Pro Val Leu Ala Ser
            100                 105                 110

Asp Arg Leu Pro Tyr Lys Asn Tyr Asp Tyr Asp Arg Val Phe Gly Ala
            115                 120                 125

Cys Cys Glu Asn Val Ile Gly Tyr Met Pro Leu Pro Val Gly Val Ile
130                 135                 140

Gly Pro Leu Val Ile Asp Gly Thr Ser Tyr His Ile Pro Met Ala Thr
145                 150                 155                 160

Thr Glu Gly Cys Leu Val Ala Ser Ala Met Arg Gly Cys Lys Ala Ile
                165                 170                 175

Asn Ala Gly Gly Gly Ala Thr Thr Val Leu Thr Lys Asp Gly Met Thr
            180                 185                 190

Arg Gly Pro Val Val Arg Phe Pro Thr Leu Lys Arg Ser Ala Ala Cys
            195                 200                 205

Lys Ile Trp Leu Asp Ser Glu Glu Gly Gln Asn Ala Ile Lys Lys Ala

```
            210                 215                 220
Phe Asn Ser Thr Ser Arg Phe Ala Arg Leu Gln His Ile Gln Thr Cys
225                 230                 235                 240

Leu Ala Gly Asp Leu Leu Phe Met Arg Phe Arg Thr Thr Thr Gly Asp
                245                 250                 255

Ala Met Gly Met Asn Met Ile Ser Lys Gly Val Glu Tyr Ser Leu Lys
            260                 265                 270

Gln Met Val Glu Glu Tyr Gly Trp Glu Asp Met Glu Val Val Ser Val
                275                 280                 285

Ser Gly Asn Tyr Cys Thr Asp Lys Lys Pro Ala Ala Ile Asn Trp Ile
            290                 295                 300

Glu Gly Arg Gly Lys Ser Val Val Ala Glu Thr Ile Pro Ala Asp
305                 310                 315                 320

Val Val Arg Lys Val Leu Lys Ser Asp Val Ser Ala Leu Val Glu Leu
                325                 330                 335

Asn Ile Ala Lys Asn Leu Val Gly Ser Ala Met Ala Gly Ser Val Ala
            340                 345                 350

Gly Phe Asn Ala His Ala Ala Asn Leu Val Thr Ala Val Phe Leu Ala
                355                 360                 365

Leu Gly Gln Asp Pro Ala Gln Asn Val Glu Ser Ser Asn Cys Ile Thr
370                 375                 380

Leu Met Lys Glu Val Asp Gly Asp Leu Arg Ile Ser Val Ser Met Pro
385                 390                 395                 400

Ser Ile Glu Val Gly Thr Ile Gly Gly Gly Thr Val Leu Glu Pro Gln
                405                 410                 415

Ala Ala Met Leu Asp Leu Leu Gly Val Arg Gly Pro His Ala Thr Ala
                420                 425                 430

Pro Gly Thr Asn Ala Arg Gln Leu Ala Arg Ile Val Ala Cys Ala Val
            435                 440                 445

Leu Ala Gly Glu Leu Ser Leu Cys Ala Ala Leu Ala Ala Gly His Leu
            450                 455                 460

Val Gln Ser His Met Thr His Asn Arg Lys Pro Ala Glu Pro Thr Lys
465                 470                 475                 480

Pro Asn Asn Leu Asp Ala Thr Asp Ile Asn Arg Leu Lys Asp Ala Ser
                485                 490                 495

Val Thr Cys Ile Lys Ser
            500

<210> SEQ ID NO 76
<211> LENGTH: 502
<212> TYPE: PRT
<213> ORGANISM: Artificial Sequence
<220> FEATURE:
<223> OTHER INFORMATION: variant HMGR

<400> SEQUENCE: 76

Pro Val Leu Thr Asn Lys Thr Val Ile Ser Gly Ser Lys Val Lys Ser
1               5                   10                  15

Leu Ser Ser Ala Gln Ser Ser Ser Gly Pro Ser Ser Ser Ser Glu
                20                  25                  30

Glu Asp Asp Ser Arg Asp Ile Glu Ser Leu Asp Lys Lys Ile Arg Pro
            35                  40                  45

Leu Glu Glu Leu Glu Ala Leu Leu Ser Ser Gly Asn Thr Lys Gln Leu
        50                  55                  60

Lys Asn Lys Glu Val Ala Ala Leu Val Ile His Gly Lys Leu Pro Leu
65                  70                  75                  80
```

```
Tyr Ala Leu Glu Lys Lys Leu Gly Asp Thr Thr Arg Ala Val Ala Val
                 85                  90                  95
Arg Arg Lys Ala Leu Ser Ile Leu Ala Glu Ala Pro Val Leu Ala Ser
            100                 105                 110
Asp Arg Leu Pro Tyr Lys Asn Tyr Asp Tyr Asp Arg Val Phe Gly Ala
            115                 120                 125
Cys Cys Glu Asn Val Ile Gly Tyr Met Pro Leu Pro Val Gly Val Ile
        130                 135                 140
Gly Pro Leu Val Ile Asp Gly Thr Ser Tyr His Ile Pro Met Ala Thr
145                 150                 155                 160
Thr Glu Gly Cys Leu Val Ala Ser Ala Met Arg Gly Cys Lys Ala Ile
                165                 170                 175
Asn Ala Gly Gly Gly Ala Thr Thr Val Leu Thr Lys Asp Gly Met Thr
            180                 185                 190
Arg Gly Pro Val Val Arg Phe Ala Thr Leu Lys Arg Ser Ala Ala Cys
            195                 200                 205
Lys Ile Trp Leu Asp Ser Glu Glu Gly Gln Asn Ala Ile Lys Lys Ala
        210                 215                 220
Phe Asn Ser Thr Ser Arg Phe Ala Arg Leu Gln His Ile Gln Pro Cys
225                 230                 235                 240
Leu Ala Gly Asp Leu Leu Phe Met Arg Phe Arg Thr Thr Thr Gly Asp
                245                 250                 255
Ala Met Gly Met Asn Met Ile Ser Lys Gly Val Glu Tyr Ser Leu Lys
            260                 265                 270
Gln Met Val Glu Glu Tyr Gly Trp Glu Asp Met Glu Val Val Ser Val
            275                 280                 285
Ser Gly Asn Tyr Cys Thr Asp Lys Lys Pro Ala Ala Ile Asn Trp Ile
        290                 295                 300
Glu Gly Arg Gly Lys Ser Val Val Ala Glu Ala Thr Ile Pro Ala Asp
305                 310                 315                 320
Val Val Arg Lys Val Leu Lys Ser Asp Val Ser Ala Leu Val Glu Leu
                325                 330                 335
Asn Ile Ala Lys Asn Leu Val Gly Ser Ala Met Ala Gly Ser Val Ala
            340                 345                 350
Gly Phe Asn Ala His Ala Ala Asn Leu Val Thr Ala Val Phe Leu Ala
            355                 360                 365
Leu Gly Gln Asp Pro Ala Gln Asn Val Glu Ser Ser Asn Cys Ile Thr
        370                 375                 380
Leu Met Lys Glu Val Asp Gly Asp Leu Arg Ile Ser Val Ser Met Pro
385                 390                 395                 400
Ser Ile Glu Val Gly Thr Ile Gly Gly Gly Thr Val Leu Glu Pro Gln
                405                 410                 415
Ala Ala Met Leu Asp Leu Leu Gly Val Arg Gly Gly His Ala Thr Ala
            420                 425                 430
Pro Gly Thr Asn Ala Arg Gln Leu Ala Arg Ile Val Ala Cys Ala Val
            435                 440                 445
Leu Ala Gly Glu Leu Ser Leu Cys Ala Ala Leu Ala Ala Gly His Leu
        450                 455                 460
Val Gln Ser His Met Thr His Asn Arg Gly Pro Ala Glu Pro Thr Lys
465                 470                 475                 480
Pro Asn Asn Leu Asp Ala Thr Asp Ile Asn Arg Leu Lys Asp Ala Ser
                485                 490                 495
Val Thr Cys Ile Lys Ser
```

```
<210> SEQ ID NO 77
<211> LENGTH: 19
<212> TYPE: DNA
<213> ORGANISM: Artificial Sequence
<220> FEATURE:
<223> OTHER INFORMATION: Synthetic Primer

<400> SEQUENCE: 77
gcgcgttggt gcggatatc                                              19

<210> SEQ ID NO 78
<211> LENGTH: 38
<212> TYPE: DNA
<213> ORGANISM: Artificial Sequence
<220> FEATURE:
<223> OTHER INFORMATION: Synthetic Primer

<400> SEQUENCE: 78
catgccatgg agcttattct gtttcctgtg tgaaattg                          38

<210> SEQ ID NO 79
<211> LENGTH: 19
<212> TYPE: DNA
<213> ORGANISM: Artificial Sequence
<220> FEATURE:
<223> OTHER INFORMATION: Synthetic Primer

<400> SEQUENCE: 79
gcgcgttggt gcggatatc                                              19

<210> SEQ ID NO 80
<211> LENGTH: 37
<212> TYPE: DNA
<213> ORGANISM: Artificial Sequence
<220> FEATURE:
<223> OTHER INFORMATION: Synthetic Primer

<400> SEQUENCE: 80
gcagcagcgg tttctttcat ggagcttatt ctgtttc                           37

<210> SEQ ID NO 81
<211> LENGTH: 37
<212> TYPE: DNA
<213> ORGANISM: Artificial Sequence
<220> FEATURE:
<223> OTHER INFORMATION: Synthetic Primer

<400> SEQUENCE: 81
gaaacagaat aagctccatg aaagaaaccg ctgctgc                           37

<210> SEQ ID NO 82
<211> LENGTH: 21
<212> TYPE: DNA
<213> ORGANISM: Artificial Sequence
<220> FEATURE:
<223> OTHER INFORMATION: Synthetic Primer

<400> SEQUENCE: 82
catgccatgg aaccgcgtgg c                                            21

<210> SEQ ID NO 83
<211> LENGTH: 19
<212> TYPE: DNA
<213> ORGANISM: Artificial Sequence
<220> FEATURE:
```

```
<223> OTHER INFORMATION: Synthetic Primer

<400> SEQUENCE: 83
gcgcgttggt gcggatatc                                                      19

<210> SEQ ID NO 84
<211> LENGTH: 21
<212> TYPE: DNA
<213> ORGANISM: Artificial Sequence
<220> FEATURE:
<223> OTHER INFORMATION: Synthetic Primer

<400> SEQUENCE: 84
catgccatgg aaccgcgtgg c                                                   21

<210> SEQ ID NO 85
<211> LENGTH: 33
<212> TYPE: DNA
<213> ORGANISM: Artificial Sequence
<220> FEATURE:
<223> OTHER INFORMATION: Synthetic Primer

<400> SEQUENCE: 85
accagcaacc gccacgctaa catgtgggaa gat                                      33

<210> SEQ ID NO 86
<211> LENGTH: 33
<212> TYPE: DNA
<213> ORGANISM: Artificial Sequence
<220> FEATURE:
<223> OTHER INFORMATION: Synthetic Primer

<400> SEQUENCE: 86
atcttcccac atgttagcgt ggcggttgct ggt                                      33

<210> SEQ ID NO 87
<211> LENGTH: 33
<212> TYPE: DNA
<213> ORGANISM: Artificial Sequence
<220> FEATURE:
<223> OTHER INFORMATION: Synthetic Primer

<400> SEQUENCE: 87
ttaaacagcc catatgccgc acccgcttat cag                                      33

<210> SEQ ID NO 88
<211> LENGTH: 33
<212> TYPE: DNA
<213> ORGANISM: Artificial Sequence
<220> FEATURE:
<223> OTHER INFORMATION: Synthetic Primer

<400> SEQUENCE: 88
ctgataagcg ggtgcggcat atgggctgtt taa                                      33

<210> SEQ ID NO 89
<211> LENGTH: 33
<212> TYPE: DNA
<213> ORGANISM: Artificial Sequence
<220> FEATURE:
<223> OTHER INFORMATION: Synthetic Primer

<400> SEQUENCE: 89
acggttgagt gtctggccat tgatcgtcat ttc                                      33

<210> SEQ ID NO 90
```

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 90
gaaatgacga tcaatggcca gacactcaac cgt                              33

<210> SEQ ID NO 91
<211> LENGTH: 33
<212> TYPE: DNA
<213> ORGANISM: Artificial Sequence
<220> FEATURE:
<223> OTHER INFORMATION: Synthetic Primer

<400> SEQUENCE: 91
tgctggaatg agcgtgccat cggagaaggt agc                              33

<210> SEQ ID NO 92
<211> LENGTH: 33
<212> TYPE: DNA
<213> ORGANISM: Artificial Sequence
<220> FEATURE:
<223> OTHER INFORMATION: Synthetic Primer

<400> SEQUENCE: 92
gctaccttct ccgatggcac gctcattcca gca                              33

<210> SEQ ID NO 93
<211> LENGTH: 33
<212> TYPE: DNA
<213> ORGANISM: Artificial Sequence
<220> FEATURE:
<223> OTHER INFORMATION: Synthetic Primer

<400> SEQUENCE: 93
aatgagcgtg gcatcgcaga aggtagccgt gat                              33

<210> SEQ ID NO 94
<211> LENGTH: 33
<212> TYPE: DNA
<213> ORGANISM: Artificial Sequence
<220> FEATURE:
<223> OTHER INFORMATION: Synthetic Primer

<400> SEQUENCE: 94
atcacggcta ccttctgcga tgccacgctc att                              33

<210> SEQ ID NO 95
<211> LENGTH: 33
<212> TYPE: DNA
<213> ORGANISM: Artificial Sequence
<220> FEATURE:
<223> OTHER INFORMATION: Synthetic Primer

<400> SEQUENCE: 95
cgtggcatcg gagaagctag ccgtgatagc tta                              33

<210> SEQ ID NO 96
<211> LENGTH: 33
<212> TYPE: DNA
<213> ORGANISM: Artificial Sequence
<220> FEATURE:
<223> OTHER INFORMATION: Synthetic Primer

<400> SEQUENCE: 96
```

-continued taagctatca cggctagctt ctccgatgcc acg                                    33

<210> SEQ ID NO 97
<211> LENGTH: 33
<212> TYPE: DNA
<213> ORGANISM: Artificial Sequence
<220> FEATURE:
<223> OTHER INFORMATION: Synthetic Primer

<400> SEQUENCE: 97
aatgcgaccg ccttggcctt tcgggcttta cgc                                    33

<210> SEQ ID NO 98
<211> LENGTH: 33
<212> TYPE: DNA
<213> ORGANISM: Artificial Sequence
<220> FEATURE:
<223> OTHER INFORMATION: Synthetic Primer

<400> SEQUENCE: 98
gcgtaaagcc cgaaaggcca aggcggtcgc att                                    33

<210> SEQ ID NO 99
<211> LENGTH: 33
<212> TYPE: DNA
<213> ORGANISM: Artificial Sequence
<220> FEATURE:
<223> OTHER INFORMATION: Synthetic Primer

<400> SEQUENCE: 99
tataatgtaa gctcagcagt gctggagaac ttc                                    33

<210> SEQ ID NO 100
<211> LENGTH: 33
<212> TYPE: DNA
<213> ORGANISM: Artificial Sequence
<220> FEATURE:
<223> OTHER INFORMATION: Synthetic Primer

<400> SEQUENCE: 100
gaagttctcc agcactgctg agcttacatt ata                                    33

<210> SEQ ID NO 101
<211> LENGTH: 33
<212> TYPE: DNA
<213> ORGANISM: Artificial Sequence
<220> FEATURE:
<223> OTHER INFORMATION: Synthetic Primer

<400> SEQUENCE: 101
ttccgtgatg acaatgctca attcttttgc ggt                                    33

<210> SEQ ID NO 102
<211> LENGTH: 33
<212> TYPE: DNA
<213> ORGANISM: Artificial Sequence
<220> FEATURE:
<223> OTHER INFORMATION: Synthetic Primer

<400> SEQUENCE: 102
accgcaaaag aattgagcat tgtcatcacg gaa                                    33

<210> SEQ ID NO 103
<211> LENGTH: 33
<212> TYPE: DNA
<213> ORGANISM: Artificial Sequence
<220> FEATURE:

<223> OTHER INFORMATION: Synthetic Primer

<400> SEQUENCE: 103
ggtcaattct tttgcgcttc tactgtggag gag                     33

<210> SEQ ID NO 104
<211> LENGTH: 33
<212> TYPE: DNA
<213> ORGANISM: Artificial Sequence
<220> FEATURE:
<223> OTHER INFORMATION: Synthetic Primer

<400> SEQUENCE: 104
ctcctccaca gtagaagcgc aaaagaattg acc                     33

<210> SEQ ID NO 105
<211> LENGTH: 33
<212> TYPE: DNA
<213> ORGANISM: Artificial Sequence
<220> FEATURE:
<223> OTHER INFORMATION: Synthetic Primer

<400> SEQUENCE: 105
actgtggagg aggaagccgc ggaggcctac aat                     33

<210> SEQ ID NO 106
<211> LENGTH: 33
<212> TYPE: DNA
<213> ORGANISM: Artificial Sequence
<220> FEATURE:
<223> OTHER INFORMATION: Synthetic Primer

<400> SEQUENCE: 106
attgtaggcc tccgcggctt cctcctccac agt                     33

<210> SEQ ID NO 107
<211> LENGTH: 33
<212> TYPE: DNA
<213> ORGANISM: Artificial Sequence
<220> FEATURE:
<223> OTHER INFORMATION: Synthetic Primer

<400> SEQUENCE: 107
aatattttat tcccggccga gaaagtgatg gaa                     33

<210> SEQ ID NO 108
<211> LENGTH: 33
<212> TYPE: DNA
<213> ORGANISM: Artificial Sequence
<220> FEATURE:
<223> OTHER INFORMATION: Synthetic Primer

<400> SEQUENCE: 108
ttccatcact ttctcggccg ggataaaat att                      33

<210> SEQ ID NO 109
<211> LENGTH: 33
<212> TYPE: DNA
<213> ORGANISM: Artificial Sequence
<220> FEATURE:
<223> OTHER INFORMATION: Synthetic Primer

<400> SEQUENCE: 109
aagaaagtcc tggcggctcg tgaagcaact cat                     33

<210> SEQ ID NO 110

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 110
atgagttgct tcacgagccg ccaggacttt ctt                              33

<210> SEQ ID NO 111
<211> LENGTH: 33
<212> TYPE: DNA
<213> ORGANISM: Artificial Sequence
<220> FEATURE:
<223> OTHER INFORMATION: Synthetic Primer

<400> SEQUENCE: 111
gacgagagtc tccttgcaga ggtcaagtat gca                              33

<210> SEQ ID NO 112
<211> LENGTH: 33
<212> TYPE: DNA
<213> ORGANISM: Artificial Sequence
<220> FEATURE:
<223> OTHER INFORMATION: Synthetic Primer

<400> SEQUENCE: 112
tgcatacttg acctctgcaa ggagactctc gtc                              33

<210> SEQ ID NO 113
<211> LENGTH: 33
<212> TYPE: DNA
<213> ORGANISM: Artificial Sequence
<220> FEATURE:
<223> OTHER INFORMATION: Synthetic Primer

<400> SEQUENCE: 113
tttatcgaaa ttttcgctca gattgatagt gaa                              33

<210> SEQ ID NO 114
<211> LENGTH: 33
<212> TYPE: DNA
<213> ORGANISM: Artificial Sequence
<220> FEATURE:
<223> OTHER INFORMATION: Synthetic Primer

<400> SEQUENCE: 114
ttcactatca atctgagcga aaatttcgat aaa                              33

<210> SEQ ID NO 115
<211> LENGTH: 33
<212> TYPE: DNA
<213> ORGANISM: Artificial Sequence
<220> FEATURE:
<223> OTHER INFORMATION: Synthetic Primer

<400> SEQUENCE: 115
gaaccagaat ttagtgcctc tcgcgtggca ttc                              33

<210> SEQ ID NO 116
<211> LENGTH: 33
<212> TYPE: DNA
<213> ORGANISM: Artificial Sequence
<220> FEATURE:
<223> OTHER INFORMATION: Synthetic Primer

<400> SEQUENCE: 116
```
gaatgccacg cgagaggcac taaattctgg ttc                                33

<210> SEQ ID NO 117
<211> LENGTH: 33
<212> TYPE: DNA
<213> ORGANISM: Artificial Sequence
<220> FEATURE:
<223> OTHER INFORMATION: Synthetic Primer

<400> SEQUENCE: 117
ttatacgaca cgcatgcgac gctggatcaa ttg                                33

<210> SEQ ID NO 118
<211> LENGTH: 33
<212> TYPE: DNA
<213> ORGANISM: Artificial Sequence
<220> FEATURE:
<223> OTHER INFORMATION: Synthetic Primer

<400> SEQUENCE: 118
caattgatcc agcgtcgcat gcgtgtcgta taa                                33

<210> SEQ ID NO 119
<211> LENGTH: 33
<212> TYPE: DNA
<213> ORGANISM: Artificial Sequence
<220> FEATURE:
<223> OTHER INFORMATION: Synthetic Primer

<400> SEQUENCE: 119
aaaatattta ccgaagctgt gcgcaggtgg gac                                33

<210> SEQ ID NO 120
<211> LENGTH: 33
<212> TYPE: DNA
<213> ORGANISM: Artificial Sequence
<220> FEATURE:
<223> OTHER INFORMATION: Synthetic Primer

<400> SEQUENCE: 120
gtcccacctg cgcacagctt cggtaaatat ttt                                33

<210> SEQ ID NO 121
<211> LENGTH: 33
<212> TYPE: DNA
<213> ORGANISM: Artificial Sequence
<220> FEATURE:
<223> OTHER INFORMATION: Synthetic Primer

<400> SEQUENCE: 121
gtgtcgctgg tggaggccct gccggatttc atg                                33

<210> SEQ ID NO 122
<211> LENGTH: 33
<212> TYPE: DNA
<213> ORGANISM: Artificial Sequence
<220> FEATURE:
<223> OTHER INFORMATION: Synthetic Primer

<400> SEQUENCE: 122
catgaaatcc ggcagggcct ccaccagcga cac                                33

<210> SEQ ID NO 123
<211> LENGTH: 33
<212> TYPE: DNA
<213> ORGANISM: Artificial Sequence
<220> FEATURE:

<223> OTHER INFORMATION: Synthetic Primer

<400> SEQUENCE: 123
gcggttaagg cccaagccca ggatatggcg gcc        33

<210> SEQ ID NO 124
<211> LENGTH: 33
<212> TYPE: DNA
<213> ORGANISM: Artificial Sequence
<220> FEATURE:
<223> OTHER INFORMATION: Synthetic Primer

<400> SEQUENCE: 124
ggccgccata tcctgggctt gggccttaac cgc        33

<210> SEQ ID NO 125
<211> LENGTH: 33
<212> TYPE: DNA
<213> ORGANISM: Artificial Sequence
<220> FEATURE:
<223> OTHER INFORMATION: Synthetic Primer

<400> SEQUENCE: 125
gaatggatcg ccaccgctca cgttccgaca ttc        33

<210> SEQ ID NO 126
<211> LENGTH: 33
<212> TYPE: DNA
<213> ORGANISM: Artificial Sequence
<220> FEATURE:
<223> OTHER INFORMATION: Synthetic Primer

<400> SEQUENCE: 126
gaatgtcgga acgtgagcgg tggcgatcca ttc        33

<210> SEQ ID NO 127
<211> LENGTH: 33
<212> TYPE: DNA
<213> ORGANISM: Artificial Sequence
<220> FEATURE:
<223> OTHER INFORMATION: Synthetic Primer

<400> SEQUENCE: 127
gaatatctga acaatgccac ccccaacacc ggt        33

<210> SEQ ID NO 128
<211> LENGTH: 33
<212> TYPE: DNA
<213> ORGANISM: Artificial Sequence
<220> FEATURE:
<223> OTHER INFORMATION: Synthetic Primer

<400> SEQUENCE: 128
accggtgttg ggggtggcat tgttcagata ttc        33

<210> SEQ ID NO 129
<211> LENGTH: 33
<212> TYPE: DNA
<213> ORGANISM: Artificial Sequence
<220> FEATURE:
<223> OTHER INFORMATION: Synthetic Primer

<400> SEQUENCE: 129
ccgttgctgc ttatggccga acacttgccg atc        33

<210> SEQ ID NO 130

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 130
gatcggcaag tgttcggcca taagcagcaa cgg                                  33

<210> SEQ ID NO 131
<211> LENGTH: 33
<212> TYPE: DNA
<213> ORGANISM: Artificial Sequence
<220> FEATURE:
<223> OTHER INFORMATION: Synthetic Primer

<400> SEQUENCE: 131
gccgaaaaag atcatgctga tttatcctgc atc                                  33

<210> SEQ ID NO 132
<211> LENGTH: 33
<212> TYPE: DNA
<213> ORGANISM: Artificial Sequence
<220> FEATURE:
<223> OTHER INFORMATION: Synthetic Primer

<400> SEQUENCE: 132
gatgcaggat aaatcagcat gatcttttc ggc                                   33

<210> SEQ ID NO 133
<211> LENGTH: 33
<212> TYPE: DNA
<213> ORGANISM: Artificial Sequence
<220> FEATURE:
<223> OTHER INFORMATION: Synthetic Primer

<400> SEQUENCE: 133
ctgaatcacg tcaacgccct gctggggaat tgt                                  33

<210> SEQ ID NO 134
<211> LENGTH: 33
<212> TYPE: DNA
<213> ORGANISM: Artificial Sequence
<220> FEATURE:
<223> OTHER INFORMATION: Synthetic Primer

<400> SEQUENCE: 134
acaattcccc agcagggcgt tgacgtgatt cag                                  33

<210> SEQ ID NO 135
<211> LENGTH: 33
<212> TYPE: DNA
<213> ORGANISM: Artificial Sequence
<220> FEATURE:
<223> OTHER INFORMATION: Synthetic Primer

<400> SEQUENCE: 135
gtcaacggcc tgctggcgaa ttgtttgctg gaa                                  33

<210> SEQ ID NO 136
<211> LENGTH: 33
<212> TYPE: DNA
<213> ORGANISM: Artificial Sequence
<220> FEATURE:
<223> OTHER INFORMATION: Synthetic Primer

<400> SEQUENCE: 136
```
ttccagcaaa caattcgcca gcaggccgtt gac                                    33

<210> SEQ ID NO 137
<211> LENGTH: 33
<212> TYPE: DNA
<213> ORGANISM: Artificial Sequence
<220> FEATURE:
<223> OTHER INFORMATION: Synthetic Primer

<400> SEQUENCE: 137
tttatgtata accaggcgga cgggttttcg att                                    33

<210> SEQ ID NO 138
<211> LENGTH: 33
<212> TYPE: DNA
<213> ORGANISM: Artificial Sequence
<220> FEATURE:
<223> OTHER INFORMATION: Synthetic Primer

<400> SEQUENCE: 138
aatcgaaaac ccgtccgcct ggttatacat aaa                                    33

<210> SEQ ID NO 139
<211> LENGTH: 33
<212> TYPE: DNA
<213> ORGANISM: Artificial Sequence
<220> FEATURE:
<223> OTHER INFORMATION: Synthetic Primer

<400> SEQUENCE: 139
tataaccagg gggacgcgtt ttcgatttcg aac                                    33

<210> SEQ ID NO 140
<211> LENGTH: 33
<212> TYPE: DNA
<213> ORGANISM: Artificial Sequence
<220> FEATURE:
<223> OTHER INFORMATION: Synthetic Primer

<400> SEQUENCE: 140
gttcgaaatc gaaaacgcgt cccctggtt ata                                     33

<210> SEQ ID NO 141
<211> LENGTH: 33
<212> TYPE: DNA
<213> ORGANISM: Artificial Sequence
<220> FEATURE:
<223> OTHER INFORMATION: Synthetic Primer

<400> SEQUENCE: 141
agcgaaaaat tgattggaga aattaagctc ctg                                    33

<210> SEQ ID NO 142
<211> LENGTH: 33
<212> TYPE: DNA
<213> ORGANISM: Artificial Sequence
<220> FEATURE:
<223> OTHER INFORMATION: Synthetic Primer

<400> SEQUENCE: 142
caggagctta atttctccaa tcaatttttc gct                                    33

<210> SEQ ID NO 143
<211> LENGTH: 33
<212> TYPE: DNA
<213> ORGANISM: Artificial Sequence
<220> FEATURE:

<223> OTHER INFORMATION: Synthetic Primer

<400> SEQUENCE: 143
gagtgtctgg gcattggtcg tcatttccaa cct                                    33

<210> SEQ ID NO 144
<211> LENGTH: 33
<212> TYPE: DNA
<213> ORGANISM: Artificial Sequence
<220> FEATURE:
<223> OTHER INFORMATION: Synthetic Primer

<400> SEQUENCE: 144
aggttggaaa tgacgaccaa tgcccagaca ctc                                    33

<210> SEQ ID NO 145
<211> LENGTH: 33
<212> TYPE: DNA
<213> ORGANISM: Artificial Sequence
<220> FEATURE:
<223> OTHER INFORMATION: Synthetic Primer

<400> SEQUENCE: 145
gctttacgct tacacggtta taatgtaagc tca                                    33

<210> SEQ ID NO 146
<211> LENGTH: 33
<212> TYPE: DNA
<213> ORGANISM: Artificial Sequence
<220> FEATURE:
<223> OTHER INFORMATION: Synthetic Primer

<400> SEQUENCE: 146
tgagcttaca ttataaccgt gtaagcgtaa agc                                    33

<210> SEQ ID NO 147
<211> LENGTH: 33
<212> TYPE: DNA
<213> ORGANISM: Artificial Sequence
<220> FEATURE:
<223> OTHER INFORMATION: Synthetic Primer

<400> SEQUENCE: 147
tatgcactag aatttgggtg gcattgttcc gtg                                    33

<210> SEQ ID NO 148
<211> LENGTH: 33
<212> TYPE: DNA
<213> ORGANISM: Artificial Sequence
<220> FEATURE:
<223> OTHER INFORMATION: Synthetic Primer

<400> SEQUENCE: 148
cacggaacaa tgccacccaa attctagtgc ata                                    33

<210> SEQ ID NO 149
<211> LENGTH: 30
<212> TYPE: DNA
<213> ORGANISM: Artificial Sequence
<220> FEATURE:
<223> OTHER INFORMATION: Synthetic Primer

<400> SEQUENCE: 149
tggttcgccg attcaggtat cgcaagtctg                                        30

<210> SEQ ID NO 150

```
<211> LENGTH: 30
<212> TYPE: DNA
<213> ORGANISM: Artificial Sequence
<220> FEATURE:
<223> OTHER INFORMATION: Synthetic Primer

<400> SEQUENCE: 150
cagacttgcg atacctgaat cggcgaacca                                    30

<210> SEQ ID NO 151
<211> LENGTH: 33
<212> TYPE: DNA
<213> ORGANISM: Artificial Sequence
<220> FEATURE:
<223> OTHER INFORMATION: Synthetic Primer

<400> SEQUENCE: 151
agtggctctc gcgtgggatt cactaaaatt gcg                                33

<210> SEQ ID NO 152
<211> LENGTH: 33
<212> TYPE: DNA
<213> ORGANISM: Artificial Sequence
<220> FEATURE:
<223> OTHER INFORMATION: Synthetic Primer

<400> SEQUENCE: 152
cgcaatttta gtgaatccca cgcgagagcc act                                33

<210> SEQ ID NO 153
<211> LENGTH: 33
<212> TYPE: DNA
<213> ORGANISM: Artificial Sequence
<220> FEATURE:
<223> OTHER INFORMATION: Synthetic Primer

<400> SEQUENCE: 153
ccggatttca tgaaaggtgc ctttgagttc tgg                                33

<210> SEQ ID NO 154
<211> LENGTH: 33
<212> TYPE: DNA
<213> ORGANISM: Artificial Sequence
<220> FEATURE:
<223> OTHER INFORMATION: Synthetic Primer

<400> SEQUENCE: 154
ccagaactca aaggcacctt tcatgaaatc cgg                                33

<210> SEQ ID NO 155
<211> LENGTH: 33
<212> TYPE: DNA
<213> ORGANISM: Artificial Sequence
<220> FEATURE:
<223> OTHER INFORMATION: Synthetic Primer

<400> SEQUENCE: 155
cccaacaccg gtatgggtgt acttaatctg atc                                33

<210> SEQ ID NO 156
<211> LENGTH: 33
<212> TYPE: DNA
<213> ORGANISM: Artificial Sequence
<220> FEATURE:
<223> OTHER INFORMATION: Synthetic Primer

<400> SEQUENCE: 156
```
gatcagatta agtacaccca taccggtgtt ggg                                33

<210> SEQ ID NO 157
<211> LENGTH: 33
<212> TYPE: DNA
<213> ORGANISM: Artificial Sequence
<220> FEATURE:
<223> OTHER INFORMATION: Synthetic Primer

<400> SEQUENCE: 157
gctagccgac tggtcggtga tgcgagagat ttt                                33

<210> SEQ ID NO 158
<211> LENGTH: 33
<212> TYPE: DNA
<213> ORGANISM: Artificial Sequence
<220> FEATURE:
<223> OTHER INFORMATION: Synthetic Primer

<400> SEQUENCE: 158
aaaatctctc gcatcaccga ccagtcggct agc                                33

<210> SEQ ID NO 159
<211> LENGTH: 33
<212> TYPE: DNA
<213> ORGANISM: Artificial Sequence
<220> FEATURE:
<223> OTHER INFORMATION: Synthetic Primer

<400> SEQUENCE: 159
catggtgatt tatccggcat cgaatgctac ctg                                33

<210> SEQ ID NO 160
<211> LENGTH: 33
<212> TYPE: DNA
<213> ORGANISM: Artificial Sequence
<220> FEATURE:
<223> OTHER INFORMATION: Synthetic Primer

<400> SEQUENCE: 160
caggtagcat tcgatgccgg ataaatcacc atg                                33

<210> SEQ ID NO 161
<211> LENGTH: 33
<212> TYPE: DNA
<213> ORGANISM: Artificial Sequence
<220> FEATURE:
<223> OTHER INFORMATION: Synthetic Primer

<400> SEQUENCE: 161
ctgaaagacc atccgggatc aacagttgaa gac                                33

<210> SEQ ID NO 162
<211> LENGTH: 33
<212> TYPE: DNA
<213> ORGANISM: Artificial Sequence
<220> FEATURE:
<223> OTHER INFORMATION: Synthetic Primer

<400> SEQUENCE: 162
gtcttcaact gttgatcccg gatggtcttt cag                                33

<210> SEQ ID NO 163
<211> LENGTH: 33
<212> TYPE: DNA
<213> ORGANISM: Artificial Sequence
<220> FEATURE:

<223> OTHER INFORMATION: Synthetic Primer

<400> SEQUENCE: 163
agcgaatcag tgtctgcaag caccgacctt aaa         33

<210> SEQ ID NO 164
<211> LENGTH: 33
<212> TYPE: DNA
<213> ORGANISM: Artificial Sequence
<220> FEATURE:
<223> OTHER INFORMATION: Synthetic Primer

<400> SEQUENCE: 164
tttaaggtcg gtgcttgcag acactgattc gct         33

<210> SEQ ID NO 165
<211> LENGTH: 33
<212> TYPE: DNA
<213> ORGANISM: Artificial Sequence
<220> FEATURE:
<223> OTHER INFORMATION: Synthetic Primer

<400> SEQUENCE: 165
cagagcttaa acagcgcata tggcgcaccc gct         33

<210> SEQ ID NO 166
<211> LENGTH: 33
<212> TYPE: DNA
<213> ORGANISM: Artificial Sequence
<220> FEATURE:
<223> OTHER INFORMATION: Synthetic Primer

<400> SEQUENCE: 166
agcgggtgcg ccatatgcgc tgtttaagct ctg         33

<210> SEQ ID NO 167
<211> LENGTH: 33
<212> TYPE: DNA
<213> ORGANISM: Artificial Sequence
<220> FEATURE:
<223> OTHER INFORMATION: Synthetic Primer

<400> SEQUENCE: 167
agcccatatg gcgcagccgc ttatcaggaa cgt         33

<210> SEQ ID NO 168
<211> LENGTH: 33
<212> TYPE: DNA
<213> ORGANISM: Artificial Sequence
<220> FEATURE:
<223> OTHER INFORMATION: Synthetic Primer

<400> SEQUENCE: 168
acgttcctga taagcggctg cgccatatgg gct         33

<210> SEQ ID NO 169
<211> LENGTH: 33
<212> TYPE: DNA
<213> ORGANISM: Artificial Sequence
<220> FEATURE:
<223> OTHER INFORMATION: Synthetic Primer

<400> SEQUENCE: 169
gatcgtcatt tccaagctga aattaagctg gcg         33

<210> SEQ ID NO 170

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 170
cgccagctta atttcagctt ggaaatgacg atc                                    33

<210> SEQ ID NO 171
<211> LENGTH: 33
<212> TYPE: DNA
<213> ORGANISM: Artificial Sequence
<220> FEATURE:
<223> OTHER INFORMATION: Synthetic Primer

<400> SEQUENCE: 171
tccaatattt tattcgcggg cgagaaagtg atg                                    33

<210> SEQ ID NO 172
<211> LENGTH: 33
<212> TYPE: DNA
<213> ORGANISM: Artificial Sequence
<220> FEATURE:
<223> OTHER INFORMATION: Synthetic Primer

<400> SEQUENCE: 172
catcactttc tcgcccgcga ataaaatatt gga                                    33

<210> SEQ ID NO 173
<211> LENGTH: 33
<212> TYPE: DNA
<213> ORGANISM: Artificial Sequence
<220> FEATURE:
<223> OTHER INFORMATION: Synthetic Primer

<400> SEQUENCE: 173
tatgcactag aatttgcgtg gcattgttcc gtg                                    33

<210> SEQ ID NO 174
<211> LENGTH: 33
<212> TYPE: DNA
<213> ORGANISM: Artificial Sequence
<220> FEATURE:
<223> OTHER INFORMATION: Synthetic Primer

<400> SEQUENCE: 174
cacggaacaa tgccacgcaa attctagtgc ata                                    33

<210> SEQ ID NO 175
<211> LENGTH: 33
<212> TYPE: DNA
<213> ORGANISM: Artificial Sequence
<220> FEATURE:
<223> OTHER INFORMATION: Synthetic Primer

<400> SEQUENCE: 175
gcggcaattt cagaagcaga atttagtggc tct                                    33

<210> SEQ ID NO 176
<211> LENGTH: 33
<212> TYPE: DNA
<213> ORGANISM: Artificial Sequence
<220> FEATURE:
<223> OTHER INFORMATION: Synthetic Primer

<400> SEQUENCE: 176
```
agagccacta aattctgctt ctgaaattgc cgc				33

<210> SEQ ID NO 177
<211> LENGTH: 33
<212> TYPE: DNA
<213> ORGANISM: Artificial Sequence
<220> FEATURE:
<223> OTHER INFORMATION: Synthetic Primer

<400> SEQUENCE: 177
ctggtggagg gcctggcgga tttcatgaaa att				33

<210> SEQ ID NO 178
<211> LENGTH: 33
<212> TYPE: DNA
<213> ORGANISM: Artificial Sequence
<220> FEATURE:
<223> OTHER INFORMATION: Synthetic Primer

<400> SEQUENCE: 178
aattttcatg aaatccgcca ggccctccac cag				33

<210> SEQ ID NO 179
<211> LENGTH: 33
<212> TYPE: DNA
<213> ORGANISM: Artificial Sequence
<220> FEATURE:
<223> OTHER INFORMATION: Synthetic Primer

<400> SEQUENCE: 179
gccaccggtc acgttgcgac attcgatgaa tat				33

<210> SEQ ID NO 180
<211> LENGTH: 33
<212> TYPE: DNA
<213> ORGANISM: Artificial Sequence
<220> FEATURE:
<223> OTHER INFORMATION: Synthetic Primer

<400> SEQUENCE: 180
atattcatcg aatgtcgcaa cgtgaccggt ggc				33

<210> SEQ ID NO 181
<211> LENGTH: 33
<212> TYPE: DNA
<213> ORGANISM: Artificial Sequence
<220> FEATURE:
<223> OTHER INFORMATION: Synthetic Primer

<400> SEQUENCE: 181
ctgaacaatg gcaccgccaa caccggtatg tgt				33

<210> SEQ ID NO 182
<211> LENGTH: 33
<212> TYPE: DNA
<213> ORGANISM: Artificial Sequence
<220> FEATURE:
<223> OTHER INFORMATION: Synthetic Primer

<400> SEQUENCE: 182
acacataccg gtgttggcgg tgccattgtt cag				33

<210> SEQ ID NO 183
<211> LENGTH: 33
<212> TYPE: DNA
<213> ORGANISM: Artificial Sequence
<220> FEATURE:

<223> OTHER INFORMATION: Synthetic Primer

<400> SEQUENCE: 183
gtacttaatc tgatcgcgtt gctgcttatg ggc 33

<210> SEQ ID NO 184
<211> LENGTH: 33
<212> TYPE: DNA
<213> ORGANISM: Artificial Sequence
<220> FEATURE:
<223> OTHER INFORMATION: Synthetic Primer

<400> SEQUENCE: 184
gcccataagc agcaacgcga tcagattaag tac 33

<210> SEQ ID NO 185
<211> LENGTH: 33
<212> TYPE: DNA
<213> ORGANISM: Artificial Sequence
<220> FEATURE:
<223> OTHER INFORMATION: Synthetic Primer

<400> SEQUENCE: 185
atgggcgaac acttggcgat cgatattctt gaa 33

<210> SEQ ID NO 186
<211> LENGTH: 33
<212> TYPE: DNA
<213> ORGANISM: Artificial Sequence
<220> FEATURE:
<223> OTHER INFORMATION: Synthetic Primer

<400> SEQUENCE: 186
ttcaagaata tcgatcgcca agtgttcgcc cat 33

<210> SEQ ID NO 187
<211> LENGTH: 33
<212> TYPE: DNA
<213> ORGANISM: Artificial Sequence
<220> FEATURE:
<223> OTHER INFORMATION: Synthetic Primer

<400> SEQUENCE: 187
gaacagatct ttctggcgag ccggttccac cat 33

<210> SEQ ID NO 188
<211> LENGTH: 33
<212> TYPE: DNA
<213> ORGANISM: Artificial Sequence
<220> FEATURE:
<223> OTHER INFORMATION: Synthetic Primer

<400> SEQUENCE: 188
atggtggaac cggctcgcca gaaagatctg ttc 33

<210> SEQ ID NO 189
<211> LENGTH: 33
<212> TYPE: DNA
<213> ORGANISM: Artificial Sequence
<220> FEATURE:
<223> OTHER INFORMATION: Synthetic Primer

<400> SEQUENCE: 189
tacctgaaag accatgcgga atcaacagtt gaa 33

<210> SEQ ID NO 190

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 190
ttcaactgtt gattccgcat ggtctttcag gta                                33

<210> SEQ ID NO 191
<211> LENGTH: 33
<212> TYPE: DNA
<213> ORGANISM: Artificial Sequence
<220> FEATURE:
<223> OTHER INFORMATION: Synthetic Primer

<400> SEQUENCE: 191
aaacaggact cggtagctct gtcgtgtaaa aaa                                33

<210> SEQ ID NO 192
<211> LENGTH: 33
<212> TYPE: DNA
<213> ORGANISM: Artificial Sequence
<220> FEATURE:
<223> OTHER INFORMATION: Synthetic Primer

<400> SEQUENCE: 192 tttttacac gacagagcta ccgagtcctg ttt                                 33

<210> SEQ ID NO 193
<211> LENGTH: 38
<212> TYPE: DNA
<213> ORGANISM: Artificial Sequence
<220> FEATURE:
<223> OTHER INFORMATION: Synthetic Primer

<400> SEQUENCE: 193
gctctagatt atataggaac cgcaacgatt agaactttt                          38

<210> SEQ ID NO 194
<211> LENGTH: 32
<212> TYPE: DNA
<213> ORGANISM: Artificial Sequence
<220> FEATURE:
<223> OTHER INFORMATION: Synthetic Primer

<400> SEQUENCE: 194
gctctagatt atatagcaac cggaacgatt ag                                 32

<210> SEQ ID NO 195
<211> LENGTH: 33
<212> TYPE: DNA
<213> ORGANISM: Artificial Sequence
<220> FEATURE:
<223> OTHER INFORMATION: Synthetic Primer

<400> SEQUENCE: 195
accagcaacc gccacccgaa catgtgggaa gat                                33

<210> SEQ ID NO 196
<211> LENGTH: 33
<212> TYPE: DNA
<213> ORGANISM: Artificial Sequence
<220> FEATURE:
<223> OTHER INFORMATION: Synthetic Primer

<400> SEQUENCE: 196
```

```
atcttcccac atgttcgggt ggcggttgct ggt                                33
```

<210> SEQ ID NO 197
<211> LENGTH: 33
<212> TYPE: DNA
<213> ORGANISM: Artificial Sequence
<220> FEATURE:
<223> OTHER INFORMATION: Synthetic Primer

<400> SEQUENCE: 197

```
ggtagccgtg atagcccaaa aaaggacctg aat                                33
```

<210> SEQ ID NO 198
<211> LENGTH: 33
<212> TYPE: DNA
<213> ORGANISM: Artificial Sequence
<220> FEATURE:
<223> OTHER INFORMATION: Synthetic Primer

<400> SEQUENCE: 198

```
attcaggtcc tttttgggc tatcacggct acc                                 33
```

<210> SEQ ID NO 199
<211> LENGTH: 33
<212> TYPE: DNA
<213> ORGANISM: Artificial Sequence
<220> FEATURE:
<223> OTHER INFORMATION: Synthetic Primer

<400> SEQUENCE: 199

```
cgtgatagct taaaaccgga cctgaatgcg acc                                33
```

<210> SEQ ID NO 200
<211> LENGTH: 33
<212> TYPE: DNA
<213> ORGANISM: Artificial Sequence
<220> FEATURE:
<223> OTHER INFORMATION: Synthetic Primer

<400> SEQUENCE: 200

```
ggtcgcattc aggtccggtt ttaagctatc acg                                33
```

<210> SEQ ID NO 201
<211> LENGTH: 33
<212> TYPE: DNA
<213> ORGANISM: Artificial Sequence
<220> FEATURE:
<223> OTHER INFORMATION: Synthetic Primer

<400> SEQUENCE: 201

```
cgcttacacc gttatcctgt aagctcagga gtg                                33
```

<210> SEQ ID NO 202
<211> LENGTH: 33
<212> TYPE: DNA
<213> ORGANISM: Artificial Sequence
<220> FEATURE:
<223> OTHER INFORMATION: Synthetic Primer

<400> SEQUENCE: 202

```
cactcctgag cttacaggat aacggtgtaa gcg                                33
```

<210> SEQ ID NO 203
<211> LENGTH: 33
<212> TYPE: DNA
<213> ORGANISM: Artificial Sequence
<220> FEATURE:

```
<223> OTHER INFORMATION: Synthetic Primer

<400> SEQUENCE: 203
cgttataatg taagcccagg agtgctggag aac                                33

<210> SEQ ID NO 204
<211> LENGTH: 33
<212> TYPE: DNA
<213> ORGANISM: Artificial Sequence
<220> FEATURE:
<223> OTHER INFORMATION: Synthetic Primer

<400> SEQUENCE: 204
gttctccagc actcctgggc ttacattata acg                                33

<210> SEQ ID NO 205
<211> LENGTH: 33
<212> TYPE: DNA
<213> ORGANISM: Artificial Sequence
<220> FEATURE:
<223> OTHER INFORMATION: Synthetic Primer

<400> SEQUENCE: 205
aaggcgttta cgacccccta tcttaagaaa gtc                                33

<210> SEQ ID NO 206
<211> LENGTH: 33
<212> TYPE: DNA
<213> ORGANISM: Artificial Sequence
<220> FEATURE:
<223> OTHER INFORMATION: Synthetic Primer

<400> SEQUENCE: 206
gactttctta agataggggg tcgtaaacgc ctt                                33

<210> SEQ ID NO 207
<211> LENGTH: 33
<212> TYPE: DNA
<213> ORGANISM: Artificial Sequence
<220> FEATURE:
<223> OTHER INFORMATION: Synthetic Primer

<400> SEQUENCE: 207
ggtcgtgaag caactcctgt cgacgagagt ctc                                33

<210> SEQ ID NO 208
<211> LENGTH: 33
<212> TYPE: DNA
<213> ORGANISM: Artificial Sequence
<220> FEATURE:
<223> OTHER INFORMATION: Synthetic Primer

<400> SEQUENCE: 208
gagactctcg tcgacaggag ttgcttcacg acc                                33

<210> SEQ ID NO 209
<211> LENGTH: 33
<212> TYPE: DNA
<213> ORGANISM: Artificial Sequence
<220> FEATURE:
<223> OTHER INFORMATION: Synthetic Primer

<400> SEQUENCE: 209
tggcattgtt ccgtgccgcg ctgggaggca cgt                                33

<210> SEQ ID NO 210
```

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 210
acgtgcctcc cagcgcggca cggaacaatg cca                                      33

<210> SEQ ID NO 211
<211> LENGTH: 33
<212> TYPE: DNA
<213> ORGANISM: Artificial Sequence
<220> FEATURE:
<223> OTHER INFORMATION: Synthetic Primer

<400> SEQUENCE: 211
atcgaaattt tcggtccgat tgatagtgaa ctg                                      33

<210> SEQ ID NO 212
<211> LENGTH: 33
<212> TYPE: DNA
<213> ORGANISM: Artificial Sequence
<220> FEATURE:
<223> OTHER INFORMATION: Synthetic Primer

<400> SEQUENCE: 212
cagttcacta tcaatcggac cgaaaatttc gat                                      33

<210> SEQ ID NO 213
<211> LENGTH: 33
<212> TYPE: DNA
<213> ORGANISM: Artificial Sequence
<220> FEATURE:
<223> OTHER INFORMATION: Synthetic Primer

<400> SEQUENCE: 213
gccgattcaa gtatcccaag tctgaacttt tac                                      33

<210> SEQ ID NO 214
<211> LENGTH: 33
<212> TYPE: DNA
<213> ORGANISM: Artificial Sequence
<220> FEATURE:
<223> OTHER INFORMATION: Synthetic Primer

<400> SEQUENCE: 214
gtaaaagttc agacttggga tacttgaatc ggc                                      33

<210> SEQ ID NO 215
<211> LENGTH: 30
<212> TYPE: DNA
<213> ORGANISM: Artificial Sequence
<220> FEATURE:
<223> OTHER INFORMATION: Synthetic Primer

<400> SEQUENCE: 215
tggttcgccg attcaggtat cgcaagtctg                                          30

<210> SEQ ID NO 216
<211> LENGTH: 30
<212> TYPE: DNA
<213> ORGANISM: Artificial Sequence
<220> FEATURE:
<223> OTHER INFORMATION: Synthetic Primer

<400> SEQUENCE: 216
```
cagacttgcg atacctgaat cggcgaacca                                              30

<210> SEQ ID NO 217
<211> LENGTH: 33
<212> TYPE: DNA
<213> ORGANISM: Artificial Sequence
<220> FEATURE:
<223> OTHER INFORMATION: Synthetic Primer

<400> SEQUENCE: 217
agtggctctc gcgtgggatt cactaaaatt gcg                                          33

<210> SEQ ID NO 218
<211> LENGTH: 33
<212> TYPE: DNA
<213> ORGANISM: Artificial Sequence
<220> FEATURE:
<223> OTHER INFORMATION: Synthetic Primer

<400> SEQUENCE: 218 cgcaattta gtgaatccca cgcgagagcc act                                           33

<210> SEQ ID NO 219
<211> LENGTH: 33
<212> TYPE: DNA
<213> ORGANISM: Artificial Sequence
<220> FEATURE:
<223> OTHER INFORMATION: Synthetic Primer

<400> SEQUENCE: 219
ccggatttca tgaaaggtgc ctttgagttc tgg                                          33

<210> SEQ ID NO 220
<211> LENGTH: 33
<212> TYPE: DNA
<213> ORGANISM: Artificial Sequence
<220> FEATURE:
<223> OTHER INFORMATION: Synthetic Primer

<400> SEQUENCE: 220
ccagaactca aaggcacctt tcatgaaatc cgg                                          33

<210> SEQ ID NO 221
<211> LENGTH: 33
<212> TYPE: DNA
<213> ORGANISM: Artificial Sequence
<220> FEATURE:
<223> OTHER INFORMATION: Synthetic Primer

<400> SEQUENCE: 221
cccaacaccg gtatgggtgt acttaatctg atc                                          33

<210> SEQ ID NO 222
<211> LENGTH: 33
<212> TYPE: DNA
<213> ORGANISM: Artificial Sequence
<220> FEATURE:
<223> OTHER INFORMATION: Synthetic Primer

<400> SEQUENCE: 222
gatcagatta agtacaccca taccggtgtt ggg                                          33

<210> SEQ ID NO 223
<211> LENGTH: 33
<212> TYPE: DNA
<213> ORGANISM: Artificial Sequence
<220> FEATURE:

<223> OTHER INFORMATION: Synthetic Primer

<400> SEQUENCE: 223
gctagccgac tggtcggtga tgcgagagat ttt              33

<210> SEQ ID NO 224
<211> LENGTH: 33
<212> TYPE: DNA
<213> ORGANISM: Artificial Sequence
<220> FEATURE:
<223> OTHER INFORMATION: Synthetic Primer

<400> SEQUENCE: 224
aaaatctctc gcatcaccga ccagtcggct agc              33

<210> SEQ ID NO 225
<211> LENGTH: 33
<212> TYPE: DNA
<213> ORGANISM: Artificial Sequence
<220> FEATURE:
<223> OTHER INFORMATION: Synthetic Primer

<400> SEQUENCE: 225
catggtgatt tatccggcat cgaatgctac ctg              33

<210> SEQ ID NO 226
<211> LENGTH: 33
<212> TYPE: DNA
<213> ORGANISM: Artificial Sequence
<220> FEATURE:
<223> OTHER INFORMATION: Synthetic Primer

<400> SEQUENCE: 226
caggtagcat tcgatgccgg ataaatcacc atg              33

<210> SEQ ID NO 227
<211> LENGTH: 33
<212> TYPE: DNA
<213> ORGANISM: Artificial Sequence
<220> FEATURE:
<223> OTHER INFORMATION: Synthetic Primer

<400> SEQUENCE: 227
ctgaaagacc atccgggatc aacagttgaa gac              33

<210> SEQ ID NO 228
<211> LENGTH: 33
<212> TYPE: DNA
<213> ORGANISM: Artificial Sequence
<220> FEATURE:
<223> OTHER INFORMATION: Synthetic Primer

<400> SEQUENCE: 228
gtcttcaact gttgatcccg gatggtcttt cag              33

<210> SEQ ID NO 229
<211> LENGTH: 33
<212> TYPE: DNA
<213> ORGANISM: Artificial Sequence
<220> FEATURE:
<223> OTHER INFORMATION: Synthetic Primer

<400> SEQUENCE: 229
agcgaatcag tgtctgcaag caccgacctt aaa              33

<210> SEQ ID NO 230

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 230
tttaaggtcg gtgcttgcag acactgattc gct                              33

<210> SEQ ID NO 231
<211> LENGTH: 33
<212> TYPE: DNA
<213> ORGANISM: Artificial Sequence
<220> FEATURE:
<223> OTHER INFORMATION: Synthetic Primer

<400> SEQUENCE: 231
cagagcttaa acagcgcata tggcgcaccc gct                              33

<210> SEQ ID NO 232
<211> LENGTH: 33
<212> TYPE: DNA
<213> ORGANISM: Artificial Sequence
<220> FEATURE:
<223> OTHER INFORMATION: Synthetic Primer

<400> SEQUENCE: 232
agcgggtgcg ccatatgcgc tgtttaagct ctg                              33

<210> SEQ ID NO 233
<211> LENGTH: 33
<212> TYPE: DNA
<213> ORGANISM: Artificial Sequence
<220> FEATURE:
<223> OTHER INFORMATION: Synthetic Primer

<400> SEQUENCE: 233
agcccatatg gcgcagccgc ttatcaggaa cgt                              33

<210> SEQ ID NO 234
<211> LENGTH: 33
<212> TYPE: DNA
<213> ORGANISM: Artificial Sequence
<220> FEATURE:
<223> OTHER INFORMATION: Synthetic Primer

<400> SEQUENCE: 234
acgttcctga taagcggctg cgccatatgg gct                              33

<210> SEQ ID NO 235
<211> LENGTH: 33
<212> TYPE: DNA
<213> ORGANISM: Artificial Sequence
<220> FEATURE:
<223> OTHER INFORMATION: Synthetic Primer

<400> SEQUENCE: 235
gatcgtcatt tccaagctga aattaagctg gcg                              33

<210> SEQ ID NO 236
<211> LENGTH: 33
<212> TYPE: DNA
<213> ORGANISM: Artificial Sequence
<220> FEATURE:
<223> OTHER INFORMATION: Synthetic Primer

<400> SEQUENCE: 236
```

```
cgccagctta atttcagctt ggaaatgacg atc                                33
```

<210> SEQ ID NO 237
<211> LENGTH: 33
<212> TYPE: DNA
<213> ORGANISM: Artificial Sequence
<220> FEATURE:
<223> OTHER INFORMATION: Synthetic Primer

<400> SEQUENCE: 237

```
tccaatattt tattcgcggg cgagaaagtg atg                                33
```

<210> SEQ ID NO 238
<211> LENGTH: 33
<212> TYPE: DNA
<213> ORGANISM: Artificial Sequence
<220> FEATURE:
<223> OTHER INFORMATION: Synthetic Primer

<400> SEQUENCE: 238

```
catcactttc tcgcccgcga ataaaatatt gga                                33
```

<210> SEQ ID NO 239
<211> LENGTH: 33
<212> TYPE: DNA
<213> ORGANISM: Artificial Sequence
<220> FEATURE:
<223> OTHER INFORMATION: Synthetic Primer

<400> SEQUENCE: 239

```
tatgcactag aatttgcgtg gcattgttcc gtg                                33
```

<210> SEQ ID NO 240
<211> LENGTH: 33
<212> TYPE: DNA
<213> ORGANISM: Artificial Sequence
<220> FEATURE:
<223> OTHER INFORMATION: Synthetic Primer

<400> SEQUENCE: 240

```
cacggaacaa tgccacgcaa attctagtgc ata                                33
```

<210> SEQ ID NO 241
<211> LENGTH: 33
<212> TYPE: DNA
<213> ORGANISM: Artificial Sequence
<220> FEATURE:
<223> OTHER INFORMATION: Synthetic Primer

<400> SEQUENCE: 241

```
gcggcaattt cagaagcaga atttagtggc tct                                33
```

<210> SEQ ID NO 242
<211> LENGTH: 33
<212> TYPE: DNA
<213> ORGANISM: Artificial Sequence
<220> FEATURE:
<223> OTHER INFORMATION: Synthetic Primer

<400> SEQUENCE: 242

```
agagccacta aattctgctt ctgaaattgc cgc                                33
```

<210> SEQ ID NO 243
<211> LENGTH: 33
<212> TYPE: DNA
<213> ORGANISM: Artificial Sequence
<220> FEATURE:

<223> OTHER INFORMATION: Synthetic Primer

<400> SEQUENCE: 243
ctggtggagg gcctggcgga tttcatgaaa att           33

<210> SEQ ID NO 244
<211> LENGTH: 33
<212> TYPE: DNA
<213> ORGANISM: Artificial Sequence
<220> FEATURE:
<223> OTHER INFORMATION: Synthetic Primer

<400> SEQUENCE: 244
aattttcatg aaatccgcca ggccctccac cag           33

<210> SEQ ID NO 245
<211> LENGTH: 33
<212> TYPE: DNA
<213> ORGANISM: Artificial Sequence
<220> FEATURE:
<223> OTHER INFORMATION: Synthetic Primer

<400> SEQUENCE: 245
gccaccggtc acgttgcgac attcgatgaa tat           33

<210> SEQ ID NO 246
<211> LENGTH: 33
<212> TYPE: DNA
<213> ORGANISM: Artificial Sequence
<220> FEATURE:
<223> OTHER INFORMATION: Synthetic Primer

<400> SEQUENCE: 246
atattcatcg aatgtcgcaa cgtgaccggt ggc           33

<210> SEQ ID NO 247
<211> LENGTH: 33
<212> TYPE: DNA
<213> ORGANISM: Artificial Sequence
<220> FEATURE:
<223> OTHER INFORMATION: Synthetic Primer

<400> SEQUENCE: 247
ctgaacaatg gcaccgccaa caccggtatg tgt           33

<210> SEQ ID NO 248
<211> LENGTH: 33
<212> TYPE: DNA
<213> ORGANISM: Artificial Sequence
<220> FEATURE:
<223> OTHER INFORMATION: Synthetic Primer

<400> SEQUENCE: 248
acacataccg gtgttggcgg tgccattgtt cag           33

<210> SEQ ID NO 249
<211> LENGTH: 33
<212> TYPE: DNA
<213> ORGANISM: Artificial Sequence
<220> FEATURE:
<223> OTHER INFORMATION: Synthetic Primer

<400> SEQUENCE: 249
gtacttaatc tgatcgcgtt gctgcttatg ggc           33

<210> SEQ ID NO 250

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 250
gcccataagc agcaacgcga tcagattaag tac                                  33

<210> SEQ ID NO 251
<211> LENGTH: 33
<212> TYPE: DNA
<213> ORGANISM: Artificial Sequence
<220> FEATURE:
<223> OTHER INFORMATION: Synthetic Primer

<400> SEQUENCE: 251
atgggcgaac acttggcgat cgatattctt gaa                                  33

<210> SEQ ID NO 252
<211> LENGTH: 33
<212> TYPE: DNA
<213> ORGANISM: Artificial Sequence
<220> FEATURE:
<223> OTHER INFORMATION: Synthetic Primer

<400> SEQUENCE: 252
ttcaagaata tcgatcgcca agtgttcgcc cat                                  33

<210> SEQ ID NO 253
<211> LENGTH: 33
<212> TYPE: DNA
<213> ORGANISM: Artificial Sequence
<220> FEATURE:
<223> OTHER INFORMATION: Synthetic Primer

<400> SEQUENCE: 253
gaacagatct ttctggcgag ccggttccac cat                                  33

<210> SEQ ID NO 254
<211> LENGTH: 33
<212> TYPE: DNA
<213> ORGANISM: Artificial Sequence
<220> FEATURE:
<223> OTHER INFORMATION: Synthetic Primer

<400> SEQUENCE: 254
atggtggaac cggctcgcca gaaagatctg ttc                                  33

<210> SEQ ID NO 255
<211> LENGTH: 33
<212> TYPE: DNA
<213> ORGANISM: Artificial Sequence
<220> FEATURE:
<223> OTHER INFORMATION: Synthetic Primer

<400> SEQUENCE: 255
tacctgaaag accatgcgga atcaacagtt gaa                                  33

<210> SEQ ID NO 256
<211> LENGTH: 33
<212> TYPE: DNA
<213> ORGANISM: Artificial Sequence
<220> FEATURE:
<223> OTHER INFORMATION: Synthetic Primer

<400> SEQUENCE: 256
```
ttcaactgtt gattccgcat ggtctttcag gta    33

<210> SEQ ID NO 257
<211> LENGTH: 33
<212> TYPE: DNA
<213> ORGANISM: Artificial Sequence
<220> FEATURE:
<223> OTHER INFORMATION: Synthetic Primer

<400> SEQUENCE: 257
aaacaggact cggtagctct gtcgtgtaaa aaa    33

<210> SEQ ID NO 258
<211> LENGTH: 33
<212> TYPE: DNA
<213> ORGANISM: Artificial Sequence
<220> FEATURE:
<223> OTHER INFORMATION: Synthetic Primer

<400> SEQUENCE: 258 tttttacac gacagagcta ccgagtcctg ttt    33

<210> SEQ ID NO 259
<211> LENGTH: 38
<212> TYPE: DNA
<213> ORGANISM: Artificial Sequence
<220> FEATURE:
<223> OTHER INFORMATION: Synthetic Primer

<400> SEQUENCE: 259
gctctagatt ataggaac cgcaacgatt agaacttt    38

<210> SEQ ID NO 260
<211> LENGTH: 32
<212> TYPE: DNA
<213> ORGANISM: Artificial Sequence
<220> FEATURE:
<223> OTHER INFORMATION: Synthetic Primer

<400> SEQUENCE: 260
gctctagatt atatagcaac cggaacgatt ag    32

<210> SEQ ID NO 261
<211> LENGTH: 33
<212> TYPE: DNA
<213> ORGANISM: Artificial Sequence
<220> FEATURE:
<223> OTHER INFORMATION: Synthetic Primer

<400> SEQUENCE: 261
accagcaacc gccacccgaa catgtgggaa gat    33

<210> SEQ ID NO 262
<211> LENGTH: 33
<212> TYPE: DNA
<213> ORGANISM: Artificial Sequence
<220> FEATURE:
<223> OTHER INFORMATION: Synthetic Primer

<400> SEQUENCE: 262
atcttcccac atgttcgggt ggcggttgct ggt    33

<210> SEQ ID NO 263
<211> LENGTH: 33
<212> TYPE: DNA
<213> ORGANISM: Artificial Sequence
<220> FEATURE:

<223> OTHER INFORMATION: Synthetic Primer

<400> SEQUENCE: 263
ggtagccgtg atagcccaaa aaaggacctg aat                              33

<210> SEQ ID NO 264
<211> LENGTH: 33
<212> TYPE: DNA
<213> ORGANISM: Artificial Sequence
<220> FEATURE:
<223> OTHER INFORMATION: Synthetic Primer

<400> SEQUENCE: 264
attcaggtcc tttttgggc tatcacggct acc                               33

<210> SEQ ID NO 265
<211> LENGTH: 33
<212> TYPE: DNA
<213> ORGANISM: Artificial Sequence
<220> FEATURE:
<223> OTHER INFORMATION: Synthetic Primer

<400> SEQUENCE: 265
cgtgatagct aaaaccgga cctgaatgcg acc                               33

<210> SEQ ID NO 266
<211> LENGTH: 33
<212> TYPE: DNA
<213> ORGANISM: Artificial Sequence
<220> FEATURE:
<223> OTHER INFORMATION: Synthetic Primer

<400> SEQUENCE: 266
ggtcgcattc aggtccggtt ttaagctatc acg                              33

<210> SEQ ID NO 267
<211> LENGTH: 33
<212> TYPE: DNA
<213> ORGANISM: Artificial Sequence
<220> FEATURE:
<223> OTHER INFORMATION: Synthetic Primer

<400> SEQUENCE: 267
cgcttacacc gttatcctgt aagctcagga gtg                              33

<210> SEQ ID NO 268
<211> LENGTH: 33
<212> TYPE: DNA
<213> ORGANISM: Artificial Sequence
<220> FEATURE:
<223> OTHER INFORMATION: Synthetic Primer

<400> SEQUENCE: 268
cactcctgag cttacaggat aacggtgtaa gcg                              33

<210> SEQ ID NO 269
<211> LENGTH: 33
<212> TYPE: DNA
<213> ORGANISM: Artificial Sequence
<220> FEATURE:
<223> OTHER INFORMATION: Synthetic Primer

<400> SEQUENCE: 269
cgttataatg taagcccagg agtgctggag aac                              33

<210> SEQ ID NO 270

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 270
gttctccagc actcctgggc ttacattata acg                                    33

<210> SEQ ID NO 271
<211> LENGTH: 33
<212> TYPE: DNA
<213> ORGANISM: Artificial Sequence
<220> FEATURE:
<223> OTHER INFORMATION: Synthetic Primer

<400> SEQUENCE: 271
aaggcgttta cgacccccta tcttaagaaa gtc                                    33

<210> SEQ ID NO 272
<211> LENGTH: 33
<212> TYPE: DNA
<213> ORGANISM: Artificial Sequence
<220> FEATURE:
<223> OTHER INFORMATION: Synthetic Primer

<400> SEQUENCE: 272
gactttctta agatagggggg tcgtaaacgc ctt                                   33

<210> SEQ ID NO 273
<211> LENGTH: 33
<212> TYPE: DNA
<213> ORGANISM: Artificial Sequence
<220> FEATURE:
<223> OTHER INFORMATION: Synthetic Primer

<400> SEQUENCE: 273
ggtcgtgaag caactcctgt cgacgagagt ctc                                    33

<210> SEQ ID NO 274
<211> LENGTH: 33
<212> TYPE: DNA
<213> ORGANISM: Artificial Sequence
<220> FEATURE:
<223> OTHER INFORMATION: Synthetic Primer

<400> SEQUENCE: 274
gagactctcg tcgacaggag ttgcttcacg acc                                    33

<210> SEQ ID NO 275
<211> LENGTH: 33
<212> TYPE: DNA
<213> ORGANISM: Artificial Sequence
<220> FEATURE:
<223> OTHER INFORMATION: Synthetic Primer

<400> SEQUENCE: 275
tggcattgtt ccgtgccgcg ctgggaggca cgt                                    33

<210> SEQ ID NO 276
<211> LENGTH: 33
<212> TYPE: DNA
<213> ORGANISM: Artificial Sequence
<220> FEATURE:
<223> OTHER INFORMATION: Synthetic Primer

<400> SEQUENCE: 276
```
acgtgcctcc cagcgcggca cggaacaatg cca                                33

<210> SEQ ID NO 277
<211> LENGTH: 33
<212> TYPE: DNA
<213> ORGANISM: Artificial Sequence
<220> FEATURE:
<223> OTHER INFORMATION: Synthetic Primer

<400> SEQUENCE: 277
atcgaaattt tcggtccgat tgatagtgaa ctg                                33

<210> SEQ ID NO 278
<211> LENGTH: 33
<212> TYPE: DNA
<213> ORGANISM: Artificial Sequence
<220> FEATURE:
<223> OTHER INFORMATION: Synthetic Primer

<400> SEQUENCE: 278
cagttcacta tcaatcggac cgaaaatttc gat                                33

<210> SEQ ID NO 279
<211> LENGTH: 33
<212> TYPE: DNA
<213> ORGANISM: Artificial Sequence
<220> FEATURE:
<223> OTHER INFORMATION: Synthetic Primer

<400> SEQUENCE: 279
gccgattcaa gtatcccaag tctgaacttt tac                                33

<210> SEQ ID NO 280
<211> LENGTH: 33
<212> TYPE: DNA
<213> ORGANISM: Artificial Sequence
<220> FEATURE:
<223> OTHER INFORMATION: Synthetic Primer

<400> SEQUENCE: 280
gtaaaagttc agacttggga tacttgaatc ggc                                33

<210> SEQ ID NO 281
<211> LENGTH: 33
<212> TYPE: DNA
<213> ORGANISM: Artificial Sequence
<220> FEATURE:
<223> OTHER INFORMATION: Synthetic Primer

<400> SEQUENCE: 281
ttttaccgta aatgccctgt ggaattttac ttc                                33

<210> SEQ ID NO 282
<211> LENGTH: 33
<212> TYPE: DNA
<213> ORGANISM: Artificial Sequence
<220> FEATURE:
<223> OTHER INFORMATION: Synthetic Primer

<400> SEQUENCE: 282
gaagtaaaat tccacagggc atttacggta aaa                                33

<210> SEQ ID NO 283
<211> LENGTH: 33
<212> TYPE: DNA
<213> ORGANISM: Artificial Sequence
<220> FEATURE:

<223> OTHER INFORMATION: Synthetic Primer

<400> SEQUENCE: 283
gtgcgcaggt gggacccgtc gctggtggag ggc                33

<210> SEQ ID NO 284
<211> LENGTH: 33
<212> TYPE: DNA
<213> ORGANISM: Artificial Sequence
<220> FEATURE:
<223> OTHER INFORMATION: Synthetic Primer

<400> SEQUENCE: 284
gccctccacc agcgacgggt cccacctgcg cac                33

<210> SEQ ID NO 285
<211> LENGTH: 33
<212> TYPE: DNA
<213> ORGANISM: Artificial Sequence
<220> FEATURE:
<223> OTHER INFORMATION: Synthetic Primer

<400> SEQUENCE: 285
tatatccgca aaaccctttg ggaacgctat ctg                33

<210> SEQ ID NO 286
<211> LENGTH: 33
<212> TYPE: DNA
<213> ORGANISM: Artificial Sequence
<220> FEATURE:
<223> OTHER INFORMATION: Synthetic Primer

<400> SEQUENCE: 286
cagatagcgt tcccaagggt ttttgcggat ata                33

<210> SEQ ID NO 287
<211> LENGTH: 33
<212> TYPE: DNA
<213> ORGANISM: Artificial Sequence
<220> FEATURE:
<223> OTHER INFORMATION: Synthetic Primer

<400> SEQUENCE: 287
aacaccggta tgtgtccact taatctgatc ccg                33

<210> SEQ ID NO 288
<211> LENGTH: 33
<212> TYPE: DNA
<213> ORGANISM: Artificial Sequence
<220> FEATURE:
<223> OTHER INFORMATION: Synthetic Primer

<400> SEQUENCE: 288
cgggatcaga ttaagtggac ataccggt gtt                33

<210> SEQ ID NO 289
<211> LENGTH: 33
<212> TYPE: DNA
<213> ORGANISM: Artificial Sequence
<220> FEATURE:
<223> OTHER INFORMATION: Synthetic Primer

<400> SEQUENCE: 289
ctgcttatgg gcgaaccctt gccgatcgat att                33

<210> SEQ ID NO 290

<211> LENGTH: 33
<212> TYPE: DNA
<213> ORGANISM: Artificial Sequence
<220> FEATURE:
<223> OTHER INFORMATION: Synthetic Primer

<400> SEQUENCE: 290
aatatcgatc ggcaagggtt cgcccataag cag                33

<210> SEQ ID NO 291
<211> LENGTH: 33
<212> TYPE: DNA
<213> ORGANISM: Artificial Sequence
<220> FEATURE:
<223> OTHER INFORMATION: Synthetic Primer

<400> SEQUENCE: 291
tggaaatttc tgaaaccaca ggactcggta cct                33

<210> SEQ ID NO 292
<211> LENGTH: 33
<212> TYPE: DNA
<213> ORGANISM: Artificial Sequence
<220> FEATURE:
<223> OTHER INFORMATION: Synthetic Primer

<400> SEQUENCE: 292
aggtaccgag tcctgtggtt tcagaaattt cca                33

<210> SEQ ID NO 293
<211> LENGTH: 39
<212> TYPE: DNA
<213> ORGANISM: Artificial Sequence
<220> FEATURE:
<223> OTHER INFORMATION: Synthetic Primer

<400> SEQUENCE: 293
aacaaaaccg tcattagcgc cagcaaggtg aagtctctg          39

<210> SEQ ID NO 294
<211> LENGTH: 39
<212> TYPE: DNA
<213> ORGANISM: Artificial Sequence
<220> FEATURE:
<223> OTHER INFORMATION: Synthetic Primer

<400> SEQUENCE: 294
cagagacttc accttgctgg cgctaatgac ggtttttgtt         39

<210> SEQ ID NO 295
<211> LENGTH: 39
<212> TYPE: DNA
<213> ORGANISM: Artificial Sequence
<220> FEATURE:
<223> OTHER INFORMATION: Synthetic Primer

<400> SEQUENCE: 295
gcccaaagct ctagcagcgc cccgtctagc agcagcgag          39

<210> SEQ ID NO 296
<211> LENGTH: 39
<212> TYPE: DNA
<213> ORGANISM: Artificial Sequence
<220> FEATURE:
<223> OTHER INFORMATION: Synthetic Primer

<400> SEQUENCE: 296

```
ctcgctgctg ctagacgggg cgctgctaga gctttgggc                                  39

<210> SEQ ID NO 297
<211> LENGTH: 39
<212> TYPE: DNA
<213> ORGANISM: Artificial Sequence
<220> FEATURE:
<223> OTHER INFORMATION: Synthetic Primer

<400> SEQUENCE: 297
gaggccctgc tgagcagcgc caacaccaag cagctgaag                                  39

<210> SEQ ID NO 298
<211> LENGTH: 39
<212> TYPE: DNA
<213> ORGANISM: Artificial Sequence
<220> FEATURE:
<223> OTHER INFORMATION: Synthetic Primer

<400> SEQUENCE: 298
cttcagctgc ttggtgttgg cgctgctcag cagggcctc                                  39

<210> SEQ ID NO 299
<211> LENGTH: 39
<212> TYPE: DNA
<213> ORGANISM: Artificial Sequence
<220> FEATURE:
<223> OTHER INFORMATION: Synthetic Primer

<400> SEQUENCE: 299
gcagcgctgg tgatccacgc taagctgcca ctgtatgcg                                  39

<210> SEQ ID NO 300
<211> LENGTH: 39
<212> TYPE: DNA
<213> ORGANISM: Artificial Sequence
<220> FEATURE:
<223> OTHER INFORMATION: Synthetic Primer

<400> SEQUENCE: 300
cgcatacagt ggcagcttag cgtggatcac cagcgctgc                                  39

<210> SEQ ID NO 301
<211> LENGTH: 39
<212> TYPE: DNA
<213> ORGANISM: Artificial Sequence
<220> FEATURE:
<223> OTHER INFORMATION: Synthetic Primer

<400> SEQUENCE: 301
gcgctggaaa agaaactggc cgatacgacg cgtgcggtc                                  39

<210> SEQ ID NO 302
<211> LENGTH: 39
<212> TYPE: DNA
<213> ORGANISM: Artificial Sequence
<220> FEATURE:
<223> OTHER INFORMATION: Synthetic Primer

<400> SEQUENCE: 302
gaccgcacgc gtcgtatcgg ccagtttctt ttccagcgc                                  39

<210> SEQ ID NO 303
<211> LENGTH: 39
<212> TYPE: DNA
<213> ORGANISM: Artificial Sequence
<220> FEATURE:
```

<223> OTHER INFORMATION: Synthetic Primer

<400> SEQUENCE: 303
gactacgacc gcgtgtttgc cgcgtgctgc gagaatgtc         39

<210> SEQ ID NO 304
<211> LENGTH: 39
<212> TYPE: DNA
<213> ORGANISM: Artificial Sequence
<220> FEATURE:
<223> OTHER INFORMATION: Synthetic Primer

<400> SEQUENCE: 304
gacattctcg cagcacgcgg caaacacgcg gtcgtagtc         39

<210> SEQ ID NO 305
<211> LENGTH: 39
<212> TYPE: DNA
<213> ORGANISM: Artificial Sequence
<220> FEATURE:
<223> OTHER INFORMATION: Synthetic Primer

<400> SEQUENCE: 305
tgctgcgaga atgtcattgc ctacatgccg ttaccggtt         39

<210> SEQ ID NO 306
<211> LENGTH: 39
<212> TYPE: DNA
<213> ORGANISM: Artificial Sequence
<220> FEATURE:
<223> OTHER INFORMATION: Synthetic Primer

<400> SEQUENCE: 306
aaccggtaac ggcatgtagg caatgacatt ctcgcagca         39

<210> SEQ ID NO 307
<211> LENGTH: 39
<212> TYPE: DNA
<213> ORGANISM: Artificial Sequence
<220> FEATURE:
<223> OTHER INFORMATION: Synthetic Primer

<400> SEQUENCE: 307
tacatgccgt taccggttgc tgtgatcggc ccgctggtc         39

<210> SEQ ID NO 308
<211> LENGTH: 39
<212> TYPE: DNA
<213> ORGANISM: Artificial Sequence
<220> FEATURE:
<223> OTHER INFORMATION: Synthetic Primer

<400> SEQUENCE: 308
gaccagcggg ccgatcacag caaccggtaa cggcatgta         39

<210> SEQ ID NO 309
<211> LENGTH: 39
<212> TYPE: DNA
<213> ORGANISM: Artificial Sequence
<220> FEATURE:
<223> OTHER INFORMATION: Synthetic Primer

<400> SEQUENCE: 309
ttaccggttg gtgtgatcgc cccgctggtc attgatggc         39

<210> SEQ ID NO 310

```
<211> LENGTH: 39
<212> TYPE: DNA
<213> ORGANISM: Artificial Sequence
<220> FEATURE:
<223> OTHER INFORMATION: Synthetic Primer

<400> SEQUENCE: 310
gccatcaatg accagcgggg cgatcacacc aaccggtaa                    39

<210> SEQ ID NO 311
<211> LENGTH: 39
<212> TYPE: DNA
<213> ORGANISM: Artificial Sequence
<220> FEATURE:
<223> OTHER INFORMATION: Synthetic Primer

<400> SEQUENCE: 311
ggcccgctgg tcattgatgc cacgagctat cacattcca                    39

<210> SEQ ID NO 312
<211> LENGTH: 39
<212> TYPE: DNA
<213> ORGANISM: Artificial Sequence
<220> FEATURE:
<223> OTHER INFORMATION: Synthetic Primer

<400> SEQUENCE: 312
tggaatgtga tagctcgtgg catcaatgac cagcgggcc                    39

<210> SEQ ID NO 313
<211> LENGTH: 39
<212> TYPE: DNA
<213> ORGANISM: Artificial Sequence
<220> FEATURE:
<223> OTHER INFORMATION: Synthetic Primer

<400> SEQUENCE: 313
ccaatggcga ccacggaagc ttgcttagtc gccagcgcc                    39

<210> SEQ ID NO 314
<211> LENGTH: 39
<212> TYPE: DNA
<213> ORGANISM: Artificial Sequence
<220> FEATURE:
<223> OTHER INFORMATION: Synthetic Primer

<400> SEQUENCE: 314
ggcgctggcg actaagcaag cttccgtggt cgccattgg                    39

<210> SEQ ID NO 315
<211> LENGTH: 39
<212> TYPE: DNA
<213> ORGANISM: Artificial Sequence
<220> FEATURE:
<223> OTHER INFORMATION: Synthetic Primer

<400> SEQUENCE: 315
gtcgccagcg ccatgcgtgc ctgtaaggcg attaacgcc                    39

<210> SEQ ID NO 316
<211> LENGTH: 39
<212> TYPE: DNA
<213> ORGANISM: Artificial Sequence
<220> FEATURE:
<223> OTHER INFORMATION: Synthetic Primer

<400> SEQUENCE: 316
```

-continued

```
ggcgttaatc gccttacagg cacgcatggc gctggcgac                                39

<210> SEQ ID NO 317
<211> LENGTH: 39
<212> TYPE: DNA
<213> ORGANISM: Artificial Sequence
<220> FEATURE:
<223> OTHER INFORMATION: Synthetic Primer

<400> SEQUENCE: 317
tgtaaggcga ttaacgccgc cggtggcgcg acgaccgtg                                 39

<210> SEQ ID NO 318
<211> LENGTH: 39
<212> TYPE: DNA
<213> ORGANISM: Artificial Sequence
<220> FEATURE:
<223> OTHER INFORMATION: Synthetic Primer

<400> SEQUENCE: 318
cacggtcgtc gcgccaccgg cggcgttaat cgccttaca                                 39

<210> SEQ ID NO 319
<211> LENGTH: 39
<212> TYPE: DNA
<213> ORGANISM: Artificial Sequence
<220> FEATURE:
<223> OTHER INFORMATION: Synthetic Primer

<400> SEQUENCE: 319
aaggcgatta acgccggcgc tggcgcgacg accgtgtta                                 39

<210> SEQ ID NO 320
<211> LENGTH: 39
<212> TYPE: DNA
<213> ORGANISM: Artificial Sequence
<220> FEATURE:
<223> OTHER INFORMATION: Synthetic Primer

<400> SEQUENCE: 320
taacacggtc gtcgcgccag cgccggcgtt aatcgcctt                                 39

<210> SEQ ID NO 321
<211> LENGTH: 39
<212> TYPE: DNA
<213> ORGANISM: Artificial Sequence
<220> FEATURE:
<223> OTHER INFORMATION: Synthetic Primer

<400> SEQUENCE: 321
gcgattaacg ccggcggtgc cgcgacgacc gtgttaacc                                 39

<210> SEQ ID NO 322
<211> LENGTH: 39
<212> TYPE: DNA
<213> ORGANISM: Artificial Sequence
<220> FEATURE:
<223> OTHER INFORMATION: Synthetic Primer

<400> SEQUENCE: 322
ggttaacacg gtcgtcgcgg caccgccggc gttaatcgc                                 39

<210> SEQ ID NO 323
<211> LENGTH: 33
<212> TYPE: DNA
<213> ORGANISM: Artificial Sequence
<220> FEATURE:
```

<223> OTHER INFORMATION: Synthetic Primer

<400> SEQUENCE: 323
gtgttaacca aggatgccat gacgcgcggt ccg       33

<210> SEQ ID NO 324
<211> LENGTH: 33
<212> TYPE: DNA
<213> ORGANISM: Artificial Sequence
<220> FEATURE:
<223> OTHER INFORMATION: Synthetic Primer

<400> SEQUENCE: 324
cggaccgcgc gtcatggcat ccttggttaa cac       33

<210> SEQ ID NO 325
<211> LENGTH: 39
<212> TYPE: DNA
<213> ORGANISM: Artificial Sequence
<220> FEATURE:
<223> OTHER INFORMATION: Synthetic Primer

<400> SEQUENCE: 325
aaggatggta tgacgcgcgc tccggtcgtc cgcttccca       39

<210> SEQ ID NO 326
<211> LENGTH: 39
<212> TYPE: DNA
<213> ORGANISM: Artificial Sequence
<220> FEATURE:
<223> OTHER INFORMATION: Synthetic Primer

<400> SEQUENCE: 326
tgggaagcgg acgaccggag cgcgcgtcat accatcctt       39

<210> SEQ ID NO 327
<211> LENGTH: 45
<212> TYPE: DNA
<213> ORGANISM: Artificial Sequence
<220> FEATURE:
<223> OTHER INFORMATION: Synthetic Primer

<400> SEQUENCE: 327
gtgttaacca aggatgccat gacgcgcgct ccggtcgtcc gcttc       45

<210> SEQ ID NO 328
<211> LENGTH: 45
<212> TYPE: DNA
<213> ORGANISM: Artificial Sequence
<220> FEATURE:
<223> OTHER INFORMATION: Synthetic Primer

<400> SEQUENCE: 328
gaagcggacg accggagcgc gcgtcatggc atccttggtt aacac       45

<210> SEQ ID NO 329
<211> LENGTH: 39
<212> TYPE: DNA
<213> ORGANISM: Artificial Sequence
<220> FEATURE:
<223> OTHER INFORMATION: Synthetic Primer

<400> SEQUENCE: 329
ccaacgctga agcgcagcgc cgcgtgtaag atttggctg       39

<210> SEQ ID NO 330

-continued

```
<211> LENGTH: 39
<212> TYPE: DNA
<213> ORGANISM: Artificial Sequence
<220> FEATURE:
<223> OTHER INFORMATION: Synthetic Primer

<400> SEQUENCE: 330
cagccaaatc ttacacgcgg cgctgcgctt cagcgttgg                            39

<210> SEQ ID NO 331
<211> LENGTH: 39
<212> TYPE: DNA
<213> ORGANISM: Artificial Sequence
<220> FEATURE:
<223> OTHER INFORMATION: Synthetic Primer

<400> SEQUENCE: 331
tggctggatt ctgaggaggc ccaaaacgcg atcaagaaa                            39

<210> SEQ ID NO 332
<211> LENGTH: 39
<212> TYPE: DNA
<213> ORGANISM: Artificial Sequence
<220> FEATURE:
<223> OTHER INFORMATION: Synthetic Primer

<400> SEQUENCE: 332
tttcttgatc gcgttttggg cctcctcaga atccagcca                            39

<210> SEQ ID NO 333
<211> LENGTH: 39
<212> TYPE: DNA
<213> ORGANISM: Artificial Sequence
<220> FEATURE:
<223> OTHER INFORMATION: Synthetic Primer

<400> SEQUENCE: 333
atccagacct gcctggccgc cgacctgctg ttcatgcgc                            39

<210> SEQ ID NO 334
<211> LENGTH: 39
<212> TYPE: DNA
<213> ORGANISM: Artificial Sequence
<220> FEATURE:
<223> OTHER INFORMATION: Synthetic Primer

<400> SEQUENCE: 334
gcgcatgaac agcaggtcgg cggccaggca ggtctggat                            39

<210> SEQ ID NO 335
<211> LENGTH: 39
<212> TYPE: DNA
<213> ORGANISM: Artificial Sequence
<220> FEATURE:
<223> OTHER INFORMATION: Synthetic Primer

<400> SEQUENCE: 335
cgcttccgca ccaccacggc cgatgcgatg ggcatgaac                            39

<210> SEQ ID NO 336
<211> LENGTH: 39
<212> TYPE: DNA
<213> ORGANISM: Artificial Sequence
<220> FEATURE:
<223> OTHER INFORMATION: Synthetic Primer

<400> SEQUENCE: 336
```

-continued

```
gttcatgccc atcgcatcgg ccgtggtggt gcggaagcg                    39

<210> SEQ ID NO 337
<211> LENGTH: 39
<212> TYPE: DNA
<213> ORGANISM: Artificial Sequence
<220> FEATURE:
<223> OTHER INFORMATION: Synthetic Primer

<400> SEQUENCE: 337
accacgggcg atgcgatggc catgaacatg atcagcaag                    39

<210> SEQ ID NO 338
<211> LENGTH: 39
<212> TYPE: DNA
<213> ORGANISM: Artificial Sequence
<220> FEATURE:
<223> OTHER INFORMATION: Synthetic Primer

<400> SEQUENCE: 338
cttgctgatc atgttcatgg ccatcgcatc gcccgtggt                    39

<210> SEQ ID NO 339
<211> LENGTH: 39
<212> TYPE: DNA
<213> ORGANISM: Artificial Sequence
<220> FEATURE:
<223> OTHER INFORMATION: Synthetic Primer

<400> SEQUENCE: 339
atgaacatga tcagcaaggc cgtcgaatat agcctgaaa                    39

<210> SEQ ID NO 340
<211> LENGTH: 39
<212> TYPE: DNA
<213> ORGANISM: Artificial Sequence
<220> FEATURE:
<223> OTHER INFORMATION: Synthetic Primer

<400> SEQUENCE: 340
tttcaggcta tattcgacgg ccttgctgat catgttcat                    39

<210> SEQ ID NO 341
<211> LENGTH: 39
<212> TYPE: DNA
<213> ORGANISM: Artificial Sequence
<220> FEATURE:
<223> OTHER INFORMATION: Synthetic Primer

<400> SEQUENCE: 341
caaatggtgg aagaatatgc ctgggaggac atggaggtt                    39

<210> SEQ ID NO 342
<211> LENGTH: 39
<212> TYPE: DNA
<213> ORGANISM: Artificial Sequence
<220> FEATURE:
<223> OTHER INFORMATION: Synthetic Primer

<400> SEQUENCE: 342
aacctccatg tcctcccagg catattcttc caccatttg                    39

<210> SEQ ID NO 343
<211> LENGTH: 39
<212> TYPE: DNA
<213> ORGANISM: Artificial Sequence
<220> FEATURE:
```

<223> OTHER INFORMATION: Synthetic Primer

<400> SEQUENCE: 343
gaggttgtct ctgtgagcgc caactattgc accgacaag          39

<210> SEQ ID NO 344
<211> LENGTH: 39
<212> TYPE: DNA
<213> ORGANISM: Artificial Sequence
<220> FEATURE:
<223> OTHER INFORMATION: Synthetic Primer

<400> SEQUENCE: 344
cttgtcggtg caatagttgg cgctcacaga gacaacctc          39

<210> SEQ ID NO 345
<211> LENGTH: 39
<212> TYPE: DNA
<213> ORGANISM: Artificial Sequence
<220> FEATURE:
<223> OTHER INFORMATION: Synthetic Primer

<400> SEQUENCE: 345
gccattaact ggattgaggc tcgcggcaaa agcgtcgtg          39

<210> SEQ ID NO 346
<211> LENGTH: 39
<212> TYPE: DNA
<213> ORGANISM: Artificial Sequence
<220> FEATURE:
<223> OTHER INFORMATION: Synthetic Primer

<400> SEQUENCE: 346
cacgacgctt tgccgcgag cctcaatcca gttaatggc          39

<210> SEQ ID NO 347
<211> LENGTH: 39
<212> TYPE: DNA
<213> ORGANISM: Artificial Sequence
<220> FEATURE:
<223> OTHER INFORMATION: Synthetic Primer

<400> SEQUENCE: 347
aactggattg agggtcgcgc caaaagcgtc gtggcagaa          39

<210> SEQ ID NO 348
<211> LENGTH: 39
<212> TYPE: DNA
<213> ORGANISM: Artificial Sequence
<220> FEATURE:
<223> OTHER INFORMATION: Synthetic Primer

<400> SEQUENCE: 348
ttctgccacg acgcttttgg cgcgaccctc aatccagtt          39

<210> SEQ ID NO 349
<211> LENGTH: 39
<212> TYPE: DNA
<213> ORGANISM: Artificial Sequence
<220> FEATURE:
<223> OTHER INFORMATION: Synthetic Primer

<400> SEQUENCE: 349
gcagaagcga ccatcccagc cgacgtggtc cgtaaggtt          39

<210> SEQ ID NO 350

```
<211> LENGTH: 39
<212> TYPE: DNA
<213> ORGANISM: Artificial Sequence
<220> FEATURE:
<223> OTHER INFORMATION: Synthetic Primer

<400> SEQUENCE: 350
aaccttacgg accacgtcgg ctgggatggt cgcttctgc                                 39

<210> SEQ ID NO 351
<211> LENGTH: 39
<212> TYPE: DNA
<213> ORGANISM: Artificial Sequence
<220> FEATURE:
<223> OTHER INFORMATION: Synthetic Primer

<400> SEQUENCE: 351
atcgcgaaaa acctggtcgc cagcgcgatg gcgggcagc                                 39

<210> SEQ ID NO 352
<211> LENGTH: 39
<212> TYPE: DNA
<213> ORGANISM: Artificial Sequence
<220> FEATURE:
<223> OTHER INFORMATION: Synthetic Primer

<400> SEQUENCE: 352
gctgcccgcc atcgcgctgg cgaccaggtt tttcgcgat                                 39

<210> SEQ ID NO 353
<211> LENGTH: 39
<212> TYPE: DNA
<213> ORGANISM: Artificial Sequence
<220> FEATURE:
<223> OTHER INFORMATION: Synthetic Primer

<400> SEQUENCE: 353
gtcggcagcg cgatggcggc cagcgtgggt ggctttaac                                 39

<210> SEQ ID NO 354
<211> LENGTH: 39
<212> TYPE: DNA
<213> ORGANISM: Artificial Sequence
<220> FEATURE:
<223> OTHER INFORMATION: Synthetic Primer

<400> SEQUENCE: 354
gttaaagcca cccacgctgg ccgccatcgc gctgccgac                                 39

<210> SEQ ID NO 355
<211> LENGTH: 45
<212> TYPE: DNA
<213> ORGANISM: Artificial Sequence
<220> FEATURE:
<223> OTHER INFORMATION: Synthetic Primer

<400> SEQUENCE: 355
ggcagcgcga tggcggccag cgtggctgcc tttaacgcac atgca                          45

<210> SEQ ID NO 356
<211> LENGTH: 45
<212> TYPE: DNA
<213> ORGANISM: Artificial Sequence
<220> FEATURE:
<223> OTHER INFORMATION: Synthetic Primer

<400> SEQUENCE: 356
```
tgcatgtgcg ttaaaggcag ccacgctggc cgccatcgcg ctgcc                45

<210> SEQ ID NO 357
<211> LENGTH: 45
<212> TYPE: DNA
<213> ORGANISM: Artificial Sequence
<220> FEATURE:
<223> OTHER INFORMATION: Synthetic Primer

<400> SEQUENCE: 357
ggcagcgcga tggcggccag cgtggctggc tttaacgcac atgca                45

<210> SEQ ID NO 358
<211> LENGTH: 45
<212> TYPE: DNA
<213> ORGANISM: Artificial Sequence
<220> FEATURE:
<223> OTHER INFORMATION: Synthetic Primer

<400> SEQUENCE: 358
tgcatgtgcg ttaaagccag ccacgctggc cgccatcgcg ctgcc                45

<210> SEQ ID NO 359
<211> LENGTH: 45
<212> TYPE: DNA
<213> ORGANISM: Artificial Sequence
<220> FEATURE:
<223> OTHER INFORMATION: Synthetic Primer

<400> SEQUENCE: 359
ggcagcgcga tggcggccag cgtgggtgcc tttaacgcac atgca                45

<210> SEQ ID NO 360
<211> LENGTH: 45
<212> TYPE: DNA
<213> ORGANISM: Artificial Sequence
<220> FEATURE:
<223> OTHER INFORMATION: Synthetic Primer

<400> SEQUENCE: 360
tgcatgtgcg ttaaaggcac ccacgctggc cgccatcgcg ctgcc                45

<210> SEQ ID NO 361
<211> LENGTH: 45
<212> TYPE: DNA
<213> ORGANISM: Artificial Sequence
<220> FEATURE:
<223> OTHER INFORMATION: Synthetic Primer

<400> SEQUENCE: 361
ggcagcgcga tggcgggcag cgtggctgcc tttaacgcac atgca                45

<210> SEQ ID NO 362
<211> LENGTH: 45
<212> TYPE: DNA
<213> ORGANISM: Artificial Sequence
<220> FEATURE:
<223> OTHER INFORMATION: Synthetic Primer

<400> SEQUENCE: 362
tgcatgtgcg ttaaaggcag ccacgctgcc cgccatcgcg ctgcc                45

<210> SEQ ID NO 363
<211> LENGTH: 39
<212> TYPE: DNA
<213> ORGANISM: Artificial Sequence
<220> FEATURE:

<223> OTHER INFORMATION: Synthetic Primer

<400> SEQUENCE: 363
gcgatggcgg gcagcgtggc tggctttaac gcacatgca                                    39

<210> SEQ ID NO 364
<211> LENGTH: 39
<212> TYPE: DNA
<213> ORGANISM: Artificial Sequence
<220> FEATURE:
<223> OTHER INFORMATION: Synthetic Primer

<400> SEQUENCE: 364
tgcatgtgcg ttaaagccag ccacgctgcc cgccatcgc                                    39

<210> SEQ ID NO 365
<211> LENGTH: 39
<212> TYPE: DNA
<213> ORGANISM: Artificial Sequence
<220> FEATURE:
<223> OTHER INFORMATION: Synthetic Primer

<400> SEQUENCE: 365
atggcgggca gcgtgggtgc ctttaacgca catgcagcg                                    39

<210> SEQ ID NO 366
<211> LENGTH: 39
<212> TYPE: DNA
<213> ORGANISM: Artificial Sequence
<220> FEATURE:
<223> OTHER INFORMATION: Synthetic Primer

<400> SEQUENCE: 366
cgctgcatgt gcgttaaagg cacccacgct gcccgccat                                    39

<210> SEQ ID NO 367
<211> LENGTH: 39
<212> TYPE: DNA
<213> ORGANISM: Artificial Sequence
<220> FEATURE:
<223> OTHER INFORMATION: Synthetic Primer

<400> SEQUENCE: 367 gcggtttttct tagccttagc tcaggaccca gcccaaaat                                   39

<210> SEQ ID NO 368
<211> LENGTH: 39
<212> TYPE: DNA
<213> ORGANISM: Artificial Sequence
<220> FEATURE:
<223> OTHER INFORMATION: Synthetic Primer

<400> SEQUENCE: 368
attttgggct gggtcctgag ctaaggctaa gaaaaccgc                                    39

<210> SEQ ID NO 369
<211> LENGTH: 39
<212> TYPE: DNA
<213> ORGANISM: Artificial Sequence
<220> FEATURE:
<223> OTHER INFORMATION: Synthetic Primer

<400> SEQUENCE: 369
ttaatgaaag aggttgacgc tgacctgcgc atcagcgtt                                    39

<210> SEQ ID NO 370

```
<211> LENGTH: 39
<212> TYPE: DNA
<213> ORGANISM: Artificial Sequence
<220> FEATURE:
<223> OTHER INFORMATION: Synthetic Primer

<400> SEQUENCE: 370
aacgctgatg cgcaggtcag cgtcaacctc tttcattaa                              39

<210> SEQ ID NO 371
<211> LENGTH: 39
<212> TYPE: DNA
<213> ORGANISM: Artificial Sequence
<220> FEATURE:
<223> OTHER INFORMATION: Synthetic Primer

<400> SEQUENCE: 371
atgccgtcta tcgaggtcgc cacgatcggc ggcggcacc                              39

<210> SEQ ID NO 372
<211> LENGTH: 39
<212> TYPE: DNA
<213> ORGANISM: Artificial Sequence
<220> FEATURE:
<223> OTHER INFORMATION: Synthetic Primer

<400> SEQUENCE: 372
ggtgccgccg ccgatcgtgg cgacctcgat agacggcat                              39

<210> SEQ ID NO 373
<211> LENGTH: 39
<212> TYPE: DNA
<213> ORGANISM: Artificial Sequence
<220> FEATURE:
<223> OTHER INFORMATION: Synthetic Primer

<400> SEQUENCE: 373
atcgaggtcg gcacgatcgc cggcggcacc gttttagaa                              39

<210> SEQ ID NO 374
<211> LENGTH: 39
<212> TYPE: DNA
<213> ORGANISM: Artificial Sequence
<220> FEATURE:
<223> OTHER INFORMATION: Synthetic Primer

<400> SEQUENCE: 374
ttctaaaacg gtgccgccgg cgatcgtgcc gacctcgat                              39

<210> SEQ ID NO 375
<211> LENGTH: 39
<212> TYPE: DNA
<213> ORGANISM: Artificial Sequence
<220> FEATURE:
<223> OTHER INFORMATION: Synthetic Primer

<400> SEQUENCE: 375
gaggtcggca cgatcggcgc cggcaccgtt ttagaaccg                              39

<210> SEQ ID NO 376
<211> LENGTH: 39
<212> TYPE: DNA
<213> ORGANISM: Artificial Sequence
<220> FEATURE:
<223> OTHER INFORMATION: Synthetic Primer

<400> SEQUENCE: 376
```

```
cggttctaaa acggtgccgg cgccgatcgt gccgacctc              39
```

<210> SEQ ID NO 377
<211> LENGTH: 39
<212> TYPE: DNA
<213> ORGANISM: Artificial Sequence
<220> FEATURE:
<223> OTHER INFORMATION: Synthetic Primer

<400> SEQUENCE: 377

```
gtcggcacga tcggcggcgc caccgtttta gaaccgcaa              39
```

<210> SEQ ID NO 378
<211> LENGTH: 39
<212> TYPE: DNA
<213> ORGANISM: Artificial Sequence
<220> FEATURE:
<223> OTHER INFORMATION: Synthetic Primer

<400> SEQUENCE: 378

```
ttgcggttct aaaacggtgg cgccgccgat cgtgccgac              39
```

<210> SEQ ID NO 379
<211> LENGTH: 39
<212> TYPE: DNA
<213> ORGANISM: Artificial Sequence
<220> FEATURE:
<223> OTHER INFORMATION: Synthetic Primer

<400> SEQUENCE: 379

```
accgttttag aaccgcaagc tgcgatgctg gatctgctg              39
```

<210> SEQ ID NO 380
<211> LENGTH: 39
<212> TYPE: DNA
<213> ORGANISM: Artificial Sequence
<220> FEATURE:
<223> OTHER INFORMATION: Synthetic Primer

<400> SEQUENCE: 380

```
cagcagatcc agcatcgcag cttgcggttc taaaacggt              39
```

<210> SEQ ID NO 381
<211> LENGTH: 39
<212> TYPE: DNA
<213> ORGANISM: Artificial Sequence
<220> FEATURE:
<223> OTHER INFORMATION: Synthetic Primer

<400> SEQUENCE: 381

```
gcgatgctgg atctgctggc cgtgcgcggc ccacatgca              39
```

<210> SEQ ID NO 382
<211> LENGTH: 39
<212> TYPE: DNA
<213> ORGANISM: Artificial Sequence
<220> FEATURE:
<223> OTHER INFORMATION: Synthetic Primer

<400> SEQUENCE: 382

```
tgcatgtggg ccgcgcacgg ccagcagatc cagcatcgc              39
```

<210> SEQ ID NO 383
<211> LENGTH: 39
<212> TYPE: DNA
<213> ORGANISM: Artificial Sequence
<220> FEATURE:

<223> OTHER INFORMATION: Synthetic Primer

<400> SEQUENCE: 383
gatctgctgg gcgtgcgcgc cccacatgca acggcccca         39

<210> SEQ ID NO 384
<211> LENGTH: 39
<212> TYPE: DNA
<213> ORGANISM: Artificial Sequence
<220> FEATURE:
<223> OTHER INFORMATION: Synthetic Primer

<400> SEQUENCE: 384
tggggccgtt gcatgtgggg cgcgcacgcc cagcagatc         39

<210> SEQ ID NO 385
<211> LENGTH: 39
<212> TYPE: DNA
<213> ORGANISM: Artificial Sequence
<220> FEATURE:
<223> OTHER INFORMATION: Synthetic Primer

<400> SEQUENCE: 385
ccacatgcaa cggccccagc caccaatgcc cgccaactg         39

<210> SEQ ID NO 386
<211> LENGTH: 39
<212> TYPE: DNA
<213> ORGANISM: Artificial Sequence
<220> FEATURE:
<223> OTHER INFORMATION: Synthetic Primer

<400> SEQUENCE: 386
cagttggcgg gcattggtgg ctggggccgt tgcatgtgg         39

<210> SEQ ID NO 387
<211> LENGTH: 39
<212> TYPE: DNA
<213> ORGANISM: Artificial Sequence
<220> FEATURE:
<223> OTHER INFORMATION: Synthetic Primer

<400> SEQUENCE: 387
gcctgcgcgg ttctggcggc tgagctgagc ctgtgcgcc         39

<210> SEQ ID NO 388
<211> LENGTH: 39
<212> TYPE: DNA
<213> ORGANISM: Artificial Sequence
<220> FEATURE:
<223> OTHER INFORMATION: Synthetic Primer

<400> SEQUENCE: 388
ggcgcacagg ctcagctcag ccgccagaac cgcgcaggc         39

<210> SEQ ID NO 389
<211> LENGTH: 39
<212> TYPE: DNA
<213> ORGANISM: Artificial Sequence
<220> FEATURE:
<223> OTHER INFORMATION: Synthetic Primer

<400> SEQUENCE: 389
tgcgccgcat tagccgcggc ccatttagtt caatctcac         39

<210> SEQ ID NO 390

<211> LENGTH: 39
<212> TYPE: DNA
<213> ORGANISM: Artificial Sequence
<220> FEATURE:
<223> OTHER INFORMATION: Synthetic Primer

<400> SEQUENCE: 390
gtgagattga actaaatggg ccgcggctaa tgcggcgca                        39

<210> SEQ ID NO 391
<211> LENGTH: 39
<212> TYPE: DNA
<213> ORGANISM: Artificial Sequence
<220> FEATURE:
<223> OTHER INFORMATION: Synthetic Primer

<400> SEQUENCE: 391
attaaccgtc tgaaggatgc cagcgtcacg tgcattaaa                        39

<210> SEQ ID NO 392
<211> LENGTH: 39
<212> TYPE: DNA
<213> ORGANISM: Artificial Sequence
<220> FEATURE:
<223> OTHER INFORMATION: Synthetic Primer

<400> SEQUENCE: 392
tttaatgcac gtgacgctgg catccttcag acggttaat                        39

<210> SEQ ID NO 393
<211> LENGTH: 33
<212> TYPE: DNA
<213> ORGANISM: Artificial Sequence
<220> FEATURE:
<223> OTHER INFORMATION: Synthetic Primer

<400> SEQUENCE: 393
ggcgatacga cgcgtggggt cgcggtgcgt cgc                              33

<210> SEQ ID NO 394
<211> LENGTH: 33
<212> TYPE: DNA
<213> ORGANISM: Artificial Sequence
<220> FEATURE:
<223> OTHER INFORMATION: Synthetic Primer

<400> SEQUENCE: 394
gcgacgcacc gcgaccccac gcgtcgtatc gcc                              33

<210> SEQ ID NO 395
<211> LENGTH: 33
<212> TYPE: DNA
<213> ORGANISM: Artificial Sequence
<220> FEATURE:
<223> OTHER INFORMATION: Synthetic Primer

<400> SEQUENCE: 395
tctacgagcc gtttcgggcg tttacagcat atc                              33

<210> SEQ ID NO 396
<211> LENGTH: 33
<212> TYPE: DNA
<213> ORGANISM: Artificial Sequence
<220> FEATURE:
<223> OTHER INFORMATION: Synthetic Primer

<400> SEQUENCE: 396

-continued gatatgctgt aaacgcccga aacggctcgt aga          33

<210> SEQ ID NO 397
<211> LENGTH: 33
<212> TYPE: DNA
<213> ORGANISM: Artificial Sequence
<220> FEATURE:
<223> OTHER INFORMATION: Synthetic Primer

<400> SEQUENCE: 397
gcagcgaatc tggttggggc ggttttctta gcc          33

<210> SEQ ID NO 398
<211> LENGTH: 33
<212> TYPE: DNA
<213> ORGANISM: Artificial Sequence
<220> FEATURE:
<223> OTHER INFORMATION: Synthetic Primer

<400> SEQUENCE: 398
ggctaagaaa accgccccaa ccagattcgc tgc          33

<210> SEQ ID NO 399
<211> LENGTH: 33
<212> TYPE: DNA
<213> ORGANISM: Artificial Sequence
<220> FEATURE:
<223> OTHER INFORMATION: Synthetic Primer

<400> SEQUENCE: 399
ccagcccaaa atgtcgggag cagcaactgc att          33

<210> SEQ ID NO 400
<211> LENGTH: 33
<212> TYPE: DNA
<213> ORGANISM: Artificial Sequence
<220> FEATURE:
<223> OTHER INFORMATION: Synthetic Primer

<400> SEQUENCE: 400
aatgcagttg ctgctcccga cattttgggc tgg          33

<210> SEQ ID NO 401
<211> LENGTH: 33
<212> TYPE: DNA
<213> ORGANISM: Artificial Sequence
<220> FEATURE:
<223> OTHER INFORMATION: Synthetic Primer

<400> SEQUENCE: 401
gcccaaaatg tcgagggcag caactgcatt acc          33

<210> SEQ ID NO 402
<211> LENGTH: 33
<212> TYPE: DNA
<213> ORGANISM: Artificial Sequence
<220> FEATURE:
<223> OTHER INFORMATION: Synthetic Primer

<400> SEQUENCE: 402
ggtaatgcag ttgctgccct cgacattttg ggc          33

<210> SEQ ID NO 403
<211> LENGTH: 33
<212> TYPE: DNA
<213> ORGANISM: Artificial Sequence
<220> FEATURE:

<223> OTHER INFORMATION: Synthetic Primer

<400> SEQUENCE: 403
gtcgagagca gcaacggcat taccttaatg aaa          33

<210> SEQ ID NO 404
<211> LENGTH: 33
<212> TYPE: DNA
<213> ORGANISM: Artificial Sequence
<220> FEATURE:
<223> OTHER INFORMATION: Synthetic Primer

<400> SEQUENCE: 404
tttcattaag gtaatgccgt tgctgctctc gac          33

<210> SEQ ID NO 405
<211> LENGTH: 33
<212> TYPE: DNA
<213> ORGANISM: Artificial Sequence
<220> FEATURE:
<223> OTHER INFORMATION: Synthetic Primer

<400> SEQUENCE: 405
ctgggcgtgc gcggcggaca tgcaacggcc cca          33

<210> SEQ ID NO 406
<211> LENGTH: 33
<212> TYPE: DNA
<213> ORGANISM: Artificial Sequence
<220> FEATURE:
<223> OTHER INFORMATION: Synthetic Primer

<400> SEQUENCE: 406
tggggccgtt gcatgtccgc cgcgcacgcc cag          33

<210> SEQ ID NO 407
<211> LENGTH: 33
<212> TYPE: DNA
<213> ORGANISM: Artificial Sequence
<220> FEATURE:
<223> OTHER INFORMATION: Synthetic Primer

<400> SEQUENCE: 407
gtgcgcggcc cacatggaac ggccccaggc acc          33

<210> SEQ ID NO 408
<211> LENGTH: 33
<212> TYPE: DNA
<213> ORGANISM: Artificial Sequence
<220> FEATURE:
<223> OTHER INFORMATION: Synthetic Primer

<400> SEQUENCE: 408
ggtgcctggg gccgttccat gtgggccgcg cac          33

<210> SEQ ID NO 409
<211> LENGTH: 33
<212> TYPE: DNA
<213> ORGANISM: Artificial Sequence
<220> FEATURE:
<223> OTHER INFORMATION: Synthetic Primer

<400> SEQUENCE: 409
gcccgtatcg tggccggcgc ggttctggcg ggt          33

<210> SEQ ID NO 410

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 410
acccgccaga accgcgccgg ccacgatacg ggc                                    33

<210> SEQ ID NO 411
<211> LENGTH: 33
<212> TYPE: DNA
<213> ORGANISM: Artificial Sequence
<220> FEATURE:
<223> OTHER INFORMATION: Synthetic Primer

<400> SEQUENCE: 411
aaccgcaagc cggcaggacc aaccaagcca aat                                    33

<210> SEQ ID NO 412
<211> LENGTH: 33
<212> TYPE: DNA
<213> ORGANISM: Artificial Sequence
<220> FEATURE:
<223> OTHER INFORMATION: Synthetic Primer

<400> SEQUENCE: 412
atttggcttg gttggtcctg ccggcttgcg gtt                                    33

<210> SEQ ID NO 413
<211> LENGTH: 33
<212> TYPE: DNA
<213> ORGANISM: Artificial Sequence
<220> FEATURE:
<223> OTHER INFORMATION: Synthetic Primer

<400> SEQUENCE: 413
ttaagcatct tagcgggggc cccggtgtta gcc                                    33

<210> SEQ ID NO 414
<211> LENGTH: 33
<212> TYPE: DNA
<213> ORGANISM: Artificial Sequence
<220> FEATURE:
<223> OTHER INFORMATION: Synthetic Primer

<400> SEQUENCE: 414
ggctaacacc ggggcccccg ctaagatgct taa                                    33

<210> SEQ ID NO 415
<211> LENGTH: 33
<212> TYPE: DNA
<213> ORGANISM: Artificial Sequence
<220> FEATURE:
<223> OTHER INFORMATION: Synthetic Primer

<400> SEQUENCE: 415
gccagcgacc gcctggggta caagaactac gac                                    33

<210> SEQ ID NO 416
<211> LENGTH: 33
<212> TYPE: DNA
<213> ORGANISM: Artificial Sequence
<220> FEATURE:
<223> OTHER INFORMATION: Synthetic Primer

<400> SEQUENCE: 416
```

```
gtcgtagttc ttgtaccoca ggcggtcgct ggc                                33
```

<210> SEQ ID NO 417
<211> LENGTH: 33
<212> TYPE: DNA
<213> ORGANISM: Artificial Sequence
<220> FEATURE:
<223> OTHER INFORMATION: Synthetic Primer

<400> SEQUENCE: 417

```
aaagaggttg acggtggcct gcgcatcagc gtt                                33
```

<210> SEQ ID NO 418
<211> LENGTH: 33
<212> TYPE: DNA
<213> ORGANISM: Artificial Sequence
<220> FEATURE:
<223> OTHER INFORMATION: Synthetic Primer

<400> SEQUENCE: 418

```
aacgctgatg cgcaggccac cgtcaacctc ttt                                33
```

<210> SEQ ID NO 419
<211> LENGTH: 33
<212> TYPE: DNA
<213> ORGANISM: Artificial Sequence
<220> FEATURE:
<223> OTHER INFORMATION: Synthetic Primer

<400> SEQUENCE: 419

```
atcggcggcg gcaccggttt agaaccgcaa ggt                                33
```

<210> SEQ ID NO 420
<211> LENGTH: 33
<212> TYPE: DNA
<213> ORGANISM: Artificial Sequence
<220> FEATURE:
<223> OTHER INFORMATION: Synthetic Primer

<400> SEQUENCE: 420

```
accttgcggt tctaaaccgg tgccgccgcc gat                                33
```

<210> SEQ ID NO 421
<211> LENGTH: 33
<212> TYPE: DNA
<213> ORGANISM: Artificial Sequence
<220> FEATURE:
<223> OTHER INFORMATION: Synthetic Primer

<400> SEQUENCE: 421

```
cgtatcgtgg cctgcggggt tctggcgggt gag                                33
```

<210> SEQ ID NO 422
<211> LENGTH: 33
<212> TYPE: DNA
<213> ORGANISM: Artificial Sequence
<220> FEATURE:
<223> OTHER INFORMATION: Synthetic Primer

<400> SEQUENCE: 422

```
ctcacccgcc agaaccccgc aggccacgat acg                                33
```

<210> SEQ ID NO 423
<211> LENGTH: 33
<212> TYPE: DNA
<213> ORGANISM: Artificial Sequence
<220> FEATURE:

<223> OTHER INFORMATION: Synthetic Primer

<400> SEQUENCE: 423
gagctgagcc tgtgcggcgc attagccgcg ggc						33

<210> SEQ ID NO 424
<211> LENGTH: 33
<212> TYPE: DNA
<213> ORGANISM: Artificial Sequence
<220> FEATURE:
<223> OTHER INFORMATION: Synthetic Primer

<400> SEQUENCE: 424
gcccgcggct aatgcgccgc acaggctcag ctc						33

<210> SEQ ID NO 425
<211> LENGTH: 33
<212> TYPE: DNA
<213> ORGANISM: Artificial Sequence
<220> FEATURE:
<223> OTHER INFORMATION: Synthetic Primer

<400> SEQUENCE: 425
tctcacatga cccacggccg caagccggca gaa						33

<210> SEQ ID NO 426
<211> LENGTH: 33
<212> TYPE: DNA
<213> ORGANISM: Artificial Sequence
<220> FEATURE:
<223> OTHER INFORMATION: Synthetic Primer

<400> SEQUENCE: 426
ttctgccggc ttgcggccgt gggtcatgtg aga						33

<210> SEQ ID NO 427
<211> LENGTH: 33
<212> TYPE: DNA
<213> ORGANISM: Artificial Sequence
<220> FEATURE:
<223> OTHER INFORMATION: Synthetic Primer

<400> SEQUENCE: 427
atgacccaca accgcgggcc ggcagaacca acc						33

<210> SEQ ID NO 428
<211> LENGTH: 33
<212> TYPE: DNA
<213> ORGANISM: Artificial Sequence
<220> FEATURE:
<223> OTHER INFORMATION: Synthetic Primer

<400> SEQUENCE: 428
ggttggttct gccggcccgc ggttgtgggt cat						33

<210> SEQ ID NO 429
<211> LENGTH: 36
<212> TYPE: DNA
<213> ORGANISM: Artificial Sequence
<220> FEATURE:
<223> OTHER INFORMATION: Synthetic Primer

<400> SEQUENCE: 429
ccagcccaaa atgtcggggg cagcaactgc attacc					36

<210> SEQ ID NO 430

```
<211> LENGTH: 36
<212> TYPE: DNA
<213> ORGANISM: Artificial Sequence
<220> FEATURE:
<223> OTHER INFORMATION: Synthetic Primer

<400> SEQUENCE: 430
ggtaatgcag ttgctgcccc cgacattttg ggctgg                                  36

<210> SEQ ID NO 431
<211> LENGTH: 45
<212> TYPE: DNA
<213> ORGANISM: Artificial Sequence
<220> FEATURE:
<223> OTHER INFORMATION: Synthetic Primer

<400> SEQUENCE: 431
ccagcccaaa atgtcgggag cagcaacggc attaccttaa tgaaa                        45

<210> SEQ ID NO 432
<211> LENGTH: 45
<212> TYPE: DNA
<213> ORGANISM: Artificial Sequence
<220> FEATURE:
<223> OTHER INFORMATION: Synthetic Primer

<400> SEQUENCE: 432
tttcattaag gtaatgccgt tgctgctccc gacattttgg gctgg                        45

<210> SEQ ID NO 433
<211> LENGTH: 42
<212> TYPE: DNA
<213> ORGANISM: Artificial Sequence
<220> FEATURE:
<223> OTHER INFORMATION: Synthetic Primer

<400> SEQUENCE: 433
gcccaaaatg tcgagggcag caacggcatt accttaatga aa                           42

<210> SEQ ID NO 434
<211> LENGTH: 42
<212> TYPE: DNA
<213> ORGANISM: Artificial Sequence
<220> FEATURE:
<223> OTHER INFORMATION: Synthetic Primer

<400> SEQUENCE: 434
tttcattaag gtaatgccgt tgctgccctc gacattttgg gc                           42

<210> SEQ ID NO 435
<211> LENGTH: 45
<212> TYPE: DNA
<213> ORGANISM: Artificial Sequence
<220> FEATURE:
<223> OTHER INFORMATION: Synthetic Primer

<400> SEQUENCE: 435
ccagcccaaa atgtcgggggg cagcaacggc attaccttaa tgaaa                       45

<210> SEQ ID NO 436
<211> LENGTH: 45
<212> TYPE: DNA
<213> ORGANISM: Artificial Sequence
<220> FEATURE:
<223> OTHER INFORMATION: Synthetic Primer

<400> SEQUENCE: 436
```

-continued

```
tttcattaag gtaatgccgt tgctgccccc gacattttgg gctgg         45
```

<210> SEQ ID NO 437
<211> LENGTH: 39
<212> TYPE: DNA
<213> ORGANISM: Artificial Sequence
<220> FEATURE:
<223> OTHER INFORMATION: Synthetic Primer

<400> SEQUENCE: 437

```
ctgggcgtgc gcggcggaca tggaacggcc ccaggcacc              39
```

<210> SEQ ID NO 438
<211> LENGTH: 39
<212> TYPE: DNA
<213> ORGANISM: Artificial Sequence
<220> FEATURE:
<223> OTHER INFORMATION: Synthetic Primer

<400> SEQUENCE: 438

```
ggtgcctggg gccgttccat gtccgccgcg cacgcccag              39
```

<210> SEQ ID NO 439
<211> LENGTH: 36
<212> TYPE: DNA
<213> ORGANISM: Artificial Sequence
<220> FEATURE:
<223> OTHER INFORMATION: Synthetic Primer

<400> SEQUENCE: 439

```
gcccgtatcg tggccggcgg ggttctggcg ggtgag                 36
```

<210> SEQ ID NO 440
<211> LENGTH: 36
<212> TYPE: DNA
<213> ORGANISM: Artificial Sequence
<220> FEATURE:
<223> OTHER INFORMATION: Synthetic Primer

<400> SEQUENCE: 440

```
ctcacccgcc agaacccgc cggccacgat acgggc                  36
```

<210> SEQ ID NO 441
<211> LENGTH: 33
<212> TYPE: DNA
<213> ORGANISM: Artificial Sequence
<220> FEATURE:
<223> OTHER INFORMATION: Synthetic Primer

<400> SEQUENCE: 441

```
atcggcggcg gcaccggttt agaaccgcaa gct                    33
```

<210> SEQ ID NO 442
<211> LENGTH: 33
<212> TYPE: DNA
<213> ORGANISM: Artificial Sequence
<220> FEATURE:
<223> OTHER INFORMATION: Synthetic Primer

<400> SEQUENCE: 442

```
agcttgcggt tctaaaccgg tgccgccgcc gat                    33
```

<210> SEQ ID NO 443
<211> LENGTH: 39
<212> TYPE: DNA
<213> ORGANISM: Artificial Sequence
<220> FEATURE:

```
<223> OTHER INFORMATION: Synthetic Primer

<400> SEQUENCE: 443
tctcacatga cccacggccg cgggccggca gaaccaacc                    39

<210> SEQ ID NO 444
<211> LENGTH: 39
<212> TYPE: DNA
<213> ORGANISM: Artificial Sequence
<220> FEATURE:
<223> OTHER INFORMATION: Synthetic Primer

<400> SEQUENCE: 444
ggttggttct gccggcccgc ggccgtgggt catgtgaga                    39

<210> SEQ ID NO 445
<211> LENGTH: 33
<212> TYPE: DNA
<213> ORGANISM: Artificial Sequence
<220> FEATURE:
<223> OTHER INFORMATION: Synthetic Primer

<400> SEQUENCE: 445
agctctagca gcggcgcgtc tagcagcagc gag                          33

<210> SEQ ID NO 446
<211> LENGTH: 33
<212> TYPE: DNA
<213> ORGANISM: Artificial Sequence
<220> FEATURE:
<223> OTHER INFORMATION: Synthetic Primer

<400> SEQUENCE: 446
ctcgctgctg ctagacgcgc cgctgctaga gct                          33

<210> SEQ ID NO 447
<211> LENGTH: 33
<212> TYPE: DNA
<213> ORGANISM: Artificial Sequence
<220> FEATURE:
<223> OTHER INFORMATION: Synthetic Primer

<400> SEQUENCE: 447
gacaagaaga tccgcgcgct ggaggagtta gag                          33

<210> SEQ ID NO 448
<211> LENGTH: 33
<212> TYPE: DNA
<213> ORGANISM: Artificial Sequence
<220> FEATURE:
<223> OTHER INFORMATION: Synthetic Primer

<400> SEQUENCE: 448
ctctaactcc tccagcgcgc ggatcttctt gtc                          33

<210> SEQ ID NO 449
<211> LENGTH: 33
<212> TYPE: DNA
<213> ORGANISM: Artificial Sequence
<220> FEATURE:
<223> OTHER INFORMATION: Synthetic Primer

<400> SEQUENCE: 449
atccacggta agctggcact gtatgcgctg gaa                          33

<210> SEQ ID NO 450
```

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 450
ttccagcgca tacagtgcca gcttaccgtg gat                                    33

<210> SEQ ID NO 451
<211> LENGTH: 33
<212> TYPE: DNA
<213> ORGANISM: Artificial Sequence
<220> FEATURE:
<223> OTHER INFORMATION: Synthetic Primer

<400> SEQUENCE: 451
atcttagcgg aggccgcggt gttagccagc gac                                    33

<210> SEQ ID NO 452
<211> LENGTH: 33
<212> TYPE: DNA
<213> ORGANISM: Artificial Sequence
<220> FEATURE:
<223> OTHER INFORMATION: Synthetic Primer

<400> SEQUENCE: 452
gtcgctggct aacaccgcgg cctccgctaa gat                                    33

<210> SEQ ID NO 453
<211> LENGTH: 33
<212> TYPE: DNA
<213> ORGANISM: Artificial Sequence
<220> FEATURE:
<223> OTHER INFORMATION: Synthetic Primer

<400> SEQUENCE: 453
gccagcgacc gcctggcgta caagaactac gac                                    33

<210> SEQ ID NO 454
<211> LENGTH: 33
<212> TYPE: DNA
<213> ORGANISM: Artificial Sequence
<220> FEATURE:
<223> OTHER INFORMATION: Synthetic Primer

<400> SEQUENCE: 454
gtcgtagttc ttgtacgcca ggcggtcgct ggc                                    33

<210> SEQ ID NO 455
<211> LENGTH: 33
<212> TYPE: DNA
<213> ORGANISM: Artificial Sequence
<220> FEATURE:
<223> OTHER INFORMATION: Synthetic Primer

<400> SEQUENCE: 455
gtcattggct acatggcgtt accggttggt gtg                                    33

<210> SEQ ID NO 456
<211> LENGTH: 33
<212> TYPE: DNA
<213> ORGANISM: Artificial Sequence
<220> FEATURE:
<223> OTHER INFORMATION: Synthetic Primer

<400> SEQUENCE: 456
```

```
cacaccaacc ggtaacgcca tgtagccaat gac                                33
```

<210> SEQ ID NO 457
<211> LENGTH: 33
<212> TYPE: DNA
<213> ORGANISM: Artificial Sequence
<220> FEATURE:
<223> OTHER INFORMATION: Synthetic Primer

<400> SEQUENCE: 457

```
ggctacatgc cgttagcggt tggtgtgatc ggc                                33
```

<210> SEQ ID NO 458
<211> LENGTH: 33
<212> TYPE: DNA
<213> ORGANISM: Artificial Sequence
<220> FEATURE:
<223> OTHER INFORMATION: Synthetic Primer

<400> SEQUENCE: 458

```
gccgatcaca ccaaccgcta acggcatgta gcc                                33
```

<210> SEQ ID NO 459
<211> LENGTH: 33
<212> TYPE: DNA
<213> ORGANISM: Artificial Sequence
<220> FEATURE:
<223> OTHER INFORMATION: Synthetic Primer

<400> SEQUENCE: 459

```
gttggtgtga tcggcgcgct ggtcattgat ggc                                33
```

<210> SEQ ID NO 460
<211> LENGTH: 33
<212> TYPE: DNA
<213> ORGANISM: Artificial Sequence
<220> FEATURE:
<223> OTHER INFORMATION: Synthetic Primer

<400> SEQUENCE: 460

```
gccatcaatg accagcgcgc cgatcacacc aac                                33
```

<210> SEQ ID NO 461
<211> LENGTH: 33
<212> TYPE: DNA
<213> ORGANISM: Artificial Sequence
<220> FEATURE:
<223> OTHER INFORMATION: Synthetic Primer

<400> SEQUENCE: 461

```
acgagctatc acattgcaat ggcgaccacg gaa                                33
```

<210> SEQ ID NO 462
<211> LENGTH: 33
<212> TYPE: DNA
<213> ORGANISM: Artificial Sequence
<220> FEATURE:
<223> OTHER INFORMATION: Synthetic Primer

<400> SEQUENCE: 462

```
ttccgtggtc gccattgcaa tgtgatagct cgt                                33
```

<210> SEQ ID NO 463
<211> LENGTH: 33
<212> TYPE: DNA
<213> ORGANISM: Artificial Sequence
<220> FEATURE:

<223> OTHER INFORMATION: Synthetic Primer

<400> SEQUENCE: 463
ggtatgacgc gcggtgcggt cgtccgcttc cca                          33

<210> SEQ ID NO 464
<211> LENGTH: 33
<212> TYPE: DNA
<213> ORGANISM: Artificial Sequence
<220> FEATURE:
<223> OTHER INFORMATION: Synthetic Primer

<400> SEQUENCE: 464
tgggaagcgg acgaccgcac cgcgcgtcat acc                          33

<210> SEQ ID NO 465
<211> LENGTH: 45
<212> TYPE: DNA
<213> ORGANISM: Artificial Sequence
<220> FEATURE:
<223> OTHER INFORMATION: Synthetic Primer

<400> SEQUENCE: 465
ggatggtatg acgcgcggtg cggtcgtccg cttcgcaacg ctgaa             45

<210> SEQ ID NO 466
<211> LENGTH: 41
<212> TYPE: DNA
<213> ORGANISM: Artificial Sequence
<220> FEATURE:
<223> OTHER INFORMATION: Synthetic Primer

<400> SEQUENCE: 466
gctgcgcttc agcgttgcga agcggacgac cgcaccgcgc g                 41

<210> SEQ ID NO 467
<211> LENGTH: 28
<212> TYPE: DNA
<213> ORGANISM: Artificial Sequence
<220> FEATURE:
<223> OTHER INFORMATION: Synthetic Primer

<400> SEQUENCE: 467
cggtccggtc gtccgcttcg caacgctg                                28

<210> SEQ ID NO 468
<211> LENGTH: 28
<212> TYPE: DNA
<213> ORGANISM: Artificial Sequence
<220> FEATURE:
<223> OTHER INFORMATION: Synthetic Primer

<400> SEQUENCE: 468
ccgctgcgct tcagcgttgc gaagcgga                                28

<210> SEQ ID NO 469
<211> LENGTH: 28
<212> TYPE: DNA
<213> ORGANISM: Artificial Sequence
<220> FEATURE:
<223> OTHER INFORMATION: Synthetic Primer

<400> SEQUENCE: 469
ctattgcagc gacaagaagg cggcagcc                                28

<210> SEQ ID NO 470

```
<211> LENGTH: 28
<212> TYPE: DNA
<213> ORGANISM: Artificial Sequence
<220> FEATURE:
<223> OTHER INFORMATION: Synthetic Primer

<400> SEQUENCE: 470
atccagttaa tggctgccgc cttcttgt                                      28

<210> SEQ ID NO 471
<211> LENGTH: 33
<212> TYPE: DNA
<213> ORGANISM: Artificial Sequence
<220> FEATURE:
<223> OTHER INFORMATION: Synthetic Primer

<400> SEQUENCE: 471
gcagaagcga ccatcgcagg cgacgtggtc cgt                                33

<210> SEQ ID NO 472
<211> LENGTH: 33
<212> TYPE: DNA
<213> ORGANISM: Artificial Sequence
<220> FEATURE:
<223> OTHER INFORMATION: Synthetic Primer

<400> SEQUENCE: 472
acggaccacg tcgcctgcga tggtcgcttc tgc                                33

<210> SEQ ID NO 473
<211> LENGTH: 33
<212> TYPE: DNA
<213> ORGANISM: Artificial Sequence
<220> FEATURE:
<223> OTHER INFORMATION: Synthetic Primer

<400> SEQUENCE: 473
gccttaggtc aggacgcagc ccaaaatgtc gag                                33

<210> SEQ ID NO 474
<211> LENGTH: 33
<212> TYPE: DNA
<213> ORGANISM: Artificial Sequence
<220> FEATURE:
<223> OTHER INFORMATION: Synthetic Primer

<400> SEQUENCE: 474
ctcgacattt tgggctgcgt cctgacctaa ggc                                33

<210> SEQ ID NO 475
<211> LENGTH: 33
<212> TYPE: DNA
<213> ORGANISM: Artificial Sequence
<220> FEATURE:
<223> OTHER INFORMATION: Synthetic Primer

<400> SEQUENCE: 475
atcagcgttt ctatggcgtc tatcgaggtc ggc                                33

<210> SEQ ID NO 476
<211> LENGTH: 33
<212> TYPE: DNA
<213> ORGANISM: Artificial Sequence
<220> FEATURE:
<223> OTHER INFORMATION: Synthetic Primer

<400> SEQUENCE: 476
```

```
gccgacctcg atagacgcca tagaaacgct gat                                      33

<210> SEQ ID NO 477
<211> LENGTH: 33
<212> TYPE: DNA
<213> ORGANISM: Artificial Sequence
<220> FEATURE:
<223> OTHER INFORMATION: Synthetic Primer

<400> SEQUENCE: 477
ggcaccgttt tagaagcgca aggtgcgatg ctg                                      33

<210> SEQ ID NO 478
<211> LENGTH: 33
<212> TYPE: DNA
<213> ORGANISM: Artificial Sequence
<220> FEATURE:
<223> OTHER INFORMATION: Synthetic Primer

<400> SEQUENCE: 478
cagcatcgca ccttgcgctt ctaaaacggt gcc                                      33

<210> SEQ ID NO 479
<211> LENGTH: 33
<212> TYPE: DNA
<213> ORGANISM: Artificial Sequence
<220> FEATURE:
<223> OTHER INFORMATION: Synthetic Primer

<400> SEQUENCE: 479
ggcaccgttt tagaagcgca aggtgcgatg ctg                                      33

<210> SEQ ID NO 480
<211> LENGTH: 33
<212> TYPE: DNA
<213> ORGANISM: Artificial Sequence
<220> FEATURE:
<223> OTHER INFORMATION: Synthetic Primer

<400> SEQUENCE: 480
cagcatcgca ccttgcgctt ctaaaacggt gcc                                      33

<210> SEQ ID NO 481
<211> LENGTH: 33
<212> TYPE: DNA
<213> ORGANISM: Artificial Sequence
<220> FEATURE:
<223> OTHER INFORMATION: Synthetic Primer

<400> SEQUENCE: 481
ctgggcgtgc gcggcgcaca tgcaacggcc cca                                      33

<210> SEQ ID NO 482
<211> LENGTH: 33
<212> TYPE: DNA
<213> ORGANISM: Artificial Sequence
<220> FEATURE:
<223> OTHER INFORMATION: Synthetic Primer

<400> SEQUENCE: 482
tggggccgtt gcatgtgcgc cgcgcacgcc cag                                      33

<210> SEQ ID NO 483
<211> LENGTH: 33
<212> TYPE: DNA
<213> ORGANISM: Artificial Sequence
<220> FEATURE:
```

<223> OTHER INFORMATION: Synthetic Primer

<400> SEQUENCE: 483
ccacatgcaa cggccgcagg caccaatgcc cgc         33

<210> SEQ ID NO 484
<211> LENGTH: 33
<212> TYPE: DNA
<213> ORGANISM: Artificial Sequence
<220> FEATURE:
<223> OTHER INFORMATION: Synthetic Primer

<400> SEQUENCE: 484
gcgggcattg gtgcctgcgg ccgttgcatg tgg         33

<210> SEQ ID NO 485
<211> LENGTH: 33
<212> TYPE: DNA
<213> ORGANISM: Artificial Sequence
<220> FEATURE:
<223> OTHER INFORMATION: Synthetic Primer

<400> SEQUENCE: 485
acccacaacc gcaaggcggc agaaccaacc aag         33

<210> SEQ ID NO 486
<211> LENGTH: 33
<212> TYPE: DNA
<213> ORGANISM: Artificial Sequence
<220> FEATURE:
<223> OTHER INFORMATION: Synthetic Primer

<400> SEQUENCE: 486
cttggttggt tctgccgcct tgcggttgtg ggt         33

<210> SEQ ID NO 487
<211> LENGTH: 33
<212> TYPE: DNA
<213> ORGANISM: Artificial Sequence
<220> FEATURE:
<223> OTHER INFORMATION: Synthetic Primer

<400> SEQUENCE: 487
cgcaagccgg cagaagcaac caagccaaat aac         33

<210> SEQ ID NO 488
<211> LENGTH: 33
<212> TYPE: DNA
<213> ORGANISM: Artificial Sequence
<220> FEATURE:
<223> OTHER INFORMATION: Synthetic Primer

<400> SEQUENCE: 488
gttatttggc ttggttgctt ctgccggctt gcg         33

<210> SEQ ID NO 489
<211> LENGTH: 33
<212> TYPE: DNA
<213> ORGANISM: Artificial Sequence
<220> FEATURE:
<223> OTHER INFORMATION: Synthetic Primer

<400> SEQUENCE: 489
gcagaaccaa ccaaggcaaa taacctggac gca         33

<210> SEQ ID NO 490

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 490
tgcgtccagg ttatttgcct tggttggttc tgc                                  33

<210> SEQ ID NO 491
<211> LENGTH: 33
<212> TYPE: DNA
<213> ORGANISM: Artificial Sequence
<220> FEATURE:
<223> OTHER INFORMATION: Synthetic Primer

<400> SEQUENCE: 491
tctctggaca agaagccccg cccgctggag gag                                  33

<210> SEQ ID NO 492
<211> LENGTH: 33
<212> TYPE: DNA
<213> ORGANISM: Artificial Sequence
<220> FEATURE:
<223> OTHER INFORMATION: Synthetic Primer

<400> SEQUENCE: 492
ctcctccagc gggcggggct tcttgtccag aga                                  33

<210> SEQ ID NO 493
<211> LENGTH: 39
<212> TYPE: DNA
<213> ORGANISM: Artificial Sequence
<220> FEATURE:
<223> OTHER INFORMATION: Synthetic Primer

<400> SEQUENCE: 493
ccgtgacatt gagtctctgc ccaagaagcc acgcccgct                            39

<210> SEQ ID NO 494
<211> LENGTH: 35
<212> TYPE: DNA
<213> ORGANISM: Artificial Sequence
<220> FEATURE:
<223> OTHER INFORMATION: Synthetic Primer

<400> SEQUENCE: 494
agtctctgcc caagaagcca cgcccgctgg aggag                                35

<210> SEQ ID NO 495
<211> LENGTH: 33
<212> TYPE: DNA
<213> ORGANISM: Artificial Sequence
<220> FEATURE:
<223> OTHER INFORMATION: Synthetic Primer

<400> SEQUENCE: 495
aagaaactgg gcgatccgac gcgtgcggtc gcg                                  33

<210> SEQ ID NO 496
<211> LENGTH: 33
<212> TYPE: DNA
<213> ORGANISM: Artificial Sequence
<220> FEATURE:
<223> OTHER INFORMATION: Synthetic Primer

<400> SEQUENCE: 496
```

```
cgcgaccgca cgcgtcggat cgcccagttt ctt                           33

<210> SEQ ID NO 497
<211> LENGTH: 33
<212> TYPE: DNA
<213> ORGANISM: Artificial Sequence
<220> FEATURE:
<223> OTHER INFORMATION: Synthetic Primer

<400> SEQUENCE: 497
gccttaagca tcttaccgga ggccccggtg tta                           33

<210> SEQ ID NO 498
<211> LENGTH: 33
<212> TYPE: DNA
<213> ORGANISM: Artificial Sequence
<220> FEATURE:
<223> OTHER INFORMATION: Synthetic Primer

<400> SEQUENCE: 498
taacaccggg gcctccggta agatgcttaa ggc                           33

<210> SEQ ID NO 499
<211> LENGTH: 28
<212> TYPE: DNA
<213> ORGANISM: Artificial Sequence
<220> FEATURE:
<223> OTHER INFORMATION: Synthetic Primer

<400> SEQUENCE: 499
agccttaagc atcttagcgc cggccccg                                 28

<210> SEQ ID NO 500
<211> LENGTH: 28
<212> TYPE: DNA
<213> ORGANISM: Artificial Sequence
<220> FEATURE:
<223> OTHER INFORMATION: Synthetic Primer

<400> SEQUENCE: 500
ctggctaaca ccggggccgg cgctaaga                                 28

<210> SEQ ID NO 501
<211> LENGTH: 33
<212> TYPE: DNA
<213> ORGANISM: Artificial Sequence
<220> FEATURE:
<223> OTHER INFORMATION: Synthetic Primer

<400> SEQUENCE: 501
atttggctgg attctccgga gggccaaaac gcg                           33

<210> SEQ ID NO 502
<211> LENGTH: 33
<212> TYPE: DNA
<213> ORGANISM: Artificial Sequence
<220> FEATURE:
<223> OTHER INFORMATION: Synthetic Primer

<400> SEQUENCE: 502
cgcgttttgg ccctccggag aatccagcca aat                           33

<210> SEQ ID NO 503
<211> LENGTH: 33
<212> TYPE: DNA
<213> ORGANISM: Artificial Sequence
<220> FEATURE:
```

<223> OTHER INFORMATION: Synthetic Primer

<400> SEQUENCE: 503
ttacagcata tccagccctg cctggccggc gac         33

<210> SEQ ID NO 504
<211> LENGTH: 33
<212> TYPE: DNA
<213> ORGANISM: Artificial Sequence
<220> FEATURE:
<223> OTHER INFORMATION: Synthetic Primer

<400> SEQUENCE: 504
gtcgccggcc aggcagggct ggatatgctg taa         33

<210> SEQ ID NO 505
<211> LENGTH: 33
<212> TYPE: DNA
<213> ORGANISM: Artificial Sequence
<220> FEATURE:
<223> OTHER INFORMATION: Synthetic Primer

<400> SEQUENCE: 505
atggtggaag aatatccctg ggaggacatg gag         33

<210> SEQ ID NO 506
<211> LENGTH: 33
<212> TYPE: DNA
<213> ORGANISM: Artificial Sequence
<220> FEATURE:
<223> OTHER INFORMATION: Synthetic Primer

<400> SEQUENCE: 506
ctccatgtcc tcccagggat attcttccac cat         33

<210> SEQ ID NO 507
<211> LENGTH: 33
<212> TYPE: DNA
<213> ORGANISM: Artificial Sequence
<220> FEATURE:
<223> OTHER INFORMATION: Synthetic Primer

<400> SEQUENCE: 507
gaagaatatg gctggccgga catggaggtt gtc         33

<210> SEQ ID NO 508
<211> LENGTH: 33
<212> TYPE: DNA
<213> ORGANISM: Artificial Sequence
<220> FEATURE:
<223> OTHER INFORMATION: Synthetic Primer

<400> SEQUENCE: 508
gacaacctcc atgtccggcc agccatattc ttc         33

<210> SEQ ID NO 509
<211> LENGTH: 33
<212> TYPE: DNA
<213> ORGANISM: Artificial Sequence
<220> FEATURE:
<223> OTHER INFORMATION: Synthetic Primer

<400> SEQUENCE: 509
tgggaggaca tggagcctgt ctctgtgagc ggc         33

<210> SEQ ID NO 510

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 510
gccgctcaca gagacaggct ccatgtcctc cca                                    33

<210> SEQ ID NO 511
<211> LENGTH: 33
<212> TYPE: DNA
<213> ORGANISM: Artificial Sequence
<220> FEATURE:
<223> OTHER INFORMATION: Synthetic Primer

<400> SEQUENCE: 511
gttctgaaga gcgaccccag cgccctggtt gag                                    33

<210> SEQ ID NO 512
<211> LENGTH: 33
<212> TYPE: DNA
<213> ORGANISM: Artificial Sequence
<220> FEATURE:
<223> OTHER INFORMATION: Synthetic Primer

<400> SEQUENCE: 512
ctcaaccagg gcgctggggt cgctcttcag aac                                    33

<210> SEQ ID NO 513
<211> LENGTH: 33
<212> TYPE: DNA
<213> ORGANISM: Artificial Sequence
<220> FEATURE:
<223> OTHER INFORMATION: Synthetic Primer

<400> SEQUENCE: 513
attaccttaa tgaaaccggt tgacggtgac ctg                                    33

<210> SEQ ID NO 514
<211> LENGTH: 33
<212> TYPE: DNA
<213> ORGANISM: Artificial Sequence
<220> FEATURE:
<223> OTHER INFORMATION: Synthetic Primer

<400> SEQUENCE: 514
caggtcaccg tcaaccggtt tcattaaggt aat                                    33

<210> SEQ ID NO 515
<211> LENGTH: 28
<212> TYPE: DNA
<213> ORGANISM: Artificial Sequence
<220> FEATURE:
<223> OTHER INFORMATION: Synthetic Primer

<400> SEQUENCE: 515
cgtttctatg ccgtctatcc cggtcggc                                          28

<210> SEQ ID NO 516
<211> LENGTH: 28
<212> TYPE: DNA
<213> ORGANISM: Artificial Sequence
<220> FEATURE:
<223> OTHER INFORMATION: Synthetic Primer

<400> SEQUENCE: 516
```

```
ccgccgatcg tgccgaccgg gatagacg                                        28
```

<210> SEQ ID NO 517
<211> LENGTH: 33
<212> TYPE: DNA
<213> ORGANISM: Artificial Sequence
<220> FEATURE:
<223> OTHER INFORMATION: Synthetic Primer

<400> SEQUENCE: 517

```
ggcggcaccg ttttaccacc gcaaggtgcg atg                                  33
```

<210> SEQ ID NO 518
<211> LENGTH: 33
<212> TYPE: DNA
<213> ORGANISM: Artificial Sequence
<220> FEATURE:
<223> OTHER INFORMATION: Synthetic Primer

<400> SEQUENCE: 518

```
catcgcacct tgcggtggta aaacggtgcc gcc                                  33
```

<210> SEQ ID NO 519
<211> LENGTH: 33
<212> TYPE: DNA
<213> ORGANISM: Artificial Sequence
<220> FEATURE:
<223> OTHER INFORMATION: Synthetic Primer

<400> SEQUENCE: 519

```
gtgcgcggcc cacatccaac ggccccaggc acc                                  33
```

<210> SEQ ID NO 520
<211> LENGTH: 33
<212> TYPE: DNA
<213> ORGANISM: Artificial Sequence
<220> FEATURE:
<223> OTHER INFORMATION: Synthetic Primer

<400> SEQUENCE: 520

```
ggtgcctggg gccgttggat gtgggccgcg cac                                  33
```

<210> SEQ ID NO 521
<211> LENGTH: 33
<212> TYPE: DNA
<213> ORGANISM: Artificial Sequence
<220> FEATURE:
<223> OTHER INFORMATION: Synthetic Primer

<400> SEQUENCE: 521

```
ggcccacatg caacgccccc aggcaccaat gcc                                  33
```

<210> SEQ ID NO 522
<211> LENGTH: 33
<212> TYPE: DNA
<213> ORGANISM: Artificial Sequence
<220> FEATURE:
<223> OTHER INFORMATION: Synthetic Primer

<400> SEQUENCE: 522

```
ggcattggtg cctggggggcg ttgcatgtgg gcc                                 33
```

What is claimed is:

1. A variant biosynthetic pathway enzyme that exhibits one or more of increased intracellular solubility, increased native folding, and reduced aggregate formation when produced recombinantly in a host cell, compared to a parent biosynthetic pathway enzyme when produced recombinantly in the host cell, wherein the parent biosynthetic pathway enzyme is
a γ-humulene synthase, and wherein said variant biosynthetic pathway enzyme is a variant γ-humulene synthase comprising an amino acid sequence having at least about 95% amino acid sequence identity to the amino acid sequence set forth in SEQ ID NO:1, wherein the variant γ-humulene synthase comprises K126P, R142G, and G227A amino acid substitutions.

2. The variant biosynthetic pathway enzyme of claim 1, wherein said variant γ-humulene synthase comprises the amino acid sequence set forth in SEQ ID NO:73.

3. The variant biosynthetic pathway enzyme of claim 1, wherein said variant γ-humulene synthase comprises the amino acid sequence set forth in SEQ ID NO:74.

4. The variant biosynthetic pathway enzyme of claim 1, wherein said variant γ-humulene synthase further comprises a set of amino acid substitutions selected from set A (G148A, G327A, and G361A), set B (F312Q, M339A, M447F), set C (M339N, S484C, and M5651), set D (A317N, A336S, S484C, and I562V), set E (A336C, T445C, S484C, 1562L, and M565L), set F (A336V, M447H, and I562T), and set G (S484A and Y566F).

5. A nucleic acid comprising a nucleotide sequence encoding the variant biosynthetic pathway enzyme of claim 1.

6. A recombinant vector comprising the nucleic acid of claim 5.

7. A recombinant host cell comprising the nucleic acid of claim 5 or the recombinant vector of claim 6.

8. The recombinant host cell of claim 7, wherein said recombinant host cell is a prokaryotic cell.

9. A method of producing an isoprenoid or isoprenoid precursor compound, the method comprising culturing the host cell of claim 8 in a suitable culture medium.

10. The method of claim 9, further comprising isolating the isoprenoid or isoprenoid precursor compound from an organic layer overlaid on the culture medium.

11. A variant biosynthetic pathway enzyme that exhibits one or more of increased intracellular solubility, increased native folding, and reduced aggregate formation when produced recombinantly in a host cell, compared to a parent biosynthetic pathway enzyme when produced recombinantly in the host cell, wherein the parent biosynthetic pathway enzyme is a truncated hydroxymethyl glutaryl-CoA reductase (tHMGR), and the variant biosynthetic pathway enzyme is a variant tHMGR comprising an amino acid sequence having at least about 95% amino acid sequence identity to the amino acid sequence set forth in SEQ ID NO:49, wherein said variant tHMGR comprises G206A, G319A, G352A, G417A, and G495A amino acid substitutions.

12. The variant biosynthetic pathway enzyme of claim 11, wherein said variant tHMGR comprises the amino acid sequence set forth in SEQ ID NO:75.

13. The variant biosynthetic pathway enzyme of claim 11, wherein said variant tHMGR comprises the amino acid sequence set forth in SEQ ID NO:76.

14. The variant biosynthetic pathway enzyme of claim 11, further comprising P200A, T239P, P428G, and K474G amino acid substitutions.

15. A nucleic acid comprising a nucleotide sequence encoding the variant biosynthetic pathway enzyme of claim 11.

16. A recombinant vector comprising the nucleic acid of claim 15.

17. A recombinant host cell comprising the nucleic acid of claim 15.

18. The recombinant host cell of claim 17, wherein said recombinant host cell is a prokaryotic cell.

19. A recombinant host cell comprising the recombinant vector of claim 16.

20. The recombinant host cell of claim 19, wherein said recombinant host cell is a prokaryotic cell.

* * * * *